US009771411B2

(12) United States Patent
Emanuel et al.

(10) Patent No.: US 9,771,411 B2
(45) Date of Patent: Sep. 26, 2017

(54) METHOD OF TREATING CANCER BY ADMINISTERING EGFR AND EGFR/IGFIR BINDING MOLECULES

(71) Applicant: BRISTOL-MYERS SQUIBB COMPANY, Princeton, NJ (US)

(72) Inventors: Stuart Emanuel, Doylestown, PA (US); Linda Engle, Framingham, MA (US); Ray Camphausen, Wayland, MA (US); Martin C. Wright, Belmont, MA (US); Ginger Chao Rakestraw, Cambridge, MA (US); Marco Gottardis, Princeton, NJ (US); Joan Carboni, Yardley, PA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 123 days.

(21) Appl. No.: 14/664,290

(22) Filed: Mar. 20, 2015

(65) Prior Publication Data

US 2015/0259398 A1    Sep. 17, 2015

Related U.S. Application Data

(62) Division of application No. 13/692,555, filed on Dec. 3, 2012, now Pat. No. 9,017,655, which is a division of application No. 12/625,217, filed on Nov. 24, 2009, now Pat. No. 8,343,501.

(60) Provisional application No. 61/200,282, filed on Nov. 26, 2008, provisional application No. 61/227,330, filed on Jul. 21, 2009, provisional application No. 61/178,279, filed on May 14, 2009, provisional application No. 61/212,966, filed on Apr. 17, 2009, provisional application No. 61/200,164, filed on Nov. 24, 2008.

(51) Int. Cl.

| | |
|---|---|
| *A61K 38/16* | (2006.01) |
| *A61K 38/39* | (2006.01) |
| *C07K 14/435* | (2006.01) |
| *C07K 14/475* | (2006.01) |
| *C07K 14/78* | (2006.01) |
| *C07K 16/28* | (2006.01) |
| *A61K 39/395* | (2006.01) |
| *A61K 45/06* | (2006.01) |
| *C07K 14/705* | (2006.01) |
| *A61K 39/00* | (2006.01) |

(52) U.S. Cl.
CPC .............. *C07K 14/78* (2013.01); *A61K 38/39* (2013.01); *A61K 39/3955* (2013.01); *A61K 45/06* (2013.01); *C07K 14/475* (2013.01); *C07K 16/2863* (2013.01); *A61K 2039/505* (2013.01); *C07K 2317/31* (2013.01); *C07K 2317/34* (2013.01); *C07K 2317/92* (2013.01); *C07K 2318/20* (2013.01); *C07K 2319/30* (2013.01)

(58) Field of Classification Search
CPC ........ A61K 38/00; A61K 38/18; A61K 38/30; C07K 14/78; C07K 14/47; C07K 14/705; C07K 14/485; C07K 14/71; C07K 2318/20; C07K 2319/30
See application file for complete search history.

(56) References Cited

U.S. PATENT DOCUMENTS

| | | |
|---|---|---|
| 3,773,919 A | 11/1973 | Boswell et al. |
| 4,863,457 A | 9/1989 | Lee |
| 4,997,652 A | 3/1991 | Wong |
| 5,164,188 A | 11/1992 | Wong |
| 5,235,041 A | 8/1993 | Cappello et al. |
| 5,443,505 A | 8/1995 | Wong et al. |
| 5,501,856 A | 3/1996 | Ohtori et al. |
| 5,514,581 A | 5/1996 | Ferrari et al. |
| 5,516,522 A | 5/1996 | Peyman et al. |
| 5,545,620 A | 8/1996 | Wahl et al. |
| 5,641,648 A | 6/1997 | Ferrari et al. |
| 5,766,242 A | 6/1998 | Wong et al. |
| 5,770,697 A | 6/1998 | Ferrari et al. |
| 5,792,742 A | 8/1998 | Gold et al. |
| 5,824,072 A | 10/1998 | Wong |
| 5,869,079 A | 2/1999 | Wong et al. |
| 5,922,676 A | 7/1999 | Pasqualini et al. |
| 6,018,030 A | 1/2000 | Ferrari et al. |

(Continued)

FOREIGN PATENT DOCUMENTS

| | | |
|---|---|---|
| CA | 2293632 A1 | 12/1998 |
| DE | 19646372 C1 | 6/1997 |

(Continued)

OTHER PUBLICATIONS

Baliwag et al. Cytokines in psoriasis. Cytokine 73: 342-350, 2015.*
Liesveld et al. "Polycythemia Vera", Merk Manual, accessed Jan. 6, 2017, 4 total pages.*
Rieux-Laucat et al. Mutations in Fas associated with human lymphoproliferative syndrome and autoimmunity. Science 268(5215): 1347-1349, 1995.*
Volkl et al. Hyperactive mTOR pathway promotes lymphoproliferation and abnormal differentiation in autoimmune lymphoproliferative syndrome. Blood 128(2): 227-238, 2016.*
Lipovsek, Dasa et al., "In-vitro protein evolution by ribosome display and mRNA display," Journal of Immunological Methods, vol. 290:51-67 (2004).

(Continued)

*Primary Examiner* — Bridget E Bunner
(74) *Attorney, Agent, or Firm* — Nelson Mullins Riley & Scarborough LLP; Jane E. Remillard, Esq.; Christopher L. Frank

(57) ABSTRACT

The present invention relates to bispecific molecules comprising an EGFR binding domain and a distinct IGFIR binding domain for use in diagnostic, research and therapeutic applications. The invention further relates to cells comprising such proteins, polynucleotide encoding such proteins or fragments thereof, and vectors comprising the polynucleotides encoding the innovative proteins. Exemplary bispecific molecules include antibody-like protein dimers based on the tenth fibronectin type III domain.

20 Claims, 57 Drawing Sheets

(56) References Cited

U.S. PATENT DOCUMENTS

| | | |
|---|---|---|
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,316,412 B1 | 11/2001 | Ginsberg et al. |
| 6,342,219 B1 | 1/2002 | Thorpe et al. |
| 6,348,333 B1 | 2/2002 | Niwa et al. |
| 6,369,116 B1 | 4/2002 | Wong et al. |
| 6,383,775 B1 | 5/2002 | Duff et al. |
| 6,462,189 B1 | 10/2002 | Koide |
| 6,518,018 B1 | 2/2003 | Szostak et al. |
| 6,524,583 B1 | 2/2003 | Thorpe et al. |
| 6,559,126 B2 | 5/2003 | Tournaire et al. |
| 6,660,492 B1 | 12/2003 | Bode et al. |
| 6,699,493 B2 | 3/2004 | Wong |
| 6,818,418 B1 | 11/2004 | Lipovsek et al. |
| 7,053,701 B2 | 5/2006 | Vice |
| 7,115,396 B2 | 10/2006 | Lipovsek et al. |
| 7,556,925 B2 | 7/2009 | Koide et al. |
| 7,598,352 B2 | 10/2009 | Koide |
| 7,847,062 B2 | 12/2010 | Chen et al. |
| 7,858,739 B2 | 12/2010 | Chen et al. |
| 7,858,759 B2 | 12/2010 | Brandt et al. |
| 8,067,201 B2 | 11/2011 | Morin et al. |
| 8,221,765 B2 | 7/2012 | Camphausen et al. |
| 8,258,265 B2 | 9/2012 | Koide |
| 8,263,741 B2 | 9/2012 | Koide |
| 8,278,419 B2 | 10/2012 | Jacobs et al. |
| 8,293,482 B2 | 10/2012 | Jacobs et al. |
| 8,324,362 B2 | 12/2012 | Chen et al. |
| 8,343,501 B2 | 1/2013 | Emanuel et al. |
| 8,420,098 B2 | 4/2013 | Camphausen et al. |
| 8,470,332 B2 | 6/2013 | Camphausen et al. |
| 8,524,244 B2 | 9/2013 | Camphausen et al. |
| 8,609,613 B2 | 12/2013 | Chen et al. |
| 8,728,483 B2 | 5/2014 | Camphausen et al. |
| 8,969,289 B2 | 3/2015 | Gosselin et al. |
| 9,017,655 B2 | 4/2015 | Emanuel et al. |
| 9,234,028 B2 | 1/2016 | Camphausen et al. |
| 9,328,157 B2 | 5/2016 | Chen et al. |
| 9,540,424 B2 | 1/2017 | Gosselin et al. |
| 9,562,089 B2 | 2/2017 | Camphausen et al. |
| 9,605,039 B2 | 3/2017 | Lipovsek et al. |
| 2002/0019517 A1 | 2/2002 | Koide |
| 2002/0061307 A1 | 5/2002 | Whitlow et al. |
| 2002/0142048 A1 | 10/2002 | Sands et al. |
| 2003/0045681 A1 | 3/2003 | Neri et al. |
| 2003/0104520 A1 | 6/2003 | Ellington et al. |
| 2003/0170753 A1 | 9/2003 | Koide |
| 2003/0186385 A1 | 10/2003 | Koide |
| 2005/0244469 A1 | 11/2005 | Whitcup et al. |
| 2005/0255548 A1 | 11/2005 | Lipovsek et al. |
| 2005/0281861 A1 | 12/2005 | Hughes et al. |
| 2006/0122162 A1 | 6/2006 | Cutler |
| 2006/0182783 A1 | 8/2006 | Hughes et al. |
| 2006/0210604 A1 | 9/2006 | Dadey et al. |
| 2006/0246059 A1 | 11/2006 | Lipovsek et al. |
| 2006/0246549 A1 | 11/2006 | Kurz et al. |
| 2006/0270604 A1 | 11/2006 | Lipovsek et al. |
| 2007/0059336 A1 | 3/2007 | Hughes et al. |
| 2007/0071575 A1 | 3/2007 | Rudduck et al. |
| 2007/0071675 A1 | 3/2007 | Wu et al. |
| 2007/0072933 A1 | 3/2007 | Peyman |
| 2007/0082365 A1 | 4/2007 | Lipovsek et al. |
| 2007/0088014 A1 | 4/2007 | Edelman et al. |
| 2007/0099879 A1 | 5/2007 | Sheibani et al. |
| 2007/0160533 A1 | 7/2007 | Chen et al. |
| 2007/0203089 A1 | 8/2007 | Rodrigues et al. |
| 2008/0015339 A1 | 1/2008 | Lipovsek et al. |
| 2008/0063651 A1 | 3/2008 | Lipovsek et al. |
| 2008/0108798 A1 | 5/2008 | Lipovsek et al. |
| 2008/0139791 A1 | 6/2008 | Lipovsek et al. |
| 2008/0193445 A1 | 8/2008 | Goetsch et al. |
| 2008/0220049 A1 | 9/2008 | Chen et al. |
| 2008/0268051 A1 | 10/2008 | Hughes et al. |
| 2009/0176654 A1 | 7/2009 | Cappuccilli et al. |
| 2009/0299040 A1 | 12/2009 | Camphausen et al. |
| 2010/0121033 A1 | 5/2010 | Camphausen et al. |
| 2010/0144599 A1 | 6/2010 | Mendlein et al. |
| 2010/0144601 A1 | 6/2010 | Jacobs et al. |
| 2010/0152063 A1 | 6/2010 | Cappuccilli et al. |
| 2010/0210511 A1 | 8/2010 | Carvajal |
| 2010/0273216 A1 | 10/2010 | Morin et al. |
| 2010/0285000 A1 | 11/2010 | Mamluk |
| 2010/0298541 A1 | 11/2010 | Wu et al. |
| 2010/0310549 A1 | 12/2010 | Chen et al. |
| 2010/0322930 A1 | 12/2010 | Kolbinger et al. |
| 2011/0021746 A1 | 1/2011 | Cappuccilli et al. |
| 2011/0034384 A1 | 2/2011 | Carvajal |
| 2011/0038866 A1 | 2/2011 | Hastewell et al. |
| 2011/0123545 A1 | 5/2011 | Marsh et al. |
| 2011/0124527 A1 | 5/2011 | Cappuccilli et al. |
| 2011/0274623 A1 | 11/2011 | Jacobs |
| 2011/0275535 A1 | 11/2011 | Loew |
| 2012/0208704 A1 | 8/2012 | Loew et al. |
| 2012/0270797 A1 | 10/2012 | Wittrup et al. |
| 2013/0079243 A1 | 3/2013 | Diem et al. |
| 2013/0079280 A1 | 3/2013 | Baca et al. |
| 2013/0096019 A1 | 4/2013 | Jacobs et al. |
| 2013/0096058 A1 | 4/2013 | Baca et al. |
| 2013/0184212 A1 | 7/2013 | Camphausen et al. |
| 2013/0237684 A1 | 9/2013 | Koide |
| 2013/0267676 A1 | 10/2013 | Koide |
| 2013/0310317 A1 | 11/2013 | Camphausen et al. |
| 2014/0038893 A1 | 2/2014 | Camphausen et al. |
| 2014/0094595 A1 | 4/2014 | Lipovsek et al. |
| 2014/0179896 A1 | 6/2014 | Chen et al. |
| 2014/0349929 A1 | 11/2014 | Camphausen et al. |
| 2015/0152147 A1 | 6/2015 | Gosselin et al. |
| 2015/0252097 A1 | 9/2015 | Camphausen et al. |
| 2016/0152688 A1 | 6/2016 | Camphausen et al. |
| 2016/0297869 A1 | 10/2016 | Chen et al. |

FOREIGN PATENT DOCUMENTS

| | | |
|---|---|---|
| EP | 0430539 A2 | 6/1991 |
| EP | 0488401 A1 | 6/1992 |
| EP | 0654256 A1 | 5/1995 |
| EP | 0962527 A1 | 12/1999 |
| EP | 0985039 B1 | 3/2000 |
| EP | 1477561 B1 | 11/2004 |
| EP | 1266025 B1 | 11/2006 |
| EP | 1137941 B1 | 8/2009 |
| EP | 2141243 A2 | 1/2010 |
| EP | 2385067 A1 | 11/2011 |
| EP | 2439212 A1 | 4/2012 |
| EP | 2379718 B1 | 3/2013 |
| JP | 4-108827 | 4/1992 |
| JP | 2001-500531 | 1/2001 |
| WO | 92/02536 A1 | 2/1992 |
| WO | 93/03172 A1 | 2/1993 |
| WO | 95/11922 A1 | 5/1995 |
| WO | 95/13765 A1 | 5/1995 |
| WO | 96/22391 A1 | 7/1996 |
| WO | 98/12226 | 3/1998 |
| WO | 98/31700 A1 | 7/1998 |
| WO | 98/56915 A2 | 12/1998 |
| WO | 99/51773 A1 | 10/1999 |
| WO | 00/34784 | 6/2000 |
| WO | 00/34787 A1 | 6/2000 |
| WO | 0107657 A1 | 2/2001 |
| WO | 01/64942 | 9/2001 |
| WO | 02/04523 A2 | 1/2002 |
| WO | 02/32925 | 4/2002 |
| WO | 02081497 A2 | 10/2002 |
| WO | 02088171 A2 | 11/2002 |
| WO | 03022858 A2 | 3/2003 |
| WO | 03072082 A1 | 9/2003 |
| WO | 03075840 A2 | 9/2003 |
| WO | 03/104418 A2 | 12/2003 |
| WO | 2005/056764 A2 | 6/2005 |
| WO | 2006/020258 A2 | 2/2006 |
| WO | 2006/091209 A2 | 8/2006 |

(56) References Cited

FOREIGN PATENT DOCUMENTS

| | | | |
|---|---|---|---|
| WO | 2007/012614 A2 | 2/2007 | |
| WO | 2007/044688 A1 | 4/2007 | |
| WO | 2007/062188 A2 | 5/2007 | |
| WO | 2007054120 A1 | 5/2007 | |
| WO | 2007/092537 A2 | 8/2007 | |
| WO | 2007/096076 A2 | 8/2007 | |
| WO | 2007/121894 A2 | 11/2007 | |
| WO | 2008/019290 A2 | 2/2008 | |
| WO | 2008/031098 A1 | 3/2008 | |
| WO | 2008/048970 A2 | 4/2008 | |
| WO | 2008/066752 A2 | 6/2008 | |
| WO | WO 2008082659 A1 | 7/2008 | * |
| WO | 2008/097497 A2 | 8/2008 | |
| WO | 2008/108986 A2 | 9/2008 | |
| WO | 2008/153745 A2 | 12/2008 | |
| WO | 2009/023184 A2 | 2/2009 | |
| WO | 2009/025806 A2 | 2/2009 | |
| WO | 2009/058379 A2 | 5/2009 | |
| WO | 2009/073115 A1 | 6/2009 | |
| WO | 2009/083804 A2 | 7/2009 | |
| WO | 2009/086116 A2 | 7/2009 | |
| WO | 2009/102421 A2 | 8/2009 | |
| WO | 2009/133208 A1 | 11/2009 | |
| WO | 2009/142773 A2 | 11/2009 | |
| WO | 2010/051274 A2 | 5/2010 | |
| WO | 2010/051310 A2 | 5/2010 | |
| WO | 2010/060095 A1 | 5/2010 | |
| WO | 2010/069913 A1 | 6/2010 | |
| WO | 2010/093627 A2 | 8/2010 | |
| WO | 2010/093771 A1 | 8/2010 | |
| WO | 2011/020033 A2 | 2/2011 | |
| WO | 2011/035202 A2 | 3/2011 | |
| WO | 2011/051333 A1 | 5/2011 | |
| WO | 2011/051466 A1 | 5/2011 | |
| WO | 2011/092233 A1 | 8/2011 | |
| WO | 2011/100700 A2 | 8/2011 | |
| WO | 2011/103105 A1 | 8/2011 | |
| WO | 2011/130324 A1 | 10/2011 | |
| WO | 2011/130328 A1 | 10/2011 | |
| WO | 2011/130354 A1 | 10/2011 | |
| WO | 2011/137319 A2 | 11/2011 | |
| WO | 2011/140086 A2 | 11/2011 | |
| WO | 2011/150133 A2 | 12/2011 | |
| WO | 2012/016245 A2 | 2/2012 | |
| WO | 2012/088006 A1 | 6/2012 | |
| WO | 2012/142515 A2 | 10/2012 | |
| WO | 2012/158678 A1 | 11/2012 | |
| WO | 2012/158739 A1 | 11/2012 | |
| WO | 2013/049275 A1 | 4/2013 | |

OTHER PUBLICATIONS

Litvinovich, Sergei V. et al., "Interactions Between Type III Domains in the 110 kDa Cell-binding Fragments of Fibronectin," J. Mol. Biol., vol. 248:611-626 (1995).

Liu, Zhihong et al., "Fine mapping of the antigen-antibody interaction of scFv215, a recombinant antibody inhibiting RNA polymerase II from *Drosophila melanogaster*," Journal of Molecular Recognition, vol. 12:103-111 (1999).

Lombardo, A. et al., "Conformational flexibility and crystallization of tandemly linked type III modules of human fibronectin," Protein Science, vol. 5:1934-1938 (1996).

Lu, Dan et al., "Simultaneous Blockade of Both the Epidermal Growth Factor Receptor and the Insulin-like Growth Factor Receptor Signaling Pathways in Cancer Cells with a Fully Human Recombinant Bispecific Antibody," The Journal of BiologicalChemistry, vol. 279(4):2856-2865 (2004).

Lu, Dan et al., "Tailoring in Vitro Selection for a Picomolar Affinity Human Antibody Directed against Vascular Endothelial Growth Factor Receptor 2 for Enhanced Neutralizing Activity," The Journal of Biological Chemistry, vol. 278(44):43496-43507(2003).

Lyden, David et al., "Impaired recruitment of bone-marrow-derived endothelial and hematopoietic precursor cells blocks tumor angiogenesis and growth," Nature Medicine, vol. 7(11):1194-1201 (2001).

Maeda, Hiroshi et al., "SMANCS and polymer-conjugated macromolecular drugs: advantages in cancer chemotherapy," Advanced Drug Delivery Reviews, vol. 46:169-185 (2001).

Main, Alison L. et al., "The Three-Dimensional Structure of the Tenth Type III Module of Fibronectin: An Insight into RGD-Mediated Interactions," Cell, vol. 71:671-678 (1992).

Mamluk, Roni et al., "Anti-tumor effect of CT-322 as an adnectin inhibitor of vascular endothelial growth factor receptor-2," mAbs, vol. 2(2):199-208 (2010).

Mao, Yong et al., "Fibronectin fibrillogenesis, a cell-mediated matrix assembly process," Matrix Biology, vol. 24:389-399 (2005).

Markland, William et al., "Iterative Optimization of High-Affinity Protease Inhibitors Using Phage Display. 1. Plasmin," Biochemistry, vol. 35:8045-8057 (1996).

Markland, William et al., "Iterative Optimization of High-Affinity Protease Inhibitors Using Phage Display. 2. Plasma Kallikrein and Thrombin," Biochemistry, vol. 35:8058-8067 (1996).

Maruyama, Kazuo et al., "Oligo-capping: a simple method to replace the cap structure of eukaryotic mRNAs with oligoribonucleotides," Gene, vol. 138:171-174 (1994).

Matsushima, Ayako et al., "Modification of *E. coli* Asparaginase with 2.4-Bis(O-Methoxypolyethylene Glycol)-6-Chloro-S-Triazine(Activated PEG2); Disapperance of Binding Ability Towards Anti-serum and Retention of Enzymic Activity," Chemistry Letters, pp. 773-776 (1980).

Mattheakis, Larry C. et al., "An in vitro polysome display system for identifying ligands from very large peptide libraries," Proc. Natl. Acad. Sci. USA, vol. 91:9022-9026 (1994).

McCleod, D. Scott et al., "Localization of VEGF Receptor-2 (KDR/Flk-1) and Effects of Blocking It in Oxygen-Induced Retinopathy," Investigative Ophthalmology & Visual Science, vol. 43(2):474-482 (2002).

McConnell, Stephen J. et al., "Tendamistat as a Scaffold for Conformationally Constrained Phage Peptide Libraries," J. Mol. Biol., vol. 250:460-470 (1995).

McPherson, Michael et al., "Drug Receptor Identification from Multiple Tissues Using Cellular-Derived mRNA Display Libraries," Chemistry & Biology, vol. 9:691-698 (2002).

Meinke, A. et al., "Cellulose-Binding Polypeptides from *Cellulomonas fimi*: Endoglucanase D (CenD), a Family A beta-1,4-Glucanase," Journal of Bacteriology, vol. 175(7):1910-1918 (1993).

Meissner, Markus et al., "Suppression of VEGFR2 Expression in Human Endothelial Cells by Dimethylfumarate Treatment: Evidence for Anti-Angiogenic Action," Journal of Investigative Dermatology, vol. 131:1356-1364 (2011).

Meyer, Rosana D. et al., "Comparative Structure-Function Analysis of VEGFR-1 and VEGFR-2, What Have We Learned from Chimeric Systems,?" Ann. N.Y. Acad. Sci., vol. 995:200-207 (2003).

Muller, Christoph W. et al., "Structure of the NF-kappaB p50 homodimer bound to DNA," Nature, vol. 373:311-317 (1995).

Muyldermans, Serge, "Single domain camel antibodies: current status," Reviews in Molecular Biotechnology, vol. 74:277-302 (2001).

Nemoto, Naoto et al., "In vitro virus: Bonding of mRNA bearing puromycin at the 3'-terminal end to the C-terminal end of its encoded protein on the ribosome in vitro," FEBS Letters, vol. 414:405-408 (1997).

Ng, Eugene W.M. et al., "Targeting angiogenesis, the underlying disorder in neovascular age-related macular degeneration," Can. J. Ophthalmol., vol. 40:352-368 (2005).

Ngo, J. Thomas et al., "Computational Complexity, Protein Structure Prediction, and the Levinthal Paradox," The Protein Folding Problem and Tertiary Structure Prediction, Merz, K. (Ed.), Birkhauser, Boston, Chapter 14, pp. 491-495 (1994).

Niemeyer, Christof M. et al., "Oligonucleotide-directed self-assembly of proteins: semisynthetic DNA—streptavidin hybrid molecules as connectors for the generation of macroscopic arrays and the construction of supramolecular bioconjugates," NucleicAcids Research, vol. 22(25):5530-5539 (1994).

Nilsen, Timothy W., "Trans-Splicing in Protozoa and Helminths," Infections Agents and Disease, vol. 1:212-218 (1992).

Nord, Karin et al., "A combinatorial library of an alpha-helical bacterial receptor domain," Prot. Eng., vol. 8:601-608 (1995).

(56) References Cited

OTHER PUBLICATIONS

Nord, Karin et al., "Binding proteins selected from combinatorial libraries of an alpha-helical bacterial receptor domain," Nature Biotechnology, vol. 15:772-777 (1997).
Notice of Opposition to European Patent No. 1137941 (Application No. 99 967 261.1), 29 pages, dated May 11, 2010.
Nygren, Per-Ake et al., "Scaffolds for engineering novel binding sites in proteins," Current Opinion in Structural Biology, vol. 7:463-469 (1997).
Parker, M.H. et al., "Antibody mimics based on human fibronectin type three domain engineered for thermostability and high-affinity binding to vascular endothelial growth factor receptor two," Protein Engineering, Design & Selection, vol. 18(9):435-444 (2005).
Partial European Search Report for Application No. 01981621.4, 5 pages, dated Feb. 25, 2005.
Patel, Neela et al., "A Selective and Oral Small Molecule Inhibitor of Vascular Epithelial Growth Factor (VEGFR)-2 and VEGFR-1 Inhibits Neovascularization and Vascular Permeability," The Journal of Pharmacology and Experimental Therapeutics, vol. 306(3):838-845 (2003).
Phillips, Anthony J., "The challenge of gene therapy and DNA delivery," Journal of Pharmacy and Pharmacology, vol. 53:1169-1174 (2001).
Plaxco, Kevin W. et al., "A Comparison of the Folding Kinetics and Thermodynamics of Two Homologous Fibronectin Type III Modules," J. Mol. Biol., vol. 270:763-770 (1997).
Plaxco, Kevin W. et al., "Rapid refolding of a proline-rich all-beta-sheet fibronectin type III module," Proc. Natl. Acad. Sci. USA, vol. 93:10703-10706 (1996).
Posey, J. et al., "A Phase I Trial of an Anti-KDR (VEGFR2) Chimeric Antibody in Patients with Liver Metastases in Colorectal Cancer (CRC)," Slides from presentation at 2002 American Society of Clinical Oncology (ASCO) Annual Meeting, 20 pages,(2002).
Potts, Jennifer R. et al., "Fibronectin structure and assembly," Current Biology, vol. 6:648-655 (1994).
Potts, Jennifer R. et al., "Structure and Function of Fibronectin Modules," Matrix Biology, vol. 15:313-320 (1996).
Proescholdt, Martin A. et al., "Vascular Endothelial Growth Factor is Expressed in Multiple Sclerosis Plaques and Can Induce Inflammatory Lesions in Experimental Allergic Encephalomyelitis Rats," Journal of Neuropathology and Experimental Neurology,vol. 61(10):914-925 (2002).
Richards, Julie et al., "Engineered Fibronectin Type III Domain with a RGDWXE Sequence Binds with Enhanced Affinity and Specificity to Human alphavbeta3 Integrin," J. Mol. Biol., vol. 326:1475-1488 (2003).
Roberts, Richard W. et al., "RNA-peptide fusions for the in vitro selection of peptides and proteins," Proc. Natl. Acad. Sci. USA, vol. 94:12297-12302 (1997).
Roberts, Richard W., "Totally in vitro protein selection using mRNA-protein fusions and ribosome display," Current Opinion in Chemical Biology, vol. 3:268-273 (1999).
Rottgen, Peter et al., "A human pancreatic secretory trypsin inhibitor presenting a hyperveriable highly constrained epitope via monovalent phagemid display," Gene, vol. 164:243-250 (1995).
Rudikoff, Stuart et al., "Single amino acid substitution altering antigen-binding specificity," Proc. Natl. Acad. Sci. USA, vol. 79:1979-1983 (1982).
Schildbach, Joel F. et al., "Contribution of a single heavy chain residue to specificity of an anti-digoxin monoclonal antibody," Protein Science, vol. 3:737-749 (1994).
Schildbach, Joel F. et al., "Heavy Chain Position 50 is a Determination of Affinity and Specificity for the Anti-digoxin Antibody 26-10," The Journal of Biological Chemistry, vol. 268(29):21739-21747 (1993).
Scott, Jamie K. et al., "Searching for Peptide Ligands with an Epitope Library," Science, vol. 249:386-390 (1990).
Shibata, K. et al., "An attempt to substitute the cell binding domain of human fibronectin in lambda phage J protein: Computer design and expression," Biochimie, vol. 75:459-465 (1993).

Shibuya, Masabumi, "Vascular endothelial growth factor receptor-2: Its unique signaling and specific ligand, VEGF-E," Cancer Sci., vol. 94(9):751-756 (2003).
Shima, David T. et al., "The Mouse Gene for Vascular Endothelial Growth Factor," The Journal of Biological Chemistry, vol. 271(7):3877-3883 (1996).
Skolnick, Jeffrey et al., "From genes to protein structure and function: novel application of computational approaches in the genomic era," Tibtech, vol. 18:34-39 (2000).
Smith, George P. et al., "Phage Display," Chem. Rev., vol. 97:391-410 (1997).
Smith, Temple et al., "The challenges of genome sequence annotation or 'The devil is in the details,'" Nature Biotechnology, vol. 15:1222-1223 (1997).
Supplementary European Search Report for Application No. 01913159.8, 3 pages, dated Dec. 21, 2004.
Supplementary European Search Report for Application No. 99967261.1, 3 pages, dated Mar. 6, 2002.
Takahashi, Satoru, "Vascular Endothelial Growth Factor (VEGF), VEGF Receptors and Their Inhibitors for Antiangiogenic Tumor Therapy," Biol. Pharm. Bull. vol. 34(12):1785-1788 (2011).
Tang, Lisa et al., "Pharmacokinetic Aspects of Biotechnology Products," Journal of Pharmaceutical Sciences, vol. 93 (9):2184-2204 (2004).
Tischer, Edmund et al., "The Human Gene for Vascular Endothelial Growth Factor," The Journal of Biological Chemistry, vol. 266(18):11947-11954 (1991).
Tokuriki, Nobuhiko et al., "Stability effects of mutations and protein evolvability," Current Opinion in Structural Biology, vol. 19:596-604 (2009).
Tramontano, Anna et al., "The Making of the Minibody: an Engineered beta-Protein for the Display of Conformationally Constrained Peptides," Journal of Molecular Recognition, vol. 7:9-24 (1994).
Trinh, Ryan et al., "Optimization of codon pair use within the (GGGGS)3 linker sequence results in enhanced protein expression," Molecular Immunology, vol. 40:717-722 (2004).
Verheul, H.M.W. et al., "Targeting Vascular Endothelial Growth Factor Blockade: Ascites and Pleural Effusion Formation," The Oncologist, vol. 5(Suppl. 1):45-50 (2000).
Vuento, Matti et al., "Purification of Fibronectin from Human Plasma by Affinity Chromatography under Non-Denaturing Conditions," Biochem. J., vol. 183:331-337 (1979).
Wang, Cheng-I et al., "Isolation of a High Affinity Inhibitor of Urokinase-type Plasminogen Activator by Phage Display of Ecotin," The Journal of Biological Chemistry, vol. 270(20):12250-12256 (1995).
Watanabe, H. et al., "Anti-vascular endothelial growth factor receptor-2 (Flk-1/KDR) antibody suppresses contact hypersensitivity," Experimental Dermatology, vol. 13:671-681 (2004).
Watanabe, Takeshi et al., "Gene Cloning of Chitinase A1 from Bacillus circulans WL-12 Revealed Its Evolutionary Relationship to Serratia Chitinase and to the Type III Homology Units of Fibronectin," The Journal of Biological Chemistry, vol. 265:15659-15665 (1990).
Wells, James A., "Additivity of Mutational Effects in Proteins," Biochemistry, vol. 29(37):8509-8517 (1990).
Williams, Alan F. et al., "The Immunoglobulin Superfamily—Domains for Cell Surface Recognition," Ann. Rev. Immunol., vol. 6:381-405 (1988).
Williams, Michael J. et al., "Solution Structures of Modular Proteins by Nuclear Magnetic Resonance," Methods in Enzymology, vol. 245:451-469 (1994).
Wilson, David S. et al., "The use of mRNA display to select high-affinity protein-binding peptides," PNAS, vol. 98 (7):3750-3755 (2001).
Written Opinion for Application No. PCT/US01/06414, 5 pages, dated Feb. 7, 2002.
Xiang, Jim et al., "Study of B72.3 combining sites by molecular modeling and site-directed mutagenesis," Protein Engineering, vo. 13(5):339-344 (2000).

(56) References Cited

OTHER PUBLICATIONS

Xu, Lihui et al., "Directed Evolution of High-Affinity Antibody Mimics Using mRNA Display," Chemistry & Biology, vol. 9:933-942 (2002).
Yang, Karen et al., "Tailoring structure-function and pharmacokinetic properties of single-chain Fv proteins by site-specific PEGylation," Protein Engineering, vol. 16(10):761-770 (2003).
Yoshiji, H. et al., "Vascular endothelial growth factor and receptor interaction is a prerequisite for murine hepatic fibrogenesis," Gut, vol. 52:1347-1354 (2003).
Zdanov, Alexander et al., Structure of a single-chain antibody variable domain (Fv) fragment complexed with a carbohydrate antigen at 1.7-A resolution, Proc. Natl. Acad. Sci. USA, vol. 91:6423-6427 (1994).
Zhou, Tianhong et al., "Development of a multi-drug delivery implant for intraocular management of proliferative vitreoretinopathy," Journal of Controlled Release, vol. 55:281-295 (1998).
Zhu, Z. et al., "Inhibition of human leukemia in an animal model with human antibodies directed against vascular endothelial growth factor receptor 2. Correlation between antibody affinity and biological activity," Leukemia, vol. 17:604-611 (2003).
Ackermann, Maximilian et al., "Anti-VEGFR2 and anti-IGF-1R-Adnectins inhibit Ewing's sarcoma A673-xenograft growth and normalize tumor vascular architecture," Angiogenesis, vol. 15:685-695 (2012).
Apte, Aaron N. et al., "Anchor-Ligated cDNA Libraries: A Technique for Generating a cDNA Library for the Immediate Cloning of the 5' Ends of mRNAs," BioTechniques, vol. 15(5):890-893 (1993).
Bae, Dong-Goo et al., "Arginine-rich Anti-vascular Endothelial Growth Factor Peptides Inhibit Tumor Growth and Metastasis by Blocking Angiogenesis," The Journal of Biological Chemistry, vol. 275(18):13588-13596 (2000).
Baggio, Rick et al., "Identification of epitope-like consensus motifs using mRNA display," Journal of Molecular Recognition, vol. 15:126-134 (2002).
Baron, Martin et al., "H NMR Assignment and Secondary Structure of the Cell Adhesion Type III Module of Fibronectin," Biochemistry, vol. 31:2068-2073 (1992).
Baron, Martin et al., "Protein modules," TIBS, vol. 16:13-17 (1991).
Batori, Vincent et al., "Exploring the potential of the monobody scaffold: effects of loop elongation on the stability of a fibronectin type III domain," Protein Engineering, vol. 15(12):1015-1020 (2002).
Bianchi, Elisabetta et al., "High Level Expression and Rational Mutagenesis of a Designed Protein, the Minibody," J. Mol. Biol., vol. 236:649-659 (1994).
Boder, Eric T. et al., "Directed evolution of antibody fragments with monovalent femtomolar antigen-binding affinity," PNAS, vol. 97(20):10701-10705 (2000).
Boder, Eric T. et al., "Yeast surface display for screening combinatorial polypeptide libraries," Nature Biotechnology, vol. 15:553-557 (1997).
Boldicke, Thomas et al., "Anti-VEGFR-2 scFvs for Cell Isolation. Single-Chain Antibodies Recognizing the Human Vascular Endothelial Growth Factor Receptor-2 (VEGFR-2/flk-1) on the Surface of Primary Endothelial Cells and Preselected CD34+ Cells fromCord Blood," Stem Cells, vol. 19:24-36 (2001).
Bork, P. et al., "The Immunoglobulin Fold, Structural Classification, Sequence Patterns and Common Core," J. Mol. Biol., vol. 242:309-320 (1994).
Bork, Peer et al., "Go hunting in sequence databases but watch out for the traps," TIG, vol. 12(10):425-427 (1996).
Bork, Peer et al., "Proposed acquisition of an animal protein domain by bacteria," Proc. Natl. Acad. Sci. USA, vol. 89:8990-8994 (1992).
Bork, Peer, "Powers and Pitfalls in Sequence Analysis: The 70% Hurdle," Genome Research, vol. 10:398-400 (2000).

Brenchley, P.E.C. et al., "Angiogenesis in inflammatory joint disease: a target for therapeutic intervention," Clin. Exp. Immunol., vol. 121:426-429 (2000).
Brenner, Steven E., "Errors in genome annotation," TIG, vol. 15(4):132-133 (1999).
Brock, Kenny V. et al., "Nucleotide sequencing of 5' and 3' termini of bovine viral diarrhea virus by RNA ligation and PCR," Journal of Virological Methods, vol. 38:39-46 (1992).
Brown, McKay et al., "Tolerance to Single, but Not Multiple, Amino Acid Replacements in Antibody VH CDR2," The Journal of Immunology, vol. 156:3285-3291 (1996).
Bruzik, James P. et al., "Spliced leader RNAs from lower eukaryotes are trans-spliced in mammalian cells," Nature, vol. 360(6405):692-695 (1992).
Caliceti, Paolo et al., "Pharmacokinetic and biodistribution properties of poly(ethylene glycol)-protein conjugates," Advanced Drug Delivery Reviews, vol. 55:1261-1277 (2003).
Campbell, Lain D. et al., "Building proteins with fibronectin type III modules, Fibronectin type III modules are versatile components of many proteins. Recent structures of module pairs show how these modules are joined together," Structure, vol. 2:333-337 (1994).
Carvalho, Jozelio Freire et al., "Vascular Endothelial Growth Factor (VEGF) in Autoimmune Diseases," Journal of Clinical Immunology, vol. 27(3):246-256 (2007).
Choy, E.H.S. Efficacy of a novel PEGylated humanized anti-TNF fragment (CDP870) in patients with rheumatoid arthritis: a phase II double-blinded, randomized, dose-escalating trial, Rheumatology, vol. 41:1133-1137 (2002).
Clackson, Tim et al., "In vitro selection from protein and peptide libraries," TibTech, vol. 12(5):173-184 (1994).
Clackson, Tim et al., "Making antibody fragments using phage display libraries," Nature, vol. 352:624-628 (1991).
Claffey, Kevin P. et al., "Vascular Endothelial Growth Factor, Regulation by Cell Differentiation and Activated Second Messenger Pathways," The Journal of Biological Chemistry, vol. 267(23):16317-16323 (1992).
Clarke, Jane et al., "Folding and Stability of a Fibronectin Type III Domain of Human Tenascin," J. Mol. Biol., vol. 270:771-778 (1997).
Connelly, Roberta J. et al., "Mitogenic properties of a bispecific single-chain Fv-Ig fusion generated from CD2-specific mAb to distinct epitopes," International Immunology, vol. 10(12):1863-1872 (1998).
Copie, Valerie et al., "Solution Structure and Dynamics of Linked Cell Attachment Modules of Mouse Fibronectin Containing the RGD and Synergy Regions: Comparison wtih the Human Fibronectin Crystal Structure," J. Mol. Biol., vol. 277:663-682 (1998).
Cota, Ernesto et al., "Two Proteins with the Same Structure Respond very Differently to Mutation: The Role of Plasticity in Protein Stability," J. Mol. Biol., vol. 302:713-725 (2000).
Cujec, Thomas P. et al., "Selection of v-Abl Tyrosine Kinase Substrate Sequences from Randomized Peptide and Cellular Proteomic Libraries Using mRNA Display," Chemistry & Biology, vol. 9:253-264 (2002).
Devlin, James J. et al., "Random Peptide Libraries: A Source of Specific Protein Binding Molecules," Science, vol. 249:404-406 (1990).
Dgene Search Results, 33 pages (2005).
Dickinson, Craig D. et al., "Crystal Structure of the Tenth Type III Cell Adhesion Module of Human Fibronectin," J. Mol. Biol., vol. 236:1079-1092 (1994).
Dickinson, Craig D. et al., "Crystals of the Cell-binding Module of Fibronectin Obtained from a Series of Recombinant Fragments Differing in Length," J. Mol. Biol., vol. 238:123-127 (1994).
Doerks, Tobias et al., "Protein annotation: detective work for function prediction," TIG, vol. 14(6):248-250 (1998).
Duan, Jinzhu, et al., "Fibronectin Type III Domain Based Monobody with High Affinity," Biochemistry, vol. 46:12656-12664 (2007).
Ely, Kathryn R. et al., "Common molecular scaffold for two unrelated RGD molecules," Protein Engineering, vol. 8 (8):823-827 (1995).

(56) References Cited

OTHER PUBLICATIONS

Emanuel, Stuart L. et al., "A fibronectin scaffold approach to bispecific inhibitors of epidermal growth factor receptor and insulin-like growth factor-I receptor," mAbs, vol. 3(1):38-48 (2011).
Emanuel, Stuart L. et al., "Adnectins as a platform for multi-specific targeted biologics: A novel bispecific inhibitor of EGFR and IGF-IR growth factor receptors," Cancer Research, vol. 70(8 Suppl. 1), Abstract 2586, 1 page, AACR 101st AnnualMeeting (2010).
Emmanuel, Stuart L. et al., "Functional activity of a bispecific Adnectin inhibitor to EGFR and IGFR," 2009 AACR Annual Meeting, Session Title: IGF-IR and P13K Pathways, Abstract No. 2813, 2 pages (2009).
European Office Action for Application No. 06013825.2, 9 pages, dated Sep. 17, 2008.
European Office Action for Application No. 09167669.2, 7 pages, dated Dec. 28, 2009.
Fenton, Bruce et al., "Pathophysiological effects of antibodies to IGF-1R and VEGFR-2 plus fractionated radiation in DU145 prostate carcinoma xenografts," Radiation Research Society 2005 Annual Meeting, Abstract No. PP109, 1 page (2005).
Ferguson, Kimberly C. et al., "The SL1 trans-spliced leader RNA performs an essential embryonic function in Caenorhabditis elegans that can also be supplied by SL2 RNA," Genes & Development, vol. 10:1543-1556 (1996).
GenBank Accession No. AAC48614, MacLeod, J.N. et al., "Fibronectin mRNA splice variant in articular cartilage lacks bases encoding the V, III-15, and I-10 protein segments," J. Biol. Chem., vol. 271(31):18954-18960 (1996), 2 pages (1996).
GenBank Accession No. CAA26536, Kornblihtt, A.R. et al., "Primary structure of human fibronectin: differential splicing may generate at least 10 polypeptides from a single gene," EMBO J., vol. 4(7):1755-1759 (1985), 7 pages (1996).
GenBank Accession No. P07589, Skorstengaard, K. et al., "Complete primary structure of bovine plasma fibronectin," Eur. J. Biochem., vol. 161(2):441-453 (1986), 9 pages (1997).
GenBank Accession No. X02761, Kornblihtt, A.R. et al., "Primary structure of human fibronectin: differential splicing may generate at least 10 polypeptides from a single gene," EMBO J., vol. 4(7):1755-1759 (1985), 4 pages (1996).
U.S. Appl. No. 15/440,730, filed Feb. 23, 2017, Dasa Lipovsek.
U.S. Appl. No. 15/404,749, filed Jan. 12, 2017, Ray Camphausen.
U.S. Appl. No. 15/363,724, filed Nov. 29, 2016, Michael L. Gosselin.
U.S. Appl. No. 15/385,222, filed Dec. 20, 2016, Ray Camphausen.
U.S. Appl. No. 11/543,316, Nov. 16, 2016.
U.S. Appl. No. 14/022,827, Jan. 31, 2017.
U.S. Appl. No. 14/022,827, Jul. 21, 2016.
U.S. Appl. No. 14/229,415, Jan. 9, 2017.
GenBank Accession No. ABB78921, Lipovsek, D. et al., "New non-antibody proteins having an immunoglobulin fold, useful in research, therapeutic or diagnostic fields, particularly as scaffolds for designing proteins with specific properties, e.g. For binding any antigen of interest," 33 pages (2005).
Ghosh, Gourisankar et al., "Structure of NF-kappaB p50 homodimer bound to a kappaB site," Nature, vol. 373:303-310 (1995).
Giusti, Angela M. et al., "Somatic diversification of S107 from an antiphosphocholine to an anti-DNA autoantibody is due to a single base change in its heavy chain variable region," Proc. Natl. Acad. Sci. USA, vol. 84:2926-2930 (1987).
Goedert, M. et al., "Cloning and sequencing of the cDNA encoding an isoform of microtubule-associated protein tau containing four tandem repeats: differential expression of tau protein mRNAs in human brain," The EMBO Journal, vol. 8(2):393-399(1989).
Grant, Richard P. et al., "Structural Requirements for Biological Activity of the Ninth and Tenth Fill Domains of Human Fibronectin," The Journal of Biological Chemistry, vol. 272(10):6159-6166 (1997).
Hamers-Casterman, C. et al., "Naturally occurring antibodies devoid of light chains," Nature, vol. 363:446-448 (1993).
Hammond, Philip W. et al., "In Vitro Selection and Characterization of Bcl-XL-binding Proteins from a Mix of Tissue-specific mRNA Display Libraries," The Journal of Biological Chemistry, vol. 276(24):20898-20906 (2001).
Harpaz, Yahouda et al., "Many of the Immunoglobulin Superfamily Domains in Cell Adhesion Molecules and Surface Receptors Belong to a New Structural Set Which is Close to That Containing Variable Domains," J. Mol. Biol., vol. 238:528-539 (1994).
Hocking, Denise C. et al., "A Novel Role for the Integrin-binding III-10 Module in Fibronectin Matrix Assembly," The Journal of Cell Biology, vol. 133(2):431-444 (1996).
Hocking, Denise C. et al., "Activation of Distinct alpha5betal-mediated Signaling Pathways by Fibronectin's Cell Adhesion and Matrix Assembly Domains," The Journal of Cell Biology, vol. 141(1):241-253 (1998).
Huang, Fei et al., "The Mechanisms of Differential Sensitivity to an Insulin-like Growth FActor-1 Receptor Inhibitor (BMS-536924) and Rationale for Combining with EGFR/HER2 Inhibitors," Cancer Res., vol. 69(1):161-170 (2009).
Huang, Hu et al., "Blockade of VEGFR1 and 2 Suppresses Pathological Angiogenesis and Vascular Leakage in the Eye," PLoS One, vol. 6(6):e21411, 14 pages, doi:10.1371/journal.pone.0021411 (2011).
Husimi, Y. et al., "Role of the Virus-type Strategy in Encoded Molecular Evolution," Progress in Biophysics and Molecular Biology, vol. 65(Suppl. 1):64 (1996).
Hynes, Richard O. et al., "Integrins: Versability, Modulation, and Signaling in Cell Adhesion," Cell, vol. 69:11-25 (1992).
International Preliminary Examination Report for Application No. PCT/US01/06414, 6 pages, dated Aug. 27, 2002.
International Preliminary Examination Report for Application No. PCT/US01/32233, 5 pages, dated Dec. 10, 2003.
International Preliminary Examination Report for Application No. PCT/U599/29317, 4 pages, dated Aug. 14, 2000.
International Preliminary Report on Patentability and Written Opinion for Application No. PCT/US2009/003192, 12 pages, dated Nov. 23, 2010.
International Preliminary Report on Patentability and Written Opinion for Application No. PCT/US2009/065765, 12 pages, dated May 24, 2011.
International Preliminary Report on Patentability and Written Opinion for Application No. PCT/US2011/034998, 10 pages, dated Nov. 6, 2012.
International Preliminary Report on Patentability for Applicaiton No. PCT/U52004/040885, 6 pages, dated Jun. 7, 2006.
International Preliminary Report on Patentability for Application No. PCT/US2011/038013, 9 pages, dated Nov. 27, 2012.
International Search Report for Application No. PCT/US01/06414, 5 pages, dated Aug. 7, 2001.
International Search Report for Application No. PCT/US01/32233, 3 pages, dated Jun. 12, 2003.
International Search Report for Application No. PCT/US04/40885, 3 pages, dated Feb. 21, 2006.
International Search Report for Application No. PCT/US2009/003192, 8 pages, dated Jun. 1, 2010.
International Search Report for Application No. PCT/US2009/065765, 7 pages, dated Apr. 23, 2010.
International Search Report for Application No. PCT/US2011/034998, 5 pages, dated Jul. 17, 2012.
International Search Report for Application No. PCT/US2011/038013, 7 pages, dated Jan. 25, 2012.
International Search Report for Application No. PCT/US99/29317, 2 pages, dated Apr. 6, 2000.
Jain, Rakesh K. et al., "Dissecting Tumour Pathophysiology Using Intravital Microscopy," Nature, vol. 2:266-276 (2002).
Jakob, W. et al., "The chick embryo chorioallantoic membrane as a bioassay for angiogenesis factors: Reactions induced by carrier materials," Exp. Path. Bd., vol. 15:241-249 (1978).
Jung, Gyoo Yeol et al., "A Functional Protein Chip for Pathway Optimization and in Vitro Metabolic Engineering," Science, vol. 304:428-431 (2004).

(56) References Cited

OTHER PUBLICATIONS

Keefe, Anthony D. et al., "Functional proteins from a random-sequence library," Nature, vol. 410:715-718 (2001).

King, Catherine A. et al., "DNA vaccines with single-chain Fv fused to fragment C of tetanus toxin induce protective immunity against lymphoma and myeloma," Nature Medicine, vol. 4(11):1281-1286 (1998).

Kohler, G. et al., "Continuous cultures of fused cells secreting antibody of predefined specificity," Nature, vol. 256:495-497 (1975).

Koide, Akiko et al., "Monobodies. Antibody Mimics Based on the Scaffold of the Fibronectin Type III Domain," Methods in Molecular Biology, vol. 352: Protein Engineering Protocols, K.M. Arndt (Ed.), Humana Press, Totowa, NJ, Chapter 6, pp. 95-109(2007).

Koide, Akiko et al., "Stabilization of a Fibronectin Type III Domain by the Removal of Unfavorable Electrostatic Interactions on the Protein Surface," Biochemistry, vol. 40:10326-10333 (2001).

Koide, Akiko et al., "The Fibronectin Type III Domain as a Scaffold for Novel Binding Proteins," J. Mol. Biol., vol. 284:1141-1151 (1998).

Koide, Shohei et al., "Directed Evolution of Fibronectin Type III Domain to Novel Ligand Binding Proteins," FASEB J., vol. 11(9 Suppl.), Poster No. M40, p. A837, (1997).

Koide, Shohei et al., "Directed Evolution of Fibronectin Type III Domain to Novel Ligand Binding Proteins," The Faseb Journal, vol. 11(9):A1155, Poster No. 1739 (1997).

Ku, Jung et al., "Alternate protein frameworks for molecular recognition," Proc. Natl. Acad. Sci. USA, vol. 92:6552-6556 (1995).

Kurz, Markus et al., "Psoralen photo-crosslinked mRNA-puromycin conjugates: a novel template for the rapid and facile preparation of mRNA-protein fusions," Nucleic Acids Research, vol. 28(18):e83, 5 pages (2000).

Kussie, Paul H. et al., "A Single Engineered Amino Acid Substitution Changes Antibody Fine Specificity," Journal of Immunology, vol. 152:146-152 (1994).

Leahy, Daniel J. et al., "2.0 A Crystal Structure of a Four-Domain Segment of Human Fibronectin Encompassing the RGD Loop and Synergy Region," Cell, vol. 84:155-164 (1996).

Leahy, Daniel J. et al., "Structure of a Fibronectin Type III Domain from Tenascin Phased by MAD Analysis of the Selenomethionyl Protein," Science, vol. 258:987-991 (1992).

Lee, Grace et al., "Strong Inhibition of Fibrogen Binding to Platelet Receptor Alpha2b beta 3 by RGD Sequences installedinto the Presentation Scaffold," Prot. Eng., vol. 6:745-754 (1993).

Lipovsek, D., "Adnectins: engineered target-binding protein therapeutics," Protein Engineering, Design & Selection, vol. 24(1-2):3-9 (2011).

Lipovsek, Dasa et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," J. Mol. Biol., 368:1024-1041 (2007).

* cited by examiner

SUMMARY OF ACTIVITY IN CELL BASED ASSAYS

| NAME | H292 pEGFR ELISA (nM) | H292 pIGFR ELISA (nM) | H292 pAKT ELISA (nM) | A431 pEGFR ICW (nM) | A431 pERK ICW (nM) |
|---|---|---|---|---|---|
| E1 | 8 | --- | | 24 | 13 |
| E1-GS10-I1 (Pegylated) | 123 | 4 | 5 | 297 | 295 |
| E1-GS10-I1 | 30 | 1 | 1 | 36 | 51 |
| I1-GS10-E1 (Pegylated) | 127 | 0.9 | 0.8 | 302 | 300 |
| I1-GS10-E1 | 42 | 1 | 1 | 93 | 99 |
| E2 | 31 | --- | | 38 | 40 |
| E2-GS10-I1 (Pegylated) | 32 | 0.3 | 0.6 | 77 | 78 |
| E2-GS10-I1 | 8 | 0.1 | 0.1 | 19 | 20 |
| I1-GS10-E2 (Pegylated) | 47 | 0.8 | 0.6 | 97 | 116 |
| I1-GS10-E2 | 8 | 0.1 | 0.1 | 11 | 15 |
| E3 | 21 | --- | | 14 | 11 |
| E3-GS10-I1 (Pegylated) | 10 | 6 | 4 | 42 | 40 |
| E3-GS10-I1 | 7 | 6 | 3 | 14 | 12 |
| I1GS10-E3 (Pegylated) | 46 | 2 | 2 | 47 | 50 |
| I1-GS10-E3 | 25 | 19 | 26 | 47 | 42 |

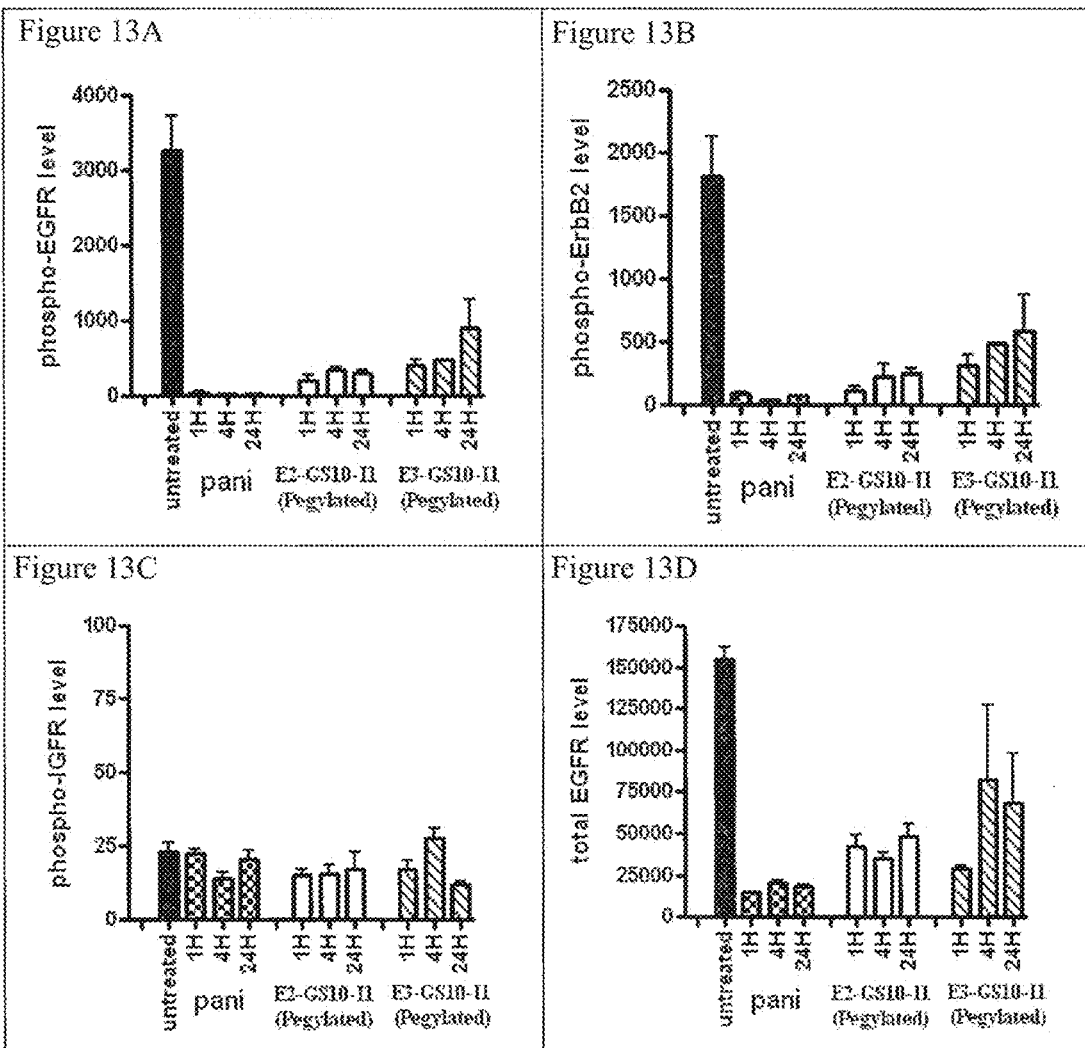

Figure 14
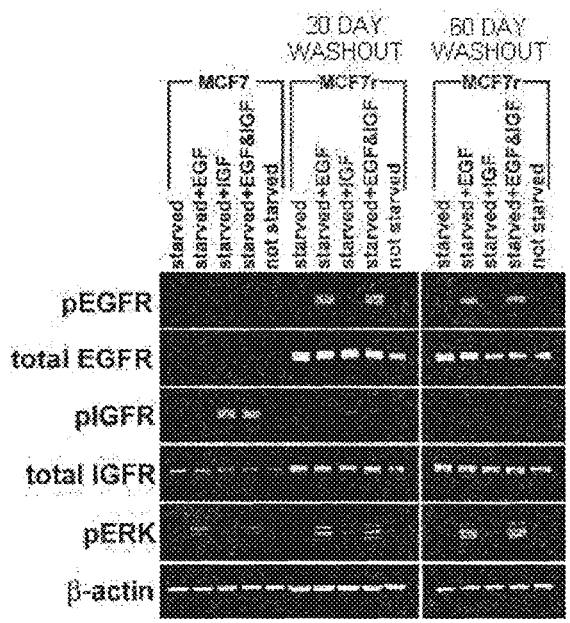
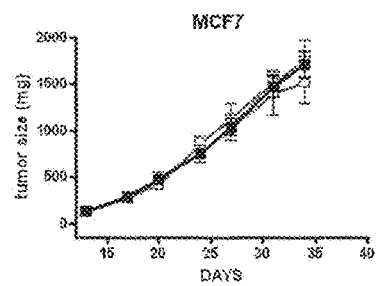
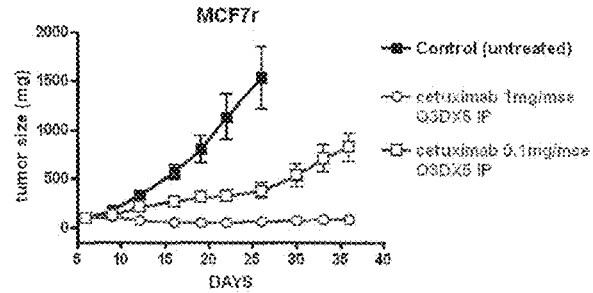

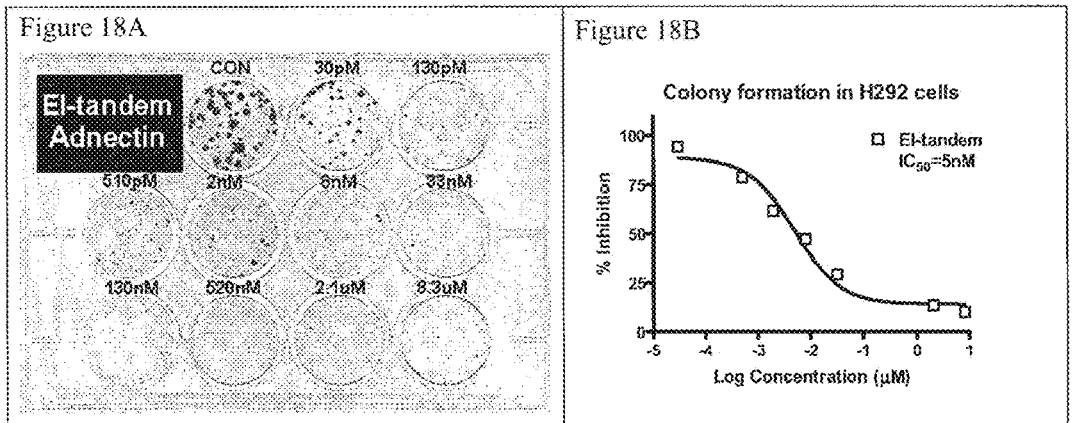
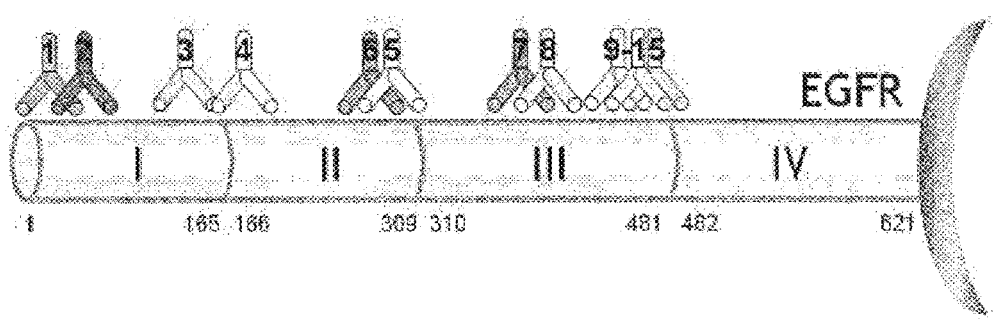
Figure 19A
Figure 19B
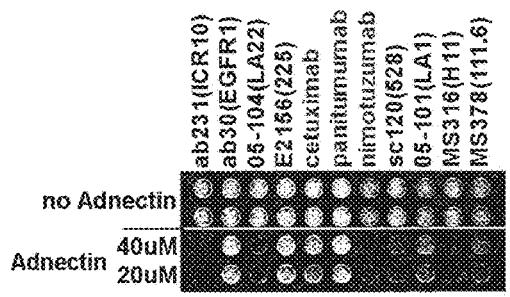

Tm = 55.2°C

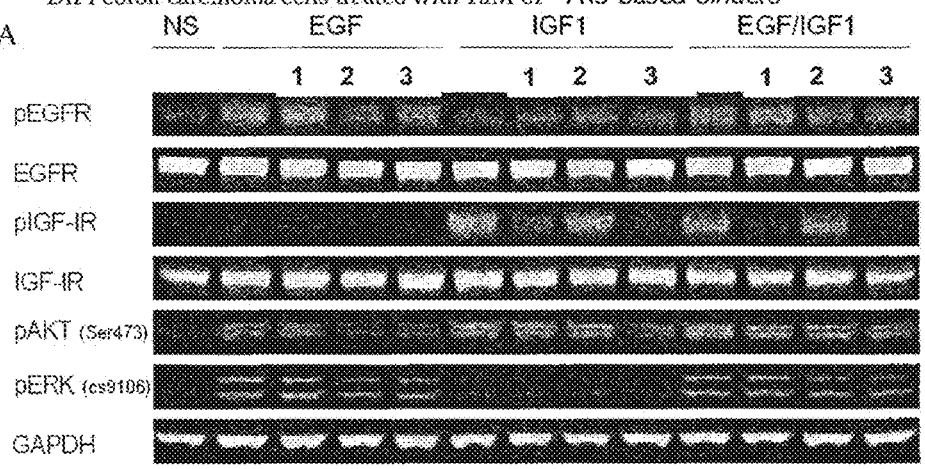
Figure 24A. DiFi colon carcinoma cells treated with 1uM of $^{10}$Fn3-based binders
(1=I1 pegylated; 2=E5 pegylated; 3=I1-GS10-E5 pegylated)
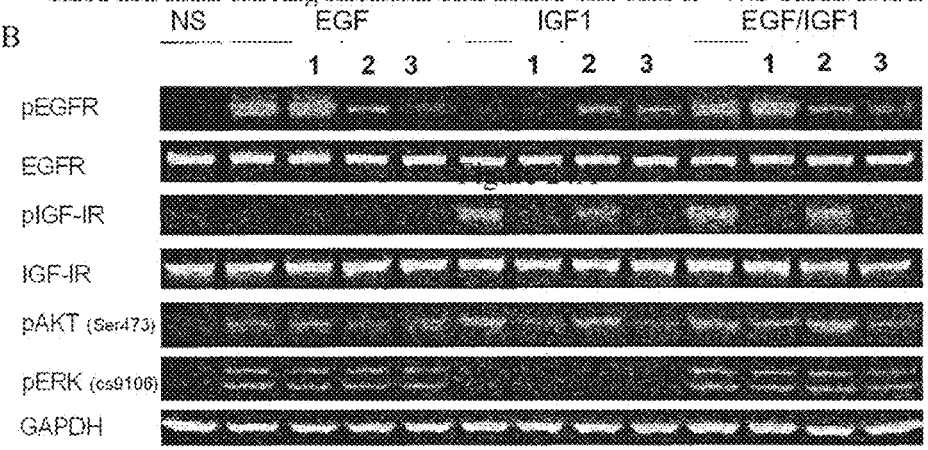
Figure 24B. H292 non-small cell lung carcinoma cells treated with 1uM of $^{10}$Fn3-based binders
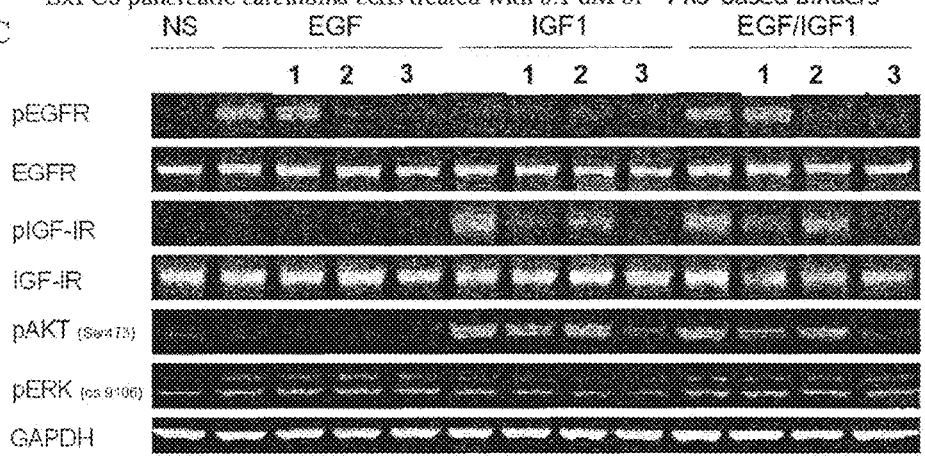
Figure 24C. BxPC3 pancreatic carcinoma cells treated with 0.1 uM of $^{10}$Fn3-based binders Abbreviations are as follows: I = I1 (unpegylated); E = E2 (unpegylated); E-I=E2-GS10-I1 (unpegylated)

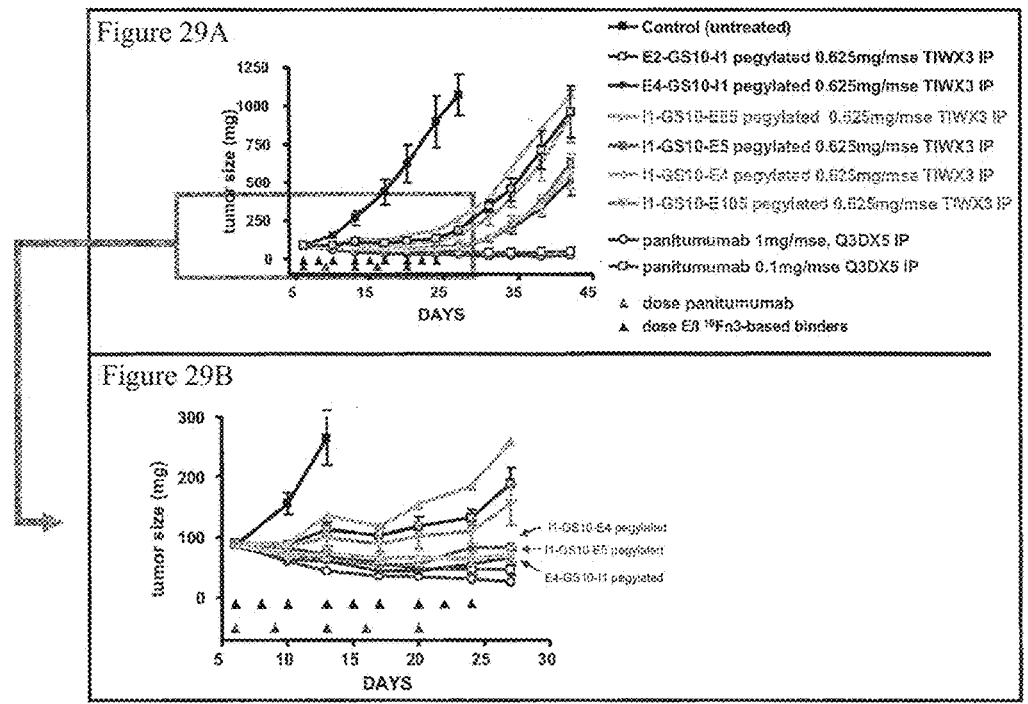
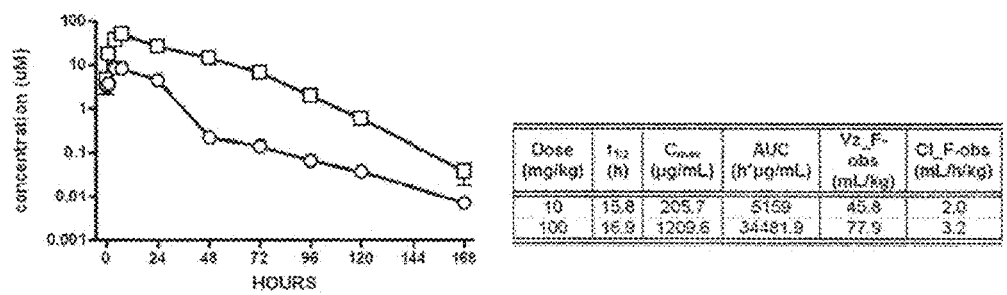
Figure 30. Pharmacokinetic profile of E2-GS10-I1 pegylated in mice
Plasma levels E2-GS10-I1 pegylated after dosing this construct at 100 mg/kg (□) and 10 mg/kg (○) by the ip route.

Figure 33A
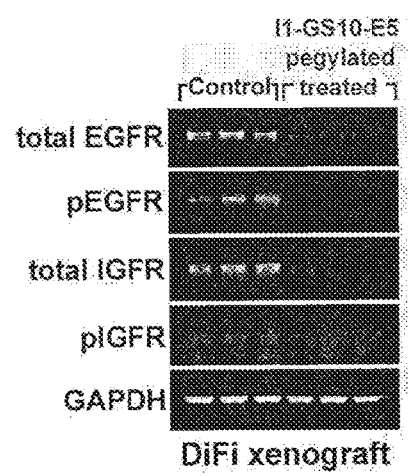
DiFi xenograft
Figure 33B
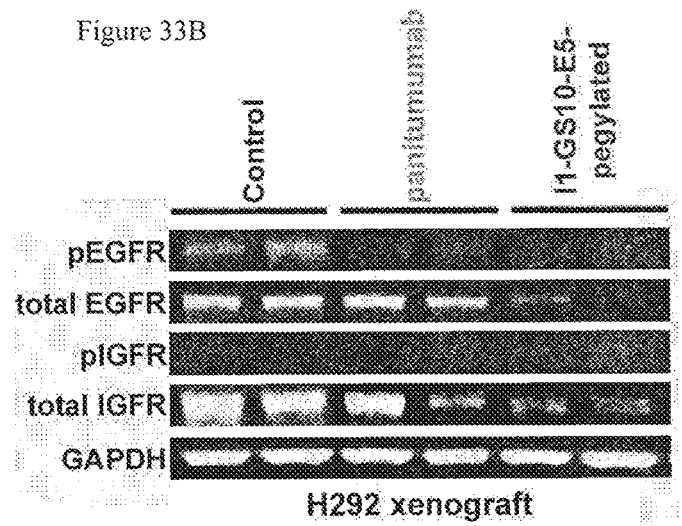
H292 xenograft
Figure 34
```
                        BC loop                              DE loop
MGVSDVPRDLEVVAATPTSLLISWQVPRPMYQYYRITYGETGGNSPVQEFTVPGGVRTATISGL
             FG loop
KPGVDYTITVYAVTDYMHSEYRQYPISINYRTEIDKPSQHHHHHH
```

Figure 43

| CLONE NAME | a<br>A431 pEGFR ICW (nM)* | b<br>A431 pERK ICW (nM)* | c<br>H292 pEGFR ELISA (nM)* | d<br>H292 pIGFR ELISA (nM)* | e<br>De-grades EGFR | f<br>De-grades IGFR | g<br>EGFR KD (nM) | h<br>IGFR KD (nM) | i<br>EGF Blocking ELISA (nM) | j<br>Inhibition of Colony Formation (nM) | k<br>Tm | l<br>% Monomer |
|---|---|---|---|---|---|---|---|---|---|---|---|---|
| E1-GS10-I1 pegylated | 297 | 295 | 123 | 4 | + | + | 57.9 | 2.43 | 238 | --- | 49 | >95% |
| E3-GS10-I1 pegylated | 42 | 40 | 10 | 6 | ++ | ++ | 10.4 | 0.74 | 89 | --- | 52.5 | >95% |
| E2-GS10-I1 pegylated | 77 | 78 | 32 | 0.3 | (-) | (-) | 10.1 | 1.17 | 25 | 560 | 57.5 | >95% |
| E4-GS10-I1 pegylated | 12±0 | 12±2 | 1.3±0.5 | 0.4±0.2 | (-) | (-) | 4.77 | 0.77 | 19.5 | 5 | 55.5 | >95% |
| E96-GS10-I1 pegylated | 61±1 | 54±21 | 10±1 | 0.4 | (-) | (-) | 24.2 | 0.86 | 43.8 | --- | 55 | >95% |
| E5-GS10-I1 pegylated | 44±1 | 47±7 | 12±4 | 0.4 | + | + | 12.4 | 1.16 | 119.3 | --- | 54.5 | >95% |
| E85-GS10-I1 pegylated | 15±0 | 15±2 | 4±1 | 0.3 | (-) | + | 4.76 | 0.75 | 65.9 | --- | 55.5 | >95% |
| E90-GS10-I1 pegylated | 65±0 | 63±9 | 10±1 | 0.4 | -- | -- | 13.5 | 1.5 | 69.1 | --- | 49.5 | >95% |
| E105-GS10-I1 pegylated | 36±0 | 61±6 | 15±4 | 0.5 | ++ | ++ | 9.28 | 1.35 | 75 | --- | 58.5 | >95% |
| E105-GS10-I1 pegylated | 61±11 | 49±17 | 16±6 | 0.5 | + | ++ | 7.65 | 1.19 | 93.8 | 1 | 56.5 | >95% |
| I1-GS10-E5 pegylated | 54±33 | 58±13 | 12±4 | 0.4±0.1 | + | ++ | 7.66 | 0.4 | 150.8 | --- | 56 | >95% |
| I1-GS10-E85 pegylated | 22±15 | 23±4 | 8±3 | 0.7±0.5 | (-) | (-) | 5.97 | 0.43 | 37.8 | --- | 58 | >95% |
| I1-GS10-E4 pegylated | 12±4 | 13±1 | 4±1 | 0.2 | (-) | (-) | 3.63 | 0.46 | 38.1 | 6 | 60 | >95% |
| I1-GS10-E105 pegylated | 53±9 | 48±3 | 13±3 | 0.5±0.2 | ++ | ++ | 4.28 | 0.37 | 61.2 | --- | 59.5 | >95% |
| I1-GS10-E112 pegylated | 116 | 94 | 16 | 0.3 | -- | -- | 3.35 | 0.38 | 104.3 | --- | 62.5 | >95% |
| cetuximab | 5±4 | 9±1 | 5±3 | --- | ++ | -- | 0.39 | --- | 1 | 770 | --- | --- |
| panitumumab | 6±4 | 5±2 | 5±2 | --- | ++ | -- | 0.05 | --- | 24.4 | 140 | --- | --- |
| nimotuzumab | >3 | >3 | >3 | --- | + | (-) | 1 | --- | 13.6 | 15,510 | --- | --- |
| I1 | --- | --- | --- | 0.4±0.2 | (-) | (-) | --- | 0.11 | --- | --- | 65.3 | >95% |

Figure 44

| Dose | Molecule | | HL_Lambda_z (hr) | Cmax (ug/mL) | AUCINF_obs (hr*ug/mL) | Cl_F_obs (mL/hr/kg) | Vz_F_obs (mL/kg) | MRTINF_obs (hr) |
|---|---|---|---|---|---|---|---|---|
| 100 mg/kg | E4-GS10-E4 pegylated | N | 3 | 3 | 3 | 3 | 3 | 3 |
| | | Mean | 18.5 | 521.1 | 20611.4 | 4.8 | 128.3 | 34.1 |
| | | SD | 2.6 | 75.7 | 2058.7 | 0.5 | 6.4 | 2.0 |
| | | Min | 16.6 | 434.2 | 18624.8 | 4.4 | 122.4 | 31.8 |
| | | Max | 21.5 | 573.0 | 22935.3 | 5.3 | 135.2 | 35.8 |
| | | CV% | 14.0 | 14.5 | 9.9 | 9.8 | 5.0 | 6.0 |
| | R-GS10-E5 pegylated | N | 3 | 3 | 3 | 3 | 3 | 3 |
| | | Mean | 20.9 | 719.5 | 25730.1 | 3.9 | 117.4 | 33.0 |
| | | SD | 2.3 | 90.4 | 2983.3 | 0.4 | 4.1 | 2.2 |
| | | Min | 18.6 | 623.7 | 23362.5 | 3.4 | 114.9 | 30.6 |
| | | Max | 23.2 | 803.4 | 29080.9 | 4.3 | 122.1 | 34.8 |
| | | CV% | 11.0 | 12.6 | 11.6 | 11.1 | 3.5 | 6.7 |
| | R-GS10-E4 pegylated | N | 3 | 3 | 3 | 3 | 3 | 3 |
| | | Mean | 15.2 | 757.1 | 28344.0 | 3.6 | 77.7 | 34.5 |
| | | SD | 0.6 | 202.9 | 2777.8 | 0.4 | 6.7 | 2.0 |
| | | Min | 14.6 | 533.9 | 25411.7 | 3.2 | 70.3 | 32.4 |
| | | Max | 15.9 | 930.4 | 30936.0 | 3.9 | 83.1 | 36.5 |
| | | CV% | 4.1 | 26.8 | 9.8 | 10.0 | 8.6 | 5.9 |
| 10 mg/kg | E4-GS10-E4 pegylated | N | 3 | 3 | 3 | 3 | 3 | 3 |
| | | Mean | 12.7 | 67.2 | 1721.2 | 6.0 | 108.4 | 19.6 |
| | | SD | 1.4 | 12.9 | 336.7 | 1.3 | 15.1 | 0.9 |
| | | Min | 11.6 | 52.5 | 1338.0 | 5.1 | 95.5 | 18.7 |
| | | Max | 14.3 | 76.8 | 1969.5 | 7.5 | 125.0 | 20.6 |
| | | CV% | 11.0 | 19.2 | 19.6 | 21.8 | 13.9 | 4.8 |
| | R-GS10-E5 pegylated | N | 3 | 3 | 2 | 2 | 2 | 2 |
| | | Mean | 19.0 | 80.9 | 2345.6 | 4.4 | 118.7 | 23.7 |
| | | SD | 1.5 | 3.2 | 526.4 | 1.0 | 17.1 | 0.6 |
| | | Min | 17.9 | 78.7 | 1973.4 | 3.7 | 106.6 | 23.3 |
| | | Max | 20.1 | 83.2 | 2717.8 | 5.1 | 130.8 | 24.1 |
| | | CV% | 8.2 | 3.9 | 22.4 | 22.4 | 14.4 | 2.5 |
| | R-GS10-E4 pegylated | N | 3 | 3 | 3 | 3 | 3 | 3 |
| | | Mean | 12.1 | 85.9 | 1857.1 | 5.6 | 96.6 | 19.6 |
| | | SD | 1.6 | 15.4 | 420.2 | 1.1 | 9.7 | 0.9 |
| | | Min | 10.7 | 69.6 | 1581.1 | 4.3 | 85.0 | 18.6 |
| | | Max | 13.8 | 100.2 | 2340.7 | 6.3 | 104.1 | 20.4 |
| | | CV% | 12.9 | 17.9 | 22.6 | 20.1 | 10.2 | 4.7 |

Figure 45A

| SEQ ID NO | Binder | % inhibition at 100nM | Amino Acid Sequence |
|---|---|---|---|
| 219 | E6 | 80.0 | MGVSDVPRDLEVVAATPTSLLISWQVPRPMYQYRITYGETGGNSPVQEFTVPYDYTITVYAVTDSYNPATHEYKY HQTPISINYRTEIDKPSQ |
| 220 | E7 | 88.4 | MGVSDVPRDLEVVAATPTSLLISWQVPRPMYQYRITYGETGGNSPVQEFTVPYDNYTATISGLKPGVDYTITVYAVTDSYNPATEEYKY HQTPISINYRTEIDKPSQ |
| 221 | E8 | 92.4 | MGVSDVPRDLEVVAATPTSLLISWQVPRPMYQYRITYGETGGNSPVQEFTVPYDLTATISGLKPGVDYTITVYAVTDSYNPAHEYKY HQFPISINYRTEIDKPSQ |
| 222 | E9 | 77.3 | MGVSDVPRDLEVVAATPTSLLISWEANPRNIQYRITYGETGGNSPVQEFTVPYEDLNTATISGLKPGVDYTITVYAVTDSYNPATHEYKY HQTPISINYRTEIDKPSQ |
| 223 | E10 | 84.7 | MGVSDVPRDLEVVAATPTSLLISWYPGERITYQYRITYGETGGNSPVQEFTVPGGVETATISGLKPGVDYTITVYAVTDYHPATYEHEY EAHPISINYRTEIDKPSQ |
| 224 | E11 | 83.7 | MGVSDVPRDLEVVAATPTSLLISWTPANKSYQYRITYGETGGMSPVQEFTVPYDGTTATISGLKPGVDYTITVYAVTDRKEHADKHTY HEYPISINYRTEIDKPSQ |
| 225 | E12 | 76.5 | MGVSDVPRDLEVVAATPTSLLISWQVPRPMYQYRITYGETGGNSPVQEFTVPHEVYTATISGLKPGVDYTITVYAVTDSYNPATEYKY HQTPISINYRTEIDKPSQ |
| 226 | E13 | 86.7 | MGVSDVPRDLEVVAATPTSLLISWQVPRPMYQYRITYGETGGNSPVQEFTVPGQYTATISGLKPGVDYTITVYAVTDSYNPATHEYKY HQTPISINYRTEIDKPSQ |
| 227 | E14 | 80.4 | MGVSDVPRDLEVVAATPTSLLISWQVPRPMYQYRITYGETGGNSPVQEFTVPYAPISGLKPGVDYTITVYAVTDSYNPATHEEKY HQTPISINYRTEIDKPSQ |
| 228 | E15 | 88.8 | MGVSDVPRDLEVVAATPTSLLISWQVPRPMYQYRITYGETGGNSPVQEFTVPHDLRTATISGLKPGVDYTITVYAVTDGSYNPATHEKY HQTPISINYRTEIDKPSQ |
| 229 | E16 | 97.7 | MGVSDVPRDLEVVAATPTSLLISWQVPRPMYQYRITYGETGPGGNSPVQEFTVPYQLYTATISGLKPGVDYTITVYAVTDHKERNGPHTY HESPISINYRTEIDKPSQ |
| 230 | E3 | 87.5 | MGVSDVPRDLEVVAATPTSLLISWLRGEHRYQYRITYGETGGRSPVQEFTVPHDLRTATISGLKPGVDYTITVYAVTMNRVEYSEYPI SINYRTEIDKPSQH |
| 231 | E1 | 85.9 | MGVSDVPRDLEVVAATPTSLLISWVAGAHYQYRITYGETGGNSPVQEFTVPHDLVTATISGLRPGVDYTITVYAVTDMKNVETERPI SINYRTEIDKPSQ |
| 232 | E17 | 75.5 | MGVSDVPRDLEVVAATPTSLLISWAQERPMYQYRITYGETGGNSPVQEFTVPGMBTATISGLRPGVDYTITVYAVTDMKPHADKPHTY HESPICINYRTEIDKPSQ |

Figure 45B

| SEQ ID NO | Binder | % inhibition at 100nM | Amino Acid Sequence |
|---|---|---|---|
| 233 | E18 | 91.1 | MGVSDVPRDLEVVAATPTSLLISWFVTHVAXQYYRITYGETGGNSPVQEFTVEGGLSTATISGLKRPGVDYTITVYAVTDYK PHADGPHTYHESFISINYRTEIDKPSQ |
| 234 | E19 | 84.6 | MGVSDVPRDLEVVAATPTSLLISWETESNAXQYYRITYGETGGNSPVQEFTVPGQIYTATISGLKRPGVDYTITVYAVTDKK PHADGPHTYHESPISINYRTEIDKPSQ |
| 235 | E20 | 80.2 | MGVSDVPRDLEVVAATPTSLLISWMTSPSVYQYYRITYGETGGNSPVQEFTVPGFVQTATISGLKRPGVDYTITVYAVTDYK EHQHAPHQYTAHPISINYRTEIDKPSQ |
| 236 | E2 | 80.5 | MGVSDVPRDLEVVAATPTSLLISWDSGRGSXQYYRITYGETGGNSPVQEFTVPGVHTATISGLKRPGVDYTITVYAVTDHK PHADGPHTYHESPISINYRTEIDKPSQ |
| 237 | E22 | 83.7 | MGVSDVPRDLEVVAATPTSLLISWSTGRTTXQYYRITYGETGGNSPVQEFTVPHDLDTATISGLKRPGVDYTITVYAVTDSY NPATHEVKYHQTPISINYRTEIDKPSQ |
| 238 | E23 | 81.1 | MGVSDVPRDLEVVAATPTSLLISWQVPRPMYQYYRITYGETGGNSPVQEFTVPYDVITATISGLKRPGVDYTITVYAVTDMM HVEYAEYPISINYRTEIDKPSQ |
| 239 | E24 | 90.3 | MGVSDVPRDLEVVAATPTSLLISWQVPRPMYQYYRITYGETGGNSPVQEFTVPSQVPTATISGLKRPGVDYTITVYAVTDSY NPATHEYKYHQTPISINYRTEIDKPSQ |
| 240 | E25 | 77.1 | MGVSDVPRDLEVVAATPTSLLISWGNYQSGGYYTYRITYGETGGNSPVQEFTVPHDLRTATISGLKRPGVDYTITVYAVTDYA YKEYQEHPISINYRTEIDKPSQ |
| 241 | E26 | 75.4 | MGVSDVPRDLEVVAATPTSLLISWWILGIPVYQYYRITYGETGGNSPVQEFTVPIDGKIATISGLKRPGVDYTITVYAVTDMM HVEYAEYPISINYRTEIDKPSQ |
| 242 | E27 | 94.6 | MGVSDVPRDLEVVAATPTSLLISWSKGSKSXQYYRITYGETGGNSPVQEFTVPYHVYTATISGLKRPGVDYTITVYAVTDYY NPATVEYIYLTTPISINYRTEIDKPSQ |
| 243 | E28 | 85.3 | MGVSDVPRDLEVVAATPTSLLISWNPGSKSXQYYRITYGETGGNSPVQEFTVGGVPTATISGLKRPGVDYTITVYAVTDFY NPDTHEYLINQYPISINYRTEIDKPSQ |
| 244 | E29 | 87.9 | MGVSDVPRDLEVVAATPTSLLISWQPGTTHXQYYRITYGETGGNSPVQEFTVPYDLMTATISGLKRPGVDYTITVYAVTDYY NPNTVEYIYLTTPISINYRTEIDKPSQ |
| 245 | E30 | 87.3 | MGVSDVPRDLEVVAATPTSLLISWAIGTLVYQYYRITYGETGGNSPVQEFTVPAGVYTATISGLKRPGVDYTITVYAVTDNY DWATHEINYHTAPISINYRTEIDKPSQ |
| 246 | E31 | 75.8 | MGVSDVPRDLEVVAATPTSLLISWTYNDGSYQYYRITYGETGGNSPVQEFTVPZAVYIATISGLKRPGVDYTITVYAVTDFY NPATVEYIXHTTPISINYRTEIDKPSQ |

Figure 45C

| SEQ ID NO | Binder | % inhibition at 100nM | Amino Acid Sequence |
|---|---|---|---|
| 247 | E32 | 86.0 | MGVSDVPRDLEVVAATPTSLLISWSLVGHYQYYRITYGETGGNSPVQEFTVPGGVRRATISGLKPGVDYTITVYAVTDYK PHALGPHTYHESPISINYRTEIDKPSQ |
| 248 | E33 | 75.8 | MGVSDVPRDLEVVAATPTSLLISWASRKHYQYYRITYGETGGNSPVQEFTVPGMLNTATISGLKPGVDYTITVYAVTDYM HVEYARYFISINYRTEIDKPSQ |
| 249 | E34 | 80.4 | MGVSDVPRDLEVVAATPTSLLISWLAPFWRYQYYRITYGETGGNSPVQEFTVPGGVRTATISGLKPGVDYTITVYAVTDYK PHADGPHTYHESPISINYRTEIDKPSQ |
| 250 | E35 | 90.2 | MGVSDVPRDLEVVAATPTSLLISWTPGHQHQYYRITYGETGGNSPVQEFTVPGQVTAPISGLKPGVDYTITVYAVTDYY NPAHHYTYTTHPISINYRTEIDKPSQ |
| 251 | E36 | 81.3 | MGVSDVPRDLEVVAATPTSLLISWESGSRTYQYYRITYGETGGNSPVQEFTVPGGVHTATISGLKTGVDYTITVYAVTDYY PHADGPHTYHEXPISINYRTEIDKPSQ |
| 252 | E37 | 80.8 | MGVSDVPRDLEVVAATPTSLLISWERTSTHYQYYRITYGETGGNSPVQEFTVPGRVTAPISGLKPGVDYTITVYAVTDYK NPAHHEYKYHQHPISINYRTEIDKPSQ |
| 253 | E38 | 89.8 | MGVSDVPRDLEVVAATPTSLLISWMARTDAVQYYRITYGETGGNSPVQEFTVPRDLETATISGLKPGVDYTITVYAVTDYY PHADGEHTYQESPISINYRTEIDKPSQ |
| 254 | E39 | 76.7 | MGVSDVPRDLEVVAATPTSLLISWQVSAFRYQYYRITYGETGGNSPVQEFTVPGMVSTATISGLKPGVDYTITVYAVTDYK PHADGPHTYSEYPISINYRTEIDKPSQ |
| 255 | E40 | 89.6 | MGVSDVPRDLEVVAATPTSLLISWVLGRRYQYYRITYGETGGNSPVQEFTVPGAVYTATISGLKPGVDYTITVYAVTDYE NPATHEYQVELTPISINYRTEIDKPSQ |
| 256 | E41 | 75.2 | MGVSDVPRDLEVVAATPTSLLISWTPFNSGHNYYRITYGETGGNSPVQEFTVPHDLTATISGLKPGVDYTITVYAVTDYY NPMTYEYTYQFTPISINYRTEIDKPSQ |
| 257 | E42 | 77.3 | MGVSDVPRDLEVVAATPTSLLISWVVPAWWMYQYYRITYGETGGNSPVQEFTVPGMLETATISGLKPGVDYTITVYAVTDYK NPTTYEYIYFYPISINYRTEIDKPSQ |
| 258 | E43 | 75.0 | MGVSDVPRDLEVVAATPTSLLISWSSGFMRYQYYRITYGETGGNSPVQEFTVPGQYXTATISGLKPGVDYTITVYAVTDYK PHADGPHTYHRSPISINYRTEIDKPSQ |
| 259 | E44 | 83.3 | MGVSDVPRDLEVVAATPTSLLISWDSEGPSYQYYRITYGETGGNSPVQEFTVPAYVTATISGLKPGVDYTITVYAVTDYY MPRTHELFFXXNPISINYRTEIDKPSQ |
| 260 | E45 | 80.4 | MGVSDVPRDLEVVAATPTSLLISWQYPRMYQYYRITYGETGGNSPVQEFTVPHDLRTATISGLKPGVDYTITVYAVTDYY DFTSNLYMTNQTPISINYRTEIDKPSQ |

Figure 45D

| SEQ ID NO | Binder | % inhibition at 100nM | Amino Acid Sequence |
|---|---|---|---|
| 261 | E46 | 77.0 | MGVSDVPRDLEVVAATPTSLLISWQGSVVYQYRITYGETGGNSPVQEFTVPRDVLTATISGLKPGVDYTITVYAVTDYK PKPDGPHIIQAVPISINYRTEIDKPSQ |
| 262 | E47 | 76.9 | MGVSDVPRDLEVVAATPTSLLISWNDASKDYQYPITYGETGGNSPVQEFTVPQVPTANISGLKPGVDYTITVYAVTDEY NEATHEYKADSTPISINYRTEIDKPSQ |
| 263 | E48 | 88.6 | MGVSDVPRDLEVVAATPTSLLISWRSSATAMQYYPITYGETGGNSPVQEFTVPGRVYTATISGLKPGVDYTITVYAVTDFF NWATHEYIYHSTPISINYRTEIDKPSQ |
| 264 | E49 | 83.5 | MGVSDVPRDLEVVAATPTSLLISWHSGPREYQYYRITYGETGGMSPVQEFTVPGQVYTATSGLKPGVDYTITVYAVTDEF NPITHAYIYYELTFISINYRTEIDKPSQ |
| 265 | E50 | 77.4 | MGVSDVPRDLEVVAATPTSLLISWTVGLSVYQYYRITYGETGGNSPVQEFTVPGKVSTATISGLKPSVDYTITVYAVTDYK PHADGPHTYREYPISINYRTEIDKPSQ |
| 266 | E51 | 82.8 | MGVSDVPRDLEVVAATPTSLLISWGGHRAVYQYYRITYGETGGNSPVQEFTVPGAVYTATISGLKPGVDYTITVYAVTDYY MPDTHEYKYRQYPISINYRTEIDKPSQ |
| 267 | E52 | 75.3 | MGVSDVPRDLEVSATPTSLLISWQVPRPMXQYYRITYGETGGNSPVQEFTVPGGVKIATISGLKPGVDYTITVYAVTDYW FKEYREDPISINYRTEIDKPSQ |
| 268 | E53 | 79.8 | MGVSDVPRDLEVVAATPTSLLISWSVGGMIYQYYRITYGETGGNSPVQEFTVPGMVYTATSGLKPGVDYTITVYAVTDYI NPATHEYKNEQTPISINYRTEIDKPSQ |
| 113, wherein X = Ser | E5 | 99.1 | MGVSDVPRDLEVVAATPTSLLISWWAPVDRYQYYRITYGETGGNSPVQEFTVPRLYYATISGLKPGVDYTITVYAVTDYK FHADGPHTYRESPISINYRTEIDKPSQ |
| 269 | E54 | 76.1 | MGVSDVPRDLEVVAATPTSLLISWKASYTGYNTYRITYGETGGNSPVQEFTVPGRDVMTATISGLKPGVDYTITVYAVTDFY MPDTHQYTYKRIPISINYRTEIDKPSQ |
| 270 | E55 | 99.1 | MGVSDVPRDLEVVAATPTSLLISWVGGVEYQYYRITYGETGGNSPVQEFTVPLDVYIATISGLKPGVDYTITVYAVTDYI NPATHEYKYEQTPISINYRTEIDKPSQ |
| 271 | E56 | 84.2 | MGVSDVPRDLEVVAATPTSLLISWISGDXHNQYYRITYGETGGNSPVQEFTVPBHLEPATISGLKPGVDYTITVYAVTDYY NPATHYYKYEQTPISINYRTEIDKPSQ |
| 272 | E57 | 75.5 | MGVSDVPRDLEVVAATPTSLLISWIVQGGRYQYYRITYGETGGNSPVQEFTVPGMVYTATISGLKPGVDYTITVYAVTDYY NPSTHEYKYHQEVSINYRTEIDKPSQ |
| 273 | E58 | 79.7 | MGVSDVPRDLEVVAATPTSLLISWSAVPMRYQYYRITYGETGGNSPVQEFTVPGGVRTATISGLKPGVDYTITVYAVTDFY NPRTHVYIYQEPISINYRTEIDKPSQ |

Figure 45E

| SEQ ID NO | Binder | % Inhibition at 100nM | Amino Acid Sequence |
|---|---|---|---|
| 274 | E59 | 76.3 | MGVSDVPRDLEVVAATPTSLLISWRARRLQYQYYRITYGETGGNSPVQEFTVPGMVETATISGLKPGVDYTITVYAVTDFY NPAHMEYTYQRTPISINYRTEIDKPSQ |
| 275 | E60 | 100.0 | MGVSDVPRDLEVVAATPTSLLISWLQPLWRYQYYRITYGETGGNSPVQEFTVPGGLDTAHISGLKPGVDYTITVYAVTDYK PHVDGPHAYHENPISINYRHEIDKPSQ |
| 276 | E61 | 79.8 | MGVSDVPRDLEVVAATPTSLLISWDASQNYQYYRITYGETGGNSPVQEFTVPGAVKTATISGLKPGVDYTITVYAVTDYY NPATHEYIYHTTPISINYRTEIDKPSQ |
| 277 | E62 | 78.9 | MGVSDVPRDLEVVAATPTSLLISWCLDGQLYQYYRITYGETGGNSPVQEFTVPGSIVTAHISGLKPGVDYTITVIAVTDWY NLATHEYNYRVTPISINYRTEIDKPSQ |
| 278 | E63 | 76.2 | MGVSDVPRDLEVVAATPTSLLISWDTSGASYQYYRITYGETGGNSPVQEFTVPFYSVYTATISGLKPGVDYTITVYAVTDYY DPDSHYYNYNMVPISINYRTEIDKPSQ |
| 279 | E64 | 78.2 | MGVSDVPRDLEVVAATPTSLLISWDSGNGTYQYYRITYGETGGNSPVQEFTVPFYRVYTATISGLKPGVDYTITVYAVTDYY NPATHEYTYELRPISINYRTEIDKPSQ |
| 280 | E65 | 80.7 | MGVSDVPRDLEVVAATPTSLLISWRPTSQVYQYYRITYGETGGNSPVQEFTVPFNVYTATISGLKPGVDYTITVYATTDFF NYATHEYIYHTIPISINYRTEIDKPSQ |
| 281 | E66 | 75.0 | MGVSDVPRDLEVVAATPTSLLISWKSYGSAYQYYRITYGETGGNSPVQEFTVPGDLQTAHISGLKPGVDYTITVYAITDYI NPDTHEYKIYHVSPISINYRTEIDKPSQ |
| 282 | E67 | 75.3 | MGVSDVPRDLEVVAATPTSLLISWSSVMGLYQYYRITYGETGGNSPVQEFTVPYDVYTATISGLKPGVDYTITVHVAVTDYY NPSTVEYKYNTTPISINYRTEIDKPSQ |
| 283 | E68 | 78.5 | MGVSDVPRDLEVVAATPTSLLISWKTEPGRHQYYRITYGETGGNSPVQEFTVPGGVRTATISGLKPGVDYTITVIAVTDWY MLVSHEYYYHTTPISINYRTEIDKPSQ |
| 284 | E69 | 85.1 | MGVSDVPRDLEVVAATPTSLLISWHAGMAVIYQYYRITYGETGGNSPVQEFTVPGDVLTATISGLKPGVDYTITVYAVTDFF NEVTHEYMYHTIFISINYRTEIDKPSQ |
| 285 | E70 | 76.8 | MGVSDVPRDLEVVAATPTSLLISWVSARGRYQYYRITYGETGGNSPVQEFTVPGGVRTATISGLKPGVDYTITVYAVTDYY NLETYEYHYYRTPISINYRHEIDKPSQ |
| 286 | E71 | 80.4 | MGVSDVPRDLEVVAATPTSLLISWFGTSSSYQYYRITYGETGGNSPVQEFTVPGDLKTATISGLKPGVDYTITVYAVTDNF NEVTHEYENHTTPISINYRTEIDKPSQ |
| 287 | E72 | 82.8 | MGVSDVPRDLEVVAATPTSLLISWATRTLYQYYRITYGETGGNSPVQEFTVPYDVHTATISGLKPGVDYTITVYAVTDYY NMVTYEYNYALTPISINYRTEIDKPSQ |

Figure 45F

| SEQ ID NO | Binder | % Inhibition at 100nM | Amino Acid Sequence |
|---|---|---|---|
| 288 | E73 | 79.8 | MGVSDVPRDLEVVATPTSLLISWTKLLGGNQYYRITYGERGGNSPVQEFTVPGSVVPTATISGLKPGVDYTITVYAVTDFY NPRTHEYQYHTTPISINYRTEIDKPSQ |
| 289 | E74 | 80.9 | MGVSDVPRDLEVVAATPTSLLISWPASGGLNQYYRITYGETGGNSPVQEFTVPGSVNTATISGLKPGVDYTITVYAVTDFY MPATHENIYRTTPISINYRTEIDKPSQ |
| 290 | E75 | 76.5 | MGVSDVPRDLEVVAATPTSLLISWAAGRATYQYYRITYGETGGNSPVQEFTVPGSVTATISGLKPGVDYTITVYAVTDFY NPATHENYIETTPISINYRTEIDKPSQ |
| 291 | E76 | 79.0 | MGVSDVPRDLEVVAATPTSLLISWYSQPLTYQYTNITYGETGGNSPVQEFTVPGSVHDVPATISLKPGVDYTITVYAVTDFY NPETHENYIHLTPISINYRTEIDKPSQ |
| 292 | E77 | 81.1 | MGVSDVPRDLEVVAAPTSLLISWSSATRPQYYRITYGETGGNSPVQEFTVPGSVRIATISGLKPGVDYTITVYAVTDFY NPTTHEYYHTTPISINYRTEIDKPSQ |
| 293 | E78 | 76.9 | MGVSDVPRDLEVVAATPTSLLISWSVERSVYQYYRITYGETGGNSPVQEFTVPGSVRTATISGLKPGVDYTITVYAVTDYY NPSTHEYNLTTPISINYRTEIDKPSQ |
| 294 | E79 | 99.2 | MGVSDVPRDLEVVAATPTSLLISWQDHSSYHQYYRITYGETGGNSPVQEFTVPGSVRIATISGLKPGVDYTITVYAVTDYF NESTHEYIYRTIPTIPISINYRTEIDKPSQ |
| 295 | E80 | 89.6 | MGVSDVPRDLEVVAATPTSLLISWSSHRKYQYYRITYGETGGNSPVQEFTVPGSVATATISGLKPGVDYTITVYAVTDYF NPDTAEYLYHATPISINYRTEIDKPSQ |
| 296 | E81 | 75.1 | MGVSDVPRDLEVVAATPTSLLISWDNMSNSYQYYRITYGETGGNSPVQEFTVPYDLKTATISGLKPGVDYTITVYAVTDYF PNTRGEHTYRESPISINYRTEIDKPSQ |
| 297 | E82 | 77.2 | MGVSDVPRDLEVVAATPTSLLISWRYLVDMYQYYRITYGETGGNSPVQEFTVPIGVLATISLKPGVDYTITVYAVTDYK PRVDGEHTYESPISINYRTEIDKPSQ |
| 298 | E83 | 90.7 | MGVSDVPRDLEVVAATPTSLLISWMFYGMSYQYYRITYGETGGNSPVQEFTVPIGVRTATISLKPGVDYTITVYAVTDYK NPATHENIYAVTFISINYRTEIDKPSQ |
| 299 | E84 | 86.5 | MGVSDVPRDLEVVAATPTSLLISWILHKMNYQYYNITYGETGGSSEGSFVQEFTVFGGSVTATISLKPGVDYTITVYAVTDYY NPATHENYDYKTTPISINYRTEIDKPSQ |
| 300 | E85 | 89.3 | MGVSDVPRDLEVVAATPTSLLISWTQGSTHYQYYNITYGETGGSMSFVQEFTVPGGSVYTATISLKPGVDYTITVYAVTDYE DRSTHEYKYKTTPISINYRTEIDKPSQ |
| Residues 1-108 of SEQ ID | E4 | 94.3 | MGVSDVPRDLEVVAATPTSLLISWHERDGSSKQYYNITYGETGGNSPVQEFTVPGGSVPTATISLKPGVDYTITVYAVTDYE NPTTHEYLYQTTPISINYRTEIDKPSQ |

Figure 45G

| SEQ ID NO: 107, wherein X = Ser | Binder | % inhibition at 100nM | Amino Acid Sequence |
|---|---|---|---|
| 301 | E86 | 84.7 | MGVSDMPRDLEVVAATPTSLLISWDSGENMQYYRITYGETGGNSPVQEFTVPGGVRTATISGLKPGVDYTITVYAVTDYY NEKTHEYNYLTIPISINYRTEIDKPSQ |
| 302 | E87 | 87.0 | MGVSDVPRDLEVVAATPTSLLISWGSPLIEYQYYRITYGETGGNSPVQEFTVPGGLSTATISGLKPGVDYTITVYAVTDYF NPATHEYTYHVSPISINYRTEIDKPSQ |
| 303 | E88 | 89.3 | MGVSDVPRDLEVVAATPTSLLISWSATNKTYQYYRITYGETGGNSPVQEFTVPGGVRTATISGLKPGVDYTITVYAVTDYF NPTTHEYITYQTTPISINYRTEIDKPSQ |
| 304 | E89 | 82.6 | MGVSDVPRDLEVVAATPTSLLISWDPAANKQYYRITYGETGGNSPVQEFTVPIDLPTATISSLKPGVDYTITVYAVTDYY NPATHQKNSQSPISINYRTEIDKPSQ |
| 305 | E90 | 81.3 | MGVSDVFRDLEVVAATPTSLLISWNWEGLPYQYYRITYGETGGNSPVQEFTVPRDVNTATISGLKPGVDYTITVYAVTDWI NPDTHEYIYHTIPISINYRTEIDKPSQ |
| 306 | E91 | 84.7 | MGVSDVPRDLEVVAATPTSLLISWSAPWRTYQYYRITYGETGGNSPVQEFTVPYDYYTATISGLKPGVRTATISGLKPGVDYTITVYAVTDLL NPNTLEYTYQRIPISINYRTEIDKPSQ |
| 307 | E92 | 88.5 | MGVSDVPRDLEVVAATPTSLLISWQAANHSYQYYRITYGETGGNSPVQEFTVPGGVRTATISGLKPGVDYTITVYAVTDFF NPVTHEYKYRTIPISINYRTEIDKPSQ |
| 308 | E93 | 76.9 | MGVSDVPRDLEVVAATPTSLLISWDSGRGSYQYYRITYGETGGNSPVQEFTVPGGVRKATISGLKPGVDYTITVYAVTDYK PRADGPHTYHEYPISPISINYRTEIDKPSQ |
| 309 | E94 | 76.7 | MGVSDVPRDLEVVAATPTSLLISWNNGGRNYQYYRITYGETGGNSPVQEFTVPRNYDYTATISGLKPGVDYTITVYAVTDYK PRADGPHTYHEYPISPISINYRTEIDKPSQ |
| 310 | E95 | 96.0 | MGVSDVPRDLEVVAATPTSLLISWVPQGMYQYYRITYGETGGNSPVQEFTVPGGVSTATISGLKPGVDYTITVYAVTDYF NPATHEYNYHSIPISINYRTEIDKPSQ |
| 311 | E96 | 91.7 | MGVSDVPRDLEVVAATPTSLLISWASNRGTYQYYRITYGETGGNSPVQEFTVPGGVSTATISGLKPGVDYTITVYAVTDAF NPTTHEYNYFTTPISINYRTEIDKPSQ |
| 312 | E97 | 89.3 | MGVSDVPRDLEVVAATPTSLLISWLPGKLRIQYYRITYGETGGNSPVQEFTVPHDLKPATISGLKPGVDYTITVYAVTDYK PRADGPHTYHESPISINYRTEIDKPSQ |
| 313 | E98 | 75.8 | MGVSDVPRDLEVVAATPTSLLISWDAPTSRYQYYRITYGETGGNSPVQEFTVPGGVRTATISGLKPGVDYTITVYAVTDYK PRADGPHTYHEYPISINYRTEIDKPSQ |

Figure 45H

| SEQ ID NO | Binder | % inhibition at 100nM | Amino Acid Sequence |
|---|---|---|---|
| 314 | E99 | 84.7 | MGVSDVPRDLEVVAATPTSLLISWDAPTSRIQYYRITYGETGGNSPVQEFTVPGGNSPVQEFTVPGGVRTATISGLKPGVDYTITVYAVTDYK PHADGPHTYHEYPISINYRTEIDKPSQ |
| 315 | E100 | 83.3 | MGVSDVPRDLEVVAATPTSLLISWTPANKSYQYYRITYGETGGNSPVQEFTVPHDLVTAHISGLKPGVDYTITVYAVTDHK PHADGPHTYHEYPISINYRTEIDKPSQ |
| 316 | E101 | 90.9 | MGVSDVPRDLEVVAATPTSLLISWDAPAVTYQYYRITYGETGGNSPVQEFTVPHDLVTATISGLKPGVDYTITVYAVTDYK PHADGPHTYHESPISINYRTEIDKPSQ |
| 317 | E102 | 80.0 | MGVSDVPRDLEVVAATPTSLLISWTPANKSYQYYRITYGETGGNSPVQEFTVPHDLVTATISGLKPGVDYTITVYAVTDHK PHADGPHTYHESPISINYRTEIDKPSQ |
| 318 | E103 | 76.3 | MGVSDVPRDLEVVAATPTSLLISWTPANKSYQYYRITYGETGGNSPVQEFTVPGGNSPVQEFTVPGGVRTATISGLKPGVDYTITVYAVTNMM HVEYSEYPISINYRTEIDKPSQ |
| 319 | E104 | 89.3 | MGVSDVPRDLEVVAATPTSLLISWDAGAVTYQYYRITYGETGGNSPVQEFTVPHDLVTAHISGLKPGVDYTITVYAVTDHK PHADGPHTYHEYPISINYRTEIDKPSQ |
| 320 | E105 | 87.0 | MGVSDVPRDLEVVAATPTSLLISWDAPTSRYQYYRITYGETGGNSPVQEFTVPGGLSTATISGLKPGVDYTITVYAVTDYK PHADGPHTYHESPISINYRTEIDKPSQ |
| 321 | E106 | 84.0 | MGVSDVPRDLEVVAATPTSLLISWDAPAVTYQYYRITYGETGGNSPVQEFTVPHDLVTAHISGLKPGVDYVITVYAVTDYK PHADGPHTYHESPISINYRTEIDKPSQ |
| 322 | E107 | 75.8 | MGVSDVPRDLEVVAATPTSLLISWDSGRGSYQYYRITYGETGGNSPVQEFTVPVYVTATISGLKPGVDYTITVYAVTDMM HVEYTEHPISINYRTEIDKPSQH |
| 323 | E108 | 80.0 | MGVSDVPRDLEVVAATPTSLLISWDAPTSRYQYYRITYGETGGNSPVQEFTVPGGNSPVQEFTVPGGVRTATISGLKPGVDYTITVYAVTDHK PHADGPHTYHESPISINYRTEIDKPSQ |
| 324 | E109 | 90.9 | MGVSDVPRDLEVVAATPTSLLISWDAPTSRYQYYRITYGETGGNSPVQEFTVPGGNSPVQEFTVPGGVKTATISGLKPGVDYTITVYAVTDYK PHADGPHTYHESPISINYRTEIDKPSQ |
| 325 | E110 | 81.3 | MGVSDVPRDLEVVAATPTSLLISWDAPTSRYQYYRITYGETGGNSPVQEFTVPHDLVTATISGLKPGVDYTITVYAVTDYK PHADGPHTYHESPISINYRTEIDKPSQ |
| 326 | E111 | 85.5 | MGVSDVPRDLEVVAATPTSLLISWDAPTSRYQYYRITYGETGGNSPVQEFTVPGGNSPVQEFTVPGGVRTATISGLKPGVDYTITVYAVTNMM HVEYSEYPISINYRTEIDKPSQ |
| 327 | E112 | 86.2 | MGVSDVPRDLEVVAATPTSLLISWDAGAVTYQYYRITYGETGGNSPVQEFTVPGGNSPVQEFTVPGGVRTATISGLKPGVDYTITVYAVTDYK PHADGPHTYHEYPISINYRTEIDKPSQ |

Figure 46

```
         1                    21        30                    51  56                       76                87
WT    EVVAATPTSLLLI SWDAPAVTVR YYRITYGETGGNSPVQEFTV PGSKST ATISGLKPGVDYTITVYAV TGRGDSPASSK      P ISINYRT
I1    EVVAATPTSLLLI SWSARLKVAR YYRITYGETGGNSPVQEFTV PKNVYT ATISGLKPGVDYTITVYAV TRFRDYQ          P ISINYRT
B1    EVVAATPTSLLLI SWVAGAEDYQ YYRITYGETGGNSPVQEFTV PHDLVT ATISGLKPGVDYTITVYAV TDMMHVEYTEH      P ISINYRT
E2    EVVAATPTSLLLI SWDSGRGSYQ YYRITYGETGGNSPVQEFTV PGPVHT ATISGLKPGVDYTITVYAV TDHKPHADGPHTYHESP  ISINYRT
E3    EVVAATPTSLLLI SWLPGKLRYQ YYRITYGETGGNSPVQEFTV PHDLRT ATISGLKPGVDYTITVYAV TNMMHVEYSEY      P ISINYRT
E4    EVVAATPTSLLLI SWHERDGSRQ YYRITYGETGGNSPVQEFTV PGGVRT ATISGLKPGVDYTITVYAV TDYFNPTTHEYIYQTTP  ISINYRT
E5    EVVAATPTSLLLI SWAPVDRYQ  YYRITYGETGGNSPVQEFTV PRDVYT ATISGLKPGVDYTITVYAV TDYKPHADGPHTYHESP  ISINYRT
E85   EVVAATPTSLLLI SWTQGSTHYQ YYRITYGETGGNSPVQEFTV PGMVYT ATISGLKPGVDYTITVYAV TDYFDRSTHEYKYRTTP  ISINYRT
E90   EVVAATPTSLLLI SWYWEGLPYQ YYRITYGETGGNSPVQEFTV PRDVNT ATISGLKPGVDYTITVYAV TDWYNPDTHEYIYHTIP  ISINYRT
E96   EVVAATPTSLLLI SWASNRGTYQ YYRITYGETGGNSPVQEFTV PGGVST ATISGLKPGVDYTITVYAV TDAFNPTTHEYNYFTTP  ISINYRT
E105  EVVAATPTSLLLI SWDAPTSRYQ YYRITYGETGGNSPVQEFTV PGGLST ATISGLKPGVDYTITVYAV TDYKPHADGPHTYHESP  ISINYRT
E113  EVVAATPTSLLLI SWDAGAVTYQ YYRITYGETGGNSPVQEFTV PGGVRT ATISGLKPGVDYTITVYAV TDYKPHADGPHTYHSYP  ISINYRT
```

Figure 47A

| SEQ ID NO | BINDER | NUCLEOTIDE SEQUENCE |
|---|---|---|
| 328 | I1 (with cys tail) | ATGGGAGTTCTGATGTGCCGCGCGACCTGGAAGTGGTTGCTGCCACCCCACCAGCCTGCTGATCAGTCGTCGGGGTCTG AAAGTTGCGCCATATTACCGCATCACTGGCGGTACCGCGAAACAGGAGGCAATAGCCCTGTCCAGGAGTTCACTGTGCCTAAAAACGTT TACCAGCTACCATCCAGCCGGCCTTAAACCTGACAGAGAAATTGACAAACCATGCCAGCACCACCACCAC CGAATTTCCATTAATTACCGCACAGAAATTGACAAACCATGCCAGCACCACCACCAC |
| 329 | E6 | ATGGGAGTTCTGATGTGCCGCGCGACCTGGAAGTGGTTGCTGCCACCCCACCAGCCTGCTGATCAGTCGCTGGCAGGTTCCGCGT CCGATGTACCAAATTACCGCATCACTGGCGGTACCGCGAAACAGGAGGCAATAGCCCTGTCCACGTGCTGTCACTGACTCCAGGTTCGCTTACGACGTT TACACAGCTACCATCCAGCGGCCTTAAACCTGAGACTCCAATTTAAACCTGTAGCTGTCACTGACTCTTACAACCCGGCT ACTCATGAATACAAATACCGGACACAGAAATTGACAAACCATGCCAGCACCATCACCAGCACCATCACCAC CACCAC |
| 330 | E7 | ATGGGAGTTCTGATGTGCCGCGCGACCTGGAAGTGGTTGCTGCCACCCCACCAGCCTGCTGATCAGCTGGCAGGTCCGCGT CCGATGTACCAAATATTACCGCATCACTGGCGGTACCGCGAAACAGGAGGCAATAGCCCTGTCCAGGAGTGCCTTACGACGTT CATACAGCTACCATCCAGCGGCCTTAAACCTGACAGAGATATCCAATTCCAATTCGTATGCTGTCACTGACTCTTACAACCCGGCT ACTCATGAATACAAATACCGGACACAGAAATTGACAAACCATGCCAGCACCATCAGCACCATCAGCACCATCACCAC CACCAC |
| 331 | E8 | ATGGGAGTTCTGATGTGCCGCGCGACCTGGAAGTGGTTGCTGCCACCCCACCAGCCTGCTGATCAGCTGGCAGGTTCCGCGT CCGATGTATCAATATTACCGCATCACTGGCGGTACCGCGAAACAGGAGGCAATAGCCCTGTCGCCAGGAGTTCACTGTGCCTTACGACGCTG ACTACAGCTACCATCCAGCGGCCTTAAACCTGACAGAGATATCCAATTACCAATTCCGTATCTGTCACTGACTCTTACAACCCGGCT ACTCATGAATACAAATACCGGACACAGAAATTGACAAACCATGCCAGCACCATCAGCACCATCAGCACCATCACCAC CACCAC |
| 332 | E9 | ATGGGAGTTCTGATGTGCCGCGCGACCTGGAAGTGGTTGCTGCCACCCCACCAGCCTGCTGATCAGCTGGGAAGCTAACCCT TCTCGTTATCAATATTACCGCATCACTGGCGGTACCGCGAAACAGGAGGCAATAGCCCTGTCGCCAGTGTCCTCAATGCCTTACGACCTG AACACAGCTACCATCAGCCGGCCTTAAACCTGACAGAGATATCCAATTACCAATTCCAATTCTTAACCCGGCT ACTCATGAATACAAATACCGGACACAGAAATTGACAAACCATGCCAGCACCATCAGCACCATCACCAC CACCAC |
| 333 | E10 | ATGGGAGTTCTGATGTGCCGCGCGACCTGGAAGTGGTTGCTGCCACCCCACCAGCCTGCTGATCAGCTGGTACCCCAGGATCT CGTACCGTACCAAATATTACCGCATCACTGGCGGTACCGCGAAACAGGAGGCAATAGCCCTGTCGCCAGTGTCCTGGTGGTGTT CGTACAGCTACCATCCAGCCGGCCTTAAACCTGACAGAGATATCCAATTACCAATTCCGTATCGTCACTGACTACTGCGTCACACTCTTACATCCGGCT ACTTACGGACATGAATACAAATACCGGACACAGAAATTGACAAACCATGCCAGCACCATCAGCACCATCAGCACCATCACCAC CACCAC |
| 334 | E11 | ATGGGAGTTCTGATGTGCCGCGCGACCTGGAAGTGGTTGCTGCCACCCCACCAGCCTGCTGATCAGCTGGGACCCCTGCTAAT AAATCTACCAATATTACCGCATCACTGGCGGTACCGCGAAACAGGAGGCAATAGCCCTGTCGCCAGTGTCCTGGTGCTTACGACGGT ACTACAGACTACCATCCAGCGGCCTTAAACCTGACAGAGAATATACCCCAATTCCAATTACCGTATCGTCACTGACCATAACCGGATGCT GACGGTCCGCATACTTACGCGACACAGAAATTGACAAACCATGCCAGCACCATCAGCACCATCACCAC CACCAC |

Figure 47B

| SEQ ID NO | BINDER | NUCLEOTIDE SEQUENCE |
|---|---|---|
| 335 | E12 | ATGGGAGTTTCTGATGTGCCGGCGACCTGGAAGTGGTTGCTGCCACCCGACCAGCCTGCTGATCAGCTGGCAGGTTCCGCGT CCGATGTACCAATATTACCGGCATCAGCGGCCTTAAACCTGGGCGTTGGGCGTTCCAATTCCAGTAGCCCTGTCCAGGAGTTCACTGTCCATGACGTT TACACAGCTACCATCAGCGGCCTTAAACCTGGGCGTTGATTATACCATCACTGTGTACTCTGACTCTTACAACCGGCT ACTCATGAATACAAATACCGGATACCATTAACCGGCACAGAAATTGACACCATCCAGCACCATCACCAC CACCAC |
| 336 | E13 | ATGGGAGTTTCTGATGTGCCGGCGACCTGGAAGTGGTTGCTGCCACCCGACCAGCCTGCTGATCAGCTGGCAGGTTCCGGGT CCGATGTACCAATATTACCGGCATCAGCGGCCTTAAACCTGGGCGAATAGCCCTGTCCAGGAGTTCACTGTCTGGTCAGTT TACCAGCTACCATCAGCGGCCTTAAACCTGGGCGTTGATTATACCATCACTGTGTATGCGTCACTGACTCTTACAACCGGCT ACTCATGAATACAAATACCGGATACCATTAATCCGGCACAGAAATTGACACCATCCAGCACCATCACCAC CACCAC |
| 337 | E14 | ATGGGAGTTTCTGATGTGCCGGCGACCTGGAAGTGGTTGCTGCCACCCGACCAGCCTGCTGATCAGCTGGCAGGTTCCGCGT CCGATGTACCAATATTACCGGCATCAGCGGCCTTAAACCTGGGCGAAACAGGAGCAATAGCCCTGTCCAGGAGTTCACTGTCCATGACGTT ACTACAGCTACCATCAGCGGCCTTAAACCTGGGCGTTGATTATACCATCACTGTGTATGCGTCACTGACTCTTACAACCGGCT ACTCATGAATACAAATACCGGATACCATTAATCCGGCACAGAAATTGACACCATCCAGCACCATCACCAC CACCAC |
| 338 | E15 | ATGGGAGTTTCTGATGTGCCGGCGACCTGGAAGTGGTTGCTGCCACCCGACCAGCCTGCTGATCAGCTGGCAGGTTCCGGGT CCGATGTACCAATATTACCGGCATCAGCGGCCTTAAACCTGGGCGAAACAGGAGCAATAGCCCTGTCCAGGAGTTCACTGTCCATGACCTG CGTACAGCTACCATCAGCGGCCTTAAACCTGGGCGTTGATTATACCATCACTGTGTATGCGTCACTGACTCTTACAACCGGCT ACTCATGAATACAAATACCGGATACCATTAATCCGGCACAGAAATTGACACCATCCAGCACCATCACCAC CACCAC |
| 339 | E16 | ATGGGAGTTTCTGATGTGCCGGCGACCTGGAAGTGGTTGCTGCCACCCGACCAGCCTGCTGATCAGCTGGCAGGTTCCGGGT CCGATGTACCAATATTACCGGCATCAGCGGCCTTAAACCTGGGCGAAACAGGAGCAATAGCCCTGCCAGGAGTTCACTGTCCTTACGACCTG GTTACAGCTACCATCAGCGGCCTTAAACCTGGGCGTTGATTATACCATCACTGTGTATGCGTCACTGACTCTTACAACCGGCT GACGGCCGCGGCATACCTACCATTAATCCGAATCACAGAAATTGACACCATCCAGCACCATCACCAC CACCAC |
| 340 | E3 | ATGGGAGTTTCTGATGTGCCGGCGACCTGGAAGTGGTTGCTGCCACCCGACCAGCCTGCTGATCAGCTGGTTGCCGGGCAAAG CTGAGGTACCAATATTACCGGCATCAGCGGCCTTAAACCTGGGCGAAACAGGAGCAATAGCCCTGTCCAGGAGTTCACTGTCCCTGATGACCTG CGTACAGCTACCATCAGCGGCCTTAAACCTGGGCGTTGATTATACCATCACTGTGTATGCGTCATATGCATGTTGAA TACTCTGAATACAAATACCGGATACCATTAATCCGGCACAGAAATTGACACCATCCAGCACCATCACCAC |
| 341 | E1 | ATGGGAGTTTCTGATGTGCCGGCGACCTGGAAGTGGTTGCTGCCACCCGACCAGCCTGCTGATCAGCTGGTGGTGCCGGGCCG GAGGACTACCAATATTACCGGCATCAGCGGCCTTAAACCTGGGCGAAACAGGAGCAATAGCCCTGCCAGGAGTTCACTGTCCCTGATGACCTG GTTACAGCTACCATCAGCGGCCTTAAACCTGGGCGTTGATTATACCATCACTGTGTATGCGTCACTGACTGATGCATGTTGAA TACACTGAACATCCAATTCCATTAATTACACAGAAATTGACACCATCCAGCACCATCACCAC |

Figure 47C

| SEQ ID NO | BINDER | NUCLEOTIDE SEQUENCE |
|---|---|---|
| 342 | E17 | ATGGGAGTTTCTGATGTGCCGGCGACCTGGAAGTGGTTGCTGCCACCCCACCAGCCTGCTGATCAGCTGCGCAGGTTCCGCGT CCGATGTACCAATATTACCGCATCACTTACGGCGACCTGGAACTGGTTGCTGCCATGGGTATGGTT CACACAGCTACCATCAGCGGCCCTTAAACCTGTGATATACCATCACTGTGTCACTGACTATAAACCGATGCT GACGGTCCGATACATTACCACCATCCGCATACCGCACAGAATTGACAAACCATCCAGCACCATCACCAC CACCAC |
| 343 | E18 | ATGGGAGTTTCTGATGTGCCGGCGACCTGGAAGTGGTTGCTGCCACCCCACCAGCCTGCTGATCAGCTGCGCAGGTTCCGTGACGGAC GTGGCCTACCAGCTACCATCAGCGGCCATCACTTACGGCGAAAACAGGAGGCAATAGCCCTGTCCAGGAGTTCACTGTCGCTGGTGGTCTG TCCACAGCTACCATCAGCGGCCTTAAACCTGGCGTTGATTATACCATCACTGTGTCACTGACTATAAACCGATGCT GACGGTCCGATACATTACCACCATCCGCATACCGCACAGAATTGACAAACCATCCAGCACCATCACCAC CACCAC |
| 344 | E19 | ATGGGAGTTTCTGATGTGCCGGCGACCTGGAAGTGGTTGCTGCCACCCCACCAGCCTGCTGATCAGCTGGAGACCGAGAGC AACGCGTACCAATATTACCGCATCACTTACGGCGAAAACAGGAGGCAATAGCCCTGTCCAGGAGTTCACTGTCCGTCCAGATC TACACAGCTACCATCAGCGGCTTAAACCTGGCGTTGATTATACCATCACTGTGTCACTGACTATAAACCGATGCT GACGGTCCGATACTTACCAGAATCCGCATACCGCACAGAATTGACAAACCATCCAGCACCATCACCAC CACCAC |
| 345 | E20 | ATGGGAGTTTCTGATGTGCCGGCGACCTGGAAGTGGTTGCTGCCACCCCACCAGCCTGCTGATCAGCTGGATGACGGTGGCCC TCGGTGTACCAATATTACCGCATCACTTACGGCGACCTGGAACTGGTTGCTGCCATGGGTATGGTT CAGACAGCTACCATCAGCGGCCTTAAACCTGGCGTTGATTATACCATCACTGTGTCACTGACTATAAAGAACATCAG CATGCTCCGCATCAGTACACTTACCATGCTCCATCCAATTTCCATCCAATTACCGCACAGAATTGACAAACCATCCAGCACCATCACCAC CACCAC |
| 346 | E2 | ATGGGAGTTTCTGATGTGCCGGCGACCTGGAAGTGGTTGCTGCCACCCCACCAGCCTGCTGATCAGCTGGGATTCAGGACGA GGTTCGTATCAATATTACCGCATCACTTACGGCGAAAACAGGAGGCAATAGCCCTGTCCAGGAGTTCACTGTGCCGGTCCGGTT CATACAGCTACCATCAGCGGCCTTAAACTCCAATTGCTGTTAATACCATCACTGTGTCACTGACTATAAACCGATGCT GACGGTCCGATACAATTACCATGGTCCAATTTCCATCCAATTACCGCACAGAATTGACAAACCATCCAGCACCATCACCAC CACCAC |
| 347 | E22 | ATGGGAGTTTCTGATGTGCCGGCGACCTGGAAGTGGTTGCTGCCACCCCACCAGCCTGCTGATCAGCTGGTCAACAGGTCGC ACAACTTATCAATATTACCGCATCACTTACGGCGAAAACAGGAGGCAATAGCCCTGTCCAGGAGTTCACTGTGCCTCATGACCTG GACACAGCTACCATCAGCGGCCTTAAACCTGGCGTTGATTATACCATCACTGTGTATCCGTGACTCTTACAAACCGGCT ACTCATGAATACAAATACCATGGTCCAATTTCCAGAATACGACACAGAATTGACAAACCATCCAGCACCATCACCAC CACCAC |
| 348 | E23 | ATGGGAGTTTCTGATGTGCCGGCGACCTGGAAGTGGTTGCTGCCACCCCACCAGCCTGCTGATCAGCTGGCAGGTTCCGCGT CCGATGTACCAATATTACCGCATCACTTACGGCGAAAACAGGAGGCAATAGCCCTGTCCAGGAGTTCACTGTCCTTACCACGTT ATCACAGCTACCATCAGCGGCCTTAAACTGGCGTTGATTATACCATCACTGTGTATCCGTGACTCTTACAATGACATGGTGAA TACGGCTGAATACCATGCCAATTTCCATTAATTACCGCACAGAAATTGACAACCCAGCACCACCAGCACCAC |

Figure 47D

| SEQ ID NO | BINDER | NUCLEOTIDE SEQUENCE |
|---|---|---|
| 349 | E24 | ATGGGAGTTTCTGATGTGCCGGCGCGACCTGGAAGTGGTTGCTGCCAGGAGTCAATCAGCTGGAATCGGCGGTCCGATGTACCAATATTACCGGCGCATCACTTACCGCGATGTGCCAGGAGTTCAGGAGGCAATAGCCCCTGTCCAGGAGTTCACTGTGCCTGGTCAGGTTCCAACCGGCTCCAACAGCTACCATCAGCGGCCCTTAAACCTGGCGTTGATTATACCATATCCGGTTGTCACTGACTCTTACAACCGGCTACTCATTGAATACCAAATACCATCAGAGAATTGACAAACCATCCAGCACCATCACCAC |
| 350 | E25 | ATGGGAGTTTCTGATGTGCCGGCGCGACCTGGAAGTGGTTGCTGCCACCGGCCACCAGCCTGTGATCAGCTGGGGCTACCAAAGTGGCGGCTATAACCTATTACCGGCGATCACTTACCGCGAAACAGGAGGCGAAACAGGAGGCAATAGCCCCTGTCCAGGAGTTCACTGTGCCTCATGACCTGCGTACAGCTACCATCAGCGGCCCTTAAACCTGGCGTTGATTATACCATGTCTGTATGCGTATACGCACCATGACATGCAATGTTGAATACCAGGAAACATTGACAAACCATCCAGCACCATCACCAC |
| 351 | E26 | ATGGGAGTTTCTGATGTGCCGGCGCGACCTGCTGCCACCAGCCTGTGATCAGCTGGATCAGTGGTGGATCGGCATCCGGGTCCGGTGTACCAATATTACCGGCGATCACTTACCGCGAAACAGGAGGCAATAGCCCCTGTCCAGGAGTTCACTGTGCCTTACGACGGTAAACAGCTACCATCAGCGGCCCTTAAACCTGGCGTTGATATACCATGTCTGTATGCGTATACGCACATGACCATCGACATGAATTGACAGAAATTGACAAACCATCCAGCACCATCACCACTACGCCTGAAATACCCTGAAATTAATTACGGACAGACAGCACCATCACCAC |
| 352 | E27 | ATGGGAGTTTCTGATGTGCCGGCGCGACCTGGAAGTGGTTGCTGCCACCAGCCTGTGATCAGCTGGTGTCGATCAGTGGTCTAAAGGTTCAAATCTTACCAATATACCATCAGCGGCCCTTAAACCTGGCGTTGATTATACCATGGCTGCCATCCGACCACTGCGTATGCGTATGCGTCACTGACTATTATAACCGGCTACTTAGCGAATGAATATACCTGAATACCCTGAATACCCTGAATACCCAATCAATAACACTTAATTACGGACAGACAGCACCATCACCAC |
| 353 | E28 | ATGGGAGTTTCTGATGTGCCGGCGCGACCTGGAAGTGGTTGCTGCCACCAGCCTGTGATCAGCTGGATCAGTGGGAATCCGGCTCCAAAAGCTACCAATATTACCGGCGATCACTTACCGCGAAACAGGAGGCAATAGCCCCTGTCCAGGAGTTCACTGACGTTCACTGACGTGCCGCGATCAGCGGCCCTTAAACCTGGCGTTGATTATACCATGTCTATGCGTATGCGTCACTGACTCTTACAATCCGGATACTCATGAATGAATATACCATGAATACCCAATCAATAATACCATCAGCACCATCACCAC |
| 354 | E29 | ATGGGAGTTTCTGATGTGCCGGCGCGACCTGGAAGTGGTTGCTGCCACCAGCCTGTGATCAGCTGGATCAGTGGCAGCTGGCAACCCGGCACCACACATATATTACCGATTATACCAGCGAAACAGGAGGCAATAGCCCCTGTCCAGGAGTTCACTGACGTGCCTACGACCTGATGACCAGCTACCATCAGCGGCCCTTAAACCTGGCGTTGATTATACCATGTCTGTATGCGTATGCGTCACTGACTATTACAACCGAATACTTATGAATGAATATACCATGAATACCCAATCAATAATACCAGCACCATCACCAC |
| 355 | E30 | ATGGGAGTTTCTGATGTGCCGGCGCGACCTGGAAGTGGTTGCTGCCACCAGCCTGTGATCAGCTGGCATCGGCACCACAACCGGCACCATCGTTACACAGCTACCAATATTACCGATCATCAGCGGCCCTTAAACCTGGCCTCCAATTTGACACACCGGAAACAGGAGGCAATAGCCCCTGTCCAGGAGTTCACTGTGTATGCGTATGCGTCACTATTACCAGCACCATCACCAC |

Figure 47L

| SEQ ID NO | BINDER | NUCLEOTIDE SEQUENCE |
|---|---|---|
| 356 | E31 | ATGGGAGTTTCTGATGTGCCGCGGACCTGGAAGTGGTTGCTGCCACCAGCCTGATCAGCTGCTGATGATGGCAGCTATCAATATTACCGGCGAACCTGGCGAAACAGGAGGCAATAGCCCTGTCCAGGAGTTCACTGTGCCTTAGGCTGTT TACACAGCTACCATCAGCGGGCGCTTAAACCTGCGTTGATTATACCACTGTGTATGCTGACTTTTACAATCCGGCT ACATATGAATACATATACCGACACAGAGAATTCCATTAATTACCGCACAGAAATTGACAAACCATCCAGCACCATCACCAC |
| 357 | E32 | ATGGGAGTTTCTGATGTGCCGCGGGACCTGGAAGTGGTTGCTGCCACCAGCCTGATCAGCTGCTGGGTCTCCTGTG CGCTTCTACCAATATTACCGGCGGGGATCACTTACGGCGAAACAGGAGGCAATAGCCCTGTCCAGGAGTTCACTGTGCCTGGTGGTGTT CATACAGCTACCATCAGCGGCGGCCTTAAACCTGGCGTTGATTATACCACTGTGTATGCTGACTACTGTAAACCGGATGCT GACGGTCCGCATACTTACCATGGAATCCCATTAATTACCGCACAGAAATTGACAAACCATCCAGCACCATCACCAC CACCAC |
| 358 | E33 | ATGGGAGTTTCTGATGTGCCGCGGGACCTGGAAGTGGTTGCTGCCACCAGCCTGATCAGCTGGGCCTTCGAGGAAG GAGTTCTACCAATATTACCGGCGATCACTTACGGCGAAACAGGAGGCAATAGCCCTGTCCAGGAGTTCACTGTGCCTGGTTGGTTG AACAAGCTACCATCAGCGGCGGCCTTAAACCTGGCGTTGATTATACCACTGTGTATGCTGACTACTGTGATGTTGAA TACGCTGAATACCAATTCCATTAATTACCGCACAGAAATTGACAAACCATCCAGCACCATCACCAC |
| 359 | E34 | ATGGGAGTTTCTGATGTGCCGCGGGACCTGGAAGTGGTTGCTGCCACCAGCCTGATCAGCTGCTGATGCAGCTGGGTTGGGCGCCTTG TGGCGGTACAGCTACCATCAGCGGCGGCCTTAAACCTGGCGTTGATTATACCACTGTGTATGCTGACTATAAACCGCATGCT CGTACAGCTACCATCAGCGGCGGCCTTAAACCTGGCGTTGATTATACCACTGTGTATGCTGACTATAAACCGCATGCT GACGGTCCGCATACTTACCATGGAATCCCATTAATTACCGCACAGAAATTGACAAACCATCCAGCACCATCACCAC CACCAC |
| 360 | E35 | ATGGGAGTTTCTGATGTGCCGCGGGACCTGGAAGTGGTTGCTGCCACCAGCCTGATCAGCTGGGACACCAGGA CATCAACATCAATATTACCGGCGATCACTTACGGCGAAACAGGAGGCAATAGCCCTGTCCAGGAGTTCACTGTGCCTGGTCAGTT ACTACAGCTACCATCAGCGGCGGCCTTAAACCTGGCGTTGATTATACCACTGTGTATGCTGACTATTACAACCGGCT ACTCACTATTACATACTTATTACGAGACTCCAATTAATACGAGACTCCAATTCCATTAATTACCGCACAGAAATTGACAAACCATCCAGCACCATCACCAC CACCAC |
| 361 | E36 | ATGGGAGTTTCTGATGTGCCGCGGGACCTGGAAGTGGTTGCTGCCACCAGCCTGATCAGCTGGGAGTCGGGGTCC AGGACGTACCATCAGCGGCGGCCTTAAACCTGGCGAAACAGGAGGCAATAGCCCTGTCCAGGAGTTCACTGTGCCTGGTGGTGTT CATACAGCTACCATCAGCGGCGGCCTTAAACCTGGCGTTGATTATACCACTGTGTATGCTGACTATAAACCGCATGCT GACGGTCCGCATACTTACCATGAATACCCAATTAATTACCGCACAGAAATGGACAAACCATCCAGCACCATCACCAC CACCAC |
| 362 | E37 | ATGGGAGTTTCTGATGTGCCGCGGGACCTGGAAGTGGTTGCTGCCACCAGCCTGATCAGCTGGGAGAGGACCTCC ACCCACTACGGTACACAGCTACCATCAGCGGGAAACAGGAGGCAATAGCCCTGTCCAGGAGTTCACTGTGCCTGGTGTGTT TACACAGCTACCATCAGCGGCGGCCTTAAACCTGGCGTTGATTATACCACTGTGTATGCTGACTACTAGAACCGGCT ACTCACATGAATACAATACAATACCAGAGCTCCAATTAATTACCGCGACAGAAATTGACAAACCATCCAGCACCATCACCAC CACCAC |

Figure 47F

| SEQ ID NO | BINDER | NUCLEOTIDE SEQUENCE |
|---|---|---|
| 363 | E38 | ATGGGAGTTTCTGATGATTACCGGCGGCGACCTGACTCACTTACGCGCGCATCACTTACCGGCTGCTGCCACCCCCACCAGCCTGCTGATCAGCTGGAATGCTGCACCGACGCTTATCAATATTACCGGCATCCGGATCAGCGGGCCCATCACTTACCGGAGGCAATAGCCCTGTCCAGGAGTTCACTGTGCCTCGTGACCTGGAAACAGCTACCAGCGGCCTTAAACCTGGCGGTTCGCCAATTCCATTAATTACCGGCACAGAAATTGACAAACCATCCAGCACCATCACCACGACGGACCCGCATACTTACCAAGAGTCGCCAATTTCCATTAATTACCGGCACAGAAATTGACAAACCATCCAGCACCATCACCACCACCAC |
| 364 | E39 | ATGGGAGTTTCTGATGTGCCGGCGACCTGGAAGTGGTTGCTGCCACCCCCACCAGCCTGCTGATCAGCTGGCAGGTGACGCGGTTCCGGTACCAGCTACCCGGCATCCGGATCAGCGGGCCCATCACTTACCGGAGGCAATAGCCCTGTCCAGGAGTTCACTGTGCCTGGTATGGTTTCTACAGCTACCAGCAGCGGGCCTTAAACCTGGCGGTTGATTATACCGACTGTGTATGCTGACTAATACCAGCACCATCAGCACTGAAGACATGAATACCAATGTCCCAATTTCCATTAATTACCGGCACAGAAATTGACAAACCATCCAGCACCATCACCACGACGGTCCGGAATACTTACTCGAGCTTACTGAGCCTTACCGGGCTGAATCTGCACTGTGCACTAATAACCATCCAGCACCATCACCACCAC |
| 365 | E40 | ATGGGAGTTTCTGATGTGTCGCGGCGACCTGGAAGTGGTTGCTGCCACCCCCACCAGCCTGCTGATCAGCTGGGTGCTGGGCAGGAGGGTGTACAGCTACCAATATTACCGGCATCCGGATCAGCGGGCCCATCACTTACCGGAGGCAATAGCCCTGTCCAGGAGTTCACTGTGCCTGGGTGCTGTTTACACAGCTACCAGCAGCGGGCCCTTAAACCTGGCGGTTGATTATACCGGACTGTGTATGCTGACTGTCACTAATTCAACCAGCTACCATGAATACAATACGGCATATCCAATTCCATTAATTACCGGCACAGAAATTGACAAACCATCCAGCACCATCACCACCAC |
| 366 | E41 | ATGGGAGTTTCTGATAATTATTACCGCCGGCGACCTGGAAGTGGTTGCTGCCACCCCCACCAGCCTGCTGATCAGCTGGACTGGACTGACTGTCCTCAGCCGACTGCTGTCTGGTATAATTATTACCGGCATCCGGATCAGCGGGCCCATCACTTACCGGAGGCAATAGCCCTGTCCAGGAGTTCACTGTGCCTGACTATTACAACCGGAATACCTACGAGCACCATCACAGACATTTACCTATCAATTCAACTCACTTACCGGCACAGAAATTGACAAACCATCCAGCACCATCACCACCAC |
| 367 | E42 | ATGGGAGTTTCTGATGTACTCTAGTCGCCGCGGCGACCTGGAAGTGGTTGCTGCCACCCCCACCAGCCTGCTGATCAGCTGGAACTGGTCCTGGTATGCCTGTGGATGAAACAGCTACCAATATTACCGGCATCCGGATCAGCGGGCCCATCACTTACCGGAGGCAATAGCCCTGTCCAGGAGTTCACTGTGCCTGGTATACCCGGACTACGTATGAATACAGCTACCATACACATATGAATACACATCCAATTCCATTAATTACCGGCACAGAAATTGACAAACCATCCAGCACCATCACCACCAC |
| 368 | E43 | ATGGGAGTTTCTGATGTGCCGGCGACCTGGAAGTGGTTGCTGCCACCCCCACCAGCCTGCTGATCAGCTGGCGGGTTCATGGCGGTCCTGGTCAGGTTTATACAGCTACCAATATTACCGGCATCCGGATCAGCGGGCCCATCACTTACCGGAGGCAATAGCCCTGTCCAGGAGTTCACTGTGCCTGACTATGCTGCACTATAAACCGGACTACGGGGTCCGCATATCACTTACCTATCCAATTCCATTAATTACCGGCACAGAAATTGACAAACCATCCAGCACCATCACCACCAC |
| 369 | E44 | ATGGGAGTTTCTGATGTGCCGGCGACCTGGAAGTGGTTGCTGCCACCCCCACCAGCCTGCTGATTCCGAAGGTCCTTCTTATTACAGCTACCAATATTATTTTTGGCAGCAATTACCGGCATCCGGATCAGCGGGCCCATCACTTACCGGAGGCAATAGCCCTGTCCAGGAGTTCACTGTGCCTTACGCTGTTTACACAGCTACCATCAGCGGGCCTTAAACCTGGCGGTTGATTATACCGGACTGTGTATGCTGACTGTCACTGACTATTACAACCGGAGAAGGCAATGAATTATTTTTGGCAGCAATTACCGGCAATATCCAATTCCATTAATTACCGGCACAGAAATTGACAAACCATCCAGCACCATCACCACCAC |

Figure 47G

| SEQ ID NO | BINDER | NUCLEOTIDE SEQUENCE |
|---|---|---|
| 370 | E45 | ATGGGAGTTTCTGATGTGCCGGCGGACCTGGAAGTGGTTGCTGCCACCAGCCTGCTGATCAGTGGCAGTTCCGGTT CCGATGTACAGCTACCAATATTACCGGCGGGACCTGGAAACAGGAGGCAATAGCCCTGTCCAGGAGTTCACTGCCTCATGACCTG CGTACAGCTACCATCAGGGGCCTTAAACCTGGCGTTGATTATACCACTGTGTATGCTGTCACTGACTATACGACCGGACA TCTAATCGTACAATTACAACAGATCCAATTTCCATTAATTACCGCACAGAAATTGACAAACCATCCCAGCACCATCACCAC CACCAC |
| 371 | E46 | ATGGGAGTTTCTGATGTGCCGGCGGACCTGGAAGTGGTTGCTGCCACCAGCCTGCTGATCAGTGGCAGTTGGGCTCG GTGGGTACAGCTACCAATATTACCGGCGGGACCTGGAAACAGGAGGCAATAGCCCTGTCCAGGAGTTCACTGTCCTGTGGAGTT CTGACAGCTACCATCAGGGCCTTAAACCTGTCTATATTACCACTGTGTATGCTGTCACTGACTATAAAACCGAAGCCT GACGGTCCACATATATACCAGCAGTGCACTCGACTCCAATTCCAATTAATTACCGCACAGAAATTGACAAACCATCCCAGCACCATCACCAC CACCAC |
| 372 | E47 | ATGGGAGTTTCTGATGTGCCGGCGGACCTGGAAGTGGTTGCTGCCACCAGCCTGCTGATCAGTGGAACCCTGCTTCT AAAGACTATCACAATATTACCGGCGGGACCTGGAAACAGGAGGCAATAGCCCTGTCCAGGAGTTCACTGTGCCTGGTCAGTTT CCGACAGCTACCATCAGCGGCCTTAAACCTGGCGTTGATTATACCACTGTGTATGCTGTCACTGACTTTTACAACCGGGCT ACTCATGAGTATAAATATGACTGACTCCAATTCCAATTAATTACCGCACAGAAATTGACAAACCATCCCAGCACCATCACCAC CACCAC |
| 373 | E48 | ATGGGAGTTTCTGATGTGCCGGCGGACCTGGAAGTGGTTGCTGCCACCAGCCTGCTGATCAGTGGAGATCATCAGCA ACCGGCTACCAATATTACCGGCGGGACCTGGAAACAGGAGGCAATAGCCCTGTCCAGGAGTTCACTGTGCCTGTGGTGTT TACACAGCTACCATCATCGGCGGCCTTAAACCTGGCGTTGATTATACCACTGTGTATGCTGTCACTGACTTTTCAACTGGGCC ACTCATTACTATTACTGACTACGAGTGACTCCAATTTCCATTAATTACCGCACAGAAATTGACAAACCATCCCAGCACCATCACCAC CACCAC |
| 374 | E49 | ATGGGAGTTTCTGATGTGCCGGCGGACCTGGAAGTGGTTGCTGCCACCAGCCTGCTGATCAGTGGCATTCCGGTCCA CCAGAAATATCAATATTACCGGCGGGACCTGGAAACAGGAGGCAATAGCCCTGTCCAGGAGTTCACTGTGCCTGGTCAGGTT TACACAGCTACCATCACCAGCGGCCTTAAACCTGACTCCAATTTCCATTAATTACCGCACAGAAATTGACAAACCATCCCAGCACCATCACCAC CACCAC |
| 375 | E50 | ATGGGAGTTTCTGATGTGCCGGCGGACCTGGAAGTGGTTGCTGCCACCAGCCTGCTGATCAGTGGACGTGGGCCTG AGCGTGTACAGCTACCATCAGGGGCCTGATATTACCGGCGGGACCTGGAAACAGGAGGCAATAGCCCTGTCCAGGAGTTCACTGTCCTGGTATGGTT TCTACAGCTACCATCAGGGGCCTTAAACCTGGCGTTAGCGTTGATTATACCACTGTGTATGCTGTCACTGACTATAAACCGATGCT GACGGTCCGCATACTTACCATGAATATCCAATTTCCATTAATTACCGCACAGAAATTGACAAACCATCCCAGCACCATCACCAC CACCAC |
| 376 | E51 | ATGGGAGTTTCTGATGTGCCGGCGGACCTGGAAGTGGTTGCTGCCACCAGCCTGCTGATCAGTGGGGGGGCACCGG GCGGTGTACAGCTACCAATATTACCGGCGGGACCTGGAAACAGGAGGCAATAGCCCTGTCCAGGAGTTCACTGTGCCTGGTCGTTT TACACAGCTACCATCAGGGGCCTTAAACCTGGCGTTGATTATACCATCACTGTGTATGCTGTCACTGACTACACCCCGGAT ACTCATGAATACAAATACCAATTAATTACCGCACAGAAATTGACAAACCATCCCAGCACCATCACCAC CACCAC |

Figure 47ll

| SEQ ID NO | BINDER | NUCLEOTIDE SEQUENCE |
|---|---|---|
| 377 | E52 | ATGGGAGTTTCTGATGTGCCGCGACCTGGAAGTGGTTCTGCCACCCCACCAGCCCTGTCCAGGAGTTCACTGTGCCTGTGGCCT CCGATGTACAGCTACCAATATTACCGCCATCCGGGCCTTAAACCTGGCGTTGATTATACCATCACTGTGTATGCTGTCACTGGTCAAGGAA CGTACAGCTACCATCAGCGGCCTTAAACCTGGCGTTGATTATACCATCACTGTGTATGCTGTCACTGACTACTGGTTCAAGGAA TACCGCGTGAAGACCCCAATTTCCATTAATTACCGCACAGAAATTGACAAGCACCATCACCAGCACCATCACCAC |
| 378 | E53 | ATGGGAGTTTCTGATGTGCCGCGACCTGGAAGTGGTTGCTGCCACCCCACCAGCCCTGTCCAGGAGTTCACTGTGCCTGGTATGGT ATGATCTACCAATATTACCGCCATCCGGCCATCAGCGGCCTTAAACCTGGCGTTGATTATACCATCACTGTGTATGCTGTCACTGGCCTGTATGGTT ACTACAGCTACCATCAGCGGCCTGGCCTTAAACCTGGCGTTGATTATACCATCACTGTGTATGCTGTCACTGACTACAACCGGCT ACTCATGAATACAAATACCAGAGACTCCAATTTCCATTAATTACCGCACAGAAATTGACAAACCATCCAGCACCATCACCAC CACCAC |
| 379 | E5 | ATGGGAGTTTCTGATGTGCCGCGACCTGGAAGTGGTTGCTGCCACCCCACCAGCCCTGTCCAGGAGTTCACTGTGCCGCCCGTC GACCGGTACCAATATTACCGCCATCCGGCCATCAGCGGCCTGGCCTTAAACCTGGCGTTGATTATACCATCACTGTGTATGCTGACGTT TACACAGCTACCATCAGCGGCCTACCATCAGCGGCCTGGCCTTAAACCTGGCGTTGATTATACCATCACTGTGTATGCTGACTATAAACCGCATGCT GACGGTCCGCATACTACAAGTACCGAGCAGAATTCCAATTTCCATTAATTACCGCACAGAAATTGACAAACCATCCAGCACCATCACCAC CACCAC |
| 380 | E5 (with Cys tail) | ATGGGAGTTTCTGATGTGCCGCGACCTGGAAGTGGTTGCTGCCACCCCACCAGCCCTGTCCAGGAGTTCACTGTGCCGCCCGTC GACCGGTACCAATATTACCGCCATCCGGCCATCAGCGGCCTGGCCTTAAACCTGGCGTTGATTATACCATCACTGTGTATGCTGACGTT TACACAGCTACCATCAGCGGCCTACCATCAGCGGCCTGGCCTTAAACCTGGCGTTGATTATACCATCACTGTGTATGCTGACTATAAACCGCATGCT GACGGTCCGCATACTACAAGTACCGAGCAGAATTCCAATTTCCATTAATTACCGCACAGAAATTGACAAACCATCCAGCACCATCACCAC CACCAC |
| 381 | E54 | ATGGGAGTTTCTGATGTGCCGCGACCTGGAAGTGGTTGCTGCCACCCCACCAGCCCTGTCCAGGAGTTCACTGTGCCTGTGACGTT ACCGGCTACAGCTATTACCGCCATCGGCCATCAGCGGCCTGGCCTTAAACCTGGCGTTGATTATACCATCACTGTGTATGCTGACTTCCTACAATCCGAT ATGACAGCTACCGCCATCAGCGGCCTGGCCTTAAACCTGGCGTTGATTATACCATCACTGTGTATGCTGACTACCGCTACAACCGGCT ACTCATCAATACAATACCAGAGACTCCAATTTCCATTAATTACCGCACAGAAATTGACAAACCATCCAGCACCATCACCAC CACCAC |
| 382 | E55 | ATGGGAGTTTCTGATGTGCCGCGACCTGGAAGTGGTTGCTGCCACCCCACCAGCCCTGTCCAGGAGTTCACTGTGCCTGGGCCAG GTCTTCTACAGCTACCGCCATCAGCGGCCTGGCCTTAAACCTGGCGTTGATTATACCATCACTGTGTATGCTGACTTGCCTTACGACGTT TACACAGCTACCGCCATCAGCGGCCTGGCCTTAAACCTGGCGTTGATTATACCATCACTGTGTATGCTGACTACTACAACCGGCT ACTCATGAATACAAATACCAGAGACTCCAATTTCCATTAATTACCGCACAGAAATTGACAAACCATCCAGCACCATCACCAC CACCAC |
| 383 | E56 | ATGGGAGTTTCTGATGTGCCGCGACCTGGAAGTGGTTGCTGCCACCCCACCAGCCCTGTCCAGGAGTTCACTGTGCCTACTGGTGAT TACCAATTACTACAAGTACCGAGCAGAATTCCAATTTCCATTAATTACCGCACAGAAATTGACAAACCATCCAGCACCATCACCAC GAAACAGCTACCGCCATCAGCGGCCTGGCCTTAAACCTGGCGTTGATTATACCATCACTGTGTATGCTGACTTCACTGACTACAACCGGCT ACTCATTACTACAAGTACCGAGCAGAATTCCAATTTCCATTAATTACCGCACAGAAATTGACAAACCATCCAGCACCATCACCAC |

Figure 47I

| SEQ ID NO | BINDER | NUCLEOTIDE SEQUENCE |
|---|---|---|
| 384 | E57 | ATGGGAGTTTCGATGTGCCGCGGACCTGGAAGTTGTTGCTGCCACCCCACCAGCCTGCTGCCAGTGGTGATCAGTGGCGAGGG GGGCGCTACCAGCTACCATCCGCAGCGGCCATTAAACCTGGCGTCCAGGAGGCAATAGCCGTGTCCAGGAGTTCACTGCTGGCTATGGTT ACTACAGCTACCATCCGCAGCGGCCATTAAACCTGGCGTGCATGCCGTGCACTGACTTCTACAACCTTCA ACTCATGAATACAAATACGATCAGATTCCCAATTCCAATTAATTACCGCACAGAAATTGACAAACCATCCAGCACCATCACCAC CACCAC |
| 385 | E58 | ATGGGAGTTTCTGATGTGCCGGGACCTGGAAGTGGTTGCTGCCACCCCACCAGCCTGCTGATCAGTGGCGGGGCCGCC TGGCGGTACCAATATTACCGCCATCAGCGGCCCTTAAACCTGGCGTTGATTATACCCATCCACTGTGTCACTGACTTTACAACCGGGT CGTACAGCTACCATCAGCGGACATATACGATCAGTTCCCAATTCCCAATTAATTACCCACAGAAATTGACAAACCATCCAGCACCATCACCAC CACCAC |
| 386 | E59 | ATGGGAGTTTCTGATGTGCCGCGGACCTGGAAGTGGTTGCTGCCACCCCACCAGCCTGATCAGTGGAGGGCCAGGCGC TTGCAGTACCAATATTACCGCCATCAGCGGCCAATAGCGAGGCAATAGCCCGTGCCAGGAGTTCACTGACTCTGCCGTGTATGGTT ACTACAGCTACCATCAGCGGCCGTTAAACCTGGCGTTGATTATACCCATCACTGTGTCACTGACTTTACAACCGGCT ACTACAGAGTACACAATATACCGCACATATCAGCGGACATATACCGCACAGAAATTGACAAACCATCCAGCACCATCACCAC CACCAC |
| 387 | E60 | ATGGGAGTTTCTGATGTGCCGCGGACCTGGAAGTGGTTGCTGCCACCCCACCAGCCTGCTGATCAGTCAGCCCTC TGGAGGTACCAATATTACCGCGACATCACTTACGCCGACATCACAGGAGGCAATACCCGTGTCCAGGAGTTCACTGCTGCCTGCTG GACACAGCTACCATCAGCGGCGTCAGCCATCAGCGGCCCTTAAACCTGGCGTTGATTATGCCGTCACTGTGTCACTGACTATAAACCGATGTT GACGGGTGCCCATGCTTACCATCAGCGGCTTACCATCAGCGGCTTACCATGAATTCCATTAATTACCGCACAGAAATTGACAAACCATCCAGCACCATCACCAC CACCAC |
| 388 | E61 | ATGGGAGTTTCTGATGTGCCGCGCGACCTGGAAGTGGTTGCTGCCACCCCACCAGCCTGCTGATCAGTGGGACGCCTCCAG GGGAACTAGCAGCTACCATCAGCGGCCCTTAAACCTGGCGTTAAACCTGCACGAGTCGTGCTGATGCGTCACTGACTTTTCAACCCGGCT AAACAGCTACCATCAGCGGCCCTTAAACCGGCCATCAGCGGCCCTTAAACCTGTGTATACCGATTAATTACCGCACAGAAATTGACAAACCATCCAGCACCATCACCAC ACTCATGAATACAATACGACTACCATCAGCGGACTACCATGAATTCCATTAATTACCGCACAGAAATTGACAAACCATCCAGCACCATCACCAC CACCAC |
| 389 | E62 | ATGGGAGTTTCTGATGTGCCGCGCGACCTGGAAGTGGTTGCTGCCACCCCACCAGCCTGATCAGTCAGCTGTTGCCTGACGGG CAGTTGTACCAGCTACCATCAGCGGCCCTTAAACCTGCCGAAACAGGAGGCAATAGCCCGTGCCAGGAGTTCACTGCTGGTTCTATC GTTACAGCTACCATCAGCGGCCCGTGAATATACCCATCAGCGGCGCCGTGAATATACCATCACTGTGTATGCCTGTCACTGACTGGTACAACCTGCG ACTCATGAATACAATACGACTACCATCAGCGACTACCATGAATTCCATTAATTACCGACAGAAATTGACAAACCATCCAGCACCATCACCAC CACCAC |
| 390 | E63 | ATGGGAGTTTCTGATGTGCCGCGCGACCTGGAAGTGGTTGCTGCCACCCCACCAGCCTGCTGATCAGTGGGACACTTCAGGT GCTTCAATACAATATTACCGCCATCAGCGGCGAAACAGGAGGCAATAGCCCGTGCCAGGAGTTCACTGCCTTACTCTGTT TACACAGCTACCATCAGCGGCCCTTAAACCTGCCGTGATTATACCCATCACTGTGTATGCGACTATTACGACCCTGAT TGGCATTATTACCAGCTACAATACGGTTCCAATTTCCAATTAATTACCGACAGAAATTGACAAACCATCCAGCACCATCACCAC CACCAC |

Figure 47J

| SEQ ID NO | BINDER | NUCLEOTIDE SEQUENCE |
|---|---|---|
| 391 | E64 | ATGGGAGTTTCTGATGTGCCGGCGACCTGGAAGTGGTTGCTGCCACCCCCACCAGCCTGCTGATCAGCTGGATTCGGTAAT GGTACTTATCAATATTACCGCATCAGCGGCCCTTACGCGGCGAAACAGGAGGCAATAGCCCTGTGTCCAGGAGTTCACTGTGCCTTGGGTT TACACAGCTACCAGCGGGGCCTTAAACCTGGCGTTGATTATACCATCACTGACTGATTATACAACCGGCT ACTCACGAATATACAATACGGACGAGCTGCGTCCAATTCCACAGAAATTGACAGAAATTGACACAGAAATTAACCGGCACCATCCAGCACCATCCAGCCACCAC CACCAC |
| 392 | E65 | ATGGGAGTTTCTGATGTGCCGGCGACCTGGAAGTGGTTGCTGCCACCCCCACCAGCCTGCTGATCAGCTGGATTCGGTACCAGC CAGGTCTACCATCACCGGCATTATTACCGCATCAGCGGCCCTTACGCGGCGAAACAGGAGGCAATAGCCCTGTGTCCAGGAGTTCACTGTGCCTTACAACGTT TACACACGAATACCAGCGGGCCTTAAACCTGGCGTTGATTATACCATCACTGTGTATGCTGTCACTGACTGTTTTAACTATGCT ACTCACGAATACAATACCGGACGAGCTGCGTCCAATTCCACAGAAATTGACACAGAAATTGACACAGAAATTAACCGGCACCATCCAGCACCATCCAGCCACCAC CACCAC |
| 393 | E66 | ATGGGAGTTTCTGATGTGCCGGCGACCTGGAAGTGGTTGCTGCCACCCCCACCAGCCTGCTGATCAGCTGGAAGTCGGTACGGG TCGGCCTACCATCACCGGCATTATTACCGGGAAACAGGAGGCCAATAGCCCGTGCCAGGAGTTCACTGTGCCTGGTGACCGG CAGACAGCTACCATCAGCGGCGTTAAACCTGGCGTTGATTATACCATCACTGTGTATGCTATCACTGACTATTACAACCGGAT ACACATGAGTATAAATAACCATGTGTCGCCACACGACAGAAATTGACAGAAATTGACACAGAAATTAACCGGCACCATCCAGCACCATCCAGCCACCAC CACCAC |
| 394 | E67 | ATGGGAGTTTCTGATGTGCCGGCGACCTGGAAGTGGTTGCTGCCACCCCCACCAGCCTGCTGATCAGCTGGATTCGGTGATG GTGTGTACCAATATTACCGCATCAGCGGCCCTTAAACCTGGCGAAACAGGAGGCAATAGCCCTGTCCAGGAGTTCACTGTGCCTTACGACGTT TACACAGCTACCAGCGGGCCTTGATTATACCATCACTGTGTATGCCTGTCACTGACTATTACAACCCTCT ACTTATGGATATACAATACGACTCACTACTTAATTCCCATTCCCATTCCGGCACACAGAAATTGACACACCATCCAGCACCATCCAGCCACCAC CACCAC |
| 395 | E68 | ATGGGAGTTTCTGATGTGCCGGCGACCTGGAAGTGGTTGCTGCCACCCCCACCAGCCTGCTGATCAGCTGGATAGCGGAAGCA GGCGGTACCATCACCGGGCATCATTACCGGCGAAACAGGAGGCAATAGCCCTGTCCAGGAGTTCACTGTGCCTGGTACAACCTGGTT CGTACAGCTACCAGCGGGCCTTAAACCTGGCGTTGATTATACCATCACTGTGTATGCTGTCACTGACTGGTACAACCACCATCCAGCACCATCCAGCCACCAC TCTGATGAATAGTATACATAGTATCATACCGCACAGAAATTGACACAGAAATTGACACAGAAATTAACCGGCACCATCCAGCACCATCCAGCCACCAC CACCAC |
| 395 | E69 | ATGGGAGTTTCTGATGTGCCGGCGACCTGGAAGTGGTTGCTGCCACCCCCACCAGCCTGCTGATCAGCTGGATGATCAGCGGCATG GCGGTGTGTACCAATATTACCGCATCAGCGGCCCTTAAACCTGGCGAAACAGGAGGCAATAGCCCTGTCCAGGAGTTCACTGTGCCTGGTGACGTT CTGACAGCTACCATCAGCGGGCCTTAAACCTGGCGTTGATTATACCATCACTGTGTATGCTGTCACTGACTGTTTCAATCGGTT ACTCACGAATACAGTATCATACCGCACAGAAATTGACACAGAAATTGACACAGAAATTAACCGGCACCATCCAGCACCATCCAGCCACCAC CACCAC |
| 396 | E70 | ATGGGAGTTTCTGATGTGCCGGCGACCTGGAAGTGGTTGCTGCCACCCCCACCAGCCTGCTGATCAGCTGGTGTCCGGAGG GGGCGGTACCAGCTACCATCACCGGGAAACAGGAGGCAATAGCCCGTGCCAGGAGTTCACTGTGCCTGGTGGTGTT CGTACAGCTACCATCAGCGGGCCTCACCACCCAATTCCAATTCCAATTCCGGCGCACACAGAAATTGACACAGAAATTAACCGGCACCATCCAGCCACCAGCCACCAC ACTTATGGATATCATTACTACTATACCGCACAGAAATTGACACAGAAATTGACACAGAAATTAACCGGCACCATCCAGCCACCAGCCACCAC CACCAC |

Figure 47K

| SEQ ID NO | BINDER | NUCLEOTIDE SEQUENCE |
|---|---|---|
| 397 | E71 | ATGGGAGTTTCTGATGTGCCGCGCGACCTGGAAGTGGTTGCTGCCACCCCACCAGCCTGCTGATCAGCTGATCAGCCTGGTGGTTCGGCACCTGTTCCTACCAATATTACCGCATCCAGGGCCATCACTTACGGCGAAACAGGAGCCAATAGCCCTGTCCAGGAGTTCACTGTGCCTGTGACCTGAAAACAGCTACCATCCAGCGGCCTTAAACCTGGCGTTGATTATACCATCACTGTGATGCTGTCACTGACTATTTAACCCGTTACTCATGAATACGAATATCATAACTACCAATTTCCATTAATTACCGCACAGAAATTGACAAACCATCCCAGCACCATCACCAC |
| 398 | E72 | ATGGGAGTTTCTGATGTGCCGCGCGACCTGGAAGTGGTTGCTGCCACCCCACCAGCCTGCTGATCAGCTGATCAGCCTGGTCCGCGACCCGGACCCGTGTACCAGCTACCATCCAGCGGCCTTACCACTTACGGCGAAACAGGAGGCCAATAGCCCTGTCCAGGAGTTCACTGTGCCTGTTACGACGTTCATACAGCTACCATCCAGCGGGCCTTAAACCTGGCGTTATACCATCACTGTATGCTGTCACTGACTATHACAACATGTTACTTATGAATACAACAACTACCATTACCGCACAGAAATTGACAAACCATCCCAGCACCATCACCAC |
| 399 | E73 | ATGGGAGTTTCTGATGTGCCGCGCGACCTGGAAGTGGTTGTTGCCACCCCACCAGCCTGCTGATCAGCTGATCAGCCAAGTGTTGGGCTGTACCAGCTACCATCCAGCGGCCTTACCACTTACGGCGAAACAGGAGGCCAATAGCCCTGTCCAGGAGTTCACTGTGCCTGTCCTGTTTACACAGCTACCATCCAGCGGGCCTTAAACCTGGCGTTGATTATACCATCACTGTGTATGCTGTCACTGACTTTCCAACCCTCGTACTTATGAATACAACAGTACCATCCCAATTTCCATTAATTACCGCACAGAAATTGACAAACCATCCCAGCACCATCACCAC |
| 400 | E74 | ATGGGAGTTTCTGATGTGCCGCGCGACCTGGAAGTGGTTGCTGCCACCCCACCAGCCTGCTGATCAGCTGATCAGCTGGAGGGCGTGTTCTGTTGGGCTGTACCAGCTACCATCCAGCGGCCTTACCACTTACGGCGAAACAGGAGGCCAATAGCCCTGTCCAGGAGTTCACTGTGCCTGGTTCTGTTAACACAGCTACCATCCAGCGGGCCTTAAACCTGGCGTTGATTATACCATCACTGTGTATGCTGTCACTGACTTTTACAACCGGCTACTTATGAGTACATATAAATACGGCGAAACAGCTACCATTACCGCACAGAAATTGACAAACCATCCCAGCACCATCACCAC |
| 401 | E75 | ATGGGAGTTTCTGATGTGCCGCGCGACCTGGAAGTGGTTGCTGCCACCCCACCAGCCTGCTGATCAGCTGATCAGCCTGGGGCGGCCGGGGCGCGCCACGGTACCAGCTACCATCCAGCGGCCTTACCACTTACGGCGAAACAGGAGGCCAATAGCCCTGTCCAGGAGTTCACTGTGCCTGTCCTTACGACGTTACTACAGCTACCATCCAGCGGGCCTTAAACCTGGCGTTGATTATACCATCACTGTATGCTGTCACTGACTTTTACAACCGGCTACTTATGAATACGAATATACTAACTACCATTACCGCACAGAAATTGACAAACCATCCCAGCACCATCACCAC |
| 402 | E76 | ATGGGAGTTTCTGATGTGCCGCGCGACCTGGAAGTGGTTGCTGCCACCCCACCAGCCTGCTGATCAGCTGATCAGCCTGGTACTCGCAGCCCTTGACGTACCAGCTACCATCCAGCGGCCTTACCACTTACGGCGAAACAGGAGGCCAATAGCCCTGTCCAGGAGTTCACTGTGCCTGTCCTCTACAACCGGAGAACACAGCTACCATCCAGCGGGCCTTAAACCTGGCGTTGATTATACCATCACTGTGTATGCTGTCACTGACTTCTACAACCGGAGACACGAATGAATACACTTACCAATTTCCATTAATTACCGCACAGAAATTGACAAACCATCCCAGCACCATCACCAC |
| 403 | E77 | ATGGGAGTTTCTGATGTGCCGCGCGACCTGGAAGTGGTTGCTGCCACCCCACCAGCCTGCTGATCAGCTGATCAGCCTGGAGTTCTGCAACAAGACCTTTACCAGCTACCATCCAGCGGCCTTACCACTTACGGCGAAACAGGAGGCCAATAGCCCTGTCCAGGAGTTCACTGTGCCTGGTGTTCAACCCGACTCGTACGTAATAGCTACCATCCAGCGGGCCTTAAACCTGGCGTTGATTATACCATCACTGTGTATGCTGTCACTGACTTTTCAACCACCATCCCAGCACCATCACCAC |

Figure 47L

| SEQ ID NO | BINDER | NUCLEOTIDE SEQUENCE |
|---|---|---|
| 404 | E78 | ATGGGAGTTTCTGATGTGCCGGCGACCTGGAAGTGGTTGCTGCCACCCCCACCAGCTGCTGATCAGCTGGTCCGCTGGTCGTGGAGAGG TCCGTGTACCAATATTACCGCATCACTGGCCCTTAAACCTGGCGGAAACAGGAGGCAATAGCCCTGTCCAGGAGTTCACTGTCCTGGTGTT CGTACAGCTACCATCAGCGGGCCTTAAACCTGGCGTTGATTATACCATCACTCACTGTGTCTATGCTGTCACTGACTATTACAACCCGTCT ACTCATGAATACAATACCTCACGGACTCCAATTTCCAATTAATTACCGCACAGAAATTGACAAACCATCCAGCACCACCATCACCAC CACCAC |
| 405 | E79 | ATGGGAGTTTCTGATGTGCCGGCGACCTGGAAGTGGTTGCTGCCACCCCCACCAGCTGCTGATCAGCTGGTCAGCTGGTCCAAGATACTCC AGTTATCATCAGCTACCGCATCACTGGCCCTTAAACCTGGCGGAAACAGGAGGCAATAGCCCTGTCCAGGAGTTCACTGTGCCTGGTGTT CGTACAGCTACCATCAGCGGGCCTTAAACCTGGCGTTGATTATACCATCACTCACTGTGTCTATGCTGTCACTGACTATTCAACCCGTCT ACCATGAATACAATACCTCATTAATTACCGCACAGAAATTGACAAACCATCCAGCACCACCATCACCAC CACCAC |
| 406 | E80 | ATGGGAGTTTCTGATGTGCCGGCGACCTGGAAGTGGTTGCTGCCACCCCCACCAGCCTGCTGATCAGCTGGTCAGCTGGTCTAGTCTCAT CGGCCGTATCAATATTACCGCATCACTGGCCCTTAAACCTGGCGGAAACAGGAGGCAATAGCCCTGTCCAGGAGTTCACTGTGCCTGGTT GCTACAGCTACCATCAGCGGGCCTTAAACCTGGCGTTGATTATACCATCACTCACTGTGTCTATGCTGTCACTGACTATTTCAACCAGAC ACTCATGAATACCTATACCAATTAATTACCGCACAGAAATTGACAAACCATCCAGCACCACCATCACCAC CACCAC |
| 407 | E81 | ATGGGAGTTTCTGATGTGCCGGCGACCTGGAAGTGGTTGCTGCCACCCCCACCAGCCTGCTGATCAGCTGGTCAGCTGGATAATAATTCT AACTCATATCAATATTACCGCATCACTGGCCCTTAAACCTGGCGGAAACAGGAGGCAATAGCCCTGTCCAGGAGTTCACTGTCCTTACGACCTG CGTACAGCTACCATCAGCGGGCCTTAAACCTGGCGTTGATTATACCATCACTCACTGTGTCTATGCTGTCACTGACTATAAACCTATACT GAGGGTGAGCTACTATCATGAATCGCACACCTATGAATTCCAATTAATTACCGCACAGAAATTGACAAACCATCCAGCACCACCATCACCAC CACCAC |
| 408 | E82 | ATGGGAGTTTCTGATGTGCCGGCGCGACCTGGAAGTGGTTGCTGCCACCCCCACCAGCCTGCTGATCAGCTGGTCAGCTGGCGGTGTGGGC CACATGTACCAATATTACCGCATCACTGGCCCTTAAACCTGGCGGAAACAGGAGGCAATAGCCCTGTCCAGGAGTTCACTGTGCCTGGTGTT CTGACAGCTACCATCAGCGGGCCTTAAACCTGGCGTTGATTATACCATCACTCACTGTGTCTATGCTGTCACTGACTATAAACCGCATGTT GACGGGCCGCACACTACTATCATGAATCGCACACCTATGAATTCCAATTAATTACCGCACAGAAATTGACAAACCATCCAGCACCACCATCACCAC CACCAC |
| 409 | E83 | ATGGGAGTTTCTGATGTGCCGGCGCGACCTGGAAGTGGTTGCTGCCACCCCCACCAGCCTGCTGATCAGCTGGTCAGCTGGATGTTCGTGGGG ATGTCTACCAATATTACCGCATCACTGGCCCTTAAACCTGGCGGAAACAGGAGGCAATAGCCCTGTCCAGGAGTTCACTGTGCCTTACGGTGTT CATACAGCTACCATCAGCGGGCCTTAAACCTGGCGTTGATTATACCATCACTCACTGTGTCTATGCTGTCACTGACTATTTCAACCGGCT ACGATGTACCTACCATCAGCGGGGGAAACAACTCCAATTAATTACCGCACAGAAATTGACAAACCATCCAGCACCACCATCACCAC CACCAC |
| 410 | E84 | ATGGGAGTTTCTGATGTCCGCGGCGACCTGAAGTGGTTCCTGCCACCCCCACCAGCTGCTGATCAGCTGGTCAGCTGGACGCTGGCACCGG AAGAACTACCAATATTACCGCATCACTGGCCCTTAAACCTGGCGGAAACAGGAGGCAATAGCCCTGTCCAGGAGTTCACTGTGCCTGGTGTT GTTACAGCTACCATCAGCGGGCCTTAAACCTGTCGACTGATTATACCATCACTCACTGTCTGTATGCTGTCACTGACTATTACAACCCGGCA ACTCATGAATACGACTACCGGAACAACTCCAATTAATTACCGCACAGAAATTGACAAACCATCCAGCACCACCATCACCAC CACCAC |

Figure 47M

| SEQ ID NO | BINDER | NUCLEOTIDE SEQUENCE |
|---|---|---|
| 411 | E85 | ATGGGAGTTTCTGATGTGCCGGGGACCTGGAAGTGGTTGCTGCCACCCCAGGCTTCTGATCAGCTGGACAAGGCAGTACTCATTACCGACAATATTACCGGATCACTTACGGCGAAACAGGAGGCAATAGCCCTGTCCAGGAGTTCACTGTCCTGTATGGTTTACACCAGCTACCATCAGCGGCCTTAAACCTGGCGTTGATTATACCATCACTGTGTATGCTGCACTGACTATTTGACGGCTCTACTCATGAGTAATAAATACCGTACGACTCCAATTTCCATTTAATTACGGCACAGAAATTGACAAACCATCCAGCACCATCACCACCACCAC |
| 412 | E4 | ATGGGAGTTTCTGATGTGCCGCGGGACCTGGAAGTGGTTGCTGCCACCCCAGGCTGATCAGCTGGACGAAGTGACGGAAGTAGACAATATTACCGGCGATCACTTACGGCGAAACAGGAGGCAATAGCCCTGTCCAGGAGTTCACTGTGGCTGGTGGTGTTCGTACAGCTACCATCAGCGGCCTTAAACCTGGCGTTGATTATACCATCACTGTGTATGCTGACTGACTATTTTAACCGGACTACACATGAATAATACATATCTTAATTACCGCACAGAAATTGACAAACCATCCAGCACCATCACCACCACCAC |
| 413 | E86 | ATGGGAGTTTCTGATGTGCCGCGGGACCTGGTGCTGCCACCCCAGCCTGCTGATCAGCTGGGACGTCCGGTGAAACAATTACCGACAATATTACCGGCGATCACTTACGGCGAAACAGGAGGCAATAGCCCTGTCCAGGAGTTCACTGTGCCTGGTGGTGTTCGTACAGCTACCATCAGCGGCCTTAAACCTGGCGTTGATTATACCATCACTGTGTATGCTCACTGACTATTACAACCCGAAGACTCATGAATAATAAATCTTACTATTCCAATTTCCATTTAATTACGGCACAGAAATTGACAAACCATCCAGCACCATCACCACCACCAC |
| 414 | E87 | ATGGGAGTTTCTGATGTGCCGCGGGACCTGGAAGTGGTTGCTGCCACCCCAGCCTGCTGATCAGCTGGGGAGCCCCTTGACAATTACCAATATTACCGGCGATCACTTACGGCGAAACAGGAGGCAATAGCCCTGTCCAGGAGTTCACTGTGCCTGTGGTCTGTCTACGAGCTACCATCAGCGGCCTTAAACCTGGCGTTGATTATACCATCACTGTGTATGCTCACTGACTATTTCAACCGGCTACCATGAATAATACACATACCAATACAAATACTTTCAGAGTCCAATTTCCATTTAATTACGGCACAGAAATTGACAAACCATCCAGCACCATCACCACCACCAC |
| 415 | E88 | ATGGGAGTTTCTGATGTGCCGCGGGACCTGGAAGTGGTTGCTGCCACCCCAGCCTGCTGATCAGCTGGTCTGCAACAAACAAAACTTACCAATATTACCGGCGATCACTTACGGCGAAACAGGAGGCAATAGCCCTGTCCAGGAGTTCACTGTGCCTGGTGTGTTCGTACAGCTACCATCAGCGGCCTTAAACCTGGCGTTGATTATACCATCACTGTGTATGCTCACTGACTATTTTAACCGGACTACACATGAATAATACATATCAATACAAATATTACTATTCCAATTTCCATTTAATTACGGCACAGAAATTGACAAACCATCCAGCACCATCACCACCACCAC |
| 416 | E89 | ATGGGAGTTTCTGATGTGCCGCGGGACCTGGAAGTGGTTGCTGCCACCCCAGCCTGCTGATCAGCTGGGATAGCCAGCTGCAAAACGGACAATATTACCGGCGATCACTTACGGCGAAACAGGAGGCAATAGCCCTGTCCAGGAGTTCACTGTGCCTGTGGTATGCCACTGACTATTACAACCGGCTCGTACAGCTACCATCAGCGGCCTTAAACCTGGCGTTGATTATACCATCACTGTGTATGCTCACTGACTATTACAACCGGCTACCCATGTCAATACAAATACTTTCCAGAGTCCAATTTCCATTTAATTACGGCACAGAAATTGACAAACCATCCAGCACCATCACCACCACCAC |
| 417 | E90 | ATGGGAGTTTCTGATGTGCCGCGGGACCTGGAAGTGGTTGCTGCCACCCCAGCCTGCTGATCAGCTGGTACTGGGAGGGGCTGCCCCTACCACCGACACTTACGGCGAAACAGGAGGCAATAGCCCTGTCCAGGAGTTCACTGTGCCTGTGGTATGCCACTGACTATTACAACCGGCTCGTACCACTCCAGCACCATCACCACCCGACTTAACACCAGCTACCATCAGCGGCCTTAAACCTGGCGTTGATTATACCATCACTGTGTATGCTCACTGACTATTACAACCGGCTACCATGAGTATATATACCATTAATTACGGCACAGAAATTGACAAACCATCCAGCACCATCACCACCACCAC |

Figure 47N

| SEQ ID NO | BINDER | NUCLEOTIDE SEQUENCE |
|---|---|---|
| 418 | E91 | ATGGGAGTTTCTGATGTGCCGCGCGACCTGGAAGTGGTTGCTGCCGCCACCAGCCTGCTGCCACCCCCACCCCCAGCAGCCTGCTGATCAGTCAGCTGGAGCGTGCCGTGG CGGACCTACCAATATTACCGCCATCACTTACCGGCGAAACAGGAGGCAATAGCCCTGTCCAGGAGTTCACTGTGCCTTACGACGTT TACACAGCTACCATCAGCTGGGCGCCTTAAACCTGGCGTTGATTATACCATCACTGGTATGCTGCACTGACTAATTTAAACCCTAAC ACGCTTGAATACAACCTACCAGGGCATTCCAATTTCCATTAAATTGACAAACCATCCAGCACCATCACCAC |
| 419 | E92 | ATGGGAGTTTCTGATGTGCCGCGCGACCTGGAAGTGGTTGCTGCCGCCACCAGCCTGCTGATCAGTCAGCTGGCAGGTGGCCAAC CACTCGTACCAATATTACCGCCATCACTTACCGGCGAAACAGGAGGCAATAGCCCTGTCCAGGAGTTCACTGTGCCTGGTGGTGTT CGTACAGCTACCATCAGCTGGGCGTTGATTATACCATCACTGGTATGTGTCACTGACTTTTCAATCCTGGC ACTCATGAATACAAATACCGTACAAATTCCATTAATTACCGCACAGAAATTGACAAACCATCCAGCACCATCACCAC |
| 420 | E93 | ATGGGAGTTTCTGATGTGCCGCGCGACCTGGAAGTGGTTGCTGCCGCCACCAGCCTGCTGATCAGCCTGCTGATCAGCTGGGGATTCAGGACGA GGTTCCTATCAATATTACCGCCATCACTTACCGGCGAAACAGGAGGCAATAGCCCGTCCAGGAGTTCACTGTGCCTGGTGGTGTT GGTACAGCTACCATCAGCTGGGCGTTGATTATACCATCACTGTGTATGCTGTCACTGACTGTGTCACTGATAAACCGCACGCT GACGGTCCGCACACTTACCATGAATATCCAATTTCCATTAATTACCGCACAGAAATTGACAAACCATCCAGCACCATCACCAC |
| 421 | E94 | ATGGGAGTTTCTGATGTGCCGCGCGACCTGGAAGTGGTTGCTGCCGCCACCAGCCTGCTGATCAGCCTGATGATCAGCTGGAATAACGGAGGA CGCAATTAGCCAATATTACCGCCATCACTTACCGGCGAAACAGGAGGCAATAGCCCGTCCAGGAGTTCACTGTGCCTTACGACGTT TACACAGCTACCATCAGCTGGGCGTTGATTATACCATCACTGTGTATGCTGTCACTGACTATAAACCGCACGCT GACGGTCCGCACACTTACCATGAATATCCAATTTCCATTAATTACCGCACAGAAATTGACAAACCATCCAGCACCATCACCAC |
| 422 | E95 | ATGGGAGTTTCTGATGTGCCGCGCGACCTGGAAGTGGTTGCTGCCGCCACCAGCCTGCTGATCAGCCTGGATCAGCTGGGGTCGTGCCGCAG GGGAGGTACCAATATTACCGCCATCACTTACCGGCGAAACAGGAGGCAATAGCCCTGTCCAGGAGTTCACTGTGCCCTGGTGGTGTT TCTACAGCTACCATCAGCTGGGCGTTGATTATACCATCACTGTGTATGCGTGCACTGACTATTCAACCGGCA ACCCATGAATACAATACCGAATTATCATTTACAACTCCAATTTCCATTAATTACCGCACAGAAATTGACAAACCATCCAGCACCATCACCAC |
| 423 | E96 | ATGGGAGTTTCTGATGTGCCGCGCGACCTGGAAGTGGTTGCTGCCGCCACCAGCCTGCTGATCAGCCTGATCAGCTGGGGCGAGCAACCGG GGGACGTACCAATATTACCGCCATCACTTACCGGCGAAACAGGAGGCAATAGCCCTGTCCAGGAGTTCACTGTGCCTGGTGGTGTT TCTACAGCTACCAATATTTACCGCCATCACTTACCGGCGAAACAGGAGGCAATAGCCCTGTCCAGGAGTTCACTGTGCCTGGTGGTGTT ACTCATGAATACAATACCGCATACTTACCATGAATCTCCAATTTCCATTAATTACCGCACAGAAATTGACAAACCATCCAGCACCATCACCAC |
| 424 | E97 | ATGGGAGTTTCTGATGTGCCGCGCGACCTGGAAGTGGTTGCTGCCGCCACCAGCCTGCTGATCAGCCTGGTTGCCGGCAAG CTGAGGTACCAATATTACCGCCATCACTTACCGGCGAAACAGGAGGCAATAGCCCTGTCCAGGAGTTCACTGTGCCTCATGACCTG CGTACAGCTACCATCAGCGGCCTTAAACCTGGCGTTGATTATACCATCACTGTGTATGCTGTCACTGACTATAAACCGCATGCT GACGGTCCGCATACTTACCATGAATCTCCAATTTCCATTAATTACCGCACAGAAATTGACAAACCATCCAGCACCATCACCAC |

Figure 47O

| SEQ ID NO | BINDER | NUCLEOTIDE SEQUENCE |
|---|---|---|
| 425 | E98 | ATGGGAGTTTCTGATGTGCCGCGACCTGGAAGTGGTTGCTGCCACCCCACCAGCCTGCTGATCAGCTGGACGCTGGTCCAACC TCCGCTACAGTACCAATATTACCGCATCACTTACGGCGAAACAGGAGGCAATAGCCCTGTCCAAGGAGTTCACTGTGCCTGGTGTT CGTACAGCTACCATCAGCGGGCTGGCGTTGTTAAACCTGGTAAGCTGTCACTGACCATAAACCGCATGCT GACGGTCCGCATACTTACCATGAAATACCCGCAATTTCCATTAATTACCGCACAGAAATTGACAAACCATCCAGCACCATCACCAC CACCAC |
| 426 | E99 | ATGGGAGTTTCTGATGTGCCGCGACCTGGAAGTGGTTGCTGCCACCCCACCAGCCTGCTGATCAGCTGGGACGCTCCAACC TCCCGCTACAGTACCAATATTACCGCATCACTTACGGGCGAAACAGGAGGCAATAGCCCTGTCCAAGGAGTTCACTGTGCCTGGTGTT CGTACAGCTACCATCAGCGGGCTTGTTATACCTGGTGTGTCACTGACTATGCTGACCATAAACCGCACGCT GACGGTCCGCACACTTACCATGAAATACCCAGCAATTTCCATTAATTACCGCACAGAAATTGACAAACCATCCAGCACCATCACCAC CACCAC |
| 427 | E100 | ATGGGAGTTTCTGATGTCCGCGACCTGGAAGTGGTTGCTGCCACCCCACCAGCCTGCTGATCAGCTGGACCTGGACCCTGCTAAT AAATCTTACCAGCTACCATCAGCGGCTGGCGTTGTTAAACCTGGTAAGCTGTCCAAGGAGTTCACTGTGCCTCATGACCTG GTTACAGCTACCATCAGCGGCTGGCGTTGTTATACCTGGTGTATGCTGACCATAAACCGCATGCT GACGGTCCGCATACTTACCATGAATACCCGCAATTTCCATTAATTACCGCACAGAAATTGACAAACCATCCAGCACCATCACCAC CACCAC |
| 428 | E101 | ATGGGAGTTTCTGATGTGCCGCGACCTGGAAGTGGTTGCTGCCACCCCACCAGCCTGCTGATCAGCTGGGACGCTCCGGCT GTTACTTACCAGCTATTACCATCAGCGGCTGGCGTCGTCCAAGGAGTTCACTGTGCCTCATGACCTG GTTACAGCTACCATCAGCGGCTGGCGTTGTTATACCTGGTGTATGCTGACTATAAACCGCATGCT GACGGTCCGCATACTTACCATGAATACCCCAATTTCCATTAATTACCGCACAGAAATTGACAAACCATCCAGCACCATCACCAC CACCAC |
| 429 | E102 | ATGGGAGTTTCTGAGTGCCGCGACCTGGAAGTGGTTGCTGCCACCCCACCAGCCTGCTGATCAGCTGGACCTGCTAAT AAATCTTACCAGCTACCATCAGCGGCTGGCGTTGTTAAACCTGGTAAGCTGTCCAAGGAGTTCACTGTGCCTCATGACCTG GTTACAGCTACCATCAGCGGCTGGCGTTGTTATACCTGGTGTATGCTGACCATAAACCGCATGCT GACGGTCCGCATACTTACCATGAATACCCGCAATTTCCATTAATTACCGCACAGAAATTGACAAACCATCCAGCACCATCACCAC CACCAC |
| 430 | E103 | ATGGGAGTTTCTGATGTGCCGCGACCTGGAAGTGGTTGCTGCCACCCCACCAGCCTGCTGATCAGCTGGACCCTGCTAAT AAATCTTACCAGCTACCATCAGCGGCTGGCGTTGTTAAACCTGGTAAGCTGTCCAAGGAGTTCACTGTGCCTCGGTGTGTT CGTACAGCTACCATCAGCGGCTTGTTATACCTGGTGTATGCTGACCATGATGCAGTTGAA TACTCCTGAATACCCAATTTCCATTAATTACCCAGCAAAACCATCCAGCACCATCACCACCAC |
| 431 | E104 | ATGGGAGTTTCTGATGTGCCGCGACCTGGAAGTGGTTGCTGCCACCCCACCAGCCTGCTGATCAGCTGGGAGACGCTGGTGCT GTTACTTACCAGCTACCATCAGCGGCTGGCGTTGTTAAACCTGGTAAGCTGTCCAAGGAGTTCACTGTGCCTCATGACCTG GTTACAGCTACCATCAGCGGCTGGCGTTATACCTGGTGTATGCTGACCATTAACCGCATGCT GACGGTCCGCATACTTACCATGAATACCCGCAATTTCCATTAATTACCGCACAGAAATTGACAAACCATCCAGCACCATCACCAC CACCAC |

Figure 47P

| SEQ ID NO | BINDER | NUCLEOTIDE SEQUENCE |
|---|---|---|
| 432 | E105 | ATGGGAGTTTCTGATGTGCCGCGCGACCTGGAAGTGGTTGCTGCCACCCCACCAGCCTGCTGATCAGCTGGAGACGCTCCAACC TCCCGCTACCAGTATTACCGCATCACTTACGGCGAACCAGGAGGCAATAGCCCTGTCCAGGAGTTCACTGTGCCTGGTGGTCTG TCCACAGCTACCATCAGCGGCCTGGCCTTAAACCTGGAATTCCAATGAATTGACTGCTCACTGACTATAAACCGCATGCT GACGGTCCGCATACTTACCATTAATTACCGCACAGAAATTGACAAACCATCCAGCACCATCACCAC CACCAC |
| 433 | E106 | ATGGGAGTTTCTGATGTGCCGCGCGACCTGGAAGTGGTTGCTGCCACCCCACCAGCCTGCTGATCAGCTGGAGACGCTCCGGCT GTTACTTACCAGTATTACCGCATCACTTACGGCGAACAGGAGGCAATAGCCCTGTCCAGGAGTCACTGTGCCTTACGACGTT TACACAGCTACCATCAGCGGCCTTAAACCTGGCTTGATTATCCACTGACTGTCACTGACTATAAACCGCATGCT GACGGTCCGCACACTTACCATTAATTACCGCACAGAAATTGACAAACCATCCAGCACCATCACCAC CACCAC |
| 434 | E107 | ATGGGAGTTTCTGATGTGCCGGACCTGGAAGTGGTTGCTGCCACCCCACCAGCCTGCTGATCAGCTGGATTCAGGACGA GGTTCCTATCCAGTATTACCGCATCACTTACGGCGAAACAGGAGGCAATAGCCCTGTCCAGGAGTTCACTGTGCCTTACGACGTT TACACAGCTACCATCAGCGGCCCTTAAACCTGGCTTGATTATACCGCACTGTCTGCACTGACTGTCACTGACTGAA TACACTGAACATTACCAATTTCCAATTAATTACCGCACAGAAATTGACAAACCATCCAGCACCATCACCAC |
| 435 | E108 | ATGGGAGTTTCTGATGGCCGCGCGACCTGGAAGTGGTTGCTGCCACCCCACCAGCCTGCTGATCAGCTGGGAGCGCTCCGGCT GTTACTTACCAGTATTACCGCATCACTTACGGCGAAACAGGAGGCAATAGCCCTGTCCAGGAGTTCACTGTGCCTGGTGTT CGTACAGCTACCATCAGCGGCCTTAAACCTGGCTTGATTATACCACTGACTGTCTGCACTGTGACTATAAACCGCATGCT GACGGTCCGCATACTTACCATTAATTACCGCACAGAAATTGACAAACCATCCAGCACCATCACCAC CACCAC |
| 436 | E109 | ATGGGAGTTTCTGATGTGCCGCGCGACCTGGAAGTGGTTGCTGCCACCCCACCAGCCTGCTGATCAGCTGGAGACGCTCCAACC TCCCGCTACCAGTATTACCGCATCACTTACGGCGAAACAGGAGGCAATAGCCCTGTCCAGGAGTTCACTGTCCCATGACCTG GTTACAGCTACCATCAGCGGCCTTAAACCTGGCTTGATTATACCACTGTGTCACTGTCACTGACTATAAACCGCATGCT GACGGTCCGCATACTTACCATTAATTACCGCACAGAAATTGACAAACCATCCAGCACCATCACCAC CACCAC |
| 437 | E110 | ATGGGAGTTTCTGATGTGCCGCGCGACCTGGAAGTGGTTGCTGCCACCCCACCAGCCTGCTGATCAGCTGGAGACGCTGGTGCT GTTACTTACCAGTATTACCGCATCACTTACGGCGAAACAGGAGGCAATAGCCCTGTCCAGGAGTTCACTGTGCCTGGTGGTGTT CGTACAGCTACCATCAGCGGCCTTAAACCTGGCTTGATTATACCACTGACTGTCACTGACTATAAACCGCATGCT GACGGTCCGCATACTTACCATTAATTACCGCACAGAAATTGACAAACCATCCAGCACCATCACCAC CACCAC |
| 438 | E111 | ATGGGAGTTTCTGATGTGGCCGCGCGACCTGGAAGTGGTTGCTGCCACCCCACCAGCCTGCTGATCAGCTGGGACGCTCCAACC TCCCGCTACCAGTATTACCGCATCACTTACGGCGAAACAGGAGGCAATAGCCCTGTCCAGGAGTTCACTGTCCCTGATGACCTG GTTACAGCTACCATCAGCGGCCTTAAACCTGGCTTGATTATACCACTGACTGTCTGTATGCTGCACTAACATGATGCATGTTGAA TACTCTGAATACCCAATTTCCAATTAATTACCGCACAGAAATTGACAAACCATCCAGCACCATCACCAC |

Figure 47Q

| SEQ ID NO | BINDER | NUCLEOTIDE SEQUENCE |
|---|---|---|
| 439 | E1.12 | ATGGGAGTTTCTGATGTGCCGGCGGACCTGGAAGTGGTTGCTGCCACCAGCCTGCTGATCAGTGGACGCTGGTGCTGTTACTTACCAGTAATTACCGGTATTACCGGAAACAGGAGGCAATAGCCCTGTCCAGGAGTTCACTGTGCCTGGTGGTGTTCGTACAGCTACCATCAGGGCCTTAAACCTGGCCGTTGATTATACCATCACTGTCTATGCTGTCACTGACTATAAACCGCACGCTGACGGTCCGCACACTTACGCACTGATAATTCCAATTAATTACCGGACAGAAATTGACAAACATCCAGCACCATCACCACCACCAC |
| 440 | E1.13 | ATGGGAGTTTCTGATGTGCCGGCGGACCTGGAAGTGGTTGCTGCCACCAGCCTGCTGATCAGTGGTATCCTGGCCAACCTACATATCAATATCAATACGGCGAAACAGGAGGCAATAGCCCTGTCCAGGAGTTCATTGTGCCTTACCTGGTTTACACAGCTACCATCAGGGCCGTTGATTATACCATCACTGTGTATGCGTCACTGACTACGCTTACAAAGAATACTCTGAATACCCAATTTCCATTAATTACCGGACAGAAATTGACAAACATCCAGCACCATCACCACCAC |
| 441 | E1.14 | ATGGGAGTTTCTGATGTGCCGGCGGACCTGGAAGTGGTTGCTGCCACCAGCCTGCTGATCAGTGGCAAAGTTCAAGCAGCCAATATCAATATCAATACGGCGAAACAGGAGGCAATAGCCCTGTCCAGGAGTTCACTGTGCCTGGTGGTGTTCGTACAGCTACCATCAGCGGCTGGCCTTAAACCTGGCGTTGATTATACCATCACTGTGTATGCTGTCACTGACTATAAACCGCATGCTGACGGTCCGCACATACTTACCATGAATTCTCCAATTTCCATTAATTACCGCACAGAAATTGACAAACCATCCCAGCACCATCACCACCAC |

Figure 48A

| SEQ ID NO | Binder | DNA SEQ |
|---|---|---|
| 442 | E3-GS10-I1 | ATGGGAGTTTCTGAATGTGCGGCGGACCTGGAAGTGGTTGCTGCCACCCCACCAGCCTGCTGATCAGCCTGGTTGCCGGGCAAG CTGAGGTACCAACAATATTACCGGCCATCCGCAGGGCCGAAACAGGAGGCAATAGCCCTGTCCAGGAGTTCACTGTGCCTCATG CGTACAGCTACAGCCATCAGCGGCCTTAAAACCTGGCGGTTGATTATACCATCACTGGAGTGTGATGTAACATGATGCAGTTGAA TACTCTGAATCTGGCAGCCAATTTCCATTAATTACCGGTTCTCGGTTCCGTTTCTGAGTGCCGATATTACCAGCCGCGGTGAGC GGCTCTGGCGCAGCCTGCTCGGGTCTGAAAGTTTACACAGCTACCATCAGCGGCCCTTAAAACCTGGCGCTTGATTATACCATG ACTGTGGCGCTAAAAACCTTTACACAGCTACCATCAGCGGCCCTTAAAACCTGGCGGTTGATTATACCATCACTGTGTATGCCATTG AGGTTCCGGACTACTCTGAATACTCTGAATACTGCCAATTTCCATTAATTACCGCACAGAAATTGACAAACCCAGCACCACCAC |
| 443 | I1-GS10-E3 | ATGGGAGTTTCTGAATGTGCCGCGGACCTGGAAGTGGTTGCTGCCACCCCACCAGCCTGCTGATCAGCCTGGTCGGGCGTCTG AAAGTTGCCGCGATACCAGCCGGCCATCCGCAGGGCCGAAACAGGAGCAATAGCCCTGTCCAGGAGTTCACTGTGCCTAAAACGTT TACACAGCTACCATCAGCGGCCCTTAAAACCTGGCGCTTGATTATACCATCACTGTGTATGCTCCGGACTACTCCGGACCAGCG CCAATTACCATTAATTACCGGTTCTCGGTTCCGTTTCTGCTGCCAGCGGCTGATGGCTGCAGGAGTTCATCGTCAGTCGCCGAGC GGCTCTGGCGCAGCCTGCTCGGGTCTGATGTGCCGAAAACAGGAGCAATAGCCCTGTCCAGGAGTTCCGCAGGAGTTCCACCGCAT GACCTGCCTACCCACGCTACCATCAGCGGCCCTTAAACCTTGAATTACCGCACAGAAATTGACAAACCAGCCAGCACCACCAC GTTGAATATCTGAATACTCTGAATACTGCCAATTTCCATTAATTACCGCACAGAAATTGACAAACCAGCCAGCACCACCAC |
| 444 | E1-GS10-I1 | ATGGGAGTTTCTGAATGCGCCGGCGACCTGGAAGTGGTTGCTGCCACCCCACCAGCCTGCTGATCAGCCTGGGTGCGGGGCG GAGGACTACCAACAATATTACCGGCCATCACTTACCGGAAAAGCGAAACAGGAGGCAATAGCCCTGTGCCAGGAGTTCACTGTGCCCTCAGAGACCTG GTTACAGCTACAGCACTCAGCAGCGCGGTTGATTATACCCATCGTGTATGCTCCGGCTATGCTGCACCTGCGATGTTGAA TACACTGAACATGAACATCCAATTTACCGGAAATTGACGACAAAAGCTAGCGGCTCTGGTTCCGCCAGCGGCTCCGGCTCCGATC GGCTCTGGCGCAGCGGGTTCGGTTCTGAATGTGCCGGCGACATCACTTACGGCGGTTGATTATACCATCACTGGTATGCCAAGG ACTGTGCCTCCGGGCCTCTAAAAACGTTTACACAGCTACCATCAGCGGCCCTTAAACCTGAATATCCTGAATACTGCCAGCACCGCCAC AGGTTCCGGACTACTCTGAATACTCTGCCAATTTCCATTAATTACCGGAGAAATTGACAAACCAGCACCACCAC |

Figure 48B

| SEQ ID NO | Binder | DNA SEQ |
|---|---|---|
| 445 | I1-GS10-E1 | ATGGGAGTTCTGATGTGCGCGCGACCTGGAAGTGGTTGCTGCCACCCCACCAGCCTGCTGATCAGCTGGTCTGCGCGTCTG AAAGTTGCGCGGATATTACCAGCGGCCTTAAACCTGACTTACGGCGAAACAGGAGGCAATAGCCTGTCCAGGAGTTCACTGTGCCTAAAAACGTT TACACAGCTACCATTAATTACCGGCACAGAATTGACAGAAGTAGCGGCTGTCACTAGGTTCCGCGACTACCAG CCAATTCCATTAATTACCGGCACAGAATTGACAGAAGTAGCGGCTCTGGTTCCGCAGCGGCTCTGGCAGC GGTTCTCGTTCCGTTCCTGATGTGCCGCGCACCAGCTGCTGATCAGCTGTGATCAGCTGGGTGGCC GGGCGGAGGACTACCAATATTACCGCGATCATAGCGGCGAAACAGGAGGCAATAGCCCTGTGTATGCGTCACTGTGCCTCAT GACCTGGTTACAGCTACCATTACGCCTTAAACCTGACTTACGGCGATATATGTGTCACTGACATGATGCAT GTTGAATACACTGAACATCCAATTTCCATTAATTACCGCACAGAAATTGACAGAACCAGCCACCACCACCAC |
| 446 | E2-GS10-I1 | ATGGGAGTTTCTGATGTGCGCGCGACCTGGAAGTGGTTGCTGCCACCCCCACCAGCCTGCTGATCAGCTGGATCAGGACGA GGTTCCTATCAATATTACCGCCATCACATCAGGGGCGAAACAGGAGGCAATAGCCCTGTCCAGGAGTTCACTGCTGTCCGGTT CATACAGCTACCATCAGCGGCCTTAAACCGGTTCATTAAACCTGACTATTACCGGCGAGAAAACCGGGAGCT GACGGTCCGCATTACCATTACCGGCAGCGGCTCTGGCAGCTGGTTCCGCAGCGGCTCTGGTTGCTGAGCAGCTAGC AGGGCTCCGCAGCCTGCTGATCAGCTGGTCTGCGCGTTCGCGATATTACCGGCGAAACAGGAGGCAATAGC ACCAGCCTGTCCAGGAGTTCACTGTGCCGCGATCAGCGGCCTTAAACCTGGCGATCACTACGGCGAAACAGGAGGCAATAGC CCTGTCCAGGAGTTCACTGTGCCTAAAAACGTTTACACAGCTACCATTACCGGCGTTGATTATATACCAATGACT GTGTATGCGTCTCACTGAGGTCCGCATTACCATTACCGCCAATTCCATTAATTACCGCACAGAAAATTGACAGAACCAGCCAC CACCACCACCAC |
| 447 | I1-GS10-E2 | ATGGGAGTTTCTGATGTGCGCGCGACCTGGAAGTGGTTGCTGCCACCCCACCAGCCTGCTGATCAGCTGGTCTGCGCGTCTG AAAGTTGCGCGGATATTACCAGCGGCCTTAAACCTGACTTACGGCGAAACAGGAGGCAATAGCCCTGTGCCTAAAAACGTT TACACAGCTACCATTACCGGCAGCGGCTCTGGCGTTGATTATACCAATGACTGTGTATGCGTCACTGAGGTTCCGCGACTACCAG CCAATTCCATTAATTACCGCACAGAATTGACAGAAGTAGCGCGGCTCTGGTTCCGCAGCGGCTCTGGCAGC GGTTCTCGGTTCCGTTCCTGATGTGCCGCGCACCAGCTGCTGATCAGCTGTGATCAGCTGGGATTCA GGACGAGGTTCCTATCAATATTACCGGCGATCATCAGCGGCGTTGATTATACCATCACTGTGTATGCGTCACTGACCATAAACCG CCGGTTCATACAGCTACCGTCCGCATTACCATTACCGCCAATTCCATTAATTACCGGACAGAAATTGACAGAACCAGCCAC CATGCGTACCATCTGCGATACTTACCATGAACTCCGCATTACCGGCAATTCCATTAATTACCGACAGAAATTGACAAACCAGCCACCAC CACCACCACCAC |
| 448 | E5-GS10-I1 | ATGGGTGTTTCTGATGTTCCGGTGAATCTGGAAGTTGTGCAGCAACCCCGACCAACCTGCTGATTCTGTTGGTGTGGGCACCGGTT GATCGTTATCGTAATTATCGGCATCACCTATGGGTGAGAAGCCCGGTAATCTCCGGTTAATTCCCTCCGGACGTT TATCCGCAACCATTAGGGTCTGAAACCGGGTGTTGATTACACCATTAACACCGGAACCGGTTAACACCGATGCA GATGGTCCGCCATATCCAGTTCCGGTTCATGAAACTGCGCGTCCGGTAGCGGCGCAGCGGTAGCGGTTTCAGGT AGCGGATCAGGATTCGTCTGGTAGCTGGTCTGCACGTCTGAAAAATGTGTACACGCCATCAGGCCAGCCAGCCGTGGCAGCCACCG ACTTCTCTGCGCAAGAATTTACCGGTGATTAGCTGGTCTGAAAAATGTGTACACGCCATCAGCCTAT TATGCGAAACCGGCCTGCGTTATTCTCTGGCCTTATTTACCGGTGATTAGCTGAAAACCTGCCGGTGACCGCGACTACACCAT GTTTATTGGCAGTGACCGTTTTGATGATTTGTGATTCAGCCGATCAGCATTCAATAGCCTGGACATCAGGCCCAT CACCATCATCAC |

Figure 48C

| SEQ ID NO | Binder | DNA SEQ |
|---|---|---|
| 449 | E85-GS10-I1 | ATGGGTGTTTCTGATGTTCCGGTGATTCAGTACCTATGGTGCAGCAACCCGACCAGCCTGCTGATTTCTTGGACCAGGGTAGC ACACATTATCAGTATTATCGCATATCCGTTCTGTGAGGTTGTTGCAGCAACCCGACCAGCCTGCTGATTTCTTGGACCAGGGTAGC TATACCGCAACCATTAGCGGTCTGAAACCGGGTGTTGATTACACCATTACCGCACCGAATATCGCATGCGTTCCCGATCCGTCC ACCCATGAATGATCAGGTTCTGGTTCTGCACGTTGGTGCACGTCTGAAAGTTGCCCGTTATTACTTATGCCGAACCTGGCGTTCAGGT AGCGGATCAGGTTCTGGTTCTGCACGTTGGTGCACGTCTGAAAGTTGTACACAGCCTGAAACCTGGCGTGGACTACACAATCACA ACTTCTCTGCTCAAGAATTTACCGTGCCAAGAATGTTCAGCCGATCAGCAGCCATCAATTATGCCGATTATCCGAACCTGGCGTAAACCGTAAACAATCACA GTTTATGCAGTGACCGTTTTCGTTGATTATCAGCCGATCAGCAGCCATCAATTATGTACAGAGATCGATAAACCGTGCCAGCATCAC CACCATCATCAC |
| 450 | E4-GS10-I1 | ATGGGTGTTTCTGATGTTCCGCGTGATCTGGAGGTTGTTGCAGCAACCCGACCAGCCTGCTGATTTCTGGCATGAACGTGAT GGTAGCCGTCAGTATTATCGCATCACCTATGGTGCAGCAACCCGGTAATTCCCGGTTCAAGGAATTTACCGTTCCGGCGGGTGTT CGTACCGCAACCATTAGCGGTCTGAAACCGGGTGTTGATTACACCATTACCGCACCGAATATCGCATGCGAAATTCAATCCGACC AGCGGATCAGGTTCTGGTTCTGCGATTAGCGGTCAGCGTCTGAAGTGCCCTGCGACGTGCCTCGTTATTACCGGTAGCACGCACACG ACTTCTCTGCTCAAGAATTACCGTGTCCGAAAATGTGTACACAGCCTGAAAGTTCTGGCTGAAACCGTGCCAGCCACTACACAATCACA GTTTATGCAGTGACCGTTTTCGTTGATTATCAGCCGATCAGCAGCCATCAATTATCGTACAGAGATCGATAAACCGTGCCAGCATCAC CACCATCATCAC |
| 451 | E90-GS10-I1 | ATGGGTGTTTCTGATGTTCCGCGTGATCTGGAGGTTGTTGCAGCAACCCGACCAGCCTGCTGATTCTGCTGTATTGGGAAGGT CTGCCGTATCAGTATTATCAGGCATCACCTATGGTGCAGCAACCCGGTAATTCTCCGGTTCAAGGAATTCACCGTTCTCGCGACTTT AATACCGCAACCATTAGCGGTCTGAAACCGGGTGTTGATTACACCATTACCGCACCGTTTTACCGCGATTGGTGTACAACCCTGAT ACCCATGAATGATCAGGTTTATCATACCGGTTCTGGTTCTGCGACGTGCCAGCGTCTGAAAGTGCCTCGTATACCGGATAAGGTAGCGGTTGCAGCCACACCG ACTTCTCTGCTGCAAGAATTACCGTGTCGGTGCCGAAAATGTGTACACAGCCATCTCGGCCGTTATTACCTTATGGGCAGAACAGGCGGAAAATAGC CCTGTGCAAGAATTACCGTGTCCGCCAAAAATGTCTGCCGAAAATGTGGACCGACTACACACAATCACA GTTTATGCAGTGACCGTTTTCGTTGATTATCAGCCGATCAGCAGCCATCAATTATCGTACAGAGATCGATAAACCGTGCCAGCATCAC CACCATCATCAC |
| 452 | E96-GS10-I1 | ATGGGTGTTTCTGATGTTCCGCGTGATCTGGAGGTTGTTGCAGCAACCCGACCAGCCTGCTGATTCTTGGCAAGCAACGT GGCACCTATCAGTATTATCCGCATCACCTATGGTGCAGCAACCCGGTAATTCCGGTTCAAGGAATTTACCGTTCCTGGGTGTT TCTAACCGCAACCATTAGCGGTCTGAAACCGGGTGTTGATTACACCATTACCGCACCGTTTACCGCGATGCATTAATCCGACC ACCCATGAATGATCAGGTTCTGGTTCTGCGATTAATCCGATTAGCGGGTCAGCGGTCAGCGTCTGAAAGTTGCCTCGTATAAGGTAGCGGTAGCCGTTCAGGT AGCGGATCAGGTTCTGGTTCTGCGATTAGCGGTCAGCGTCTGAAAGTTGCCTCGACGTGCCTGGAAGTGTGGCAGCCACACCG ACTTCTCTGCTCAAGAATTACCGTGTCGGTGCCGAAAATGTGGCCGTTATTACCTTATGGCGAAACAGGCGGAAATAGC CCTGTGCAAGAATTACCGTGCCGTGCCGAAAATGTGGACCGATCAGCAGCCACTACACAATCACA GTTTATGCAGTGACCGTTTCGTTGATTATCAGCCGATCAGCAGCATCAATTATCGTACAGAGATCGATAAACCGTGCCAGCATCAC CACCATCATCAC |

Figure 48D

| SEQ ID NO | Binder | DNA SEQ |
|---|---|---|
| 453 | E105-GS10-I1 | ATGGGGTGTTTCTGATGTTCCGGTGATCTGAGGTTGTTGCAGCAACCCGACCAGCCTGCTGATTCTTGGGATGCACCGACCTCTCGTTAATCAGTATTATCGCATCACCTATGGTGAGGTGAAACCGGTAATTCTCCGGTTACCGTTCCTGGCGGTCTGAGCAGCCGCAACCATTAGCGGTCTGAAACCGGTTGATTACAACCATTACCGTTCCGGATTACCGCACCGGTTCAGATGAAGGTCCGCATACCTACCGTTCTGGTTCATGAAGCCCGAAATTGATAAAGTAGCGGTGGTTCAGGTAGCGGATCAGTTCCGGTTCTGCGTAGTGGTGCACGTCTGAAAATTTGTACACAGCCGGTTATTACCGTTATTACTATGCGAAACAGGCGGAAATAGCACTTCTCTGCTGATTAGCTCGGATTTACCGTGCCGGAAGAATTTACCGCTATTATGGCTGAAAGGCGGACTACACAATCACACCTGTGCAAGAATTACCGTGCCGGAAAAATGTACACAGCCGATCAGCCGTGAAACCTGGCGTGATAAACCGTGCCAGCATCACAGTTTATGCAGTGCAGTTCCGGGTTCGTGATTATCAGCCGATTATCGTACACAGATGATCAGAATCGATAAACCGTGCCAGCATCACCACCATCATCAC |
| 454 | E112-GS10-I1 | ATGGGTGTTTCTGATGTTCCGGTGATCTGAGGTTGTTGCAGCAACCCGACCAGCCTGCTGATTTCTGGGATGCAGGTGCAGTTACCTATCAGTATTATCGCATCACCTATGGTGAAACCGGTAATTCTCCGGTTACCGTTCCTGGCGGTCTGAGCCGTTTACCGTTCTGAAACCGGTGTCTGAAACCGGTTATTACACCATTACCGCACCGGTTCAGATGAAGGTCCGCATACCTACCGTTCTGGTTCATGAAGCCCGAAATTGATAAAGTAGCGGTGGTTCAGGTAGCGGATCAGGTTCCGGTTCTGCGTAGTGGTGCACGTCTGGAAAATGTACACAGCCGGTTATTACCGTTATTACTATGCGAAACAGGCGGAAATAGCACTTCTCTGCTGATTAGCTCGGATTTACCGTTCCGGAAGAATTTACCGCTATTATGGCCGTGAAGGTTGTACACAGCCGGTTATTACCGTTATTACCATCTCTGGCCGATCAGCCGTGAAACCTGGCGTGATAAACCGTGCCAGCATCACGTTTATGCAGTGCAGTTCCGGGTTCGTGATTATCAGCCGATTATCGTACACAGATGATCAGCCGTGAAACCTGGCGTGATAAACCGTGCCAGCATCACCACCATCATCAC |
| 455 | I1-GS10-E5 | ATGGGTGTTTCTGATGTTCCGCGTGATCTGCTGATTGCGCTGATTAGCCTGATTAGCGAAAATGTTAAAGTTGCCGGTTATTACCGTTAATTACACCATTAGCGGTTACACCGTTCCGGGTAATTCTCCGGTTACCGTTCAGTTATGCAGTTATCAGTATACCGGAACCCATTAACGTTGATAAAGTAGAAGTCGGTTCGGTGAGCGGTTCAGTGCGGTTCACTGCTGATTCTGGTTCTCGGTGAGTCCGATTAGCGGCAGCGTGCCTGCTGCAGCGGAAAACGGCGAAATAGCACCATGCGCCGGCTGATCGGCAAAATTCCCGGTTATACCGGGCCGCACATCAGGTTTAAACCAAACCTGGGTGGACATATGGCCGTGAAGTTATGCCGTGACCGAATTATAAACCGCATGTGTATACCCAGATGGGGTCGCAGATATTCATCAGAAAGCCCGGATCTCTATCATCATAATATGGCCGCACCGTCTATCAATTATCGCACAGCCGAATTATCGATCACCATCATCAC |
| 456 | I1-GS10-E85 | ATGGGTGTTTCTGATGTTCCGCGTGATCTGCTGATTGCGCTGATTAGCCTGATTAGCGAAAATGTTAAAGTTGCCGGTTATTACCGTTAATTACACCATTAGCGGTCTGAAAACCGGTTATTACCGGTTATTACCGTTCAGTTATGCAGTTATCAGTGAAAGTGGCCTGCCAGCTCTGGTAGCGGTTCAGTTACCGTGCGGTTCAGATAGCGGTTCAGATAGCGGTTCAGATTCTGGTAGCGGTTCAGATAGCGGTTCAGATAGCGGAAATAGCCGCTGGTGCAGATAACCTGTGCAAGAATAGCCCGGTTATGCCGTGAACCAGTTACCCACCATCACAGAATTGGCAAAATCACGAGGGTATACCGGCACATTAGCGGCTACTACCAATCACTATCGAATACCCAGAATCGATCCTATCAATTATCGATCAACAGATTCTATCAATTATCGATCAGCACGTGTCAGCATCACCACCATCATCAC |

Figure 48E

| SEQ ID NO | Binder | DNA SEQ |
|---|---|---|
| 457 | I1-GS10-E4 | ATGGGTGTTTCTGATGTTCCGGTGATCTGGAAGTTGTTGCAGCAACCCGACCAGCCTGCTGATTAGCTGGTCTGCACGGTCTG AAAGTTGCCCGTTATTATCGCATTAGCCGGTGTCTGAAACCGGGTGTTGATTACAGCGGTGAAACCGGTAATTCCGTTCCGAAAAATGTT TATACGCAACCATTAACTAGCGGTCTGAAACCGGGTGTTGATTACAGCGGTGAAACCGGTTTATGCAGTTACCCGTTTCGTGATTATCAG CCGATTAGCCATTAACTATCGCGAGCGTTTCAGACGTTCAGTATTATCGCATCAGTATTTCGGTTAGAAGTAGCGGTCGGTTCTGGTAGT GGTAGCGGCAGCCGTTTCAGACGTTTCAGTATTATCGCATCAGTATTTCGGTTAGAAGTAGCGGTCGGTTCTGGTCTGATTCTGGCATGCA CGTGATGTAGCCCGCTGACAGGTATTATCGGCAGACAGCGGGAAATAGCCCTGCTGCAAGAATTCACCGTACCGGT GGTGTTCGTACCGCCACCGAATATATTTATCAGACCCGATCTCTATCAATTATCGCACAGAGATCGATAAACCGTGTCAGCATCAC CCGACCACCCGAGAATATATTTATCAGACCCGATCTCTATCAATTATCGCACAGAGATCGATAAACCGTGTCAGCATCAC CACCATCATCAC |
| 458 | I1-GS10-E105 | ATGGGTGTTTCTGATGTTCCGGTGATCTGGAAGTTGTTGCAGCAACCCGACCAGCCTGCTGATTAGCTGGTCTGCACGTCTG AAAGTTGCCCGTTATTATCGCCATTAGCCGGTGTCTGAAACCGGGTGTTGATTACAGCGGTGAAACCGGTAATTCCGTTCCGAAAAATGTT TATACGCAACCATTAACTAGCGGTCTGAAACCGGGTGTTGATTACAGCGGTGAAACCGGTTTATGCAGTTACCCGTTTCGTGATTATCAG CCGATTAGCAATTAGCGATAACGCGAAATTGATAAAGTAGCGGTCGGTTCTGGTAGT GGTAGCGGCAGCCGTTTATCAGACGTTATTATCGCATCAGTATTATCGCATCAGTATTTCGGTTAGAAGTAGCGGTCGGTTCTGGTCTGATGCA CCGACCAGCCGTTATCAGCGCCACACAATAGCCCTGCGGAAATAGCCATCACAGTTATGCCGTCAAGAATTCACCGTAAAACCG GGTCTGAGCACGGTCCGCATACCTATCATGAAAAGCCCGATCTCTATCAAATTATCGCACAGAGATCCGATAAACCGTGTCAGCATCAC CATGCAGATGGTCCGCATACTATCATGAAAAGCCCGATCTCTATCAAATTATCGCACAGAGATCCGATAAACCGTGTCAGCATCAC CACCATCATCAC |
| 459 | I1-GS10-E112 | ATGGGTGTTTCTGATGTTCCGGTGATCTGGAAGTTGTTGCAGCAACCCGACCAGCCTGCTGATTAGCTGGTCTGCACGTCTG AAAGTTGCCCGTTATTATCGCGGTCTGAAACCGGGTGTTGATTACAGCGGTGAAACCGGTAATTCCGTTCCGAAAATGTT TATACGCAACCATTAACTAGCGATTAACTGGTGAACCGGGTGATTACAGCGGTGAAACCGGTTTATGCAGTTACCCGTTTCGTGATTATCAG CCGATTAGCATTAACTATCGGCAGCGTTTCAGACTAGTATTATCGCATCAGTATTATCGCATCAGTATTTCGGTTAGAAGTAGCGGTCGGTTCTGGTAGT GGTGCAGTAGTTACCTATCAGACGCCACAATTCCTGGTTTAAAAGCCCAATATTCACCGTTATGCCGTGACCGATTATAAACCG GGTGTTCGTACCGCCACATTAACCATCATGAATATCCTATCAAATTATCGCACAGAGATCGATAAACCGTGCAGCATCAC CATCAGATGGTCCCGCATACTATCATGAATATCCTATCAAATTATCGCACAGAGATCGATAAACCGTGCAGCATCAC CACCATCATCAC |
| 460 | I1-GSGCGS8-E5 | ATGGGCGGTGAGTGAGTTCCGGTGATCTGGAAGTGGTTGCAGCAACCCGACCGAGCCTGCTGATTAGCTGGTCTGCCCGCTG AAAGTGGCACGTTATTACGGCATTAGCGGGTAACTCTCCGGTTCAGGAATTACGTGCGGCACCGTAATCCGGGTTCCGATTACCAG TATACCGCAACGATTAGCGGTGTGATTATACCCGTTGATTATACCCGTTCTCGGAAGGCTTCGGCTCGCCCAAGCACCGTTCCAG CCGATTAGCATCAACTATCGAGCTCTACCGCGACTATCGATTATCCAGGGCTGCAAGCGATCGATTGCGCAGGAGTTCT GGCAGTGGTAGCGGTAGCGGCCTTTACCGGCGACATCGGTAGCGGTTGTTGCAGCGGACCCTCTGCGCAGCGGCAGCGCCGACCCAACGCCTCGGGT CGGTGGATCGGTAGCGGCTACCAGTATTACCGGCGACATCACCTATGCGGAAGTTGGCAGGACGATTACCGGTAACAGCCGTTACCGGTAACGGCTACCGGT GATGTTATACCGCGATACCAATCAGACGCTACCACGGACACCGATACCACGCCGAAAAGCCTTTGACTACACGACTATTACCGATTAAAACCG CATGCCGATGGTCCGCATAGCCGATTACCGATTACCGATTACCGATTAAAAGCCTTACCGACCATCAACATCAC |

Figure 48F

| SEQ ID NO | Binder | DNA SEQ |
|---|---|---|
| 461 | T1-GS10-E5-GSGC | ATGGGCGTGAGTGATGTTCCGCGTGATCTGGAAGTGGTTGCAGCAACGAGAGCCTGCTGATTAGCCTGGTCTGCCCGCCTG AAAGTGGCACGTTATTACCGCCATCGGCGGTAACGGGCGGTAACAGGGCGGTTCAGGAATTTACCGTGCCGAAAAATGTT TATACCGCAACGATTCTGGCCTGAAACGGGTGTGCGATTATACCATCACGGCGGTTACGCGGTACGCGGTTCCGCGATTACCAG CCGATTAGCATCAACTATCGTAAGCGACTATCGACTATGGAAATTGAAAAAGGCAGTGGTAGCCAGCGGTTCTGGCAGTGGTAGC GGCTCTGGTAGTGTAAGCGACGTCCCGCGATCTGGAAGTTGTTGCAGCGAGTTGGTTGCCGACGAGCCTGCAAGAATCTCCGGTGCCGAGC CCGGTGGATCGTTATACCGGCGACGATTATTACCGCTATGCCCGGGCCGGTTCTGAAACGGGTGATTTATCCGGACCAGTGGTTGCCATCACCATCAC |
| 462 | T1(S62C)-GS10-E5 | ATGGGCGTGAGTGATGTTCCGCGTGATCTGGAAGTGGTTGCAGCAACCCCGACGAGCCTGCTGATTAGCCTGGTCTGCCCGCCTG AAAGTGGCACGTTATTACCGCCATCGACGGCGGTAACGGGCGGTAACAGCGGCGTTCAGGAATTTACCGTGCCGAAAAATGTT TATACCGCAACGATTTGCCGGTCTGAAACGGGTGTGGATTATACCATCACGGCGGTTACGCGGTTCCGCGATTACCAG CCGATTAGCATCAACTATCGTAAGCGACGTATCGACTATGGAAATTGAAAAAGGCAGTGGTAGCGGTAGGCCAGCGGTTCTGGCAGTGGTAGC GGCTCTGGTAGTGTAAGCGACGTCCCGCGACCTGGAAGTTGTTGCAGCGACGTGGTAACTCCCGGTGACGAGCCTGCAAGAATTCCGATTAAACCG GATGTTTATACCGCGACGATTCTGGTCTGAAACGGGTACACCGGATTATCAATACGGACGAACATCACCATCACCATCAC |
| 463 | T1-GS10-E5(S62C) | ATGGGCGTGAGTGATGTTCCGCGTGATCTGGAAGTGGTTGCAGCAACCCCGACGAGCCTGCTGATTAGCCTGGTCTGCCCGCCTG AAAGTGGCACGTTATTACCGCCATCGACGGCGGTAACGGGCGGTAACAGGGCGTTCAGGAATTTACCGTGCCGAAAAATGTT TATACCGCAACGATTAGCGCCTGAAACGGGTGTGGATTATACCATCACGGCGGTTACGCGGTTCCGCGATTACCAG CCGATTAGCATCAACTATCGTAAGCGACGTATCGACTATGGAAATTGAAAAAGGCAGTGGTAGCCAGCGGTTCTGGCAGTGGTAGC GGCTCTGGTAGTGATCGTTACCGACGTATTACCGACGTATTACCCGGAAGTTGTTGCAGCCCCGGTGTAACAGCCCGGTGCTGACGAGCCTGCAAGAATTACCGATTAAACCG GATGTTTATACCGCGACCGATTTGGTCCGCACGATTATCGGTACACCGGATTATCAATATCGGACCAACATCACCATCACCATCAC |

Figure 48G

| SEQ ID NO | Binder | DNA SEQ |
|---|---|---|
| 464 | L1(S91C)-GS10-E5 | ATGGGGCGTGAGTGATGTTCCGCGTGATCTGGAAGTGGTTGCAGCAACCCGACGAGCTGCTGATTAGCTGGTCTGCCGCCTGAAAGTGGCACGTTATTACCGGCATCACCTACGGCGAAACCGGTAACTCTCCGGTTCAGGAATTTACCGTGCCGAAAAATGTTTATACCGCAACGATTAGCGGCCTGAAACCGGGTGTGGATTATACCATCACGGTGTACCGGTTACCGGTTTCCGCGATTACCAGCCGATTTGCATCAACTATCGTAAGCGGGGCAAATTGAAAAGGCAGTGGTAGTGGTAGCGGCCTGGACGGCCGACCTGCAAGAGCCTGCTGATCTCTTGGTGGCCGGCTCTGGTAGTGTAAGCGATATTACCCAGTGACCATCTCTGGTCTGGAAGTTGCAGCGACGCCGAAGACCGGTAACAGCCGGTGGTACAGATTACCGTTTACCCGGTTGCAAGAACATCACCATCACCATCACCCGGTGGACGCGTTATACCGCGACCATCTCTGGTCTGGAAGTTGCAGCGACGCCGAAGACCGGTAACAGCCGGTTGGTTACAGATTAGGTGTAGCATCCAGAACCGGTGAATCTCCGATTAGTATCAATTATCGGAACATCACCATCACCATCAC |
| 465 | L1-GS10-E5(S91C) | ATGGGCGTGAGCGATGTTCCGCGTGATCTGGAAGTGGTTGCAGCAACCCGACGAGCTGCTGATTAGCTGGTCTGCCGCCTGAAAGTGGCACGTTATTACCGGCATCACCTACGGCGAAACCGGTAACAGTCCGGTTCAGGAATTTACCGTGCCGAAAAATGTTTATACCGCAACGATTAGCGGCCTGAAACCGGGTGTGGATTATACCATCACGGTGTACCGGTTACCGGTTTCCGCGATTACCAGCCGATTAGCATCAACTATCGTAAGCGGGCTCTGGTAGTGGTAGCGGTAGCGGCCTGGACGGCCGACCAGCCGCTGCTGATCAGTTGGTGGGCCCCGGTGGGATCGTTATACCGCGACCATCTCTGGTCTGGAAGTTGCAGCGACGCCGAAGACCGGTAACAGCCGGTTGGTTACAGATTACCGCGACCATCTCTGGTCTGGAAGTTGCAGCGACGCCGAAGACCGGTAACAGCCGGTTGGTTACAGATTACCGGTTACCGCGGTTACAGATTACCGGTTACGATTATACCGGAACATCAATTATCGATCGATCCGGTAGCATCCGAATCACCATCACCATCAC |

METHOD OF TREATING CANCER BY ADMINISTERING EGFR AND EGFR/IGFIR BINDING MOLECULES

RELATED APPLICATIONS

This application is a divisional of U.S. patent application Ser. No. 13/692,555, filed Dec. 3, 2012 (now U.S. Pat. No. 9,017,655), which is a divisional of U.S. patent application Ser. No. 12/625,217, filed Nov. 24, 2009 (now U.S. Pat. No. 8,343,501), which claims benefit of U.S. Provisional Application Nos. 61/200,164, filed Nov. 24, 2008; 61/200,282, filed Nov. 26, 2008; 61/212,966, filed Apr. 17, 2009; 61/178,279, filed May 14, 2009; and 61/227,330, filed Jul. 21, 2009. The aforementioned applications are hereby incorporated by reference.

FIELD OF THE INVENTION

The present invention relates to EGFR binding domains and bispecific molecules comprising an EGFR binding domain and a distinct IGFIR binding domain for use in diagnostic, research and therapeutic applications. The invention further relates to cells comprising such proteins, polynucleotide encoding such proteins or fragments thereof, and vectors comprising the polynucleotides encoding the innovative proteins. Exemplary EGFR binding domains and bispecific molecules include antibody-like protein dimers based on the tenth fibronectin type III domain.

INTRODUCTION

Activation of receptor tyrosine kinase signaling is central to cancer development (see e.g., Grimberg A. Cancer Biol Ther. 2003 2(6):630-5 and Mendelsohn J. J Clin Oncol. 2003 21(14):2787-99). Receptor tyrosine kinases have a conserved domain structure including an extracellular domain, a transmembrane domain and an intracellular tyrosine kinase domain. The extracellular domain can bind to a ligand, such as to a polypeptide growth factor or to a cell membrane-associated molecule. Typically, either ligand binding or ligand binding induced dimerization of receptor tyrosine kinases activates the intracellular catalytic tyrosine kinase domain of the receptor and subsequent signal transduction.

Examples of receptor tyrosine kinases include, but are not limited to ERBB receptors (e.g., EGFR, ERBB2, ERBB3, ERBB4), erythropoietin-producing hepatocellular (EPH) receptors, fibroblast growth factor (FGF) receptors (e.g., FGFR1, FGFR2, FGFR3, FGFR4, FGFR5), platelet-derived growth factor (PDGF) receptors (e.g., PDGFR-A, PDGFR-B), vascular endothelial growth factor (VEGF) receptors (e.g., VEGFR1/FLT1, VEGFR2/FLK1, VEGF3), tyrosine kinase with immunoglobulin-like and EGF-like domains (TIE) receptors, insulin-like growth factor (IGF) receptors (e.g., INS-R, IGFIR, IR-R), Discoidin Domain (DD) receptors, receptor for c-Met (MET), recepteur d'origine nantais (RON); also known as macrophage stimulating 1 receptor, Flt3 fins-related tyrosine kinase 3 (Flt3), colony stimulating factor 1 (CSF1) receptor, adhesion related kinase receptor (e.g., Ax1), receptor for c-kit (KIT) and insulin receptor related (IRR) receptors.

Inhibition of receptor tyrosine kinases has emerged as an effective treatment strategy for certain human malignancies (for a review see Roussidis A E, In Vivo. 2002 16(6):459-69). While targeted monotherapy may initially be effective in treating cancer, therapeutic resistance often follows, possibly as a result of upregulation of other signaling cascades (see e.g., Nahta R et al., Breast Cancer Res. 2006 8(6):215 and Horn L et al., Clin Lung Cancer. 2007 8:S68-73). Accordingly, there exists a need for developing improved cancer therapeutics.

SUMMARY OF THE INVENTION

In one aspect, the application provides EGFR binding tenth fibronectin type III domains ($^{10}$Fn3) having novel sequences. EGFR binding $^{10}$Fn3 having a consensus sequence are also provided. Such EGFR binding $^{10}$Fn3 may be monomeric or may be included as part of a fusion protein.

In another aspect, the application provides bispecific molecules that bind EGFR and IGFIR, referred to herein as "E/I binders". E/I binders encompassed by the invention include bispecific antibodies and dimers of ligand binding scaffold proteins (e.g., tendamistat, affibody, fibronectin type III domain, anticalin, tetranectin, and ankyrin). When constructed as a single polypeptide chain, the E/I binders may be constructed in any orientation, e.g., from N-terminus to C-terminus either in the E-I arrangement or the I-E arrangement.

In one aspect, antibody-like protein dimers are provided comprising an EGFR binding $^{10}$Fn3 covalently or non-covalently linked to an IGFIR binding $^{10}$Fn3. The $^{10}$Fn3 bind their target (EGFR or IGFIR) with a $K_D$ of less than 500 nM. Each of the individual $^{10}$Fn3 independently has an amino acid sequence at least 70, 80, 85, 90, 95, 98, or 100% identical to SEQ ID NO: 32, wherein n is an integer from 1-20, o is an integer from 1-20, and p is an integer from 1-40. In some embodiments, n is an integer from 8-12, o is an integer from 4-8, and p is an integer from 4-28. In some embodiments, n is 10, o is 6, and p is 12.

In some embodiments, the antibody-like protein dimers comprise IGFIR binding $^{10}$Fn3 covalently linked to EGFR binding $^{10}$Fn3 via a polypeptide linker or a polyethylene glycol moiety. In some embodiments, the antibody-like protein dimer comprises an amino acid sequence at least 80, 90, 95, or 100% identical to any one of SEQ ID NOs: 20-31, 53-58, 87-92, 98-105, 118-133, 149-154, 164-169, 179-184, 192-197, 205-210 and 211-216.

In some embodiments, the E/I binder comprises an amino acid sequence having any one of SEQ ID NOs: 20-31, 53-58, 87-92, 98-105, 118-133, 149-154, 164-169, 179-184, 192-197, 205-210 and 211-216, wherein (i) the EGFR binding $^{10}$Fn3 and/or the IGF-IR binding $^{10}$Fn3 comprises a $^{10}$Fn3 scaffold having from has anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the corresponding scaffold amino acids of SEQ ID NO: 1, and/or (ii) the EGFR binding $^{10}$Fn3 has anywhere from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the corresponding loop sequences of any one of SEQ ID NOs: 5-8, 52, 66-68, 106-108, 112-114, 140-142, 155-157, 170-172, 182, 185-187, 198-200, or 219-327 and/or the IGF-IR binding $^{10}$Fn3 has anywhere from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the corresponding loop sequences of SEQ ID NO: 3.

In one aspect, pharmaceutically acceptable compositions are provided comprising an antibody-like protein dimer as described herein and a pharmaceutically acceptable carrier, wherein the composition is essentially pyrogen free.

In a further aspect, methods for treating hyperproliferative disorders, such as cancer, in a subject are provided comprising administering to a subject in need thereof a therapeutically effective amount of a pharmaceutically acceptable composition comprising an antibody-like protein dimer as described herein.

In another aspect, the application provides a nucleic acid encoding an antibody-like protein dimer as described herein. Also provided is a vector comprising a nucleic acid encoding an antibody-like dimer as described herein. Suitable vectors include, for example, expression vectors. Also provided are host cells comprising a nucleic, vector, or expression vector, comprising a nucleic acid encoding an antibody-like protein dimer as described herein. Suitable host cells include prokaryotic and eukaryotic host cells. Exemplary prokaryotic cells are bacterial cells, such as *E. coli*. Exemplary eukaryotic cells are mammalian cells, such as CHO cells. Also provided are methods for producing an antibody-like protein dimer as described herein, comprising culturing a host cell comprising a nucleic, vector, or expression vector, comprising a nucleic acid encoding the antibody-like protein dimer and recovering the expressed antibody-like protein dimer from the culture.

BRIEF DESCRIPTION OF THE DRAWINGS

FIG. 12A: Preclinical antitumor activity in the H292 human tumor xenograft model. Mean tumor sizes calculated from groups of 8 mice is shown in mg for control animals (■), E3-GS10-I1 (w/PEG) dosed at 100 mg/kg (○), E2-GS10-I1 (with PEG) dosed at 100 mg/kg (□), panitumumab dosed at 1 mg/mouse (Δ) or 0.1 mg/mouse (∇). The letter a on the x-axis indicates doses of E/I binders administered and the p indicates doses of panitumumab administered. FIG. 12B: Average weight change is shown for each group over the course of the study. Symbols are as described in FIG. 12A legend.

FIGS. 13A-13D. Pharmacodynamic effects in the H292 NSCLC tumor xenograft model. Levels of the indicated analytes were determined in tumor lysates as described in Example 12. (FIG. 13A) phosph-EGFR, (FIG. 13B) phospho-ErbB2, (FIG. 13C) phospho-IGFR, and (FIG. 13D) total EGFR. Checkered bars=panitumumab, empty bars=E2-GS10-I1 (with PEG), hatched bats=E3-GS10-I1 (with PEG).

FIG. 14. Western blot analysis of MCF7r cells compared to MCF7 parental cells.

FIGS. 15A and 15B. MCF7 (FIG. 15A) and MCF7r (FIG. 15B) human tumor xenograft studies in nude mice. Mean tumor size is shown for both studies calculated from 8 mice per group.

FIGS. 18A and 18B. Colony formation assay with H292 NSCLC cells. FIG. 18A. Representative data is shown from a single plate. FIG. 18B. IC50 from one E/I $^{10}$Fn3-based binder is shown with error bars calculated from triplicate measurements.

FIGS. 19A and 19B. Epitope mapping assay. Location of epitope binding for various EGFR binding antibodies are shown in FIG. 19A. A description of the antibodies is provided in Example 18, Table 11. The left column of table 11 provides a number for each anti-EGFR antibody which correlates with the numbered antibodies shown in FIG. 19A. FIG. 19B shows an exemplary epitope mapping assay as described in Example 18.

FIGS. 24A-24C. Inhibition of ligand stimulated signaling by $^{10}$Fn3-based binders (pegylated). Effect of E/I $^{10}$Fn3-based binder (I1-GS10-E5 pegylated) on receptor activation and cell signaling in DiFi (FIG. 24A), H292 (FIG. 24B) or BxPC3 (FIG. 24C) cells. Cells were serum starved and treated for 2 hours with 1 μM $^{10}$Fn3-based binders before stimulation with either EGF, IGF1 or a combination of EGF+IGF1. GAPDH was probed to illustrate equal loading in all lanes.

FIGS. 29A and 29B. H292 xenograft study using E/I 10Fn3-based binders as compared to panitumumab. H292 xenografts were either untreated (■) or dosed three times a week with $^{10}$Fn3-based binders formulated in PBS with the individual constructs as described in the figure or dosed every three days i.p. with panitumumab at 1 mg/mouse (○) or 0.1 mg/mouse (□). Actual doses of $^{10}$Fn3-based binders and panitumumab (▲) are indicated on the x-axis with the panitumumab doses closest to the x-axis below the triangles indicating doses of $^{10}$Fn3-based binders. FIG. 29A shows measurements out to day 43. FIG. 29B shows measurements out to day 27.

FIG. 30. Pharmaokinectic parameters profile of E2-GS10-I1pegylated in mice.

FIGS. 33A and 33B. Measurement of pharmacodynamic endpoints in tumors. At the end of treatment, tumors were removed 4 hours following the final dose from DiFi xenograft model (FIG. 33A) and H292 xenograft model (FIG. 33B) and examined for levels of phospho-EGFR, phospho-IGFR, total EGFR and total IGFR. Equal amounts of total protein lysate was loaded into each lane of the gels and blots were also probed with GAPDH to demonstrate equal loading across all lanes.

FIG. 34. Sequence of anti-EGFR binder 679F09 (SEQ ID NO: 490). Loop residues which were varied are underlined.

FIG. 43. Table summarizing various characteristics of E/I $^{10}$Fn3-based binders as described in Example 22.

FIG. 44. Table summarizing various pharmacokinetic parameters of E/I $^{10}$Fn3-based binders as described in Example 30.

FIGS. 45A-H. Amino acid sequences of E monomers as described in Example 32. The BC, DE and FG loops in each sequence are underlined.

FIG. 46. Alignment of wild-type core sequence (amino acids 9-94 of SEQ ID NO: 1) with I1 core (SEQ ID NO:65), E1 core (SEQ ID NO:66), E2 core (SEQ ID NO:67), E3 core (SEQ ID NO:68), E4 core (SEQ ID NO:108), E5 core (SEQ ID NO:114), E85 core (SEQ ID NO:141), E90 core (SEQ ID NO:156), E96 core (SEQ ID NO:171), E105 core (SEQ ID NO:186), and E112 core (SEQ ID NO:199). The BC, DE and FG loops in the wild-type sequences are shown in bold and underlined. The amino acid residues actually changed in comparison to wild-type for the I and E cores are shown i bold and underlined.

FIGS. 47A-Q. Nucleic acid sequences of E and I monomers. Unless otherwise specified, the nucleotide sequences encode a monomer having an N+10 N-terminal extension, a Ser tail, and a His tag.

FIGS. 48A-G. Nucleic acid sequence of E/I $^{10}$Fn3-based binders. All nucleotide sequences encode an E/I $^{10}$Fn3-based binder having an N+10 N-terminal extension on the first monomer in the construct and a Cys tail and His tag on the second monomer in the construct. GS10 is SEQ ID NO: 11; GSGCGS8 is SEQ ID NO: 218; and GSGC is SEQ ID NO: 489.

DETAILED DESCRIPTION OF THE INVENTION

Definitions

Figure 1:
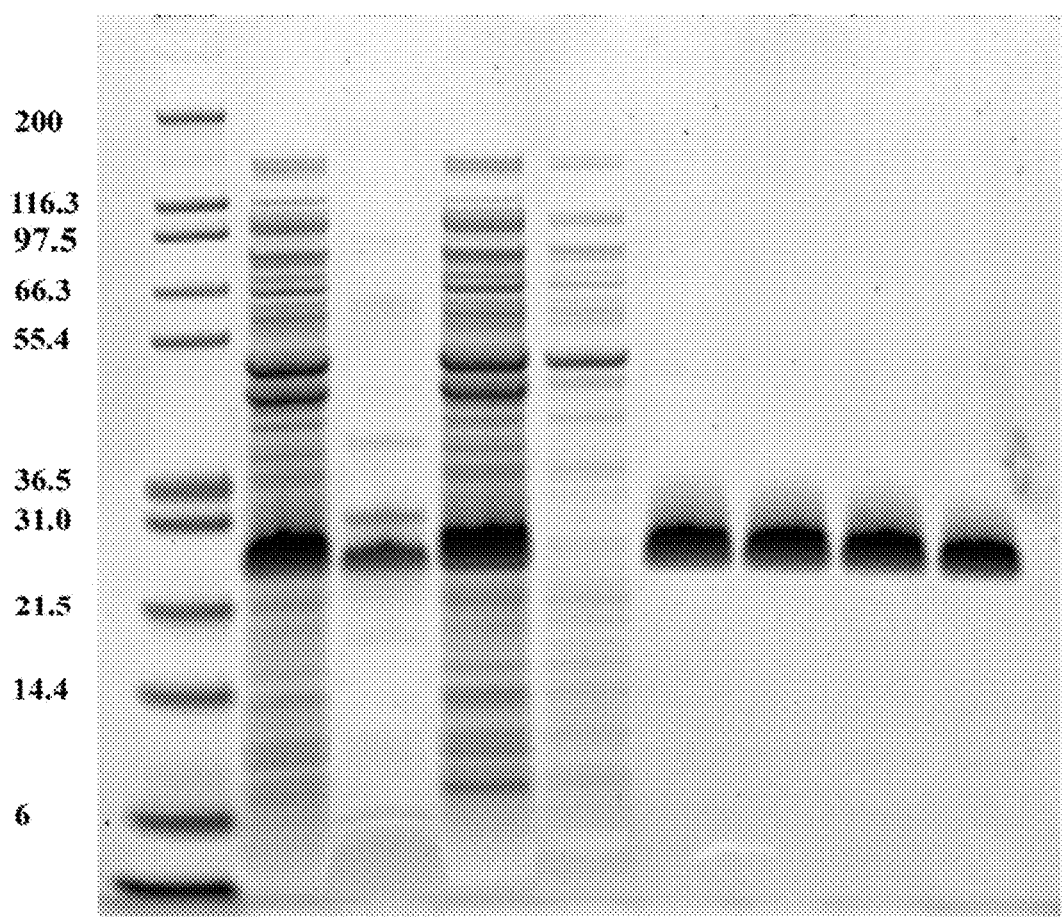
FIG. 1. SDS-PAGE Analysis of I1-GS10-E2. Samples from the lysis of HMS174(DE3) bacterial cell pellet from which I1-GS10-E2 was expressed and purified by a HisTrap chromatography column were run on a 4-12% NuPAGE minigel and stained by Sypro-Orange and visualized by STORM imager. Mark 12 molecular weight standards (Lane 1); Lysate-soluble (Lane 2); Lysate-insoluble (Lane 3); HisTrap load (Lane 4); HisTrap non-bound (Lane 5); Pooled HisTrap Eluate (Lane 6); Dialyzed into 50 mM NaOAc, 150 mM NaCl, pH 4.5 (Lane 7); Dialyzed into PBS (Lane 8); Dialyzed into Tris, 150 mM NaCl, pH 8.5 (Lane 9).

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The terms "comprise" and "comprising" are used in the inclusive, open sense, meaning that additional elements may be included.

The term "including" is used to mean "including but not limited to". "Including" and "including but not limited to" are used interchangeably.

The term "antibody-like protein" refers to a non-immunoglobulin protein having an "immunoglobulin-like fold", i.e., comprises about 80-150 amino acid residues that are structurally organized into a set of beta or beta-like strands, forming beta sheets, where the beta or beta-like strands are connected by intervening loop portions. The beta sheets form the stable core of the antibody-like protein, while creating two "faces" composed of the loops that connect the beta or beta-like strands. As described herein, these loops can be varied to create customized ligand binding sites, and such variations can be generated without disrupting the overall stability of the protein. An example of such an antibody-like protein is a "fibronectin-based scaffold protein", by which is meant a polypeptide based on a fibronectin type III domain (Fn3). In one aspect, an antibody-like protein is based on a tenth fibronectin type III domain ($^{10}$Fn3).

By a "polypeptide" is meant any sequence of two or more amino acids, regardless of length, post-translation modification, or function. "Polypeptide," "peptide," and "protein" are used interchangeably herein.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the time to disease progression (TTP) and/or determining the response rates (RR).

The half-life of an amino acid sequence or compound can generally be defined as the time taken for the serum concentration of the polypeptide to be reduced by 50% in vivo due to, e.g., degradation of the sequence or compound and/or clearance or sequestration of the sequence or compound by natural mechanisms. The half-life can be determined in any manner known in the art, such as by pharmacokinetic analysis. See e.g., M Gibaldi & D Perron "Pharmacokinetics", published by Marcel Dekker, 2nd Rev. edition (1982).

The term "E/I binder" refers to a bispecific molecule that comprises an EGFR binding domain and a distinct IGFIR binding domain. The two domains may be covalently or non-covalently linked. An exemplary E/I binder is an antibody-like dimer comprising an EGFR binding $^{10}$Fn3 and an IGFIR binding $^{10}$Fn3, i.e., an E/I $^{10}$Fn3 based binder.

Overview

The epidermal growth factor receptor (EGFR) and insulin-like growth factor receptor (IFGR) play key roles in the tumorigenesis of several types of human cancer. Inhibition of either receptor effectively reduces tumor growth in pre-clinical models as well as clinically. Blocking the EGFR pathway induces switching to the IGFR pathway to drive growth with in vitro tumor models. Therefore, blocking both receptors simultaneously may achieve superior efficacy to blocking either pathway alone by overcoming pathway switching. In exemplary embodiments, the activity of an E/I binder is synergistic in comparison to the monomeric components of the E/I binder.

The specification describes, inter alia, bispecific molecules that bind EGFR and IGFIR, referred to herein as "E/I binders". Applicants have discovered that such bispecific molecules inhibit proliferation of a cancer model cell line with greater potency than the corresponding. monospecific binders (see e.g., Example 9 and FIG. 8).

E/I binders will be useful in numerous therapeutic applications, especially in the treatment of cancer. In addition to therapeutic applications, E/I binders may be used in any circumstance where it is desirable to detect EGFR and/or IGFIR.

E/I binders have an EGFR binding domain and a distinct IGFIR binding domain. Typical binding domains include antibodies; therefore, bispecific antibodies may be generated to function as E/I binders. Bispecific antibodies comprising complementary pairs of $V_H$ and $V_L$ regions are known in the art. These bispecific antibodies comprise two pairs of $V_H$ and $V_L$, each $V_{H/L}$ pair binding to a single antigen. (see e.g., Hu et al., Cancer Res. 1996 56:3055-306; Neri et al., J. Mol. Biol. 1995 246:367-373; Atwell et al., Mol. Immunol. 1996 33:1301-1312; and Carter et al., Protein Sci. 1997 6:781-788). An exemplary bispecific antibody is a diabody, i.e., a small antibody fragment with two antigen-binding sites, which fragments comprise a heavy-chain variable domain connected to a light-chain variable domain in the same polypeptide chain (Hollinger et al., Proc. Natl. Acad. Sci. USA 1993 90: 6444-6448).

E/I binders also encompass dimers of ligand binding scaffold proteins. Scaffold proteins are well described in the literature and include, e.g., tendamistat, affibody, fibronecctin type III domain, anticalin, tetranectin, and ankyrin. Additional scaffold proteins that may be used to generate E/I binders are reviewed in Binz et al., Nature Biotech 23:1257-1268 (2005). Scaffold proteins are based on a rigid core structure or 'framework' that is important in determining and stabilizing the three-dimensional structure. In between the fixed or conserved residues of the scaffold lie variable regions such as loops, surfaces or cavities that can be randomized to alter ligand binding. A large diversity of amino acids is provided in the variable regions between the fixed scaffold residues to provide specific binding to a target molecule.

An exemplary ligand binding scaffold protein is based on a fibronectin type III domain (Fn3). Fibronectin is a large protein which plays essential roles in the formation of extracellular matrix and cell-cell interactions; it consists of many repeats of three types (types I, II, and III) of small domains.

Fn3 is small, monomeric, soluble, and stable. It lacks disulfide bonds and, therefore, is stable under reducing conditions. The overall structure of Fn3 resembles the immunoglobulin fold. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face and loops BC, DE, and FG are located on the opposing face. Any or all of loops AB, BC, CD, DE, EF and FG may participate in ligand binding. There are at least 15 different modules of Fn3, and while the sequence homology between the molecules is low, they all share a high similarity in tertiary structure.

Adnectins™ (Adnexus, a Bristol-Myers Squibb R&D Company) are ligand binding scaffold proteins based on the tenth fibronectin type III domain, i.e., the tenth module of Fn3, ($^{10}$Fn3). The amino acid sequence of a naturally occurring human $^{10}$Fn3 is set forth in SEQ ID NO: 1.

```
                                        (SEQ ID NO: 1)
VSDVPRDLEVVAATPTSLLISWDAPAVTVRYYRITYGETGGNSPVQEF

TVPGSKSTATISGLKPGVDYTITVYAVTGRGDSPASSKPISINYRT
(BC, FG, and DE loops are emphasized)
```

In SEQ ID NO:1, the AB loop corresponds to residues 15-16, the BC loop corresponds to residues 21-30, the CD loop corresponds to residues 39-45, the DE loop corresponds to residues 51-56, the EF loop corresponds to residues 60-66, and the FG loop corresponds to residues 76-87. (Xu et al., Chemistry & Biology 2002 9:933-942). The BC, DE and FG loops align along one face of the molecule and the AB, CD and EF loops align along the opposite face of the molecule. In SEQ ID NO: 1, beta strand A corresponds to residues 9-14, beta strand B corresponds to residues 17-20, beta strand C corresponds to residues 31-38, beta strand D corresponds to residues 46-50, beta strand E corresponds to residues 57-59, beta strand F corresponds to residues 67-75, and beta strand G corresponds to residues 88-94. The strands are connected to each other through the corresponding loop, e.g., strands A and B are connected via loop AB in the formation strand A, loop AB, strand B, etc. Residues involved in forming the hydrophobic core (the "core amino acid residues") include the amino acids corresponding to the following amino acids of SEQ ID NO: 1: L8, V10, A13, L18, I20, W22, Y32, I34, Y36, F48, V50, A57, I59, L62, Y68, I70, V72, A74, I88, I90 and Y92, wherein the core amino acid residues are represented by the single letter amino acid code followed by the position at which they are located within SEQ ID NO: 1. See e.g., Dickinson et al., J. Mol. Biol. 236: 1079-1092 (1994).

As described above, amino acid residues corresponding to residues 21-30, 51-56, and 76-87 of SEQ ID NO: 1 define the BC, DE and FG loops, respectively. However, it should be understood that not every residue within the loop region needs to be modified in order to achieve a $^{10}$Fn3 binder having strong affinity for a desired target, such as IGF-IR or EGFR. For example, in many of the examples described herein, only residues corresponding to amino acids 23-30, 52-55 and 77-86 of SEQ ID NO: 1 were modified to produce high affinity $^{10}$Fn3 binders (see FIG. 46. Accordingly, in certain embodiments, the BC loop may be defined by amino acids corresponding to residues 23-30 of SEQ ID NO: 1, the DE loop may be defined by amino acids corresponding to residues 52-55 of SEQ ID NO: 1, and the FG loop may be defined by amino acids corresponding to residues 77-86 of SEQ ID NO: 1.

$^{10}$Fn3 are structurally and functionally analogous to antibodies, specifically the variable region of an antibody. While $^{10}$Fn3 domains may be described as "antibody mimics" or "antibody-like proteins", they do offer a number of advantages over conventional antibodies. In particular, they exhibit better folding and thermo stability properties as compared to antibodies, and they lack disulphide bonds, which are known to impede or prevent proper folding under certain conditions. Exemplary E/I $^{10}$Fn3 based binders are predominantly monomeric with Tm's averaging ~50° C.

The BC, DE, and FG loops of $^{10}$Fn3 are analogous to the complementary determining regions (CDRs) from immunoglobulins. Alteration of the amino acid sequence in these loop regions changes the binding specificity of $^{10}$Fn3. The protein sequences outside of the CDR-like loops are analogous to the framework regions from immunoglobulins and play a role in the structural conformation of the $^{10}$Fn3. Alterations in the framework-like regions of $^{10}$Fn3 are permissible to the extent that the structural conformation is not so altered as to disrupt ligand binding. Methods for generating $^{10}$Fn3 ligand specific binders have been described in PCT Publication Nos. WO 00/034787, WO 01/64942, and WO 02/032925, disclosing high affinity TNFα binders, PCT Publication No. WO 2008/097497, disclosing high affinity VEGFR2 binders, and PCT Publication No. WO 2008/066752, disclosing high affinity IGFIR binders. Additional references discussing $^{10}$Fn3 binders and methods of selecting binders include PCT Publication Nos. WO 98/056915, WO 02/081497, and WO 2008/031098 and U.S. Publication No. 2003186385.

Antibody-like proteins based on the $^{10}$Fn3 scaffold can be defined generally by the sequence: VSDVPRDLEVVAATPTSLLI(X)$_n$YYRITYGETGGNSPVQEFTV(X)$_o$ATISGLKPGVDYTITV YAV(X)$_p$ISINYRT (SEQ ID NO: 32), wherein n is an integer from 1-20, o is an integer from 1-20, and p is an integer from 1-40. The BC, DE, and FG loops are represented by (X)$_n$, (X)$_o$, and (X)$_p$, respectively.

$^{10}$Fn3 generally begin with the amino acid residue corresponding to number 1 of SEQ ID NO: 1. However, domains with amino acid deletions are also encompassed by the invention. In some embodiments, amino acid residues corresponding to the first eight amino acids of SEQ ID NO: 1 are deleted. Additional sequences may also be added to the N- or C-terminus. For example, an additional MG sequence may be placed at the N-terminus of $^{10}$Fn3. The M will usually be cleaved off, leaving a G at the N-terminus. In some embodiments, sequences may be placed at the C-terminus of the $^{10}$Fn3 domain, e.g., EIDKPSQ (SEQ ID NO: 9), EIDKPCQ (SEQ ID NO: 10), EGSGS (SEQ ID NO: 96) or EGSGC (SEQ ID NO: 97).

The non-ligand binding sequences of $^{10}$Fn3, i.e., the "$^{10}$Fn3 scaffold", may be altered provided that the $^{10}$Fn3 retains ligand binding function and/or structural stability. In some embodiments, one or more of Asp 7, Glu 9, and Asp 23 are replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (See, PCT Publication No. WO 02/04523). A variety of additional alterations in the $^{10}$Fn3 scaffold that are either beneficial or neutral have been disclosed. See, for example, Batori et al., Protein Eng. 2002 15(12):1015-20; Koide et al., Biochemistry 2001 40(34): 10326-33.

The $^{10}$Fn3 scaffold may be modified by one or more conservative substitutions. As many as 5%, 10%, 20% or even 30% or more of the amino acids in the $^{10}$Fn3 scaffold may be altered by a conservative substitution without substantially altering the affinity of the $^{10}$Fn3 for a ligand. For example, the scaffold modification preferably reduces the binding affinity of the $^{10}$Fn3 binder for a ligand by less than 100-fold, 50-fold, 25-fold, 10-fold, 5-fold, or 2-fold. It may be that such changes will alter the immunogenicity of the $^{10}$Fn3 in vivo, and where the immunogenicity is decreased, such changes will be desirable. As used herein, "conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., Atlas of Protein Sequence and Structure 5:345-352 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

E Binders

In one aspect, the disclosure provides antibody-like proteins comprising an EGFR binding $^{10}$Fn3 domain. In certain embodiments, an EGFR binding $^{10}$Fn3 may be provided as part of a fusion protein or multimer. For example, an EGFR binding $^{10}$Fn3 may be covalently or non-covalently linked to at least a second $^{10}$Fn3 binding domain. The second $^{10}$Fn3 binding domain may bind to EGFR or to a different target. In an exemplary embodiment, an EGFR binding $^{10}$Fn3 may be covalently or non-covalently linked to an IGF-IR binding $^{10}$Fn3.

In exemplary embodiments, the EGFR binding $^{10}$Fn3 proteins described herein bind to EGFR with a K$_D$ of less than 500 nM, 100 nM, 50 nM, 10 nM, 1 nM, 500 pM, 100 pM. 100 pM, 50 pM or 10 pM.

In exemplary embodiments, the BC loop of the EGFR binding $^{10}$Fn3 proteins correspond to amino acids 23-30 of SEQ ID NO: 1, the DE loop of the EGFR binding $^{10}$Fn3 proteins correspond to amino acids 52-55 of SEQ ID NO: 1, and the FG loop of the EGFR binding $^{10}$Fn3 proteins correspond to amino acids 77-86 of SEQ ID NO: 1.

In one embodiment, the invention provides an EGFR binding $^{10}$Fn3 comprising a BC loop having a YQ at the positions corresponding to amino acids 29 and 30 of SEQ ID NO: 1.

In another embodiment, the invention provides an EGFR binding $^{10}$Fn3 comprising a BC loop having a YQ at the positions corresponding to amino acids 29 and 30 of SEQ ID NO: 1 and an FG loop that is fifteen amino acids in length, e.g., an FG loop that is extended in length by five amino acids due to an insertion of five amino acids between residues corresponding to amino acids 77-86 of SEQ ID NO: 1.

In another embodiment, the invention provides an EGFR binding $^{10}$Fn3 comprising a BC loop having a YQ at the positions corresponding to amino acids 29 and 30 of SEQ ID NO: 1 and a DE loop having a V, I, L, M or A residue at the position corresponding to amino acid 54 of SEQ ID NO: 1.

In another embodiment, the invention provides an EGFR binding $^{10}$Fn3 comprising a BC loop having a YQ at the positions corresponding to amino acids 29 and 30 of SEQ ID NO: 1, a DE loop having a V, I, L, M or A residue at the position corresponding to amino acid 54 of SEQ ID NO: 1, and an FG loop that is fifteen amino acids in length, e.g., an FG loop that is extended in length by five amino acids due to an insertion of five amino acids between residues corresponding to amino acids 77-86 of SEQ ID NO: 1.

In another embodiment, the invention provides an EGFR binding $^{10}$Fn3 comprising a BC loop having a YQ at the positions corresponding to amino acids 29 and 30 of SEQ ID NO: 1 and an FG loop comprising a D or N at the position corresponding to amino acid 77 of SEQ ID NO: 1.

In another embodiment, the invention provides an EGFR binding $^{10}$Fn3 comprising a BC loop having a YQ at the positions corresponding to amino acids 29 and 30 of SEQ ID NO: 1 and an FG loop (i) that is fifteen amino acids in length, e.g., an FG loop that is extended in length by five amino acids due to an insertion of five amino acids between residues corresponding to amino acids 77-86 of SEQ ID NO: 1 and (ii) comprises a D or N at the position corresponding to amino acid 77 of SEQ ID NO: 1.

In another embodiment, the invention provides an EGFR binding $^{10}$Fn3 comprising a DE loop comprising a V, I, L, M or A residue at the position corresponding to amino acid 54 of SEQ ID NO: 1 and an FG loop comprising a D or N at the position corresponding to amino acid 77 of SEQ ID NO: 1.

In another embodiment, the invention provides an EGFR binding $^{10}$Fn3 comprising a DE loop comprising a V, I, L, M or A residue at the position corresponding to amino acid 54 of SEQ ID NO: 1 and an FG loop (i) that is fifteen amino acids in length, e.g., an FG loop that is extended in length by five amino acids due to an insertion of five amino acids between residues corresponding to amino acids 77-86 of SEQ ID NO: 1 and (ii) comprises a D or N at the position corresponding to amino acid 77 of SEQ ID NO: 1.

In another embodiment, the invention provides an EGFR binding $^{10}$Fn3 comprising a BC loop having a YQ at the positions corresponding to amino acids 29 and 30 of SEQ ID NO: 1, a DE loop comprising a V, I, L, M or A residue at the position corresponding to amino acid 54 of SEQ ID NO: 1, and an FG loop comprising a D or N at the position corresponding to amino acid 77 of SEQ ID NO: 1.

In another embodiment, the invention provides an EGFR binding $^{10}$Fn3 comprising a BC loop having a YQ at the positions corresponding to amino acids 29 and 30 of SEQ ID NO: 1, a DE loop comprising a V, I, L, M or A residue at the position corresponding to amino acid 54 of SEQ ID NO: 1, and an FG loop (i) that is fifteen amino acids in length, e.g., an FG loop that is extended in length by five amino acids due to an insertion of five amino acids between residues corresponding to amino acids 77-86 of SEQ ID NO: 1 and (ii) comprises a D or N at the position corresponding to amino acid 77 of SEQ ID NO: 1.

In another embodiment, the invention provides an EGFR binding $^{10}$Fn3 comprising a BC loop comprising the amino acid sequence XXXXXXYQ, a DE loop comprising the amino acid sequence XX(V/I/L/M/A)X, and an FG loop comprising the amino acid sequence (D/N)X$_n$, wherein X is any amino acid and n is 9-14 amino acids. In an exemplary embodiment, n is 14 amino acids.

In another embodiment, the invention provides an EGFR binding $^{10}$Fn3 comprising a BC loop corresponding to amino acids 23-30 of SEQ ID NO: 1 comprising the amino acid sequence XXXXXXYQ, a DE loop corresponding to amino acids 52-55 of SEQ ID NO: 1 comprising the amino acid sequence XX(V/I/L/M/A)X, and an FG loop corresponding to amino acids 77-86 of SEQ ID NO: 1 comprising the amino acid sequence (D/N)X$_n$, wherein X is any amino acid and n is 9-14 amino acids. In an exemplary embodiment, n is 14 amino acids.

In another embodiment, the invention provides an EGFR binding $^{10}$Fn3 comprising a BC loop comprising the amino acid sequence XXXXXXYQ, a DE loop comprising the amino acid sequence XX(V/I/L/M/A)X, and an FG loop comprising an amino acid sequence selected from:

```
i.
(D/N)(Y/M)(Y/A/M)(Y/H/F)(K/Q/V)(E/P/R)(Y/T/K)X (E/Y/Q)(Y/G/H);
and ii.
D(Y/F/W)(Y/F/K)(N/D/P)(P/H/L)(A/T/V)(T/D/S)

(H/Y/G)(E/P/V)(Y/H)(T/K/I)(Y/F)(H/N/Q)(T/Q/E)

(T/S/I);
``` wherein X is any amino acid.

In another embodiment, the invention provides an EGFR binding $^{10}$Fn3 comprising a BC loop comprising the amino acid sequence XXXXXXYQ, a DE loop comprising the amino acid sequence (G/Y/H)(D/M/G)(V/L/I)X, and an FG loop comprising an amino acid sequence (D/N)(Y/M)(Y/A/M)(Y/H/F)(K/Q/V)(E/P/R)(Y/T/K)X(E/Y/Q)(Y/G/H), wherein X is any amino acid.

In another embodiment, the invention provides an EGFR binding $^{10}$Fn3 comprising a BC loop comprising the amino acid sequence XXXXXXYQ, a DE loop comprising the amino acid sequence (G/Y/H)(D/M/G)(V/L/I)X, and an FG loop comprising an amino acid sequence D(Y/F/W)(Y/F/K)(N/D/P)(P/H/L)(A/T/V)(T/D/S)(H/Y/G)(E/P/V)(Y/H)(T/K/I)(Y/F)(H/N/Q)(T/Q/E)(T/S/I), wherein X is any amino acid.

In another embodiment, the invention provides an EGFR binding $^{10}$Fn3 comprising a BC loop comprising the amino acid sequence XXXXXXYQ, a DE loop comprising the amino acid sequence XX(V/I/L/M/A)X, and an FG loop comprising an amino acid sequence selected from:

```
                                       (SEQ ID NO: 473)
i.      DY(A/Y)GKPYXEY;

(SEQ ID NO: 474)
ii.     DY(A/Y)Y(K/R/Q/T)PYXEY;

(SEQ ID NO: 475)
iii.    (D/N)Y(A/Y)(Y/F)(K/R/Q/T)EYXE(Y/H);

(SEQ ID NO: 476)
iv.     DYY(H/Y)X(R/K)X(E/T)YX;

(SEQ ID NO: 477)
v.      DYY(H/Y)(K/H/Q)(R/K)T(E/T)Y(G/P);

(SEQ ID NO: 478)
vi.     (D/N)MMHV(E/D)YXEY;

(SEQ ID NO: 479)
vii.    DYMHXXYXEY;
and
```

-continued viii. D(M/Y)YHX(K/R)X(V/I/L/M)YG; (SEQ ID NO: 480)

wherein X is any amino acid.

In another embodiment, the invention provides an EGFR binding $^{10}$Fn3 comprising a BC loop comprising the amino acid sequence XXXXXXYQ, a DE loop comprising the amino acid sequence XX(V/I/L/M/A)X, and an FG loop comprising an amino acid sequence selected from:

i. D(Y/F)(Y/F)NPXTHEYXYXXX; (SEQ ID NO: 481)

ii. D(Y/F)(Y/F)D(P/L)X(T/S)HXYXYXXX; (SEQ ID NO: 482)
and iii. D(Y/F)(K/R)PHXDGPH(T/I)YXE(S/Y); (SEQ ID NO: 483)

wherein X is any amino acid.

In another embodiment, the invention provides an EGFR binding $^{10}$Fn3 comprising a BC loop comprising the amino acid sequence XXXXXXYQ, a DE loop comprising the amino acid sequence XX(V/I/L/M/A)X, and an FG loop comprising the amino acid sequence (D/N)(M/Y)(M/A/W)(H/F/Y)(V/K)EY(A/Q/R/S/T)E(Y/H/D), wherein X is any amino acid.

In another embodiment, the invention provides an EGFR binding $^{10}$Fn3 comprising a BC loop comprising the amino acid sequence XXXXXXYQ, a DE loop comprising the amino acid sequence XX(V/I/L/M/A)X, and an FG loop comprising the amino acid sequence D(Y/F/W)(Y/F/K)(N/P/D)(P/H/L)X(T/D/S)(H/G/Y)(E/P/Y)(Y/H)XYXXX, wherein X is any amino acid.

In various embodiments, the DE loop of the EGFR binding $^{10}$Fn3 may comprise the sequence (G/Y/H)(D/M/G)(V/L/I)X.

In another embodiment, the invention provides an EGFR binding $^{10}$Fn3 comprising an FG loop comprising an amino acid sequence selected from:

i. D(Y/F)(Y/F)NPXTHEYXYXXX; (SEQ ID NO: 481)

ii. D(Y/F)(Y/F)D(P/L)X(T/S)HXYXYXXX; (SEQ ID NO: 482)
and iii. D(Y/F)(K/R)PHXDGPH(T/I)YXE(S/Y); (SEQ ID NO: 483)

wherein X is any amino acid.

In certain embodiments, the EGFR binding $^{10}$Fn3 comprises any of the consensus sequences provided above, with the proviso that the EGFR binding $^{10}$Fn3 does not comprise one or more of the following sequences:

i. VSDVPRDLEVVAATPTSLLISWQVPRPMYQRYYRITYGETG (SEQ ID NO: 484)

GNSPVQEFTVPGGVRTATISGLKPGVDYTITVYAVTDYMHS

EYRQYPISINYRT,
and ii. VSDVPRDLEVVAATPTSLLISWQVPRPMYQYYRITYGETGG (SEQ ID NO: 485)

NSPVQEFTVPGGVRTATISGLKPGVDYTITVYAVTDYMHSE

YRQYPISINYRT,
and iii. VSDVPRDLEVVAATPTSLLISWQVPRPMYQRYYRITYGETG (SEQ ID NO: 486)

GNSPVQEFTVPGGVRTATISGLKPGVDYTITVYAVTDYMHS

EYRQYPISINYRTEIDKPCQ.

In certain embodiments, an EGFR binding $^{10}$Fn3 comprising one of the consensus sequences provided above has at least 40%, 50%, 60%, 70%, 75%, or 80% identity to SEQ ID NO: 1. In certain embodiments, the overall structure of an EGFR binding $^{10}$Fn3 comprising one of the consensus sequences provided above resembles the immunoglobulin fold. In certain embodiment, an EGFR binding $^{10}$Fn3 comprising one of the consensus sequences provided above further comprises the core amino acid residues of the scaffold. In certain embodiments, an EGFR binding $^{10}$Fn3 comprising one of the consensus sequences provided above has at least 70%, 75%, 80%, 85%, 90%, 95%, 97%, 98%, or 99% identity to any one of SEQ ID NOs: 5-8, 52, 66-68, 106-108, 112-114, 140-142, 155-157, 170-172, 182, 185-187, 198-200, or 219-327. In certain embodiments, an EGFR binding $^{10}$Fn3 comprising one of the consensus sequences provided above has at least 70%, 75%, 80%, 85%, 90%, 95%, 97%, 98%, or 99% identity to the amino acid sequence of amino acid residues corresponding to E9 of SEQ ID NO: 1 through T94 of SEQ ID NO: 1 of any one of SEQ ID NOs: 5-8, 52, 66-68, 106-108, 112-114, 140-142, 155-157, 170-172, 182, 185-187, 198-200, or 219-327. In certain embodiments, the EGFR binding $^{10}$Fn3 comprising one of the consensus sequences provided above comprises a $^{10}$Fn3 scaffold having from has anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the scaffold amino acids residues of SEQ ID NO: 1.

In certain embodiments, the invention provides an EGFR binding $^{10}$Fn3 comprising a BC loop having the amino acid sequence set forth in amino acids 23-30, a DE loop having the amino acid sequence set forth in amino acids 52-55, and an FG loop having the amino acid sequence set forth in amino acids 77-86 of any one of SEQ ID NOs: 219-327. In certain embodiments, the invention provides an EGFR binding $^{10}$Fn3 comprising a BC loop having the amino acid sequence set forth in amino acids 21-30, a DE loop having the amino acid sequence set forth in amino acids 51-56, and an FG loop having the amino acid sequence set forth in amino acids 76-87 of any one of SEQ ID NOs: 219-327. In certain embodiments, the invention provides an EGFR binding $^{10}$Fn3 comprising an amino acid sequence at least 60%, 75%, 80%, 85%, 90%, 95%, or 98% identical to any one of SEQ ID NOs: 219-327.

In one embodiment, an antibody-like protein is provided comprising a tenth fibronectin type III domain ($^{10}$Fn3) that binds EGFR with a $K_D$ of less than 500 nM and comprises a BC loop having the amino acid sequence set forth in amino acids 21-30 of SEQ ID NO: 5, a DE loop having the amino acid sequence set forth in amino acids 51-56 of SEQ ID NO: 5, and an FG loop having the amino acid sequence set forth in amino acids 76-92 of SEQ ID NO: 5. In some embodiments, the EGFR binding $^{10}$Fn3 comprises a BC loop having the amino acid sequence X$_g$DSGRGSYQX$_h$ (SEQ ID NO: 40), a DE loop having the amino acid sequence X$_i$GPVHX$_j$ (SEQ ID NO: 42), and an FG loop having the amino acid sequence X$_k$DHKPHADGPHTYHEX$_l$ (SEQ ID NO: 44); wherein X is any amino acid and g, h, i, j, k, and l are integers independently selected from 0 to 5. In some embodiments, the EGFR binding $^{10}$Fn3 comprises a BC loop having the amino acid sequence SWDSGRGSYQ (SEQ ID NO: 39), a DE loop having the amino acid sequence PGPVHT (SEQ ID NO: 41), and an FG loop having the amino acid sequence TDHKPHADGPHTYHESP (SEQ ID NO: 43). In some embodiments, the EGFR binding $^{10}$Fn3 has an amino acid sequence at least 80, 90, 95, or 100% identical to SEQ ID NOs: 5 or 6.

In one embodiment, an antibody-like protein is provided comprising a tenth fibronectin type III domain ($^{10}$Fn3) that binds EGFR with a K$_D$ of less than 500 nM and comprises a BC loop having the amino acid sequence set forth in amino acids 21-30 of SEQ ID NO: 7, a DE loop having the amino acid sequence set forth in amino acids 51-56 of SEQ ID NO: 7, and an FG loop having the amino acid sequence set forth in amino acids 76-87 of SEQ ID NO: 7. In some embodiments, the EGFR binding $^{10}$Fn3 comprises a BC loop having the amino acid sequence X$_m$VAGAEDYQX$_n$ (SEQ ID NO: 34), a DE loop having the amino acid sequence X$_o$HDLVX$_p$ (SEQ ID NO: 36), and an FG loop having the amino acid sequence X$_q$DMMHVEYTEHX$_r$ (SEQ ID NO: 38); wherein X is any amino acid and m, n, o, p, q, and r are integers independently selected from 0 to 5. In some embodiments, the EGFR binding $^{10}$Fn3 comprises a BC loop having the amino acid sequence SWVAGAEDYQ (SEQ ID NO: 33), a DE loop having the amino acid sequence PHDLVT (SEQ ID NO: 35), and an FG loop having the amino acid sequence TDMMHVEYTEHP (SEQ ID NO: 37). In some embodiments, the EGFR binding $^{10}$Fn3 has an amino acid sequence at least 80, 90, 95, or 100% identical to SEQ ID NO: 7 or 8.

In one embodiment, an antibody-like protein is provided comprising a tenth fibronectin type III domain ($^{10}$Fn3) that binds EGFR with a K$_D$ of less than 500 nM and comprises a BC loop having the amino acid sequence set forth in amino acids 23-30 of SEQ ID NO: 82, a DE loop having the amino acid sequence set forth in amino acids 51-55 of SEQ ID NO: 82, and an FG loop having the amino acid sequence set forth in amino acids 76-86 of SEQ ID NO: 82. In some embodiments, the EGFR binding $^{10}$Fn3 comprises a BC loop having the amino acid sequence X$_s$LPGKLRYQX$_t$ (SEQ ID NO: 60), a DE loop having the amino acid sequence X$_u$HDLRX$_w$ (SEQ ID NO: 62), and an FG loop having the amino acid sequence X$_y$NMMHVEYSEYX$_z$ (SEQ ID NO: 64); wherein X is any amino acid and s, t, u, w, y and z are integers independently selected from 0 to 5. In some embodiments, the EGFR binding $^{10}$Fn3 comprises a BC loop having the amino acid sequence LPGKLRYQ (resdiues 3-13 of SEQ ID NO: 59), a DE loop having the amino acid sequence PHDLR (residues 1-5 of SEQ ID NO: 61), and an FG loop having the amino acid sequence TNMMHVEYSEY (residues 1-11 of SEQ ID NO: 63). In some embodiments, the EGFR binding $^{10}$Fn3 has an amino acid sequence at least 80, 90, 95, or 100% identical to SEQ ID NO: 52 or 82.

In one embodiment, an antibody-like protein is provided comprising a tenth fibronectin type III domain ($^{10}$Fn3) that binds EGFR with a K$_D$ of less than 500 nM and comprises a BC loop having the amino acid sequence set forth in amino acids 23-30 of SEQ ID NO: 106, a DE loop having the amino acid sequence set forth in amino acids 51-55 of SEQ ID NO: 106, and an FG loop having the amino acid sequence set forth in amino acids 76-86 of SEQ ID NO: 106. In some embodiments, the EGFR binding $^{10}$Fn3 comprises a BC loop having the amino acid sequence X$_g$HERDGSRQX$_h$ (SEQ ID NO: 134), a DE loop having the amino acid sequence X$_i$GGVRX$_j$ (SEQ ID NO: 135), and an FG loop having the amino acid sequence X$_k$DYFNPTTHEYIYQTX$_l$ (SEQ ID NO: 136); wherein X is any amino acid and g, h, i, j, k and l are integers independently selected from 0 to 5. In some embodiments, the EGFR binding $^{10}$Fn3 comprises a BC loop having the amino acid sequence SWHERDGSRQ (SEQ ID NO: 109), a DE loop having the amino acid sequence PGGVRT (SEQ ID NO: 110), and an FG loop having the amino acid sequence TDYFNPTTHEYIYQTTP (SEQ ID NO: 111). In some embodiments, the EGFR binding $^{10}$Fn3 has an amino acid sequence at least 80, 90, 95, or 100% identical to any one of SEQ ID NOs: 106-108.

In one embodiment, an antibody-like protein is provided comprising a tenth fibronectin type III domain ($^{10}$Fn3) that binds EGFR with a K$_D$ of less than 500 nM and comprises a BC loop having the amino acid sequence set forth in amino acids 23-30 of SEQ ID NO: 112, a DE loop having the amino acid sequence set forth in amino acids 51-55 of SEQ ID NO: 112, and an FG loop having the amino acid sequence set forth in amino acids 76-86 of SEQ ID NO: 112. In some embodiments, the EGFR binding $^{10}$Fn3 comprises a BC loop having the amino acid sequence X$_g$WAPVDRYQX$_h$ (SEQ ID NO: 137), a DE loop having the amino acid sequence X$_i$RDVYX$_j$ (SEQ ID NO: 138), and an FG loop having the amino acid sequence X$_k$DYKPHADGPHTYHESX$_l$ (SEQ ID NO: 139); wherein X is any amino acid and g, h, i, j, k and l are integers independently selected from 0 to 5. In some embodiments, the EGFR binding $^{10}$Fn3 comprises a BC loop having the amino acid sequence SWWAPVDRYQ (SEQ ID NO: 115), a DE loop having the amino acid sequence PRDVYT (SEQ ID NO: 116), and an FG loop having the amino acid sequence TDYKPHADGPHTYHESP (SEQ ID NO: 117). In some embodiments, the EGFR binding $^{10}$Fn3 has an amino acid sequence at least 80, 90, 95, or 100% identical to any one of SEQ ID NOs: 112-114.

In one embodiment, an antibody-like protein is provided comprising a tenth fibronectin type III domain ($^{10}$Fn3) that binds EGFR with a K$_D$ of less than 500 nM and comprises a BC loop having the amino acid sequence set forth in amino acids 13-22 of SEQ ID NO: 141, a DE loop having the amino acid sequence set forth in amino acids 43-48 of SEQ ID NO: 141, and an FG loop having the amino acid sequence set forth in amino acids 68-84 of SEQ ID NO: 141. In some embodiments, the EGFR binding $^{10}$Fn3 comprises a BC loop having the amino acid sequence X$_g$TQGSTHYQX$_h$ (SEQ ID NO: 146), a DE loop having the amino acid sequence X$_i$GMVYX$_j$ (SEQ ID NO: 147), and an FG loop having the amino acid sequence X$_k$DYFDRSTHEYKYRTX$_l$ (SEQ ID NO: 148); wherein X is any amino acid and g, h, i, j, k and l are integers independently selected from 0 to 5. In some embodiments, the EGFR binding $^{10}$Fn3 comprises a BC loop having the amino acid sequence SWTQGSTHYQ (SEQ ID NO: 143), a DE loop having the amino acid sequence PGMVYT (SEQ ID NO: 144), and an FG loop having the amino acid sequence TDYFDRSTHEYKYRTTP (SEQ ID NO: 145). In some embodiments, the EGFR binding $^{10}$Fn3 has an amino acid sequence at least 80, 90, 95, or 100% identical to any one of SEQ ID NOs: 140-142.

In one embodiment, an antibody-like protein is provided comprising a tenth fibronectin type III domain ($^{10}$Fn3) that binds EGFR with a $K_D$ of less than 500 nM and comprises a BC loop having the amino acid sequence set forth in amino acids 13-22 of SEQ ID NO: 156, a DE loop having the amino acid sequence set forth in amino acids 43-48 of SEQ ID NO: 156, and an FG loop having the amino acid sequence set forth in amino acids 68-84 of SEQ ID NO: 156. In some embodiments, the EGFR binding $^{10}$Fn3 comprises a BC loop having the amino acid sequence $X_g$YWEGLPYQX$_h$ (SEQ ID NO: 161), a DE loop having the amino acid sequence $X_i$RDVNX$_j$ (SEQ ID NO: 162), and an FG loop having the amino acid sequence $X_k$DWYNPDTHEYIYHTIX$_l$ (SEQ ID NO: 163); wherein X is any amino acid and g, h, i, j, k and l are integers independently selected from 0 to 5. In some embodiments, the EGFR binding $^{10}$Fn3 comprises a BC loop having the amino acid sequence SWYWEGLPYQ (SEQ ID NO: 158), a DE loop having the amino acid sequence PRDVNT (SEQ ID NO: 159), and an FG loop having the amino acid sequence TDWYNPDTHEYIYHTIP (SEQ ID NO: 160). In some embodiments, the EGFR binding $^{10}$Fn3 has an amino acid sequence at least 80, 90, 95, or 100% identical to any one of SEQ ID NOs: 155-157.

In one embodiment, an antibody-like protein is provided comprising a tenth fibronectin type III domain ($^{10}$Fn3) that binds EGFR with a $K_D$ of less than 500 nM and comprises a BC loop having the amino acid sequence set forth in amino acids 13-22 of SEQ ID NO: 171, a DE loop having the amino acid sequence set forth in amino acids 43-48 of SEQ ID NO: 171, and an FG loop having the amino acid sequence set forth in amino acids 68-84 of SEQ ID NO: 171. In some embodiments, the EGFR binding $^{10}$Fn3 comprises a BC loop having the amino acid sequence $X_g$ASNRGTYQX$_h$ (SEQ ID NO: 176), a DE loop having the amino acid sequence $X_i$GGVSX$_j$ (SEQ ID NO: 177), and an FG loop having the amino acid sequence $X_k$DAFNPTTHEYNYFTTX$_l$ (SEQ ID NO: 178); wherein X is any amino acid and g, h, i, j, k and l are integers independently selected from 0 to 5. In some embodiments, the EGFR binding $^{10}$Fn3 comprises a BC loop having the amino acid sequence SWASNRGTYQ (SEQ ID NO: 173), a DE loop having the amino acid sequence PGGVST (SEQ ID NO: 174), and an FG loop having the amino acid sequence TDAFNPTTHEYNYFTTP (SEQ ID NO: 175). In some embodiments, the EGFR binding $^{10}$Fn3 has an amino acid sequence at least 80, 90, 95, or 100% identical to any one of SEQ ID NOs: 170-172.

In one embodiment, an antibody-like protein is provided comprising a tenth fibronectin type III domain ($^{10}$Fn3) that binds EGFR with a $K_D$ of less than 500 nM and comprises a BC loop having the amino acid sequence set forth in amino acids 13-22 of SEQ ID NO: 186, a DE loop having the amino acid sequence set forth in amino acids 43-48 of SEQ ID NO: 186, and an FG loop having the amino acid sequence set forth in amino acids 68-84 of SEQ ID NO: 186. In some embodiments, the EGFR binding $^{10}$Fn3 comprises a BC loop having the amino acid sequence $X_g$DAPTSRYQX$_h$ (SEQ ID NO: 190), a DE loop having the amino acid sequence $X_i$GGLSX$_j$ (SEQ ID NO: 191), and an FG loop having the amino acid sequence $X_k$DYKPHADGPHTYHESX$_l$ (SEQ ID NO: 139); wherein X is any amino acid and g, h, i, j, k and l are integers independently selected from 0 to 5. In some embodiments, the EGFR binding $^{10}$Fn3 comprises a BC loop having the amino acid sequence SWDAPTSRYQ (SEQ ID NO: 188), a DE loop having the amino acid sequence PGGLST (SEQ ID NO: 189), and an FG loop having the amino acid sequence TDYKPHADGPHTYHESP (SEQ ID NO: 117). In some embodiments, the EGFR binding $^{10}$Fn3 has an amino acid sequence at least 80, 90, 95, or 100% identical to any one of SEQ ID NOs: 185-187.

In one embodiment, an antibody-like protein is provided comprising a tenth fibronectin type III domain ($^{10}$Fn3) that binds EGFR with a $K_D$ of less than 500 nM and comprises a BC loop having the amino acid sequence set forth in amino acids 13-22 of SEQ ID NO: 199, a DE loop having the amino acid sequence set forth in amino acids 43-48 of SEQ ID NO: 199, and an FG loop having the amino acid sequence set forth in amino acids 68-84 of SEQ ID NO: 199. In some embodiments, the EGFR binding $^{10}$Fn3 comprises a BC loop having the amino acid sequence $X_g$DAGAVTYQX$_h$ (SEQ ID NO: 203), a DE loop having the amino acid sequence $X_i$GGVRX$_j$ (SEQ ID NO: 135), and an FG loop having the amino acid sequence $X_k$DYKPHADGPHTYHEYX$_l$ (SEQ ID NO: 204); wherein X is any amino acid and g, h, i, j, k and l are integers independently selected from 0 to 5. In some embodiments, the EGFR binding $^{10}$Fn3 comprises a BC loop having the amino acid sequence SWDAGAVTYQ (SEQ ID NO: 201), a DE loop having the amino acid sequence PGGVRT (SEQ ID NO: 110), and an FG loop having the amino acid sequence TDYKPHADGPHTYHEYP (SEQ ID NO: 202). In some embodiments, the EGFR binding $^{10}$Fn3 has an amino acid sequence at least 80, 90, 95, or 100% identical to any one of SEQ ID NOs: 198-200.

In certain embodiments, an EGFR binding $^{10}$Fn3 domain is covalently or non-covalently linked to an EGF-IR binding $^{10}$Fn3 domain. In exemplary embodiments, the IGF-IR binding $^{10}$Fn3 may comprise a BC loop having the amino acid sequence set forth in amino acids 21-30 of SEQ ID NO: 3, a DE loop having the amino acid sequence set forth in amino acids 51-56 of SEQ ID NO: 3, and an FG loop having the amino acid sequence set forth in amino acids 76-83 of SEQ ID NO: 3. In some embodiments, the IGF-IR binding $^{10}$Fn3 comprises a BC loop having the amino acid sequence $X_a$SARLKVAX$_b$ (SEQ ID NO: 46), a DE loop having the amino acid sequence $X_c$KNVYX$_d$ (SEQ ID NO: 48), and an FG loop having the amino acid sequence $X_e$RFRDYQX$_f$ (SEQ ID NO: 50), wherein X is any amino acid and a, b, c, d, e, f, g, h, i, j, k, and l are integers independently selected from 0 to 5, or wherein a is 2 and b-f are 1, or wherein a-f are zero. In some embodiments, the IGF-IR binding $^{10}$Fn3 has an amino acid sequence at least 80, 90, 95, 98, 99, or 100% identical to SEQ ID NO: 3. In certain embodiments, the IGF-IR binding $^{10}$Fn3 comprises a $^{10}$Fn3 scaffold having from has anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the scaffold amino acid residues of SEQ ID NO: 1. In certain embodiments, the IGF-IR binding $^{10}$Fn3 has anywhere from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the corresponding loop sequences of SEQ ID NO: 3.

$^{10}$Fn3 E/I Binders

One aspect of the disclosure provides E/I binders constructed from antibody-like protein multimers. In some embodiments, an antibody-like protein multimer comprises at least one EGFR binding $^{10}$Fn3 covalently or non-covalently linked to at least one IGFIR binding $^{10}$Fn3. In certain embodiments, the E/I binders described herein may be constructed as a single polypeptide chain wherein the E and I subunits may be in either orientation, e.g., from N-terminus to C-terminus, in the E-I orientation or in the I-E orientation.

The disclosure relates, in part, to the surprising discovery that multiple $^{10}$Fn3 joined via a polypeptide linker correctly fold independently of each other, retain high affinity binding, and that each of the domains retains its functional properties (see e.g., Examples 5-10). Additionally, these E/I $^{10}$Fn3 based binders demonstrate desirable biophysical properties such as low aggregation and high melting temperature ($T_m$) (see e.g., Example 4). The Examples characterize a variety of E/I $^{10}$Fn3 based binders. An exemplary IGFIR binding $^{10}$Fn3 is set forth in SEQ ID NO: 4. Exemplary EGFR binding $^{10}$Fn3 are set forth in SEQ ID NOs: 6, 8, 52, 107, 113, 140, 155, 170, 185 and 198.

In some embodiments, an E/I binder comprises an EGFR binding $^{10}$Fn3 and an IGFIR binding $^{10}$Fn3, independently having an amino acid sequence at least 40, 50, 60, 70, or 80% identical to the human $^{10}$Fn3 domain, shown in SEQ ID NO: 1. Much of the variability will generally occur in one or more of the loops.

In some embodiments, an E/I binder comprises an EGFR binding $^{10}$Fn3 and an IGFIR binding $^{10}$Fn3, independently having an amino acid sequence at least 70, 80, 85, 90, 95, 98, or 100% identical to SEQ ID NO: 32, wherein n is an integer from 1-20, o is an integer from 1-20, and p is an integer from 1-40. In some embodiments, n is an integer from 8-12, o is an integer from 4-8, and p is an integer from 4-28. In some embodiments, n is 10, o is 6, and p is 12.

In some embodiments, the disclosure provides multimers of $^{10}$Fn3 having at least one loop selected from loop BC, DE, and FG with an altered amino acid sequence relative to the sequence of the corresponding loop of the human $^{10}$Fn3. By "altered" is meant one or more amino acid sequence alterations relative to a template sequence (corresponding human fibronectin domain) and includes amino acid additions, deletions, and substitutions. Altering an amino acid sequence may be accomplished through intentional, blind, or spontaneous sequence variation, generally of a nucleic acid coding sequence, and may occur by any technique, for example, PCR, error-prone PCR, or chemical DNA synthesis. In some embodiments, an amino acid sequence is altered by substituting with or adding naturally occurring amino acids.

In some embodiments, one or more loops selected from BC, DE, and FG may be extended or shortened in length relative to the corresponding human fibronectin loop. In particular, the FG loop of the human $^{10}$Fn3 is 12 residues long, whereas the corresponding loop in antibody heavy chains ranges from 4-28 residues. To optimize antigen binding, therefore, the length of the FG loop of $^{10}$Fn3 may be altered in length as well as in sequence to obtain the greatest possible flexibility and affinity in antigen binding.

In some embodiments of the $^{10}$Fn3 molecules, the altered BC loop has up to 10 amino acid substitutions, up to 9 amino acid deletions, up to 10 amino acid insertions, or a combination of substitutions and deletions or insertions. In some embodiments, the altered DE loop has up to 6 amino acid substitutions, up to 5 amino acid deletions, up to 14 amino acid insertions or a combination of substitutions and deletions or insertions. In some embodiments, the FG loop has up to 12 amino acid substitutions, up to 11 amino acid deletions, up to 28 amino acid insertions or a combination of substitutions and deletions or insertions.

Naturally occurring $^{10}$Fn3 comprises an "arginine-glycine-aspartic acid" (RGD) integrin-binding motif in the FG loop. Preferred multimers of $^{10}$Fn3 lack an RGD integrin-binding motif.

In some embodiments, an E/I binder is an antibody-like protein dimer comprising a) an EGFR binding $^{10}$Fn3 comprising a BC loop having the amino acid sequence set forth in amino acids 21-30 of SEQ ID NO: 5, a DE loop having the amino acid sequence set forth in amino acids 51-56 of SEQ ID NO: 5, and an FG loop having the amino acid sequence set forth in amino acids 76-92 of SEQ ID NO: 5; covalently or non-covalently linked to b) an IGFIR binding $^{10}$Fn3 comprising a BC loop having the amino acid sequence set forth in amino acids 21-30 of SEQ ID NO: 3, a DE loop having the amino acid sequence set forth in amino acids 51-56 of SEQ ID NO: 3, and an FG loop having the amino acid sequence set forth in amino acids 76-83 of SEQ ID NO: 3. In some embodiments, the EGFR binding $^{10}$Fn3 has an amino acid sequence at least 80, 90, 95, 98, 99, or 100% identical to SEQ ID NO: 5. In some embodiments, the IGFIR binding $^{10}$Fn3 has an amino acid sequence at least 80, 90, 95, 98, 99, or 100% identical to SEQ ID NO: 3. In some embodiments, the E/I binder comprises an amino acid sequence at least 80, 85, 90, 95, 98, 99, or 100% identical to SEQ ID NOs: 20, 21, 23, 24, 90, 92, 101 or 103.

In some embodiments, an E/I binder is an antibody-like protein dimer comprising a) an EGFR binding $^{10}$Fn3 comprising a BC loop having the amino acid sequence set forth in amino acids 21-30 of SEQ ID NO: 7, a DE loop having the amino acid sequence set forth in amino acids 51-56 of SEQ ID NO: 7, and an FG loop having the amino acid sequence set forth in amino acids 76-87 of SEQ ID NO: 7; covalently or non-covalently linked to b) an IGFIR binding $^{10}$Fn3 comprising a BC loop having the amino acid sequence set forth in amino acids 21-30 of SEQ ID NO: 3, a DE loop having the amino acid sequence set forth in amino acids 51-56 of SEQ ID NO: 3, and an FG loop having the amino acid sequence set forth in amino acids 76-83 of SEQ ID NO: 3. In some embodiments, the EGFR binding $^{10}$Fn3 has an amino acid sequence at least 80, 90, 95, 98, or 100% identical to SEQ ID NO: 7. In some embodiments, the IGFIR binding $^{10}$Fn3 has an amino acid sequence at least 80, 90, 95, 98, or 100% identical to SEQ ID NO: 3. In some embodiments, the E/I binder comprises an amino acid sequence at least 80, 85, 90, 95, 98, or 100% identical to SEQ ID NOs: 26, 27, 29, 30, 89, 91, 100 or 102.

In some embodiments, an E/I binder is an antibody-like protein dimer comprising a) an EGFR binding $^{10}$Fn3 comprising a BC loop having the amino acid sequence set forth in amino acids 21-30 of SEQ ID NO: 82, a DE loop having the amino acid sequence set forth in amino acids 51-56 of SEQ ID NO: 82, and an FG loop having the amino acid sequence set forth in amino acids 76-87 of SEQ ID NO: 82; covalently or non-covalently linked to b) an IGFIR binding $^{10}$Fn3 comprising a BC loop having the amino acid sequence set forth in amino acids 21-30 of SEQ ID NO: 3, a DE loop having the amino acid sequence set forth in amino acids 51-56 of SEQ ID NO: 3, and an FG loop having the amino acid sequence set forth in amino acids 76-83 of SEQ ID NO: 3. In some embodiments, the EGFR binding $^{10}$Fn3 has an amino acid sequence at least 80, 90, 95, 98, or 100% identical to SEQ ID NO: 82. In some embodiments, the IGFIR binding $^{10}$Fn3 has an amino acid sequence at least 80, 90, 95, 98, or 100% identical to SEQ ID NO: 3. In some embodiments, the E/I binder comprises an amino acid sequence at least 80, 85, 90, 95, 98, or 100% identical to SEQ ID NOs: 53, 54, 87, 88, 98, 99, 104 or 105.

In some embodiments, an E/I binder is an antibody-like protein dimer comprising a) an EGFR binding $^{10}$Fn3 comprising a BC loop having the amino acid sequence set forth in amino acids 21-30 of SEQ ID NO: 106, a DE loop having the amino acid sequence set forth in amino acids 51-56 of SEQ ID NO: 106, and an FG loop having the amino acid sequence set forth in amino acids 76-92 of SEQ ID NO: 106; covalently or non-covalently linked to b) an IGFIR binding $^{10}$Fn3 comprising a BC loop having the amino acid sequence set forth in amino acids 21-30 of SEQ ID NO: 3, a DE loop having the amino acid sequence set forth in amino acids 51-56 of SEQ ID NO: 3, and an FG loop having the amino acid sequence set forth in amino acids 76-83 of SEQ ID NO: 3. In some embodiments, the EGFR binding $^{10}$Fn3 has an amino acid sequence at least 80, 90, 95, 98, or 100% identical to SEQ ID NO: 106. In some embodiments, the IGFIR binding $^{10}$Fn3 has an amino acid sequence at least 80, 90, 95, 98, or 100% identical to SEQ ID NO: 3. In some embodiments, the E/I binder comprises an amino acid sequence at least 80, 85, 90, 95, 98, or 100% identical to SEQ ID NOs: 118-125.

In some embodiments, an E/I binder is an antibody-like protein dimer comprising a) an EGFR binding $^{10}$Fn3 comprising a BC loop having the amino acid sequence set forth in amino acids 21-30 of SEQ ID NO: 112, a DE loop having the amino acid sequence set forth in amino acids 51-56 of SEQ ID NO: 112, and an FG loop having the amino acid sequence set forth in amino acids 76-92 of SEQ ID NO: 112; covalently or non-covalently linked to b) an IGFIR binding $^{10}$Fn3 comprising a BC loop having the amino acid sequence set forth in amino acids 21-30 of SEQ ID NO: 3, a DE loop having the amino acid sequence set forth in amino acids 51-56 of SEQ ID NO: 3, and an FG loop having the amino acid sequence set forth in amino acids 76-83 of SEQ ID NO: 3. In some embodiments, the EGFR binding $^{10}$Fn3 has an amino acid sequence at least 80, 90, 95, 98, or 100% identical to SEQ ID NO: 112. In some embodiments, the IGFIR binding $^{10}$Fn3 has an amino acid sequence at least 80, 90, 95, 98, or 100% identical to SEQ ID NO: 3. In some embodiments, the E/I binder comprises an amino acid sequence at least 80, 85, 90, 95, 98, or 100% identical to SEQ ID NOs: 126-133.

In some embodiments, an E/I binder is an antibody-like protein dimer comprising a) an EGFR binding $^{10}$Fn3 comprising a BC loop having the amino acid sequence set forth in amino acids 13-22 of SEQ ID NO: 141, a DE loop having the amino acid sequence set forth in amino acids 43-48 of SEQ ID NO: 141, and an FG loop having the amino acid sequence set forth in amino acids 68-84 of SEQ ID NO: 141; covalently or non-covalently linked to b) an IGFIR binding $^{10}$Fn3 comprising a BC loop having the amino acid sequence set forth in amino acids 21-30 of SEQ ID NO: 3, a DE loop having the amino acid sequence set forth in amino acids 51-56 of SEQ ID NO: 3, and an FG loop having the amino acid sequence set forth in amino acids 76-83 of SEQ ID NO: 3. In some embodiments, the EGFR binding $^{10}$Fn3 has an amino acid sequence at least 80, 90, 95, 98, or 100% identical to SEQ ID NO: 140, 141, 142 or 300. In some embodiments, the IGFIR binding $^{10}$Fn3 has an amino acid sequence at least 80, 90, 95, 98, or 100% identical to SEQ ID NO: 3. In some embodiments, the E/I binder comprises an amino acid sequence at least 80, 85, 90, 95, 98, or 100% identical to SEQ ID NOs: 149-154.

In some embodiments, an E/I binder is an antibody-like protein dimer comprising a) an EGFR binding $^{10}$Fn3 comprising a BC loop having the amino acid sequence set forth in amino acids 13-22 of SEQ ID NO: 156, a DE loop having the amino acid sequence set forth in amino acids 43-48 of SEQ ID NO: 156, and an FG loop having the amino acid sequence set forth in amino acids 68-84 of SEQ ID NO: 156; covalently or non-covalently linked to b) an IGFIR binding $^{10}$Fn3 comprising a BC loop having the amino acid sequence set forth in amino acids 21-30 of SEQ ID NO: 3, a DE loop having the amino acid sequence set forth in amino acids 51-56 of SEQ ID NO: 3, and an FG loop having the amino acid sequence set forth in amino acids 76-83 of SEQ ID NO: 3. In some embodiments, the EGFR binding $^{10}$Fn3 has an amino acid sequence at least 80, 90, 95, 98, or 100% identical to SEQ ID NO: 155, 156, 157 or 305. In some embodiments, the IGFIR binding $^{10}$Fn3 has an amino acid sequence at least 80, 90, 95, 98, or 100% identical to SEQ ID NO: 3. In some embodiments, the E/I binder comprises an amino acid sequence at least 80, 85, 90, 95, 98, or 100% identical to SEQ ID NOs: 158-166.

In some embodiments, an E/I binder is an antibody-like protein dimer comprising a) an EGFR binding $^{10}$Fn3 comprising a BC loop having the amino acid sequence set forth in amino acids 13-22 of SEQ ID NO: 171, a DE loop having the amino acid sequence set forth in amino acids 43-48 of SEQ ID NO: 171, and an FG loop having the amino acid sequence set forth in amino acids 68-84 of SEQ ID NO: 171; covalently or non-covalently linked to b) an IGFIR binding $^{10}$Fn3 comprising a BC loop having the amino acid sequence set forth in amino acids 21-30 of SEQ ID NO: 3, a DE loop having the amino acid sequence set forth in amino acids 51-56 of SEQ ID NO: 3, and an FG loop having the amino acid sequence set forth in amino acids 76-83 of SEQ ID NO: 3. In some embodiments, the EGFR binding $^{10}$Fn3 has an amino acid sequence at least 80, 90, 95, 98, or 100% identical to SEQ ID NO: 170, 171, 172 or 311. In some embodiments, the IGFIR binding $^{10}$Fn3 has an amino acid sequence at least 80, 90, 95, 98, or 100% identical to SEQ ID NO: 3. In some embodiments, the E/I binder comprises an amino acid sequence at least 80, 85, 90, 95, 98, or 100% identical to SEQ ID NOs: 179-184.

In some embodiments, an E/I binder is an antibody-like protein dimer comprising a) an EGFR binding $^{10}$Fn3 comprising a BC loop having the amino acid sequence set forth in amino acids 13-22 of SEQ ID NO: 186, a DE loop having the amino acid sequence set forth in amino acids 43-48 of SEQ ID NO: 186, and an FG loop having the amino acid sequence set forth in amino acids 68-84 of SEQ ID NO: 186; covalently or non-covalently linked to b) an IGFIR binding $^{10}$Fn3 comprising a BC loop having the amino acid sequence set forth in amino acids 21-30 of SEQ ID NO: 3, a DE loop having the amino acid sequence set forth in amino acids 51-56 of SEQ ID NO: 3, and an FG loop having the amino acid sequence set forth in amino acids 76-83 of SEQ ID NO: 3. In some embodiments, the EGFR binding $^{10}$Fn3 has an amino acid sequence at least 80, 90, 95, 98, or 100% identical to SEQ ID NO: 185, 186, 187 or 320. In some embodiments, the IGFIR binding $^{10}$Fn3 has an amino acid sequence at least 80, 90, 95, 98, or 100% identical to SEQ ID NO: 3. In some embodiments, the E/I binder comprises an amino acid sequence at least 80, 85, 90, 95, 98, or 100% identical to SEQ ID NOs: 192-197.

In some embodiments, an E/I binder is an antibody-like protein dimer comprising a) an EGFR binding $^{10}$Fn3 comprising a BC loop having the amino acid sequence set forth in amino acids 13-22 of SEQ ID NO: 199, a DE loop having the amino acid sequence set forth in amino acids 43-48 of SEQ ID NO: 199, and an FG loop having the amino acid sequence set forth in amino acids 68-84 of SEQ ID NO: 199; covalently or non-covalently linked to b) an IGFIR binding $^{10}$Fn3 comprising a BC loop having the amino acid sequence set forth in amino acids 21-30 of SEQ ID NO: 3, a DE loop having the amino acid sequence set forth in amino acids 51-56 of SEQ ID NO: 3, and an FG loop having the amino acid sequence set forth in amino acids 76-83 of SEQ ID NO: 3. In some embodiments, the EGFR binding $^{10}$Fn3 has an amino acid sequence at least 80, 90, 95, 98, or 100% identical to SEQ ID NO: 198, 199, 200 or 327. In some embodiments, the IGF1R binding $^{10}$Fn3 has an amino acid sequence at least 80, 90, 95, 98, or 100% identical to SEQ ID NO: 3. In some embodiments, the E/I binder comprises an amino acid sequence at least 80, 85, 90, 95, 98, or 100% identical to SEQ ID NOs: 205-210.

In some embodiments, an E/I binder is an antibody-like protein dimer comprising an IGF1R binding $^{10}$Fn3 comprising a BC loop having the amino acid sequence $X_a$SARLK-VA$X_b$ (SEQ ID NO: 46), a DE loop having the amino acid sequence $X_c$KNVY$X_d$ (SEQ ID NO: 48), and an FG loop having the amino acid sequence $X_e$RFRDYQ$X_f$ (SEQ ID NO: 50); covalently or non-covalently linked to an EGFR binding $^{10}$Fn3 comprising a BC loop having the amino acid sequence $X_g$DSGRGSY$X_h$ (SEQ ID NO: 40), a DE loop having the amino acid sequence $X_i$GPVH$X_j$ (SEQ ID NO: 42), and an FG loop having the amino acid sequence $X_k$DHKPHADGPHTYHE$X_l$(SEQ ID NO: 44); wherein X is any amino acid and a, b, c, d, e, f, g, h, i, j, k, and l are integers independently selected from 0 to 5. In some embodiments, a, g, and l are 2; b-f and i-k are 1; and h is zero. In some embodiments, a-l are zero.

In some embodiments, an E/I binder is an antibody-like protein dimer comprising an IGF1R binding $^{10}$Fn3 comprising a BC loop having the amino acid sequence SWSAR-LKVAR (SEQ ID NO: 45), a DE loop having the amino acid sequence PKNVYT (SEQ ID NO: 47), and an FG loop having the amino acid sequence TRFRDYQP (SEQ ID NO: 49); covalently or non-covalently linked to an EGFR binding $^{10}$Fn3 comprising a BC loop having the amino acid sequence SWDSGRGSYQ (SEQ ID NO: 39), a DE loop having the amino acid sequence PGPVHT (SEQ ID NO: 41), and an FG loop having the amino acid sequence TDHKPHADGPHTYHESP (SEQ ID NO: 43).

In some embodiments, an E/I binder is an antibody-like protein dimer comprising an IGF1R binding $^{10}$Fn3 comprising a BC loop having the amino acid sequence $X_a$SARLK-VA$X_b$ (SEQ ID NO: 46), a DE loop having the amino acid sequence $X_c$KNVY$X_d$ (SEQ ID NO: 48), and an FG loop having the amino acid sequence $X_e$RFRDYQ$X_f$ (SEQ ID NO: 50); covalently or non-covalently linked to an EGFR binding $^{10}$Fn3 comprising a BC loop having the amino acid sequence $X_m$VAGAEDYQ$X_n$ (SEQ ID NO: 34), a DE loop having the amino acid sequence $X_o$HDLV$X_p$ (SEQ ID NO: 36), and an FG loop having the amino acid sequence $X_q$DMMHVEYTEH$X_r$ (SEQ ID NO: 38); wherein X is any amino acid and a, b, c, d, e, f, m, n, o, p, q, and r are integers from 0 to 5, independently. In some embodiments, a and m are 2; b-f and o-r are 1; and n is zero. In some embodiments, a-f and m-r are zero.

In some embodiments, an E/I binder is an antibody-like protein dimer comprising an IGF1R binding $^{10}$Fn3 comprising a BC loop having the amino acid sequence SWSAR-LKVAR (SEQ ID NO: 45), a DE loop having the amino acid sequence PKNVYT (SEQ ID NO: 47), and an FG loop having the amino acid sequence TRFRDYQP (SEQ ID NO: 49); covalently or non-covalently linked to an EGFR binding $^{10}$Fn3 comprising a BC loop having the amino acid sequence SWVAGAEDYQ (SEQ ID NO: 33), a DE loop having the amino acid sequence PHDLVT (SEQ ID NO: 35), and an FG loop having the amino acid sequence TDMM-HVEYTEHP (SEQ ID NO: 37).

In some embodiments, an E/I binder is an antibody-like protein dimer comprising an IGF1R binding $^{10}$Fn3 comprising a BC loop having the amino acid sequence $X_a$SARLK-VA$X_b$ (SEQ ID NO: 46), a DE loop having the amino acid sequence $X_c$KNVY$X_d$ (SEQ ID NO: 48), and an FG loop having the amino acid sequence $X_e$RFRDYQ$X_f$ (SEQ ID NO: 50); covalently or non-covalently linked to an EGFR binding $^{10}$Fn3 comprising a BC loop having the amino acid sequence $X_s$LPGKLRYQ$X_t$ (SEQ ID NO: 60), a DE loop having the amino acid sequence $X_u$HDLR$X_w$ (SEQ ID NO: 62), and an FG loop having the amino acid sequence $X_y$NMMHVEYSEY$X_z$ (SEQ ID NO: 64); wherein X is any amino acid and a, b, c, d, e, f, s, t, u, w, y, and z are integers from 0 to 5, independently. In some embodiments, a and s are 2; b-f, u, w, y and z are 1; and t is zero. In some embodiments, a-f, s-u, w, y and z are zero.

In some embodiments, an E/I binder is an antibody-like protein dimer comprising an IGF1R binding $^{10}$Fn3 comprising a BC loop having the amino acid sequence SWSAR-LKVAR (SEQ ID NO: 45), a DE loop having the amino acid sequence PKNVYT (SEQ ID NO: 47), and an FG loop having the amino acid sequence TRFRDYQP (SEQ ID NO: 49); covalently or non-covalently linked to an EGFR binding $^{10}$Fn3 comprising a BC loop having the amino acid sequence SWLPGKLRYQ (SEQ ID NO: 59), a DE loop having the amino acid sequence PHDLRT (SEQ ID NO: 61), and an FG loop having the amino acid sequence TNMM-HVEYSEYP (SEQ ID NO: 63).

In some embodiments, an E/I binder is an antibody-like protein dimer comprising an IGF1R binding $^{10}$Fn3 comprising a BC loop having the amino acid sequence $X_a$SARLK-VA$X_b$ (SEQ ID NO: 46), a DE loop having the amino acid sequence $X_c$KNVY$X_d$ (SEQ ID NO: 48), and an FG loop having the amino acid sequence $X_e$RFRDYQ$X_f$ (SEQ ID NO: 50); covalently or non-covalently linked to an EGFR binding $^{10}$Fn3 comprising a BC loop having the amino acid sequence $X_g$HERDGSRQ$X_h$ (SEQ ID NO: 134), a DE loop having the amino acid sequence $X_i$GGVR$X_j$ (SEQ ID NO: 135), and an FG loop having the amino acid sequence $X_k$DYFNPTTHEYIYQTT$X_l$ (SEQ ID NO: 136); wherein X is any amino acid and a, b, c, d, e, f, g, h, i, j, k and l are integers from 0 to 5, independently. In some embodiments, a and g are 2; b-f and i-l are 1; and h is zero. In some embodiments, a-l are zero.

In some embodiments, an E/I binder is an antibody-like protein dimer comprising an IGF1R binding $^{10}$Fn3 comprising a BC loop having the amino acid sequence SWSAR-LKVAR (SEQ ID NO: 45), a DE loop having the amino acid sequence PKNVYT (SEQ ID NO: 47), and an FG loop having the amino acid sequence TRFRDYQP (SEQ ID NO: 49); covalently or non-covalently linked to an EGFR binding $^{10}$Fn3 comprising a BC loop having the amino acid sequence SWHERDGSRQ (SEQ ID NO: 109), a DE loop having the amino acid sequence PGGVRT (SEQ ID NO: 110), and an FG loop having the amino acid sequence TDYFNPTTHEYIYQTTP (SEQ ID NO: 111).

In some embodiments, an E/I binder is an antibody-like protein dimer comprising an IGF1R binding $^{10}$Fn3 comprising a BC loop having the amino acid sequence $X_a$SARLK-VA$X_b$ (SEQ ID NO: 46), a DE loop having the amino acid sequence $X_c$KNVY$X_d$ (SEQ ID NO: 48), and an FG loop having the amino acid sequence $X_e$RFRDYQ$X_f$ (SEQ ID NO: 50); covalently or non-covalently linked to an EGFR binding $^{10}$Fn3 comprising a BC loop having the amino acid sequence $X_g$WAPVDRYQ$X_h$ (SEQ ID NO: 137), a DE loop having the amino acid sequence $X_i$RDVY$X_j$ (SEQ ID NO: 138), and an FG loop having the amino acid sequence $X_k$DYKPHADGPHTYHES$X_l$ (SEQ ID NO: 139); wherein X is any amino acid and a, b, c, d, e, f, g, h, i, j, k and l are integers from 0 to 5, independently. In some embodiments, a and g are 2; b-f and i-l are 1; and h is zero. In some embodiments, a-l are zero.

In some embodiments, an E/I binder is an antibody-like protein dimer comprising an IGFIR binding $^{10}$Fn3 comprising a BC loop having the amino acid sequence SWSARLKVAR (SEQ ID NO: 45), a DE loop having the amino acid sequence PKNVYT (SEQ ID NO: 47), and an FG loop having the amino acid sequence TRFRDYQP (SEQ ID NO: 49); covalently or non-covalently linked to an EGFR binding $^{10}$Fn3 comprising a BC loop having the amino acid sequence SWWAPVDRYQ (SEQ ID NO: 115), a DE loop having the amino acid sequence PRDVYT (SEQ ID NO: 116), and an FG loop having the amino acid sequence TDYKPHADGPHTYHESP (SEQ ID NO: 117).

In some embodiments, an E/I binder is an antibody-like protein dimer comprising an IGFIR binding $^{10}$Fn3 comprising a BC loop having the amino acid sequence X$_a$SARLKVAX$_b$ (SEQ ID NO: 46), a DE loop having the amino acid sequence X$_c$KNVYX$_d$ (SEQ ID NO: 48), and an FG loop having the amino acid sequence X$_e$RFRDYQX$_f$ (SEQ ID NO: 50); covalently or non-covalently linked to an EGFR binding $^{10}$Fn3 comprising a BC loop having the amino acid sequence X$_g$TQGSTHYQX$_h$ (SEQ ID NO: 146), a DE loop having the amino acid sequence X$_i$GMVYX$_j$ (SEQ ID NO: 147), and an FG loop having the amino acid sequence X$_k$DYFDRSTHEYKYRTTX$_l$ (SEQ ID NO: 148); wherein X is any amino acid and a, b, c, d, e, f, g, h, i, j, k and l are integers from 0 to 5, independently. In some embodiments, a and g are 2; b-f and i-l are 1; and h is zero. In some embodiments, a-l are zero.

In some embodiments, an E/I binder is an antibody-like protein dimer comprising an IGFIR binding $^{10}$Fn3 comprising a BC loop having the amino acid sequence SWSARLKVAR (SEQ ID NO: 45), a DE loop having the amino acid sequence PKNVYT (SEQ ID NO: 47), and an FG loop having the amino acid sequence TRFRDYQP (SEQ ID NO: 49); covalently or non-covalently linked to an EGFR binding $^{10}$Fn3 comprising a BC loop having the amino acid sequence SWTQGSTHYQ (SEQ ID NO: 143), a DE loop having the amino acid sequence PGMVYT (SEQ ID NO: 144), and an FG loop having the amino acid sequence TDYFDRSTHEYKYRTTP (SEQ ID NO: 145).

In some embodiments, an E/I binder is an antibody-like protein dimer comprising an IGFIR binding $^{10}$Fn3 comprising a BC loop having the amino acid sequence X$_a$SARLKVAX$_b$ (SEQ ID NO: 46), a DE loop having the amino acid sequence X$_c$KNVYX$_d$ (SEQ ID NO: 48), and an FG loop having the amino acid sequence X$_e$RFRDYQX$_f$ (SEQ ID NO: 50); covalently or non-covalently linked to an EGFR binding $^{10}$Fn3 comprising a BC loop having the amino acid sequence X$_g$YWEGLPYQX$_h$ (SEQ ID NO: 161), a DE loop having the amino acid sequence X$_i$RDVNX$_j$ (SEQ ID NO: 162), and an FG loop having the amino acid sequence X$_k$DWYNPDTHEYIYHTIX$_l$ (SEQ ID NO: 163); wherein X is any amino acid and a, b, c, d, e, f, g, h, i, j, k and l are integers from 0 to 5, independently. In some embodiments, a and g are 2; b-f and i-l are 1; and h is zero. In some embodiments, a-l are zero.

In some embodiments, an E/I binder is an antibody-like protein dimer comprising an IGFIR binding $^{10}$Fn3 comprising a BC loop having the amino acid sequence SWSARLKVAR (SEQ ID NO: 45), a DE loop having the amino acid sequence PKNVYT (SEQ ID NO: 47), and an FG loop having the amino acid sequence TRFRDYQP (SEQ ID NO: 49); covalently or non-covalently linked to an EGFR binding $^{10}$Fn3 comprising a BC loop having the amino acid sequence SWYWEGLPYQ (SEQ ID NO: 158), a DE loop having the amino acid sequence PRDVNT (SEQ ID NO: 159), and an FG loop having the amino acid sequence TDWYNPDTHEYIYHTIP (SEQ ID NO: 160).

In some embodiments, an E/I binder is an antibody-like protein dimer comprising an IGFIR binding $^{10}$Fn3 comprising a BC loop having the amino acid sequence X$_a$SARLKVAX$_b$ (SEQ ID NO: 46), a DE loop having the amino acid sequence X$_c$KNVYX$_d$ (SEQ ID NO: 48), and an FG loop having the amino acid sequence X$_e$RFRDYQX$_f$ (SEQ ID NO: 50); covalently or non-covalently linked to an EGFR binding $^{10}$Fn3 comprising a BC loop having the amino acid sequence X$_g$ASNRGTYQX$_h$ (SEQ ID NO: 176), a DE loop having the amino acid sequence X$_i$GGVSX$_j$ (SEQ ID NO: 177), and an FG loop having the amino acid sequence X$_k$DAFNPTTHEYNYFTTX$_l$ (SEQ ID NO: 178); wherein X is any amino acid and a, b, c, d, e, f, g, h, i, j, k and l are integers from 0 to 5, independently. In some embodiments, a and g are 2; b-f and i-l are 1; and h is zero. In some embodiments, a-l are zero.

In some embodiments, an E/I binder is an antibody-like protein dimer comprising an IGFIR binding $^{10}$Fn3 comprising a BC loop having the amino acid sequence SWSARLKVAR (SEQ ID NO: 45), a DE loop having the amino acid sequence PKNVYT (SEQ ID NO: 47), and an FG loop having the amino acid sequence TRFRDYQP (SEQ ID NO: 49); covalently or non-covalently linked to an EGFR binding $^{10}$Fn3 comprising a BC loop having the amino acid sequence SWASNRGTYQ (SEQ ID NO: 173), a DE loop having the amino acid sequence PGGVST (SEQ ID NO: 174), and an FG loop having the amino acid sequence TDAFNPTTHEYNYFTTP (SEQ ID NO: 175).

In some embodiments, an E/I binder is an antibody-like protein dimer comprising an IGFIR binding $^{10}$Fn3 comprising a BC loop having the amino acid sequence X$_a$SARLKVAX$_b$ (SEQ ID NO: 46), a DE loop having the amino acid sequence X$_c$KNVYX$_d$ (SEQ ID NO: 48), and an FG loop having the amino acid sequence X$_e$RFRDYQX$_f$ (SEQ ID NO: 50); covalently or non-covalently linked to an EGFR binding $^{10}$Fn3 comprising a BC loop having the amino acid sequence X$_g$DAPTSRYQX$_h$ (SEQ ID NO: 190), a DE loop having the amino acid sequence X$_i$GGLSX$_j$ (SEQ ID NO: 191), and an FG loop having the amino acid sequence X$_k$DYKPHADGPHTYHESX$_l$ (SEQ ID NO: 139); wherein X is any amino acid and a, b, c, d, e, f, g, h, i, j, k and l are integers from 0 to 5, independently. In some embodiments, a and g are 2; b-f and i-l are 1; and h is zero. In some embodiments, a-l are zero.

In some embodiments, an E/I binder is an antibody-like protein dimer comprising an IGFIR binding $^{10}$Fn3 comprising a BC loop having the amino acid sequence SWSARLKVAR (SEQ ID NO: 45), a DE loop having the amino acid sequence PKNVYT (SEQ ID NO: 47), and an FG loop having the amino acid sequence TRFRDYQP (SEQ ID NO: 49); covalently or non-covalently linked to an EGFR binding $^{10}$Fn3 comprising a BC loop having the amino acid sequence SWDAPTSRYQ (SEQ ID NO: 188), a DE loop having the amino acid sequence PGGLST (SEQ ID NO: 189), and an FG loop having the amino acid sequence TDYKPHADGPHTYHESP (SEQ ID NO: 117).

In some embodiments, an E/I binder is an antibody-like protein dimer comprising an IGFIR binding $^{10}$Fn3 comprising a BC loop having the amino acid sequence X$_a$SARLKVAX$_b$ (SEQ ID NO: 46), a DE loop having the amino acid sequence X$_c$KNVYX$_d$ (SEQ ID NO: 48), and an FG loop having the amino acid sequence X$_e$RFRDYQX$_f$ (SEQ ID NO: 50); covalently or non-covalently linked to an EGFR binding ¹⁰Fn3 comprising a BC loop having the amino acid sequence X$_g$DAGAVTYQX$_h$ (SEQ ID NO: 203), a DE loop having the amino acid sequence X$_i$GGVRX$_j$ (SEQ ID NO: 135), and an FG loop having the amino acid sequence X$_k$DYKPHADGPHTYHEYX$_l$ (SEQ ID NO: 204); wherein X is any amino acid and a, b, c, d, e, f, g, h, i, j, k and l are integers from 0 to 5, independently. In some embodiments, a and g are 2; b-f and i-l are 1; and h is zero. In some embodiments, a-l are zero.

In some embodiments, an E/I binder is an antibody-like protein dimer comprising an IGFIR binding ¹⁰Fn3 comprising a BC loop having the amino acid sequence SWSARLKVAR (SEQ ID NO: 45), a DE loop having the amino acid sequence PKNVYT (SEQ ID NO: 47), and an FG loop having the amino acid sequence TRFRDYQP (SEQ ID NO: 49); covalently or non-covalently linked to an EGFR binding ¹⁰Fn3 comprising a BC loop having the amino acid sequence SWDAGAVTYQ (SEQ ID NO: 201), a DE loop having the amino acid sequence PGGVRT (SEQ ID NO: 110), and an FG loop having the amino acid sequence TDYKPHADGPHTYHEYP (SEQ ID NO: 202).

In some embodiments, an E/I binder is an antibody-like protein dimer comprising a) an IGFIR binding ¹⁰Fn3 comprising a BC loop having the amino acid sequence set forth in amino acids 23-29 of SEQ ID NO: 3, a DE loop having the amino acid sequence set forth in amino acids 52-55 of SEQ ID NO: 3, and an FG loop having the amino acid sequence set forth in amino acids 77-82 of SEQ ID NO: 3; covalently or non-covalently linked to b) an EGFR binding ¹⁰Fn3 comprising a BC, DE and FG loop as set forth in any one of SEQ ID NOs: 219-327 (see e.g., FIG. 45 wherein the BC, DE and FG loop sequences for each EGFR binding ¹⁰Fn3 are underlined). In some embodiments, an E/I binder is an antibody-like protein dimer comprising a) an IGFIR binding ¹⁰Fn3 comprising a BC loop having the amino acid sequence set forth in amino acids 23-29 of SEQ ID NO: 3, a DE loop having the amino acid sequence set forth in amino acids 52-55 of SEQ ID NO: 3, and an FG loop having the amino acid sequence set forth in amino acids 77-82 of SEQ ID NO: 3; covalently or non-covalently linked to b) an EGFR binding ¹⁰Fn3 comprising a BC loop having the amino acid sequence set forth in amino acids corresponding to amino acid residues 23-30 of SEQ ID NO: 1 of any one of SEQ ID NOs: 5-8, 52, 66-68, 106-108, 112-114, 140-142, 155-157, 170-172, 182, 185-187, 198-200, or 219-327, a DE loop having the amino acid sequence set forth in amino acids corresponding to amino acid residues 52-55 of SEQ ID NO: 1 of any one of SEQ ID NOs: 5-8, 52, 66-68, 106-108, 112-114, 140-142, 155-157, 170-172, 182, 185-187, 198-200, or 219-327, and an FG loop having the amino acid sequence set forth in amino acids corresponding to amino acid residues 77-86 of SEQ ID NO: 15-8, 52, 66-68, 106-108, 112-114, 140-142, 155-157, 170-172, 182, 185-187, 198-200, or 219-327. In some embodiments, the EGFR binding ¹⁰Fn3 of the antibody-like protein dimer comprises an amino acid sequence at least 80, 90, 95, or 100% identical to the amino acid sequence of amino acid residues corresponding to E9 of SEQ ID NO: 1 through T94 of SEQ ID NO: 1 of any one of SEQ ID NOs: 5-8, 52, 66-68, 106-108, 112-114, 140-142, 155-157, 170-172, 182, 185-187, 198-200, or 219-327. In some embodiments, the IGFIR binding ¹⁰Fn3 of the antibody-like protein dimer has an amino acid sequence at least 80, 90, 95, 98, 99, or 100% identical to the amino acid sequence of amino acid residues corresponding to E9 of SEQ ID NO: 1 through T94 of SEQ ID NO: 1 of SEQ ID NO: 3. In some embodiments, the E/I binder comprises an amino acid sequence at least 80, 85, 90, 95, 98, 99, or 100% identical to any one of SEQ ID NOs: 20-31, 53-58, 87-92, 98-105, 118-133, 149-154, 164-169, 179-184, 192-197, 205-210 and 211-216.

Preferably, X as defined herein is a naturally occurring amino acid.

In certain embodiments, the E binders, or the E and/or I monomers of the E/I binders described herein may contain a Ser to Cys amino acid substitution at a position corresponding to serine 62 or serine 91 of SEQ ID NO: 1.

In certain aspects, the disclosure provides short peptide sequences that mediate EGFR binding. Examples of such sequences include the amino acid residues that correspond to the BC, DE, and FG loops from SEQ ID NOs: 5, 7, 82, 106, 112, 141, 156, 171, 186 and 199. Other examples of such sequences include the amino acid residues that correspond to the BC, DE, and FG loops from SEQ ID NOs: 219-327. In some embodiments, the peptides bind to their respective ligand with a dissociation constant ($K_D$) of less than 500 nM, 100 nM, 50 nM, 5 nM or less. Such sequences may mediate ligand binding in an isolated form or when inserted into a particular protein structure, such as an immunoglobulin or immunoglobulin-like domain.

In one embodiment, an antibody-like protein dimer comprises a polypeptide having the structure A-B-C, wherein A is a polypeptide comprising, consisting essentially of, or consisting of a ¹⁰Fn3 domain that binds to EGFR, B is a polypeptide linker, and C is a polypeptide comprising, consisting essentially of, or consisting of a ¹⁰Fn3 domain that binds to IGF-IR. In another embodiment, a antibody-like protein dimer comprises a polypeptide having the structure A-B-C, wherein A is a polypeptide comprising, consisting essentially of, or consisting of a ¹⁰Fn3 domain that binds to IGF-IR, B is a polypeptide linker, and C is a polypeptide comprising, consisting essentially of, or consisting of a ¹⁰Fn3 domain that binds to EGFR. Specific examples of antibody-like protein dimers having the structure A-B-C are polypeptides comprising (i) a polypeptide having an amino acid sequence set forth in any one of SEQ ID NOs: 20-31, 53-58, 87-92, 98-105, 118-133, 149-154, 164-169, 179-184, 192-197, 205-210 and 211-216, or (ii) a polypeptide comprising an amino acid sequence at least 85%, 90%, 95%, 97%, 98%, or 99% identical to any one of the amino acid sequences set forth in SEQ ID NOs: 20-31, 53-58, 87-92, 98-105, 118-133, 149-154, 164-169, 179-184, 192-197, 205-210 and 211-216.

In certain embodiments, the A or C region is a polypeptide comprising a ¹⁰Fn3 domain that binds to EGFR; wherein the ¹⁰Fn3 domain has the structure from N-terminus to C-terminus: beta strand A, loop AB, beta strand B, loop BC, beta strand C, loop CD, beta strand D, loop DE, beta strand E, loop EF, beta strand F, loop FG, beta strand G; wherein: (i) the BC loop has the amino acid sequence of SEQ ID NO: 33 or 34, the DE loop has the amino acid sequence of SEQ ID NO: 35 or 36, and the FG loop has the amino acid sequence of SEQ ID NO: 37 or 38, (ii) the BC loop has the amino acid sequence of SEQ ID NO: 39 or 40, the DE loop has the amino acid sequence of SEQ ID NO: 41 or 42, and the FG loop has the amino acid sequence of SEQ ID NO: 43 or 44, (iii) the BC loop has the amino acid sequence of SEQ ID NO: 59 or 60, the DE loop has the amino acid sequence of SEQ ID NO: 61 or 62, and the FG loop has the amino acid sequence of SEQ ID NO: 63 or 64, (iv) the BC loop has the amino acid sequence of SEQ ID NO: 109 or 134, the DE loop has the amino acid sequence of SEQ ID NO: 110 or 135, and the FG loop has the amino acid sequence of SEQ ID NO: 111 or 136, (v) the BC loop has the amino acid sequence of SEQ ID NO: 115 or 137, the DE loop has the amino acid sequence of SEQ ID NO: 116 or 138, and the FG loop has the amino acid sequence of SEQ ID NO: 117 or 139, (vi) the BC loop has the amino acid sequence of SEQ ID NO: 143 or 146, the DE loop has the amino acid sequence of SEQ ID NO: 144 or 147, and the FG loop has the amino acid sequence of SEQ ID NO: 145 or 148, (vii) the BC loop has the amino acid sequence of SEQ ID NO: 158 or 161, the DE loop has the amino acid sequence of SEQ ID NO: 159 or 162, and the FG loop has the amino acid sequence of SEQ ID NO: 160 or 163, (viii) the BC loop has the amino acid sequence of SEQ ID NO: 173 or 176, the DE loop has the amino acid sequence of SEQ ID NO: 174 or 177, and the FG loop has the amino acid sequence of SEQ ID NO: 175 or 178, (ix) the BC loop has the amino acid sequence of SEQ ID NO: 188 or 190, the DE loop has the amino acid sequence of SEQ ID NO: 189 or 191, and the FG loop has the amino acid sequence of SEQ ID NO: 117 or 139, (x) the BC loop has the amino acid sequence of SEQ ID NO: 201 or 203, the DE loop has the amino acid sequence of SEQ ID NO: 110 or 135, and the FG loop has the amino acid sequence of SEQ ID NO: 202 or 204, or (xi) the BC, DE and FG loops have the amino acid sequences as set forth in any one of SEQ ID NOs: 219-327 (see e.g., FIG. 45 wherein the BC, DE and FG loops for each of SEQ ID NOs: 219-327 are underlined); wherein the $^{10}$Fn3 domain folds into an antibody heavy chain variable region-like structure; and wherein the polypeptide binds to EGFR with a $K_D$ of less than 100 nM. The $^{10}$Fn3 domain that binds to EGFR preferably folds into a structure wherein the 7 beta strands are distributed between two beta sheets that pack against each other forming a stable core and wherein the beta strands are connected by the six loops which are solvent exposed. In exemplary embodiments, the $^{10}$Fn3 domain is from 80-150 amino acids in length.

In exemplary embodiments, the A or C region is a $^{10}$Fn3 domain that binds to EGFR with a $K_D$ of less than 100 nM having a sequence selected from the group consisting of SEQ ID NO: 83-85 and 466-472 as set forth below:

(SEQ ID NO: 83)
<u>EVVAAT</u>X$_{n1}$<u>SLLI</u>X$_{a1}$SWVAGAEDYQX$_{a2}$<u>YYRITYGE</u>X$_{n2}$<u>QEFTV</u>X$_{a3}$
PHDLVTX$_{a4}$<u>ATI</u>X$_{n3}$<u>DYTITVYAV</u>X$_{a5}$TDMMHVEYTEHPX$_{a6}$<u>ISINYRT</u>;

(SEQ ID NO: 84)
<u>EVVAAT</u>X$_{n1}$<u>SLLI</u>X$_{a1}$SWDSGRGSYQX$_{a2}$<u>YYRITYGE</u>X$_{n2}$<u>QEFTV</u>X$_{a3}$
PGPVHTX$_{a4}$<u>ATI</u>X$_{n3}$<u>DYTITVYAV</u>X$_{a5}$TDHKPHADGPHTYHESPX$_{a6}$
<u>ISINYRT</u>;
or (SEQ ID NO: 85)
<u>EVVAAT</u>X$_{n1}$<u>SLLI</u>X$_{a1}$SWLPGKLRYQX$_{a2}$<u>YYRITYGE</u>X$_{n2}$<u>QEFTV</u>X$_{a3}$
PHDLRTX$_{a4}$<u>ATI</u>X$_{n3}$<u>DYTITVYAV</u>X$_{a5}$TNMMHVEYSEYPX$_{a6}$<u>ISINYRT</u>.

(SEQ ID NO: 466)
<u>EVVAAT</u>X$_{n1}$<u>SLLI</u>X$_{a1}$SWHERDGSRQX$_{a2}$<u>YYRITYGE</u>X$_{n2}$<u>QEFTV</u>X$_{a3}$
PGGVRTX$_{a4}$<u>ATI</u>X$_{n3}$<u>DYTITVYAV</u>X$_{a5}$TDYFNPTTHEYIYQTTPX$_{a6}$
<u>ISINYRT</u>.

(SEQ ID NO: 467)
<u>EVVAAT</u>X$_{n1}$<u>SLLI</u>X$_{a1}$SWWAPVDRYQX$_{a2}$<u>YYRITYGE</u>X$_{n2}$<u>QEFTV</u>X$_{a3}$
PRDVYTX$_{a4}$<u>ATI</u>X$_{n3}$<u>DYTITVYAV</u>X$_{a5}$TDYKPHADGPHTYHESPX$_{a6}$
<u>ISINYRT</u>.

(SEQ ID NO: 468)
<u>EVVAAT</u>X$_{n1}$<u>SLLI</u>X$_{a1}$SWTQGSTHYQX$_{a2}$<u>YYRITYGE</u>X$_{n2}$<u>QEFTV</u>X$_{a3}$
PGMVYTX$_{a4}$<u>ATI</u>X$_{n3}$<u>DYTITVYAV</u>X$_{a5}$TDYFDRSTHEYKYRTTPX$_{a6}$
<u>ISINYRT</u>.

(SEQ ID NO: 469)
<u>EVVAAT</u>X$_{n1}$<u>SLLI</u>X$_{a1}$SWYWEGLPYQX$_{a2}$<u>YYRITYGE</u>X$_{n2}$<u>QEFTV</u>X$_{a3}$
PRDVNTX$_{a4}$<u>ATI</u>X$_{n3}$<u>DYTITVYAV</u>X$_{a5}$TDWYNPDTHEYIYHTIPX$_{a6}$
<u>ISINYRT</u>.

(SEQ ID NO: 470)
<u>EVVAAT</u>X$_{n1}$<u>SLLI</u>X$_{a1}$SWASNRGTYQX$_{a2}$<u>YYRITYGE</u>X$_{n2}$<u>QEFTV</u>X$_{a3}$
PGGVSTX$_{a4}$<u>ATI</u>X$_{n3}$<u>DYTITVYAV</u>X$_{a5}$TDAFNPTTHEYNYFTTPX$_{a6}$
<u>ISINYRT</u>.

(SEQ ID NO: 471)
<u>EVVAAT</u>X$_{n1}$<u>SLLI</u>X$_{a1}$SWDAPTSRYQX$_{a2}$<u>YYRITYGE</u>X$_{n2}$<u>QEFTV</u>X$_{a3}$
PGGLSTX$_{a4}$<u>ATI</u>X$_{n3}$<u>DYTITVYAV</u>X$_{a5}$TDYKPHADGPHTYHESPX$_{a6}$
<u>ISINYRT</u>.

(SEQ ID NO: 472)
<u>EVVAAT</u>X$_{n1}$<u>SLLI</u>X$_{a1}$SWDAGAVTYQX$_{a2}$<u>YYRITYGE</u>X$_{n2}$<u>QEFTV</u>X$_{a3}$
PGGVRTX$_{a4}$<u>ATI</u>X$_{n3}$<u>DYTITVYAV</u>X$_{a5}$TDYKPHADGPHTYHEYPX$_{a6}$
<u>ISINYRT</u>.

In SEQ ID NOs: 83-85 and 466-472, the BC, DE and FG loops have a fixed sequence as shown in bold, or a sequence at least 75%, 80%, 85%, 90%, 95%, 97%, 98%, or 99% identical to the sequences shown in bold, the AB loop is represented by $X_{n1}$, the CD is represented by $X_{n2}$, and EF loop is represented by $X_{n3}$, and the beta strands A-G are underlined. X represents any amino acid and the subscript following the X represents an integer of the number of amino acids. In particular, n1 may be anywhere from 1-15, 2-15, 1-10, 2-10, 1-8, 2-8, 1-5, 2-5, 1-4, 2-4, 1-3, 2-3, or 1-2 amino acids; n2 and n3 may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids; and a1-a6 may each independently comprise from 0-10, 0-5, 1-10, 1-5, or 2-5 amino acids. In preferred embodiments, n1 is 2 amino acids, n2 is 7 amino acids, n3 is 7 amino acids, and a1-a6 is 0 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 1. In an exemplary embodiment, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 1. In certain embodiments, the core amino acid residues are fixed and any substitutions, conservative substitutions, deletions or additions occur at residues other than the core amino acid residues. In certain embodiments, the EGFR binder is represented by one of the following amino acid sequences:

(SEQ ID NO: 66)
<u>EVVAAT</u>PTSLLISWVAGAEDYQ<u>YYRITYGE</u>TGGNSP<u>VQEFTV</u>PHDLV<u>TAT</u>
<u>ISGLKPG</u>V<u>DYTITVYAV</u>TDMMHVEYTEHPI<u>SINYRT</u>;

```
                                              (SEQ ID NO: 67)
EVVAATPTSLLISWDSGRGSYQYYRITYGETGGNSPVQEFTVPGPVHTAT

ISGLKPGVDYTITVYAVTDHKPHADGPHTYHESPISINYRT;

(SEQ ID NO: 68)
EVVAATPTSLLISWLPGKLRYQYYRITYGETGGNSPVQEFTVPHDLRTAT

ISGLKPGVDYTITVYAVTNMMHVEYSEYPISINYRT;

(SEQ ID NO: 108)
EVVAATPTSLLISWHERDGSRQYYRITYGETGGNSPVQEFTVPGGVRTAT

ISGLKPGVDYTITVYAVTDYFNPTTHEYIYQTTPISINYRT;
or (SEQ ID NO: 114)
EVVAATPTSLLISWWAPVDRYQYYRITYGETGGNSPVQEFTVPRDVYTAT

ISGLKPGVDYTITVYAVTDYKPHADGPHTYHESPISINYRT.

(SEQ ID NO: 141)
EVVAATPTSLLISWTQGSTHYQYYRITYGETGGNSPVQEFTVPGMVYTAT

ISGLKPGVDYTITVYAVTDYFDRSTHEYKYRTTPISINYRT (SEQ ID NO: 156)
EVVAATPTSLLISWYWEGLPYQYYRITYGETGGNSPVQEFTVPRDVNTAT

ISGLKPGVDYTITVYAVTDWYNPDTHEYIYHTIPISINYRT (SEQ ID NO: 171)
EVVAATPTSLLISWASNRGTYQYYRITYGETGGNSPVQEFTVPGGVSTAT

ISGLKPGVDYTITVYAVTDAFNPTTHEYNYFTTPISINYRT (SEQ ID NO: 186)
EVVAATPTSLLISWDAPTSRYQYYRITYGETGGNSPVQEFTVPGGLSTAT

ISGLKPGVDYTITVYAVTDYKPHADGPHTYHESPISINYRT

E112
                                             (SEQ ID NO: 199)
EVVAATPTSLLISWDAGAVTYQYYRITYGETGGNSPVQEFTVPGGVRTAT

ISGLKPGVDYTITVYAVTDYKPHADGPHTYHEYPISINYRT
```

In SEQ ID NOs: 66-68, 108, 114, 141, 156, 171, 186 and 199, the sequence of the BC, DE and FG loops have a fixed sequence as shown in bold, or a sequence at least 75%, 80%, 85%, 90%, 95%, 97%, 98%, or 99% identical to the sequences shown in bold, and the remaining sequence which is underlined (e.g., the sequence of the 7 beta strands and the AB, CD and EF loops) has anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the corresponding amino acids shown in SEQ ID NO: 66-68, 108, 114, 141, 156, 171, 186 and 199. In certain embodiments, the core amino acid residues are fixed and any substitutions, conservative substitutions, deletions or additions occur at residues other than the core amino acid residues. The $^{10}$Fn3 domain that binds to EGFR may optionally comprise an N-terminal extension of from 1-20, 1-15, 1-10, 1-8, 1-5, 1-4, 1-3, 1-2, or 1 amino acids in length. Exemplary N-terminal extensions include (represented by the single letter amino acid code) M, MG, G, MGVSDVPRDL (SEQ ID NO: 69), GVSDVPRDL (SEQ ID NO: 70), and VSDVPRDL (SEQ ID NO: 71), or N-terminal truncations of any one of SEQ ID NOs: 69, 70, or 71. Other suitable N-terminal extensions include, for example, $X_n$S-DVPRDL (SEQ ID NO: 72), $X_n$DVPRDL (SEQ ID NO: 73), $X_n$VPRDL (SEQ ID NO: 74), $X_n$PRDL (SEQ ID NO: 75), $X_n$RDL (SEQ ID NO: 76), $X_n$DL (SEQ ID NO: 77), or $X_n$L, wherein n=0, 1 or 2 amino acids, wherein when n=1, X is Met or Gly, and when n=2, X is Met-Gly. The $^{10}$Fn3 domain that binds to EGFR may optionally comprise a C-terminal tail. Exemplary C-terminal tails include polypeptides that are from 1-20, 1-15, 1-10, 1-8, 1-5, 1-4, 1-3, 1-2, or 1 amino acids in length. Specific examples of C-terminal tails include EIDKPSQ (SEQ ID NO: 9), EIDKPCQ (SEQ ID NO: 10), and EIDK (SEQ ID NO: 78). In other embodiments, suitable C-terminal tails may be a C-terminally truncated fragment of SEQ ID NOs: 9, 10 or 78, including, for example, one of the following amino acid sequences (represented by the single letter amino acid code): E, EI, EID, EIDKP (SEQ ID NO: 79), EIDKPS (SEQ ID NO: 80), or EIDKPC (SEQ ID NO: 81). Other suitable C-terminal tails include, for example, ES, EC, EGS, EGC, EGSGS (SEQ ID NO: 96), EGSGC (SEQ ID NO: 97), or EIEK (SEQ ID NO: 217). In certain embodiments, the $^{10}$Fn3 domain that binds to EGFR comprises both an N-terminal extension and a C-terminal tail. In exemplary embodiments, the A region comprises an N-terminal extension beginning with Gly or Met-Gly and a C-terminal extension that does not contain a cysteine residue and the B region comprises an N-terminal extension that does not start with a Met and a C-terminal extension that comprises a cysteine residue. Specific examples of $^{10}$Fn3 domains that bind to EGFR are polypeptides comprising (i) a polypeptide having an amino acid sequence set forth in any one of SEQ ID NOs: 5-8, 52, 66-68, 82-85, 106-108, 112-114, 140-142, 155-157, 170-172, 185-187, 198-200, and 219-327, or (ii) a polypeptide comprising an amino acid sequence at least 85%, 90%, 95%, 97%, 98%, or 99% identical to the amino acid sequence set forth in any one of SEQ ID NOs: 5-8, 52, 66-68, 82-85, 106-108, 112-114, 140-142, 155-157, 170-172, 185-187, 198-200, and 219-327.

In certain embodiments, the A or C region is a polypeptide comprising a $^{10}$Fn3 domain that binds to IGF-IR, wherein the $^{10}$Fn3 domain has the structure from N-terminus to C-terminus: beta strand A, loop AB, beta strand B, loop BC, beta strand C, loop CD, beta strand D, loop DE, beta strand E, loop EF, beta strand F, loop FG, beta strand G, wherein the BC loop has the amino acid sequence of SEQ ID NO: 45 or 46, the DE loop has the amino acid sequence of SEQ ID NO: 47 or 48, and the FG loop has the amino acid sequence of SEQ ID NO: 49 or 50, wherein the $^{10}$Fn3 domain folds into an antibody heavy chain variable region-like structure, and wherein the polypeptide binds to IGF-IR with a $K_D$ of less than 100 nM. The $^{10}$Fn3 domain that binds to IGF-IR preferably folds into a structure wherein the 7 beta strands are distributed between two beta sheets that pack against each other forming a stable core and wherein the beta strands are connected by the six loops which are solvent exposed. In exemplary embodiments, the $^{10}$Fn3 domain is from 80-150 amino acids in length.

In exemplary embodiments, the A or C region is a $^{10}$Fn3 domain that binds to IGF-IR with a $K_D$ of less than 100 nM having the sequence set forth below:

```
                                              (SEQ ID NO: 86)
EVVAATX_{n1}SLLIX_{a1}SWSARLKVARX_{a2}YYRITYGEX_{n2}QEFTVX_{a3}

PKNVYTX_{a4}ATIX_{n3}DYTITVYAVX_{a5}TRFRDYQPX_{a6}ISINYRT.
```

In SEQ ID NO: 86, the BC, DE and FG loops have a fixed sequence as shown in bold, or a sequence at least 75%, 80%, 85%, 90%, 95%, 97%, 98%, or 99% identical to the sequences shown in bold, the AB loop is represented by $X_{n1}$, the CD loop is represented by $X_{n2}$, and the EF loop is represented by $X_{n3}$, and the beta strands A-G are underlined.

X represents any amino acid and the subscript following the X represents an integer of the number of amino acids. In particular, n1 may be anywhere from 1-15, 2-15, 1-10, 2-10, 1-8, 2-8, 1-5, 2-5, 1-4, 2-4, 1-3, 2-3, or 1-2 amino acids; n2 and n3 may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids; and a1-a6 may each independently comprise from 0-10, 0-5, 1-10, 1-5, or 2-5 amino acids. In preferred embodiments, n1 is 2 amino acids, n2 is 7 amino acids, n3 is 7 amino acids, and a1-a6 is 0 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 1. In an exemplary embodiment, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 1. In certain embodiments, the core amino acid residues are fixed and any substitutions, conservative substitutions, deletions or additions occur at residues other than the core amino acid residues. In certain embodiments, the IGF-IR binder is represented by the following amino acid sequence:

(SEQ ID NO: 65)
EVVAATPTSLLISWSARLKVARYYRITYGETGGNSPVQEFTVPKNVYTAT

ISGLKPGVDYTITVYAVTRFRDYQPISINYRT.

In SEQ ID NO: 65, the sequence of the BC, DE and FG loops have a fixed sequence as shown in bold, or a sequence at least 75%, 80%, 85%, 90%, 95%, 97%, 98%, or 99% identical to the sequences shown in bold, and the remaining sequence which is underlined (e.g., the sequence of the 7 beta strands and the AB, CD and EF loops) has anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the corresponding amino acids shown in SEQ ID NO: 65. In certain embodiments, the core amino acid residues are fixed and any substitutions, conservative substitutions, deletions or additions occur at residues other than the core amino acid residues. The $^{10}$Fn3 domain that binds to IGF-IR may optionally comprise an N-terminal extension of from 1-20, 1-15, 1-10, 1-8, 1-5, 1-4, 1-3, 1-2, or 1 amino acids in length. Exemplary N-terminal extensions include (represented by the single letter amino acid code) M, MG, G, MGVSDVPRDL (SEQ ID NO: 69), GVSDVPRDL (SEQ ID NO: 70), and VSDVPRDL (SEQ ID NO: 71), or N-terminal truncations of any one of SEQ ID NOs: 69, 70, or 71. Other suitable N-terminal extensions include, for example, $X_n$SDVPRDL (SEQ ID NO: 72), $X_n$DVPRDL (SEQ ID NO: 73), $X_n$VPRDL (SEQ ID NO: 74), $X_n$PRDL (SEQ ID NO: 75), $X_n$RDL (SEQ ID NO: 76), $X_n$DL (SEQ ID NO: 77), or $X_n$L, wherein n=0, 1 or 2 amino acids, wherein when n=1, X is Met or Gly, and when n=2, X is Met-Gly. The $^{10}$Fn3 domain that binds to IGF-IR may optionally comprise a C-terminal tail. Exemplary C-terminal tails include polypeptides that are from 1-20, 1-15, 1-10, 1-8, 1-5, 1-4, 1-3, 1-2, or 1 amino acids in length. Specific examples of C-terminal tails include EIDKPSQ (SEQ ID NO: 9), EIDKPCQ (SEQ ID NO: 10), and EIDK (SEQ ID NO: 78). In other embodiments, suitable C-terminal tails may be a C-terminally truncated fragment of SEQ ID NOs: 9, 10 or 78, including, for example, one of the following amino acid sequences (represented by the single letter amino acid code): E, EI, EID, EIDKP (SEQ ID NO: 79), EIDKPS (SEQ ID NO: 80), or EIDKPC (SEQ ID NO: 81). Other suitable C-terminal tails include, for example, ES, EC, EGS, EGC, EGSGS (SEQ ID NO: 96), EGSGC (SEQ ID NO: 97), or EIEK (SEQ ID NO: 217). In certain embodiments, the $^{10}$Fn3 domain that binds to IGF-IR comprises both an N-terminal extension and a C-terminal tail. In exemplary embodiments, the A region comprises an N-terminal extension beginning with Gly or Met-Gly and a C-terminal extension that does not contain a cysteine residue and the B region comprises an N-terminal extension that does not start with a Met and a C-terminal extension that comprises a cysteine residue. Specific examples of $^{10}$Fn3 domains that bind to IGF-IR are polypeptides comprising (i) a polypeptide having an amino acid sequence set forth in any one of SEQ ID NOs: 3, 4, 65 or 86, or (ii) a polypeptide comprising an amino acid sequence at least 85%, 90%, 95%, 97%, 98%, or 99% identical to the amino acid sequence set forth in any one of SEQ ID NOs: 3, 4, 65 or 86.

The B region is a linker as described further herein. In exemplary embodiments, the B region is a polypeptide linker. Exemplary polypeptide linkers include polypeptides having from 1-20, 1-15, 1-10, 1-8, 1-5, 1-4, 1-3, or 1-2 amino acids. Specific examples of suitable polypeptide linkers are described further herein and include, for example, linkers having a sequence selected from the group consisting of SEQ ID NOs: 11-19, 51, 93-95 and 218. In certain embodiments, the linker may be a C-terminal tail polypeptide as described herein, an N-terminal extension polypeptide as described herein, or a combination thereof.

In one embodiment, an antibody-like protein dimer comprises a polypeptide having the structure $X_1$-A-$X_2$-B-$X_3$-C-$X_4$, wherein $X_1$ is an optional N-terminal extension, A is a $^{10}$Fn3 domain that binds to EGFR, $X_2$ is an optional C-terminal tail, B is a polypeptide linker, $X_3$ is an optional N-terminal extension, C is a $^{10}$Fn3 domain that binds to IGF-IR, and $X_4$ is an optional C-terminal tail. In another embodiment, an antibody-like protein dimer comprises a polypeptide having the structure $X_1$-A-$X_2$-B-$X_3$-C-$X_4$, wherein $X_1$ is an optional N-terminal extension, A is a $^{10}$Fn3 domain that binds to IGF-IR, $X_2$ is an optional C-terminal tail, B is a polypeptide linker, $X_3$ is an optional N-terminal extension, C is a $^{10}$Fn3 domain that binds to EGFR, and $X_4$ is an optional C-terminal tail. Specific examples of suitable N-terminal extensions and C-terminal tails are described above. In certain embodiments, one or more of $X_1$, $X_2$, B, $X_3$ or $X_4$ may comprise an amino acid residue suitable for pegylation, such as a cysteine or lysine residue. In exemplary embodiments, $X_4$ comprises at least one amino acid suitable for pegylation, such as a cysteine or lysine residue. Specific examples of suitable polypeptide linkers are described further below. Specific examples of antibody-like protein dimers having the structure $X_1$-A-$X_2$-B-$X_3$-C-$X_4$ are polypeptides comprising (i) a polypeptide having the amino acid sequence set forth in any one of SEQ ID NOs: 20-31, 53-58, 87-92, 98-105, 118-133, 149-154, 164-169, 179-184, 192-197, 205-210 and 211-216, or (ii) a polypeptide comprising an amino acid sequence at least 85%, 90%, 95%, 97%, 98%, or 99% identical to the amino acid sequence set forth in any one of SEQ ID NOs: 20-31, 53-58, 87-92, 98-105, 118-133, 149-154, 164-169, 179-184, 192-197, 205-210 and 211-216.

In certain embodiments, it may be desirable to tune the potency of one $^{10}$Fn3 binding domain relative to the other $^{10}$Fn3 binding domain in the antibody-like protein dimers described herein. For example, if the binding affinity of the first $^{10}$Fn3 domain is significantly higher than the binding affinity of the second $^{10}$Fn3 domain, the biological effect of the first $^{10}$Fn3 domain could overwhelm the effects of the second of second $^{10}$Fn3 domain. Accordingly, in certain embodiments, it may be desirable for the binding affinities of the first and second $^{10}$Fn3 domains of an antibody-like protein dimer to be similar to each other, e.g., binding affinities within 100-fold, 30-fold, 10-fold, 3-fold, 1-fold, 0.3-fold or 0.1-fold, of each other, or binding affinities within 0.1-fold to 10-fold, within 0.3-fold to 10-fold, within 0.1-fold to 3-fold, within 0.3-fold to 3-fold, within 0.1-fold to 1-fold, within 0.3-fold to 1-fold, within 1-fold to 10-fold, within 3-fold to 10-fold, within 3-fold to 30-fold, or within 1-fold to 3-fold of each other.

Conjugation

Multimers of antibody-like proteins may be covalently or non-covalently linked. In some embodiments, an EGFR binding $^{10}$Fn3 may be directly or indirectly linked to an IGFIR binding $^{10}$Fn3 via a polypeptide linker. Suitable linkers for joining Fn3 are those which allow the separate domains to fold independently of each other forming a three dimensional structure that permits high affinity binding to a target molecule.

The disclosure provides a number of suitable linkers that meet these requirements, including glycine-serine based linkers, glycine-proline based linkers, as well as the linker having the amino acid sequence PSTSTST (SEQ ID NO: 12). The Examples described herein demonstrate that Fn3 domains joined via polypeptide linkers retain their target binding function. In some embodiments, the linker is a glycine-serine based linker. These linkers comprise glycine and serine residues and may be between 8 and 50, 10 and 30, and 10 and 20 amino acids in length. Examples include linkers having an amino acid sequence GSGSGSGSGSGSGSGSGSGS (SEQ ID NO: 11), GSGSGSGSGS (SEQ ID NO: 13), GGGGS GGGGS GGGGS (SEQ ID NO: 14), GGGGS GGGGS GGGGS GGGGS (SEQ ID NO: 15), GGGGS GGGGS GGGGS GGGGS GGGGS (SEQ ID NO: 16), or GGGGSGGGGSGGGSG (SEQ ID NO: 17). In some embodiments, the linker is a glycine-proline based linker. These linkers comprise glycine and proline residues and may be between 3 and 30, 10 and 30, and 3 and 20 amino acids in length. Examples include linkers having an amino acid sequence GPGPGPG (SEQ ID NO: 18), GPGPGPG-PGPG (SEQ ID NO: 19), and GPG (SEQ ID NO: 51). In some embodiments, the linker is a proline-alanine based linker. These linkers comprise proline and alanine residues and may be between 3 and 30, 10 and 30, 3 and 20 and 6 and 18 amino acids in length. Examples of such linkers include SEQ ID NOs: 93, 94 and 95. It is contemplated, that the optimal linker length and amino acid composition may be determined by routine experimentation by methods well known in the art.

In some embodiments, multimers of antibody-like proteins are linked via a polypeptide linker having a protease site that is cleavable by a protease in the blood or target tissue. Such embodiments can be used to release two or more therapeutic proteins for better delivery or therapeutic properties or more efficient production compared to separately producing such proteins.

Additional linkers or spacers, e.g., SEQ ID NOs: 9 and 10, may be introduced at the C-terminus of a Fn3 domain between the Fn3 domain and the polypeptide linker. Additional linkers or spacers may be introduced at the N-terminus of a Fn3 domain between the Fn3 domain and the polypeptide linker.

In some embodiments, multimers of antibody-like proteins may be directly or indirectly linked via a polymeric linker. Polymeric linkers can be used to optimally vary the distance between each protein moiety to create a protein with one or more of the following characteristics: 1) reduced or increased steric hindrance of binding of one or more protein domain when binding to a protein of interest, 2) increased protein stability or solubility, 3) decreased protein aggregation, and 4) increased overall avidity or affinity of the protein.

In some embodiments, multimers of antibody-like proteins are linked via a biocompatible polymer such as a polymeric sugar. The polymeric sugar can include an enzymatic cleavage site that is cleavable by an enzyme in the blood or target tissue. Such embodiments can be used to release two or more therapeutic proteins for better delivery or therapeutic properties or more efficient production compared to separately producing such proteins In some embodiments, multimers of antibody-like proteins are linked via a polyoxyalkylene, in particular a polyethylene glycol (PEG) moiety. Antibody-like proteins may comprise a cysteine containing linker, such as the linker set forth in SEQ ID NO: 10, 81, 97 or 218. PEG may be conjugated to the cysteine moiety in the linker sequence and may operably link the two domains.

Pharmacokinetic Moieties

In one aspect, the disclosure provides E binders and E/I binders further comprising a pharmacokinetic (PK) moiety. In some embodiments, the E/I binder is a multimer of antibody-like proteins, in particular, a dimer of an EGFR binding $^{10}$Fn3 and an IGFIR binding $^{10}$Fn3. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). E binders and E/I binders may be attached to a moiety that reduces the clearance rate of the polypeptide in a mammal (e.g., mouse, rat, or human) by greater than three-fold relative to the unmodified polypeptide. Other measures of improved pharmacokinetics may include serum half-life, which is often divided into an alpha phase and a beta phase. Either or both phases may be improved significantly by addition of an appropriate moiety.

Moieties that tend to slow clearance of a protein from the blood include polyoxyalkylene moieties (e.g., polyethylene glycol); sugars (e.g., sialic acid); and well-tolerated protein moieties (e.g., Fc, Fc fragments, transferrin, or serum albumin).

In some embodiments, the PK moiety is a serum albumin binding protein such as those described in U.S. Publication Nos. 2007/0178082 and 2007/0269422.

In some embodiments, the PK moiety is a serum immunoglobulin binding protein such as those described in U.S. Publication No. 2007/0178082.

In some embodiments, the PK moiety is polyethylene glycol (PEG).

The serum clearance rate of a PK-modified antibody-like protein multimer may be decreased by about 10%, 20%, 30%, 40%, 50%, 60%, 70%, 80%, or even 90%, relative to the clearance rate of the unmodified E/I binders. The PK-modified multimer may have a half-life ($t_{1/2}$) which is enhanced relative to the half-life of the unmodified multimer. The half-life of PK-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified multimer. In some embodiments, the multimer half-life is determined in vitro, such as in a buffered saline solution or in serum. In other embodiments, the multimer half-life is an in vivo half life, such as the half-life of the multimer in the serum or other bodily fluid of an animal.

In some embodiments, a PK moiety is linked to an antibody-like protein multimer via at least one disulfide bond, a peptide bond, a polypeptide, a polymeric sugar, or a polyethylene glycol moiety. Exemplary polypeptide linkers include PSTSTST (SEQ ID NO: 12), EIDKPSQ (SEQ ID NO: 9), and GS linkers, such as GSGSGSGSGS (SEQ ID NO: 13) and multimers thereof.

Binding/Screening

The disclosure provides E binders and E/I binders, in particular, antibody-like protein multimers such as a dimer of an EGFR binding $^{10}$Fn3 and an IGFIR binding $^{10}$Fn3. Binding to EGFR or IGFIR may be assessed in terms of equilibrium constants (e.g., dissociation, $K_D$) and in terms of kinetic constants (e.g., on rate constant, $k_{on}$ and off rate constant, $k_{off}$). In some embodiments, an antibody-like protein monomer or multimer will bind to EGFR with a $K_D$ of less than 500 nM, 100 nM, 50 nM, 5 nM or less. In some embodiments, an antibody-like protein multimer will bind to IGFIR with a $K_D$ of less than 500 nM, 100 nM, 50 nM, 5 nM or less. Higher $K_D$ values may be tolerated where the $k_{off}$ is sufficiently low or the $k_{on}$ is sufficiently high.

E binders and E/I binders may bind to any part of EGFR, including the extracellular domain of a EGFR, in particular the ligand binding domain of EGFR. Binding of E binders and E/I binders to EGFR may disrupt the interaction of EGFR with one or more ligands, including TGF-alpha and EGF, and/or disrupt receptor dimerization. In some embodiments, E binders and E/I binders compete with an anti-EGFR antibody for binding to EGFR. The anti-EGFR antibody may be selected from any known anti-EGFR antibody including panitumumab (Amgen), nimotuzumab (YM Biosciences), zalutumumab (Genmab), EMD72000 (Merck KGaA), and cetuximab (ImClone Systems).

In some embodiments, E binders and E/I binders inhibit downstream signaling of EGFR. EGFR ligand binding leads to homo- or heterodimeric receptor dimerization with EGFR or another HER family member. Dimerization promotes receptor autophosphorylation, which in turn leads to the activation of several signaling pathways.

E/I binders may bind to any part of IGFIR, including the extracellular domain of a IGFIR, in particular the ligand binding domain of IGFIR. Binding of E/I binders to IGFIR may disrupt the interaction of IGFIR with one or more ligands, e.g., IGF-I and IGF-II; and/or disrupt assembly of receptor heterotetramers. In some embodiments, E/I binders compete with an anti-IGFIR antibody for binding to IGFIR. The anti-IGFIR antibody may be selected from any known anti-IGFIR antibody.

In some embodiments, E/I binders inhibit downstream signaling of IGFIR. The IGF-I receptor is composed of two types of subunits: an alpha subunit (a 130-135 kDa protein that is entirely extracellular and functions in ligand binding) and a beta subunit (a 95-kDa transmembrane protein, with transmembrane and cytoplasmic domains). IGFIR is initially synthesized as a single chain proreceptor polypeptide that is processed by glycosylation, proteolytic cleavage, and covalent bonding to assemble into a mature 460-kDa heterotetramer comprising two alpha-subunits and two beta-subunits. The beta subunit(s) possesses ligand-activated tyrosine kinase activity.

EGFR and IGFIR receptor signaling independently activates the MAPK pathway, including the phosphorylation of MEK. Another activated pathway is the phosphatidylinositol 3-kinase (PI3K) pathway, including phosphorylation of AKT. Receptor signaling is transduced to the nucleus, resulting in the activation of various transcription factors.

Screening assays may be designed to identify and characterize E binders and E/I binders. Binding assays, such as surface plasmon resonance and ELISA, and assays that detect activated signaling pathways are well-known in the art, see e.g., Example 5. Various antibodies, including many that are commercially available, have been produced which specifically bind to phosphorylated, activated isoforms of EGFR and IGFIR, see e.g., Examples 6 and 7. Downstream signaling events may also be used as an indicator of receptor inhibition, such as by measuring levels of AKT phosphorylation, see e.g., Example 8. Cell proliferation assays are also a useful method for characterizing the ability of candidate E/I binders to bind and inhibit EGFR and IGFIR signaling, see e.g., Example 9.

Polymer Conjugation

Conjugation to a biocompatible polymer may be used to link antibody-like protein multimers and/or to improve the pharmacokinetics of the proteins. The identity, size and structure of the polymer is selected so as to improve the circulation half-life of the multimer or decrease the antigenicity of the multimer without an unacceptable decrease in activity.

Examples of polymers useful in the invention include, but are not limited to, poly(alkylene glycols) such as polyethylene glycol (PEG). The polymer is not limited to a particular structure and can be linear (e.g., alkoxy PEG or bifunctional PEG), or non-linear such as branched, forked, multi-armed (e.g., PEGs attached to a polyol core), and dendritic.

Typically, PEG and other water-soluble polymers (i.e., polymeric reagents) are activated with a suitable activating group appropriate for coupling to a desired site on the polypeptide. Thus, a polymeric reagent will possess a reactive group for reaction with the polypeptide. Representative polymeric reagents and methods for conjugating these polymers to an active moiety are well-known in the art and further described in Zalipsky, S., et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992), and in Zalipsky (1995) Advanced Drug Reviews 16: 157-182.

Typically, the weight-average molecular weight of the polymer is from about 100 Daltons to about 150,000 Daltons. Exemplary weight-average molecular weights for the biocompatible polymer include about 20,000 Daltons, about 40,000 Daltons, about 60,000 Daltons and about 80,000 Daltons. Branched versions of the biocompatible polymer having a total molecular weight of any of the foregoing can also be used.

In some embodiments, the polymer is PEG. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_{n-1}$CH$_2$CH$_2$OH, where n is 20 to 2300 and X is H or a terminal modification, e.g., a C$_{1-4}$ alkyl. PEG can contain further chemical groups which are necessary for binding reactions, which result from the chemical synthesis of the molecule; or which act as a spacer for optimal distance of parts of the molecule. In addition, such a PEG can consist of one or more PEG side-chains which are linked together. PEGs with more than one PEG chain are called multiarmed or branched PEGs. Branched PEG are described in, for example, European Published Application No. 473084A and U.S. Pat. No. 5,932,462.

To effect covalent attachment of the polymer molecule(s) to a polypeptide, the hydroxyl end groups of the polymer molecule must be provided in activated form, i.e. with reactive functional groups. Suitably activated polymer molecules are commercially available, e.g. from Nektar Therapeutics, Inc., Huntsville, Ala., USA; PolyMASC Pharmaceuticals plc, UK; or SunBio Corporation, Anyang City, South Korea. Alternatively, the polymer molecules can be activated by conventional methods known in the art, e.g. as disclosed in WO 90/13540. Specific examples of activated PEG polymers include the following linear PEGs: NHS-PEG, SPA-PEG, SSPA-PEG, SBA-PEG, SS-PEG, SSA-PEG, SC-PEG, SG-PEG, SCM-PEG, NOR-PEG, BTC-PEG, EPDX-PEG, NCO-PEG, NPC-PEG, CDI-PEG, ALD-PEG, TRES-PEG, VS-PEG, OPSS-PEG, IODO-PEG, and MAL-PEG, and branched PEGs, such as PEG2-NHS, PEG2-MAL, and those disclosed in U.S. Pat. Nos. 5,932,462 and 5,643,575, both of which are incorporated herein by reference.

In some embodiments where PEG molecules are conjugated to cysteine residues on an antibody-like protein multimer, the cysteine residues are native to the protein, whereas in other embodiments, one or more cysteine residues are engineered into the protein. Mutations may be introduced into a protein coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework based on which binding polypeptides are designed and evolved has been solved (see Himanen et al., Nature. (2001) 20-27; 414(6866):933-8) and thus the surface-exposed residues identified. In some embodiments, cysteine residues are introduced into antibody-like protein multimers at or near the N- and/or C-terminus, or within loop regions. Pegylation of cysteine residues may be carried out using, for example, PEG-maleiminde, PEG-vinylsulfone, PEG-iodoacetamide, or PEG-orthopyridyl disulfide.

In some embodiments, the pegylated antibody-like protein multimer comprises a PEG molecule covalently attached to the alpha amino group of the N-terminal amino acid. Site specific N-terminal reductive amination is described in Pepinsky et al., (2001) JPET, 297,1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) J. Biol. Chem. 254, 12579, and in Chamow et al., (1994) Bioconjugate Chem. 5, 133.

In another embodiment, pegylated antibody-like protein multimer comprises one or more PEG molecules covalently attached to a linker, which in turn is attached to the alpha amino group of the amino acid residue at the N-terminus of the binding polypeptide. Such an approach is disclosed in U.S. Publication No. 2002/0044921 and PCT Publication No. WO 94/01451.

In some embodiments, an antibody-like protein multimer is pegylated at the C-terminus. A protein may be pegylated at the C-terminus by the introduction of C-terminal azidomethionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, *Bioconjug Chem.* 2004; 15(5):1005-1009.

Conventional separation and purification techniques known in the art can be used to purify PEGylated antibody-like protein multimers, such as size exclusion (e.g., gel filtration) and ion exchange chromatography. Products may also be separated using SDS-PAGE. Products that may be separated include mono-, di-, tri-, poly- and un-pegylated binding polypeptide, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity.

In some embodiments, the pegylated antibody-like protein multimers will preferably retain at least about 25%, 50%, 60%, 70%, 80%, 85%, 90%, 95% or 100% of the biological activity associated with the unmodified protein. In some embodiments, biological activity refers to its ability to bind to EGFR and IGFIR, as assessed by K$_D$, k$_{on}$ or k$_{off}$. In some embodiments, the pegylated antibody-like protein multimer shows an increase in binding to EGFR and/or IGFIR relative to unpegylated protein.

Deimmunization of Binding Polypeptides

The amino acid sequences of E binders and E/I binders, in particular, antibody-like protein multimers, such as a dimer of an EGFR binding $^{10}$Fn3 and an IGFIR binding $^{10}$Fn3, may be altered to eliminate one or more B- or T-cell epitopes. A protein, or a multimer of proteins, may be deimmunized to render it non-immunogenic, or less immunogenic, to a given species. Deimmunization can be achieved through structural alterations to the protein. Any deimmunization technique known to those skilled in the art can be employed, see e.g., WO 00/34317, the disclosure of which is incorporated herein in its entirety.

In one embodiment, the sequences of the E binders and E/I binders can be analyzed for the presence of MHC class II binding motifs. For example, a comparison may be made with databases of MHC-binding motifs such as, for example by searching the "motifs" database on the worldwide web at sitewehil.wehi.edu.au. Alternatively, MHC class II binding peptides may be identified using computational threading methods such as those devised by Altuvia et al. (J. Mol. Biol. 249 244-250 (1995)) whereby consecutive overlapping peptides from the polypeptide are testing for their binding energies to MHC class II proteins. Computational binding prediction algorithms include iTope™, Tepitope, SYF-PEITHI, EpiMatrix (EpiVax), and MHCpred. In order to assist the identification of MHC class II-binding peptides, associated sequence features which relate to successfully presented peptides such as amphipathicity and Rothbard motifs, and cleavage sites for cathepsin B and other processing enzymes can be searched for.

Having identified potential (e.g. human) T-cell epitopes, these epitopes are then eliminated by alteration of one or more amino acids, as required to eliminate the T-cell epitope. Usually, this will involve alteration of one or more amino acids within the T-cell epitope itself. This could involve altering an amino acid adjacent the epitope in terms of the primary structure of the protein or one which is not adjacent in the primary structure but is adjacent in the secondary structure of the molecule. The usual alteration contemplated will be amino acid substitution, but it is possible that in certain circumstances amino acid addition or deletion will be appropriate. All alterations can be accomplished by recombinant DNA technology, so that the final molecule may be prepared by expression from a recombinant host, for example by well established methods, but the use of protein chemistry or any other means of molecular alteration may also be used.

Once identified T-cell epitopes are removed, the deimmunized sequence may be analyzed again to ensure that new T-cell epitopes have not been created and, if they have, the epitope(s) can be deleted.

Not all T-cell epitopes identified computationally need to be removed. A person skilled in the art will appreciate the significance of the "strength" or rather potential immunogenicity of particular epitopes. The various computational methods generate scores for potential epitopes. A person skilled in the art will recognize that only the high scoring epitopes may need to be removed. A skilled person will also recognize that there is a balance between removing potential epitopes and maintaining binding affinity of the protein. Therefore, one strategy is to sequentially introduce substitutions into the protein and then test for antigen binding and immunogenicity.

In one aspect, the deimmunized protein is less immunogenic (or rather, elicits a reduced HAMA response) than the original protein in a human subject. Assays to determine immunogenicity are well within the knowledge of the skilled person. Art-recognized methods of determining immune response can be performed to monitor a HAMA response in a particular subject or during clinical trials. Subjects administered deimmunized protein can be given an immunogenicity assessment at the beginning and throughout the administration of said therapy. The HAMA response is measured, for example, by detecting antibodies to the deimmunized protein in serum samples from the subject using a method known to one in the art, including surface plasmon resonance technology (BIAcore) and/or solid-phase ELISA analysis. Alternatively, in vitro assays designed to measure a T-cell activation event are also indicative of immunogenicity.

Additional Modifications

In certain embodiments, E binders and E/I binders, in particular, antibody-like protein multimers such as a dimer of an EGFR binding $^{10}$Fn3 and an IGFIR binding $^{10}$Fn3, may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified E binders and E/I binders may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogenicity of the protein. See, e.g., Raju et al. Biochemistry. 2001 Jul. 31; 40(30):8868-76. Effects of such non-amino acid elements on the functionality of an E binder or E/I binder may be tested for its antagonizing role in EGFR and IGFIR signaling function.

In some embodiments, E binders and E/I binders are modified to enhance antigen-dependent cell-mediated cytotoxicity (ADCC) and/or complement dependent cytotoxicity (CDC). In some embodiments, the E/I binder is a dimer of an EGFR binding $^{10}$Fn3 and an IGFIR binding $^{10}$Fn3, further comprising an Fc region. In some embodiments, the Fc region is a variant that enhances ADCC or CDC. The Fc region variant may comprise a human Fc region sequence (e.g., a human IgG1, IgG2, IgG3 or IgG4 Fc region) comprising an amino acid modification (e.g., a substitution) at one or more amino acid positions, including positions 256, 290, 298, 312, 326, 330, 333, 334, 360, 378 or 430, wherein the numbering of the residues in the Fc region is that of the EU index as in Kabat.

Vectors & Polynucleotides Embodiments

Also included in the present disclosure are nucleic acid sequences encoding any of the proteins described herein. As appreciated by those skilled in the art, because of third base degeneracy, almost every amino acid can be represented by more than one triplet codon in a coding nucleotide sequence. In addition, minor base pair changes may result in a conservative substitution in the amino acid sequence encoded but are not expected to substantially alter the biological activity of the gene product. Therefore, a nucleic acid sequence encoding a protein described herein may be modified slightly in sequence and yet still encode its respective gene product.

Exemplary nucleic acids encoding the E/I binders described herein include nucleic acids having SEQ ID NOs: 442-465 or nucleic acids having a sequence at least 80%, 85%, 90%, 95%, 97%, 98%, 99% or 100% identical to any one of SEQ ID NOs: 442-465. Isolated nucleic acids which differ from the nucleic acids as set forth in SEQ ID NOs: 442-465 due to degeneracy in the genetic code are also within the scope of the invention. Also provided are E/I binders comprising an I monomer encoded by a nucleotide sequence at least 80%, 85%, 90%, 95%, 97%, 98%, 99% or 100% identical to SEQ ID NO: 328 and/or E/I binders comprising an E monomer encoded by a nucleotide sequence at 80%, 85%, 90%, 95%, 97%, 98%, 99% or 100% identical to any one of SEQ ID NOs: 329-441 or 495. Also provided are E binders encoded by a nucleotide sequence at 80%, 85%, 90%, 95%, 97%, 98%, 99% or 100% identical to any one of SEQ ID NOs: 329-441 or 495. In certain embodiments, the nucleotide sequences encoding the E/I binders, an E monomer, or an I monomer do not contain a sequence encoding a 6× His tag (SEQ ID NO: 487).

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc Natl Acad Sci USA. 2003 100(2):438-42; Sinclair et al. Protein Expr Purif. 2002 (1):96-105; Connell N D. Curr Opin Biotechnol. 2001 (5):446-9; Makrides et al. Microbiol Rev. 1996 60(3):512-38; and Sharp et al. Yeast. 1991 7(7):657-78.

General techniques for nucleic acid manipulation are within the purview of one skilled in the art and are also described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding a protein is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated. Suitable regulatory elements are well-known in the art.

The proteins described herein may be produced as a fusion protein with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, lpp, or heat-stable enterotoxin II leaders. For yeast secretion, the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in PCT Publication No. WO 90/13646. In mammalian cell expression, mammalian signal sequences as well as viral secretory leaders, for example, the herpes simplex gD signal, are available. The DNA for such precursor regions may be ligated in reading frame to DNA encoding the protein.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the multivalent antibody. One useful transcription termination component is the bovine growth hormone polyadenylation region. See PCT Publication No. WO 94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N.Y., 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). In some instance it will be desired to produce proteins in vertebrate cells, such as for glycosylation, and the propagation of vertebrate cells in culture (tissue culture) has become a routine procedure. Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. For many applications, the small size of the protein multimers described herein would make *E. coli* the preferred method for expression.

Protein Production

Host cells are transformed with the herein-described expression or cloning vectors for protein production and cultured in conventional nutrient media modified as appropriate for inducing promoters, selecting transformants, or amplifying the genes encoding the desired sequences.

The host cells used to produce the proteins of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-translation systems. For such purposes, the nucleic acids encoding the proteins must be modified to allow in vitro transcription to produce mRNA and to allow cell-free translation of the mRNA in the particular cell-free system being utilized. Exemplary eukaryotic cell-free translation systems include, for example, mammalian or yeast cell-free translation systems, and exemplary prokaryotic cell-free translation systems include, for example, bacterial cell-free translation systems.

Proteins disclosed herein can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, proteins may be exchanged into different buffers and/or concentrated by any of a variety of methods known to the art, including, but not limited to, filtration and dialysis.

The purified proteins are preferably at least 85% pure, more preferably at least 95% pure, and most preferably at least 98% pure. Regardless of the exact numerical value of the purity, the proteins are sufficiently pure for use as a pharmaceutical product.

Imaging, Diagnostic and Other Applications

The E binders described herein can be detectably labeled and used to contact cells expressing EGFR for imaging or diagnostic applications. The E/I binders described herein can be detectably labeled and used to contact cells expressing EGFR and/or IGFIR for imaging or diagnostic applications. Any method known in the art for conjugating a protein to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

In certain embodiments, the E binders and E/I binders described herein are further attached to a label that is able to be detected (e.g., the label can be a radioisotope, fluorescent compound, enzyme or enzyme co-factor). The label may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. An E binder or E/I binder affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety.

E binders and E/I binders also are useful as affinity purification agents. In this process, the proteins are immobilized on a suitable support, such a Sephadex resin or filter paper, using methods well known in the art. The proteins can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

E binders are useful in methods for detecting EGFR in a sample. E/I binders also are useful in methods for detecting EGFR and/or IGFIR in a sample. The sample will often by a biological sample, such as a biopsy, and particularly a biopsy of a tumor, a suspected tumor. The sample may be from a human or other mammal. The E binder or E/I binder may be labeled with a labeling moiety, such as a radioactive moiety, a fluorescent moiety, a chromogenic moiety, a chemiluminescent moiety, or a hapten moiety; and may be immobilized on a solid support. Detection may be carried out using any technique known in the art, such as, for example, radiography, immunological assay, fluorescence detection, mass spectroscopy, or surface plasmon resonance.

Therapeutic/In Vivo Uses

The E binders described herein are also useful in methods for treating conditions which respond to an inhibition of EGFR biological activity. The E/I binders described herein are also useful in methods for treating conditions which respond to an inhibition of EGFR and/or IGFIR biological activity. EGFR and IGFIR are involved either directly or indirectly in the signal transduction pathways of various cell activities, including proliferation, adhesion and migration, as well as differentiation.

In one aspect, the application provides methods for treating a subject afflicted with a hyperproliferative disorder with a therapeutically effective amount of an E binder or an E/I binder. In particular, E binders and E/I binders are useful for the treatment and/or prophylaxis of tumors and/or tumor metastases. In exemplary embodiments, the E/I binder is an antibody-like protein multimer such as a dimer of an EGFR binding $^{10}$Fn3 and an IGFIR binding $^{10}$Fn3.

In some embodiments, pharmaceutical compositions comprising E binders or E/I binders are administered to a subject afflicted with a tumor, including but not limited to, a brain tumor, tumor of the urogenital tract, tumor of the lymphatic system, stomach tumor, laryngeal tumor, monocytic leukemia, lung adenocarcinoma, small-cell lung carcinoma, pancreatic cancer, glioblastoma and breast carcinoma; or a cancerous disease, including but not limited to, squamous cell carcinoma, bladder cancer, stomach cancer, liver cancer, kidney cancer, colorectal cancer, breast cancer, head cancer, neck cancer, oesophageal cancer, gynecological cancer, thyroid cancer, lymphoma, chronic leukemia and acute leukemia.

An E binder or an E/I binder can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described herein. Techniques and dosages for administration vary depending on the type of specific polypeptide and the specific condition being treated but can be readily determined by the skilled artisan.

Additional Agents that May be Used with E/I Binders

One aspect of the application provides combinations of E binder or E/I binders and an additional therapeutic agent, such as a cytotoxic agent. In some embodiments, an E binder or E/I binder is linked to a cytotoxic agent. Such embodiments can be prepared by in vitro or in vivo methods as appropriate. In vitro methods include conjugation chemistry well know in the art, such as conjugation to cysteine and lysine residues. In order to link a cytotoxic agent to a polypeptide, a linking group or reactive group is used. Suitable linking groups are well known in the art and include disulfide groups, thioether groups, acid labile groups, photolabile groups, peptidase labile groups and esterase labile groups. Cytotoxic agents can also be linked to E binders or E/I binders through an intermediary carrier molecule such as serum albumin Exemplary cytotoxic agents that may be linked to E binders or E/I binders, include maytansinoids, taxanes, analogs of CC-1065, bacterial toxin, plant toxin, ricin, abrin, a ribonuclease (RNase), DNase I, a protease, Staphylococcal enterotoxin-A, pokeweed antiviral protein, gelonin, diphtherin toxin, *Pseudomonas* exotoxin, *Pseudomonas* endotoxin, Ranpimase (Rap), Rap (N69Q), methotrexate, daunorubicin, doxorubicin, vincristine, vinblastine, melphalan, mitomycin C, chlorambucil, and calicheamicin.

In other therapeutic treatments or compositions, E binders or E/I binders are co-administered, or administered sequentially, with one or more additional therapeutic agents. Suitable therapeutic agents include, but are not limited to, cytotoxic or cytostatic agents, such as cancer therapeutic agents.

Cancer therapeutic agents are those agents that seek to kill or limit the growth of cancer cells while having minimal effects on the patient. Thus, such agents may exploit any difference in cancer cell properties (e.g., metabolism, vascularization or cell-surface antigen presentation) from healthy host cells. Therapeutic agents that can be combined with E/I binders for improved anti-cancer efficacy include diverse agents used in oncology practice (Reference: Cancer, Principles & Practice of Oncology, DeVita, V. T., Hellman, S., Rosenberg, S. A., 6th edition, Lippincott-Raven, Philadelphia, 2001), such as doxorubicin, epirubicin, cyclophosphamide, trastuzumab, capecitabine, tamoxifen, toremifene, letrozole, anastrozole, fulvestrant, exemestane, goserelin, oxaliplatin, carboplatin, cisplatin, dexamethasone, antide, bevacizumab, 5-fluorouracil, leucovorin, levamisole, irinotecan, etoposide, topotecan, gemcitabine, vinorelbine, estramustine, mitoxantrone, abarelix, zoledronate, streptozocin, rituximab, idarubicin, busulfan, chlorambucil, fludarabine, imatinib, cytarabine, ibritumomab, tositumomab, interferon alpha-2b, melphalam, bortezomib, altretamine, asparaginase, gefitinib, erlonitib, anti-EGF receptor antibody (e.g., cetuximab or panitumab), ixabepilone, epothilones or derivatives thereof, platinum agents (such as carboplatin, oxaliplatin, cisplatin), taxanes (such as paclitaxel, docetaxel), and camptothecin.

Therapeutic Formulations and Modes of Administration

The present application provides methods for treating conditions which respond to an inhibition of EGFR and/or IGFIR biological activity. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

In some embodiments, the E binders and E/I binders are pharmaceutically acceptable to a mammal, in particular a human. A "pharmaceutically acceptable" polypeptide refers to a polypeptide that is administered to an animal without significant adverse medical consequences. Examples of pharmaceutically acceptable E binders and E/I binders include $^{10}$Fn3 domains that lack the integrin-binding domain (RGD) and $^{10}$Fn3 domains that are essentially endotoxin free or have very low endotoxin levels.

Therapeutic compositions may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique using nucleic acids encoding E binders or E/I binders, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; a liquid for intravenous, subcutaneous or parenteral administration; or a gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the E binder or E/I binder is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or less frequently (e.g., once every other day, once or twice weekly, or monthly). In addition, as is known in the art, adjustments for age as well as the body weight, general health, sex, diet, time of administration, drug interaction, and the severity of the disease may be necessary, and will be ascertainable with routine experimentation by those skilled in the art.

Exemplification

The invention now being generally described will be more readily understood by reference to the following examples which are included merely for purposes of illustration of certain aspects and embodiments of the present invention, and are not intended to limit the invention in any way.

Summary of Sequences

Many of the sequences referenced in this application are summarized in the table below. Unless otherwise specified, N-terminal extensions are indicated with a single underline, C-terminal tails are indicated with a double underline, and linker sequences are indicated in bold.

| SEQ ID NO: | Description | Sequence |
|---|---|---|
| 1 | WT human $^{10}$Fn3 domain | VSDVPRDLEVVAATPTSLLISWDAPAVTVRYY RITYGETGGNSPVQEFTVPGSKSTATISGLKPGV DYTITVYAVTGRGDSPASSKPISINYRT |
| 2 | Variant human $^{10}$Fn3 with the integrin binding motif removed (RGD changed to SGE; changes from SEQ ID NO: 1 are underlined) | VSDVPRDLEVVAATPTSLLISWDAPAVTVRYY RITYGETGGNSPVQEFTVPGSKSTATISGLKPGV DYTITVYAVTGSGESPASSKPISINYRT |
| 3 | I1 IGF-IR monomer with N-terminal extension (N + 8) and no tail | VSDVPRDLEVVAATPTSLLISWSARLKVARYY RITYGETGGNSPVQEFTVPKNVYTATISGLKPG VDYTITVYAVTRFRDYQPISINYRT |
| 4 | I1 IGF-IR monomer with N-terminal extension (N + 10) and Ser tail with His tag | MGVSDVPRDLEVVAATPTSLLISWSARLKVAR YYRITYGETGGNSPVQEFTVPKNVYTATISGLK PGVDYTITVYAVTRFRDYQPISINYRTEIDKPSQ HHHHHH |
| 5 | E2 EGFR monomer with N-terminal extension (N + 8) and no tail | VSDVPRDLEVVAATPTSLLISWDSGRGSYQYY RITYGETGGNSPVQEFTVPGPVHTATISGLKPG VDYTITVYAVTDHKPHADGPHTYHESPISINYR T |
| 6 | E2 EGFR monomer with N-terminal extension (N + 10) and Ser tail with his tag | MGVSDVPRDLEVVAATPTSLLISWDSGRGSYQ YYRITYGETGGNSPVQEFTVPGPVHTATISGLK PGVDYTITVYAVTDHKPHADGPHTYHESPISIN YRTEIDKPSQHHHHHH |
| 7 | E1 EGFR monomer with N-terminal extension (N + 8) and no tail | VSDVPRDLEVVAATPTSLLISWVAGAEDYQYY RITYGETGGNSPVQEFTVPHDLVTATISGLKPG VDYTITVYAVTDMMHVEYTEHPISINYRT |
| 8 | E1 EGFR monomer with N-terminal extension (N + 10) and Ser tail with his tag | MGVSDVPRDLEVVAATPTSLLISWVAGAEDYQ YYRITYGETGGNSPVQEFTVPHDLVTATISGLK PGVDYTITVYAVTDMMHVEYTEHPISINYRTEI DKPSQHHHHHH |
| 9 | Ser tail | EIDKPSQ |
| 10 | Cys tail | EIDKPCQ |
| 11 | (GS)$_{10}$ Linker | GSGSGSGSGSGSGSGSGSGS |
| 12 | Fn Based Linker | PSTSTST |
| 13 | (GS)$_5$ Linker | GSGSGSGSGS |
| 14 | (GGGGS)$_3$ Linker | GGGGS GGGGS GGGGS |
| 15 | (GGGGS)$_4$ Linker | GGGGS GGGGS GGGGS GGGGS |
| 16 | (GGGGS)5 Linker | GGGGS GGGGS GGGGS GGGGS GGGGS |
| 17 | G$_4$SG$_4$SG$_3$SG Linker | GGGGS GGGGS GGGSG |
| 18 | Linker | GPGPGPG |
| 19 | Linker | GPGPGPGPGPG |
| 20 | I1-GS10-E2: I/E tandem having I1 (with N-terminal extension (N + 8) and short tail) fused via GS$_{10}$ linker (GS10 is | VSDVPRDLEVVAATPTSLLISWSARLKVARYY RITYGETGGNSPVQEFTVPKNVYTATISGLKPG VDYTITVYAVTRFRDYQPISINYRTEIDKGSGS GSGSGSGSGSGSGSGSVSDVPRDLEVVAATPT |

| SEQ ID NO: | Description | Sequence |
|---|---|---|
|  | SEQ ID NO: 11) to E2 (with N-terminal extension (N + 8) and no tail) | SLLISWDSGRGSYQYYRITYGETGGNSPVQEFT VPGPVHTATISGLKPGVDYTITVYAVTDHKPHA DGPHTYHESPISINYRT |
| 21 | I1-GS10-E2: I/E tandem having I1 (with N-terminal extension (N + 10) and short tail) fused via GS₁₀ linker (GS10 is SEQ ID NO: 11) to E2 (with N-terminal extension (N + 8) and Ser tail) | MGVSDVPRDLEVVAATPTSLLISWSARLKVAR YYRITYGETGGNSPVQEFTVPKNVYTATISGLK PGVDYTITVYAVTRFRDYQPISINYRTEIDKGSG SGSGSGSGSGSGSGSGSVSDVPRDLEVVAATP TSLLISWDSGRGSYQYYRITYGETGGNSPVQEF TVPGPVHTATISGLKPGVDYTITVYAVTDHKPH ADGPHTYHESPISINYRTEIDKPSQ |
| 22 | I1-GS10-E2: I/E tandem I1 (with N-terminal extension (N + 10) and short tail) fused via GS₁₀ linker (GS10 is SEQ ID NO: 11) to E2 (with N-terminal extension (N + 8) and Ser tail with his tag) | MGVSDVPRDLEVVAATPTSLLISWSARLKVAR YYRITYGETGGNSPVQEFTVPKNVYTATISGLK PGVDYTITVYAVTRFRDYQPISINYRTEIDKGSG SGSGSGSGSGSGSGSGSVSDVPRDLEVVAATP TSLLISWDSGRGSYQYYRITYGETGGNSPVQEF TVPGPVHTATISGLKPGVDYTITVYAVTDHKPH ADGPHTYHESPISINYRTEIDKPSQHHHHHH |
| 23 | E2-GS10-I1: E/I tandem having E2 (with N-terminal extension (N + 8) and short tail) fused via GS₁₀ linker (GS10 is SEQ ID NO: 11) to I1 (with N-terminal extension (N + 8) and Ser tail) | VSDVPRDLEVVAATPTSLLISWDSGRGSYQYY RITYGETGGNSPVQEFTVPGPVHTATISGLKPG VDYTITVYAVTDHKPHADGPHTYHESPISINYR TEIDKGSGSGSGSGSGSGSGSGSGSVSDVPRD LEVVAATPTSLLISWSARLKVARYYRITYGETG GNSPVQEFTVPKNVYTATISGLKPGVDYTITVY AVTRFRDYQPISINYRTEIDKPSQ |
| 24 | E2-GS10-I1: E/I tandem having E2 (with N-terminal extension (N + 10) and short tail) fused via GS₁₀ linker (GS10 is SEQ ID NO: 11) to I1 (with N-terminal extension (N + 8) and Ser tail) | MGVSDVPRDLEVVAATPTSLLISWDSGRGSYQ YYRITYGETGGNSPVQEFTVPGPVHTATISGLK PGVDYTITVYAVTDHKPHADGPHTYHESPISIN YRTEIDKGSGSGSGSGSGSGSGSGSGSVSDVP RDLEVVAATPTSLLISWSARLKVARYYRITYGE TGGNSPVQEFTVPKNVYTATISGLKPGVDYTIT VYAVTRFRDYQPISINYRTEIDKPSQ |
| 25 | E2-GS10-I1: E/I tandem having E2 (with N-terminal extension (N + 10) and short tail) fused via GS₁₀ linker (GS10 is SEQ ID NO: 11) to I1 (with N-terminal extension (N + 8) and Ser tail with his tag) | MGVSDVPRDLEVVAATPTSLLISWDSGRGSYQ YYRITYGETGGNSPVQEFTVPGPVHTATISGLK PGVDYTITVYAVTDHKPHADGPHTYHESPISIN YRTEIDKGSGSGSGSGSGSGSGSGSGSVSDVP RDLEVVAATPTSLLISWSARLKVARYYRITYGE TGGNSPVQEFTVPKNVYTATISGLKPGVDYTIT VYAVTRFRDYQPISINYRTEIDKPSQHHHHHH |
| 26 | I1-GS10-E1: I/E tandem having I1 (with N-terminal extension (N + 8) and short tail) fused via GS₁₀ linker (GS10 is SEQ ID NO: 11) to E1 (with N-terminal extension (N + 8) and no tail) | VSDVPRDLEVVAATPTSLLISWSARLKVARYY RITYGETGGNSPVQEFTVPKNVYTATISGLKPG VDYTITVYAVTRFRDYQPISINYRTEIDKGSGS GSGSGSGSGSGSGSGSVSDVPRDLEVVAATPT SLLISWVAGAEDYQYYRITYGETGNSPVQEFT VPHDLVTATISGLKPGVDYTITVYAVTDMMHV EYTEHPISINYRT |
| 27 | I1-GS10-E1: I/E tandem having I1 (with N-terminal extension (N + 10) and short tail) fused via GS₁₀ linker (GS10 is SEQ ID NO: 11) to E1 (with N-terminal extension (N + 8) and Ser tail) | MGVSDVPRDLEVVAATPTSLLISWSARLKVAR YYRITYGETGGNSPVQEFTVPKNVYTATISGLK PGVDYTITVYAVTRFRDYQPISINYRTEIDKGSG SGSGSGSGSGSGSGSGSVSDVPRDLEVVAATP TSLLISWVAGAEDYQYYRITYGETGNSPVQEF TVPHDLVTATISGLKPGVDYTITVYAVTDMMH VEYTEHPISINYRTEIDKPSQ |
| 28 | I1-GS10-E1: I/E tandem having I1 (with N-terminal extension (N + 10) and short tail) fused via GS₁₀ linker (GS10 is SEQ ID NO: 11) to E1 (with N-terminal extension (N + 8) and Ser tail with his tag) | MGVSDVPRDLEVVAATPTSLLISWSARLKVAR YYRITYGETGGNSPVQEFTVPKNVYTATISGLK PGVDYTITVYAVTRFRDYQPISINYRTEIDKGSG SGSGSGSGSGSGSGSGSVSDVPRDLEVVAATP TSLLISWVAGAEDYQYYRITYGETGNSPVQEF TVPHDLVTATISGLKPGVDYTITVYAVTDMMH VEYTEHPISINYRTEIDKPSQHHHHHH |
| 29 | E1-GS10-I1: E/I tandem having E1 (with N-terminal extension (N + 8) and short tail) fused via GS₁₀ linker (GS10 is SEQ ID NO: 11) to I1 (with N-terminal extension (N + 8) and no tail) | VSDVPRDLEVVAATPTSLLISWVAGAEDYQYY RITYGETGGNSPVQEFTVPHDLVTATISGLKPG VDYTITVYAVTDMMHVEYTEHPISINYRTEIDK GSGSGSGSGSGSGSGSGSGSVSDVPRDLEVVA ATPTSLLISWSARLKVARYYRITYGETGGNSPV QEFTVPKNVYTATISGLKPGVDYTITVYAVTRF RDYQPISINYRT |

| SEQ ID NO: | Description | Sequence |
|---|---|---|
| 30 | E1-GS10-I1: E/I tandem having E1 (with N-terminal extension (N + 10) and short tail) fused via GS₁₀ linker (GS10 is SEQ ID NO: 11) to I1 (with N-terminal extension (N + 8) and Ser tail) | MGVSDVPRDLEVVAATPTSLLISWVAGAEDYQ YYRITYGETGGNSPVQEFTVPHDLVTATISGLK PGVDYTITVYAVTDMMHVEYTEHPISINYRTEI DKGSGSGSGSGSGSGSGSGSGSVSDVPRDLEV VAATPTSLLISWSARLKVARYYRITYGETGGNS PVQEFTVPKNVYTATISGLKPGVDYTITVYAVT RFRDYQPISINYRTEIDKPSQ |
| 31 | E1-GS10-I1: E/I tandem having E1 (with N-terminal extension (N + 10) and short tail) fused via GS₁₀ linker (GS10 is SEQ ID NO: 11) to I1 (with N-terminal extension (N + 8) and Ser tail with his tag) | MGVSDVPRDLEVVAATPTSLLISWVAGAEDYQ YYRITYGETGGNSPVQEFTVPHDLVTATISGLK PGVDYTITVYAVTDMMHVEYTEHPISINYRTEI DKGSGSGSGSGSGSGSGSGSGSVSDVPRDLEV VAATPTSLLISWSARLKVARYYRITYGETGGNS PVQEFTVPKNVYTATISGLKPGVDYTITVYAVT RFRDYQPISINYRTEIDKPSQHHHHHH |
| 32 | ¹⁰Fn3 scaffold, wherein the BC, DE, and FG loops are represented by (X)$_n$, (X)$_o$, and (X)$_p$, respectively, and n is an integer from 1-20, o is an integer from 1-20, and p is an integer from 1-40 | VSDVPRDLEVVAATPTSLLI(X)$_n$YYRITYGETGGNSPVQEFTV(X)$_o$ATISGLKP GVDYTITVYAV(X)$_p$ISINYRT |
| 33 | BC loop sequence from EGFR binder E1 | SWVAGAEDYQ |
| 34 | BC loop sequence from EGFR binder E1, wherein X is any amino acid and m and n are independently selected from 0 to 5 amino acids | X$_m$VAGAEDYQX$_n$ |
| 35 | DE loop sequence from EGFR binder E1 | PHDLVT |
| 36 | DE loop sequence from EGFR binder E1, wherein X is any amino acid and o and p are independently selected from 0 to 5 amino acids | X$_o$HDLVX$_p$ |
| 37 | FG loop sequence from EGFR binder E1 | TDMMHVEYTEHP |
| 38 | FG loop sequence from EGFR binder E1, wherein X is any amino acid and q and r are independently selected from 0 to 5 amino acids | X$_q$DMMHVEYTEHX$_r$ |
| 39 | BC loop sequence from EGFR binder E2 | SWDSGRGSYQ |
| 40 | BC loop sequence from EGFR binder E2, wherein X is any amino acid and g and h are independently selected from 0 to 5 amino acids | X$_g$DSGRGSYQX$_h$ |
| 41 | DE loop sequence from EGFR binder E2 | PGPVHT |
| 42 | DE loop sequence from EGFR binder E2, wherein X is any amino acid and i and j are independently selected from 0 to 5 amino acids | X$_i$GPVHX$_j$ |
| 43 | FG loop sequence from EGFR binder E2 | TDHKPHADGPHTYHESP |
| 44 | FG loop sequence from EGFR binder E2, wherein X is any amino acid and k and l are | X$_k$DHKPHADGPHTYHEX$_l$ |

| SEQ ID NO: | Description | Sequence |
|---|---|---|
| | independently selected from 0 to 5 amino acids | |
| 45 | BC loop sequence from IGF-IR binder I1 | SWSARLKVAR |
| 46 | BC loop sequence from IGF-IR binder I1, wherein X is any amino acid and a and b are independently selected from 0 to 5 amino acids | $X_a$SARLKVA$X_b$ |
| 47 | DE loop sequence from IGF-IR binder I1 | PKNVYT |
| 48 | DE loop sequence from IGF-IR binder I1, wherein X is any amino acid and c and d are independently selected from 0 to 5 amino acids | $X_c$KNVY$X_d$ |
| 49 | FG loop sequence from IGF-IR binder I1 | TRFRDYQP |
| 50 | FG loop sequence from IGF-IR binder I1, wherein X is any amino acid and e and f are independently selected from 0 to 5 amino acids | $X_e$RFRDYQ$X_f$ |
| 51 | Linker | GPG |
| 52 | E3 EGFR monomer with N-terminal extension (N + 10), Ser tail and his tag | MGVSDVPRDLEVVAATPTSLLISWLPGKLRYQYYRITYGETGGNSPVQEFTVPHDLRTATISGLKPGVDYTITVYAVTNMMHVEYSEYPISINYRTEIDKPSQHHHHHH |
| 53 | E3-GS10-I1: E/I tandem having E3 (with N-terminal extension (N + 10) and short tail) fused via GS₁₀ linker (GS10 is SEQ ID NO: 11) to I1 (with N-terminal extension (N + 8) and Cys tail with his tag) | MGVSDVPRDLEVVAATPTSLLISWLPGKLRYQYYRITYGETGGNSPVQEFTVPHDLRTATISGLKPGVDYTITVYAVTNMMHVEYSEYPISINYRTEIDKGSGSGSGSGSGSGSGSGSGSVSDVPRDLEVVAATPTSLLISWSARLKVARYYRITYGETGGNSPVQEFTVPKNVYTATISGLKPGVDYTITVYAVTRFRDYQPISINYRTEIDKPCQHHHHHH |
| 54 | I1-GS10-E3: I/E tandem having I1 with N-terminal extension (N + 10) and short tail) fused via GS₁₀ linker (GS10 is SEQ ID NO: 11) to E3 (with N-terminal extension (N + 8) and Cys tail with his tag) | MGVSDVPRDLEVVAATPTSLLISWSARLKVARYYRITYGETGGNSPVQEFTVPKNVYTATISGLKPGVDYTITVYAVTRFRDYQPISINYRTEIDKGSGSGSGSGSGSGSGSGSGSVSDVPRDLEVVAATPTSLLISWLPGKLRYQYYRITYGETGGNSPVQEFTVPHDLRTATISGLKPGVDYTITVYAVTNMMHVEYSEYPISINYRTEIDKPCQHHHHHH |
| 55 | E1-GS10-I1: E/I tandem having E1 (with N-terminal extension (N + 10) and short tail) fused via GS₁₀ linker (GS10 is SEQ ID NO: 11) to I1 (with N-terminal extension (N + 8) and Cys tail with his tag) | MGVSDVPRDLEVVAATPTSLLISWVAGAEDYQYYRITYGETGGNSPVQEFTVPHDLVTATISGLKPGVDYTITVYAVTDMMHVEYTEHPISINYRTEIDKGSGSGSGSGSGSGSGSGSGSVSDVPRDLEVVAATPTSLLISWSARLKVARYYRITYGETGGNSPVQEFTVPKNVYTATISGLKPGVDYTITVYAVTRFRDYQPISINYRTEIDKPCQHHHHHH |
| 56 | E2-GS10-I1: E/I tandem having E2 (with N-terminal extension (N + 10) and short tail) fused via GS₁₀ linker (GS10 is SEQ ID NO: 11) to I1 (with N-terminal extension (N + 8) and Cys tail with his tag) | MGVSDVPRDLEVVAATPTSLLISWDSGRGSYQYYRITYGETGGNSPVQEFTVPGPVHTATISGLKPGVDYTITVYAVTDHKPHADGPHTYHESPISINYRTEIDKGSGSGSGSGSGSGSGSGSGSVSDVPRDLEVVAATPTSLLISWSARLKVARYYRITYGETGGNSPVQEFTVPKNVYTATISGLKPGVDYTITVYAVTRFRDYQPISINYRTEIDKPCQHHHHHH |
| 57 | I1-GS10-E1: I/E tandem having I1 (with N-terminal extension (N + 10) and short | MGVSDVPRDLEVVAATPTSLLISWSARLKVARYYRITYGETGGNSPVQEFTVPKNVYTATISGLKPGVDYTITVYAVTRFRDYQPISINYRTEIDKGSG |

| SEQ ID NO: | Description | Sequence |
|---|---|---|
| | tail) fused via GS$_{10}$ linker (GS10 is SEQ ID NO: 11) to E1 (with N-terminal extension (N + 8) and Cys tail with his tag) | SGSGSGSGSGSGSGSGSVSDVPRDLEVVAATP TSLLISWVAGAEDYQYRITYGETGGNSPVQEF TVPHDLVTATISGLKPGVDYTITVYAVTDMMH VEYTEHPISINYRT<u>EIDKPCQ</u>HHHHHH |
| 58 | I1-GS10-E2: I/E tandem having I1 (with N-terminal extension (N + 10) and short tail) fused via GS$_{10}$ linker (GS10 is SEQ ID NO: 11) to E2 (with N-terminal extension (N + 8) and Cys tail with his tag) | <u>MGVSDVPRDL</u>EVVAATPTSLLISWSARLKVAR YYRITYGETGGNSPVQEFTVPKNVYTATISGLK PGVDYTITVYAVTRFRDYQPISINYRT<u>EIDK</u>GSG SGSGSGSGSGSGSGSGSVSDVPRDLEVVAATP TSLLISWDSGRGSYQYRITYGETGGNSPVQEF TVPGPVHTATISGLKPGVDYTITVYAVTDHKPH ADGPHTYHESPISINYRT<u>EIDKPCQ</u>HHHHHH |
| 59 | BC loop sequence from EGFR binder E3 | SWLPGKLRYQ |
| 60 | BC loop sequence from EGFR binder E3, wherein X is any amino acid and s and t are independently selected from 0 to 5 amino acids | X$_s$LPGKLRYQX$_t$ |
| 61 | DE loop sequence from EGFR binder E3 | PHDLRT |
| 62 | DE loop sequence from EGFR binder E3, wherein X is any amino acid and u and w are independently selected from 0 to 5 amino acids | X$_u$HDLRX$_w$ |
| 63 | FG loop sequence from EGFR binder E3 | TNMMHVEYSEYP |
| 64 | DE loop sequence from EGFR binder E3, wherein X is any amino acid and y and z are independently selected from 0 to 5 amino acids | X$_y$NMMHVEYSEYX$_z$ |
| 65 | I1 IGF-IR monomer core sequence: I1 without N-terminal extension or C-terminal tail | EVVAATPTSLLISWSARLKVARYYRITYGETGG NSPVQEFTVPKNVYTATISGLKPGVDYTITVYA VTRFRDYQPISINYRT |
| 66 | E1 EGFR monomer core sequence: E1 without N-terminal extension or C-terminal tail | EVVAATPTSLLISWVAGAEDYQYRITYGETG GNSPVQEFTVPHDLVTATISGLKPGVDYTITVY AVTDMMHVEYTEHPISINYRT |
| 67 | E2 EGFR monomer core sequence: E2 without N-terminal extension or C-terminal tail | EVVAATPTSLLISWDSGRGSYQYRITYGETGG NSPVQEFTVPGPVHTATISGLKPGVDYTITVYA VTDHKPHADGPHTYHESPISINYRT |
| 68 | E3 EGFR monomer core sequence: SEQ ID NO: 82 without N-terminal extension or C-terminal tail | EVVAATPTSLLISWLPGKLRYQYYRITYGETGG NSPVQEFTVPHDLRTATISGLKPGVDYTITVYA VTNMMHVEYSEYPISINYRT |
| 69 | Exemplary N-terminal extension (N + 10) | MGVSDVPRDL |
| 70 | Exemplary N-terminal extension | GVSDVPRDL |
| 71 | Exemplary N-terminal extension (N + 8) | VSDVPRDL |
| 72 | Exemplary N-terminal extension, wherein X is any amino acid and n is 0, 1 or 2, preferably when n = 1, X is Met | X$_n$SDVPRDL |

-continued

| SEQ ID NO: | Description | Sequence |
|---|---|---|
| | or Gly and when n = 2, X is Met-Gly | |
| 73 | Exemplary N-terminal extension, wherein X is any amino acid and n is 0, 1 or 2, preferably when n = 1, X is Met or Gly and when n = 2, X is Met-Gly | $X_n$DVPRDL |
| 74 | Exemplary N-terminal extension, wherein X is any amino acid and n is 0, 1 or 2, preferably when n = 1, X is Met or Gly and when n = 2, X is Met-Gly | $X_n$VPRDL |
| 75 | Exemplary N-terminal extension, wherein X is any amino acid and n is 0, 1 or 2, preferably when n = 1, X is Met or Gly and when n = 2, X is Met-Gly | $X_n$PRDL |
| 76 | Exemplary N-terminal extension, wherein X is any amino acid and n is 0, 1 or 2, preferably when n = 1, X is Met or Gly and when n = 2, X is Met-Gly | $X_n$RDL |
| 77 | Exemplary N-terminal extension, wherein X is any amino acid and n is 0, 1 or 2, preferably when n = 1, X is Met or Gly and when n = 2, X is Met-Gly | $X_n$DL |
| 78 | Short tail | EIDK |
| 79 | Exemplary C-terminal tail | EIDKP |
| 80 | Exemplary C-terminal tail | EIDKPS |
| 81 | Exemplary C-terminal tail | EIDKPC |
| 82 | E3 EGFR monomer with N-terminal extension (N + 8) and no tail | VSDVPRDLEVVAATPTSLLISWLPGKLRYQYY RITYGETGGNSPVQEFTVPHDLRTATISGLKPG VDYTITVYAVTNMMHVEYSEYPISINYRT |
| 87 | E3-GS10-I1: E/I tandem having E3 (with N-terminal extension (N + 8) and short tail) fused via GS10 linker (GS10 is SEQ ID NO: 11) to I1 (with N-terminal extension (N + 8) and Cys tail) | VSDVPRDLEVVAATPTSLLISWLPGKLRYQYY RITYGETGGNSPVQEFTVPHDLRTATISGLKPG VDYTITVYAVTNMMHVEYSEYPISINYRTEIDK GSGSGSGSGSGSGSGSGSGSVSDVPRDLEVVA ATPTSLLISWSARLKVARYYRITYGETGGNSPV QEFTVPKNVYTATISGLKPGVDYTITVYAVTRF RDYQPISINYRTEIDKPCQ |
| 88 | I1-GS10-E3: I/E tandem having I1 (with N-terminal extension (N + 8) and short tail) fused via GS10 linker (GS10 is SEQ ID NO: 11) to E3 (with N-terminal extension (N + 8) and Cys tail) | VSDVPRDLEVVAATPTSLLISWSARLKVARYY RITYGETGGNSPVQEFTVPKNVYTATISGLKPG VDYTITVYAVTRFRDYQPISINYRTEIDKGSGS GSGSGSGSGSGSGSGSVSDVPRDLEVVAATPT SLLISWLPGKLRYQYYRITYGETGGNSPVQEFT VPHDLRTATISGLKPGVDYTITVYAVTNMMHV EYSEYPISINYRTEIDKPCQ |
| 89 | E1-GS10-I1: E/I tandem having E1 (with N-terminal extension (N + 8) and short tail) fused via GS10 linker (GS10 is SEQ ID NO: 11) to I1 (with N-terminal extension (N + 8) and Cys tail) | VSDVPRDLEVVAATPTSLLISWVAGAEDYQYY RITYGETGGNSPVQEFTVPHDLVTATISGLKPG VDYTITVYAVTDMMHVEYTEHPISINYRTEIDK GSGSGSGSGSGSGSGSGSGSVSDVPRDLEVVA ATPTSLLISWSARLKVARYYRITYGETGGNSPV QEFTVPKNVYTATISGLKPGVDYTITVYAVTRF RDYQPISINYRTEIDKPCQ |
| 90 | E2-GS10-I1: E/I tandem having E2 (with N-terminal | VSDVPRDLEVVAATPTSLLISWDSGRGSYQYY RITYGETGGNSPVQEFTVPGPVHTATISGLKPG |

| SEQ ID NO: | Description | Sequence |
|---|---|---|
| | extension (N + 8) and short tail) fused via GS₁₀ linker (GS10 is SEQ ID NO: 11) to I1 (with N-terminal extension (N + 8) and Cys tail) | VDYTITVYAVTDHKPHADGPHTYHESPISINYR TEIDKGSGSGSGSGSGSGSGSGSGSVSDVPRD LEVVAATPTSLLISWSARLKVARYYRITYGETG GNSPVQEFTVPKNVYTATISGLKPGVDYTITVY AVTRFRDYQPISINYRTEIDKPCQ |
| 91 | I1-GS10-E1: I/E tandem having I1 (with N-terminal extension (N + 8) and short tail) fused via GS₁₀ linker (GS10 is SEQ ID NO: 11) to E1 (with N-terminal extension (N + 8) and Cys tail) | VSDVPRDLEVVAATPTSLLISWSARLKVARYY RITYGETGGNSPVQEFTVPKNVYTATISGLKPG VDYTITVYAVTRFRDYQPISINYRTEIDKGSGS GSGSGSGSGSGSGSVSDVPRDLEVVAATPT SLLISWVAGAEDYQYYRITYGETGGNSPVQEFT VPHDLVTATISGLKPGVDYTITVYAVTDMMHV EYTEHPISINYRTEIDKPCQ |
| 92 | I1-GS10-E2: I/E tandem having I1 (with N-terminal extension (N + 8) and short tail) fused via GS₁₀ linker (GS10 is SEQ ID NO: 11) to E2 (with N-terminal extension (N + 8) and Cys tail) | VSDVPRDLEVVAATPTSLLISWSARLKVARYY RITYGETGGNSPVQEFTVPKNVYTATISGLKPG VDYTITVYAVTRFRDYQPISINYRTEIDKGSGS GSGSGSGSGSGSGSVSDVPRDLEVVAATPT SLLISWDSGRGSYQYYRITYGETGGNSPVQEFT VPGPVHTATISGLKPGVDYTITVYAVTDHKPHA DGPHTYHESPISINYRTEIDKPCQ |
| 93 | PA3 Linker | PAPAPA |
| 94 | PA6 Linker | PAPAPAPAPAPA |
| 95 | PA9 Linker | PAPAPAPAPAPAPAPA |
| 96 | Modified Ser tail | EGSGS |
| 97 | Modified Cys tail | EGSGC |
| 98 | E3-(PA)ₙ-I1: E/I tandem having E3 (with N-terminal extension (N + 8) and an E tail) fused via (PA)ₙ linker ((PA)ₙ is SEQ ID NO: 488) to I1 (with N-terminal extension (N + 8) and a modified Ser or Cys tail), wherein n = 3, 6 or 9, and X = Ser or Cys | VSDVPRDLEVVAATPTSLLISWLPGKLRYQYY RITYGETGGNSPVQEFTVPHDLRTATISGLKPG VDYTITVYAVTNMMHVEYSEYPISINYRTE(PA)ₙ VSDVPRDLEVVAATPTSLLISWSARLKVARYY RITYGETGGNSPVQEFTVPKNVYTATISGLKPG VDYTITVYAVTRFRDYQPISINYRTEGSGX |
| 99 | I1-(PA)ₙ-E3: I/E tandem having I1 (with N-terminal extension (N + 8) and an E tail) fused via (PA)ₙ linker ((PA)ₙ is SEQ ID NO: 488) to E3 (with N-terminal extension (N + 8) and a modified Ser or Cys tail), wherein n = 3, 6 or 9, and X = Ser or Cys | VSDVPRDLEVVAATPTSLLISWSARLKVARYY RITYGETGGNSPVQEFTVPKNVYTATISGLKPG VDYTITVYAVTRFRDYQPISINYRTE(PA)ₙVSDV PRDLEVVAATPTSLLISWLPGKLRYQYYRITYG ETGGNSPVQEFTVPHDLRTATISGLKPGVDYTI TVYAVTNMMHVEYSEYPISINYRTEGSGX |
| 100 | E1-(PA)ₙ-I1: E/I tandem having E1 (with N-terminal extension (N + 8) and an E tail) fused via (PA)ₙ linker ((PA)ₙ is SEQ ID NO: 488) to I1 (with N-terminal extension (N + 8) and a modified Ser or Cys tail), wherein n = 3, 6 or 9, and X = Ser or Cys | VSDVPRDLEVVAATPTSLLISWVAGAEDYQYY RITYGETGGNSPVQEFTVPHDLVTATISGLKPG VDYTITVYAVTDMMHVEYTEHPISINYRTE(PA)ₙ VSDVPRDLEVVAATPTSLLISWSARLKVARYY RITYGETGGNSPVQEFTVPKNVYTATISGLKPG VDYTITVYAVTRFRDYQPISINYRTEGSGX |
| 101 | E2-(PA)ₙ-I1: E/I tandem having E2 (with N-terminal extension (N + 8) and an E tail) fused via (PA)ₙ linker ((PA)ₙ is SEQ ID NO: 488) to I1 (with N-terminal extension (N + 8) and a modified Ser or Cys tail), wherein n = 3, 6 or 9, and X = Ser or Cys | VSDVPRDLEVVAATPTSLLISWDSGRGSYQYY RITYGETGGNSPVQEFTVPGPVHTATISGLKPG VDYTITVYAVTDHKPHADGPHTYHESPISINYR TE(PA)ₙVSDVPRDLEVVAATPTSLLISWSARLK VARYYRITYGETGGNSPVQEFTVPKNVYTATIS GLKPGVDYTITVYAVTRFRDYQPISINYRTEGS GX |
| 102 | I1-(PA)ₙ-E1: I/E tandem having I1 (with N-terminal extension (N + 8) and an E tail) fused via (PA)ₙ linker ((PA)ₙ is | VSDVPRDLEVVAATPTSLLISWSARLKVARYY RITYGETGGNSPVQEFTVPKNVYTATISGLKPG VDYTITVYAVTRFRDYQPISINYRTE(PA)ₙVSDV PRDLEVVAATPTSLLISWVAGAEDYQYYRITY |

| SEQ ID NO: | Description | Sequence |
|---|---|---|
| | SEQ ID NO: 488) to E1 (with N-terminal extension (N + 8) and a modified Ser or Cys tail), wherein n = 3, 6 or 9, and X = Ser or Cys | GETGGNSPVQEFTVPHDLVTATISGLKPGVDYT ITVYAVTDMMHVEYTEHPISINYRTEGSGX |
| 103 | I1-(PA)$_n$-E2: I/E tandem having I1 (with N-terminal extension (N + 8) and an E tail) fused via (PA)$_n$ linker ((PA)$_n$ is SEQ ID NO: 488) to E2 (with N-terminal extension (N + 8) and a modified Ser or Cys tail), wherein n = 3, 6 or 9, and X = Ser or Cys | VSDVPRDLEVVAATPTSLLISWSARLKVARYY RITYGETGGNSPVQEFTVPKNVYTATISGLKPG VDYTITVYAVTRFRDYQPISINYRTE(PA)$_n$VSDV PRDLEVVAATPTSLLISWDSGRGSYQYYRITYG ETGGNSPVQEFTVPGPVHTATISGLKPGVDYTI TVYAVTDHKPHADGPHTYHESPISINYRTEGSGX |
| 104 | E3-GS10-I1: E/I tandem having E3 (with N-terminal extension (N + 8) and short tail) fused via GS$_{10}$ linker (GS10 is SEQ ID NO: 11) to I1 (with N-terminal extension (N + 8) and Ser tail) | VSDVPRDLEVVAATPTSLLISWLPGKLRYQYY RITYGETGGNSPVQEFTVPHDLRTATISGLKPG VDYTITVYAVTNMMHVEYSEYPISINYRTEIDK GSGSGSGSGSGSGSGSGSGSVSDVPRDLEVVA ATPTSLLISWSARLKVARYYRITYGETGGNSPV QEFTVPKNVYTATISGLKPGVDYTITVYAVTRF RDYQPISINYRTEIDKPSQ |
| 105 | I1-GS10-E3: I/E tandem having I1 with N-terminal extension (N + 8) and short tail) fused via GS$_{10}$ linker (GS10 is SEQ ID NO: 11) to E3 (with N-terminal extension (N + 8) and Ser tail) | VSDVPRDLEVVAATPTSLLISWSARLKVARYY RITYGETGGNSPVQEFTVPKNVYTATISGLKPG VDYTITVYAVTRFRDYQPISINYRTEIDKGSGS GSGSGSGSGSGSGSGSVSDVPRDLEVVAATPT SLLISWLPGKLRYQYYRITYGETGGNSPVQEFT VPHDLRTATISGLKPGVDYTITVYAVTNMMHV EYSEYPISINYRTEIDKPSQ |
| 106 | E4 EGFR monomer with N-terminal extension (N + 8) and no tail | VSDVPRDLEVVAATPTSLLISWHERDGSRQYY RITYGETGGNSPVQEFTVPGGVRTATISGLKPG VDYTITVYAVTDYFNPTTHEYIYQTTPISINYRT |
| 107 | E4 EGFR monomer with N-terminal extension (N + 10) and a Ser with His tag | MGVSDVPRDLEVVAATPTSLLISWHERDGSRQ YYRITYGETGGNSPVQEFTVPGGVRTATISGLK PGVDYTITVYAVTDYFNPTTHEYIYQTTPISINY RTEIDKPSQHHHHHH |
| 108 | E4 EGFR monomer core sequence: E4 without N-terminal extension or C-terminal tail | EVVAATPTSLLISWHERDGSRQYYRITYGETGG NSPVQEFTVPGGVRTATISGLKPGVDYTITVYA VTDYFNPTTHEYIYQTTPISINYRT |
| 109 | BC loop sequence from EGFR binder E4 | SWHERDGSRQ |
| 110 | DE loop sequence from EGFR binder E4 | PGGVRT |
| 111 | FG loop sequence from EGFR binder E4 | TDYFNPTTHEYIYQTTP |
| 112 | E5 EGFR monomer with N-terminal extension (N + 8) and no tail | VSDVPRDLEVVAATPTSLLISWWAPVDRYQYY RITYGETGGNSPVQEFTVPRDVYTATISGLKPG VDYTITVYAVTD YKPHADGPHTYHES PIS INYR T |
| 113 | E5 EGFR monomer with N-terminal extension (N + 10) and a modified Ser or Cys tail, wherein X = Ser or Cys; may optionally comprise a 6X His tag (SEQ ID NO: 487) | MGVSDVPRDLEVVAATPTSLLISWWAPVDRYQ YYRITYGETGGNSPVQEFTVPRDVYTATISGLK PGVDYTITVYAVTDYKPHADGPHTYHESPISIN YRTEIDKPXQ |
| 114 | E5 EGFR monomer core sequence: E5 without N-terminal extension or C-terminal tail | EVVAATPTSLLISWWAPVDRYQYYRITYGETG GNSPVQEFTVPRDVYTATISGLKPGVDYTITVY AVTDYKPHADGPHTYHESPISINYRT |
| 115 | BC loop sequence from EGFR binder E5 | SWWAPVDRYQ |

| SEQ ID NO: | Description | Sequence |
|---|---|---|
| 116 | DE loop sequence from EGFR binder E5 | PRDVYT |
| 117 | FG loop sequence from EGFR binder E5 | TDYKPHADGPHTYHESP |
| 118 | E4-GS10-I1: E/I tandem having E4 (with N-terminal extension (N + 8) and short tail) fused via GS10 linker (GS10 is SEQ ID NO: 11) to I1 (with N-terminal extension (N + 8) and no tail) | VSDVPRDLEVVAATPTSLLISWHERDGSRQYY RITYGETGGNSPVQEFTVPGGVRTATISGLKPG VDYTITVYAVTDYFNPTTHEYIYQTTPISINYRT EIDKGSGSGSGSGSGSGSGSGSGSVSDVPRDL EVVAATPTSLLISWSARLKVARYYRITYGETGG NSPVQEFTVPKNVYTATISGLKPGVDYTITVYA VTRFRDYQPISINYRT |
| 119 | E4-GS10-I1: E/I tandem having E4 (with N-terminal extension (N + 8) and short tail) fused via GS10 linker (GS10 is SEQ ID NO: 11) to I1 (with N-terminal extension (N + 8) and modified Ser or Cys tail), wherein X = Ser or Cys; may optionally comprise a 6X His tag (SEQ ID NO: 487) | VSDVPRDLEVVAATPTSLLISWHERDGSRQYY RITYGETGGNSPVQEFTVPGGVRTATISGLKPG VDYTITVYAVTDYFNPTTHEYIYQTTPISINYRT EIDKGSGSGSGSGSGSGSGSGSGSVSDVPRDL EVVAATPTSLLISWSARLKVARYYRITYGETGG NSPVQEFTVPKNVYTATISGLKPGVDYTITVYA VTRFRDYQPISINYRTEIDKPXQ |
| 120 | E4-GS10-I1: E/I tandem having E4 (with N-terminal extension (N + 10) and short tail) fused via GS10 linker (GS10 is SEQ ID NO: 11) to I1 (with N-terminal extension (N + 8) and Cys tail) with his tag | MGVSDVPRDLEVVAATPTSLLISWHERDGSRQ YYRITYGETGGNSPVQEFTVPGGVRTATISGLK PGVDYTITVYAVTDYFNPTTHEYIYQTTPISINY RTEIDKGSGSGSGSGSGSGSGSGSGSVSDVPR DLEVVAATPTSLLISWSARLKVARYYRITYGET GGNSPVQEFTVPKNVYTATISGLKPGVDYTITV YAVTRFRDYQPISINYRTEIDKPCQHHHHHH |
| 121 | E4-(PA)$_n$-I1: E/I tandem having E4 (with N-terminal extension (N + 8) and an E tail) fused via (PA)$_n$ linker ((PA)$_n$ is SEQ ID NO: 488) to I1 (with N-terminal extension (N + 8) and modified Ser or Cys tail), wherein n = 3, 6 or 9, and X = Ser or Cys; may optionally comprise a 6X His tag (SEQ ID NO: 487) | VSDVPRDLEVVAATPTSLLISWHERDGSRQYY RITYGETGGNSPVQEFTVPGGVRTATISGLKPG VDYTITVYAVTDYFNPTTHEYIYQTTPISINYRT E(PA)$_n$VSDVPRDLEVVAATPTSLLISWSARLKV ARYYRITYGETGGNSPVQEFTVPKNVYTATISG LKPGVDYTITVYAVTRFRDYQPISINYRTEIDKP CQHHHHHH |
| 122 | I1-GS10-E4: I/E tandem having I1 (with N-terminal extension (N + 8) and short tail) fused via GS10 linker (GS10 is SEQ ID NO: 11) to E4 (having N-terminal extension (N + 8) and no tail) | VSDVPRDLEVVAATPTSLLISWSARLKVARYY RITYGETGGNSPVQEFTVPKNVYTATISGLKPG VDYTITVYAVTRFRDYQPISINYRTEIDKGSGS GSGSGSGSGSGSGSGSVSDVPRDLEVVAATPT SLLISWHERDGSRQYYRITYGETGGNSPVQEFT VPGGVRTATISGLKPGVDYTITVYAVTDYFNPT THEYIYQTTPISINYRT |
| 123 | I1-GS10-E4: I/E tandem having I1 (with N-terminal extension (N + 8) and short tail) fused via GS10 linker (GS10 is SEQ ID NO: 11) to E4 (with N-terminal extension (N + 8) and modified Ser or Cys tail), wherein X = Ser or Cys; may optionally comprise a 6X His tag (SEQ ID NO: 487) | VSDVPRDLEVVAATPTSLLISWSARLKVARYY RITYGETGGNSPVQEFTVPKNVYTATISGLKPG VDYTITVYAVTRFRDYQPISINYRTEIDKGSGS GSGSGSGSGSGSGSGSVSDVPRDLEVVAATPT SLLISWHERDGSRQYYRITYGETGGNSPVQEFT VPGGVRTATISGLKPGVDYTITVYAVTDYFNPT THEYIYQTTPISINYRTEIDKPXQ |
| 124 | I1-GS10-E4: I/E tandem having I1 (with N-terminal extension (N + 10) and short tail) fused via GS10 linker (GS10 is SEQ ID NO: 11) to E4 (with N-terminal extension (N + 8) and a Cys tail) with his tag | MGVSDVPRDLEVVAATPTSLLISWSARLKVAR YYRITYGETGGNSPVQEFTVPKNVYTATISGLK PGVDYTITVYAVTRFRDYQPISINYRTEIDKGSG SGSGSGSGSGSGSGSGSVSDVPRDLEVVAATP TSLLISWHERDGSRQYYRITYGETGGNSPVQEF TVPGGVRTATISGLKPGVDYTITVYAVTDYFNP TTHEYIYQTTPISINYRTEIDKPCQHHHHHH |

| SEQ ID NO: | Description | Sequence |
|---|---|---|
| 125 | I1-(PA)ₙ-E4: I/E tandem having I1 (with N-terminal extension (N + 8) and an E tail) fused via (PA)ₙ linker ((PA)ₙ is SEQ ID NO: 488) to E4 (with N-terminal extension (N + 8) and modified Ser or Cys tail), wherein n = 3, 6 or 9, and X = Ser or Cys; may optionally comprise a 6X His tag (SEQ ID NO: 487) | VSDVPRDLEVVAATPTSLLISWSARLKVARYY RITYGETGGNSPVQEFTVPKNVYTATISGLKPG VDYTITVYAVTRFRDYQPISINYRTE(PA)ₙVSDV PRDLEVVAATPTSLLISWHERDGSRQYYRITYG ETGNSPVQEFTVPGGVRTATISGLKPGVDYTI TVYAVTDYFNPTTHEYIYQTTPISINYRTEIDKP XQ |
| 126 | E5-GS10-I1: E/I tandem having E5 (with N-terminal extension (N + 8) and short tail) fused via GS10 linker (GS10 is SEQ ID NO: 11) to I1 (with N-terminal extension (N + 8) and no tail) | VSDVPRDLEVVAATPTSLLISWWAPVDRYQYY RITYGETGGNSPVQEFTVPRDVYTATISGLKPG VDYTITVYAVTDYKPHADGPHTYHESPISINYR TEIDKGSGSGSGSGSGSGSGSGSGSVSDVPRD LEVVAATPTSLLISWSARLKVARYYRITYGETG GNSPVQEFTVPKNVYTATISGLKPGVDYTITVY AVTRFRDYQPISINYRT |
| 127 | E5-GS10-I1: E/I tandem having E5 (with N-terminal extension (N + 8) and short tail) fused via GS10 linker (GS10 is SEQ ID NO: 11) to I1 (with N-terminal extension (N + 8) and modified Ser or Cys tail), wherein X = Ser or Cys; may optionally comprise a 6X His tag (SEQ ID NO: 487) | VSDVPRDLEVVAATPTSLLISWWAPVDRYQYY RITYGETGGNSPVQEFTVPRDVYTATISGLKPG VDYTITVYAVTDYKPHADGPHTYHESPISINYR TEIDKGSGSGSGSGSGSGSGSGSGSVSDVPRD LEVVAATPTSLLISWSARLKVARYYRITYGETG GNSPVQEFTVPKNVYTATISGLKPGVDYTITVY AVTRFRDYQPISINYRTEIDKPXQ |
| 128 | E5-GS10-I1: E/I tandem having E5 (with N-terminal extension (N + 10) and short tail) fused via GS10 linker (GS10 is SEQ ID NO: 11) to I1 (with N-terminal extension (N + 8) and a Cys tail), with a His tag | MGVSDVPRDLEVVAATPTSLLISWWAPVDRYQ YYRITYGETGGNSPVQEFTVPRDVYTATISGLK PGVDYTITVYAVTDYKPHADGPHTYHESPISIN YRTEIDKGSGSGSGSGSGSGSGSGSGSVSDVP RDLEVVAATPTSLLISWSARLKVARYYRITYGE TGGNSPVQEFTVPKNVYTATISGLKPGVDYTIT VYAVTRFRDYQPISINYRTEIDKPCQHHHHHH |
| 129 | E5-(PA)ₙ-I1: E/I tandem having E5 (with N-terminal extension (N + 8) and an E tail) fused via (PA)ₙ linker ((PA)ₙ is SEQ ID NO: 488) to I1 (with N-terminal extension (N + 8) and modified Ser or Cys tail), wherein n = 3, 6 or 9, and X = Ser or Cys; may optionally comprise a 6X His tag (SEQ ID NO: 487) | VSDVPRDLEVVAATPTSLLISWWAPVDRYQYY RITYGETGGNSPVQEFTVPRDVYTATISGLKPG VDYTITVYAVTDYKPHADGPHTYHESPISINYR TE(PA)ₙVSDVPRDLEVVAATPTSLLISWSARLK VARYYRITYGETGGNSPVQEFTVPKNVYTATIS GLKPGVDYTITVYAVTRFRDYQPISINYRTEIDK PXQ |
| 130 | I1-GS10-E5: I/E tandem having I1 (with N-terminal extension (N + 8) and short tail) fused via GS10 linker (GS10 is SEQ ID NO: 11) to E5 (with N-terminal extension (N + 8) and no tail) | VSDVPRDLEVVAATPTSLLISWSARLKVARYY RITYGETGGNSPVQEFTVPKNVYTATISGLKPG VDYTITVYAVTRFRDYQPISINYRTEIDKGSGS GSGSGSGSGSGSGSGSVSDVPRDLEVVAATPT SLLISWWAPVDRYQYYRITYGETGGNSPVQEF TVPRDVYTATISGLKPGVDYTITVYAVTDYKPH ADGPHTYHESPISINYRT |
| 131 | I1-GS10-E5: I/E tandem having I1 (with N-terminal extension (N + 8) and short tail) fused via GS10 linker (GS10 is SEQ ID NO: 11) to E5 (with N-terminal extension (N + 8) and modified Ser or Cys tail), wherein X = Ser or Cys; may optionally comprise a 6X His tag (SEQ ID NO: 487) | VSDVPRDLEVVAATPTSLLISWSARLKVARYY RITYGETGGNSPVQEFTVPKNVYTATISGLKPG VDYTITVYAVTRFRDYQPISINYRTEIDKGSGS GSGSGSGSGSGSGSGSVSDVPRDLEVVAATPT SLLISWWAPVDRYQYYRITYGETGGNSPVQEF TVPRDVYTATISGLKPGVDYTITVYAVTDYKPH ADGPHTYHESPISINYRTEIDKPXQ |
| 132 | I1-GS10-E5: I/E tandem having I1 (with N-terminal extension (N + 10) and short tail) fused via GS10 linker | MGVSDVPRDLEVVAATPTSLLISWSARLKVAR YYRITYGETGGNSPVQEFTVPKNVYTATISGLK PGVDYTITVYAVTRFRDYQPISINYRTEIDKGSG SGSGSGSGSGSGSGSGSVSDVPRDLEVVAATP |

| SEQ ID NO: | Description | Sequence |
|---|---|---|
| | (GS10 is SEQ ID NO: 11) to E5 (with N-terminal extension (N + 8) and a Cys tail) with a His tag | TSLLISWWAPVDRYQYYRITYGETGGNSPVQE FTVPRDVYTATISGLKPGVDYTITVYAVTDYKP HADGPHTYHESPISINYRTEIDKPCQHHHHHH |
| 133 | I1-(PA)$_n$-E5: YE tandem having I1 (with N-terminal extension (N + 8) and an E tail) fused via (PA)$_n$ linker ((PA)$_n$ is SEQ ID NO: 488) to E5 (with N-terminal extension (N + 8) and modified Ser or Cys tail), wherein n = 3, 6 or 9, and X = Ser or Cys; may optionally comprise a 6X His tag (SEQ ID NO: 487) | MGVSDVPRDLEVVAATPTSLLISWSARLKVAR YYRITYGETGGNSPVQEFTVPKNVYTATISGLK PGVDYTITVYAVTRFRDYQPISINYRTE(PA)$_n$VS DVPRDLEVVAATPTSLLISWWAPVDRYQYYRI TYGETGGNSPVQEFTVPRDVYTATISGLKPGVD YTITVYAVTDYKPHADGPHTYHESPISINYRTEI DKPXQ |
| 134 | BC loop sequence from EGFR binder E4, wherein X is any amino acid and g and h are independently selected from 0 to 5 amino acids | X$_g$HERDGSRQX$_h$ |
| 135 | DE loop sequence from EGFR binder E4, wherein X is any amino acid and i and j are independently selected from 0 to 5 amino acids | X$_i$GGVRX$_j$ |
| 136 | FG loop sequence from EGFR binder E4, wherein X is any amino acid and k and l are independently selected from 0 to 5 amino acids | X$_k$DYFNPTTHEYIYQTTX$_l$ |
| 137 | BC loop sequence from EGFR binder E5, wherein X is any amino acid and g and h are independently selected from 0 to 5 amino acids | X$_g$WAPVDRYQX$_h$ |
| 138 | DE loop sequence from EGFR binder E5, wherein X is any amino acid and i and j are independently selected from 0 to 5 amino acids | X$_i$RDVYX$_j$ |
| 139 | FG loop sequence from EGFR binder E5, wherein X is any amino acid and k and l are independently selected from 0 to 5 amino acids | X$_k$DYKPHADGPHTYHESX$_l$ |
| 140 | E85 EGFR monomer with N-terminal extension (N + 10) and Ser tail with his tag | MGVSDVPRDLEVVAATPTSLLISWTQGSTHYQ YYRITYGETGGNSPVQEFTVPGMVYTATISGLK PGVDYTITVYAVTDYFDRSTHEYKYRTTPISIN YRTEIDKPSQHHHHHH |
| 141 | E85 EGFR monomer core: E85 monomer without N-terminal extension or C-terminal tail | EVVAATPTSLLISWTQGSTHYQYYRITYGETGG NSPVQEFTVPGMVYTATISGLKPGVDYTITVYA VTDYFDRSTHEYKYRTTPISINYRT |
| 142 | E85 EGFR monomer, wherein X$_1$ is selected from the group consisting of SEQ ID NOs: 69-77 and X$_2$ is selected from the group consisting of SEQ ID NOs: 9, 10, or 78-81; in exemplary embodiments, X$_1$ is SEQ ID NO: 69 or 71 and X$_2$ is SEQ ID NO: 9 or 10; may optionally comprise a his tag | X$_1$EVVAATPTSLLISWTQGSTHYQYYRITYGET GGNSPVQEFTVPGMVYTATISGLKPGVDYTITV YAVTDYFDRSTHEYKYRTTPISINYRTX$_2$ |
| 143 | BC loop sequence from EGFR binder E85 | SWTQGSTHYQ |

| SEQ ID NO: | Description | Sequence |
|---|---|---|
| 144 | DE loop sequence from EGFR binder E85 | PGMVYT |
| 145 | FG loop sequence from EGFR binder E85 | TDYFDRSTHEYKYRTTP |
| 146 | BC loop sequence from EGFR binder E85, wherein X is any amino acid and g and h are independently selected from 0 to 5 amino acids | X$_g$TQGSTHYQX$_h$ |
| 147 | DE loop sequence from EGFR binder E85, wherein X is any amino acid and i and j are independently selected from 0 to 5 amino acids | X$_i$GMVYX$_j$ |
| 148 | FG loop sequence from EGFR binder E85, wherein X is any amino acid and k and l are independently selected from 0 to 5 amino acids | X$_k$DYFDRSTHEYKYRTTX$_l$ |
| 149 | E85-GS10-I1: E/I tandem having E85 (with N-terminal extension (N + 10) and a short tail) fused via GS linker (GS10 is SEQ ID NO: 11) to I1 (with N-terminal extension (N + 8) and Cys tail) with a 6X His tag (SEQ ID NO: 487) | MGVSDVPRDLEVVAATPTSLLISWTQGSTHYQ YYRITYGETGGNSPVQEFTVPGMVYTATISGLK PGVDYTITVYAVTDYFDRSTHEYKYRTTPISIN YRTEIDKGSGSGSGSGSGSGSGSGSGSVSDVP RDLEVVAATPTSLLISWSARLKVARYYRITYGE TGGNSPVQEFTVPKNVYTATISGLKPGVDYTIT VYAVTRFRDYQPISINYRTEIDKPCQHHHHHH |
| 150 | E85-GS10-I1 core, wherein X$_1$ is optional and when present is selected from the group consisting of SEQ ID NOs: 69-77, X$_2$ is optional and when present is selected from the group consisting of SEQ ID NOs: 9, 10, or 78-81, and n = 3, 6 or 9; in exemplary embodiments, X$_1$ is SEQ ID NO: 69 or 71 and X$_2$ is SEQ ID NO: 9 or 10 | X$_1$EVVAATPTSLLISWTQGSTHYQYYRITYGET GGNSPVQEFTVPGMVYTATISGLKPGVDYTITV YAVTDYFDRSTHEYKYRTTPISINYRTEIDKGS GSGSGSGSGSGSGSGSGSVSDVPRDLEVVAAT PTSLLISWSARLKVARYYRITYGETGGNSPVQE FTVPKNVYTATISGLKPGVDYTITVYAVTRFRD YQPISINYRTX$_2$ |
| 151 | E85-(PA)?+0-I1 core, wherein X$_1$ is optional and when present is selected from the group consisting of SEQ ID NOs: 69-77, X$_2$ is optional and when present is selected from the group consisting of SEQ ID NOs: 9, 10, or 78-81, and n = 3, 6 or 9; in exemplary embodiments, X$_1$ is SEQ ID NO: 69 or 71 and X$_2$ is SEQ ID NO: 9 or 10 | X$_1$EVVAATPTSLLISWTQGSTHYQYYRITYGET GGNSPVQEFTVPGMVYTATISGLKPGVDYTITV YAVTDYFDRSTHEYKYRTTPISINYRTE(PA)$_n$VS DVPRDLEVVAATPTSLLISWSARLKVARYYRIT YGETGGNSPVQEFTVPKNVYTATISGLKPGVD YTITVYAVTRFRDYQPISINYRTX$_2$ |
| 152 | I1-GS10-E85: I/E tandem having I1 (with N-terminal extension (N + 10) and a short tail) fused via GS10 linker (GS10 is SEQ ID NO: 11) to E85 (with N-terminal extension (N + 8) and Cys tail) with a 6X His tag (SEQ ID NO: 487) | MGVSDVPRDLEVVAATPTSLLISWSARLKVAR YYRITYGETGGNSPVQEFTVPKNVYTATISGLK PGVDYTITVYAVTRFRDYQPISINYRTEIDKGSG SGSGSGSGSGSGSGSGSVSDVPRDLEVVAATP TSLLISWTQGSTHYQYYRITYGETGGNSPVQEF TVPGMVYTATISGLKPGVDYTITVYAVTDYFD RSTHEYKYRTTPISINYRTEIDKPCQHHHHHH |
| 153 | I1-GS10-E85 core, wherein X$_1$ is optional and when present is selected from the group consisting of SEQ ID NOs: 69-77, X$_2$ is optional and when | X$_1$EVVAATPTSLLISWSARLKVARYYRITYGET GGNSPVQEFTVPKNVYTATISGLKPGVDYTITV YAVTRFRDYQPISINYRTEIDKGSGSGSGSGSG SGSGSGSGSVSDVPRDLEVVAATPTSLLISWTQ GSTHYQYYRITYGETGGNSPVQEFTVPGMVYT |

| SEQ ID NO: | Description | Sequence |
|---|---|---|
| | present is selected from the group consisting of SEQ ID NOs: 9, 10, or 78-81, and n = 3, 6 or 9; in exemplary embodiments, $X_1$ is SEQ ID NO: 69 or 71 and $X_2$ is SEQ ID NO: 9 or 10 | ATISGLKPGVDYTITVYAVTDYFDRSTHEYKYR TTPISINYRTX$_2$ |
| 154 | I1-(PA)$_n$-E85 core, wherein $X_1$ is optional and when present is selected from the group consisting of SEQ ID NOs: 69-77, $X_2$ is optional and when present is selected from the group consisting of SEQ ID NOs: 9, 10, or 78-81, and n = 3, 6 or 9; in exemplary embodiments, $X_1$ is SEQ ID NO: 69 or 71 and $X_2$ is SEQ ID NO: 9 or 10 | X$_1$EVVAATPTSLLISWSARLKVARYYRITYGET GGNSPVQEFTVPKNVYTATISGLKPGVDYTITV YAVTRFRDYQPISINYRTE(PA)$_n$VSDVPRDLEV VAATPTSLLISWTQGSTHYQYYRITYGETGGNS PVQEFTVPGMVYTATISGLKPGVDYTITVYAVT DYFDRSTHEYKYRTTPISINYRTX$_2$ |
| 155 | E90 EGFR monomer with N-terminal extension (N + 10) and Ser tail with his tag | MGVSDVPRDLEVVAATPTSLLISWYWEGLPYQ YYRITYGETGGNSPVQEFTVPRDVNTATISGLK PGVDYTITVYAVTDWYNPDTHEYIYHTIPISINY RTEIDKPSQHHHHHH |
| 156 | E90 EGFR monomer core: E90 monomer without N-terminal extension or C-terminal tail | EVVAATPTSLLISWYWEGLPYQYYRITYGETG GNSPVQEFTVPRDVNTATISGLKPGVDYTITVY AVTDWYNPDTHEYIYHTIPISINYRT |
| 157 | E90 EGFR monomer, wherein $X_1$ is selected from the group consisting of SEQ ID NOs: 69-77 and $X_2$ is selected from the group consisting of SEQ ID NOs: 9, 10, or 78-81; in exemplary emobidments, $X_1$ is SEQ ID NO: 69 or 71 and $X_2$ is SEQ ID NO: 9 or 10; may optionally comprise a his tag | X$_1$EVVAATPTSLLISWYWEGLPYQYYRITYGET GGNSPVQEFTVPRDVNTATISGLKPGVDYTITV YAVTDWYNPDTHEYIYHTIPISINYRTX$_2$ |
| 158 | BC loop sequence from EGFR binder E90 | SWYWEGLPYQ |
| 159 | DE loop sequence from EGFR binder E90 | PRDVNT |
| 160 | FG loop sequence from EGFR binder E90 | TDWYNPDTHEYIYHTIP |
| 161 | BC loop sequence from EGFR binder E90, wherein X is any amino acid and g and h are independently selected from 0 to 5 amino acids | X$_g$YWEGLPYQX$_h$ |
| 162 | DE loop sequence from EGFR binder E90, wherein X is any amino acid and i and j are independently selected from 0 to 5 amino acids | X$_i$RDVNX$_j$ |
| 163 | FG loop sequence from EGFR binder E90, wherein X is any amino acid and k and l are independently selected from 0 to 5 amino acids | X$_k$DWYNPDTHEYIYHTIX$_l$ |
| 164 | E90-GS10-I1: E/I tandem having E90 (with N-terminal extension (N + 10) and a short tail) fused via GS10 linker (GS10 is SEQ ID NO: 11) to | MGVSDVPRDLEVVAATPTSLLISWYWEGLPYQ YYRITYGETGGNSPVQEFTVPRDVNTATISGLK PGVDYTITVYAVTDWYNPDTHEYIYHTIPISINY RTEIDKGSGSGSGSGSGSGSGSGSVSDVPR DLEVVAATPTSLLISWSARLKVARYYRITYGET |

| SEQ ID NO: | Description | Sequence |
|---|---|---|
|  | I1 (with N-terminal extension (N + 8) and Cys tail) with a 6X His tag (SEQ ID NO: 487) | GGNSPVQEFTVPKNVYTATISGLKPGVDYTITV YAVTRFRDYQPISINYRTEIDKPCQHHHHHH |
| 165 | E90-GS10-I1 core, wherein X₁ is optional and when present is selected from the group consisting of SEQ ID NOs: 69-77, X₂ is optional and when present is selected from the group consisting of SEQ ID NOs: 9, 10, or 78-81, and n = 3, 6 or 9; in exemplary embodiments, X₁ is SEQ ID NO: 69 or 71 and X₂ is SEQ ID NO: 9 or 10 | X₁EVVAATPTSLLISWYWEGLPYQYYRITYGET GGNSPVQEFTVPRDVNTATISGLKPGVDYTITV YAVTDWYNPDTHEYIYHTIPISINYRTEIDKGSG SGSGSGSGSGSGSGSGSGSVSDVPRDLEVVAATP TSLLISWSARLKVARYYRITYGETGGNSPVQEF TVPKNVYTATISGLKPGVDYTITVYAVTRFRDY QPISINYRTX₂ |
| 166 | E90-(PA)ₙ-I1 core, wherein X1 is optional and when present is selected from the group consisting of SEQ ID NOs: 69-77, X₂ is optional and when present is selected from the group consisting of SEQ ID NOs: 9, 10, or 78-81, and n = 3, 6 or 9; in exemplary embodiments, X₁ is SEQ ID NO: 69 or 71 and X₂ is SEQ ID NO: 9 or 10 | X₁EVVAATPTSLLISWYWEGLPYQYYRITYGET GGNSPVQEFTVPRDVNTATISGLKPGVDYTITV YAVTDWYNPDTHEYIYHTIPISINYRTE(PA)ₙVS DVPRDLEVVAATPTSLLISWSARLKVARYYRIT YGETGGNSPVQEFTVPKNVYTATISGLKPGVD YTITVYAVTRFRDYQPISINYRTX₂ |
| 167 | I1-GS10-E90: UE tandem having I1 (with N-terminal extension (N + 10) and a short tail) fused via GS10 linker (GS10 is SEQ ID NO: 11) to E90 (with N-terminal extension (N + 8) and Cys tail) with a 6X His tag (SEQ ID NO: 487) | MGVSDVPRDLEVVAATPTSLLISWSARLKVAR YYRITYGETGGNSPVQEFTVPKNVYTATISGLK PGVDYTITVYAVTRFRDYQPISINYRTEIDKGSG SGSGSGSGSGSGSGSGSGSVSDVPRDLEVVAATP TSLLISWYWEGLPYQYYRITYGETGGNSPVQEF TVPRDVNTATISGLKPGVDYTITVYAVTDWYN PDTHEYIYHTIPISINYRTEIDKPCQHHHHHH |
| 168 | I1-GS10-E90 core, wherein X₁ is optional and when present is selected from the group consisting of SEQ ID NOs: 69-77, X₂ is optional and when present is selected from the group consisting of SEQ ID NOs: 9, 10, or 78-81, and n = 3, 6 or 9; in exemplary embodiments, X₁ is SEQ ID NO: 69 or 71 and X₂ is SEQ ID NO: 9 or 10 | X₁EVVAATPTSLLISWSARLKVARYYRITYGET GGNSPVQEFTVPKNVYTATISGLKPGVDYTITV YAVTRFRDYQPISINYRTEIDKGSGSGSGSGSG SGSGSGSVSDVPRDLEVVAATPTSLLISWY WEGLPYQYYRITYGETGGNSPVQEFTVPRDVN TATISGLKPGVDYTITVYAVTDWYNPDTHEYIY HTIPISINYRTX₂ |
| 169 | I1-(PA)ₙ-E90 core, wherein X₁ is optional and when present is selected from the group consisting of SEQ ID NOs: 69-77, X₂ is optional and when present is selected from the group consisting of SEQ ID NOs: 9, 10, or 78-81, and n = 3, 6 or 9; in exemplary embodiments, X₁ is SEQ ID NO: 69 or 71 and X₂ is SEQ ID NO: 9 or 10 | X₁EVVAATPTSLLISWSARLKVARYYRITYGET GGNSPVQEFTVPKNVYTATISGLKPGVDYTITV YAVTRFRDYQPISINYRTE(PA)ₙVSDVPRDLEV VAATPTSLLISWYWEGLPYQYYRITYGETGGN SPVQEFTVPRDVNTATISGLKPGVDYTITVYAV TDWYNPDTHEYIYHTIPISINYRTX₂ |
| 170 | E96 EGFR monomer with N-terminal extension (N + 10) and Ser tail with his tag | MGVSDVPRDLEVVAATPTSLLISWASNRGTYQ YYRITYGETGGNSPVQEFTVPGGVSTATISGLK PGVDYTITVYAVTDAFNPTTHEYNYFTTPISINY RTEIDKPSQHHHHHH |
| 171 | E96 EGFR monomer core: E96 monomer without N-terminal extension or C-terminal tail | EVVAATPTSLLISWASNRGTYQYYRITYGETGG NSPVQEFTVPGGVSTATISGLKPGVDYTITVYA VTDAFNPTTHEYNYFTTPISINYRT |

| SEQ ID NO: | Description | Sequence |
|---|---|---|
| 172 | E96 EGFR monomer, wherein X₁ is selected from the group consisting of SEQ ID NOs: 69-77 and X₂ is selected from the group consisting of SEQ ID NOs: 9, 10, or 78-81; in exemplary emobidments, X₁ is SEQ ID NO: 69 or 71 and X₂ is SEQ ID NO: 9 or 10; may optionally comprise a his tag | X₁EVVAATPTSLLISWASNRGTYQYYRITYGET GGNSPVQEFTVPGGVSTATISGLKPGVDYTITV YAVTDAFNPTTHEYNYFTTPISINYRTX₂ |
| 173 | BC loop sequence from EGFR binder E96 | SWASNRGTYQ |
| 174 | DE loop sequence from EGFR binder E96 | PGGVST |
| 175 | FG loop sequence from EGFR binder E96 | TDAFNPTTHEYNYFTTP |
| 176 | BC loop sequence from EGFR binder E96, wherein X is any amino acid and g and h are independently selected from 0 to 5 amino acids | X_gASNRGTYQX_h |
| 177 | DE loop sequence from EGFR binder E96, wherein X is any amino acid and i and j are independently selected from 0 to 5 amino acids | X_iGGVSX_j |
| 178 | FG loop sequence from EGFR binder E96, wherein X is any amino acid and k and l are independently selected from 0 to 5 amino acids | X_kDAFNPTTHEYNYFTTX_l |
| 179 | E96-GS10-I1: E/I tandem having E96 (with N-terminal extension (N + 10) and a short tail) fused via GS10 linker (GS10 is SEQ ID NO: 11) to I1 (with N-terminal extension (N + 8) and Cys tail) with a 6X His tag (SEQ ID NO: 487) | MGVSDVPRDLEVVAATPTSLLISWASNRGTYQ YYRITYGETGGNSPVQEFTVPGGVSTATISGLK PGVDYTITVYAVTDAFNPTTHEYNYFTTPISINY RTEIDKGSGSGSGSGSGSGSGSGSGSVSDVPR DLEVVAATPTSLLISWSARLKVARYYRITYGET GGNSPVQEFTVPKNVYTATISGLKPGVDYTITV YAVTRFRDYQPISINYRTEIDKPCQHHHHHH |
| 180 | E96-GS10-I1 core, wherein X₁ is optional and when present is selected from the group consisting of SEQ ID NOs: 69-77, X₂ is optional and when present is selected from the group consisting of SEQ ID NOs: 9, 10, or 78-81, and n = 3, 6 or 9; in exemplary embodiments, X₁ is SEQ ID NO: 69 or 71 and X₂ is SEQ ID NO: 9 or 10 | X₁EVVAATPTSLLISWASNRGTYQYYRITYGET GGNSPVQEFTVPGGVSTATISGLKPGVDYTITV YAVTDAFNPTTHEYNYFTTPISINYRTEIDKGSG SGSGSGSGSGSGSGSVSDVPRDLEVVAATP TSLLISWSARLKVARYYRITYGETGGNSPVQEF TVPKNVYTATISGLKPGVDYTITVYAVTRFRDY QPISINYRTX₂ |
| 181 | E96-(PA)ₙ-I1 core, wherein X1 is optional and when present is selected from the group consisting of SEQ ID NOs: 69-77, X2 is optional and when present is selected from the group consisting of SEQ ID NOs: 9, 10, or 78-81, and n = 3, 6 or 9; in exemplary embodiments, X₁ is SEQ ID NO: 69 or 71 and X₂ is SEQ ID NO: 9 or 10 | X₁EVVAATPTSLLISWASNRGTYQYYRITYGET GGNSPVQEFTVPGGVSTATISGLKPGVDYTITV YAVTDAFNPTTHEYNYFTTPISINYRTE(PA)ₙVS DVPRDLEVVAATPTSLLISWSARLKVARYYRIT YGETGGNSPVQEFTVPKNVYTATISGLKPGVD YTITVYAVTRFRDYQPISINYRTX₂ |
| 182 | I1-GS10-E96: UE tandem having I1 (with N-terminal extension (N + 10) and a short | MGVSDVPRDLEVVAATPTSLLISWSARLKVAR YYRITYGETGGNSPVQEFTVPKNVYTATISGLK PGVDYTITVYAVTRFRDYQPISINYRTEIDKGSG |

-continued

| SEQ ID NO: | Description | Sequence |
|---|---|---|
|  | tail) fused via GS10 linker (GS10 is SEQ ID NO: 11) to E96 (with N-terminal extension (N + 8) and Cys tail) with a 6X His tag (SEQ ID NO: 487) | SGSGSGSGSGSGSGSGSVSDVPRDLEVVAATP TSLLISWASNRGTYQYYRITYGETGGNSPVQEF TVPGGVSTATISGLKPGVDYTITVYAVTDAFNP TTHEYNYFTTPISINYRT<u>EIDKPCQ</u>HHHHHH |
| 183 | I1-GS10-E96 core, wherein $X_1$ is optional and when present is selected from the group consisting of SEQ ID NOs: 69-77, $X_2$ is optional and when present is selected from the group consisting of SEQ ID NOs: 9, 10, or 78-81, and n = 3, 6 or 9; in exemplary embodiments, $X_1$ is SEQ ID NO: 69 or 71 and $X_2$ is SEQ ID NO: 9 or 10 | $X_1$EVVAATPTSLLISWSARLKVARYYRITYGET GGNSPVQEFTVPKNVYTATISGLKPGVDYTITV YAVTRFRDYQPISINYRT<u>EIDK</u>GSGSGSGSGSG SGSGSGSGSVSDVPRDLEVVAATPTSLLISWAS NRGTYQYYRITYGETGGNSPVQEFTVPGGVST ATISGLKPGVDYTITVYAVTDAFNPTTHEYNYF TTPISINYRT$X_2$ |
| 184 | I1-(PA)$_n$-E96 core, wherein $X_1$ is optional and when present is selected from the group consisting of SEQ ID NOs: 69-77, $X_2$ is optional and when present is selected from the group consisting of SEQ ID NOs: 9, 10, or 78-81, and n = 3, 6 or 9; in exemplary embodiments, $X_1$ is SEQ ID NO: 69 or 71 and $X_2$ is SEQ ID NO: 9 or 10 | $X_1$EVVAATPTSLLISWSARLKVARYYRITYGET GGNSPVQEFTVPKNVYTATISGLKPGVDYTITV YAVTRFRDYQPISINYRT<u>E</u>(PA)$_n$VSDVPRDLEV VAATPTSLLISWASNRGTYQYYRITYGETGGNS PVQEFTVPGGVSTATISGLKPGVDYTITVYAVT DAFNPTTHEYNYFTTPISINYRT$X_2$ |
| 185 | E105 EGFR monomer with N-terminal extension (N + 10) and Ser tail with his tag | <u>MG</u>VSDVPRDLEVVAATPTSLLISWDAPTSRYQ YYRITYGETGGNSPVQEFTVPGGLSTATISGLKP GVDYTITVYAVTDYKPHADGPHTYHESPISINY RT<u>EIDKPSQ</u>HHHHHH |
| 186 | E105 EGFR monomer core: E105 monomer without N-terminal extension or C-terminal tail | EVVAATPTSLLISWDAPTSRYQYYRITYGETGG NSPVQEFTVPGGLSTATISGLKPGVDYTITVYA VTDYKPHADGPHTYHESPISINYRT |
| 187 | E105 EGFR monomer, wherein $X_1$ is selected from the group consisting of SEQ ID NOs: 69-77 and $X_2$ is selected from the group consisting of SEQ ID NOs: 9, 10, or 78-81; in exemplary emobidments, $X_1$ is SEQ ID NO: 69 or 71 and $X_2$ is SEQ ID NO: 9 or 10; may optionally comprise a his tag | $X_1$EVVAATPTSLLISWDAPTSRYQYYRITYGET GGNSPVQEFTVPGGLSTATISGLKPGVDYTITV YAVTDYKPHADGPHTYHESPISINYRT$X_2$ |
| 188 | BC loop sequence from EGFR binder E105 | SWDAPTSRYQ |
| 189 | DE loop sequence from EGFR binder E105 | PGGLST |
| 117 | FG loop sequence from EGFR binder E105 | TDYKPHADGPHTYHESP |
| 190 | BC loop sequence from EGFR binder E105, wherein X is any amino acid and g and h are independently selected from 0 to 5 amino acids | $X_g$DAPTSRYQ$X_h$ |
| 191 | DE loop sequence from EGFR binder E105, wherein X is any amino acid and i and j are independently selected from 0 to 5 amino acids | $X_i$GGLS$X_j$ |

| SEQ ID NO: | Description | Sequence |
|---|---|---|
| 139 | FG loop sequence from EGFR binder E105, wherein X is any amino acid and k and l are independently selected from 0 to 5 amino acids | $X_k$DYKPHADGPHTYHES$X_l$ |
| 192 | E105-GS10-I1: E/I tandem having E105 (with N-terminal extension (N + 10) and a short tail) fused via GS10 linker (GS10 is SEQ ID NO: 11) to I1 (with N-terminal extension (N + 8) and Cys tail) with a 6X His tag (SEQ ID NO: 487) | MGVSDVPRDLEVVAATPTSLLISWDAPTSRYQ YYRITYGETGGNSPVQEFTVPGGLSTATISGLKP GVDYTITVYAVTDYKPHADGPHTYHESPISINY RTEIDKGSGSGSGSGSGSGSGSGSGSVSDVPR DLEVVAATPTSLLISWSARLKVARYYRITYGET GGNSPVQEFTVPKNVYTATISGLKPGVDYTITV YAVTRFRDYQPISINYRTEIDKPCQHHHHHH |
| 193 | E105-GS10-I1 core, wherein $X_1$ is optional and when present is selected from the group consisting of SEQ ID NOs: 69-77, $X_2$ is optional and when present is selected from the group consisting of SEQ ID NOs: 9, 10, or 78-81, and n = 3, 6 or 9; in exemplary embodiments, $X_1$ is SEQ ID NO: 69 or 71 and $X_2$ is SEQ ID NO: 9 or 10 | $X_1$EVVAATPTSLLISWDAPTSRYQYYRITYGET GGNSPVQEFTVPGGLSTATISGLKPGVDYTITV YAVTDYKPHADGPHTYHESPISINYRTEIDKGS GSGSGSGSGSGSGSGSVSDVPRDLEVVAAT PTSLLISWSARLKVARYYRITYGETGGNSPVQE FTVPKNVYTATISGLKPGVDYTITVYAVTRFRD YQPISINYRT$X_2$ |
| 194 | E105-(PA)$_n$-I1 core, wherein X1 is optional and when present is selected from the group consisting of SEQ ID NOs: 69-77, $X_2$ is optional and when present is selected from the group consisting of SEQ ID NOs: 9, 10, or 78-81, and n = 3, 6 or 9; in exemplary embodiments, $X_1$ is SEQ ID NO: 69 or 71 and $X_2$ is SEQ ID NO: 9 or 10 | $X_1$EVVAATPTSLLISWDAPTSRYQYYRITYGET GGNSPVQEFTVPGGLSTATISGLKPGVDYTITV YAVTDYKPHADGPHTYHESPISINYRTE(PA)$_n$V SDVPRDLEVVAATPTSLLISWSARLKVARYYRI TYGETGGNSPVQEFTVPKNVYTATISGLKPGVD YTITVYAVTRFRDYQPISINYRT$X_2$ |
| 195 | I1-GS10-E105: UE tandem having I1 (with N-terminal extension (N + 10) and a short tail) fused via GS10 linker (GS10 is SEQ ID NO: 11) to E105 (with N-terminal extension (N + 8) and Cys tail) with a 6X His tag (SEQ ID NO: 487) | MGVSDVPRDLEVVAATPTSLLISWSARLKVAR YYRITYGETGGNSPVQEFTVPKNVYTATISGLK PGVDYTITVYAVTRFRDYQPISINYRTEIDKGSG SGSGSGSGSGSGSVSDVPRDLEVVAATP TSLLISWDAPTSRYQYYRITYGETGGNSPVQEF TVPGGLSTATISGLKPGVDYTITVYAVTDYKPH ADGPHTYHESPISINYRTEIDKPCQHHHHHH |
| 196 | I1-GS10-E105 core, wherein $X_1$ is optional and when present is selected from the group consisting of SEQ ID NOs: 69-77, $X_2$ is optional and when present is selected from the group consisting of SEQ ID NOs: 9, 10, or 78-81, and n = 3, 6 or 9; in exemplary embodiments, $X_1$ is SEQ ID NO: 69 or 71 and $X_2$ is SEQ ID NO: 9 or 10 | $X_1$EVVAATPTSLLISWSARLKVARYYRITYGET GGNSPVQEFTVPKNVYTATISGLKPGVDYTITV YAVTRFRDYQPISINYRTEIDKGSGSGSGSGSG SGSGSGSGSVSDVPRDLEVVAATPTSLLISWDA PTSRYQYYRITYGETGGNSPVQEFTVPGGLSTA TISGLKPGVDYTITVYAVTDYKPHADGPHTYH ESPISINYRT$X_2$ |
| 197 | I1-(PA)$_n$-E105 core, wherein $X_1$ is optional and when present is selected from the group consisting of SEQ ID NOs: 69-77, $X_2$ is optional and when present is selected from the group consisting of SEQ ID NOs: 9, 10, or 78-81, and n = 3, 6 or 9; in exemplary embodiments, $X_1$ is SEQ ID NO: 69 or 71 and $X_2$ is SEQ ID NO: 9 or 10 | $X_1$EVVAATPTSLLISWSARLKVARYYRITYGET GGNSPVQEFTVPKNVYTATISGLKPGVDYTITV YAVTRFRDYQPISINYRTE(PA)$_n$VSDVPRDLEV VAATPTSLLISWDAPTSRYQYYRITYGETGGNS PVQEFTVPGGLSTATISGLKPGVDYTITVYAVT DYKPHADGPHTYHESPISINYRT$X_2$ |

-continued

| SEQ ID NO: | Description | Sequence |
|---|---|---|
| 198 | E112 EGFR monomer with N-terminal extension (N + 10) and Ser tail with his tag | MGVSDVPRDLEVVAATPTSLLISWDAGAVTYQ YYRITYGETGGNSPVQEFTVPGGVRTATISGLK PGVDYTITVYAVTDYKPHADGPHTYHEYPISIN YRTEIDKPSQHHHHHH |
| 199 | E112 EGFR monomer core: E112 monomer without N-terminal extension or C-terminal tail | EVVAATPTSLLISWDAGAVTYQYYRITYGETG GNSPVQEFTVPGGVRTATISGLKPGVDYTITVY AVTDYKPHADGPHTYHEYPISINYRT |
| 200 | E112 EGFR monomer, wherein $X_1$ is selected from the group consisting of SEQ ID NOs: 69-77 and $X_2$ is selected from the group consisting of SEQ ID NOs: 9, 10, or 78-81; in exemplary emobidments, $X_1$ is SEQ ID NO: 69 or 71 and $X_2$ is SEQ ID NO: 9 or 10; may optionally comprise a his tag | $X_1$EVVAATPTSLLISWDAGAVTYQYYRITYGET GGNSPVQEFTVPGGVRTATISGLKPGVDYTITV YAVTDYKPHADGPHTYHEYPISINYRT$X_2$ |
| 201 | BC loop sequence from EGFR binder E112 | SWDAGAVTYQ |
| 110 | DE loop sequence from EGFR binder E112 | PGGVRT |
| 202 | FG loop sequence from EGFR binder E112 | TDYKPHADGPHTYHEYP |
| 203 | BC loop sequence from EGFR binder E112, wherein X is any amino acid and g and h are independently selected from 0 to 5 amino acids | $X_g$DAGAVTYQ$X_h$ |
| 135 | DE loop sequence from EGFR binder E112, wherein X is any amino acid and i and j are independently selected from 0 to 5 amino acids | $X_i$GGVR$X_j$ |
| 204 | FG loop sequence from EGFR binder E112, wherein X is any amino acid and k and l are independently selected from 0 to 5 amino acids | $X_k$DYKPHADGPHTYHEY$X_l$ |
| 205 | E112-GS10-I1: E/I tandem having E112 (with N-terminal extension (N + 10) and a short tail) fused via GS10 linker (GS10 is SEQ ID NO: 11) to I1 (with N-terminal extension (N + 8) and Cys tail) with a 6X His tag (SEQ ID NO: 487) | MGVSDVPRDLEVVAATPTSLLISWDAGAVTYQ YYRITYGETGGNSPVQEFTVPGGVRTATISGLK PGVDYTITVYAVTDYKPHADGPHTYHEYPISIN YRTEIDKGSGSGSGSGSGSGSGSGSGSVSDVP RDLEVVAATPTSLLISWSARLKVARYYRITYGE TGGNSPVQEFTVPKNVYTATISGLKPGVDYTIT VYAVTRFRDYQPISINYRTEIDKPCQHHHHHH |
| 206 | E112-GS10-I1 core, wherein $X_1$ is optional and when present is selected from the group consisting of SEQ ID NOs: 69-77, $X_2$ is optional and when present is selected from the group consisting of SEQ ID NOs: 9, 10, or 78-81, and n = 3, 6 or 9; in exemplary embodiments, $X_1$ is SEQ ID NO: 69 or 71 and $X_2$ is SEQ ID NO: 9 or 10 | $X_1$EVVAATPTSLLISWDAGAVTYQYYRITYGET GGNSPVQEFTVPGGVRTATISGLKPGVDYTITV YAVTDYKPHADGPHTYHEYPISINYRTEIDKGS GSGSGSGSGSGSGSGSGSVSDVPRDLEVVAAT PTSLLISWSARLKVARYYRITYGETGGNSPVQE FTVPKNVYTATISGLKPGVDYTITVYAVTRFRD YQPISINYRT$X_2$ |
| 207 | E112-(PA)$_n$-I1 core, wherein X1 is optional and when present is selected from the group consisting of SEQ | $X_1$EVVAATPTSLLISWDAGAVTYQYYRITYGET GGNSPVQEFTVPGGVRTATISGLKPGVDYTITV YAVTDYKPHADGPHTYHEYPISINYRTE(PA)$_n$V SDVPRDLEVVAATPTSLLISWSARLKVARYYRI |

| SEQ ID NO: | Description | Sequence |
|---|---|---|
|  | NOs: 69-77, X$_2$ is optional and when present is selected from the group consisting of SEQ ID NOs: 9, 10, or 78-81, and n = 3, 6 or 9; in exemplary embodiments, X$_1$ is SEQ ID NO: 69 or 71 and X$_2$ is SEQ ID NO: 9 or 10 | TYGETGGNSPVQEFTVPKNVYTATISGLKPGVD YTITVYAVTRFRDYQPISINYRTX$_2$ |
| 208 | I1-GS10-E112: I/E tandem having I1 (with N-terminal extension (N + 10) and a short tail) fused via GS10 linker (GS10 is SEQ ID NO: 11) to E112 (with N-terminal extension (N + 8) and Cys tail) with a 6X His tag (SEQ ID NO: 487) | MGVSDVPRDLEVVAATPTSLLISWSARLKVAR YYRITYGETGGNSPVQEFTVPKNVYTATISGLK PGVDYTITVYAVTRFRDYQPISINYRTEIDKGSG SGSGSGSGSGSGSGSGSVSDVPRDLEVVAATP TSLLISWDAGAVTYQYYRITYGETGGNSPVQEF TVPGGVRTATISGLKPGVDYTITVYAVTDYKPH ADGPHTYHEYPISINYRTEIDKPCQHHHHHH |
| 209 | I1-GS10-E112 core, wherein X$_1$ is optional and when present is selected from the group consisting of SEQ ID NOs: 69-77, X$_2$ is optional and when present is selected from the group consisting of SEQ ID NOs: 9, 10, or 78-81, and n = 3, 6 or 9; in exemplary embodiments, X$_1$ is SEQ ID NO: 69 or 71 and X$_2$ is SEQ ID NO: 9 or 10 | X$_1$EVVAATPTSLLISWSARLKVARYYRITYGET GGNSPVQEFTVPKNVYTATISGLKPGVDYTITV YAVTRFRDYQPISINYRTEIDKGSGSGSGSGSG SGSGSGSVSDVPRDLEVVAATPTSLLISWDA GAVTYQYYRITYGETGGNSPVQEFTVPGGVRT ATISGLKPGVDYTITVYAVTDYKPHADGPHTY HEYPISINYRTX$_2$ |
| 210 | I1-(PA)$_n$-E112 core, wherein X$_1$ is optional and when present is selected from the group consisting of SEQ ID NOs: 69-77, X$_2$ is optional and when present is selected from the group consisting of SEQ ID NOs: 9, 10, or 78-81, and n = 3, 6 or 9; in exemplary embodiments, X$_1$ is SEQ ID NO: 69 or 71 and X$_2$ is SEQ ID NO: 9 or 10 | X$_1$EVVAATPTSLLISWSARLKVARYYRITYGET GGNSPVQEFTVPKNVYTATISGLKPGVDYTITV YAVTRFRDYQPISINYRTE(PA)$_n$VSDVPRDLEV VAATPTSLLISWDAGAVTYQYYRITYGETGGN SPVQEFTVPGGVRTATISGLKPGVDYTITVYAV TDYKPHADGPHTYHEYPISINYRTX$_2$ |
| 211 | I1-GSGCGS8-E5: I/E tandem having I1 (with N-terminal extension (N + 10) and a modified short tail) fused via GSGCGS8 linker (GSGCGS8 is SEQ ID NO: 218) to E5 (with N-terminal extension (N + 8) and an E tail) with an optional 6X His tag (SEQ ID NO: 487) | MGVSDVPRDLEVVAATPTSLLISWSARLKVAR YYRITYGETGGNSPVQEFTVPKNVYTATISGLK PGVDYTITVYAVTRFRDYQPISINYRTEIEKGSG CGSGSGSGSGSGSGSVSDVPRDLEVVAATP TSLLISWWAPVDRYQYYRITYGETGGNSPVQE FTVPRDVYTATISGLKPGVDYTITVYAVTDYKP HADGPHTYHESPISINYRTEHHHHHH |
| 212 | I1-GS10-E5-GSGC: I/E tandem having I1 (with N-terminal extension (N + 10) and a modified short tail) fused via GS10 linker (GS10 is SEQ ID NO: 11) to E5 (with N-terminal extension (N + 8) and a modified Cys tail) with an optional 6X His tag (SEQ ID NO: 487) | MGVSDVPRDLEVVAATPTSLLISWSARLKVAR YYRITYGETGGNSPVQEFTVPKNVYTATISGLK PGVDYTITVYAVTRFRDYQPISINYRTEIEKGSG SGSGSGSGSGSGSGSVSDVPRDLEVVAATP TSLLISWWAPVDRYQYYRITYGETGGNSPVQE FTVPRDVYTATISGLKPGVDYTITVYAVTDYKP HADGPHTYHESPISINYRTEGSGCHHHHHH |
| 213 | I1(S62C)-GS10-E5: I/E tandem having I1 (with N-terminal extension (N + 10), an S62C substitution (boxed), and a modified short tail) fused via GS10 linker (GS10 is SEQ ID NO: 11) to E5 (with N-terminal extension (N + 8) and an E tail) with an optional 6X | MGVSDVPRDLEVVAATPTSLLISWSARLKVAR YYRITYGETGGNSPVQEFTVPKNVYTATICGLK PGVDYTITVYAVTRFRDYQPISINYRTEIEKGSG SGSGSGSGSGSGSGSVSDVPRDLEVVAATP TSLLISWWAPVDRYQYYRITYGETGGNSPVQE FTVPRDVYTATISGLKPGVDYTITVYAVTDYKP HADGPHTYHESPISINYRTEHHHHHH |

| SEQ ID NO: | Description | Sequence |
|---|---|---|
| | His tag (SEQ ID NO: 487); position 62 refers to the amino acid corresponding to position 62 of SEQ ID NO: 1 | |
| 214 | I1-GS10-E5(S62C): I/E tandem having I1 (with N-terminal extension (N + 10) and a modified short tail) fused via GS10 linker (GS10 is SEQ ID NO: 11) to E5 (with N-terminal extension (N + 8), an S62C substitution (boxed), and an E tail) with an optional 6X His tag (SEQ ID NO: 487); position 62 refers to the amino acid corresponding to position 62 of SEQ ID NO: 1 | MGVSDVPRDLEVVAATPTSLLISWSARLKVAR YYRITYGETGGNSPVQEFTVPKNVYTATISGLK PGVDYTITVYAVTRFRDYQPISINYRT<u>E</u>IEKGSG SGSGSGSGSGSGSGSGSGSVSDVPRDLEVVAATP TSLLISWWAPVDRYQYYRITYGETGGNSPVQE FTVPRDVYTATI[C]GLKPGVDYTITVYAVTDYKP HADGPHTYHESPISINYRT<u>E</u>HHHHHH |
| 215 | I1(S91C)-GS10-E5: I/E tandem having I1 (with N-terminal extension (N + 10), an S91C substitution (boxed), and a modified short tail) fused via GS10 linker (GS10 is SEQ ID NO: 11) to E5 (with N-terminal extension (N + 8) and an E tail) with an optional 6X His tag (SEQ ID NO: 487); position 91 refers to the amino acid corresponding to position 91 of SEQ ID NO: 1 | MGVSDVPRDLEVVAATPTSLLISWSARLKVAR YYRITYGETGGNSPVQEFTVPKNVYTATISGLK PGVDYTITVYAVTRFRDYQPI[C]NYRT<u>E</u>IEKGS GSGSGSGSGSGSGSGSGSVSDVPRDLEVVAAT PTSLLISWWAPVDRYQYYRITYGETGGNSPVQ EFTVPRDVYTATISGLKPGVDYTITVYAVTDYK PHADGPHTYHESPISINYRT<u>E</u>HHHHHH |
| 216 | I1-GS10-E5(S91C): I/E tandem having I1 (with N-terminal extension (N + 10) and a modified short tail) fused via GS10 linker (GS10 is SEQ ID NO: 11) to E5 (with N-terminal extension (N + 8), an S91C substitution (boxed), and an E tail) with an optional 6X His tag (SEQ ID NO: 487); position 91 refers to the amino acid corresponding to position 91 of SEQ ID NO: 1 | MGVSDVPRDLEVVAATPTSLLISWSARLKVAR YYRITYGETGGNSPVQEFTVPKNVYTATISGLK PGVDYTITVYAVTRFRDYQPISINYRT<u>E</u>IEKGSG SGSGSGSGSGSGSGSGSVSDVPRDLEVVAATP TSLLISWWAPVDRYQYYRITYGETGGNSPVQE FTVPRDVYTATISGLKPGVDYTITVYAVTDYKP HADGPHTYHESPONYRT<u>E</u>HHHHHH |
| 217 | Modified short tail | EIEK |
| 218 | GSGCGS8 Linker | GSGCGSGSGSGSGSGSGSGS |

EXAMPLE 1

In Cell Western Assay to Screen for EGFR Activity

In Cell Western assays were developed to screen various single $^{10}$Fn3 clones for the ability to inhibit EGFR activity in order to identify those that could be linked with IGF1R $^{10}$Fn3 binders to construct E/I binders. In Cell Western assays were also used to screen and determine relative potency of specific E/I $^{10}$Fn3 binders. Two In Cell Western assays were developed to measure 1) inhibition of EGF-stimulated EGFR phosphorylation or 2) inhibition of EGF-stimulated ERK phosphorylation. Cells were seeded into poly-D-lysine coated 96-well microtiter plates (Becton Dickinson, Franklin Lakes, N.J.) at 24,000 cells/well for A431 epidermoid carcinoma or FaDu head & neck carcinoma cells and allowed to adhere overnight. Cells were washed once and then incubated for 24 hours in serum free media. Serial dilutions of the $^{10}$Fn3-based binders were next applied to the cells and incubated for 2-3 hours prior to stimulation with 100 ng/ml EGF for 10 minutes. Following stimulation, cells were fixed for 20 minutes in PBS containing 3.7% formaldehyde and then permeabilized in PBS containing 0.1% triton-X-100 for 15 minutes. Cells were blocked for one hour in Odyssey blocker (Li-Cor Biosciences, Lincoln, Nebr.) and incubated with antibodies to detect either EGFR phosphorylated on tyrosine 1068 (Cell Signaling, Beverly, Mass.) and β-actin (Sigma, St. Louis, Mo.) or pERK (MAP kinase phosphorylated on tyrosine 202/threonine 204) and total ERK (Santa Cruz Biotechnology, Santa Cruz, Calif.). After washing three times in PBS containing 0.1% tween-20, secondary antibodies were added (Invitrogen, Carlsbad, Calif. or Rockland, Gilbertsville, Pa.). Cells were washed three times in PBS containing 0.1% tween-20 and imaged on a Li-Cor Odyssey Infrared Imaging System (Li-Cor Biosciences, Lincoln, Nebr.). Each clone was assayed in duplicate or triplicate and values were normalized to β-actin for the pEGFR assay and total ERK for the pERK assay. IC50 values were calculated from linear regression analysis of percent inhibition of maximum signal minus background.

Figures 8, 9:
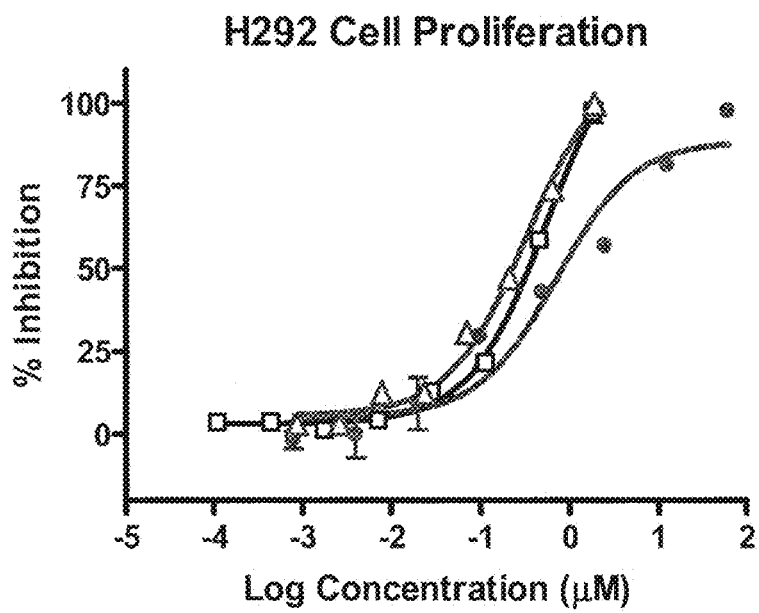
FIG. 8. Inhibition of H292 cell proliferation. Cells were treated with either ● I1, □ E1, or Δ E1-GS10-I1 HTPP preparations and percent inhibition of proliferation was determined.
FIG. 9. Summarizes IC50 values in cell based functional assays for isolated EGFR mononectins, E/I $^{10}$Fn3-based binders with serine at the C-terminal position without PEG added and E/I $^{10}$Fn3-based binders with cysteine at the C-terminal position conjugated to a 40 kDa branched PEG. Representative data is shown.

Results yielded various $^{10}$Fn3 clones that had ability to inhibit activity of EGFR, and showed that certain specific E/I $^{10}$Fn3 binders possessed similar activity to the example shown in FIG. 9.

EXAMPLE 2

Expression of $^{10}$Fn3-based binders

E/I binders were produced by covalently linking an EGFR-binding $^{10}$Fn3 to an IGFIR-binding $^{10}$Fn3 using a glycine-serine linker, thereby generating $^{10}$Fn3 dimers, wherein each $^{10}$Fn3 domain binds to a different target. The IGFIR-binding $^{10}$Fn3 (I1) was previously described as SEQ ID NO: 226 in PCT Publication No. WO 2008/066752. Two novel EGFR-binding $^{10}$Fn3 (E2 and E1) were identified by screening an RNA-protein fusion library, as described in PCT Publication No. WO 2008/066752, for binders to EGFR-Fc (R&D Systems, Minneapolis, Minn.). The following examples describe results using a variety of His-tagged E/I $^{10}$Fn3-based binders (non-pegylated): E2-GS10-I1 (SEQ ID NO: 25), E1-GS10-I1 (SEQ ID NO: 31), I1-GS10-E1 (SEQ ID NO: 28), and I1-GS10-E2 (SEQ ID NO: 22).

The following examples also describe results with the following pegylated, His-tagged E/I $^{10}$Fn3-based binders: E1-GS10-I1 (SEQ ID NO: 55), E2-GS10-I1 (SEQ ID NO: 56), E3-GS10-I1 (SEQ ID NO: 53), I1-GS10-E1 (SEQ ID NO: 57), I1-GS10-E2 (SEQ ID NO: 58), I1-GS10-E3 (SEQ ID NO: 54), E4-GS10-I1 (SEQ ID NO: 120), I1-GS10-E4 (SEQ ID NO: 124), E5-GS10-I1 (SEQ ID NO: 128), I1-GS10-E5 (SEQ ID NO: 132), E85-GS10-I1 (SEQ ID NO: 149), I1-GS10-E85 (SEQ ID NO: 152), E90-GS10-I1 (SEQ ID NO: 164), E96-GS10-I1 (SEQ ID NO: 179), E105-GS10-I1 (SEQ ID NO: 192), I1-GS10-E105 (SEQ ID NO: 195), E112-GS10-I1 (SEQ ID NO: 205), I1-GS10-E112 (SEQ ID NO: 208), I1-GSGCGS8-E5 (SEQ ID NO: 211), I1-GS10-E5-GSGC (SEQ ID NO: 212), I1 (S62C)-GS10-E5 (SEQ ID NO: 213), I1-GS10-E5(S62C) (SEQ ID NO: 214), I1 (S91C)-GS10-E5 (SEQ ID NO: 215), and I1-GS10-E5 (S91C) (SEQ ID NO: 216).

The examples also describe results using a His-tagged IGFRIR $^{10}$Fn3-based binder, I1 (SEQ ID NO: 4), and ten His-tagged EGFR $^{10}$Fn3-based binders, E2 (SEQ ID NO: 6), E1 (SEQ ID NO: 8), E3 (SEQ ID NO: 52), E4 (SEQ ID NO: 107), E5 (SEQ ID NO: 113, wherein X=Ser and with a His tag at the C-terminus), E5 pegylated (SEQ ID NO: 113, wherein X=Cys and with a His tag at the C-terminus), E85 (SEQ ID NO: 140), E90 (SEQ ID NO: 155), E96 (SEQ ID NO: 170), E105 (SEQ ID NO: 185), and E112 (SEQ ID NO: 198). Examples 32 also describes a variety of E monomers having the sequences set forth in FIG. 45 and including a His tag at the C-terminus.

The various $^{10}$Fn3-based binders were purified using a high throughput protein production process (HTPP). Selected binders were cloned into the pET9d vector in order to generate His$_6$ tag (SEQ ID NO: 487) fusions. DNA was transformed into *E. coli* HMS174(DE3), and cells were inoculated in 5 ml LB medium containing 50 μg/mL kanamycin in a 24-well format and grown at 37° C. overnight. Fresh 5 ml LB medium (50 μg/mL kanamycin) cultures were prepared for inducible expression by aspirating 200 μl from the overnight culture and dispensing it into the appropriate well. The cultures were grown at 37° C. until A$_{600}$ 0.6-0.9. After induction with 1 mM isopropyl-β-thio-galactoside (IPTG), the culture was grown for another 6 hours at 30° C. and harvested by centrifugation for 10 minutes at 3220×g at 4° C. Cell pellets were frozen at 80° C.

Cell pellets (in 24-well format) were lysed by resuspension in 450 μl of Lysis buffer (50 mM NaH$_2$PO$_4$, 0.5 M NaCl, 1× Complete™ Protease Inhibitor Cocktail-EDTA free (Roche), 1 mM PMSF, 10 mM CHAPS, 40 mM imidazole, 1 mg/ml lysozyme, 30 ug/ml DNAse, 2 μg/ml aprotonin, pH 8.0) and shaken at room temperature for 1 hour. Lysates were clarified and re-racked into a 96-well format by transfer into a 96-well Whatman GF/D Unifilter fitted with a 96-well, 650 μl catch plate and centrifuged for 5 minutes at 200×g. The clarified lysates were transferred to a 96-well Ni-Chelating Plate that had been equilibrated with equilibration buffer (50 mM NaH$_2$PO$_4$, 0.5 M NaCl, 10 mM CHAPS, 40 mM imidazole, pH 8.0) and incubated for 5 minutes. Unbound material was removed by vacuum. The resin was washed 2×0.3 ml/well with Wash buffer #1 (50 mM NaH$_2$PO$_4$, 0.5 M NaCl, 5 mM CHAPS, 40 mM imidazole, pH 8.0) with each wash removed by vacuum. Next, the resin was washed with 3×0.3 ml/well with PBS with each wash step removed by vacuum. Prior to elution, each well was washed with 50 μl Elution buffer (PBS+20 mM EDTA), incubated for 5 minutes, and the wash discarded by vacuum. Protein was eluted by applying an additional 100 μl of Elution buffer to each well. After a 30 minute incubation at room temperature, the plate(s) were centrifuged for 5 minutes at 200×g and eluted protein collected in 96-well catch plates containing 5 μl of 0.5 M MgCl$_2$ affixed to the bottom of the Ni-plates. Eluted protein was quantified using a BCA Protein assay with SEQ ID NO: 2 as the protein standard.

HTPP yielded active $^{10}$Fn3-based binders that were expressed in a soluble form and purified from the soluble fraction of the bacterial cytosol. FIG. 1 depicts an exemplary SDS-PAGE analysis from one of the E/I $^{10}$Fn3-based binders. SEC analysis on a Superdex 200 5/150 GL in a mobile phase of 100 mM NaPO4, 100 mM NaSO4, 150 mM NaCl, pH 6.8 (GE Healthcare) demonstrated predominantly monomeric proteins (see Example 4).

In addition, midscale expression and purification of select $^{10}$Fn3-based binders was performed. The selected binders, fused to a His$_6$ tag (SEQ ID NO: 487), were cloned into a pET9d or pET29 vector and expressed in *E. coli* HMS174 (DE3) or BL212(DE3) (EMD Biosciences, San Diego, Calif.) cells. 20 ml of an inoculum culture (generated from a single plated colony) was used to inoculate 1 liter of LB medium containing 50 μg/mL kanamycin. The culture was grown at 37° C. until A$_{600}$ 0.6-1.0. After induction with 1 mM isopropyl-β-thiogalactoside (IPTG), the culture was grown for another 6 hours at 30° C. Alternatively, expression was carried out at 18° C. after initial growth at 37° C. using autoinduction media ("ONE" medium, EMD Biosciences, San Diego, Calif.). Cell pellets were harvested by centrifugation for 30 minutes at ≥10,000×g at 4° C. and frozen at 80° C. The cell pellet was resuspended in 25 mL of lysis buffer (20 mM NaH$_2$PO$_4$, 0.5 M NaCl, 1× Complete™ Protease Inhibitor Cocktail-EDTA free (Roche), pH 7.4) using an Ultra-turrax homgenizer on ice. Cell lysis was achieved by high pressure homogenization (≥18,000 psi) using a Model M-110S Microfluidizer (Microfluidics). The soluble fraction was separated by centrifugation for 30 minutes at 23,300×g at 4° C. The supernatant was clarified via 0.45 μm filter. The clarified lysate was loaded onto a HisTrap column (GE) pre-equilibrated with 20 mM NaH$_2$PO$_4$, 0.5 M NaCl, pH 7.4. The column was then washed with 25 column volumes of 20 mM NaH$_2$PO$_4$, 0.5 M NaCl, pH 7.4, followed by 20 column volumes of 20 mM NaH$_2$PO$_4$, 0.5 M NaCl, 25 mM imidazole, pH 7.4, and then 35 column volumes of 20 mM NaH$_2$PO$_4$, 0.5 M NaCl, 40 mM imidazole, pH 7.4. Protein was eluted with 15 column volumes of 20 mM NaH$_2$PO$_4$, 0.5 M NaCl, 500 mM imidazole, pH 7.4, fractions pooled based on absorbance at A$_{280}$ and dialyzed against 1×PBS, 50 mM Tris, 150 mM NaCl, pH 8.5 or 50 mM NaOAc, 150 mM NaCl, pH4.5. Any precipitate was removed by filtering at 0.22 μm.

Midscale expression and purification yielded highly pure and active proteins that were expressed in a soluble form and purified from the soluble fraction of the bacterial cytosol. SEC analysis on a Superdex 200 10/30GL in a mobile phase of 100 mM NaPO$_4$, 100 mM NaSO$_4$, 150 mM NaCl, pH 6.8 (GE Healthcare) demonstrated predominantly monomeric proteins (see Example 4).

EXAMPLE 3

Pegylation of E/I $^{10}$Fn3-Based Binders

Multi-valent fibronectin based scaffold proteins, such as E/I $^{10}$Fn3-based binders, can be pegylated with various sizes and types of PEG. To allow for pegylation, the protein is typically modified near the C-terminus by a single point mutation of an amino acid, typically a serine, to a cysteine. PEGylation of the protein at the single cysteine residue is accomplished through conjugation with various maleimide-derivatized PEG forms by combining the derivitized-PEG reagent with the protein solution and incubating. Progress and confirmation of the PEGylation conjugation reaction can be confirmed by SDS-PAGE and/or SE-HPLC methods that separate the non-PEGylated protein from the PEGylated protein.

For example, the construct E2-GS10-I1 (SEQ ID NO: 25) was pegylated by replacing a serine that was at position 221 with a cysteine. The resulting construct, SEQ ID NO: 56, was then conjugated with a maleimide-derivatized 40 kDa branched PEG (NOF America Corporation, White Plains, N.Y.). The derivatized PEG reagent was mixed with the protein construct in solution and incubated at pH 7.40 at Room temperature until the reaction was complete, typically 30 minutes or overnight at 4° C. The pH was lowered to pH 4.5 or pH 5.0 by dialysis or rapid desalting using size exclusion column chromatography into in 50 NaOAc, 150 mM NaCl buffer. The mixture of products and excess reactants from the PEGylation reaction were then loaded onto a cation exchange chromatography column at the lowered pH and eluted with a 150 mM to 1 M NaCl gradient. Studies to confirm the pegylation were also conducted as described in the paragraph above. The conjugations can be performed with the His tagged or the His-Tag free versions of the protein.

On occasions in which E coli endotoxin contamination needed to be depleted in the sample, two methods used either separately or in conjunction with one another were empoloyed. The first was to wash the cation exchange column with typically 5 column volumes NaOAc buffer supplemented with 0.5% Triton X-100, followed by 20 column volumes (or more) of the same buffer without Triton X-100. Additionally or in place of this procedure, the protein was passed very slowly through a Sartorius Sartobind® Q filter (Sartorius Stedim Biotech Bohemia, N.Y.).

Two of the E/I $^{10}$Fn3-based binders, E2-GS10-I1-cys (with his) (SEQ ID NO: 56) and E3-GS10-I1-Cys (with his) (SEQ ID NO: 53), were pegylated using an alternative procedure. Five ml of an inoculum culture of BL21(DE3) E. coli cells containing a T7 ploymerase driven pET29 plasmid encoding either E2-GS10-I1-cys (with his) or E3-GS10-I1-Cys (with his), were generated from a single plated colony and used to inoculate 1 liter of auto-induction media ("ONE" medium, EMD Biosciences, San Diego, Calif.) containing 50 μg/mL kanamycin. Expression was carried out at 18° C. after initial growth at 37° C. and harvested by centrifugation for 10 minutes at ~10,000×g at 4° C. Cell pellets were frozen at 80° C. The cell pellet was resuspended in 10 mL of lysis buffer (20 mM NaH$_2$PO$_4$, 0.5 M NaCl, 5 mM Immidazole, pH 7.4) and mechanically lysed using an Avestin homgenizer. The soluble fraction was separated by centrifugation for 15 minutes at 23,300×g at 4° C. The supernatant was decanted and the pellet was solubilized in Lysis buffer (above) supplemented with 4 M to 6 M guanidine hydrochloride (GdnHCl). Solubilized protein was then purified on a suitably sized NiNTA column (Qiagen, Inc.) pre-equilibrated with the GdnHCL supplemented Lysis Buffer. The column was then washed with 5 to 10 column volumes of the same buffer, followed by elution with the same buffer supplemented with 300 mM Immidazole. The fractions eluted off the column containing the protein of interest were diluted to 2-3 mgs/mL protein and then combined with a 1.2-1.5 molar excess of solid NEM-PEG (40 kDa branched or other). The mixture was allowed to react at room temperature for 30 minutes or until the reaction was complete. The entire reaction volume was then placed into a dialysis bag (5,000 Da Molecular Weight cutoff) and the mixture was subjected to a dialysis refolding process. For example, this process may consist of two 10-16 hour 500:1 (buffer: dialysate) dialysis exchanges against 50 mM NaOAc, 150 mm NaCl, pH 4.5. The dialysate from this procedure contains properly folded, PEGylated materials plus excess reactants. The mixture of products and excess reactants from the PEGylation reaction were clarified via centrifugation or filtration prior to loading them onto a cation exchange chromatography column (SP Sepharose or Resource S, GE Healthcare). The column was developed with 150 mM to 1 M NaCl gradient in the NaOAc background buffer. Studies to confirm the pegylation were conducted as described above.

EXAMPLE 4

Biophysical Characterization of $^{10}$Fn3-Based Binders

Standard size exclusion chromatography (SEC) was performed on the proteins purified from the HTPP and the midscale processes (0.1 to 1 μg of protein for HTPP and 10-50 ug for midscale). SEC of HTPP derived material was performed using a Superdex 200 5/150 column (GE Healthcare) or on a Superdex 200 10/30 column (GE Healthcare) for midscaled material on an Agilent 1100 or 1200 HPLC system with UV detection at A$_{214}$ nm and A$_{280}$ nm and with fluorescence detection (excitation=$_{280}$ nm, emission=$_{350}$ nm). A buffer of 100 mM sodium sulfate, 100 mM sodium phosphate, 150 mM sodium chloride, pH 6.8 at appropriate flow rate of the SEC column employed. Gel filtration standards (Bio-Rad Laboratories, Hercules, Calif.) were used for molecular weight calibration.

The results of the SEC on the HTPP purified $^{10}$Fn3-based binders showed predominantly monomeric proteins and elution in the approximate range of 25 kDa vs. globular Gel Filtration standards (BioRad).

Figure 2A:
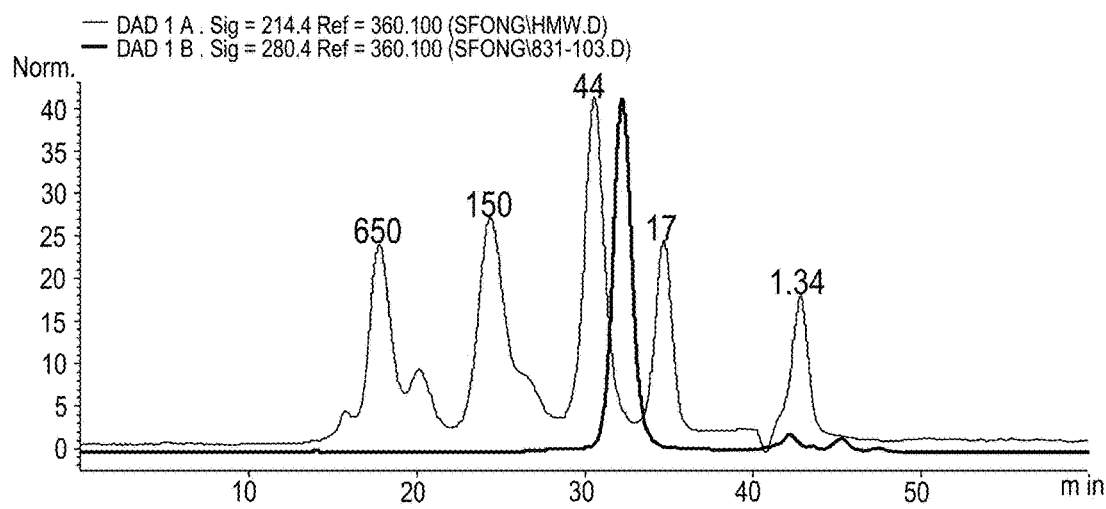
FIG. 2A. SEC Analysis of midscale purified I1-GS10-E2. 22 μg of HisTrap purified I1-GS10-E2 dialyzed into PBS, pH 7.4 was loaded onto a Superdex 200 10/30 SEC Column (GE Healthcare) with a mobile phase of 100 mM $NaPO_4$, 100 mM $NaSO_4$, 150 mM NaCl, pH 6.8 and measured using A280. I1-GS10-E2 eluted predominantly as a single monomeric species at a molecular weight range of approximately 24.6 kDa vs. globular Gel Filtration standards (BioRad).
Figure 2B:
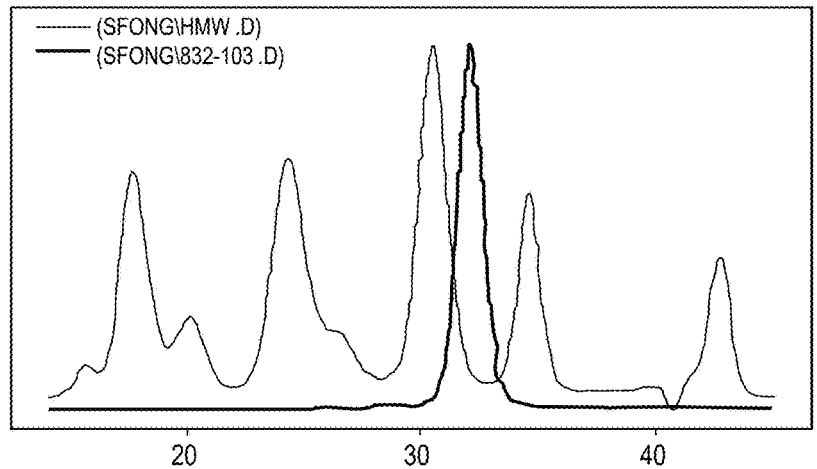
FIG. 2B. SEC analysis of E2-GS10-I1.

The results of the SEC on the midscaled purified $^{10}$Fn3-based binders showed predominantly monomeric proteins and elution in the approximate range of 25 kDa vs. globular Gel Filtration standards (BioRad). FIG. 2 depicts exemplary SEC profiles for E/I $^{10}$Fn3-based binders (I1-GS10-E2 in FIG. 2A and E2-GS10-I1 in FIG. 2B).

Select midscale $^{10}$Fn3-based binders were further analyzed by LC-MS (Water's 2695 liquid chromatography HPLC system coupled with Waters Q-TOF API mass spectrometer, Waters Corporation, Milford, Mass.). Samples were diluted to approximately 0.5 mg/ml with HPLC grade water. Approximately 5 µl of diluted sample was injected onto a Jupiter C18 column (Catalog number 00G-4053-80, Phenomenex). Buffer A: 0.02% TFA+0.08% formic acid in HPLC grade water. Buffer B: 0.02% TFA+0.08% formic acid in HPLC grade acetonitrile. Sample was eluted with gradient (Table 1) at flow rate 0.2 ml/minutes.

TABLE 1

| Time | % A | B % |
|---|---|---|
| 0 | 95 | 5 |
| 5.00 | 75 | 25 |
| 25.00 | 55 | 45 |
| 30.00 | 5 | 95 |
| 32.00 | 95 | 5 |
| 45.00 | 95 | 5 |

HPLC elution was split at approximately to 1:1 ratio and half sent to UV detector and the other half to mass spectrometer. Mass spectrometer had the following instrument settings: capillary voltage 3.5 KV, cone voltage 40, source temperature 80° C., desolvation temperature 250° C., desolvation gas flow 450 and multi channel photo detector voltage 2200. Raw spectra were deconvoluted with MaxEn1 (Waters Corporation).

The molecular weight of I1-GS10-E2 (SEQ ID NO: 22) as measured by LC-MS is 24,445 Dalton, which is within 1 Dalton from the molecular weight calculated from the amino acid composition. This indicates that the protein has the correct amino acid composition and the N terminal methionine is processed. There is no other post translational modification on the protein.

Figure 3A:
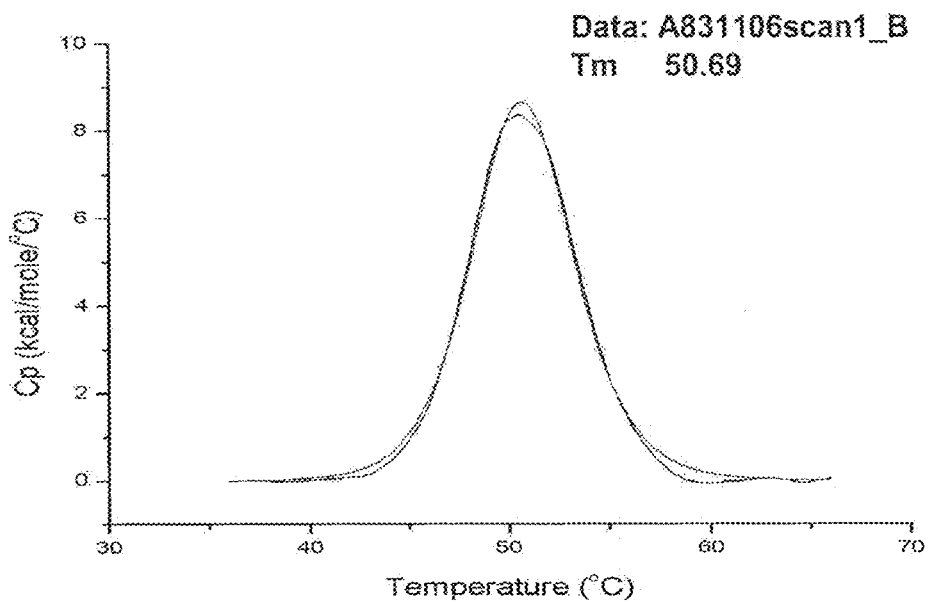
FIG. 3A. Differential Scanning calorimetry (DSC) of midscale purified I1-GS10-E2 in PBS was performed to determine the $T_m$. A 1 mg/mL solution of I1-GS10-E2 was scanned from 5° C. to 95° C. at a rate of 1 degree per minute under 3 atm pressure. The data was analyzed versus a control run of the PBS buffer.
Figure 3B:
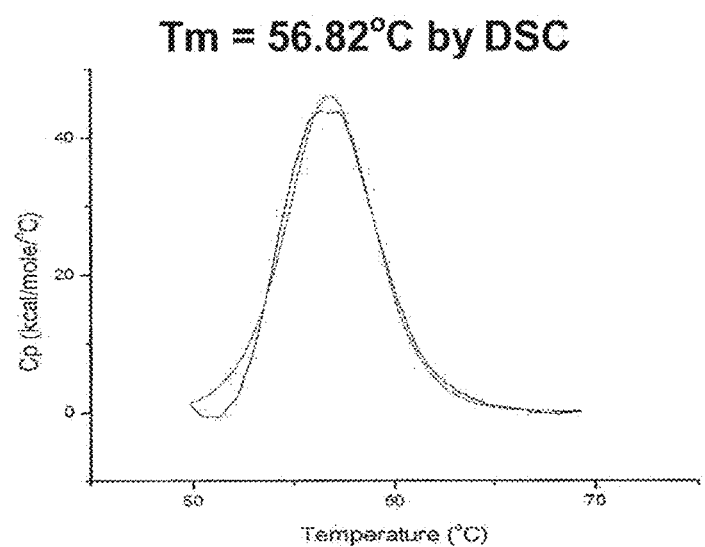
FIG. 3B. DSC of E2-GS10-I1.

Differential Scanning calorimetry (DSC) analysis of the midscaled I1-GS10-E2 was performed to determine the $T_m$. A 1 mg/ml solution was scanned in a N-DSC II calorimeter (calorimetry Sciences Corp) by ramping the temperature from 5° C. to 95° C. at a rate of 1 degree per minute under 3 atm pressure. The data was analyzed versus a control run of the appropriate buffer using a best fit using Orgin Software (OrginLab Corp). The results of this assay demonstrate that the E/I binder has a $T_m$ of 50.69° C. (see FIG. 3A). Using the same methods, the $T_m$ of E2-GS10-I1 (with Peg) was determined to be 50.72° C. and the $T_m$ of E2-GS10-I1 (without Peg) was determined to be 56.82° C. (see FIG. 3B).

EXAMPLE 5

Determination of Binding Affinity

Surface plasmon resonance (BIAcore) analysis was performed on solution-phase $^{10}$Fn3-based binders in order to determine off-rates and/or binding affinities using captured EGFR-Fc and IGF1R-Fc. The extracellular domain of human IGF1R (aa 1-932) was cloned into a mammalian expression vector containing the hinge and constant regions of human IgG1. Transient transfection of the plasmid produced a fusion protein, IGF1R-Fc which was subsequently purified by Protein A chromatography. Recombinant human EGFR-Fc (aa 1-645 of the extracellular domain of human EGFR fused to human Fc) was purchased from R&D systems (Minneapolis, Minn.). IGF1R-Fc was captured on immobilized Protein A whereas EGFR-Fc was captured on immobilized anti-human antibody.

In a typical experiment, anti-human IgG was immobilized on flow cells 1 and 2 of a CM5 chip following the manufacturer's recommendations (GE Healthcare, Piscataway, N.J.). EGFR-Fc (50 nM) was injected at 5 uL for 2 minutes on flow cell 2 (Fc2). Two 30 second injections of 3 M $MgCl_2$ were used for regeneration of the bound EGFR-Fc from the anti-human IgG surface. Protein A was diluted to 80 ug/mL in acetate pH 4.5 and immobilized to ~3000 RU on flow cells 3 and 4 of a CM5 chip surface. Approximately 1300 RU of IGF1R-Fc was captured on Fc 4. Two 30 second injections of 50 mM glycine pH 1.5 were used to regenerate the surface between samples.

A concentration series of 100 nM to 1 nM of HTPP purified protein (three data points collected) or 300 nM to 0.05 nM of midscale purified protein (eleven data points collected) was evaluated for binding to EGFR-Fc or IGF1R-Fc. Sensorgrams were obtained at each concentration and were evaluated using Biacore T100 Evaluation Software, Version 1.1.1 (GE healthcare/Biacore) to determine the rate constants $k_a$ ($k_{on}$) and $k_d$ ($k_{off}$). For the HTPP evaluation the off-rate was fitted from the 3 point curves. The affinity $K_D$ was calculated from the ratio of rate constants $k_{off}/k_{on}$.

The EGFR $^{10}$Fn3-based binders were evaluated for specificity in a similar format using anti-human IgG to capture HER2-Fc. The $^{10}$Fn3-based binders did not show any discernible binding to captured HER2-Fc under conditions where robust binding was seen for EGFR-Fc.

As shown in Table 2, both domains of the E/I $^{10}$Fn3-based binders are functional, retaining their binding properties to the respective targets. The off rates shown in Table 2 are from midscale material and are similar to the qualitative results obtained with the HTPP material.

TABLE 2

Summary of binding constants for $^{10}$Fn3-based binders

| Target | Protein | ka (1/Ms) | kd (1/s) | $K_D$ (nM) |
|---|---|---|---|---|
| EGFR-Fc | E1 | 1.19E+05 | 1.18E-03 | 9.92 |
|  |  | 1.43E+05 | 1.89E-03 | 13.2 |
|  | E1-GS10-I1 | 6.29E+04 | 4.74E-04 | 7.53 |
|  |  | 3.82E+04 | 3.89E-04 | 10.17 |
|  | I1-GS10-E1 | 1.26E+05 | 6.03E-04 | 4.8 |
|  |  | 4.13E+04 | 4.25E-04 | 10.28 |
|  | E2 | 3.73E+05 | 2.72E-04 | 0.73 |
|  |  | 3.27E+05 | 3.2E-04 | 0.98 |
|  | E2-GS10-I1 | 3.93E+05 | 1.75E-04 | 0.45 |
|  |  | 3.75E+05 | 1.67E-04 | 0.45 |
|  | I1-GS10-E2 | 6.47E+05 | 1.42E-04 | 0.22 |
|  |  | 3.90E+05 | 1.14E-04 | 0.29 |
|  | E3 | 2.83E+05 | 3.98E-04 | 3.4 |
|  |  |  |  | 1.4 |
|  | E3-GS10-I1 | 3.49E+05 | 2.29E-04 | 0.66 |
|  | I1-GS10-E3 | 1.17E+05 | 2.91E-04 | 2.48 |
| IGF1R-Fc | I1 | 3.84E+06 | 4.34E-04 | 0.11 |
|  | E1-GS10-I1 | 5.13E+05 | 3.38E-04 | 0.66 |
|  | I1-GS10-E1 | 1.47E+06 | 3.98E-04 | 0.27 |
|  | E2-GS10-I1 | 1.24E+06 | 3.95E-04 | 0.32 |
|  | I1-GS10-E2 | 3.82E+06 | 4.79E-04 | 0.13 |
|  | E3-GS10-I1 | 1.8E+06 | 2.09E-04 | 0.12 |
|  | I1-GS10-E3 | 1.37E+06 | 4.54E-05 | 0.03 |

EXAMPLE 6

Inhibition of IGFR Activity in H292 Cells

The ability of E/I $^{10}$Fn3-based binders to inhibit phosphorylation of IGF1R on tyrosine 1131 was determined using an H292 cell in vitro assay. Briefly, 65×10$^3$ H292 cells were plated in 96-well microplates (Biocoat Poly-D-Lysine coated 96-well plate, cat#356640, Becton Dickinson, Franklin Lakes, N.J.) in RPMI-1640 culture medium containing 10 mM Hepes pH 7.4 and 10% fetal bovine serum. Cells were allowed to adhere for 24 hours at 37° C., 5% $CO_2$. The next day cells were washed once with 200 microliters per well of serum free RPMI-1640 and incubated overnight in 100 µL per well of serum free RPMI-1640. Serial dilutions of HTPP material was added and cells were incubated for an additional 3 hours. Cells were stimulated with 100 ng/ml of IGF-1 (cat#500-P11, PeproTech, Rocky Hill, N.J.) for 10 minutes at 37° C. Media was dumped from the plate and 100 µL of cell lysis buffer (Cell Signaling cat#9803, Beverly, Mass.) was added to each well. Cells were incubated at room temperature for 15 minutes to allow lysis and lysate was transferred to a phospho-IGFR ELISA (cat#7302, Cell Signaling, Beverly, Mass.). The manufacturer's procedure was followed to carry out the ELISA.

Figure 4:
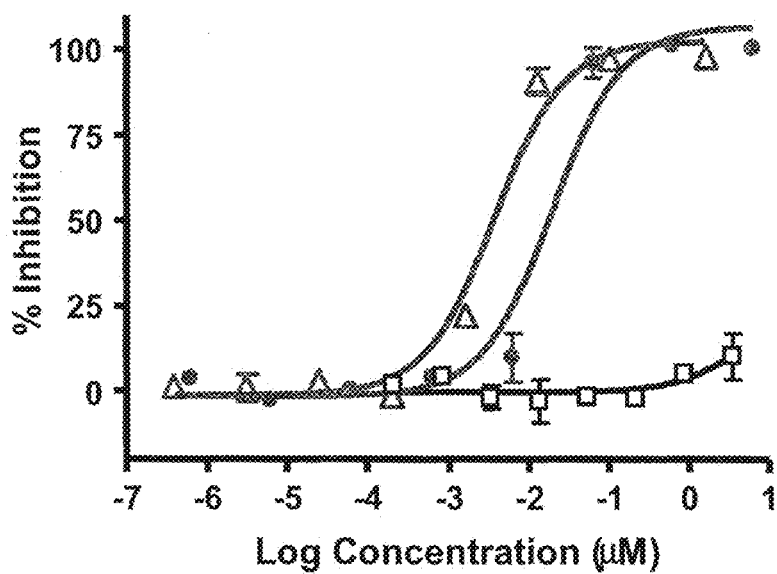
FIG. 4. Inhibition of IGFR activity in H292 cells. Cells were stimulated with 100 ng/mL of IGF-1 and 100 ng/mL of EGF and treated with either ● I1, □ E1, or Δ E1-GS10-I1 HTPP preparations. Phosphorylation of IGF1R on tyrosine 1131 was determined by ELISA.

As demonstrated in FIG. 4, His tagged E1-GS10-I1 inhibited IGF1-stimulated phosphorylation of the IGF1R ($IC_{50}$=0.004 uM) with comparable potency to the isolated IGF1R binder, I1 ($IC_{50}$=0.018 uM). The EGFR binder, E1, alone had very little effect on IGF1R phosphorylation ($IC_{50}$>3.5 uM). As shown in FIG. 9, additional E/I binders demonstrated ability to inhibit IGF1R-stimulated phosphorylation with an IC50 in the range of 0.1 nM to 19 nM, including several pegylated E/I binders that were tested. In particular, for the pegylated E/I binders E1-GS10-I1, and I1-GS10-E1, inhibition of pIGFR was shown at 0.9 nM and 4 nM, respectively. For pegylated E/I binders E2-GS1041 and I1-GS10-E2, inhibition of pIGFR was shown at 0.3 nM and 0.8 nM, respectively.

EXAMPLE 7

Inhibition of EGFR Activity in H292 Cells

The ability of E/I $^{10}$Fn3-based binders to inhibit phosphorylation of the EGFR on tyrosine 1068 was determined using an H292 cell in vitro assay. The assay was carried out as described in Example 6, except that cells were stimulated with 100 ng/ml of EGF (cat#236-EG-200, R & D Systems, Minneapolis, Minn.) and a phospho-EGFR ELISA was performed (cat#7240, Cell Signaling, Beverly, Mass.). The manufacturer's procedure was followed to carry out the ELISA.

Figure 5:
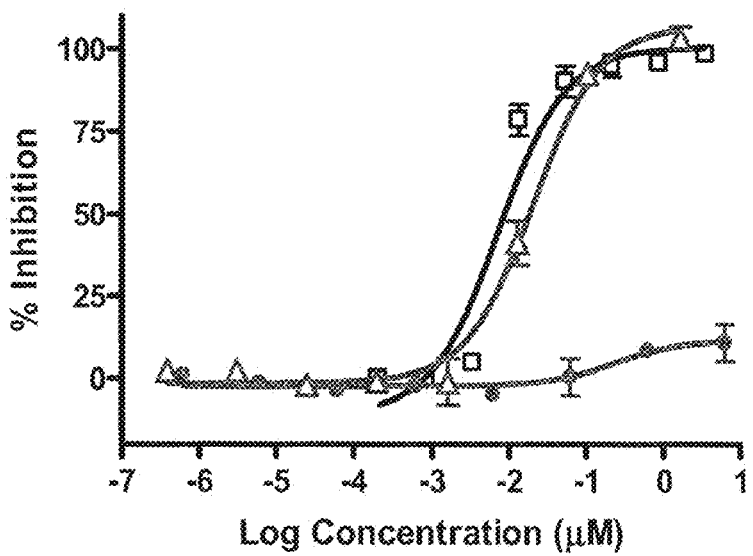
FIG. 5. Inhibition of EGFR activity in H292 cells. Cells were stimulated with 100 ng/mL of IGF-1 and 100 ng/mL of EGF and treated with either ● I1, □ E1, or Δ E1-GS10-I1 HTPP preparations. Phosphorylation of EGFR on tyrosine 1068 was determined by ELISA.
Figure 11:
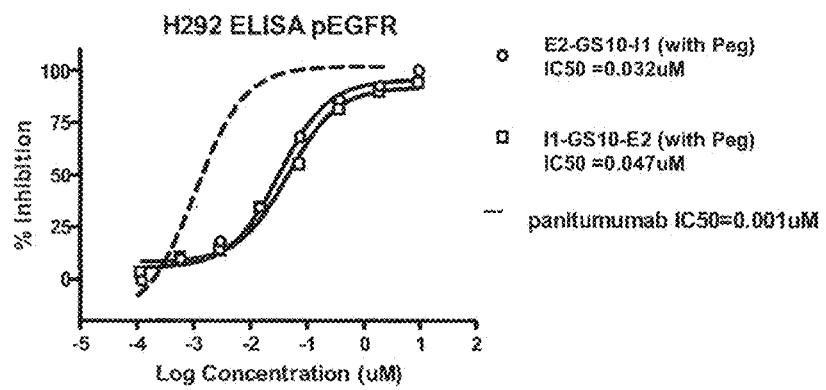
FIG. 11. Inhibition of EGF-stimulated EGFR phosphorylation in H292 cells. Both constructs demonstrated comparable activity in the H292 cell assay for inhibiting EGFR. E2-GS10-I1 (with PEG) (○), I1-GS10-E2 (with PEG) (□), panitumumab (----).

As demonstrated in FIG. 5, His-tagged E1-GS10-I1 inhibited EGF-stimulated phosphorylation of the EGFR ($IC_{50}$=0.020 uM) with comparable potency to the isolated EGFR binder, E1 ($IC_{50}$=0.007 uM). The IGF1R binder, I1 alone had very little effect on EGFR phosphorylation ($IC_{50}$>6.21 uM). As shown in FIG. 9, additional E/I binders demonstrated ability to inhibit EGF-stimulated phosphorylation with an IC50 in the range of 7 nM to 127 nM, including several pegylated E/I binders that were tested. In particular, for pegylated E2-GS10-I1 and I1-GS10-E2, inhibition of pEGFR was shown at 32 nM and 47 nM, respectively. Similar data is shown in FIG. 11 for the pegylated E/I binders E2-GS10-I1, and I1-GS10-E2.

EXAMPLE 8

Inhibition of EGF+IGF1-Induced pAKT in H292 Cells

The ability of E/I $^{10}$Fn3-based binders to inhibit phosphorylation of AKT on serine 473 was determined using an H292 cell in vitro assay. The assay was carried out as described in Example 6, except that cells were simultaneously stimulated with both EGF and IGF1 as described above and lysates were analyzed with a phospho-AKT ELISA (cat#7160, Cell Signaling, Beverly, Mass.). The manufacturer's procedure was followed to carry out the ELISA.

Figure 6:
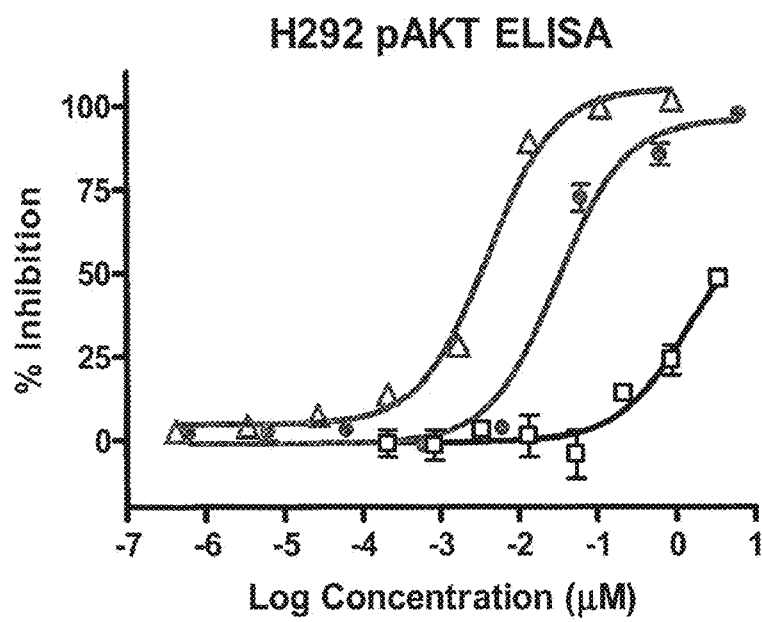
FIG. 6. Inhibition of AKT phosphorylation in H292 cells. Cells were stimulated with 100 ng/mL of IGF-1 and 100 ng/mL of EGF and treated with either ● I1, □ E1, or Δ E1-GS10-I1 HTPP preparations. Phosphorylation of AKT on serine 473 was determined by ELISA.

Signal transduction at EGFR and IGF1R feeds into the PI3K-AKT signaling pathway and stimulates phosphorylation of AKT. As demonstrated in FIG. 6, E1-GS10-I1 inhibited EGF and IGF1-stimulated phosphorylation of AKT in H292 cells. The E/I $^{10}$Fn3-based binder was slightly more potent in its ability to block AKT activation ($IC_{50}$=0.004 uM) than the IGF1R binder, I1, by itself ($IC_{50}$=0.031 uM). The EGFR binder, E1, exhibited only modest activity in its ability to block AKT activation by both ligands ($IC_{50}$=1.28 uM). As shown in FIG. 9, additional E/I binders demonstrated ability to inhibit EGF and IGF1-stimulated phosphorylation of AKT with an IC50 in the range of 0.1 nM to 26 nM, including several pegylated E/I binders that were tested.

EXAMPLE 9

Inhibition of Cell Proliferation in RH41 and H292 Cells

E/I $^{10}$Fn3-based binders were evaluated for antiproliferative activity in the H292 non-small cell lung carcinoma cell line, which depends on EGFR signaling for growth, or the RH41 Ewing sarcoma cell line, which depends on IGF1R signaling for growth. Antiproliferative activity of binders was assessed in monolayer cultures by staining cellular DNA with the CyQuantNF fluorescent stain (cat#C35006, Invitrogen, Carlsbad, Calif.). Briefly, 2×10$^3$ H292 or 5×10$^3$ RH41 cells were plated into 96-well microplates (View Plates 96F cat#6005225, Perkin Elmer, Waltham, Mass.) in RPMI-1640 culture medium containing 10 mM Hepes pH 7.4 and 10% fetal bovine serum and allowed to adhere for 24 hours at 37° C., 5% $CO_2$. Cells were maintained as exponentially growing monolayers and remained in logarithmic growth phase during the period of the assay without reaching confluence during the course of the assay. Twenty-four hours after plating, serial dilutions of midscale material was added and cells were incubated for an additional 72 hours. Following this incubation, cells were treated with CyQuantNF reagent and allowed to incorporate dye into cellular DNA for 1 hour at 37° C. Total DNA was quantified by reading fluorescence at 485 nm excitation and 530 nm emission on a CytoFluor 4000 instrument (Applied Biosystems, Framingham, Mass.). Total time that cells were exposed to drug was 72 hours. Standard compounds were included in each experiment to verify assay performance and reproducibility. Linear regression analysis of the percent of inhibition by test compound was used to determine $IC_{50}$ values.

Figure 7:
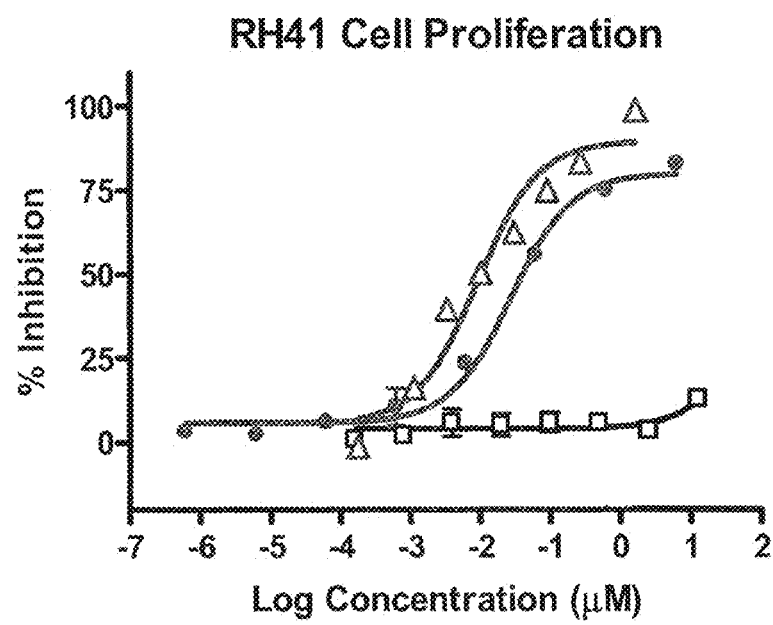
FIG. 7. Inhibition of RH41 cell proliferation. Cells were treated with either ● I1, □ E1, or Δ E1-GS10-I1 HTPP preparations and percent inhibition of proliferation was determined.

As demonstrated in FIG. 7, in RH41 cells, His-tagged E1-GS10-I1 inhibited proliferation with comparable potency ($IC_{50}$=0.009 uM) to the IGFR binder, I1 ($IC_{50}$=0.028 uM). The EGFR binder, E1, by itself had very little effect on the proliferation in this cell line ($IC_{50}$>12.5 uM).

As demonstrated in FIG. 8, in H292 cells, His-tagged E2-GS10-I1 inhibited proliferation with greater potency ($IC_{50}$=0.329 uM) than the IGFR binder, I1, ($IC_{50}$=0.699 uM) or the EGFR binder, E2 ($IC_{50}$=0.553 uM). See Table 4 below for the IC50 values for the E and I monomers.

EXAMPLE 10

Competitive EGF Ligand Binding Assay

The E/I binders E1-GS10-I1, I1-GS10-E1, E2-GS10-I1 and I1-GS10-E2 (HTPP material) were tested in an EGF ligand binding cell-based competition assay in A431 cells and compared to EGFR $^{10}$Fn3-based binders E1 and E2 (midscale material). A431 cells were plated at 15000 cells/well in 96-well plates in DMEM+10% FBS and incubated 48 hours. Cells were washed with starvation media (DMEM+0.1% BSA) and incubated in starvation media for 1 hour. Starvation media was removed and replaced with $^{10}$Fn3-based binders that were diluted in starvation media and cells were pre-incubated for 30 minutes at 37° C. to allow proteins to bind to EGF receptors on cell surfaces. 10 nM final concentration of Europium (Eu)-labeled EGF (Perkin Elmer, Boston, Mass.) diluted in starvation media was added to pre-incubated cells and plates were incubated for 3 hours at 4° C. in the dark. Plates were washed twice with cold PBS and 50 ul/well of Enhancement solution (Perkin Elmer, Boston, Mass.) was added to plates and incubated 1 hour at 37° C. Plates were read on the Flexstation II (Molecular Devices). The data was plotted with Softmax plus software and IC50 values, i.e., the concentration of $^{10}$Fn3-based binders required to inhibit 50% of the Eu-EGF ligand from binding to the EGF receptor on the cell surfaces, were calculated.

The results for E2 and E1 compared with E2-GS10-I1, I1-GS10-E2, E1-GS10-I1 and I1-GS10-E1 are summarized in Table 3. This data indicates that the E/I $^{10}$Fn3-based binders compete with, and inhibit the binding of, EGF to the EGFR receptor on A431 cells with similar potency to the EGFR $^{10}$Fn3-based binders. See Table 4 below for the IC50 values for the E and I monomers.

TABLE 3

Summary of IC50 values for inhibition of EGF Binding to EGFR on A431 cell surfaces

| Protein | IC50 (nM) |
| --- | --- |
| E2 | 7 |
| E1 | 14 |
| E2-GS10-I1 | 1.8 |
| I1-GS10-E2 | 1.4 |
| E1-GS10-I1 | 14.6 |
| I1-GS10-E1 | 7 |

EXAMPLE 11

Activation and Signaling Activity in Cell-Based Assays

Target effects of the various E/I $^{10}$Fn3-based binders were evaluated in DiFi colon carcinoma cells by immunoblotting. Cells were seeded at 4×10$^5$ cells in each 25 cm$^2$ flask and incubated overnight at 37° C. in 5% $CO_2$. The next day, treatments were initiated and cells were further incubated for various times from 1.5 to 120 hours. Cells were then lysed in HNTG (50 mM Hepes, 150 mM NaCl, 0.5% triton-X-100, 8% glycerol, 2 mM $Na_3VO_4$, 1.5 mM $MgCl_2$, 1 mM EDTA containing the protease inhibitors AEBSF, aprotinin, leupeptin, bestatin, pepstatin-A and E64) and total protein was quantified with the BCA protein assay (Pierce, Waltham, Mass.). Levels of total EGFR, total IGF1R and the phosphorylation state of the EGFR, MAP kinase protein ERK1/2 isoforms, was detected by SDS-PAGE analysis of 20 micrograms of total protein followed by transfer of proteins to nitrocellulose and immunoblotting with specific antibodies. Blots were also probed with β-actin to demonstrate equal loading of each sample.

Figure 10:
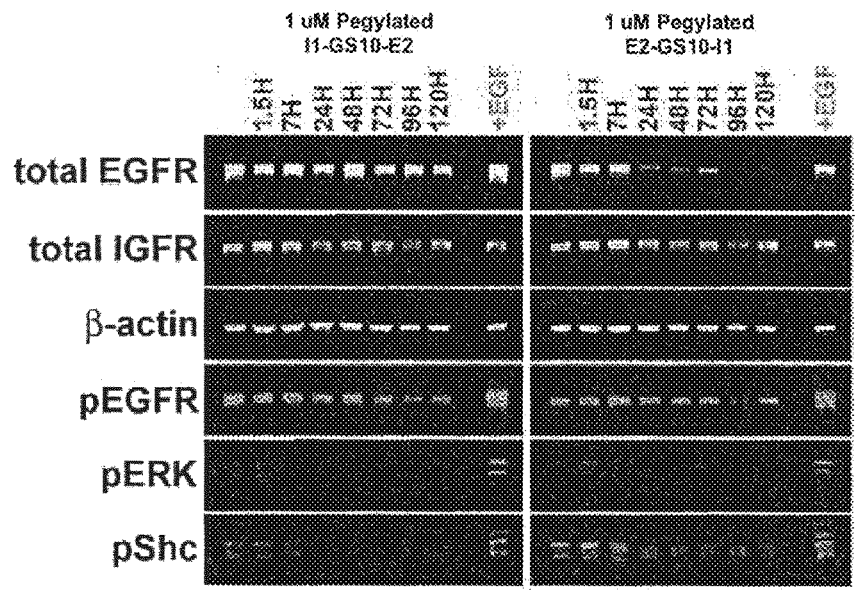
FIG. 10. Immunoblot analysis of PEGylated E/I $^{10}$Fn3-based binder with E2 in the N-terminal and C-terminal positions. Despite both constructs demonstrating comparable activity in the H292 cell assay for inhibiting EGFR, the E/I $^{10}$Fn3-based binder with E2 at the C-terminal position did not degrade EGFR while the E/I $^{10}$Fn3-based binder with E2 at the N-terminal position did. Both constructs show very weak to no IGFR degradation in this cell line. β-actin was included to demonstrate equal loading across all lanes. The phosphorylation state of EGFR, ERK and Shc was also examined.

The pegylated E/I $^{10}$Fn3-based binders E1-GS10-I1 (SEQ ID NO: 55), E2-GS10-I1 (SEQ ID NO: 56), and E3-GS10-I1 (SEQ ID NO: 53), demonstrated the ability to degrade EGFR in this assay. In addition, for E3-GS10-I1 (SEQ ID NO: 53), degradation of IGF1R was also observed. The effect on EGFR degradation for the pegylated binder E2-GS10-I1 is shown in FIG. 10, as are other effects on signaling molecules. Additionally, the non-pegylated version of the binder E2-GS10-I1 demonstrated similar EGFR degradation (data not shown). FIG. 10 shows that for the pegylated binder I1-GS10-E2, there was no EGFR degradation. Table 4 below summarizes various properties of the E monomers.

TABLE 4

Summary of properties of E monomers.
EGFR

| Monomer | BIAcore KD IC50 | Neutralizes EGF Binding IC50 | Inhibition of pEGFR IC50 | Inhibition of pERK IC50 | Inhibition of H292 Proliferation IC50 |
| --- | --- | --- | --- | --- | --- |
| E1 | 14.6 nM | 0.53 nM | 18 nM | 17 nM | 18 nM |
| E2 | 1.4 nM | 1.46 nM | 20 nM | 40 nM | 30 nM |
| E3 | 0.72 nM | 0.87 nM | 11 nM | 97 nM | 26 nM |

EXAMPLE 12

Evaluation of Certain E/I $^{10}$Fn3-Based Binders on H292 Tumor Xenografts Grown in Nude Mice The pegylated E/I binders E2-GS10-I1 and E3-GS10-I1 as well as the monoclonal antibody panitumumab were evaluated in an H292 tumor xenograft model. For in vivo models, panitumumab was obtained as the marketed drug and E/I binders were purified as described above. In vitro activity of all E/I binders was validated prior to administration in animals by testing functionality of each end in the EGF-stimulated pEGFR and the IGF1-stimulated pIGFR assay in H292 cells. E/I binders were diluted in phosphate buffered saline (PBS) at the beginning of the experiment and stored at 2-4° C. for the duration of each study. Both compounds were administered i.p. in a total volume of 500 μl/inj/mouse and were equilibrated to room temperature prior to administration.

Mice and tumor propagation. Female athymic (nude) mice 5-6 weeks of age were obtained from Harlan Sprague-Dawley Co. (Indianapolis, Ind.). and were quarantined for approximately 3 weeks prior to their use for tumor propagation or drug efficacy testing. The animals were provided food and water ad libitum. Animal care was performed in keeping with AAALAC and Bristol-Myers Squibb guidelines. Tumors were propagated by subcutaneous (s.c.) implantation in nude mice. Tumor passages occurred approximately every two to four weeks.

In vivo antitumor testing. Estimated tumor weight was calculated using the formula: Tumor weight (mg)=(w$^2$*l)/2; where w=width and l=length in mm. Antitumor activity was evaluated in terms of % tumor growth inhibition (TGI) where a % TGI of >50% was considered active. Relative % tumor growth inhibition was calculated as % TGI=[(C$_t$−T$_t$)/(C$_t$−C$_0$)]×100 where C$_t$=median tumor weight of control mice at time t in days after tumor implant, T$_t$=median tumor weight of treated mice at time t, C$_0$=median tumor weight of control mice at time 0. % TGI value was calculated at various time points beginning after 1.5 tumor volume doubling times and sustained over a time period of 3 tumor volume doubling times (TVDT) where possible. Where, TVDT=median time (days) for control tumors to reach target size—median time (days) for control tumors to reach half the target size. The definition of a cured mouse was one whose tumor was undetectable, or <35 mg, when assessed more than 10 TVDTs post-treatment. The dose of a compound which yielded the maximum therapeutic effect, was termed the optimal dose (OD). Treatment groups (typically 8 mice) with more than one death attributable to drug toxicity were considered to have had excessively toxic treatments and their data were not used in the evaluation of antitumor activity. The maximum tolerated dose (MTD) is defined as the dose level immediately below which excessive toxicity (i.e. more than one death) occurred. Treated mice dying prior to having their tumors reach target size were considered to have died from drug toxicity. Statistical evaluations of data were performed using Gehan's generalized Wilcoxon test (Gehan, E A, A Generalized Wilcoxon Test for Comparing Arbitrarily Slightly-Censored Samples, Biometrika 52:203-223, 1965).

Measurement of pharmacodynamic endpoints in tumors. Tumors were harvested from untreated or drug treated mice and snap frozen in liquid nitrogen. Samples were weighed and homogenized in 10 µl of lysis buffer (50 mM Hepes, 150 mM NaCl, 0.5% triton-X-100, 8% glycerol, 2 mM Na$_3$VO$_4$, 1.5 mM MgCl$_2$, 1 mM EDTA containing one complete mini protease inhibitor tablet Sigma #S8820 per 15 ml buffer and phosphatase inhibitor cocktail Sigma #P5726) for each mg of tissue. Tissues were minced in a 100 mm petri dish with two scalpels, transferred to Falcon#2059 polypropylene round bottom tubes and macerated with a hand held homogenizer for 30 seconds. Homogenate was transferred to 1.5 ml eppendorf tubes and centrifuged at 15000×g for 2 minutes in a microfuge. Clarified supernatant was transferred to a new tube and total protein concentration was determined with the Pierce BCA protein assay (Pierce Biotechnology). Samples were analyzed by immunoblotting or on a Meso scale MSD Sector Imager 6000 multi spot assay system as recommended by the manufacturer (Meso Scale Discovery, Gaithersburg, Md.).

Figure 12A:
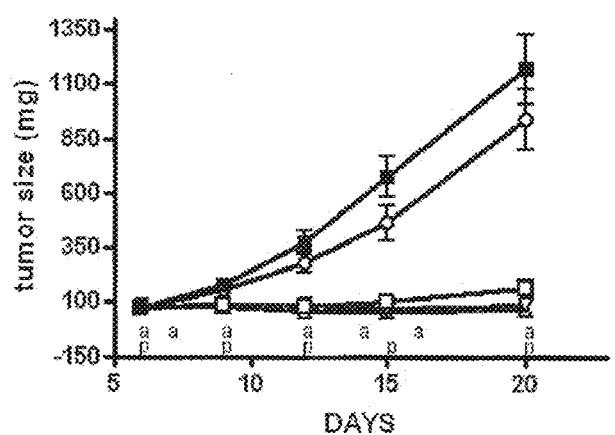
FIGS. 12A and 12B. Results of tumor xenograft studies.

The pegylated E/I binders E2-GS10-I1 and E3-GS10-I1 were tested in an H292 NSCLC in athymic mice. Tumors were implanted subcutaneously with 1 mm$^3$ H292 tumor fragments in the hind flank and allowed to establish to a size of 50-150 mg prior to initiation of treatment on Day 6 post-tumor implant. The pegylated E/I binders were administered i.p. at a dose of 100 mg/kg on a TIWX3 schedule to assess antitumor activity. Panitumumab was obtained as marketed drug and administered i.p. at its optimal dose of 1 mg/mouse and at a lower dose of 0.1 mg/mouse on a Q3DX5 schedule. Mean tumor sizes calculated from groups of 8 mice are shown in FIG. 12A. The 1 mg/mouse and 0.1 mg/mouse doses of panitumumab were both active by % TGI with values of 101% and 100%, respectively and these values were significantly different from control animals (p=0.0002, Table 5). Pegylated E2-GS10-I1 was also significantly active by % TGI with a value of 96% (p=0.0005). Pegylated E3-GS10-I1 was not active in this study with a % TGI value of 31% that was not statistically different from the control group (p=0.416). Post dosing analysis indicated that approximately two thirds of the pegylated E3-GS10-I1 was aggregated (66.64% aggregation/33.36% monomer for one batch and 72.53% aggregation/27.47% monomer for another batch) which could account for the poor activity of pegylated E3-GS10-I1 in this assay. In contrast, the pegylated E2-GS10-I1 showed only a small percentage of aggregation in post dosing studies (1.79% aggregation/98.21% monomer).

Figure 12B:
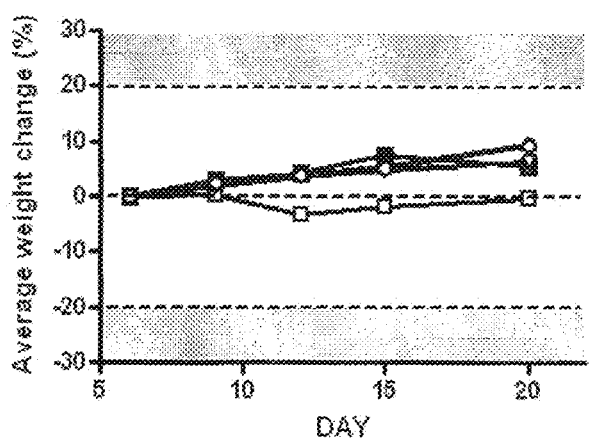

All treatments were well tolerated with no treatment related deaths or excessive weight loss over the course of the study. Clinical observations revealed no evidence of toxicity and the average weight change over the course of therapy was within acceptable limits (FIG. 12B).

TABLE 5

Results of the H292 human tumor xenograft study

| Group | Compound | Schedule, Route | Dose (mg/kg) | AVE weight change (g) | % TGI | p value for % TGI | Outcome by % TGI |
|---|---|---|---|---|---|---|---|
| 1 | Control (untreated) | — | — | 5.3 | — | 1.0 | — |
| 2 | panitumumab | q3dx5; 6 ip$^a$ | 1 mg/mse | 9.6 | 101 | 0.0002 | A |
| 3 | panitumumab | q3dx5; 6 ip$^a$ | 0.1 mg/mse | 6.3 | 100 | 0.0002 | A |
| 4 | E2-GS10-I1 (w/PEG) | TIWx3; 6 ip$^a$ | 100 | −0.1 | 94 | 0.0005 | A |
| 5 | E3-GS10-I1 (w/PEG) | TIWx3; 6 ip$^a$ | 100 | 9.5 | 28 | 0.416 | I |

$^a$Vehicle was phosphate buffered saline.
Abbreviations used are as follows: ip, intraperitoneal route; % TGI, relative % tumor growth inhibition calculated as % TGI = [(Ct − Tt)/(Ct − C0)] × 100 where Ct = median tumor weight of control mice at time t in days after tumor implant, Tt = median tumor weight of treated mice at time t, C0 = median tumor weight of control mice at time 0. % TGI value was calculated at two points as the average inhibition of Day 12 and Day 20. Outcome, a treatment regimen was considered active if it produced a statistically significant % TGI value of >50%; q3dx5; 6, compound was administered every three days for five doses starting on the sixth day after tumor implant; TIWx3; 6, compound was administered three times a week for three weeks starting on the sixth day after tumor implant. p values were calculated on Day 20 relative to the control group in a two tailed paired analysis with 8 measurements per group. Outcome by % TGI, A = active and I = inactive.

Pharmacodynamic endpoints from the H292 tumor study. Samples of tumors from untreated control, panitumumab and E/I binder treated groups were analyzed for levels of phosphorylated EGFR, ErbB2 and IGFR that would indicate target suppression. Tumors were also analyzed for levels of total EGFR to determine if EGF receptor degradation occurred. On day 20, a final treatment was administered and tumors were removed from 2 animals at 1 hour after dosing, 3 animals at 4 hours after dosing and 3 animals at 24 hours after dosing. All treatments showed marked suppression of phosphorylated EGFR and ErbB2 while the basal levels of phosphorylated IGFR were too low to discern a difference in this study (FIG. 13). All treatments showed a reduction in the amount of total EGFR indicating degradation of the receptor had occurred.

EXAMPLE 13

Selection and Characterization of MCF7 Cells Resistant to IGF1R Inhibitor

MCF7 cells (American Type Culture Collection, Cat No. HTB-22, Manassas, Va.) were cultured in RPMI medium containing 10 mM hepes and 10% FBS at 37° C. in the presence of 5% $CO_2$. The small molecule IGF1R inhibitor BMS-754807 was added to the culture medium and the concentration increased at stepwise increments over a period of 10 months until the cells exhibited continued proliferation in the presence of 200 mM BMS-754807. The resistant cells were designated MCF7r and the IC50 for BMS-754807 was 1239 nM compared to 120 nM for the parental MCF7 cells as measured in a proliferation assay carried out as previously described (Carboni et al., Cancer Res. 69: 161-170 (2009)). The drug was then removed from the culture medium and the MCF7r cells were passaged in complete medium for an additional 20 or 60 days to remove all traces of residual BMS-754807. Analysis of the MCF7r cells by immunoblotting revealed that EGFR was significantly overexpressed in the resistant cells compared to the parental MCF7 cells (FIG. 14). In addition, when MCF7 and MCF7r cells were serum starved and then stimulated with EGF for 7 minutes, phosphorylated EGFR could not be detected in the parental MCF7 cells (probably due to low levels of EGFR) but was strongly visible in MCF7r cells. In serum starved cells stimulated with IGF ligand, phosphorylated IGFR was seen in the parental MCF7 cells but despite the slightly higher levels of total IGFR present in the MCF7r cells almost no pIGFR was observed. This shows that the IGFR in the resistant MCF7r cells lost the ability to activate IGFR in response to IGF1 stimulation (FIG. 14). Activation of the MAP kinase pathway in response to EGF stimulation was stronger in the MCF7r cells as measured by pERK activation.

EXAMPLE 14

Antitumor Studies in MCF7 and MCF7r Xenografts

MCF7r cells were scaled up in T75 flasks and isolated by centrifugation. Viable cell numbers were measured by trypan blue exclusion with a Vi-CELL XR (Beckman Coulter, Fullerton, Calif.), resuspended in PBS to $5 \times 10^6$ viable cells/ml and implanted subcutaneously in the hind flank of athymic mice in a volume of 0.2 ml. For MCF7 and MCF7r tumor growth, all mice were supplemented with 0.25 mg 90 day release pellets of 17-β-estradiol (Innovative Research of America, Sarasota, Fla., Cat. No. NE-121). Tumors were propagated until they reached a median size of 500-1000 mg when they were excised and 1 $mm^3$ fragments were reimplanted in the hind flank of new athymic mice. Tumors were adapted for solid tumor growth by serial trocar passage in mice through at least four rounds of growth during which tumor volume doubling time and take rate were monitored for each passage. Growth characteristics were observed to determine if the xenografts exhibited acceptable properties to serve as a reliable, reproducible model. The MCF7r tumor type demonstrated an acceptable take rate and doubling time and therefore satisfied the criteria for use as a xenograft model. The MCF7 parental tumor model had been previously established using the same techniques. For the MCF7 parental xenograft, 1 $mm^3$ tumor fragments were implanted subcutaneously in the hind flank and allowed to establish to a size of 50-150 mg prior to initiation of treatment on Day 13 post-tumor implant. Cetuximab was obtained as marketed drug and administered i.p. at its optimal dose of 1 mg/mouse and at a lower dose of 0.1 mg/mouse on a Q3DX5 schedule (doses administered on Day 13, 16, 19, 22, 25). Mean tumor sizes calculated from groups of 8 mice are shown in FIG. 15A. In the MCF7 xenograft model, neither the 1 mg/mouse or the 0.1 mg/mouse dose of cetuximab was active by % TGI with values of −9% and 3.2%, respectively and the tumor sizes were not statistically different from the control group (Table 6).

For the MCF7r resistant xenograft, 1 $mm^3$ tumor fragments were implanted subcutaneously in the hind flank and allowed to establish to a size of 50-150 mg prior to initiation of treatment on Day 6 post-tumor implant. Cetuximab was obtained as marketed drug and administered i.p. at its optimal dose of 1 mg/mouse and at a lower dose of 0.1 mg/mouse on a Q3DX5 schedule (doses administered on Day 6, 9, 12, 15, 18). Mean tumor sizes calculated from groups of 8 mice are shown in FIG. 15B. In the MCF7r xenograft model, doses of cetuximab were active by % TGI with values of 105% and 75%, respectively. The high dose of cetuximab had a TGI value over 100% which indicates that it caused tumor regression below the starting size at the initiation of treatment. Both doses resulted in a statistically significant difference in tumor size compared to the control group (Table 7).

TABLE 6

Results of the MCF7 human breast carcinoma tumor xenograft study.

| Group | Compound | Schedule, Route | Dose (mg/mouse) | % TGI | p value for % TGI | Outcome by % TGI |
|---|---|---|---|---|---|---|
| 1 | Control (untreated) | — | — | — | 1.0 | — |
| 2 | cetuximab | q3dx5; 13 ip[a] | 1 mg/mse | −9 | 0.223 | I |
| 3 | cetuximab | q3dx5; 13 ip[a] | 0.1 mg/mse | 3.2 | 0.220 | I |

[a]Vehicle was phosphate buffered saline.
Abbreviations used are as follows: ip, intraperitoneal route; % TGI, relative % tumor growth inhibition calculated as % TGI = [(Ct − Tt)/(Ct − C0)] × 100 where Ct = median tumor weight of control mice at time t in days after tumor implant, Tt = median tumor weight of treated mice at time t, C0 = median tumor weight of control mice at time 0. % TGI value was calculated at three points as the average inhibition of Day 20, 24 and Day 27. Outcome, a treatment regimen was considered active if it produced a statistically significant % TGI value of >50%; q3dx5; 13, compound was administered every three days for six doses starting on the thirteenth day after tumor implant. p values were calculated on Day 24 relative to the control group in a two tailed paired analysis with 8 measurements per group. Outcome by % TGI, A = active and I = inactive.

TABLE 7

Results of the MCF7r human breast carcinoma tumor xenograft study.

| Group | Compound | Schedule, Route | Dose (mg/kg) | % TGI | p value for % TGI | Outcome by % TGI |
|---|---|---|---|---|---|---|
| 1 | Control (untreated) | — | — | — | 1.0 | — |
| 2 | cetuximab | q3dx5; 6 ip[a] | 1 mg/mse | 105 | 0.001 | A |
| 3 | cetuximab | q3dx5; 6 ip[a] | 0.1 mg/mse | 75 | 0.024 | A |

See footnotes to Table 6. p values were calculated on Day 19 relative to the control group in a two tailed paired analysis with 8 measurements per group.

EXAMPLE 15

Antitumor Studies in GEO Xenografts

Figure 16:
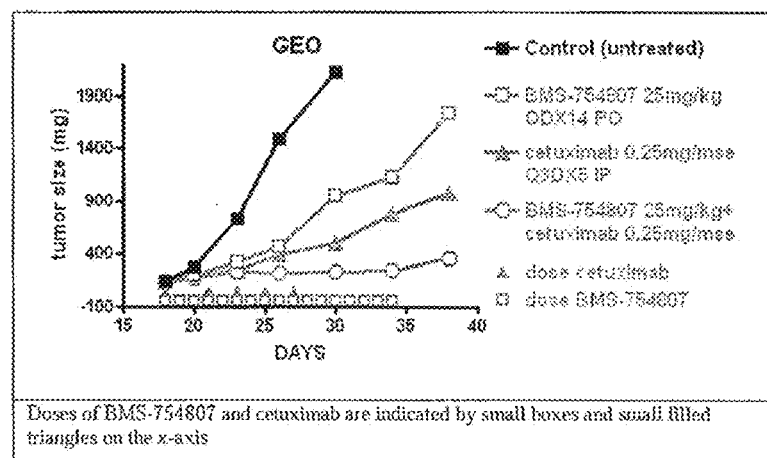
FIG. 16. GEO human tumor xenograft studies in nude mice.
Figure 17:
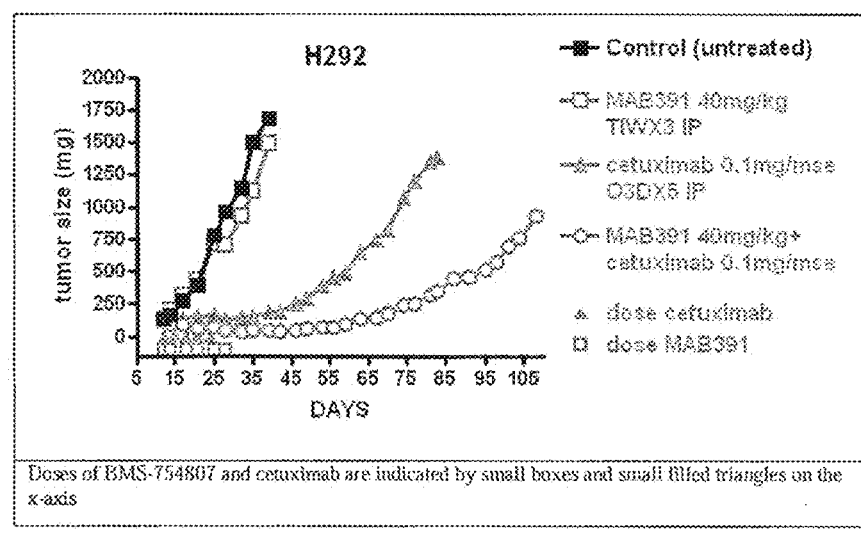
FIG. 17. H292 human tumor xenograft studies in nude mice.

GEO tumors were established by implanting 1 mm$^3$ tumor fragments subcutaneously in the hind flank of athymic mice and allowing them to reach a size of 50-150 mg prior to initiation of treatment on Day 18 post-tumor implant. Cetuximab was administered ip at 0.25 mg/mouse on a Q3DX5 schedule (doses administered on Day 18, 21, 24, 27, 30). The IGFR kinase inhibitor BMS-754807 was administered at 25 mg/kg on a QDX21 schedule. Mean tumor sizes calculated from groups of 8 mice are shown in FIG. 16. Cetuximab was active at 0.25 mg/mouse with a % TGI value of 67%. BMS-754807 was active with a % TGI of 80% and the combination of the two was considerably more active then either agent alone with a % TGI of 94% (Table 8). All treatment groups were statistically different from the control group on Day 26 (Table 8).

establish to a size of 50-150 mg prior to initiation of treatment on Day 12 post-tumor implant. Cetuximab was administered ip at 0.1 mg/mouse on a Q3DX5 schedule. MAB391 is an antibody to IGF1R (R&D Systems, Minneapolis, Minn., Cat. No. MAB391) and was administered at a dose of 40 mg/kg on a BIWX3 schedule. Mean tumor sizes calculated from groups of 8 mice are shown in FIG. 17. Cetuximab was active at 0.1 mg/mouse with a % TGI value of 95.1% and MAB391 was inactive at 40 mg/kg with a % TGI value of 10.5% (Table 9). Mice dosed with the combination of cetuximab and MAB391 exhibited a % TGI value of 109.2% indicating tumor regression in the combination group (Table 9). After dosing ceased, tumors regrew in the cetuximab treated group more rapidly than in the group treated with the combination of cetuximab and MAB391 (FIG. 17).

TABLE 8

Results of the GEO human colon carcinoma tumor xenograft study.

| | | Cetuximab | | BMS-754807 | | | | |
|---|---|---|---|---|---|---|---|---|
| Group | Schedule, Route | Dose (mg/mouse) | Schedule, Route | Dose (mg/kg) | % TGI | p value | Outcome by % TGI | Synergy |
| 1 | Control (untreated) | — | — | — | — | — | — | — |
| 2 | q3dx5; 6 ip[a] | 0.25 mg/mse | — | | 80 | | A | — |
| 3 | — | — | qdx21; 18[b] | 25 | 67 | | A | — |
| 4 | q3dx5; 6 ip[a] | 0.25 mg/mse | qdx21; 18[b] | 25 | 94 | | A | YES |

[a]Vehicle for cetuximab was phosphate buffered saline.
Vehicle for BMS-754807 was 50% polyethylene glycol 400, 50% water.
Abbreviations used are as described in Table 6 and synergy is defined as statistically significant activity that is better than either agent in the combination demonstrated on its own. Outcome by % TGI, A = active and I = inactive.

EXAMPLE 16

Antitumor Studies in H292 Xenografts

H292 cells were implanted subcutaneously in the hind flank of athymic mice as 1 mm$^3$ fragments and allowed to

TABLE 9

Results of the H292 human NSCLC tumor xenograft study.

| | | Cetuximab | | MAB391 | | | | |
|---|---|---|---|---|---|---|---|---|
| Group | Schedule, Route | Dose (mg/mouse) | Schedule, Route | Dose (mg/kg) | % TGI | p value | Outcome by % TGI | Synergy |
| 1 | Control (untreated) | — | — | — | — | — | — | — |
| 2 | q3dx5; 12 ip[a] | 0.1 mg/mse | — | | 95.1 | | A | — |

TABLE 9-continued

Results of the H292 human NSCLC tumor xenograft study.

| | Cetuximab | | MAB391 | | | | | |
|---|---|---|---|---|---|---|---|---|
| Group | Schedule, Route | Dose (mg/mouse) | Schedule, Route | Dose (mg/kg) | % TGI | p value | Outcome by % TGI | Synergy |
| 3 | — | — | BIWx3; 12[a] | 40 | 10.5 | | I | — |
| 4 | q3dx5; 12 ip[a] | 0.1 mg/mse | BIWx3; 12[a] | 40 | 109.2 | | A | YES |

[a]Vehicle for cetuximab and MAB391 was phosphate buffered saline.
Abbreviations used are as described in Table 6 and 8.

EXAMPLE 17

Colony Formation Assay

To determine the effects of test compounds on the ability to inhibit colony formation of H292 cells, 400 cells were seeded into 24-well plates (Becton-Dickinson, Franklin Lakes, N.J., Cat. No. 351143) in complete medium and allowed to adhere overnight. The next day medium was removed and replaced with medium containing 2% FBS. Test compound was diluted into medium containing 2% FBS and added to cells in serial dilutions. Cells were incubated at 37° C. for 14 days. After 14 days, media was discarded and wells rinsed once with 2 ml PBS. Cells were stained with 0.5 ml Coomassie Stain Solution (Bio-Rad, Hercules, Calif., Cat. No. 161-0436) for 20 min. The stain was aspirated and wells were washed quickly with 1× Destain Solution Coomassie R-250 (Bio-Rad, Cat. No. 161-0438). A final rinse with 1 ml water per well was carried out and plates were inverted and allowed to dry. Colonies consisting of (at least) 50 cells or larger were counted by eye under low power magnification (10×-20×). All samples were tested in triplicate and IC50 values were calculated from linear regression of the percent inhibition of control. Representative results for a PEGylated E/I binder are shown in FIG. 18 and IC50 values for various E/I $^{10}$Fn3-based binders, monospecific IGF1R $^{10}$Fn3-based binder, and EGFR antibody is shown in Table 10.

TABLE 10

IC50 values of various E/I $^{10}$Fn3-based binders, monospecific IGF1R $^{10}$Fn3-based binder, and EGFR antibody in the colony formation assay.

| SAMPLE | IC50 (nM) |
|---|---|
| E4-GS10-I1 (with Peg) | 5 |
| I1-GS10-E5 (with Peg) | 1 |
| I1-GS10-E4 | 6 |
| E2-GS10-I1 (with Peg) | 560 |
| I1 monomer (with Peg) | 15,510 |
| panitumumab | 140 |

EXAMPLE 18

Epitope Mapping Assay

An epitope mapping assay was developed utilizing commercially available antibodies where the binding site on the EGFR extracellular domain is roughly known according to various literature reports. The antibodies used in this assay are listed in Table 11 and FIG. 19A depicts how antibodies were localized to approximate binding domains on EGFR. The assay is a variation of the In Cell Western assay previously described and assesses the ability of EGFR $^{10}$Fn3-based binders preincubated with A431 or other cells expressing EGFR to block binding of the detection antibodies from the panel listed in Table 11. The assay was carried out as follows: A431 cells in log phase growth were harvested by trypsinization and seeded in a 96 well plate at 24,000 cells/well in a total volume of 100 μl/well. The next day, media was dumped and the EGFR $^{10}$Fn3-based binders diluted in cold DMEM base media were added to the plate and allowed to bind for 1 hour at 4° C. to prevent internalization of EGFR. After binding, cells were washed with 0.2 ml PBS+0.1% Tween-20 and fixed for 20 minutes in PBS+3.7% formaldehyde at room temp. Cells were blocked in 0.2 ml of Odyssey blocking buffer for 1 hour at room temp. Next, primary antibodies were diluted in 50 μl of Odyssey blocker per well and incubated for 1-2 hours at room temp. Primary antibodies were dumped by inverting the plate, and each well washed 3× with 200 μl of PBS+0.1% Tween-20. Secondary antibodies are the same ones used in the In Cell Western assay and were appropriate for the species of antibody being detected. These secondary antibodies were diluted (1:800) in Odyssey Blocker+0.2% Tween-20 and added in a volume of 50 μl per well along with TOPRO3 (Invitrogen, Carlsbad, Calif., cat#T3605) diluted at (1:3000) to counterstain cells for normalization. Cells were incubated on bench for 1 hour at room temp. Secondary antibody was dumped out and each well washed 4× with 200 μl of PBS+0.1% Tween-20 for 5 minutes at room temp. Plates were imaged on a Licor instrument at 160 μm resolution, medium quality, focus offset of 3 mm, intensity of 5. This assay was also carried out with the marketed drug antibodies cetuximab, panitumumab and nimotuzumab to determine if the EGFR$^{10}$Fn3-based binders were interfering with their binding to EGFR on A431 cells. Representative results are shown in FIG. 19B.

TABLE 11

Commercially available antibodies to the extracellular domain of EGFR.

| | Clone | SUPPLIER and cat# | SPECIES | BINDS | EPITOPE | Binding motif |
|---|---|---|---|---|---|---|
| 1 | | Abcam ab38165 | Rab | h | Peptide AA 42-58 | linear |
| 2 | E234 | Abcam ab32198 | Rab | h, mu, rat | Peptide AA 40-80 (No ICC) | linear |
| 3 | N-20 | Santa Cruz#31155 | Goat IgG | h | AA 110-160 | linear |
| 4 | ICR10 | Abcam ab231 Santa Cruz #57095 | Rat IgG2a | h(HN5) | AA 124-176[b], neutralizing[e] | conf |
| 5 | EGFR1 | Abcam ab30 Chemicon MAB88910 Labvision MS-311 | Mu IgG1 | h(A431) | AA 176-294, neutralizing[b] ab30&MAB88910@(1 mg/ml) | conf |
| 6 | 199.12 | Labvision MS-396-P | Mu IgG2a | h | AA 124-176, non-neutralizing[b] | conf |
| 7 | LA22 | Upstate 05-104 | Mu IgG2a | h(A431) | AA 351-364, neutralizing[a] | linear |
| 8 | | Abcam ab15669 | Rab | Mu, rat | Peptide AA376-394[d] | linear |
| 9 | 225 | Sigma E2156 Labvision MS-269-P | Mu IgG1 | h(A431) | AA 294-475, neutralizing[b,c] | conf |
| 10 | 528 | Abcam ab3103 Santa Cruz#120 Labvision MS-268-P | Mu IgG2a | h(A431) | AA 294-475, neutralizing[b,c] | conf |
| 11 | B1D8 | Labvision MS-666-P | Mu IgG2a | h(A431) | AA 294-475[b] | conf |
| 12 | LA1 | Upstate 05-101 | Mu IgG1 | h | neutralizing | |
| 13 | H11 | Labvision MS-316-P | Mu IgG1 | h | AA 294-475, non-neutralizing[b] | linear |
| 14 | 111.6 | Labvision MS-378-P Imgenex IMG-80179 | Mu IgG1 | h | AA 294-475, neutralizing[b] | linear |
| 15 | 29.1 | Sigma E2760 Abcam ab10414 | Mu IgG1 | h(A431) | External carbohydrate non-neutralizing | |

Abbreviations: conf: epitope conformationally specific; linear: epitope independent of conformation.
[a]JBC 264(1989)17469 Ala351-Asp364,
[b]J Immunological Methods 287(2004)147,
[c]Mol Biol Med1(1983)511,
[d]Raised against a peptide to mouse EGFR [FKGDSFTRTPPLDPRELEI (SEQ ID NO: 491)],
[e]Int J Oncol 4(1994)277.
[f][EEKKVCQGTSNKLTQLGTFEDHFLSLQRMFNNCEVVLGNLEITYVQRNYDLSFLK-TIQEVAGYVLIALNTVERIPLENLQIIRGNMYYENSYALAVLSNY (SEQ ID NO: 492)],
[g]Ile-Gln-Cys-Ala-His-Tyr-Ile-Asp-Gly-Pro-His-Cys (SEQ ID NO: 493) (amino acids 580-591).
[h]Cancer Cell 7(2005)301.

Using various approaches, we have confirmed that the EGFR monomer E3 binds to domain I of EGFR. Since other E monomers have similar properties in various experiments, it is thought that the other E monomers also bind to domain I of EGFR.

EXAMPLE 19

Properties of I Monomers

BIAcore Analysis of the Soluble Fibronectin-Based Scaffold Proteins

The kinetics of I monomers binding to the target was measured using BIAcore 2000 or 3000 biosensors (Pharmacia Biosensor). A capture assay was developed utilizing an IGF-IR-Fc fusion. A similar reagent had been described by Forbes et al. (Forbes et al. 2002, European J. Biochemistry, 269, 961-968). The extracellular domain of human IGF-IR (aa 1-932) was cloned into a mammalian expression vector containing the hinge and constant regions of human IgG1. Transient transfection of the plasmid produced a fusion protein, IGF-IR-Fc which was subsequently purified by Protein A chromatography and captured on Protein A immobilized on Biasensor CM5 chips by amine coupling. The kinetic analysis involved the capture of IGF-IR-Fc on Protein A followed by injection of the fibronectin-based scaffold protein in solution and regeneration of the Protein A surface by glycine pH 2.0. Sensorgrams were obtained at each concentration and were evaluated using a program Biaevaluation, BIA Evaluation 2.0 (BIAcore), to determine the rate constants $k_a$ ($k_{on}$) and $k_d$ ($k_{off}$) The dissociation constant, $K_D$ was calculated from the ratio of rate constants $k_{off}/k_{on}$. Typically, a concentration series (2 uM to 0 uM) of purified fibronectin-based scaffold protein was evaluated for binding to protein A captured human IGF-IR-Fc fusion protein.

For experiments determining binding to human insulin receptor, recombinant human insulin receptor (IR) and recombinant human VEGF-R2-Fc were directly coupled to a CM5 Biasensor chip by amine group linkage following standard procedures recommended by Biacore (Uppsala, Sweden). In brief, 60 ug/mL of IR diluted in acetate 4.5 was coupled/immobilized to a level of 8300 RU and 11.9 ug/mL of VEGF-R2-Fc diluted in acetate 5.0 was immobilized to a level of 9700 RU on flow cells 2 and 3. A blank reference surface was prepared on FC1. Specific binding to either IR or VEGF-R2-Fc was calculated by subtracting the binding observed to the blank reference flow cell 1. Fibronectin-based scaffold proteins were diluted to 10 uM in HBS-EP (10 mM Hepes, 150 mM NaCl, 3 mM EDTA, 0.05% Surfactant P20) and injected at 20 uL/min for 3 minutes over the flow cells at 25° C. and dissociation was observed over 10 mins.

Cell-Based Receptor Blocking Assay

The human breast adenocarcinoma MCF-7 (ATCC, Manassas, Va.) was plated in 24 well plates at a concentration of 50,000 cells per well in RPMI 1640 (Invitrogen, Carlsbad, Calif.) containing 10% fetal bovine serum (Hyclone, Logan, Utah). The following day, cells were washed in binding buffer consisting of RPMI 1640 containing 0.1% BSA (Sigma, St. Louis, Mo.), and then pre-incubated for 30 minutes on ice in 200 μL binding buffer containing IGF-IR competitor. After the pre-incubation period, 40 pM [$^{125}$I]-IGF-I (Perkin Elmer, Wellesley, Mass.), equivalent to approximately 60000 counts per minute, was added to each well and allowed to incubate for an additional three hours on ice with gentle agitation. The wells were then washed with ice cold PBS containing 0.1% BSA. Cells were lysed with 500 μL buffer consisting of 0.1% SDS+0.5 N NaOH. Radioactivity of the lysates was measured using a Wallac 1470 Gamma Counter (Perkin Elmer, Wellesley, Mass.), and the data were analyzed using SigmaPlot (Systat Software, Point Richmond, Calif.).

pIGFR Assay

Fibronectin-based scaffold proteins fused to Fc were evaluated for their ability to inhibit IGF-1R phosphorylation in Rh41 human rhabdomyosarcoma cells. A Western Blot was employed to assess the ability of the I monomer to inhibit IGF-1R phosphorylation in Rh41 human rhabdomyosarcoma cells. Cells were stimulated with IGF-I, IGF-II, insulin ligands (50 ng/ml), or no stimulation (NS) and then treated with various concentrations of the I monomer. Membranes were probed with phospho-specific antibodies.

Cellular Proliferation in Rh41 (Human Rhabdomyosarcoma and H929 Human Multiple Myeloma)

Proliferation was evaluated by incorporation of [$^3$H]-thymidine into DNA after a 72 hour exposure to reagents. Rh41 cells were plated at a density of 3500 cells/well in 96-well microtiter plates and 24 hours later they were exposed to a range of I monomer concentrations. After 72 hours incubation at 37° C., cells were pulsed with 4 μCi/ml [$^3$H]-thymidine (Amersham Pharmacia Biotech, UK) for 3 hours, trypsinized, harvested onto UniFilter-96, GF/B plates (Perkin Elmer, Boston, Mass.) and scintillation was measured on a TopCount NXT (Packard, Conn.). Results are expressed as an IC50, which is the drug concentration required to inhibit cell proliferation by 50% to that of untreated control cells Data represents the average of triplicate wells with standard deviations shown.

Results of the characterization of the I monomer are shown below in Table 12.

TABLE 12

Properties of I monomers.
IGFR

| Monomer | BIAcore KD IC50 | Neutralizes IGF Binding IC50 | Inhibition of pIGFR IC50 | Inhibition of RH41 Proliferation IC50 |
| --- | --- | --- | --- | --- |
| I1 | 0.11 nM | 8 nM | 0.2 nM | 28 nM |

EXAMPLE 20

Additional Characteristics of Monospecific and Bispecific EGFR and IGF-IR $^{10}$Fn3-Based Binders $^{10}$Fn3-based binders that bound either EGFR or IGF-IR were identified using the biochemical selection technique of mRNA display in which a protein is covalently attached to its coding nucleic acid sequences. $^{10}$Fn3-based proteins-mRNA fusion populations that bound either IGF-IR or EGFR when the receptors were presented at concentrations from 1 to 10 nM were cloned into E. coli and expressed as $^{10}$Fn3-based proteins. A subset of target binders that blocked EGFR or IGF-IR signaling and had suitable biophysical properties were identified (Table 13). These initial clones were optimized for target binding affinity and cellular potency with additional mRNA selection at increasingly lower target concentrations and selection for lower dissociation rate constants. IC$_{50}$ values obtained during the selection procedures ranged from 9 to 304 nM, illustrating the opportunity for choosing molecules from a wide range of potency values for the construction of bi-specific $^{10}$Fn3-based binders. EGFR $^{10}$Fn3-based binders were tested by In-Cell Western screening assays for the blockade of phosphorylation of EGFR and ERK, a downstream signaling molecule of EGFR activation (methods similar to Example 1). Analogous studies were performed on optimized IGF-IR binders. Optimized EGFR-binding clones (E3, E1, and E2) inhibited EGFR phosphorylation on Y1068 and downstream phosphorylation of ERK on Y204 of p42/p44 in vitro with IC$_{50}$ values ranging from 9 to 40 nM, potencies that were more than 100-fold higher than the parental EGFR clone (Table 13, methods similar to Example 1).

I1 bound to IGF-IR with a K$_D$ value of 0.11 nM and inhibited IGF-I-stimulated IGF-IR phosphorylation with an IC$_{50}$ of 0.2 nM (Table 13, methods similar to Example 6). The optimized IGF-IR and EGFR single-domain $^{10}$Fn3-based binders were >95% monomeric based on size exclusion chromatography, had melting temperatures >56° C. (Table 13, methods similar to Example 4), and exhibited minimal immunogenic potential as predicted from EpiMatrix (<7 for five out of six loops), a matrix-based algorithm for T-cell epitope mapping (De Groot A S, Moise L (2007) Prediction of immunogenicity for therapeutic proteins: state of the art. Curr Opin Drug Discovery Devel 10:332-340). The $^{10}$Fn3-based binders E1, E2, and E3 were selected for further development, and had EGFR binding constants in the range of 0.7 to 10 nM as determined from Biacore assay (Table 13, methods similar to Example 5). EGFR-binding of these $^{10}$Fn3-based binders was competitive for EGF binding to EGFR (Table 13) as measured by a displacement assay using Europium labeled EGF (methods similar to Example 10). Similarly, IGF-I binding to IGF-IR was inhibited by I1 (Table 13, methods similar to Example 19).

Biophysical Characterization of Bi-Specific $^{10}$Fn3-based binders. T$_m$ values of selected E/I $^{10}$Fn3-based binders ranged from 49-58° C. and their SEC profiles indicated the protein was >90% monomer (Table 14, methods similar to Example 4). Monospecific $^{10}$Fn3-based binders and E/I $^{10}$Fn3-based binders showed comparable binding affinities, although T$_m$ values decreased slightly when the single domain $^{10}$Fn3-based binders were linked together (Tables 13 and 14). To increase serum half life for in vivo applications, E/I $^{10}$Fn3-based binders were PEGylated with a 40 kDa branched PEG (methods similar to Example 3). PEGylation of E/I $^{10}$Fn3-based binders resulted in a 10- to 20-fold reduction of binding affinity relative to the un-PEGylated constructs due to decreased association rate constants but did not decrease T$_m$. Furthermore, PEGylation did not markedly reduce inhibition of EGFR/IGF-IR phosphorylation in cells. The PEGylated E-I orientation (wherein the EGFR binder is at the N terminus, and IGF1R is at the C terminus) exhibited slightly lower IC$_{50}$ values for the inhibition of EGFR and IGF-IR phosphorylation by ELISA compared to the I-E orientation. While minor differences in the K$_D$ values and biological activity were found between PEGylated E-I orientation, vs the I-E orientation, there were no consistent trends.

TABLE 13

Properties of Monospecific $^{10}$Fn3-based binders Relevant to the Construction of E/I $^{10}$Fn3-based binders.

| Name | $T_m$ °C. | SEC Monomer % | EGFR KD nM | IGF-IR KD nM | A431 pEGFR IC$_{50}$, nM | A431 pERK IC$_{50}$, nM | H292 pEGFR IC$_{50}$, nM | H292 pIGF-IR IC$_{50}$, nM | Competition EGFR/IGF-IR IC$_{50}$, nM |
|---|---|---|---|---|---|---|---|---|---|
| E-parent | 56 | ND | 42.5 |  | 2580 | 2370 | 1148 ± 21 | ND | 29 ± 12.73 |
| E3 | 60 | >80 | 3.4 | NA | 15 ± 8 | 11 ± 7 | 22 ± 1 | >7000 | 4.75 ± 1.77 |
| E1 | 64 | >95 | 9.92 | NA | 24 ± 7 | 13 ± 3 | 9 ± 2 | >3400 | 15.9 ± 2.97 |
| E2 | 72 | >95 | 0.7 | NA | 38 ± 15 | 40 ± 9 | 31 ± 1 | >3400 | 9.4 ± 3.68 |
| I-parent | ND | ND | NA | 1.8 | ND | ND | ND | ND | 13** |
| I1 | 61.5 | >95 | >6210 | 0.11 | NA | NA | NA | 0.2 | 8** |

ND, not done; NA, not applicable; SEC, size exclusion chromatography.
*IC$_{50}$ values for EGFR and ERK phosphorylation levles in A431 cells were determined by In-Cell Western assay (ICW). Phosphorylation levels of EGFR and IGF-IR in H292 cells were determined by Enzyme-linked immunosorbent assay (ELISA).
**Competition for IGF-IR binding. Standard deviations are from 3-6 experiments.

TABLE 14

Properties of the E/I $^{10}$Fn3-based binders.

| Name | $T_m$ °C. | EGFR $K_D$ nM | IGF-IR $K_D$ nM | H292 pEGFR IC$_{50}$, nM | H292 pIGF-IR IC$_{50}$, nM | A431 pERK IC$_{50}$, nM | A431 pEGFR IC$_{50}$, nM | EGF-EGFR Competition IC$_{50}$, nM |
|---|---|---|---|---|---|---|---|---|
| E3-GS10-I1 | 52 | 0.7 | 0.1 | 7 | 6 | 12 | 14 | 25 ± 6.5 |
| E3-GS10-I1-PEG | 52.5 | 10.4 | 0.74 | 10 | 6 | 40 | 42 | 80.5 ± 12.02 |
| E1-GS10-I1 | 48 | 3.8 | 0.8 | 30 | 1 | 51 | 36 | 51 |
| E1-GS10-I1-PEG | 49 | 57.9 | 2.4 | 123 | 4 | 295 | 297 | 396 ± 223 |
| E2-GS10-I1 | 56 | 0.5 | 0.2 | 8 | 0.1 | 20 | 19 | 2.1 ± 0.57 |
| E2-GS10-I1-PEG | 57.5 | 10.1 | 1.17 | 32 | 0.3 | 78 | 77 | 56.5 ± 24.5 |
| I1-GS10-E2-PEG | 60 | 3.6 | 0.46 | 47 | 0.8 | 118 | 97 | 128 ± 4.95 |

$T_m$ measurements are from thermal scanning flurometry. $K_D$ values are from Biacore binding assays using recombinant EGFR or IGF-IR domains adsorbed on the chip. In-Cell Western assays (ICW) were conducted to determine the ability of EI-Tandems to inhibit the phosphorylation of EGFR or ERK in A431 cells. Enzyme-linked immunosorbent assays (ELISA) were used to determine the phosphorylation of EGFR or IGF-IR in H292 cells.

EXAMPLE 21

Species Cross-Reactivity of E/I $^{10}$Fn3-based binders

Pegylated E/I $^{10}$Fn3-based binders were analyzed for their binding affinities to EGFR from mouse, rat and monkey using surface plasmon resonance (BIAcore) analysis (methods identical to Example 5). Mouse EGFR was purchased from R&D systems (Minneapolis, Minn.), rat EGFR was produced in house, and monkey EGFR was purchased from KEMP (Frederick, Md.)

As shown in Table 15, all pegylated E/I $^{10}$Fn3-based binders bound to mouse, rat and monkey EGFR with low nanomolar affinities indicating that all pegylated E/I binders are cross-reactive with human, mouse, rat and monkey EGFR.

TABLE 15

| Analyte | KD (nM) (mouse EGFR) | KD (nM) (rat EGFR) | KD (nM) (monkey EGFR) |
|---|---|---|---|
| I1-GS10-E105 (pegylated) | 2.7 | 2.9 | 4.4 |
| I1-GS10-E5 (pegylated) | 3.4 | 3.6 | 5.1 |
| I1-GS10-E4 (pegylated) | 5.5 | 3.7 | 3.9 |

TABLE 15-continued

| Analyte | KD (nM) (mouse EGFR) | KD (nM) (rat EGFR) | KD (nM) (monkey EGFR) |
|---|---|---|---|
| E4-GS10-I1 (pegylated) | 6.9 | 5.6 | 5.7 |
| E2-GS10-I1 (pegylated) | 9.6 | 9.6 | 18.0 |
| I1-GS10-E85 (pegylated) | 13.9 | 10.7 | 7.0 |

EXAMPLE 22

Characterization of Additional E/I $^{10}$Fn3-Based Binders

FIG. 43 summarizes various characteristics of additional E/I $^{10}$Fn3-based binders.

The pegylated E/I $^{10}$Fn3-based binders were tested to determine inhibition of EGF induced EGFR and ERK phosphorylation in A431, using methods as previously described in Example 1. Results demonstrated that the pegylated E/I $^{10}$Fn3-based binders inhibited EGF induced EGFR phosphorylation with IC50's ranging from 12 nM-297 nM and phosphorylation of ERK with IC50's ranging from 12 nM-295 nM (FIG. 43, columns a and b).

The ability of the pegylated E/I $^{10}$Fn3-based binders to inhibit IGFR and EGFR activity was also examined in H292 cells using methods previously described in Examples 6 and 7. Results indicated that the pegylated E/I $^{10}$Fn3-based binders inhibited IGFR activity with IC50's ranging from 0.2 nM-6 nM (FIG. 43, column d) and inhibited EGFR activity with IC50's ranging from 1.3 nM-123 nM (FIG. 43, columns c).

The pegylated E/I $^{10}$Fn3-based binders were tested to determine if they could induce degradation of EGFR and IGFR in Difi cells as shown in columns e and f of FIG. 43. Cells were treated with 1 uM of pegylated E/I $^{10}$Fn3-based binders and harvested at time points starting at 7 hrs and ending at 120 hrs and levels of EGFR and IGF1R were determine by Western blot analysis. The strength of degradation was scored as either (+) indicating the tandem degraded that receptor but the degradation was not sustained and receptor expression reappeared during the time course or (++) which indicates the tandem degraded the receptor and sustained that degradation throughout the time course. Results (FIG. 43, column e and f) demonstrated that the pegylated E/I $^{10}$Fn3-based binders displayed various patterns of EGFR and IGF1R degradation; degradation of only IGFR, degradation of both EGFR and IGFR or no degradation of either receptor. No tandem tested displayed the ability to degrade only EGFR.

The binding affinity of the pegylated E/I $^{10}$Fn3-based binders for EGFR and IGF1R was assessed by surface Plasmon resonance (BIAcore) analysis as previously described in Example 5. Results demonstrated that the pegylated E/I $^{10}$Fn3-based binders bound to EGFR with affinities ranging between 3.35 nM-57.9 nM and bound to IGF1R with affinities ranging between 0.37 nM-2.43 nM (FIG. 43, columns g and h).

The pegylated E/I $^{10}$Fn3-based binders were tested to determine their potency for blocking EGF binding to EGFR on the surface of A431 cells using methods previously described in Example 10. The pegylated E/I $^{10}$Fn3-based binders blocked EGF binding to A431 cells with IC50's ranging from 19.5 nM to 238 nM (FIG. 43, column i).

The pegylated E/I $^{10}$Fn3-based binders were assessed for their ability to inhibit colony formation of H292 cells using methods described in Example 17. As shown in FIG. 43, column j, the pegylated E/I $^{10}$Fn3-based binders inhibited colony formation with IC50 values ranging from 1 nM-560 nM and three of the four pegylated E/I $^{10}$Fn3-based binders tested were 23-140 fold more potent than the anti-EGFR monoclonal antibody panitumumab. The fourth pegylated E/I $^{10}$Fn3-based binders was 4 fold less potent than panitumuab. The pegylated I1 monomer was only marginally active in inhibiting colony formation in H292 with an IC50>15 uM and this is expected since H292 cell growth is predominantly driven by EGFR signaling and not IGF1R signaling.

Figure 20:
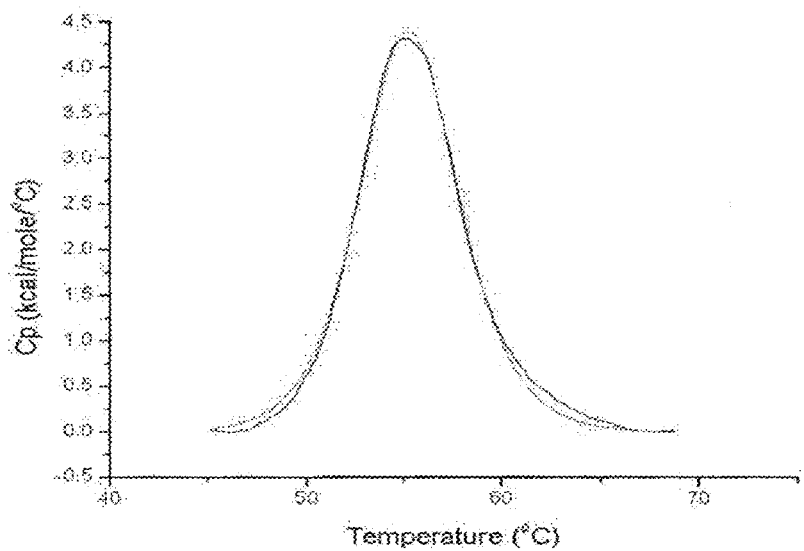
FIG. 20. DSC analysis of the E/I $^{10}$Fn3-based binder, I1-GS10-E5 pegylated, measured with a scan range of 15-95° C. at 1 mg/ml protein concentration in PBS, resulted in a Tm measurement of 55.2° C.

The melting temperature was assessed for pegylated E/I $^{10}$Fn3-based binders by DSC (as previously described in Example 4) or thermal dye melt methodology. For thermal dye melt assessment, the pegylated E/I $^{10}$Fn3-based binders were diluted to 0.2 mg/mL in 50 mM NaAc buffer pH 4.5. Each sample was spiked with 1 uL of the 200× Sypro Orange in DMSO buffer for a final concentration of 0.5% dye. Each sample was loaded into the 96 well tray and coated with 5 uL of silicone oil. The tray was spun down at 1,000 RPM and loaded onto the Bio-Rad CFX96 system and the following method was selected: 25° C. for 10 minutes+Plate Read 25° C. to 95° C. @ 0.5° C. increments for 15 minutes+Plate Read. Data analysis was performed for the inflection point with the CFX software. As shown in FIG. 43, column k, all pegylated E/I $^{10}$Fn3-based binders had similar Tm measurements, ranging from 49-62.5 degrees celsius. Tm measurements for the pegylated E/I $^{10}$Fn3-based binders were independent of concentration and remained consistent at all concentrations tested. DSC analysis of an exemplary binder, I1-GS10-E5 pegylated, measured with a scan range of 15-95° C. at 1 mg/ml protein concentration in PBS, resulted in a Tm measurement of 55.2° C. as shown in FIG. 20.

Size exclusion chromatography (SEC) was performed on the pegylated E/I $^{10}$Fn3-based binders as previously described in Example 4. SEC analysis revealed that all of the pegylated E/I $^{10}$Fn3-based binders were >95% monomeric as shown in FIG. 43 (column 1 of Table).

EXAMPLE 23

Biochemical and Biophysical Properties of E/I $^{10}$Fn3-Based Binder I1-GS10-E5 Pegylated with Selected Amino Acid Changes I1-GS10-E5 pegylated was constructed without the 6HIS tag (SEQ ID NO: 487) and also with various alterations to the linker region. In addition, a global change was made to all the constructs wherein the C-terminal tail of the first monomer had a single point change of the aspartic acid to glutamic acid (D to an E). Several clones were made with selected serine residues mutated to cysteines (S to C) to provide for alternate PEGylation sites. The effect of these changes on biochemical and biophysical properties of the molecule were compared and are summarized in Table 16. Methods for measuring inhibition of pEGFR are described in Example 7, pIGFR in Example 6, pERK in Example 1, Tm in Example 4, EGFR and IGFR KD in Example 5. Detailed analysis of the binding kinetics were also carried out on these clones and are presented in Tables 17 and 18 (using methods similar to those described in Example 5).

TABLE 16

| CLONE NAME | pEGFR IC50 (nM) | pIGFR IC50 (nM) | pERK IC50 (nM) | Tm (° C.) | EGFR KD (nM) | IGFR KD (nM) | SEC % mono |
|---|---|---|---|---|---|---|---|
| I1-GS10-E5 pegylated | 28 | 2.2 | 12 | 56 | 2.7 | 0.25 | 96 |
| I1-GS10-E5 pegylated[1] | 30 | 1.2 | 11 | 56.8 | Sticky[9] | 0.23 | 94.1 |
| I1-GSGCGS8-E5[3] | 19.8 | 1.4 | 8 | 54.8 | 4 | 0.29 | 95.2 |
| I1-GS10-E5-GSGC[4] | 28.7 | 1.2 | 19 | 55 | 1.4 | 0.25 | 92.7 |
| I1 (S62C)-GS10-E5[5] | 21 | 1.9 | 10 | 55.5 | 8.7 | 0.7 | 97.45 |
| I1-GS10-E5 (S62C)[6] | 68.4 | 2.2 | 30 | 56 | 1.7 | 0.26 | 96.12 |

TABLE 16-continued

| CLONE NAME | pEGFR IC50 (nM) | pIGFR IC50 (nM) | pERK IC50 (nM) | Tm (° C.) | EGFR KD (nM) | IGFR KD (nM) | SEC % mono |
|---|---|---|---|---|---|---|---|
| I1 (S91C)-GS10-E5[7] | 22.7 | 6.2 | 15 | 52 | 17 | 7.16 | 95.98 |
| I1-GS10-E5(S91C)[8] | 22.6 | 2.1 | 29 | 50.5 | 17.9 | 0.28 | 93.39 |

[1]No His Tag was used for this construct.
(2) a global change was made to all the alternative constructs of I1-GS10-E5 pegylated, wherein the C-terminal tail of the first monomer had a single point change of aspartic acid to glutamic acid (D to an E).
[3]The I1 monomer linked with GSGC (SEQ ID NO: 489) plus GS8 (SEQ ID NO: 494), to E5.
[4]I1 linked with GS10 to E5 with GSGC (SEQ ID NO: 489) at the tail of E5.
[5]I1 linked with GS10 to E5, wherein the I1 has a single point change of serine to cysteine at position 62.
[6]I1 linked with GS10 to E5, wherein the E5 has a single point change of serine to cysteine at position 62.
[7]I1 linked with GS10 to E5, wherein the I1 has a single point change of serine to cysteine at position 91.
[8]I1 linked with GS10 to E5, wherein the E5 has a single point change of serine to cysteine at position 91.
[9]This construct demonstrated non-specific binding to the flow cell so an accurate determination of affinity was not possible in this experiment.

TABLE 17

Biacore binding of altered I1-GS10-E5 Pegylated clones to EGFR645-Fc.

| Description | ka (1/Ms) | kd (1/s) | Kd (nm) | Δka (fold) | Δkd (fold) | ΔKd (fold) |
|---|---|---|---|---|---|---|
| I1-GS10-E5 Pegylated | 2.93 ± 0.67E+04 | 7.24 ± 3.14E−05 | 2.69 ± 1.53 | — | — | — |
| I1-GS10-E5 pegylated | 2.27E+04 | 1.49E−04 | 6.6 | 0.8 | 0.5 | 0.4 |
| I1-GS10-E5 pegylated[1] | Non-specific binding to reference cell surface at higher analyte concentrations (600 nM, 200 nM prohibited kinetic value determination) | | | | | |
| ALTERNATIVE CLONES[2] | | | | | | |
| I1-GSGCGS8-E5[3] | 2.94E+04 | 1.18E−04 | 4.0 | 1.0 | 0.6 | 0.7 |
| I1-GS10-E5-GSGC[4] | 3.34E+04 | 4.52E−05 | 1.4 | 1.1 | 1.6 | 2.0 |
| I1(S62C)-GS10-E5[5] | 2.28E+04 | 1.99E−04 | 8.7 | 0.8 | 0.4 | 0.3 |
| I1-GS10-E5(S62C)[6] | 1.78E+04 | 3.04E−05 | 1.7 | 0.6 | 2.4 | 1.6 |
| I1(S91C)-GS10-E5[7] | 1.96E+04 | 3.34E−04 | 17.0 | 0.7 | 0.2 | 0.2 |
| I1-GS10-E5(S91C)[8] | 1.08E+04 | 1.93E−04 | 17.9 | 0.4 | 0.4 | 0.2 |

[1]No His Tag was used for this construct.
[2]a global change was made to all the alternative constructs of I1-GS10-E5 pegylated, wherein the C-terminal tail of the first monomer had a single point change of aspartic acid to glutamic acid (D to an E).
[3]The I1 monomer linked with GSGC (SEQ ID NO: 489) plus GS8 (SEQ ID NO: 494), to E5.
[4]I1 linked with GS10 to E5 with GSGC (SEQ ID NO: 489) at the tail of E5.
[5]I1 linked with GS10 to E5, wherein the I1 has a single point change of serine to cysteine at position 62.
[6]I1 linked with GS10 to E5, wherein the E5 has a single point change of serine to cysteine at position 62.
[7]I1 linked with GS10 to E5, wherein the I1 has a single point change of serine to cysteine at position 91.
[8]I1 linked with GS10 to E5, wherein the E5 has a single point change of serine to cysteine at position 91.

TABLE 18

Biacore binding of altered I1-GS10-E5 Pegylated clones to IGF1R-Fc.

| Description | ka (1/Ms) | kd (1/s) | Kd (nm) | Δka (fold) | Δkd (fold) | ΔKd (fold) |
|---|---|---|---|---|---|---|
| I1-GS10-E5 pegylated | 1.04 ± 0.04E+06 | 2.62 ± 0.21E−04 | 0.25 ± 0.01 | — | — | — |
| I1-GS10-E5 pegylated | 1.10E+06 | 2.78E−04 | 0.25 | 1.1 | 0.9 | 1.0 |
| I1-GS10-E5 pegylated[1] | 1.28E+06, 1.22E+06 | 2.88E−04, 2.76E−04 | 0.22, 0.23 | 1.2 | 0.9 | 1.1 |
| ALTERNATIVE CLONES[2] | | | | | | |
| I1-GSGCGS8-E5[3] | 8.52E+05 | 2.45E−04 | 0.29 | 0.8 | 1.1 | 0.9 |
| I1-GS10-E5-GSGC[4] | 1.07E+06 | 2.65E−04 | 0.25 | 1.0 | 1.0 | 1.0 |
| I1(S62C)-GS10-E5[5] | 3.34E+05 | 2.34E−04 | 0.70 | 0.3 | 1.1 | 0.4 |
| I1-GS10-E5(S62C)[6] | 1.07E+06 | 2.79E−04 | 0.26 | 1.0 | 0.9 | 1.0 |
| I1(S91C)-GS10-E5[7] | 8.22E+04 | 5.89E−04 | 7.16 | 0.1 | 0.4 | 0.04 |
| I1-GS10-E5(S91C)[8] | 9.86E+05 | 2.81E−04 | 0.28 | 0.9 | 0.9 | 0.9 |

[1]No His Tag was used for this construct.
[2]a global change was made to all the alternative constructs of I1-GS10-E5 pegylated, wherein the C-terminal tail of the first monomer had a single point change of aspartic acid to glutamic acid (D to an E).
[3]The I1 monomer linked with GSGC (SEQ ID NO: 489) plus GS8 (SEQ ID NO: 494), to E5.
[4]I1 linked with GS10 to E5 with GSGC (SEQ ID NO: 489) at the tail of E5.
[5]I1 linked with GS10 to E5, wherein the I1 has a single point change of serine to cysteine at position 62.
[6]I1 linked with GS10 to E5, wherein the E5 has a single point change of serine to cysteine at position 62.
[7]I1 linked with GS10 to E5, wherein the I1 has a single point change of serine to cysteine at position 91.
[8]I1 linked with GS10 to E5, wherein the E5 has a single point change of serine to cysteine at position 91.

EXAMPLE 24

Inhibition of Shared Downstream Signaling Pathways of EGFR and IGFR

Figure 21:
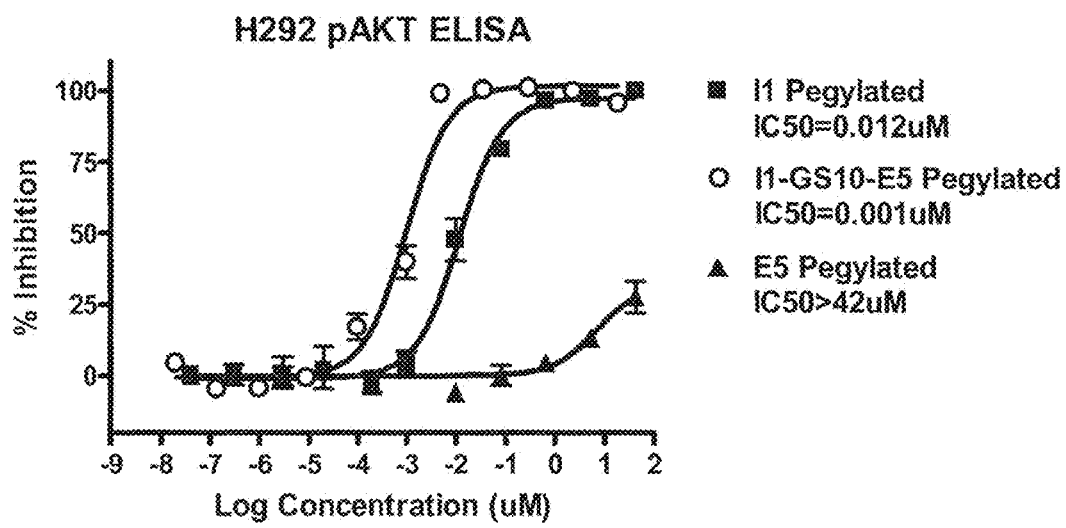
FIG. 21. Evaluation of E/I $^{10}$Fn3-based binders for inhibition of AKT phosphorylation in H292 cells as measured by ELISA. I1-GS10-E5-pegylated (○) was more potent than I1-pegylated alone (■) or E5-pegylated alone (▲) for blocking IGF1-stimulated AKT phosphorylation.

Inhibition of downstream signaling pathways were analyzed with a pAKT ELISA identical to those previously described in Example 8. Results of this study demonstrate that I1-GS10-E5 pegylated is more potent than I1 pegylated alone at blocking IGF1-stimulated AKT activation in H292 cells. E5 pegylated, the EGFR monospecific binder alone did not efficiently prevent activation of AKT by IGF1 stimulation (FIG. 21).

EXAMPLE 25

Figure 22:
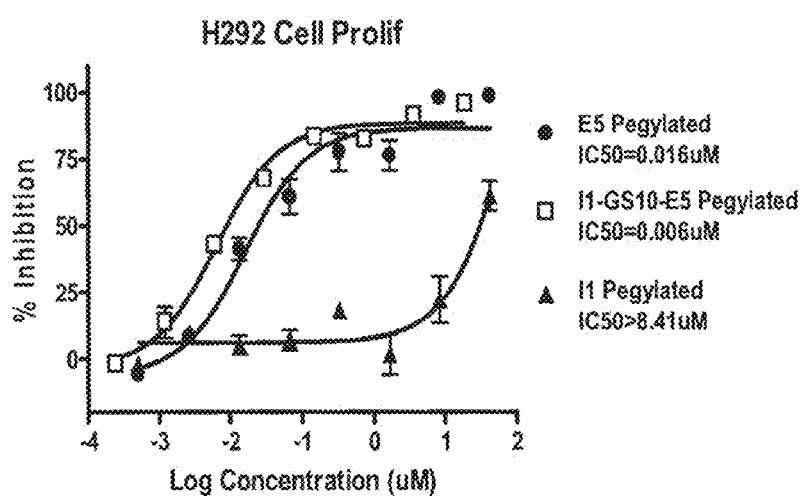
FIG. 22. Evaluation of E/I $^{10}$Fn3-based binders for inhibition of cell proliferation in H292 cells. I1-GS10-E5-pegylated (□) was more potent than I1-pegylated alone (▲) and E5-pegylated alone (●) had only weak effects for inhibiting the growth of H292 cells. Assays were carried out in triplicate. Representative data is shown.
Figure 23:
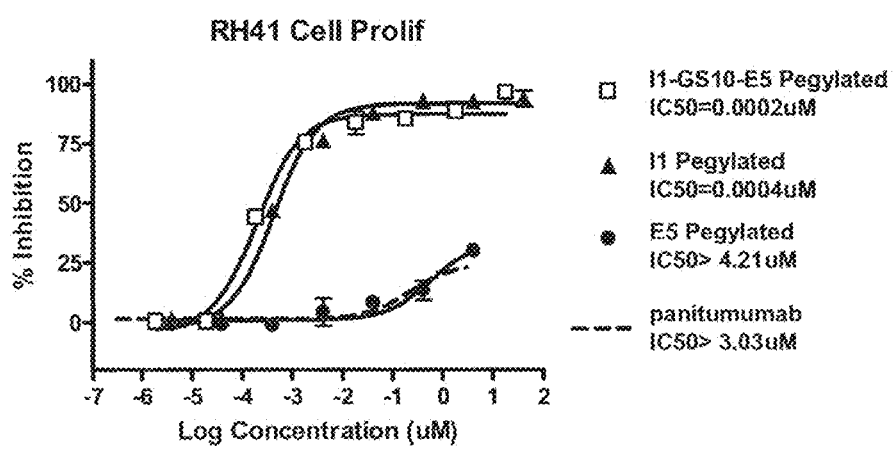
FIG. 23. Evaluation of E/I $^{10}$Fn3-based binders for inhibition of cell proliferation in RH41 cells. I1-GS10-E5-pegylated (□) was slightly more potent than I1-pegylated alone (▲) and E5-pegylated alone (●) or panitumumab (dashed line) had almost no effect for inhibiting the growth of RH41 cells. Assays were carried out in triplicate. Representative data is shown.

Inhibition of Cell Proliferation by $^{10}$Fn3-Based Binders and Comparator Antibody H292 and RH41 cell proliferation experiments were conducted as described in Example 9. The EGFR monospecific $^{10}$Fn3-based binder E5-pegylated inhibited proliferation of H292 cells with an IC50 value of 0.016 μM. The IGFR monospecific $^{10}$Fn3-based binder I1-pegylated had an IC50 value of >8.4 μM while the E/I $^{10}$Fn3-based binder I1-GS10-E5 pegylated was slightly more potent with an IC50 value of 0.006 μM (FIG. 22). The H292 cell line is of lung cancer origin and sensitive to inhibition of IGFR and EGFR ((Akashi Y, et al. (2008) Enhancement of the antitumor activity of ionising radiation by nimotuzumab, a humanised monoclonal antibody to the epidermal growth factor receptor, in non-small cell lung cancer cell lines of differing epidermal growth factor receptor status. Br. J. Cancer 98:749-755; and Buck E, et al. (2008) Feedback mechanisms promote cooperativity for small molecule inhibitors of epidermal and insulin-like growth factor receptors. Cancer Res. 68:8322-8332.)) In contrast, only the I1-GS10-E5 pegylated binder and the I1-pegylated binder inhibited the proliferation of RH41 cells (IC50 values were 0.0002 and 0.0004 μM, respectively, FIG. 23). This was expected, since RH41 is a pediatric rhabdomyosarcoma cell line that is known to be driven predominantly by IGFR signaling ((Huang F, et al. (2009). The mechanisms of differential sensitivity to an insulin-like growth factor-1 receptor inhibitor (BMS-536924) and rationale for combining with EGFR/HER2 inhibitors. Cancer Res. 69:161-170)) and thus not sensitive to EGFR blockade.

EXAMPLE 26

Inhibition of Receptor Activation and Downstream Signaling In Vitro by Pegylated and Non-Pegylated $^{10}$Fn3-Based Binders In order to understand the dynamics of EGFR/IGFR signaling and its inhibition by I1-GS10-E5 pegylated, DiFi, H292 or BxPC3 cells were serum-starved, exposed to 1 μM or 0.1 μM E5 pegylated, I1 pegylated, or I1-GS10-E5 pegylated, or vehicle control for 2 hours, then stimulated with either EGF, IGF-I, or EGF+IGF-I for 10 min. Cells were cultured in vitro, serum starved overnight and then exposed to $^{10}$Fn3-based binders for 2 hours prior to stimulation with 100 ng/ml of EGF or IGF. Cell lysates were prepared in lysis buffer (1% Triton X-100, 5% glycerol, 0.15 M NaCl, 20 mM Tris-HCl pH 7.6, Complete Protease Inhibitor Cocktail Tablets [Roche, Indianapolis, Ind.] and Phosphatase Inhibitor Cocktail 2 [Sigma-Aldrich Corp.]). Lysates (30 μg) were resolved by SDS-PAGE, transferred to membranes, and immunoblotted with antibodies to phospho-EGFR and total EGFR (Santa Cruz Biotechnology, Carlsbad, Calif.), phospho-AKT (Ser 473), phospho-p44/42 MAPK (Thr202/Tyr204) (Cell Signaling Technology, Beverly, Mass.), or total actin (Chemicon International, Temecula, Calif.) in Odyssey Blocking Buffer with 0.1% Tween 20 (LI-COR Biosciences, Lincoln, Nebr.). Membranes were incubated with the appropriate secondary antibodies. Protein visualization was performed using a LI-COR Biosciences Odyssey infrared imaging system.

As shown in FIG. 24, the basal levels of phosphorylated EGFR, IGF-IR, and AKT were nearly undetectable after serum deprivation. In DiFi cells, neither I1-GS10-E5 pegylated or E5 pegylated (monospecific EGFR binder) are able to completely suppress EGF-stimulated EGFR phosphorylation. In H292 and BxPC3 cells there is strong inhibition of EGFR phosphorylation by both I1-GS10-E5 pegylated and E5 pegylated. In DiFi and BxPC3 cells, I1-GS10-E5 pegylated blocks IGF-stimulated IGFR phosphorylation more than I1 pegylated (monospeciific IGFR binder) by itself. In H292 cells, IGF-stimulation cross activates the EGFR only when EGFR is blocked. I1-GS10-E5 pegylated inhibited EGF-stimulated pAKT in DiFi; increased pAKT in EGF-stimulated H292 and in BxPC3 EGF did not activate pAKT. In DiFi, H292 and BxPC3 cells I1-GS10-E5 pegylated inhibited IGF-stimulated pIGFR more than the individual E5 pegylated and I1 pegylated by themselves. I1-GS10-E5 pegylated had very little if any effect on EGF-stimulated pERK in DiFi, H292 or BxPC3. IGF-stimulation did not induce pERK in any cell line examined.

Figure 25:
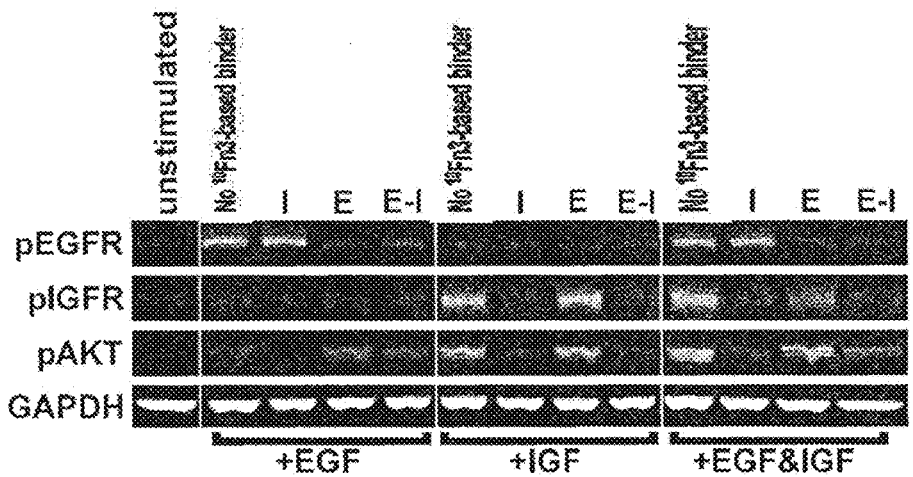
FIG. 25. Inhibition of ligand stimulated signaling in H292 cells by $^{10}$Fn3-based binders (unpegylated). Effect of E/I $^{10}$Fn3-based binder (E2-GS10-I1) on receptor activation and cell signaling in H292 cells. Cells were serum starved and treated for 2 hours with 1 μm $^{10}$Fn3-based binders before stimulation with either EGF, IGF1 or a combination of EGF+IGF1. GAPDH was probed to illustrate equal loading in all lanes FIGS. 26A and 26B. Competition binding studies with E/I $^{10}$Fn3-based binders.

In another experiment with unPEGylated_$^{10}$Fn3-based binders, H292 cells were serum-starved, exposed to 1 μM unPEGylated monospecific EGFR binder E2, IGFR binder I1, or E2-GS10-I1, or vehicle control for 1 hour, then stimulated with either EGF, IGF-I, or EGF+IGF-I for 10 min. The basal levels of phosphorylated EGFR, IGFR, and AKT were nearly undetectable after serum deprivation (FIG. 25). Stimulation with EGF induced EGFR phosphorylation, but did not transactivate IGFR. EGFR phosphorylation was blocked by the E2, and E2-GS10-I1, but not I1. Similarly, stimulation with IGF-I induced strong phosphorylation of IGFR that was blocked by I1 and E2-GS10-I1, but not by E2. EGF stimulation only slightly increased AKT phosphorylation, but IGF-I or EGF+IGF-I strongly induced phosphorylation of AKT that was suppressed to basal levels by both I1 and E2-GS10-I1. The combination of IGF-I and EGF induced AKT phosphorylation more than either growth factor alone. E2 partially reduced pAKT induced by the combination of EGF and IGF-I. However, I1 showed the most dramatic reduction in pAKT, suggesting that stimulation with EGF+IGF-I led to strong AKT phosphorylation through the IGFR pathway. Surprisingly, blockade of the EGFR pathway by E2 followed by stimulation with EGF ligand actually increased the phosphorylation of AKT, perhaps as a result of EGFR-independent activation of AKT ((Dobashi Y, et al. (2009) EGFR-dependent and independent activation of Akt/mTOR cascade in bone and soft tissue tumors. Mod Pathol (Epub Ahead of Print)). These results illustrate the complex cross-talk between the EGFR and IGFR pathways and feed-back mechanisms.

EXAMPLE 27

Competition Binding Studies with E/I $^{10}$Fn3-Based Binders

Figure 26A:
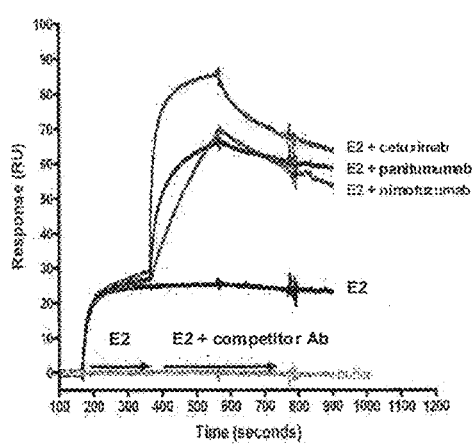
FIG. 26A. The EGFR $^{10}$Fn3-based binder does not compete for binding of EGFR antibodies to EGFR. Initial injection of the EGFR $^{10}$Fn3-based binder shows binding to EGFR on the surface of the chip. A second injection of EGFR $^{10}$Fn3-based binder mixed with an equal amount of cetuximab, panitumumab, or nimotuzumab shows no competition for binding of antibodies to EGFR by the EGFR $^{10}$Fn3-based binder.

For Biacore competition experiments, EGFR-Fc (3 μg/mL in Na-acetate pH 5.0) was immobilized on the Biacore CM5 chip surface using standard EDC/NHS amide coupling chemistry to a surface density of 300 RU. EGFR antibodies were obtained as a marketed drug and competition between monospecific EGFR binder E2 and antibodies for binding to EGFR-Fc was assessed by binding 450 nM E2 (30 µL/min, 200 s contact time), immediately followed by 450 nM E2 alone, or a mixture of 450 nM E2 plus 450 nM cetuximab, panitumumab, or nimotuzumab (30 µL/min, 200 sec contact time). The surface was successfully regenerated between cycles using two 10 sec pulses of 50 mM NaOH at a flow rate of 30 µL/min. Initial injection of E2 shows binding to EGFR on the surface of the chip. A second injection of E2 mixed with an equal amount of cetuximab, panitumumab, or nimotuzumab shows no competition for binding of antibodies to EGFR by E2 (FIG. 26A).

Figure 26B:
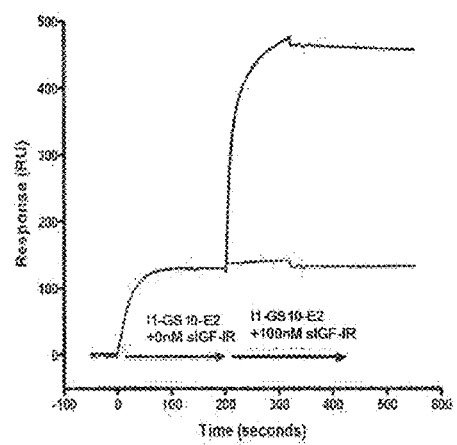
FIG. 26B. The E/I $^{10}$Fn3-based binder can bind EGFR and IGF-IR simultaneously. Initial injection of the E/I $^{10}$Fn3-based binder shows binding to EGFR immobilized on the chip surface. A second injection of the E/I $^{10}$Fn3-based binder soluble IGF-IR shows binding of sIGF-IR to other end of the immobilized E/I $^{10}$Fn3-based binder.

Surface plasmon resonance (BIAcore) analysis was utilized to demonstrate simultaneous engagement of captured EGFR-Fc and solution phase IGF1R by E/I $^{10}$Fn3-based binders. Recombinant human EGFR-Fc (aa 1-645 of the extracellular domain of human EGFR fused to human Fc) was purchased from R&D systems (Minneapolis, Minn.). Recombinant IGF1R (aa 1-932 of human IGF1R propeptide, proteolytically cleaved and disulfide linked) was purchased from R&D systems (Minneapolis, Minn.). To demonstrate simultaneous engagement, anti-human IgG was immobilized on flow cells 1 and 2 of a CM5 chip following the manufacturer's recommendations (GE Healthcare, Piscataway, N.J.). EGFR-Fc (50 nM) was captured on flow cell 2 at 10 uL/min for 2 minutes. Binding of E/I $^{10}$Fn3-based binders to EGFR-Fc was achieved by injecting $^{10}$Fn3-based protein samples (100 nM) over both flow cells at 10 uL/min for 2 minutes. Simultaneous engagement of EGFR-Fc and IGF1R was probed by subsequently injecting IGF1R (0,100 nM) over both flow cells at 30 uL/min for 2 minutes. Dissociation of the complex was monitored for 300 seconds. Two 30 second injections of 3 M MgCl$_2$ were used for regeneration of the bound complex from the anti-human IgG surface. Biacore T100 Evaluation Software, Version 2.0.1 (GE healthcare/Biacore) was utilized to overlay sensograms and remove airspikes. As shown in FIG. 26B, both domains of the E/I $^{10}$Fn3-based binder are functional and able to bind to EGFR-Fc and IGF1R simultaneously.

Binding specificity of E2-GS10-I1 pegylated to HER family receptors was assessed by Biacore as described in Example 5. HER-2-Fc, HER-3-Fc and HER-4-Fc (R&D Systems) was captured on the surface of the CM5 chip with anti-human IgG. E2-GS10-I1 pegylated did not show any discernible binding to other HER family members under conditions where robust binding was seen for EGFR-Fc (HER-1) (Table 19).

TABLE 19

Binding affinity of E2-GS10-I1 pegylated to extracellular domains of HER family of receptors.

| Name | EGFR-Fc K$_D$, nM* | HER-2-Fc K$_D$, nM | HER-3-Fc K$_D$, nM | HER-4-Fc K$_D$, nM |
|---|---|---|---|---|
| E2-GS10-I1 pegylated | 10.1 | >1000 | >1000 | >1000 |

EXAMPLE 28

Measurement of Plasma Biomarkers

Figure 27A:
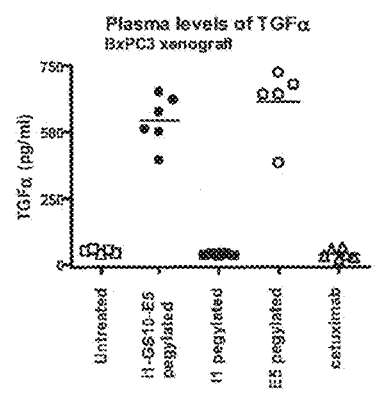
FIGS. 27A-27C. TGFα plasma levels 4 hours after last dose of xenograft studies. Plasma samples taken at the end of treatment from the BxPC3 (FIG. 27A), GEO (FIG. 27B) and H441 (FIG. 27C) xenograft studies described in Table 24 were analyzed for circulating levels of TGFα.
Figure 27B:
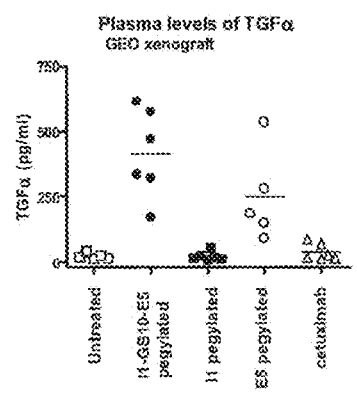
Figure 27C:
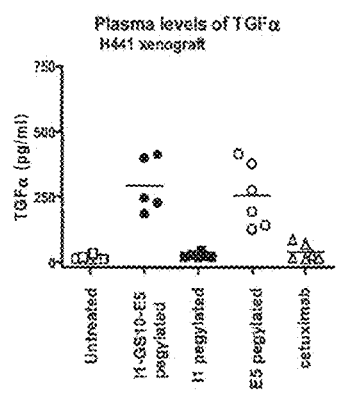
Figure 28A:
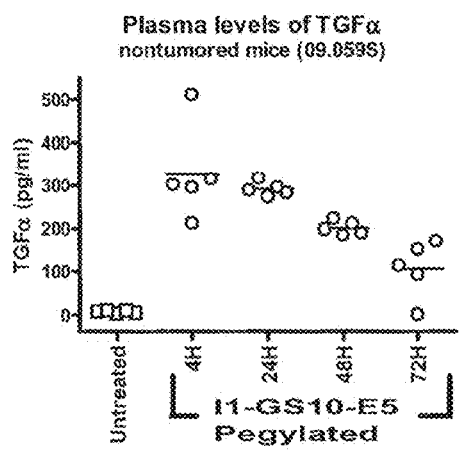
FIGS. 28A and 28B. TGFα and IGF1 plasma levels in non tumor bearing nude mice after dosing with I1-GS10-E5 pegylated. Non-tumor bearing mice were given a single dose of I1-GS10-E5 pegylated $^{10}$Fn3-based binder and analyzed for circulating levels of TGFα (FIG. 28A) and IGF1 (FIG. 28B).
Figure 28B:
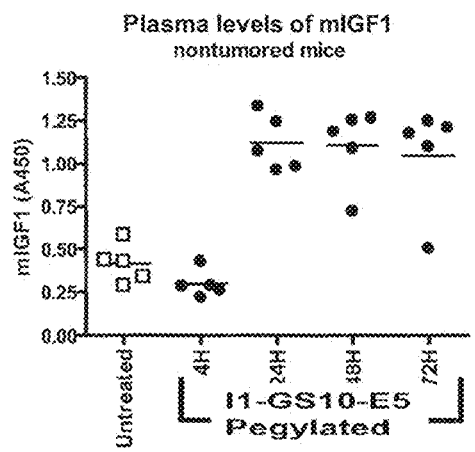

Levels of soluble biomarkers TGFα and mIGF1 were measured in mouse plasma at the end of xenograft studies or in non tumor bearing mice at various times following treatment. Blood was obtained by terminal cardiac puncture into tubes containing EDTA as an anticoagulant. Plasma was prepared by centrifuging blood at 1300×g for 10 minutes at 4 degrees C. and removing the clarified supernatant to a separate tube. TGFα levels were measured in 0.1 ml of plasma, mIGF1 levels were measured in 0.02 ml plasma with an ELISA assay as recommended by manufacturer (R&D Systems, Minneapolis, Minn.). Plasma levels of TGFα were increased in mice treated with I1-GS10-E5 pegylated or the monospecific EGFR binder E5 pegylated but not cetuximab (FIG. 27A-C). The TGFα could be secreted from the human tumor or may represent endogenous mouse TGFα. Due to the high homology between human and mouse TGFα (93% amino acid identity) the ELISA may cross react with mouse TGFα. Furthermore, human TGFα secreted by the implanted tumor can bind to the mouse EGFR. Because I1-GS10-E5 pegylated and E5 pegylated can bind both human and mouse EGFR, all host and tumor EGFR binding sites are blocked by these $^{10}$Fn3-based binders while cetuximab does not bind mouse EGFR. To determine if these $^{10}$Fn3-based binders cause increases in endogenouse mouse TGFα and if the ELISA cross reacts with mouse TGFα, non-tumor bearing nude mice were dosed with I1-GS10-E5 pegylated at 100 mg/kg and plasma samples were taken at 4, 24, 48, 72 hours post dose. Increases in mouse TGFα were in fact observed that persisted out past 72 hours (FIG. 28A). Plasma samples from non-tumored mice were also tested for mIGF1 with a mouse specific ELISA and increases in this ligand were also observed (FIG. 28B).

EXAMPLE 29

Results of In Vivo Human Tumor Xenograft Studies for Various E/I $^{10}$Fn3-Based Binders Several E/I $^{10}$Fn3-based binders were evaluated in a head-to-head H292 NSCLC study (methods described in Example 12) at a lower dose than previously used so that differences in relative activity could be ascertained. Efficacy of the E/I $^{10}$Fn3-based binders E2-GS10-I1 pegylated, E4-GS10-I1 pegylated, I1-GS10-E5 pegylated, I1-GS10-E85 pegylated, I1-GS10-E4 pegylated, I1-GS10-E105 pegylated at a single dose of 0.625 mg/mouse and panitumumab at two doses (1 mg/mouse and 0.1 mg/mouse) were compared.

Both doses of panitumumab and all E/I $^{10}$Fn3-based binders evaluated in this study were active by a tumor growth inhibition (TGI) endpoint. During the dosing phase, E4-GS10-I1 pegylated, I1-GS10-E5 pegylated, I1-GS10-E4 pegylated and panitumumab all caused tumor regression (Table 20, TGI values greater than 100%) while E2-GS10-I1 pegylated, I1-GS10-E85 pegylated and I1-GS10-E105 pegylated caused tumor growth inhibition (Table 20, TGI values up to 100%). Differences in activity were statistically significant when compared to the control group. All treatments were well tolerated with no treatment related deaths or excessive weight loss over the course of the study. Comparison of the efficacy of the E/I $^{10}$Fn3-based binders and panitumumab are presented in Table 20 below and in FIG. 29. In FIG. 29A, measurements out to day 43 shows the pattern of regrowth of the tumors after dosing ceased. FIG. 29B shows measurements out to day 27 and the y-axis is expanded to illustrate the relative differences in activity among the treatment groups.

TABLE 20

In vivo antitumor activity in the H292 NSCLC study

| Group | Compound | Schedule, Route | Dose (mg/kg) | AVE weight change (g) | % TGI | p value for % TGI | Outcome by % TGI |
|---|---|---|---|---|---|---|---|
| 1 | Control (untreated) | — | — | 3.36 | — | 1.0 | — |
| 2 | panitumumab | q3dx5; 6 ip[a] | 1 mg/mse | 5.19 | 107 | 0.0023 | A |
| 3 | panitumumab | q3dx5; 6 ip[a] | 0.1 mg/mse | 5.9 | 105 | 0.0029 | A |
| 4 | E2-GS10-I1 pegylated | TIWX3; 6 ip[a] | 0.625 mg/mse | −1.4 | 93 | 0.0067 | A |
| 5 | E4-GS10-I1 pegylated | TIWX3; 6 ip[a] | 0.625 mg/mse | −0.23 | 105 | 0.0023 | A |
| 6 | I1-GS10-E5 pegylated | TIWX3; 6 ip[a] | 0.625 mg/mse | −2.92 | 103 | 0.0033 | A |
| 7 | I1-GS10-E85 pegylated | TIWX3; 6 ip[a] | 0.625 mg/mse | 1.08 | 86 | 0.0114 | A |
| 8 | I1-GS10-E4 pegylated | TIWX3; 6 ip[a] | 0.625 mg/mse | −1.21 | 103 | 0.0034 | A |
| 9 | I1-GS10-E105 pegylated | TIWX3; 6 ip[a] | 0.625 mg/mse | −1.54 | 95 | 0.0035 | A |

[a]Vehicle was phosphate buffered saline.

Abbreviations used are as follows: ip, intraperitoneal route; % TGI, relative % tumor growth inhibition calculated as % TGI = [($C_t$ − $T_t$)/($C_t$ − $C_0$)] × 100 where $C_t$ = median tumor weight of control mice at time t in days after tumor implant, $T_t$ = median tumor weight of treated mice at time t, $C_0$ = median tumor weight of control mice at time 0. % TGI value was calculated at two points as the average inhibition of Day 20, Day 24 and Day 27. Outcome, a treatment regimen was considered active if it produced a statistically significant % TGI value of >50%; q3dx5; 6, compound was administered every three days for six doses starting on the sixth day after tumor implant; 6 on/1 off; 6, compound was administered once a day for 6 days then no treatment for 1 day and this regimen started on the sixth day after tumor implant. p values were calculated on Day 20 relative to the control group in a two tailed paired analysis with 8 measurements per group.

Further in vivo studies were carried out with selected E/I $^{10}$Fn3-based binders below, in various xenograft models using the methods described in Example 12. A description of the various xenograft models is as follows: H292 is a non-small cell lung carcinoma (NSCLC) and is described in more detail Example 12; MCF7r breast carcinoma is described in Example 14; and GEO colon carcinoma is described in Example 15. The DiFi human colon carcinoma expresses high levels of activated EGFR and also expresses IGFR; RH41 is a pediatric rhabdomyosarcoma cell line that is known to be driven predominantly by IGFR signaling (Huang F, et al. ((2009)) The mechanisms of differential sensitivity to an insulin-like growth factor-1 receptor inhibitor (BMS-536924) and rationale for combining with EGFR/HER2 inhibitors. Cancer Res. 69:161-170) and thus is not sensitive to EGFR blockade; Cal27 is a human head and neck carcinoma expressing high levels of EGFR and moderate levels of IGFR; BxPC3 is a human pancreatic carcinoma; and H441 is a NSCLC.

Figure 32:
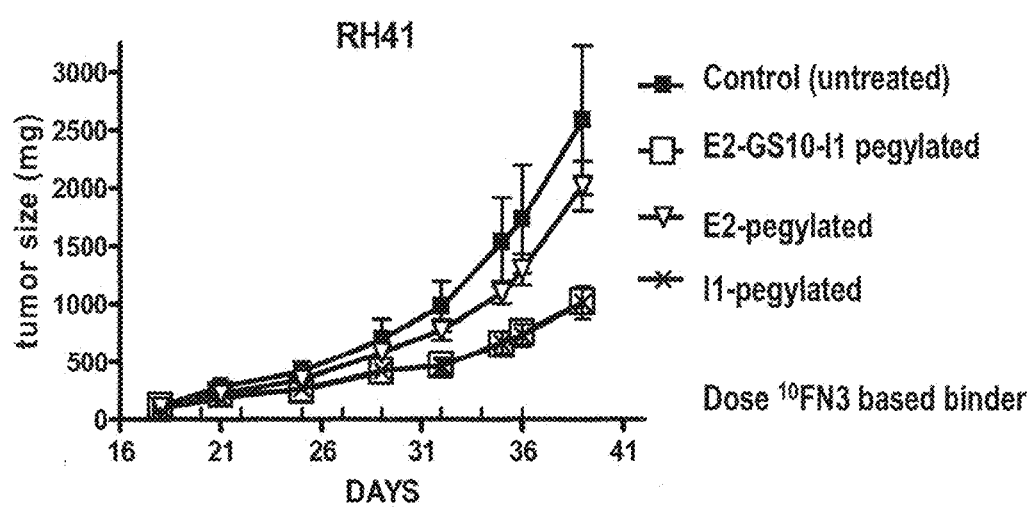
FIG. 32. Antitumor efficacy of E2-GS10-I1 pegylated in the RH41 model.
Figure 35:
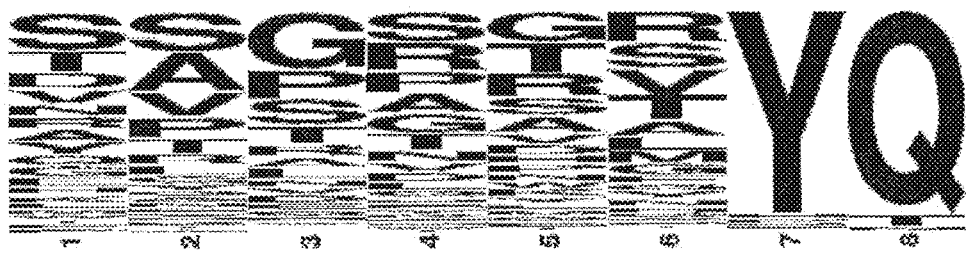
FIG. 35. BC loop Sequence Analysis I. Frequency of amino acids at each position in the BC loop from EGFR binding sequences. Image created using WebLogo (Crooks G E, Hon G, Chandonia J M, Brenner S E. WebLogo: A sequence logo generator. *Genome Research,* 14:1188-1190, 2004).
Figure 36:
FIG. 36. DE loop Sequence Analysis 1. Frequency of amino acids at each position in the DE loop from EGFR binding sequences (263 unique DE loop sequences analyzed).
Figure 37:
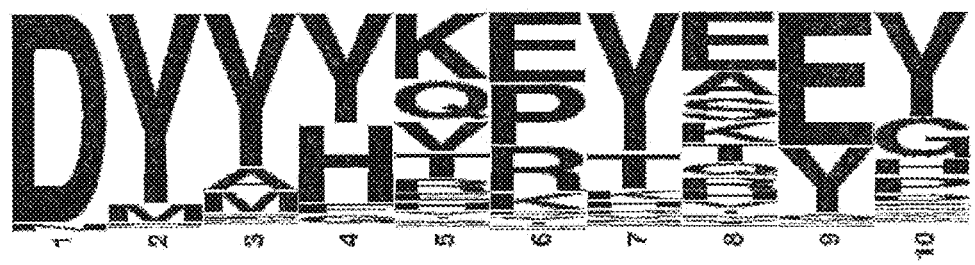
FIG. 37. FG loop (10-aa length) Sequence Analysis I. Frequency of amino acids at each position in the FG loop from EGFR binding sequences with 10-amino acid long FG loops (228 unique 10-amino acid long FG loops analyzed).
Figure 38:
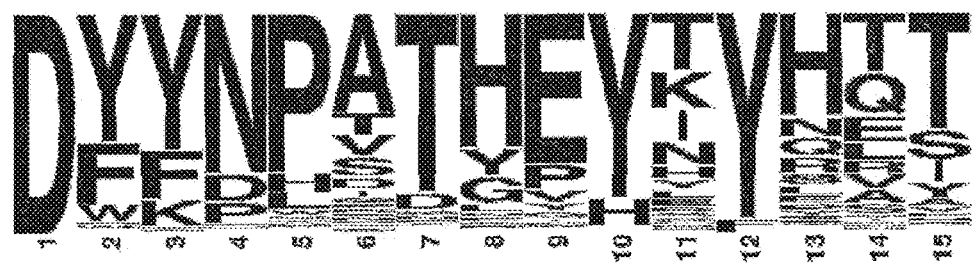
FIG. 38. FG loop (15-aa length) Sequence Analysis I. Frequency of amino acids at each position in the FG loop from EGFR binding sequences with 15-amino acid long FG loops (349 unique 15-amino acid long FG loops analyzed).
Figure 39:
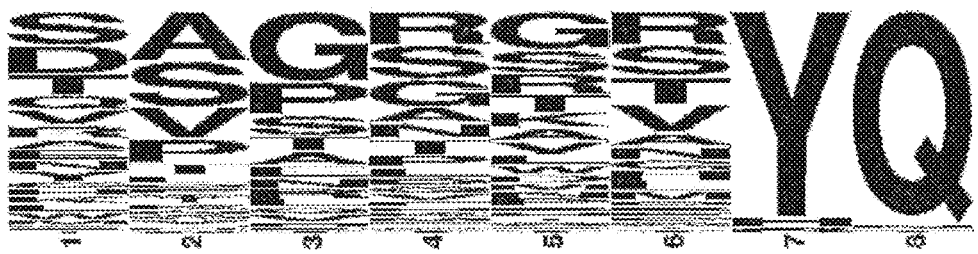
FIG. 39. BC loop Sequence Analysis II. Frequency of amino acids at each position in the BC loop from all "potent" sequences (85 unique BC loop sequences analyzed).
Figure 40:
FIG. 40. DE loop Sequence Analysis II. Frequency of amino acids at each position in the DE loop from all "potent" sequences (60 unique DE loop sequences analyzed).
Figure 41:
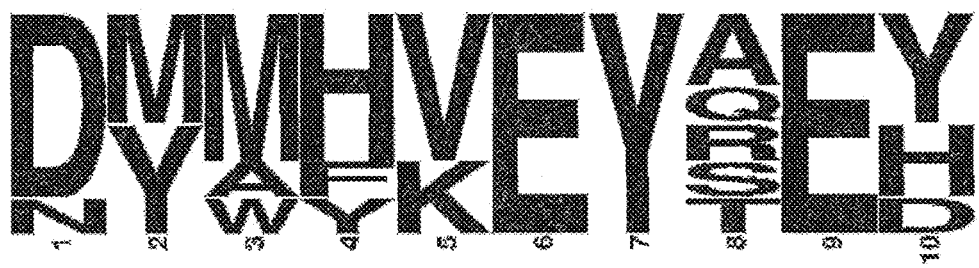
FIG. 41. FG loop (10-aa length) Sequence Analysis II. Frequency of amino acids at each position in the FG loop from all "potent" sequences with 10-amino acid long FG loops (6 unique 10-amino acid long FG loops analyzed).
Figure 42:
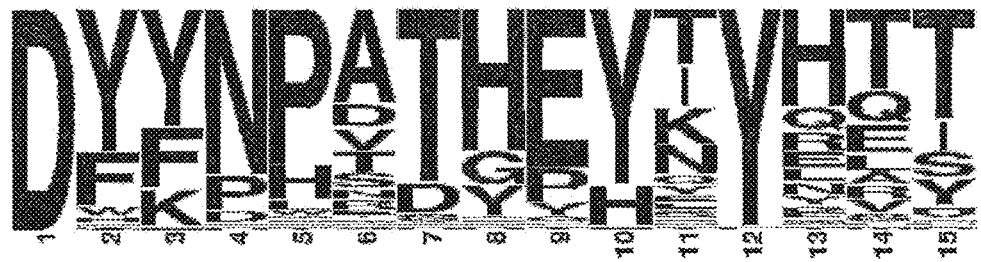
FIG. 42. FG loop (15-aa length) Sequence Analysis II. Frequency of amino acids at each position in the FG loop from all "potent" sequences with 15-amino acid long FG loops (65 unique 15-amino acid long FG loops analyzed).

Comparison of the efficacy of selected E/I $^{10}$Fn3-based binders are presented in Table 21. In these efficacy studies, all of the E/I $^{10}$Fn3-based binders showed equivalent activity to panitumumab and all treatments were able to regress H292 tumors below their starting size as indicated by % TGI values over 100%. In the DiFi study, panitumumab regressed tumors at the 1 mg/mouse dose and was active at the 0.1 mg/mouse dose while all of the E/I $^{10}$Fn3-based binders were inactive although the I1-GS10-E5 pegylated showed some inhibition of tumor growth (TGI =43.8%). In the RH41 study, panitumumab was not active at either dose, the E2-pegylated construct was not active while the E/I $^{10}$Fn3-based binders and the I1-pegylated construct were all active. FIG. 32 shows antitumor efficacy in the RH41 model for a representative construct E2-GS10-I1 pegylated (data also shown in Table 22). In the Cal27 study panitumumab regressed tumors at the 1 mg/mouse dose and was active at the 0.1 mg/mouse dose but among the E/I $^{10}$Fn3-based binders only the I1-GS10-E5 pegylated E/I $^{10}$Fn3-construct was active.

Results of human tumor xenograft studies with I1-GS10-E5 pegylated and individual I1 and E5 components designed to assess synergy are presented in Table 22. These combination (synergy) studies were structured such that the individual pieces of the E/I $^{10}$Fn3-based binders (ie., IGFR and EGFR monospecific pegylated versions) were included so antitumor effects beyond the contribution of isolated ends could be discerned. In the MCF7r study, I1 pegylated was not active while the E5 pegylated, (E5 pegylated+I1 pegylated) and the I1-GS10-E5 pegylated clones were all active and exhibited similar activity meaning that all of the antitumor activity likely comes from inhibition of EGFR and blocking the IGFR pathway did not provide any enhancement. Cetuximab regressed tumors at the 1 mg/mouse dose and was not active at the 0.1 mg/mouse dose. BMS-754807 was also not active showing that blocking the IGFR pathway with a small molecule inhibitor did not result in efficacy in this model.

In the BxPC3 study, I1 pegylated was not active while the E5 pegylated and (E5 pegylated+I1 pegylated) clones were active (TGI=61.2% and 68.8%, respectively). The I1-GS10-E5 pegylated clone was more active (TGI=78%) than the individual pieces it is made from and the difference was statistically significant by a two tailed paired t-test showing that it has synergistic activity in this model. Cetuximab was active at all doses studied but adding in IGFR inhibition by combining it with the I1-pegylated did not result in synergy.

In the GEO study, I1 pegylated was not active while the E5 pegylated and (E5 pegylated+I1 pegylated) and I1-GS10-E5 pegylated clones were active (TGI=83.5%, 92.1 and 92.1%, respectively). While there may have been some enhancement provided by combining EGFR and IGFR inhibition together in this model, the difference was not significantly better than the E5 pegylated by itself. Cetuximab was active at both doses studied but adding in IGFR inhibition by combining it with the I1-pegylated did not result in synergy.

In the H441 study, I1 pegylated and E5 pegylated were not active on their own but (E5 pegylated+I1 pegylated) was active (TGI=54.5%). The I1-GS10-E5 pegylated clone was more active (TGI=69.2%) than the individual pieces it is made from but the differences were not statistically significant showing that it provides enhanced activity but not synergy in this model. Cetuximab was active at the 1 mg/mouse dose and was not active at the 0.1 mg/mouse dose. Adding in IGFR inhibition by combining it with the I1-pegylated did not result in any enhancement in this model.

TABLE 21

In vivo results of selected E/I $^{10}$Fn3-based binders

| Group | Compound | Schedule | Dose (mg/kg)[a] | AVE weight change (g) | % TGI | p value for % TGI | Outcome by % TGI |
|---|---|---|---|---|---|---|---|
| In vivo antitumor activity in the H292 study ||||||||
| 1 | Control (untreated) | — | — | 5.7 | — | 1.0 | — |
| 2 | panitumumab | Q3dx5; 6 ip[a] | 1 mg/mse | 5.0 | 104 | 0.0006 | A |
| 3 | panitumumab | Q3dx5; 6 ip[a] | 0.1 mg/mse | 1.5 | 102 | 0.0005 | A |
| 4 | E4-GS10-I1 pegylated | TIWX3; 6 | 2 mg/mse | −4.86 | 105 | 0.0004 | A |
| 5 | I1-GS10-E5 pegylated | TIWX3; 6 | 2 mg/mse | −10.0 | 102 | 0.0006 | A |
| 6 | I1-GS10-E4 pegylated | TIWX3; 6 | 2 mg/mse | −1.41 | 105 | 0.0005 | A |
| In vivo antitumor activity in the DiFi study ||||||||
| 1 | Control (untreated) | — | — | −0.5 | — | 1.0 | — |
| 2 | panitumumab | Q3dx5; 6 ip[a] | 1 mg/mse | 5.3 | 109.7 | 0.006 | A |
| 3 | panitumumab | Q3dx5; 6 ip[a] | 0.1 mg/mse | 2.6 | 99.9 | 0.005 | A |
| 4 | E4-GS10-I1 pegylated | TIWX3; 6 | 3 mg/mse | −10.8 | −1.1 | 0.815 | I |
| 5 | I1-GS10-E5 pegylated | TIWX3; 6 | 3 mg/mse | −16.4 | 43.8 | 0.310 | I |
| 6 | I1-GS10-E4 pegylated | TIWX3; 6 | 3 mg/mse | −8.5 | 1.4 | 0.977 | I |
| In vivo antitumor activity in the RH41study ||||||||
| 1 | Control (untreated) | — | — | 7.2 | — | 1.0 | — |
| 2 | panitumumab | q3dx5; 6 ip[a] | 1 mg/mse | 10.7 | 16.5 | 0.721 | I |
| 3 | panitumumab | q3dx5; 6 ip[a] | 0.1 mg/mse | 8.6 | 38.4 | 0.563 | I |
| 4 | E4-GS10-I1 pegylated | TIWX3; 6 | 2.5 mg/mse | −5.3 | 72.7 | 0.02 | A |
| 5 | I1-GS10-E5 pegylated | TIWX3; 6 | 2.5 mg/mse | −7.8 | 68 | 0.019 | A |
| 6 | I1-GS10-E4 pegylated | TIWX3; 6 | 2.5 mg/mse | −2.9 | 64.5 | 0.018 | A |
| 7 | Control (untreated) | — | — | 12.3 | — | 1.0 | — |
| 8 | E2-GS10-I1 pegylated | TIWX3; 18 | 2.5 mg/mse | −1.8 | 58.6 | 0.044 | A |
| 9 | E2-pegylated | TIWX3; 18 | 1.25 mg/mse | 5.9 | 20.2 | 0.530 | I |
| 10 | I1 pegylated | TIWX3; 18 | 1.25 mg/mse | 7.1 | 58.6 | 0.025 | A |
| In vivo antitumor activity in the Cal27 study ||||||||
| 1 | Control (untreated) | — | — | 9.4 | — | 1.0 | — |
| 2 | Panitumumab | q3dx5; 6 ip[a] | 1 mg/mse | 6.1 | 109.8 | 0.0006 | A |
| 3 | panitumumab | q3dx5; 6 ip[a] | 0.1 mg/mse | 5.8 | 72.9 | 0.003 | A |
| 4 | E4-GS10-I1 pegylated | TIWX3; 6 | 2 mg/mse | −1.2 | −11.4 | 0.587 | I |
| 5 | I1-GS10-E5 pegylated | TIWX3; 6 | 2 mg/mse | −11.6 | 57.6 | 0.037 | A |
| 6 | I1-GS10-E4 pegylated | TIWX3; 6 | 2 mg/mse | −2.2 | −9.2 | 0.177 | I |

[a]Vehicle was phosphate buffered saline for all treatments.
Abbreviations used are as follows: ip, intraperitoneal route; po, oral route; % TGI, relative % tumor growth inhibition calculated as % TGI = [(Ct − Tt)/(Ct − C0)] × 100 where Ct = median tumor weight of control mice at time t in days after tumor implant, Tt = median tumor weight of treated mice at time t, C0 = median tumor weight of control mice at time 0. % TGI value was calculated at two points as the average inhibition on Day 19 and 23 for H292, Day 39 and 41 for DiFi, Day 34 and 37 for RH41 for groups 1-6 and Day 35, 36 and 39 for groups 7-10, Day 18 and 20 for Cal27. Outcome, a treatment regimen was considered active if it produced a statistically significant % TGI value of >50%; q3dx5; 6, compound was administered every three days for six doses starting on the sixth day after tumor implant; TIWX3; 6, compound was administered three times a week for 3 weeks and this regimen started on the sixth day after tumor implant. p values were calculated relative to the control group in a two tailed paired analysis with 8 measurements per group on Day 23 for H292, Day 39 for DiFi, Day 37 for RH41 for groups 1-6 and Day 39 for groups 7-10 and Day 20 for Cal27.

TABLE 22

Summary of in vivo experiments with $^{10}$Fn3-based binders and comparators

| Group | Compound | Schedule | Dose (mg/kg)[a] | AVE weight change (g) | % TGI | p value for % TGI | Outcome by % TGI |
|---|---|---|---|---|---|---|---|
| In vivo antitumor activity in the MCF7r study ||||||||
| 1 | Control (untreated) | — | — | 6.1 | — | 1.0 | — |
| 2 | I1 pegylated[a] | TIWX3; 7 | 50 mg/kg, ip | 17.1 | −40.8 | 0.195 | I |
| 3 | E5 pegylated[a] | TIWX3; 7 | 50 mg/kg, ip | 5.1 | 75.8 | 0.007 | A |
| 4 | E5 pegylated[a] + I1 pegylated[a] | TIWX3; 7 | 50 mg/kg, ip | −3.0 | 81.8 | <0.0001 | A |
| 5 | I1-GS10-E5 pegylated[a] | TIWX3; 7 | 100 mg/kg, ip | −4.5 | 78 | 0.009 | A |
| 6 | cetuximab[a] | Q3DX5; 7 | 1 mg/mse, ip | 11.7 | 105.4 | 0.0009 | A |
| 7 | cetuximab[a] | Q3DX5; 7 | 0.1 mg/mse, ip | 7.5 | 34.3 | 0.031 | I |
| 8 | BMS-754807[b] | QDX14; 7 | 50 mg/kg, po | −4.0 | 44.5 | 0.146 | I |
| In vivo antitumor activity in the BxPC3 study ||||||||
| 1 | Control (untreated) | — | — | 3.1 | — | 1.0 | — |
| 2 | I1 pegylated | TIWX3; 9 | 50 mg/kg, ip | 4.3 | 14.3 | 0.315 | I |
| 3 | E5 pegylated | TIWX3; 9 | 50 mg/kg, ip | −5.3 | 61.2 | 0.0003 | A |

TABLE 22-continued

Summary of in vivo experiments with $^{10}$Fn3-based binders and comparators

| Group | Compound | Schedule | Dose (mg/kg)[a] | AVE weight change (g) | % TGI | p value for % TGI | Outcome by % TGI |
|---|---|---|---|---|---|---|---|
| 4 | E5 pegylated + I1 pegylated | TIWX3; 9 | 50 mg/kg, ip | −4.9 | 68.8 | 0.0019 | A |
| 5 | I1-GS10-E5 pegylated | TIWX3; 9 | 100 mg/kg, ip | −14.0 | 78.0 | 0.0002 | A |
| 6 | cetuximab | Q3DX5; 9 | 1 mg/mse, ip | 5.2 | 62.6 | 0.0026 | A |
| 7 | cetuximab | Q3DX5; 9 | 0.25 mg/mse, ip | 2.5 | 62.8 | 0.0005 | A |
| 8 | cetuximab + I1 pegylated | Q3DX5; 9 TIWX3; 9 | 1 mg/mse, ip 50 mg/kg, ip | 3.6 | 62.1 | 0.0005 | A |
| | | In vivo antitumor activity in the GEO study | | | | | |
| 1 | Control (untreated) | — | — | 7.5 | — | 1.0 | — |
| 2 | I1 pegylated | TIWX3; 9 | 50 mg/kg, ip | −7.2 | 26.8 | 0.594 | I |
| 3 | E5 pegylated | TIWX3; 9 | 50 mg/kg, ip | 9.7 | 83.5 | 0.0028 | A |
| 4 | E5 pegylated + I1 pegylated | TIWX3; 9 | 50 mg/kg, ip | 5.4 | 92.1 | 0.0005 | A |
| 5 | I1-GS10-E5 pegylated | TIWX3; 9 | 100 mg/kg, ip | −7.3 | 92.1 | 0.0006 | A |
| 6 | cetuximab | Q3DX5; 9 | 1 mg/mse, ip | 7.7 | 91.8 | 0.0008 | A |
| 7 | cetuximab | Q3DX5; 9 | 0.25 mg/mse, ip | 7.8 | 92.0 | 0.0007 | A |
| 8 | cetuximab + I1 pegylated | Q3DX5; 9 TIWX3; 9 | 1 mg/mse, ip 50 mg/kg, ip | 7.1 | 91.3 | 0.0006 | A |
| | | In vivo antitumor activity in the H441 study | | | | | |
| 1 | Control (untreated) | — | — | 12.4 | — | 1.0 | — |
| 2 | I1 pegylated | TIWX3; 9 | 50 mg/kg, ip | 11.5 | 30.8 | 0.701 | I |
| 3 | E5 pegylated | TIWX3; 9 | 50 mg/kg, ip | −8.8 | 43.1 | 0.292 | I |
| 4 | E5 pegyalted + I1 pegylated | TIWX3; 9 | 50 mg/kg, ip | −0.8 | 54.5 | 0.011 | A |
| 5 | I1-GS10-E5 pegylated | TIWX3; 9 | 100 mg/kg, ip | −3.9 | 69.2 | 0.022 | A |
| 6 | cetuximab | Q3DX5; 9 | 1 mg/mse, ip | 12.6 | 65.2 | 0.002 | A |
| 7 | cetuximab | Q3DX5; 9 | 0.25 mg/mse, ip | 13.7 | 43.9 | 0.110 | I |
| 8 | cetuximab + I1 pegylated | Q3DX5; 9 TIWX3; 9 | 1 mg/mse, ip 50 mg/kg, ip | 10.2 | 66.7 | 0.060 | I |

[a]Vehicle was phosphate buffered saline for all treatments.
Abbreviations used are as follows: ip, intraperitoneal route; po, oral route; % TGI, relative % tumor growth inhibition calculated as % TGI = [(Ct − Tt)/(Ct − C0)] × 100 where Ct = median tumor weight of control mice at time t in days after tumor implant, Tt = median tumor weight of treated mice at time t, C0 = median tumor weight of control mice at time 0. % TGI value was calculated at two points as the average inhibition on Day 22 and 26 for MCF7r, Day 23 and 27 for BxPC3, Day 29 and 31 for GEO and Day 17 for H441. Outcome, a treatment regimen was considered active if it produced a statistically significant % TGI value of >50%; q3dx5; 6, compound was administered every three days for six doses starting on the sixth day after tumor implant; TIWX3; 6, compound was administered three times a week for 3 weeks and this regimen started on the sixth day after tumor implant. p values were calculated relative to the control group in a two tailed paired analysis with 8 measurements per group on Day 26 for MCF7r, Day 27 for BxPC3, Day 29 for GEO and Day17 for H441.

EXAMPLE 30

Pharmacokinetic Profile of Various E/I $^{10}$Fn3-Based Binders in Mice

The pharmacokinetic profiles of the pegylated E/I $^{10}$Fn3-based binder, E2-GS10-I1, were assessed in mice via intraperitoneal injection. Three nude mice per dose group were dosed with E2-GS10-I1, formulated in PBS, at 10 and 100 mg/kg, ip and plasma samples were collected in citrate phosphate dextrose solution at pre dosing, 0.5, 2, 4, 8, 12, 24, 48, 72, 96, 144, and 168 hours post dosing. Plasma samples were assessed for pegylated E2-GS10-I1 Fn3-based binder levels using a quantitative electrochemiluminescence (ECL) assay developed to detect and quantitate the pegylated E/I $^{10}$Fn3-based binder in plasma samples. In this assay, a mouse monoclonal antibody with specificity toward the EGFR binding region was adsorbed to Meso Scale Discovery plates overnight at 4° C. to allow capture of the pegylated E/I $^{10}$Fn3-based binder in the plasma samples. The plasma samples were added to the plates and incubated at 22° C. for 1 h. The captured pegylated E/I $^{10}$Fn3-based binder was detected by a rabbit polyclonal antibody specific to the scaffold region of the E/I $^{10}$Fn3-based binder, mixed with a goat anti-rabbit antibody linked with a SULFO-TAG. Following a wash to remove unbound SULFO-TAG reagent, a read buffer was added and ECL detection was used. The level of pegylated E2-GS10-I1 in plasma samples was calculated based on comparison to a 4-parameter fit of a standard curve of the pegylated E2-GS10-I1 Fn3-based binder.

Mice administered 10 or 100 mg/kg interperitoneally (ip) of pegylated E2-GS10-I1 resulted in peak levels of approximately 200 and 1700 μg/mL, respectively, indicating dose-proportional pharmacokinetics (FIG. 30). Pharmacokinetic parameters for FIG. 30 were calculated in a similar fashion to those described in the paragraph below (note that "T ½" is interchangeable with "HL_lambda_z" and AUC is interchangeable with "AUCINF_obs". The half-life of pegylated E2-GS10-I1 in mice was 15.75±1.52 h (FIG. 30). Based on these pharmacokinetic parameters, administration of 100 mg/kg three times weekly (TIW) in human tumor xenograft studies was able to maintain drug levels 10- to 100-fold higher than the in vitro IC50 value.

Figure 31:
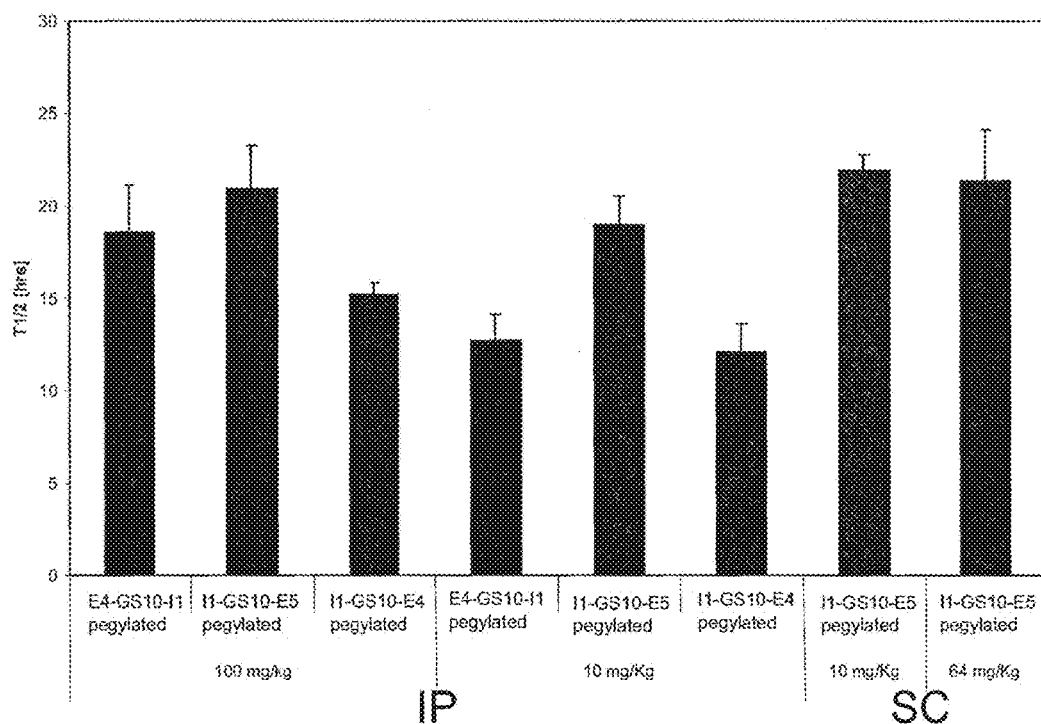
FIG. 31. Comparison of half-life at 100 mg/kg and 10 mg/kg IP, and 10 mg/kg and 64 mg/kg SC in various E/I $^{10}$Fn3-based binders.

Additional pharmacokinetic experiments were conducted on several pegylated E/I $^{10}$Fn3-based binders, where mice were administered 10 or 100 mg/kg interperitoneally (ip) and, for the pegylated I1-GS10-E5, 10 or 64 mg/kg subcutaneously (sc), plasma was collected and analyzed as described above to measure the levels of pegylated E/I $^{10}$Fn3-based binders. The pharmacokinetic parameters of these various E/I $^{10}$Fn3-based binders were obtained by non-compartmental analysis of plasma (serum) concentration vs. time data. WinNonlin software (version 5.1, Pharsight Corp. Mountain View Calif.) was used to calculate the terminal half-life (HL_lambda_z), maximum observed concentration (Cmax), the area under the curve from time zero extrapolated to infinity (AUCINF_obs), clearance (CL_F_obs), volume of distribution based on the terminal phase (Vz_F_obs) and the mean residence time extrapolated to infinity (MRTINF_obs). Results showed that the half life for the pegylated E/I $^{10}$Fn3-based binders were between 12.1-20.9 hours, as shown in FIG. 44 and FIG. 31.

EXAMPLE 31

Pharmacodynamics

Samples were taken from the H292 and the DiFi xenograft models described in Table 21 at the end of the study and processed as outlined under Measurement of pharmacodynamic endpoints in tumors in Example 12 for analysis of total levels of EGFR and IGFR protein and phosphorylated EGFR and IGFR. Target effects of I1-GS10-E5-pegylated and panitumumab were evaluated by immunoblotting as described in Example 11. In FIG. 33A, levels of total EGFR, pEGFR and total IGFR were lower in I1-GS10-E5-pegylated treated tumors than in untreated tumors at the end of the DiFi xenograft model. In FIG. 33B, levels of pEGFR were lower in tumors treated with panitumumab and I1-GS10-E5-pegylated. Levels of total EGFR were lower only in I1-GS10-E5-pegylated treated tumors but not in panitumumab treated tumors. Levels of total IGFR were lower in both I1-GS10-E5-pegylated treated tumors and in one panitumumab treated tumor but not the other. The amount of pIGFR in these models was too low to detect differences following treatment. Immunoblots were probed with GAPDH to demonstrate equal loading of protein.

EXAMPLE 32

EGFR $^{10}$Fn3-Based Binders Optimization and Consensus Sequence Analysis

The $^{10}$Fn3-based binder 679F09 (as described in PCT WO 2009/102421) (FIG. 34) was identified as a binder to EGFR ectodomain-Fc fusion protein (R&D Systems). Binding activity was selected using a bead coated with EGFR-Fc and $^{10}$Fn3-based binders coupled to their nucleic acid coding sequence (see e.g., Xu et al., Directed Evolution of High-Affinity Antibody Mimics Using MRNA Display, Chem. Biol. 9: 933-942 (2002)). More potent variants of the parental EGFR binder 679F09 having alterations to the amino acid sequences in the BC, DE and FG loops were also identified.

Sequence Analysis I: All $^{10}$Fn3-Based Binders Selected for High-Affinity Binding to EGFR In order to reveal sequence patterns that defined strong affinity for EGFR, all unique EGFR binding sequences (1044) were analyzed using several methods. First, the sequences were analyzed by the frequency of amino acids at each position in the loops (FIGS. 35-38). Only unique sequences for each loop were analyzed.

From the above sequence analysis, the following broad sequence motif was defined:
Sequence Motif #1
(a) BC loop: "YQ" in positions 7-8 (i.e., corresponding to positions 29 and 30 of SEQ ID NO: 1)
(b) DE loop: aliphatic residue ("V/I/L/M/A") in position 3 (i.e., corresponding to position 54 of SEQ ID NO: 1)
(c) FG loop: "D/N" in position 1 (i.e., corresponding to position 77 of SEQ ID NO: 1)

All 1044 sequences analyzed, except one, follow the FG loop sequence pattern (c). Of all unique sequences analyzed, 90% follow pattern (a) for the BC loop, and 95% follow pattern (b) for the DE loop. All sequences analyzed, except four, follow at least two of the three patterns above. In addition, the 15-amino acid FG loop length is a noteworthy sequence feature.

In addition to the broad Sequence Motif #1 defined above, the data in FIGS. 35-38 were used to define a second sequence motif based on the dominant residues at each position. Residues were included in this motif if the sum of the top 3 most frequent amino acids had a greater than 50% frequency.

Sequence Motif #2
(a) BC loop: XXXXXXYQ (same as Motif #1), wherein X is any amino acid
(b) DE loop: (G/Y/H)(D/M/G)(V/L/I)X, wherein X is any amino acid
(c) FG loop, 10 amino acid length: (D/N)(Y/M)(Y/A/M)(Y/H/F)(K/Q/V)(E/P/R)(Y/T/K)X(E/Y/Q)(Y/G/H), wherein X is any amino acid
(d) FG loop, 15 amino acid length: D(Y/F/W)(Y/F/K)(N/D/P)(P/H/L)(A/T/V)(T/D/S)(H/Y/G)(E/P/V)(Y/H)(T/K/I)(Y/F)(H/N/Q)(T/Q/E)(T/S/I)

The analysis methods used to define Sequence Motifs #1 and #2 evaluate each residue position within a loop separately. To reveal any sequence motifs spanning multiple residues within a loop, the $^{10}$Fn3-based binders were subjected to further analysis. In this analysis, the loop sequences were aligned using ClustalW (Thompson J D et al. CLUSTAL W: improving the sensitivity of progressive multiple sequence alignment through sequence weighting, position-specific gap penalties and weight matrix choice. *Nucleic Acids Research* 22: 4673-4680, 1994). From this alignment, families of sequences were grouped using manual inspection. For the BC and DE loops, sequence patterns similar to Sequence Motifs #1 and #2 were observed. However, additional sequence motifs could be defined for the 10 and 15 amino acid long FG loops.

Sequence Motif #3
(a) FG loop, 10 amino acid length
(1) DY(A/Y)GKPYXEY (SEQ ID NO: 473), wherein X is any amino acid
(2) DY(A/Y)Y(K/R/Q/T)PYXEY (SEQ ID NO: 474), wherein X is any amino acid
(3) (D/N)Y(A/Y)(Y/F)(K/R/Q/T)EYXE(Y/H) (SEQ ID NO: 475), wherein X is any amino acid
(4) DYY(H/Y)X(R/K)X(E/T)YX (SEQ ID NO: 476), wherein X is any amino acid
(5) DYY(H/Y)(K/H/Q)(R/K)T(E/T)Y(G/P) (SEQ ID NO: 477)
(6) (D/N)MMHV(E/D)YXEY (SEQ ID NO: 478), wherein X is any amino acid
(7) DYMHXXYXEY (SEQ ID NO: 479) (like FG loop of 679F09), wherein X is any amino acid
(8) D(M/Y)YHX(K/R)X(V/I/L/M)YG (SEQ ID NO: 480), wherein X is any amino acid
(b) FG loop, 15 amino acid length
(1) D(Y/F)(Y/F)NPXTHEYXYXXX (SEQ ID NO: 481), wherein X is any amino acid
(2) D(Y/F)(Y/F)D(P/L)X(T/S)HXYXYXXX (SEQ ID NO: 482), wherein X is any amino acid
(3) D(Y/F)(K/R)PHXDGPH(T/I)YXE(S/Y) (SEQ ID NO: 483), wherein X is any amino acid Sequence Analysis II: $^{10}$Fn3-Based Binders Showing More Potent Inhibition of EGFR Phosphorylation Another overall sequence analysis was performed on the subset of $^{10}$Fn3-based binders that showed the most potent activity in a cell-based assay (as opposed to Sequence Analysis I, which was performed on all binders selected for high-affinity binding to EGFR through Profusion). Because many of the binders were only run through single-point cell-based assays, binders that showed greater than 75% inhibition of EGFR phosphorylation at a fixed concentration of 100 nM were included in this analysis. The percent inhibition at a given concentration is related to the IC50 by: % inhibition=100× concentration/(concentration+IC50).

Normally, an IC50 is calculated by fitting the data for % inhibition at various concentrations. However, given that only a single data point is available for each binder, it is inappropriate to use this single data point to calculate an IC50. Therefore, the percent inhibition of EGFR signaling at a single concentration point was used as an approximation of the potency of the binder. Although a binder may show 75% inhibition at a concentration of 100 nM, increasing the concentration will allow the clone to show 100% inhibition at a higher concentration. The % inhibition is inversely related to the IC50; i.e., the higher the % inhibition, the lower the IC50 and the more potent the binder. If a binder showed 75% inhibition at a concentration of 100 nM, we considered this to be a "potent" binder for the purposes of Sequence Analysis II. However, the binders which showed less than 75% inhibition at 100 nM concentration for the most part still bind to EGFR and still have an effect on EGFR signaling. For instance, the anti-EGFR monoclonal antibody Nimotuzumab (Friedlander E et al. ErbB-directed immunotherapy: antibodies in current practice and promising new agents. *Immunol Lett* 116: 126-140, 2008) is currently under development as a therapeutic, but it shows <5% inhibition at a 100 nM concentration in the EGFR phosphorylation assay (data not shown). The sequences of all "potent" binders assayed and their % inhibition of EGFR phosphorylation at 100 nM concentration is shown in FIG. 45.

The total number of unique $^{10}$Fn3-based binders that showed >75% inhibition at 100 nM concentration was 111. As before, the sequences first were analyzed by the frequency of amino acids at each position in the loops (FIGS. 39-42). Since these binders are a subset of all the binders selected for high affinity binding to EGFR during Profusion, they also follow Sequence Motif #1 (see above). All "potent" sequences analyzed follow the FG loop sequence pattern ("D/N" in position 1). Of all unique "potent" sequences analyzed, 93% follow the pattern for the BC loop ("YQ" in positions 7-8), and 98% follow the pattern for the DE loop (aliphatic residue ("V/I/L/M/A") in position 3). All "potent" sequences analyzed follow at least two of the three patterns of Sequence Motif #1.

Of note, the 15-amino acid FG loop length also appears to be highly represented in the most "potent" binders. While 15-amino acid long FG loops represent only 55% of all binders selected for high affinity binding to EGFR (Sequence Analysis I), 15-amino acid FG loops represent 86% of the binders with >50% inhibition of EGFR phosphorylation at 100 nM concentration, and 91% of the binders with >75% inhibition ("potent" binders in Sequence Analysis II). Therefore, the longer 15-amino acid FG loop appears to be a sequence pattern associated with greater potency.

Of the 111 "potent" sequences analyzed, only 10 contain 10-amino acid long FG loops, and 6 of those are unique. Therefore, a single sequence motif can encompass every "potent" 10-amino acid FG loop sequence. Sequence Motif #4 was defined based on these 6 sequences.

Sequence Motif #4

FG loop, 10-amino acid length, "potent" binders (D/N)(M/Y)(M/A/W)(H/F/Y)(V/K)EY(A/Q/R/S/T)E(Y/H/D)

The sequence analysis of the "potent" binders with 15-amino acid FG loops also further illuminated which residue positions were most conserved, allowing Sequence Motif #5 to be defined. An "X" in this sequence motif denotes positions where there are no three dominant amino acids.

Sequence Motif #5

FG loop, 15-amino acid length, "potent" binders D(Y/F/W)(Y/F/K)(N/P/D)(P/H/L)X(T/D/S)(H/G/Y)(E/P/Y)(Y/H)XYXXX, wherein X is any amino acid All of the EGFR binders that were analyzed are progeny of the parent 679F09 and constitute a sequence "family," i.e. they are all related in sequence according to the aforementioned sequence motifs. Various members of the 679F09 family of binders can tolerate a T51I scaffold mutation and retain binding activity. Therefore, a T51I scaffold mutation could be combined with any of the aforementioned sequence motifs to also yield a binder with high affinity binding to EGFR.

Finally, it should be noted that amino acids with similar properties can often be substituted into protein sequences with little or no effect on structure or function. This indeed is the case for $^{10}$Fn3-based binders as well, where conservative amino acid substitutions in either the loop or scaffold regions can still lead to binders which bind to EGFR. For instance, substituting "Y" for "H" in the second position of the FG loop of binder E98 yields binder E99, and both binders show similar potency in inhibiting EGFR phosphorylation (FIG. 45).

We Claim:

1. A method for treating a cancer associated with epidermal growth factor receptor (EGFR) signaling in a subject comprising administering to a subject in need thereof a therapeutically effective amount of an antibody-like protein comprising a tenth fibronectin type III domain ($^{10}$Fn3) that binds EGFR with a $K_D$ of less than 500 nM, wherein the EGFR binding $^{10}$Fn3 comprises a BC loop having the amino acid sequence $X_g$WAPVDRYQX$_h$ (SEQ ID NO: 137), a DE loop having the amino acid sequence $X_i$RDVYX$_j$ (SEQ ID NO: 138), and an FG loop having the amino acid sequence $X_k$DYKPHADGPHTYHESX$_l$ (SEQ ID NO: 139); and
   wherein X is any amino acid and a, b, c, d, e, f, g, h, i, j, k, and l are integers independently selected from 0 to 5.

2. The method of claim 1, wherein the EGFR binding $^{10}$Fn3 comprises a BC loop having the amino acid sequence SWWAPVDRYQ (SEQ ID NO: 115), a DE loop having the amino acid sequence PRDVYT (SEQ ID NO: 116), and an FG loop having the amino acid sequence TDYKPHADGPHTYHESP (SEQ ID NO: 117).

3. The method of claim 1, wherein the antibody-like protein further comprises a second tenth fibronectin type III domain ($^{10}$Fn3).

4. The method of claim 3, wherein the second $^{10}$Fn3 is covalently linked to the EGFR binding $^{10}$Fn3 via a polypeptide linker or a polyethylene glycol moiety.

5. The method of claim 3, wherein the second $^{10}$Fn3 binds to IGF-IR.

6. The method of claim 5, wherein the IGF-IR binding $^{10}$Fn3 comprises a BC loop having the amino acid sequence $X_a$SARLKVAX$_b$ (SEQ ID NO: 46), a DE loop having the amino acid sequence $X_c$KNVYX$_d$ (SEQ ID NO: 48), and an FG loop having the amino acid sequence $X_e$RFRDYQX$_f$ (SEQ ID NO: 50).

7. The method of claim 6, wherein the IGF-IR binding $^{10}$Fn3 comprises a BC loop having the amino acid sequence SWSARLKVAR (SEQ ID NO: 45), a DE loop having the amino acid sequence PKNVYT (SEQ ID NO: 47), and an FG loop having the amino acid sequence TRFRDYQP (SEQ ID NO: 49).

8. The method of claim 1, wherein the antibody-like protein further comprises one or more pharmacokinetic (PK) moieties.

9. The method of claim 1, wherein the cancer is selected from the group consisting of: brain cancer, urogenital tract cancer, lymphatic cancer, stomach cancer, laryngeal cancer, monocytic leukemia, lung adenocarcinoma, small-cell lung carcinoma, pancreatic cancer, glioblastoma, squamous cell carcinoma, bladder cancer, liver cancer, kidney cancer, colorectal cancer, breast cancer, head cancer, neck cancer, oesophageal cancer, gynecological cancer, thyroid cancer, lymphoma, chronic leukemia, and acute leukemia.

10. The method of claim 1, further comprising administering one or more additional therapeutic agents.

11. The method of claim 10, wherein the one or more additional therapeutic agents is a cancer therapeutic agent.

12. A method of treating a cancer associated with epidermal growth factor receptor (EGFR) and/or insulin-like growth factor 1 receptor (IGF-1R) signaling in a subject comprising administering to a subject in need thereof a therapeutically effective amount of an antibody-like protein comprising:
   (a) a tenth fibronectin type III domain ($^{10}$Fn3) that binds EGFR with a $K_D$ of less than 500 nM, wherein the EGFR binding $^{10}$Fn3 comprises a BC loop having the amino acid sequence $X_g$WAPVDRYQX$_h$ (SEQ ID NO: 137), a DE loop having the amino acid sequence $X_i$RDVYX$_j$ (SEQ ID NO: 138), and an FG loop having the amino acid sequence $X_k$DYKPHADGPHTYHESX$_l$ (SEQ ID NO: 139), and
   (b) a $^{10}$Fn3 that binds IGF-1R comprising a BC loop having the amino acid sequence $X_a$SARLKVAX$_b$ (SEQ ID NO: 46), a DE loop having the amino acid sequence $X_c$KNVYX$_d$ (SEQ ID NO: 48), and an FG loop having the amino acid sequence $X_e$RFRDYQX$_f$ (SEQ ID NO: 50),
   wherein X is any amino acid and a, b, c, d, e, f, g, h, i, j, k, and l are integers independently selected from 0 to 5.

13. The method of claim 12, wherein the IGF-IR binding $^{10}$Fn3 comprises a BC loop having the amino acid sequence SWSARLKVAR (SEQ ID NO: 45), a DE loop having the amino acid sequence PKNVYT (SEQ ID NO: 47), and an FG loop having the amino acid sequence TRFRDYQP (SEQ ID NO: 49).

14. The method of claim 13, wherein the EGFR binding $^{10}$Fn3 has an amino acid sequence at least 90% identical to SEQ ID NO: 112, and the IGF-IR binding $^{10}$Fn3 has an amino acid sequence at least 90% identical to SEQ ID NO: 3.

15. The method of claim 14, wherein the EGFR binding $^{10}$Fn3 comprises the amino acid sequence set forth in SEQ ID NO: 112 and the IGF-IR binding $^{10}$Fn3 comprises the amino acid sequence set forth in SEQ ID NO: 3.

16. The method of claim 13, wherein the antibody-like protein comprises an amino acid sequence at least 90% identical to any one of SEQ ID NOs: 126-132.

17. The method of claim 16, wherein the antibody-like protein comprises an amino acid sequence at least 90% identical to SEQ ID NO: 130.

18. The method of claim 17, wherein the antibody-like protein comprises the amino acid sequence of SEQ ID NO: 130.

19. The method of claim 12, wherein the antibody-like protein further comprises one or more pharmacokinetic (PK) moieties.

20. The method of claim 12, further comprising administering one or more additional therapeutic agents.

* * * * *

SEQUENCE LISTING

<160> NUMBER OF SEQ ID NOS: 495

<210> SEQ ID NO 1
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

```
Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr
                85                  90
```

<210> SEQ ID NO 2
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Ser Gly Glu
 65                  70                  75                  80

Ser Pro Ala Ser Ser Lys Pro Ile Ser Ile Asn Tyr Arg Thr
                85                  90
```

<210> SEQ ID NO 3
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Val Ser Asp Val Pro Arg Asp Leu Glu Val Val Ala Ala Thr Pro Thr
 1               5                  10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
            35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Arg Phe Arg Asp
 65                  70                  75                  80

Tyr Gln Pro Ile Ser Ile Asn Tyr Arg Thr
                85                  90
```

<210> SEQ ID NO 4
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 4

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Pro Ser Gln His His His His His
            100                 105

<210> SEQ ID NO 5
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Val Ser Asp Val Pro Arg Asp Leu Glu Val Val Ala Ala Thr Pro Thr
1               5                   10                  15

Ser Leu Leu Ile Ser Trp Asp Ser Gly Arg Gly Ser Tyr Gln Tyr Tyr
            20                  25                  30

Arg Ile Thr Tyr Gly Glu Thr Gly Gly Asn Ser Pro Val Gln Glu Phe
        35                  40                  45

Thr Val Pro Gly Pro Val His Thr Ala Thr Ile Ser Gly Leu Lys Pro
    50                  55                  60

Gly Val Asp Tyr Thr Ile Thr Val Tyr Ala Val Thr Asp His Lys Pro
65                  70                  75                  80

His Ala Asp Gly Pro His Thr Tyr His Glu Ser Pro Ile Ser Ile Asn
                85                  90                  95

Tyr Arg Thr

<210> SEQ ID NO 6
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Pro Val His Thr Ala Thr Ile Ser Gly Leu
    50                  55                  60

Lys Pro Gly Val Asp Tyr Thr Ile Thr Val Tyr Ala Val Thr Asp His
65                  70                  75                  80
```

```
Lys Pro His Ala Asp Gly Pro His Thr Tyr His Glu Ser Pro Ile Ser
                85                  90                  95

Ile Asn Tyr Arg Thr Glu Ile Asp Lys Pro Ser Gln His His His His
            100                 105                 110

His His
```

<210> SEQ ID NO 7
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Val Ser Asp Val Pro Arg Asp Leu Glu Val Val Ala Ala Thr Pro Thr
1               5                   10                  15

Ser Leu Leu Ile Ser Trp Val Ala Gly Ala Glu Asp Tyr Gln Tyr Tyr
            20                  25                  30

Arg Ile Thr Tyr Gly Glu Thr Gly Gly Asn Ser Pro Val Gln Glu Phe
        35                  40                  45

Thr Val Pro His Asp Leu Val Thr Ala Thr Ile Ser Gly Leu Lys Pro
    50                  55                  60

Gly Val Asp Tyr Thr Ile Thr Val Tyr Ala Val Thr Asp Met Met His
65                  70                  75                  80

Val Glu Tyr Thr Glu His Pro Ile Ser Ile Asn Tyr Arg Thr
                85                  90
```

<210> SEQ ID NO 8
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Gly Val Ser Asp Val Pro Arg Asp Leu Glu Val Val Ala Ala Thr
1               5                   10                  15

Pro Thr Ser Leu Leu Ile Ser Trp Val Ala Gly Ala Glu Asp Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro His Asp Leu Val Thr Ala Thr Ile Ser Gly Leu
    50                  55                  60

Lys Pro Gly Val Asp Tyr Thr Ile Thr Val Tyr Ala Val Thr Asp Met
65                  70                  75                  80

Met His Val Glu Tyr Thr Glu His Pro Ile Ser Ile Asn Tyr Arg Thr
                85                  90                  95

Glu Ile Asp Lys Pro Ser Gln His His His His His
            100                 105
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 9

Glu Ile Asp Lys Pro Ser Gln
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Ile Asp Lys Pro Cys Gln
1               5

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Gly Ser Gly Ser Gly Ser Gly Ser Gly Ser Gly Ser Gly Ser
1               5                   10                  15

Gly Ser Gly Ser
            20

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Ser Thr Ser Thr Ser Thr
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ser Gly Ser Gly Ser Gly Ser Gly Ser
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Gly Ser Gly Gly Gly Ser Gly Gly Gly Gly Ser
1               5                   10                  15
```

-continued

```
<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Gly Ser Gly Gly Gly Ser Gly Gly Gly Gly Ser Gly
1               5                   10                  15

Gly Gly Gly Ser
            20

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser Gly Gly Gly Ser Gly Gly Gly Ser Gly
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Pro Gly Pro Gly Pro Gly
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Pro Gly Pro Gly Pro Gly Pro Gly Pro Gly
1               5                   10

<210> SEQ ID NO 20
<211> LENGTH: 213
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 20

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Arg Phe Arg Asp
65                  70                  75                  80

Tyr Gln Pro Ile Ser Ile Asn Tyr Arg Thr Glu Ile Asp Lys Gly Ser
                85                  90                  95

Gly Ser Gly Ser Gly Ser Gly Ser Gly Ser Gly Ser Gly Ser Gly Ser
            100                 105                 110

Gly Ser Val Ser Asp Val Pro Arg Asp Leu Glu Val Val Ala Ala Thr
        115                 120                 125

Pro Thr Ser Leu Leu Ile Ser Trp Asp Ser Gly Arg Gly Ser Tyr Gln
    130                 135                 140

Tyr Tyr Arg Ile Thr Tyr Gly Glu Thr Gly Gly Asn Ser Pro Val Gln
145                 150                 155                 160

Glu Phe Thr Val Pro Gly Pro Val His Thr Ala Thr Ile Ser Gly Leu
                165                 170                 175

Lys Pro Gly Val Asp Tyr Thr Ile Thr Val Tyr Ala Val Thr Asp His
            180                 185                 190

Lys Pro His Ala Asp Gly Pro His Thr Tyr His Glu Ser Pro Ile Ser
        195                 200                 205

Ile Asn Tyr Arg Thr
        210

<210> SEQ ID NO 21
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
```

```
                   100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Asp Ser Gly Arg Gly Ser
        130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Gly Pro Val His Thr Ala Thr Ile Ser
                165                 170                 175

Gly Leu Lys Pro Gly Val Asp Tyr Thr Ile Thr Val Tyr Ala Val Thr
            180                 185                 190

Asp His Lys Pro His Ala Asp Gly Pro His Thr Tyr His Glu Ser Pro
        195                 200                 205

Ile Ser Ile Asn Tyr Arg Thr Glu Ile Asp Lys Pro Ser Gln
    210                 215                 220

<210> SEQ ID NO 22
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Asp Ser Gly Arg Gly Ser
        130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Gly Pro Val His Thr Ala Thr Ile Ser
                165                 170                 175

Gly Leu Lys Pro Gly Val Asp Tyr Thr Ile Thr Val Tyr Ala Val Thr
            180                 185                 190

Asp His Lys Pro His Ala Asp Gly Pro His Thr Tyr His Glu Ser Pro
```

```
                195                 200                 205

Ile Ser Ile Asn Tyr Arg Thr Glu Ile Asp Lys Pro Ser Gln His His
    210                 215                 220

His His His His
225

<210> SEQ ID NO 23
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Val Ser Asp Val Pro Arg Asp Leu Glu Val Val Ala Ala Thr Pro Thr
1               5                   10                  15

Ser Leu Leu Ile Ser Trp Asp Ser Gly Arg Gly Ser Tyr Gln Tyr Tyr
            20                  25                  30

Arg Ile Thr Tyr Gly Glu Thr Gly Gly Asn Ser Pro Val Gln Glu Phe
        35                  40                  45

Thr Val Pro Gly Pro Val His Thr Ala Thr Ile Ser Gly Leu Lys Pro
    50                  55                  60

Gly Val Asp Tyr Thr Ile Thr Val Tyr Ala Val Thr Asp His Lys Pro
65                  70                  75                  80

His Ala Asp Gly Pro His Thr Tyr His Glu Ser Pro Ile Ser Ile Asn
                85                  90                  95

Tyr Arg Thr Glu Ile Asp Lys Gly Ser Gly Ser Gly Ser Gly Ser Gly
            100                 105                 110

Ser Gly Ser Gly Ser Gly Ser Gly Ser Val Ser Asp Val Pro
            115                 120                 125

Arg Asp Leu Glu Val Val Ala Ala Thr Pro Thr Ser Leu Leu Ile Ser
    130                 135                 140

Trp Ser Ala Arg Leu Lys Val Ala Arg Tyr Tyr Arg Ile Thr Tyr Gly
145                 150                 155                 160

Glu Thr Gly Gly Asn Ser Pro Val Gln Glu Phe Thr Val Pro Lys Asn
                165                 170                 175

Val Tyr Thr Ala Thr Ile Ser Gly Leu Lys Pro Gly Val Asp Tyr Thr
            180                 185                 190

Ile Thr Val Tyr Ala Val Thr Arg Phe Arg Asp Tyr Gln Pro Ile Ser
        195                 200                 205

Ile Asn Tyr Arg Thr Glu Ile Asp Lys Pro Ser Gln
    210                 215                 220

<210> SEQ ID NO 24
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
            20                  25                  30

Tyr Tyr Arg Ile Thr Tyr Gly Glu Thr Gly Gly Asn Ser Pro Val Gln
```

```
            35                  40                  45
Glu Phe Thr Val Pro Gly Pro Val His Thr Ala Thr Ile Ser Gly Leu
 50                  55                  60
Lys Pro Gly Val Asp Tyr Thr Ile Thr Val Tyr Ala Val Thr Asp His
 65                  70                  75                  80
Lys Pro His Ala Asp Gly Pro His Thr Tyr His Glu Ser Pro Ile Ser
                 85                  90                  95
Ile Asn Tyr Arg Thr Glu Ile Asp Lys Gly Ser Gly Ser Gly Ser Gly
                100                 105                 110
Ser Gly Ser Gly Ser Gly Ser Gly Ser Gly Ser Gly Ser Val Ser Asp
                115                 120                 125
Val Pro Arg Asp Leu Glu Val Val Ala Ala Thr Pro Thr Ser Leu Leu
130                 135                 140
Ile Ser Trp Ser Ala Arg Leu Lys Val Ala Arg Tyr Tyr Arg Ile Thr
145                 150                 155                 160
Tyr Gly Glu Thr Gly Gly Asn Ser Pro Val Gln Glu Phe Thr Val Pro
                165                 170                 175
Lys Asn Val Tyr Thr Ala Thr Ile Ser Gly Leu Lys Pro Gly Val Asp
                180                 185                 190
Tyr Thr Ile Thr Val Tyr Ala Val Thr Arg Phe Arg Asp Tyr Gln Pro
                195                 200                 205
Ile Ser Ile Asn Tyr Arg Thr Glu Ile Asp Lys Pro Ser Gln
                210                 215                 220

<210> SEQ ID NO 25
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Gly Val Ser Asp Val Pro Arg Asp Leu Glu Val Val Ala Ala Thr
 1                5                  10                  15
Pro Thr Ser Leu Leu Ile Ser Trp Asp Ser Gly Arg Gly Ser Tyr Gln
                 20                  25                  30
Tyr Tyr Arg Ile Thr Tyr Gly Glu Thr Gly Gly Asn Ser Pro Val Gln
                 35                  40                  45
Glu Phe Thr Val Pro Gly Pro Val His Thr Ala Thr Ile Ser Gly Leu
 50                  55                  60
Lys Pro Gly Val Asp Tyr Thr Ile Thr Val Tyr Ala Val Thr Asp His
 65                  70                  75                  80
Lys Pro His Ala Asp Gly Pro His Thr Tyr His Glu Ser Pro Ile Ser
                 85                  90                  95
Ile Asn Tyr Arg Thr Glu Ile Asp Lys Gly Ser Gly Ser Gly Ser Gly
                100                 105                 110
Ser Gly Ser Gly Ser Gly Ser Gly Ser Gly Ser Gly Ser Val Ser Asp
                115                 120                 125
Val Pro Arg Asp Leu Glu Val Val Ala Ala Thr Pro Thr Ser Leu Leu
130                 135                 140
Ile Ser Trp Ser Ala Arg Leu Lys Val Ala Arg Tyr Tyr Arg Ile Thr
145                 150                 155                 160
Tyr Gly Glu Thr Gly Gly Asn Ser Pro Val Gln Glu Phe Thr Val Pro
                165                 170                 175
```

```
Lys Asn Val Tyr Thr Ala Thr Ile Ser Gly Leu Lys Pro Gly Val Asp
                180                 185                 190

Tyr Thr Ile Thr Val Tyr Ala Val Thr Arg Phe Arg Asp Tyr Gln Pro
            195                 200                 205

Ile Ser Ile Asn Tyr Arg Thr Glu Ile Asp Lys Pro Ser Gln His His
    210                 215                 220

His His His His
225

<210> SEQ ID NO 26
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
            35                  40                  45

Thr Val Pro Lys Asn Val Tyr Thr Ala Thr Ile Ser Gly Leu Lys Pro
        50                  55                  60

Gly Val Asp Tyr Thr Ile Thr Val Tyr Ala Val Thr Arg Phe Arg Asp
65                  70                  75                  80

Tyr Gln Pro Ile Ser Ile Asn Tyr Arg Thr Glu Ile Asp Lys Gly Ser
                85                  90                  95

Gly Ser Gly Ser Gly Ser Gly Ser Gly Ser Gly Ser Gly Ser Gly Ser
            100                 105                 110

Gly Ser Val Ser Asp Val Pro Arg Asp Leu Glu Val Val Ala Ala Thr
            115                 120                 125

Pro Thr Ser Leu Leu Ile Ser Trp Val Ala Gly Ala Glu Asp Tyr Gln
        130                 135                 140

Tyr Tyr Arg Ile Thr Tyr Gly Glu Thr Gly Gly Asn Ser Pro Val Gln
145                 150                 155                 160

Glu Phe Thr Val Pro His Asp Leu Val Thr Ala Thr Ile Ser Gly Leu
                165                 170                 175

Lys Pro Gly Val Asp Tyr Thr Ile Thr Val Tyr Ala Val Thr Asp Met
            180                 185                 190

Met His Val Glu Tyr Thr Glu His Pro Ile Ser Ile Asn Tyr Arg Thr
            195                 200                 205

<210> SEQ ID NO 27
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30
```

```
Tyr Tyr Arg Ile Thr Tyr Gly Glu Thr Gly Asn Ser Pro Val Gln
        35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Ile Asp Lys
                 85                  90                  95

Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Val Ala Gly Ala Glu Asp
130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro His Asp Leu Val Thr Ala Thr Ile Ser
                165                 170                 175

Gly Leu Lys Pro Gly Val Asp Tyr Thr Ile Thr Val Tyr Ala Val Thr
            180                 185                 190

Asp Met Met His Val Glu Tyr Thr Glu His Pro Ile Ser Ile Asn Tyr
            195                 200                 205

Arg Thr Glu Ile Asp Lys Pro Ser Gln
210                 215

<210> SEQ ID NO 28
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Gly Val Ser Asp Val Pro Arg Asp Leu Glu Val Val Ala Ala Thr
 1               5                  10                  15

Pro Thr Ser Leu Leu Ile Ser Trp Ser Ala Arg Leu Lys Val Ala Arg
                 20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Ile Asp Lys
                 85                  90                  95

Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Val Ala Gly Ala Glu Asp
130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro His Asp Leu Val Thr Ala Thr Ile Ser
                165                 170                 175
```

```
Gly Leu Lys Pro Gly Val Asp Tyr Thr Ile Thr Val Tyr Ala Val Thr
            180                 185                 190

Asp Met Met His Val Glu Tyr Thr Glu His Pro Ile Ser Ile Asn Tyr
            195                 200                 205

Arg Thr Glu Ile Asp Lys Pro Ser Gln His His His His His
    210                 215                 220

<210> SEQ ID NO 29
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Val Ser Asp Val Pro Arg Asp Leu Glu Val Val Ala Ala Thr Pro Thr
1               5                   10                  15

Ser Leu Leu Ile Ser Trp Val Ala Gly Ala Glu Asp Tyr Gln Tyr Tyr
            20                  25                  30

Arg Ile Thr Tyr Gly Glu Thr Gly Gly Asn Ser Pro Val Gln Glu Phe
        35                  40                  45

Thr Val Pro His Asp Leu Val Thr Ala Thr Ile Ser Gly Leu Lys Pro
    50                  55                  60

Gly Val Asp Tyr Thr Ile Thr Val Tyr Ala Val Thr Asp Met Met His
65                  70                  75                  80

Val Glu Tyr Thr Glu His Pro Ile Ser Ile Asn Tyr Arg Thr Glu Ile
                85                  90                  95

Asp Lys Gly Ser Gly Ser Gly Ser Gly Ser Gly Ser Gly Ser Gly Ser
            100                 105                 110

Gly Ser Gly Ser Gly Ser Val Ser Asp Val Pro Arg Asp Leu Glu Val
            115                 120                 125

Val Ala Ala Thr Pro Thr Ser Leu Leu Ile Ser Trp Ser Ala Arg Leu
        130                 135                 140

Lys Val Ala Arg Tyr Tyr Arg Ile Thr Tyr Gly Glu Thr Gly Gly Asn
145                 150                 155                 160

Ser Pro Val Gln Glu Phe Thr Val Pro Lys Asn Val Tyr Thr Ala Thr
                165                 170                 175

Ile Ser Gly Leu Lys Pro Gly Val Asp Tyr Thr Ile Thr Val Tyr Ala
            180                 185                 190

Val Thr Arg Phe Arg Asp Tyr Gln Pro Ile Ser Ile Asn Tyr Arg Thr
        195                 200                 205

<210> SEQ ID NO 30
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Gly Val Ser Asp Val Pro Arg Asp Leu Glu Val Val Ala Ala Thr
1               5                   10                  15

Pro Thr Ser Leu Leu Ile Ser Trp Val Ala Gly Ala Glu Asp Tyr Gln
            20                  25                  30

Tyr Tyr Arg Ile Thr Tyr Gly Glu Thr Gly Gly Asn Ser Pro Val Gln
        35                  40                  45
```

Glu Phe Thr Val Pro His Asp Leu Val Thr Ala Thr Ile Ser Gly Leu
    50                  55                  60

Lys Pro Gly Val Asp Tyr Thr Ile Thr Val Tyr Ala Val Thr Asp Met
 65                  70                  75                  80

Met His Val Glu Tyr Thr Glu His Pro Ile Ser Ile Asn Tyr Arg Thr
                85                  90                  95

Glu Ile Asp Lys Gly Ser Gly Ser Gly Ser Gly Ser Gly Ser Gly Ser
                100                 105                 110

Gly Ser Gly Ser Gly Ser Gly Ser Val Ser Asp Val Pro Arg Asp Leu
            115                 120                 125

Glu Val Val Ala Ala Thr Pro Thr Ser Leu Leu Ile Ser Trp Ser Ala
    130                 135                 140

Arg Leu Lys Val Ala Arg Tyr Tyr Arg Ile Thr Tyr Gly Glu Thr Gly
145                 150                 155                 160

Gly Asn Ser Pro Val Gln Glu Phe Thr Val Pro Lys Asn Val Tyr Thr
                165                 170                 175

Ala Thr Ile Ser Gly Leu Lys Pro Gly Val Asp Tyr Thr Ile Thr Val
                180                 185                 190

Tyr Ala Val Thr Arg Phe Arg Asp Tyr Gln Pro Ile Ser Ile Asn Tyr
            195                 200                 205

Arg Thr Glu Ile Asp Lys Pro Ser Gln
    210                 215

<210> SEQ ID NO 31
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Gly Val Ser Asp Val Pro Arg Asp Leu Glu Val Val Ala Ala Thr
 1               5                   10                  15

Pro Thr Ser Leu Leu Ile Ser Trp Val Ala Gly Ala Glu Asp Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro His Asp Leu Val Thr Ala Thr Ile Ser Gly Leu
    50                  55                  60

Lys Pro Gly Val Asp Tyr Thr Ile Thr Val Tyr Ala Val Thr Asp Met
 65                  70                  75                  80

Met His Val Glu Tyr Thr Glu His Pro Ile Ser Ile Asn Tyr Arg Thr
                85                  90                  95

Glu Ile Asp Lys Gly Ser Gly Ser Gly Ser Gly Ser Gly Ser Gly Ser
                100                 105                 110

Gly Ser Gly Ser Gly Ser Gly Ser Val Ser Asp Val Pro Arg Asp Leu
            115                 120                 125

Glu Val Val Ala Ala Thr Pro Thr Ser Leu Leu Ile Ser Trp Ser Ala
    130                 135                 140

Arg Leu Lys Val Ala Arg Tyr Tyr Arg Ile Thr Tyr Gly Glu Thr Gly
145                 150                 155                 160

Gly Asn Ser Pro Val Gln Glu Phe Thr Val Pro Lys Asn Val Tyr Thr
                165                 170                 175

Ala Thr Ile Ser Gly Leu Lys Pro Gly Val Asp Tyr Thr Ile Thr Val

```
                180               185               190
Tyr Ala Val Thr Arg Phe Arg Asp Tyr Gln Pro Ile Ser Ile Asn Tyr
                    195               200               205

Arg Thr Glu Ile Asp Lys Pro Ser Gln His His His His His
        210               215               220

<210> SEQ ID NO 32
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(40)
<223> OTHER INFORMATION: Any amino acid; this region may encompass 1-20
      residues
<220> FEATURE:
<221> NAME/KEY: MOD_RES
<222> LOCATION: (61)..(80)
<223> OTHER INFORMATION: Any amino acid; this region may encompass 1-20
      residues
<220> FEATURE:
<221> NAME/KEY: MOD_RES
<222> LOCATION: (100)..(139)
<223> OTHER INFORMATION: Any amino acid; this region may encompass 1-40
      residues

<400> SEQUENCE: 32

Val Ser Asp Val Pro Arg Asp Leu Glu Val Val Ala Ala Thr Pro Thr
1               5                   10                  15

Ser Leu Leu Ile Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Tyr Tyr Arg Ile Thr Tyr Gly Glu
            35                  40                  45

Thr Gly Gly Asn Ser Pro Val Gln Glu Phe Thr Val Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Ala Thr Ile Ser Gly Leu Lys Pro Gly Val Asp Tyr Thr Ile Thr Val
                85                  90                  95

Tyr Ala Val Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Ile Ser Ile Asn Tyr
        130                 135                 140

Arg Thr
145

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Trp Val Ala Gly Ala Glu Asp Tyr Gln
1               5                   10
```

```
<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (14)..(18)
<223> OTHER INFORMATION: Any amino acid; this region may encompass 0-5
      residues

<400> SEQUENCE: 34

Xaa Xaa Xaa Xaa Xaa Val Ala Gly Ala Glu Asp Tyr Gln Xaa Xaa Xaa
1               5                   10                  15

Xaa Xaa

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro His Asp Leu Val Thr
1               5

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (10)..(14)
<223> OTHER INFORMATION: Any amino acid; this region may encompass 0-5
      residues

<400> SEQUENCE: 36

Xaa Xaa Xaa Xaa Xaa His Asp Leu Val Xaa Xaa Xaa Xaa Xaa
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Asp Met Met His Val Glu Tyr Thr Glu His Pro
1               5                   10

<210> SEQ ID NO 38
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (16)..(20)
<223> OTHER INFORMATION: Any amino acid; this region may encompass 0-5
      residues

<400> SEQUENCE: 38

Xaa Xaa Xaa Xaa Xaa Asp Met Met His Val Glu Tyr Thr Glu His Xaa
1               5                   10                  15

Xaa Xaa Xaa Xaa
            20

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Trp Asp Ser Gly Arg Gly Ser Tyr Gln
1               5                   10

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (14)..(18)
<223> OTHER INFORMATION: Any amino acid; this region may encompass 0-5
      residues

<400> SEQUENCE: 40

Xaa Xaa Xaa Xaa Xaa Asp Ser Gly Arg Gly Ser Tyr Gln Xaa Xaa Xaa
1               5                   10                  15

Xaa Xaa

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Gly Pro Val His Thr
1               5
```

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (10)..(14)
<223> OTHER INFORMATION: Any amino acid; this region may encompass 0-5
      residues

<400> SEQUENCE: 42

Xaa Xaa Xaa Xaa Xaa Gly Pro Val His Xaa Xaa Xaa Xaa Xaa
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Asp His Lys Pro His Ala Asp Gly Pro His Thr Tyr His Glu Ser
1               5                   10                  15

Pro

<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (20)..(24)
<223> OTHER INFORMATION: Any amino acid; this region may encompass 0-5
      residues

<400> SEQUENCE: 44

Xaa Xaa Xaa Xaa Xaa Asp His Lys Pro His Ala Asp Gly Pro His Thr
1               5                   10                  15

Tyr His Glu Xaa Xaa Xaa Xaa Xaa
            20

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Trp Ser Ala Arg Leu Lys Val Ala Arg

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (13)..(17)
<223> OTHER INFORMATION: Any amino acid; this region may encompass 0-5
      residues

<400> SEQUENCE: 46

Xaa Xaa Xaa Xaa Xaa Ser Ala Arg Leu Lys Val Ala Xaa Xaa Xaa Xaa
1               5                   10                  15

Xaa

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Lys Asn Val Tyr Thr
1               5

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (10)..(14)
<223> OTHER INFORMATION: Any amino acid; this region may encompass 0-5
      residues

<400> SEQUENCE: 48

Xaa Xaa Xaa Xaa Xaa Lys Asn Val Tyr Xaa Xaa Xaa Xaa Xaa
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Arg Phe Arg Asp Tyr Gln Pro
1               5

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (12)..(16)
<223> OTHER INFORMATION: Any amino acid; this region may encompass 0-5
      residues

<400> SEQUENCE: 50

Xaa Xaa Xaa Xaa Xaa Arg Phe Arg Asp Tyr Gln Xaa Xaa Xaa Xaa Xaa
1               5                   10                  15

<210> SEQ ID NO 51
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Pro Gly
1

<210> SEQ ID NO 52
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Gly Val Ser Asp Val Pro Arg Asp Leu Glu Val Val Ala Ala Thr
1               5                   10                  15

Pro Thr Ser Leu Leu Ile Ser Trp Leu Pro Gly Lys Leu Arg Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro His Asp Leu Arg Thr Ala Thr Ile Ser Gly Leu
    50                  55                  60

Lys Pro Gly Val Asp Tyr Thr Ile Thr Val Tyr Ala Val Thr Asn Met
65                  70                  75                  80

Met His Val Glu Tyr Ser Glu Tyr Pro Ile Ser Ile Asn Tyr Arg Thr
                85                  90                  95

Glu Ile Asp Lys Pro Ser Gln His His His His His
                100                 105

<210> SEQ ID NO 53
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 53

Met Gly Val Ser Asp Val Pro Arg Asp Leu Glu Val Val Ala Ala Thr
1               5                   10                  15

Pro Thr Ser Leu Leu Ile Ser Trp Leu Pro Gly Lys Leu Arg Tyr Gln
            20                  25                  30

Tyr Tyr Arg Ile Thr Tyr Gly Glu Thr Gly Asn Ser Pro Val Gln
                35                  40                  45

Glu Phe Thr Val Pro His Asp Leu Arg Thr Ala Thr Ile Ser Gly Leu
50                  55                  60

Lys Pro Gly Val Asp Tyr Thr Ile Thr Val Tyr Ala Val Thr Asn Met
65                  70                  75                  80

Met His Val Glu Tyr Ser Glu Tyr Pro Ile Ser Ile Asn Tyr Arg Thr
                85                  90                  95

Glu Ile Asp Lys Gly Ser Gly Ser Gly Ser Gly Ser Gly Ser Gly Ser
                100                 105                 110

Gly Ser Gly Ser Gly Ser Gly Ser Val Ser Asp Val Pro Arg Asp Leu
            115                 120                 125

Glu Val Val Ala Ala Thr Pro Thr Ser Leu Leu Ile Ser Trp Ser Ala
130                 135                 140

Arg Leu Lys Val Ala Arg Tyr Tyr Arg Ile Thr Tyr Gly Glu Thr Gly
145                 150                 155                 160

Gly Asn Ser Pro Val Gln Glu Phe Thr Val Pro Lys Asn Val Tyr Thr
                165                 170                 175

Ala Thr Ile Ser Gly Leu Lys Pro Gly Val Asp Tyr Thr Ile Thr Val
            180                 185                 190

Tyr Ala Val Thr Arg Phe Arg Asp Tyr Gln Pro Ile Ser Ile Asn Tyr
                195                 200                 205

Arg Thr Glu Ile Asp Lys Pro Cys Gln His His His His His
            210                 215                 220

<210> SEQ ID NO 54
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
                35                  40                  45

Glu Phe Thr Val Pro Lys Asn Val Tyr Thr Ala Thr Ile Ser Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
                100                 105                 110

Gly Ser Gly Ser Val Ser Asp Val Pro Arg Asp Leu Glu Val Val Ala
            115                 120                 125
```

Ala Thr Pro Thr Ser Leu Leu Ile Ser Trp Leu Pro Gly Lys Leu Arg
        130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro His Asp Leu Arg Thr Ala Thr Ile Ser
                165                 170                 175

Gly Leu Lys Pro Gly Val Asp Tyr Thr Ile Thr Val Tyr Ala Val Thr
                180                 185                 190

Asn Met Met His Val Glu Tyr Ser Glu Tyr Pro Ile Ser Ile Asn Tyr
        195                 200                 205

Arg Thr Glu Ile Asp Lys Pro Cys Gln His His His His His
    210                 215                 220

<210> SEQ ID NO 55
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Gly Val Ser Asp Val Pro Arg Asp Leu Glu Val Val Ala Ala Thr
1               5                   10                  15

Pro Thr Ser Leu Leu Ile Ser Trp Val Ala Gly Ala Glu Asp Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro His Asp Leu Val Thr Ala Thr Ile Ser Gly Leu
        50                  55                  60

Lys Pro Gly Val Asp Tyr Thr Ile Thr Val Tyr Ala Val Thr Asp Met
65                  70                  75                  80

Met His Val Glu Tyr Thr Glu His Pro Ile Ser Ile Asn Tyr Arg Thr
                85                  90                  95

Glu Ile Asp Lys Gly Ser Gly Ser Gly Ser Gly Ser Gly Ser Gly Ser
                100                 105                 110

Gly Ser Gly Ser Gly Ser Val Ser Asp Val Pro Arg Asp Leu
            115                 120                 125

Glu Val Val Ala Ala Thr Pro Thr Ser Leu Leu Ile Ser Trp Ser Ala
        130                 135                 140

Arg Leu Lys Val Ala Arg Tyr Tyr Arg Ile Thr Tyr Gly Glu Thr Gly
145                 150                 155                 160

Gly Asn Ser Pro Val Gln Glu Phe Thr Val Pro Lys Asn Val Tyr Thr
                165                 170                 175

Ala Thr Ile Ser Gly Leu Lys Pro Gly Val Asp Tyr Thr Ile Thr Val
            180                 185                 190

Tyr Ala Val Thr Arg Phe Arg Asp Tyr Gln Pro Ile Ser Ile Asn Tyr
        195                 200                 205

Arg Thr Glu Ile Asp Lys Pro Cys Gln His His His His His
    210                 215                 220

<210> SEQ ID NO 56
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Pro Val His Thr Ala Thr Ile Ser Gly Leu
    50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Gly Ser Gly Ser Gly Ser Gly
            100                 105                 110

Ser Gly Ser Gly Ser Gly Ser Gly Ser Gly Ser Val Ser Asp
        115                 120                 125

Val Pro Arg Asp Leu Glu Val Val Ala Ala Thr Pro Thr Ser Leu Leu
    130                 135                 140

Ile Ser Trp Ser Ala Arg Leu Lys Val Ala Arg Tyr Tyr Arg Ile Thr
145                 150                 155                 160

Tyr Gly Glu Thr Gly Gly Asn Ser Pro Val Gln Glu Phe Thr Val Pro
                165                 170                 175

Lys Asn Val Tyr Thr Ala Thr Ile Ser Gly Leu Lys Pro Gly Val Asp
            180                 185                 190

Tyr Thr Ile Thr Val Tyr Ala Val Thr Arg Phe Arg Asp Tyr Gln Pro
        195                 200                 205

Ile Ser Ile Asn Tyr Arg Thr Glu Ile Asp Lys Pro Cys Gln His His
    210                 215                 220

His His His His
225

<210> SEQ ID NO 57
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser

```
                    100                 105                 110
Gly Ser Gly Ser Val Ser Asp Val Pro Arg Asp Leu Glu Val Val Ala
            115                 120                 125

Ala Thr Pro Thr Ser Leu Leu Ile Ser Trp Val Ala Gly Ala Glu Asp
        130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro His Asp Leu Val Thr Ala Thr Ile Ser
                    165                 170                 175

Gly Leu Lys Pro Gly Val Asp Tyr Thr Ile Thr Val Tyr Ala Val Thr
                180                 185                 190

Asp Met Met His Val Glu Tyr Thr Glu His Pro Ile Ser Ile Asn Tyr
            195                 200                 205

Arg Thr Glu Ile Asp Lys Pro Cys Gln His His His His His
        210                 215                 220

<210> SEQ ID NO 58
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
        115                 120                 125

Ala Thr Pro Thr Ser Leu Leu Ile Ser Trp Asp Ser Gly Arg Gly Ser
    130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Gly Pro Val His Thr Ala Thr Ile Ser
                165                 170                 175

Gly Leu Lys Pro Gly Val Asp Tyr Thr Ile Thr Val Tyr Ala Val Thr
            180                 185                 190

Asp His Lys Pro His Ala Asp Gly Pro His Thr Tyr His Glu Ser Pro
        195                 200                 205

Ile Ser Ile Asn Tyr Arg Thr Glu Ile Asp Lys Pro Cys Gln His His
    210                 215                 220

His His His His
225
```

```
<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Trp Leu Pro Gly Lys Leu Arg Tyr Gln
1               5                   10

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (14)..(18)
<223> OTHER INFORMATION: Any amino acid; this region may encompass 0-5
      residues

<400> SEQUENCE: 60

Xaa Xaa Xaa Xaa Xaa Leu Pro Gly Lys Leu Arg Tyr Gln Xaa Xaa Xaa
1               5                   10                  15

Xaa Xaa

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro His Asp Leu Arg Thr
1               5

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (10)..(14)
<223> OTHER INFORMATION: Any amino acid; this region may encompass 0-5
      residues

<400> SEQUENCE: 62

Xaa Xaa Xaa Xaa Xaa His Asp Leu Arg Xaa Xaa Xaa Xaa Xaa
1               5                   10
```

```
<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Asn Met Met His Val Glu Tyr Ser Glu Tyr Pro
1               5                   10

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (16)..(20)
<223> OTHER INFORMATION: Any amino acid; this region may encompass 0-5
      residues

<400> SEQUENCE: 64

Xaa Xaa Xaa Xaa Xaa Asn Met Met His Val Glu Tyr Ser Glu Tyr Xaa
1               5                   10                  15

Xaa Xaa Xaa Xaa
            20

<210> SEQ ID NO 65
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Val Ala Ala Thr Pro Thr Ser Leu Leu Ile Ser Trp Ser Ala
1               5                   10                  15

Arg Leu Lys Val Ala Arg Tyr Tyr Arg Ile Thr Tyr Gly Glu Thr Gly
            20                  25                  30

Gly Asn Ser Pro Val Gln Glu Phe Thr Val Pro Lys Asn Val Tyr Thr
        35                  40                  45

Ala Thr Ile Ser Gly Leu Lys Pro Gly Val Asp Tyr Thr Ile Thr Val
    50                  55                  60

Tyr Ala Val Thr Arg Phe Arg Asp Tyr Gln Pro Ile Ser Ile Asn Tyr
65                  70                  75                  80

Arg Thr

<210> SEQ ID NO 66
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66
```

Glu Val Val Ala Ala Thr Pro Thr Ser Leu Leu Ile Ser Trp Val Ala
1               5                   10                  15

Gly Ala Glu Asp Tyr Gln Tyr Tyr Arg Ile Thr Tyr Gly Glu Thr Gly
            20                  25                  30

Gly Asn Ser Pro Val Gln Glu Phe Thr Val Pro His Asp Leu Val Thr
        35                  40                  45

Ala Thr Ile Ser Gly Leu Lys Pro Gly Val Asp Tyr Thr Ile Thr Val
    50                  55                  60

Tyr Ala Val Thr Asp Met Met His Val Glu Tyr Thr Glu His Pro Ile
65                  70                  75                  80

Ser Ile Asn Tyr Arg Thr
                85

<210> SEQ ID NO 67
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Val Ala Ala Thr Pro Thr Ser Leu Leu Ile Ser Trp Asp Ser
1               5                   10                  15

Gly Arg Gly Ser Tyr Gln Tyr Tyr Arg Ile Thr Tyr Gly Glu Thr Gly
            20                  25                  30

Gly Asn Ser Pro Val Gln Glu Phe Thr Val Pro Gly Val His Thr
        35                  40                  45

Ala Thr Ile Ser Gly Leu Lys Pro Gly Val Asp Tyr Thr Ile Thr Val
    50                  55                  60

Tyr Ala Val Thr Asp His Lys Pro His Ala Asp Gly Pro His Thr Tyr
65                  70                  75                  80

His Glu Ser Pro Ile Ser Ile Asn Tyr Arg Thr
                85                  90

<210> SEQ ID NO 68
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Val Ala Ala Thr Pro Thr Ser Leu Leu Ile Ser Trp Leu Pro
1               5                   10                  15

Gly Lys Leu Arg Tyr Gln Tyr Tyr Arg Ile Thr Tyr Gly Glu Thr Gly
            20                  25                  30

Gly Asn Ser Pro Val Gln Glu Phe Thr Val Pro His Asp Leu Arg Thr
        35                  40                  45

Ala Thr Ile Ser Gly Leu Lys Pro Gly Val Asp Tyr Thr Ile Thr Val
    50                  55                  60

Tyr Ala Val Thr Asn Met Met His Val Glu Tyr Ser Glu Tyr Pro Ile
65                  70                  75                  80

Ser Ile Asn Tyr Arg Thr
                85

<210> SEQ ID NO 69
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Met Gly Val Ser Asp Val Pro Arg Asp Leu
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Val Ser Asp Val Pro Arg Asp Leu
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Val Ser Asp Val Pro Arg Asp Leu
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid; this region may encompass 0-2
      residues

<400> SEQUENCE: 72

Xaa Xaa Ser Asp Val Pro Arg Asp Leu
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid; this region may encompass 0-2
      residues

<400> SEQUENCE: 73

Xaa Xaa Asp Val Pro Arg Asp Leu
1               5

<210> SEQ ID NO 74
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid; this region may encompass 0-2
      residues

<400> SEQUENCE: 74

Xaa Xaa Val Pro Arg Asp Leu
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid; this region may encompass 0-2
      residues

<400> SEQUENCE: 75

Xaa Xaa Pro Arg Asp Leu
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid; this region may encompass 0-2
      residues

<400> SEQUENCE: 76

Xaa Xaa Arg Asp Leu
1               5

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid; this region may encompass 0-2
      residues

<400> SEQUENCE: 77

Xaa Xaa Asp Leu
1

<210> SEQ ID NO 78
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 78

Glu Ile Asp Lys
1

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Ile Asp Lys Pro
1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Ile Asp Lys Pro Ser
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Glu Ile Asp Lys Pro Cys
1               5

<210> SEQ ID NO 82
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Val Ser Asp Val Pro Arg Asp Leu Glu Val Val Ala Ala Thr Pro Thr
1               5                   10                  15

Ser Leu Leu Ile Ser Trp Leu Pro Gly Lys Leu Arg Tyr Gln Tyr Tyr
                20                  25                  30

Arg Ile Thr Tyr Gly Glu Thr Gly Gly Asn Ser Pro Val Gln Glu Phe
        35                  40                  45

Thr Val Pro His Asp Leu Arg Thr Ala Thr Ile Ser Gly Leu Lys Pro
    50                  55                  60

Gly Val Asp Tyr Thr Ile Thr Val Tyr Ala Val Thr Asn Met Met His
65                  70                  75                  80

Val Glu Tyr Ser Glu Tyr Pro Ile Ser Ile Asn Tyr Arg Thr
                85                  90
```

```
<210> SEQ ID NO 83
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid; this region may encompass
      1-15, 2-15, 1-10, 2-10, 1-8, 2-8, 1-5, 2-5, 1-4, 2-4, 1-3, 2-3 or
      1-2 residues
<220> FEATURE:
<221> NAME/KEY: MOD_RES
<222> LOCATION: (26)..(35)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (46)..(55)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (64)..(83)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (89)..(98)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (105)..(114)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (118)..(137)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (147)..(156)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (169)..(178)
<223> OTHER INFORMATION: Any amino acid; this region may encompass 0-10,
      0-5, 1-10, 1-5 or 2-5 residues

<400> SEQUENCE: 83

Glu Val Val Ala Ala Thr Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa
            20                  25                  30

Xaa Xaa Xaa Ser Trp Val Ala Gly Ala Glu Asp Tyr Gln Xaa Xaa Xaa
        35                  40                  45

Xaa Xaa Xaa Xaa Xaa Xaa Xaa Tyr Tyr Arg Ile Thr Tyr Gly Glu Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Gln Glu Phe Thr Val Xaa Xaa Xaa Xaa Xaa Xaa Xaa Xaa
                85                  90                  95

Xaa Xaa Pro His Asp Leu Val Thr Xaa Xaa Xaa Xaa Xaa Xaa Xaa Xaa
```

```
            100                 105                 110
Xaa Xaa Ala Thr Ile Xaa Xaa Xaa Xaa Xaa Xaa Xaa Xaa Xaa
            115                 120                 125

Xaa Xaa Xaa Xaa Xaa Xaa Xaa Xaa Asp Tyr Thr Ile Thr Val Tyr
        130                 135                 140

Ala Val Xaa Xaa Xaa Xaa Xaa Xaa Xaa Xaa Xaa Thr Asp Met Met
145                 150                 155                 160

His Val Glu Tyr Thr Glu His Pro Xaa Xaa Xaa Xaa Xaa Xaa Xaa
                165                 170                 175

Xaa Xaa Ile Ser Ile Asn Tyr Arg Thr
        180                 185

<210> SEQ ID NO 84
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid; this region may encompass 1-15,
      2-15, 1-10, 2-10, 1-8, 2-8, 1-5, 2-5, 1-4, 2-4, 1-3, 2-3 or
      1-2 residues
<220> FEATURE:
<221> NAME/KEY: MOD_RES
<222> LOCATION: (26)..(35)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (46)..(55)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (64)..(83)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (89)..(98)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (105)..(114)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (118)..(137)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (147)..(156)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (174)..(183)
<223> OTHER INFORMATION: Any amino acid; this region may encompass 0-10,
      0-5, 1-10, 1-5 or 2-5 residues

<400> SEQUENCE: 84

Glu Val Val Ala Ala Thr Xaa Xaa Xaa Xaa Xaa Xaa Xaa Xaa Xaa Xaa
1               5                   10                  15
```

```
Xaa Xaa Xaa Xaa Xaa Ser Leu Leu Ile Xaa Xaa Xaa Xaa Xaa Xaa
                20                  25                  30

Xaa Xaa Xaa Ser Trp Asp Ser Gly Arg Gly Ser Tyr Gln Xaa Xaa Xaa
            35                  40                  45

Xaa Xaa Xaa Xaa Xaa Xaa Xaa Tyr Tyr Arg Ile Thr Tyr Gly Glu Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Gln Glu Phe Thr Val Xaa Xaa Xaa Xaa Xaa Xaa Xaa Xaa
                85                  90                  95

Xaa Xaa Pro Gly Pro Val His Thr Xaa Xaa Xaa Xaa Xaa Xaa Xaa Xaa
            100                 105                 110

Xaa Xaa Ala Thr Ile Xaa Xaa Xaa Xaa Xaa Xaa Xaa Xaa Xaa Xaa Xaa
            115                 120                 125

Xaa Xaa Xaa Xaa Xaa Xaa Xaa Xaa Asp Tyr Thr Ile Thr Val Tyr
        130                 135                 140

Ala Val Xaa Xaa Xaa Xaa Xaa Xaa Xaa Xaa Xaa Thr Asp His Lys
145                 150                 155                 160

Pro His Ala Asp Gly Pro His Thr Tyr His Glu Ser Pro Xaa Xaa Xaa
                165                 170                 175

Xaa Xaa Xaa Xaa Xaa Xaa Xaa Ile Ser Ile Asn Tyr Arg Thr
            180                 185                 190

<210> SEQ ID NO 85
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid; this region may encompass 1-15,
      2-15, 1-10, 2-10, 1-8, 2-8, 1-5, 2-5, 1-4, 2-4, 1-3, 2-3 or
      1-2 residues
<220> FEATURE:
<221> NAME/KEY: MOD_RES
<222> LOCATION: (26)..(35)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (46)..(55)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (64)..(83)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (89)..(98)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (105)..(114)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (118)..(137)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
```

```
<220> FEATURE:
<221> NAME/KEY: MOD_RES
<222> LOCATION: (147)..(156)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (169)..(178)
<223> OTHER INFORMATION: Any amino acid; this region may encompass 0-10,
      0-5, 1-10, 1-5 or 2-5 residues

<400> SEQUENCE: 85

Glu Val Val Ala Ala Thr Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa
            20                  25                  30

Xaa Xaa Xaa Ser Trp Leu Pro Gly Lys Leu Arg Tyr Gln Xaa Xaa Xaa
            35                  40                  45

Xaa Xaa Xaa Xaa Xaa Xaa Xaa Tyr Tyr Arg Ile Thr Tyr Gly Glu Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Gln Glu Phe Thr Val Xaa Xaa Xaa Xaa Xaa Xaa Xaa
            85                  90                  95

Xaa Xaa Pro His Asp Leu Arg Thr Xaa Xaa Xaa Xaa Xaa Xaa Xaa
            100                 105                 110

Xaa Xaa Ala Thr Ile Xaa Xaa Xaa Xaa Xaa Xaa Xaa Xaa Xaa Xaa
            115                 120                 125

Xaa Xaa Xaa Xaa Xaa Xaa Xaa Xaa Asp Tyr Thr Ile Thr Val Tyr
            130                 135                 140

Ala Val Xaa Xaa Xaa Xaa Xaa Xaa Xaa Xaa Xaa Thr Asn Met Met
145                 150                 155                 160

His Val Glu Tyr Ser Glu Tyr Pro Xaa Xaa Xaa Xaa Xaa Xaa Xaa
                165                 170                 175

Xaa Xaa Ile Ser Ile Asn Tyr Arg Thr
            180                 185

<210> SEQ ID NO 86
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid; this region may encompass 1-15,
      2-15, 1-10, 2-10, 1-8, 2-8, 1-5, 2-5, 1-4, 2-4, 1-3, 2-3 or
      1-2 residues
<220> FEATURE:
<221> NAME/KEY: MOD_RES
<222> LOCATION: (26)..(35)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (46)..(55)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (64)..(83)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
```

```
<220> FEATURE:
<221> NAME/KEY: MOD_RES
<222> LOCATION: (89)..(98)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (105)..(114)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (118)..(137)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (147)..(156)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (165)..(174)
<223> OTHER INFORMATION: Any amino acid; this region may encompass 0-10,
      0-5, 1-10, 1-5 or 2-5 residues

<400> SEQUENCE: 86

Glu Val Val Ala Ala Thr Xaa Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa Xaa
            20                  25                  30

Xaa Xaa Xaa Ser Trp Ser Ala Arg Leu Lys Val Ala Arg Xaa Xaa Xaa
        35                  40                  45

Xaa Xaa Xaa Xaa Xaa Xaa Xaa Tyr Tyr Arg Ile Thr Tyr Gly Glu Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Gln Glu Phe Thr Val Xaa Xaa Xaa Xaa Xaa Xaa Xaa Xaa
                85                  90                  95

Xaa Xaa Pro Lys Asn Val Tyr Thr Xaa Xaa Xaa Xaa Xaa Xaa Xaa Xaa
            100                 105                 110

Xaa Xaa Ala Thr Ile Xaa Xaa Xaa Xaa Xaa Xaa Xaa Xaa Xaa Xaa Xaa
        115                 120                 125

Xaa Xaa Xaa Xaa Xaa Xaa Xaa Xaa Asp Tyr Thr Ile Thr Val Tyr
    130                 135                 140

Ala Val Xaa Xaa Xaa Xaa Xaa Xaa Xaa Xaa Thr Arg Phe Arg
145                 150                 155                 160

Asp Tyr Gln Pro Xaa Xaa Xaa Xaa Xaa Xaa Xaa Xaa Xaa Ile Ser
                165                 170                 175

Ile Asn Tyr Arg Thr
            180

<210> SEQ ID NO 87
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Val Ser Asp Val Pro Arg Asp Leu Glu Val Val Ala Ala Thr Pro Thr
1               5                   10                  15
```

```
Ser Leu Leu Ile Ser Trp Leu Pro Gly Lys Leu Arg Tyr Gln Tyr Tyr
            20                  25                  30

Arg Ile Thr Tyr Gly Glu Thr Gly Asn Ser Pro Val Gln Glu Phe
         35                  40                  45

Thr Val Pro His Asp Leu Arg Thr Ala Thr Ile Ser Gly Leu Lys Pro
 50                  55                  60

Gly Val Asp Tyr Thr Ile Thr Val Tyr Ala Val Thr Asn Met Met His
 65                  70                  75                  80

Val Glu Tyr Ser Glu Tyr Pro Ile Ser Ile Asn Tyr Arg Thr Glu Ile
             85                  90                  95

Asp Lys Gly Ser Gly Ser Gly Ser Gly Ser Gly Ser Gly Ser
            100                 105                 110

Gly Ser Gly Ser Gly Ser Val Ser Asp Val Pro Arg Asp Leu Glu Val
            115                 120                 125

Val Ala Ala Thr Pro Thr Ser Leu Leu Ile Ser Trp Ser Ala Arg Leu
130                 135                 140

Lys Val Ala Arg Tyr Tyr Arg Ile Thr Tyr Gly Glu Thr Gly Gly Asn
145                 150                 155                 160

Ser Pro Val Gln Glu Phe Thr Val Pro Lys Asn Val Tyr Thr Ala Thr
                165                 170                 175

Ile Ser Gly Leu Lys Pro Gly Val Asp Tyr Thr Ile Thr Val Tyr Ala
            180                 185                 190

Val Thr Arg Phe Arg Asp Tyr Gln Pro Ile Ser Ile Asn Tyr Arg Thr
            195                 200                 205

Glu Ile Asp Lys Pro Cys Gln
210                 215

<210> SEQ ID NO 88
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Val Ser Asp Val Pro Arg Asp Leu Glu Val Val Ala Ala Thr Pro Thr
1               5                  10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
         35                  40                  45

Thr Val Pro Lys Asn Val Tyr Thr Ala Thr Ile Ser Gly Leu Lys Pro
 50                  55                  60

Gly Val Asp Tyr Thr Ile Thr Val Tyr Ala Val Thr Arg Phe Arg Asp
 65                  70                  75                  80

Tyr Gln Pro Ile Ser Ile Asn Tyr Arg Thr Glu Ile Asp Lys Gly Ser
             85                  90                  95

Gly Ser Gly Ser Gly Ser Gly Ser Gly Ser Gly Ser Gly Ser
            100                 105                 110

Gly Ser Val Ser Asp Val Pro Arg Asp Leu Glu Val Val Ala Ala Thr
            115                 120                 125

Pro Thr Ser Leu Leu Ile Ser Trp Leu Pro Gly Lys Leu Arg Tyr Gln
130                 135                 140

Tyr Tyr Arg Ile Thr Tyr Gly Glu Thr Gly Gly Asn Ser Pro Val Gln
145                 150                 155                 160
```

```
Glu Phe Thr Val Pro His Asp Leu Arg Thr Ala Thr Ile Ser Gly Leu
                165                 170                 175

Lys Pro Gly Val Asp Tyr Thr Ile Thr Val Tyr Ala Val Thr Asn Met
            180                 185                 190

Met His Val Glu Tyr Ser Glu Tyr Pro Ile Ser Ile Asn Tyr Arg Thr
        195                 200                 205

Glu Ile Asp Lys Pro Cys Gln
    210                 215
```

<210> SEQ ID NO 89
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Val Ser Asp Val Pro Arg Asp Leu Glu Val Val Ala Ala Thr Pro Thr
1               5                   10                  15

Ser Leu Leu Ile Ser Trp Val Ala Gly Ala Glu Asp Tyr Gln Tyr Tyr
            20                  25                  30

Arg Ile Thr Tyr Gly Glu Thr Gly Gly Asn Ser Pro Val Gln Glu Phe
            35                  40                  45

Thr Val Pro His Asp Leu Val Thr Ala Thr Ile Ser Gly Leu Lys Pro
    50                  55                  60

Gly Val Asp Tyr Thr Ile Thr Val Tyr Ala Val Thr Asp Met Met His
65                  70                  75                  80

Val Glu Tyr Thr Glu His Pro Ile Ser Ile Asn Tyr Arg Thr Glu Ile
                85                  90                  95

Asp Lys Gly Ser Gly Ser Gly Ser Gly Ser Gly Ser Gly Ser Gly Ser
            100                 105                 110

Gly Ser Gly Ser Gly Ser Val Ser Asp Val Pro Arg Asp Leu Glu Val
        115                 120                 125

Val Ala Ala Thr Pro Thr Ser Leu Leu Ile Ser Trp Ser Ala Arg Leu
    130                 135                 140

Lys Val Ala Arg Tyr Tyr Arg Ile Thr Tyr Gly Glu Thr Gly Gly Asn
145                 150                 155                 160

Ser Pro Val Gln Glu Phe Thr Val Pro Lys Asn Val Tyr Thr Ala Thr
                165                 170                 175

Ile Ser Gly Leu Lys Pro Gly Val Asp Tyr Thr Ile Thr Val Tyr Ala
            180                 185                 190

Val Thr Arg Phe Arg Asp Tyr Gln Pro Ile Ser Ile Asn Tyr Arg Thr
        195                 200                 205

Glu Ile Asp Lys Pro Cys Gln
    210                 215
```

<210> SEQ ID NO 90
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Val Ser Asp Val Pro Arg Asp Leu Glu Val Val Ala Ala Thr Pro Thr
1               5                   10                  15
```

```
Ser Leu Leu Ile Ser Trp Asp Ser Gly Arg Gly Ser Tyr Gln Tyr Tyr
             20                  25                  30

Arg Ile Thr Tyr Gly Glu Thr Gly Gly Asn Ser Pro Val Gln Glu Phe
             35                  40                  45

Thr Val Pro Gly Pro Val His Thr Ala Thr Ile Ser Gly Leu Lys Pro
 50                  55                  60

Gly Val Asp Tyr Thr Ile Thr Val Tyr Ala Val Thr Asp His Lys Pro
 65                  70                  75                  80

His Ala Asp Gly Pro His Thr Tyr His Glu Ser Pro Ile Ser Ile Asn
             85                  90                  95

Tyr Arg Thr Glu Ile Asp Lys Gly Ser Gly Ser Gly Ser Gly Ser Gly
            100                 105                 110

Ser Gly Ser Gly Ser Gly Ser Gly Ser Val Ser Asp Val Pro
            115                 120                 125

Arg Asp Leu Glu Val Val Ala Ala Thr Pro Thr Ser Leu Leu Ile Ser
130                 135                 140

Trp Ser Ala Arg Leu Lys Val Ala Arg Tyr Tyr Arg Ile Thr Tyr Gly
145                 150                 155                 160

Glu Thr Gly Gly Asn Ser Pro Val Gln Glu Phe Thr Val Pro Lys Asn
                165                 170                 175

Val Tyr Thr Ala Thr Ile Ser Gly Leu Lys Pro Gly Val Asp Tyr Thr
            180                 185                 190

Ile Thr Val Tyr Ala Val Thr Arg Phe Arg Asp Tyr Gln Pro Ile Ser
            195                 200                 205

Ile Asn Tyr Arg Thr Glu Ile Asp Lys Pro Cys Gln
    210                 215                 220

<210> SEQ ID NO 91
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Val Ser Asp Val Pro Arg Asp Leu Glu Val Val Ala Ala Thr Pro Thr
 1               5                  10                  15

Ser Leu Leu Ile Ser Trp Ser Ala Arg Leu Lys Val Ala Arg Tyr Tyr
             20                  25                  30

Arg Ile Thr Tyr Gly Glu Thr Gly Gly Asn Ser Pro Val Gln Glu Phe
             35                  40                  45

Thr Val Pro Lys Asn Val Tyr Thr Ala Thr Ile Ser Gly Leu Lys Pro
 50                  55                  60

Gly Val Asp Tyr Thr Ile Thr Val Tyr Ala Val Thr Arg Phe Arg Asp
 65                  70                  75                  80

Tyr Gln Pro Ile Ser Ile Asn Tyr Arg Thr Glu Ile Asp Lys Gly Ser
             85                  90                  95

Gly Ser Gly Ser Gly Ser Gly Ser Gly Ser Gly Ser Gly Ser Gly Ser
            100                 105                 110

Gly Ser Val Ser Asp Val Pro Arg Asp Leu Glu Val Val Ala Ala Thr
            115                 120                 125

Pro Thr Ser Leu Leu Ile Ser Trp Val Ala Gly Ala Glu Asp Tyr Gln
130                 135                 140

Tyr Tyr Arg Ile Thr Tyr Gly Glu Thr Gly Gly Asn Ser Pro Val Gln
```

```
                145                 150                 155                 160
Glu Phe Thr Val Pro His Asp Leu Val Thr Ala Thr Ile Ser Gly Leu
                165                 170                 175

Lys Pro Gly Val Asp Tyr Thr Ile Thr Val Tyr Ala Val Thr Asp Met
                180                 185                 190

Met His Val Glu Tyr Thr Glu His Pro Ile Ser Ile Asn Tyr Arg Thr
                195                 200                 205

Glu Ile Asp Lys Pro Cys Gln
                210                 215

<210> SEQ ID NO 92
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Val Ser Asp Val Pro Arg Asp Leu Glu Val Val Ala Ala Thr Pro Thr
  1               5                  10                  15

Ser Leu Leu Ile Ser Trp Ser Ala Arg Leu Lys Val Ala Arg Tyr Tyr
                 20                  25                  30

Arg Ile Thr Tyr Gly Glu Thr Gly Gly Asn Ser Pro Val Gln Glu Phe
             35                  40                  45

Thr Val Pro Lys Asn Val Tyr Thr Ala Thr Ile Ser Gly Leu Lys Pro
         50                  55                  60

Gly Val Asp Tyr Thr Ile Thr Val Tyr Ala Val Thr Arg Phe Arg Asp
 65                  70                  75                  80

Tyr Gln Pro Ile Ser Ile Asn Tyr Arg Thr Glu Ile Asp Lys Gly Ser
                 85                  90                  95

Gly Ser Gly Ser Gly Ser Gly Ser Gly Ser Gly Ser Gly Ser Gly Ser
                100                 105                 110

Gly Ser Val Ser Asp Val Pro Arg Asp Leu Glu Val Val Ala Ala Thr
             115                 120                 125

Pro Thr Ser Leu Leu Ile Ser Trp Asp Ser Gly Arg Gly Ser Tyr Gln
         130                 135                 140

Tyr Tyr Arg Ile Thr Tyr Gly Glu Thr Gly Gly Asn Ser Pro Val Gln
145                 150                 155                 160

Glu Phe Thr Val Pro Gly Pro Val His Thr Ala Thr Ile Ser Gly Leu
                165                 170                 175

Lys Pro Gly Val Asp Tyr Thr Ile Thr Val Tyr Ala Val Thr Asp His
                180                 185                 190

Lys Pro His Ala Asp Gly Pro His Thr Tyr His Glu Ser Pro Ile Ser
                195                 200                 205

Ile Asn Tyr Arg Thr Glu Ile Asp Lys Pro Cys Gln
                210                 215                 220

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Pro Ala Pro Ala Pro Ala
```

```
1               5

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Pro Ala Pro Ala Pro Ala Pro Ala Pro Ala Pro Ala
1               5                   10

<210> SEQ ID NO 95
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Pro Ala Pro Ala Pro Ala Pro Ala Pro Ala Pro Ala Pro Ala Pro Ala
1               5                   10                  15

Pro Ala

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Glu Gly Ser Gly Ser
1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Glu Gly Ser Gly Cys
1               5

<210> SEQ ID NO 98
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (96)..(113)
<223> OTHER INFORMATION: This region may encompass 3, 6, or 9 "Pro-Ala"
      repeats
<220> FEATURE:
<221> NAME/KEY: MOD_RES
<222> LOCATION: (208)..(208)
<223> OTHER INFORMATION: Ser or Cys

<400> SEQUENCE: 98
```

```
Val Ser Asp Val Pro Arg Asp Leu Glu Val Val Ala Ala Thr Pro Thr
1               5                   10                  15

Ser Leu Leu Ile Ser Trp Leu Pro Gly Lys Leu Arg Tyr Gln Tyr Tyr
            20                  25                  30

Arg Ile Thr Tyr Gly Glu Thr Gly Gly Asn Ser Pro Val Gln Glu Phe
        35                  40                  45

Thr Val Pro His Asp Leu Arg Thr Ala Thr Ile Ser Gly Leu Lys Pro
50                  55                  60

Gly Val Asp Tyr Thr Ile Thr Val Tyr Ala Val Thr Asn Met Met His
65                  70                  75                  80

Val Glu Tyr Ser Glu Tyr Pro Ile Ser Ile Asn Tyr Arg Thr Glu Pro
                85                  90                  95

Ala Pro Ala Pro Ala Pro Ala Pro Ala Pro Ala Pro Ala Pro Ala Pro
                100                 105                 110

Ala Val Ser Asp Val Pro Arg Asp Leu Glu Val Val Ala Ala Thr Pro
            115                 120                 125

Thr Ser Leu Leu Ile Ser Trp Ser Ala Arg Leu Lys Val Ala Arg Tyr
130                 135                 140

Tyr Arg Ile Thr Tyr Gly Glu Thr Gly Gly Asn Ser Pro Val Gln Glu
145                 150                 155                 160

Phe Thr Val Pro Lys Asn Val Tyr Thr Ala Thr Ile Ser Gly Leu Lys
                165                 170                 175

Pro Gly Val Asp Tyr Thr Ile Thr Val Tyr Ala Val Thr Arg Phe Arg
                180                 185                 190

Asp Tyr Gln Pro Ile Ser Ile Asn Tyr Arg Thr Glu Gly Ser Gly Xaa
            195                 200                 205
```

<210> SEQ ID NO 99
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (92)..(109)
<223> OTHER INFORMATION: This region may encompass 3, 6, or 9 "Pro-Ala"
      repeats
<220> FEATURE:
<221> NAME/KEY: MOD_RES
<222> LOCATION: (208)..(208)
<223> OTHER INFORMATION: Ser or Cys

<400> SEQUENCE: 99

```
Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
50                  55                  60

Gly Val Asp Tyr Thr Ile Thr Val Tyr Ala Val Thr Arg Phe Arg Asp
65                  70                  75                  80

Tyr Gln Pro Ile Ser Ile Asn Tyr Arg Thr Glu Pro Ala Pro Ala Pro
                85                  90                  95

Ala Pro Ala Pro Ala Pro Ala Pro Ala Pro Ala Pro Ala Val Ser Asp
```

```
              100                 105                 110
Val Pro Arg Asp Leu Glu Val Val Ala Ala Thr Pro Thr Ser Leu Leu
            115                 120                 125

Ile Ser Trp Leu Pro Gly Lys Leu Arg Tyr Gln Tyr Tyr Arg Ile Thr
        130                 135                 140

Tyr Gly Glu Thr Gly Gly Asn Ser Pro Val Gln Glu Phe Thr Val Pro
145                 150                 155                 160

His Asp Leu Arg Thr Ala Thr Ile Ser Gly Leu Lys Pro Gly Val Asp
                165                 170                 175

Tyr Thr Ile Thr Val Tyr Ala Val Thr Asn Met Met His Val Glu Tyr
            180                 185                 190

Ser Glu Tyr Pro Ile Ser Ile Asn Tyr Arg Thr Glu Gly Ser Gly Xaa
        195                 200                 205
```

<210> SEQ ID NO 100
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (96)..(113)
<223> OTHER INFORMATION: This region may encompass 3, 6, or 9 "Pro-Ala"
      repeats
<220> FEATURE:
<221> NAME/KEY: MOD_RES
<222> LOCATION: (208)..(208)
<223> OTHER INFORMATION: Ser or Cys

<400> SEQUENCE: 100

```
Val Ser Asp Val Pro Arg Asp Leu Glu Val Val Ala Ala Thr Pro Thr
1               5                   10                  15

Ser Leu Leu Ile Ser Trp Val Ala Gly Ala Glu Asp Tyr Gln Tyr Tyr
            20                  25                  30

Arg Ile Thr Tyr Gly Glu Thr Gly Gly Asn Ser Pro Val Gln Glu Phe
        35                  40                  45

Thr Val Pro His Asp Leu Val Thr Ala Thr Ile Ser Gly Leu Lys Pro
    50                  55                  60

Gly Val Asp Tyr Thr Ile Thr Val Tyr Ala Val Thr Asp Met Met His
65                  70                  75                  80

Val Glu Tyr Thr Glu His Pro Ile Ser Ile Asn Tyr Arg Thr Glu Pro
                85                  90                  95

Ala Pro Ala Pro Ala Pro Ala Pro Ala Pro Ala Pro Ala Pro Ala Pro
            100                 105                 110

Ala Val Ser Asp Val Pro Arg Asp Leu Glu Val Val Ala Ala Thr Pro
        115                 120                 125

Thr Ser Leu Leu Ile Ser Trp Ser Ala Arg Leu Lys Val Ala Arg Tyr
    130                 135                 140

Tyr Arg Ile Thr Tyr Gly Glu Thr Gly Gly Asn Ser Pro Val Gln Glu
145                 150                 155                 160

Phe Thr Val Pro Lys Asn Val Tyr Thr Ala Thr Ile Ser Gly Leu Lys
                165                 170                 175

Pro Gly Val Asp Tyr Thr Ile Thr Val Tyr Ala Val Thr Arg Phe Arg
            180                 185                 190

Asp Tyr Gln Pro Ile Ser Ile Asn Tyr Arg Thr Glu Gly Ser Gly Xaa
        195                 200                 205
```

```
<210> SEQ ID NO 101
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (101)..(118)
<223> OTHER INFORMATION: This region may encompass 3, 6, or 9 "Pro-Ala"
      repeats
<220> FEATURE:
<221> NAME/KEY: MOD_RES
<222> LOCATION: (213)..(213)
<223> OTHER INFORMATION: Ser or Cys

<400> SEQUENCE: 101

Val Ser Asp Val Pro Arg Asp Leu Glu Val Val Ala Ala Thr Pro Thr
1               5                   10                  15

Ser Leu Leu Ile Ser Trp Asp Ser Gly Arg Gly Ser Tyr Gln Tyr Tyr
            20                  25                  30

Arg Ile Thr Tyr Gly Glu Thr Gly Gly Asn Ser Pro Val Gln Glu Phe
        35                  40                  45

Thr Val Pro Gly Pro Val His Thr Ala Thr Ile Ser Gly Leu Lys Pro
    50                  55                  60

Gly Val Asp Tyr Thr Ile Thr Val Tyr Ala Val Thr Asp His Lys Pro
65                  70                  75                  80

His Ala Asp Gly Pro His Thr Tyr His Glu Ser Pro Ile Ser Ile Asn
                85                  90                  95

Tyr Arg Thr Glu Pro Ala Pro Ala Pro Ala Pro Ala Pro Ala Pro Ala
            100                 105                 110

Pro Ala Pro Ala Pro Ala Val Ser Asp Val Pro Arg Asp Leu Glu Val
        115                 120                 125

Val Ala Ala Thr Pro Thr Ser Leu Leu Ile Ser Trp Ser Ala Arg Leu
    130                 135                 140

Lys Val Ala Arg Tyr Tyr Arg Ile Thr Tyr Gly Glu Thr Gly Gly Asn
145                 150                 155                 160

Ser Pro Val Gln Glu Phe Thr Val Pro Lys Asn Val Tyr Thr Ala Thr
                165                 170                 175

Ile Ser Gly Leu Lys Pro Gly Val Asp Tyr Thr Ile Thr Val Tyr Ala
            180                 185                 190

Val Thr Arg Phe Arg Asp Tyr Gln Pro Ile Ser Ile Asn Tyr Arg Thr
        195                 200                 205

Glu Gly Ser Gly Xaa
    210

<210> SEQ ID NO 102
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (92)..(109)
<223> OTHER INFORMATION: This region may encompass 3, 6, or 9 "Pro-Ala"
      repeats
<220> FEATURE:
<221> NAME/KEY: MOD_RES
<222> LOCATION: (208)..(208)
<223> OTHER INFORMATION: Ser or Cys
```

<400> SEQUENCE: 102

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Arg Phe Arg Asp
65                  70                  75                  80

Tyr Gln Pro Ile Ser Ile Asn Tyr Arg Thr Glu Pro Ala Pro Ala Pro
                85                  90                  95

Ala Pro Ala Pro Ala Pro Ala Pro Ala Pro Ala Pro Val Ser Asp
            100                 105                 110

Val Pro Arg Asp Leu Glu Val Val Ala Ala Thr Pro Thr Ser Leu Leu
            115                 120                 125

Ile Ser Trp Val Ala Gly Ala Glu Asp Tyr Gln Tyr Tyr Arg Ile Thr
        130                 135                 140

Tyr Gly Glu Thr Gly Gly Asn Ser Pro Val Gln Glu Phe Thr Val Pro
145                 150                 155                 160

His Asp Leu Val Thr Ala Thr Ile Ser Gly Leu Lys Pro Gly Val Asp
                165                 170                 175

Tyr Thr Ile Thr Val Tyr Ala Val Thr Asp Met Met His Val Glu Tyr
            180                 185                 190

Thr Glu His Pro Ile Ser Ile Asn Tyr Arg Thr Glu Gly Ser Gly Xaa
        195                 200                 205

<210> SEQ ID NO 103
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (92)..(109)
<223> OTHER INFORMATION: This region may encompass 3, 6, or 9 "Pro-Ala"
      repeats
<220> FEATURE:
<221> NAME/KEY: MOD_RES
<222> LOCATION: (213)..(213)
<223> OTHER INFORMATION: Ser or Cys

<400> SEQUENCE: 103

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Arg Phe Arg Asp
65                  70                  75                  80

Tyr Gln Pro Ile Ser Ile Asn Tyr Arg Thr Glu Pro Ala Pro Ala Pro
                85                  90                  95

```
Ala Pro Ala Pro Ala Pro Ala Pro Ala Pro Ala Val Ser Asp
            100                 105                 110

Val Pro Arg Asp Leu Glu Val Val Ala Ala Thr Pro Thr Ser Leu Leu
            115                 120                 125

Ile Ser Trp Asp Ser Gly Arg Gly Ser Tyr Gln Tyr Tyr Arg Ile Thr
130                 135                 140

Tyr Gly Glu Thr Gly Gly Asn Ser Pro Val Gln Glu Phe Thr Val Pro
145                 150                 155                 160

Gly Pro Val His Thr Ala Thr Ile Ser Gly Leu Lys Pro Gly Val Asp
                165                 170                 175

Tyr Thr Ile Thr Val Tyr Ala Val Thr Asp His Lys Pro His Ala Asp
            180                 185                 190

Gly Pro His Thr Tyr His Glu Ser Pro Ile Ser Ile Asn Tyr Arg Thr
            195                 200                 205

Glu Gly Ser Gly Xaa
    210

<210> SEQ ID NO 104
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Val Ser Asp Val Pro Arg Asp Leu Glu Val Val Ala Ala Thr Pro Thr
1               5                   10                  15

Ser Leu Leu Ile Ser Trp Leu Pro Gly Lys Leu Arg Tyr Gln Tyr Tyr
            20                  25                  30

Arg Ile Thr Tyr Gly Glu Thr Gly Gly Asn Ser Pro Val Gln Glu Phe
        35                  40                  45

Thr Val Pro His Asp Leu Arg Thr Ala Thr Ile Ser Gly Leu Lys Pro
    50                  55                  60

Gly Val Asp Tyr Thr Ile Thr Val Tyr Ala Val Thr Asn Met Met His
65                  70                  75                  80

Val Glu Tyr Ser Glu Tyr Pro Ile Ser Ile Asn Tyr Arg Thr Glu Ile
                85                  90                  95

Asp Lys Gly Ser Gly Ser Gly Ser Gly Ser Gly Ser Gly Ser Gly Ser
            100                 105                 110

Gly Ser Gly Ser Gly Ser Val Ser Asp Val Pro Arg Asp Leu Glu Val
            115                 120                 125

Val Ala Ala Thr Pro Thr Ser Leu Leu Ile Ser Trp Ser Ala Arg Leu
130                 135                 140

Lys Val Ala Arg Tyr Tyr Arg Ile Thr Tyr Gly Glu Thr Gly Gly Asn
145                 150                 155                 160

Ser Pro Val Gln Glu Phe Thr Val Pro Lys Asn Val Tyr Thr Ala Thr
            165                 170                 175

Ile Ser Gly Leu Lys Pro Gly Val Asp Tyr Thr Ile Thr Val Tyr Ala
            180                 185                 190

Val Thr Arg Phe Arg Asp Tyr Gln Pro Ile Ser Ile Asn Tyr Arg Thr
            195                 200                 205

Glu Ile Asp Lys Pro Ser Gln
    210                 215
```

```
<210> SEQ ID NO 105
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Arg Phe Arg Asp
65                  70                  75                  80

Tyr Gln Pro Ile Ser Ile Asn Tyr Arg Thr Glu Ile Asp Lys Gly Ser
                85                  90                  95

Gly Ser Gly Ser Gly Ser Gly Ser Gly Ser Gly Ser Gly Ser Gly Ser
            100                 105                 110

Gly Ser Val Ser Asp Val Pro Arg Asp Leu Glu Val Val Ala Ala Thr
        115                 120                 125

Pro Thr Ser Leu Leu Ile Ser Trp Leu Pro Gly Lys Leu Arg Tyr Gln
    130                 135                 140

Tyr Tyr Arg Ile Thr Tyr Gly Glu Thr Gly Gly Asn Ser Pro Val Gln
145                 150                 155                 160

Glu Phe Thr Val Pro His Asp Leu Arg Thr Ala Thr Ile Ser Gly Leu
                165                 170                 175

Lys Pro Gly Val Asp Tyr Thr Ile Thr Val Tyr Ala Val Thr Asn Met
            180                 185                 190

Met His Val Glu Tyr Ser Glu Tyr Pro Ile Ser Ile Asn Tyr Arg Thr
        195                 200                 205

Glu Ile Asp Lys Pro Ser Gln
    210                 215

<210> SEQ ID NO 106
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Val Ser Asp Val Pro Arg Asp Leu Glu Val Val Ala Ala Thr Pro Thr
1               5                   10                  15

Ser Leu Leu Ile Ser Trp His Glu Arg Asp Gly Ser Arg Gln Tyr Tyr
            20                  25                  30

Arg Ile Thr Tyr Gly Glu Thr Gly Gly Asn Ser Pro Val Gln Glu Phe
        35                  40                  45

Thr Val Pro Gly Gly Val Arg Thr Ala Thr Ile Ser Gly Leu Lys Pro
    50                  55                  60

Gly Val Asp Tyr Thr Ile Thr Val Tyr Ala Val Thr Asp Tyr Phe Asn
65                  70                  75                  80

Pro Thr Thr His Glu Tyr Ile Tyr Gln Thr Thr Pro Ile Ser Ile Asn
```

Tyr Arg Thr

<210> SEQ ID NO 107
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Gly Val Ser Asp Val Pro Arg Asp Leu Glu Val Val Ala Ala Thr
1               5                   10                  15

Pro Thr Ser Leu Leu Ile Ser Trp His Glu Arg Asp Gly Ser Arg Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Phe Asn Pro Thr Thr His Glu Tyr Ile Tyr Gln Thr Thr Pro Ile Ser
                85                  90                  95

Ile Asn Tyr Arg Thr Glu Ile Asp Lys Pro Ser Gln His His His His
            100                 105                 110

His His

<210> SEQ ID NO 108
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Val Val Ala Ala Thr Pro Thr Ser Leu Leu Ile Ser Trp His Glu
1               5                   10                  15

Arg Asp Gly Ser Arg Gln Tyr Tyr Arg Ile Thr Tyr Gly Glu Thr Gly
            20                  25                  30

Gly Asn Ser Pro Val Gln Glu Phe Thr Val Pro Gly Gly Val Arg Thr
        35                  40                  45

Ala Thr Ile Ser Gly Leu Lys Pro Gly Val Asp Tyr Thr Ile Thr Val
    50                  55                  60

Tyr Ala Val Thr Asp Tyr Phe Asn Pro Thr Thr His Glu Tyr Ile Tyr
65                  70                  75                  80

Gln Thr Thr Pro Ile Ser Ile Asn Tyr Arg Thr
                85                  90

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Trp His Glu Arg Asp Gly Ser Arg Gln

```
1               5                   10
```

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

```
Pro Gly Gly Val Arg Thr
1               5
```

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

```
Thr Asp Tyr Phe Asn Pro Thr Thr His Glu Tyr Ile Tyr Gln Thr Thr
1               5                   10                  15

Pro
```

<210> SEQ ID NO 112
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Val Ser Asp Val Pro Arg Asp Leu Glu Val Val Ala Ala Thr Pro Thr
1               5                   10                  15

Ser Leu Leu Ile Ser Trp Trp Ala Pro Val Asp Arg Tyr Gln Tyr Tyr
                20                  25                  30

Arg Ile Thr Tyr Gly Glu Thr Gly Gly Asn Ser Pro Val Gln Glu Phe
            35                  40                  45

Thr Val Pro Arg Asp Val Tyr Thr Ala Thr Ile Ser Gly Leu Lys Pro
        50                  55                  60

Gly Val Asp Tyr Thr Ile Thr Val Tyr Ala Val Thr Asp Tyr Lys Pro
65                  70                  75                  80

His Ala Asp Gly Pro His Thr Tyr His Glu Ser Pro Ile Ser Ile Asn
                85                  90                  95

Tyr Arg Thr
```

<210> SEQ ID NO 113
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (107)..(107)
<223> OTHER INFORMATION: Ser or Cys

<400> SEQUENCE: 113

```
Met Gly Val Ser Asp Val Pro Arg Asp Leu Glu Val Val Ala Ala Thr
```

```
               1               5                  10                 15
    Pro Thr Ser Leu Leu Ile Ser Trp Trp Ala Pro Val Asp Arg Tyr Gln
                        20                  25                  30

Tyr Tyr Arg Ile Thr Tyr Gly Glu Thr Gly Gly Asn Ser Pro Val Gln
                   35                  40                  45

Glu Phe Thr Val Pro Arg Asp Val Tyr Thr Ala Thr Ile Ser Gly Leu
              50                  55                  60

Lys Pro Gly Val Asp Tyr Thr Ile Thr Val Tyr Ala Val Thr Asp Tyr
    65                  70                  75                  80

Lys Pro His Ala Asp Gly Pro His Thr Tyr His Glu Ser Pro Ile Ser
                        85                  90                  95

Ile Asn Tyr Arg Thr Glu Ile Asp Lys Pro Xaa Gln
                       100                 105
```

```
<210> SEQ ID NO 114
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114
```

```
    Glu Val Val Ala Ala Thr Pro Thr Ser Leu Leu Ile Ser Trp Trp Ala
    1               5                  10                  15

Pro Val Asp Arg Tyr Gln Tyr Tyr Arg Ile Thr Tyr Gly Glu Thr Gly
                        20                  25                  30

Gly Asn Ser Pro Val Gln Glu Phe Thr Val Pro Arg Asp Val Tyr Thr
                   35                  40                  45

Ala Thr Ile Ser Gly Leu Lys Pro Gly Val Asp Tyr Thr Ile Thr Val
              50                  55                  60

Tyr Ala Val Thr Asp Tyr Lys Pro His Ala Asp Gly Pro His Thr Tyr
    65                  70                  75                  80

His Glu Ser Pro Ile Ser Ile Asn Tyr Arg Thr
                        85                  90
```

```
<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ser Trp Trp Ala Pro Val Asp Arg Tyr Gln
1               5                  10
```

```
<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Pro Arg Asp Val Tyr Thr
1               5
```

```
<210> SEQ ID NO 117
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Thr Asp Tyr Lys Pro His Ala Asp Gly Pro His Thr Tyr His Glu Ser
1               5                   10                  15

Pro

<210> SEQ ID NO 118
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Val Ser Asp Val Pro Arg Asp Leu Glu Val Val Ala Ala Thr Pro Thr
1               5                   10                  15

Ser Leu Leu Ile Ser Trp His Glu Arg Asp Gly Ser Arg Gln Tyr Tyr
                20                  25                  30

Arg Ile Thr Tyr Gly Glu Thr Gly Gly Asn Ser Pro Val Gln Glu Phe
                35                  40                  45

Thr Val Pro Gly Gly Val Arg Thr Ala Thr Ile Ser Gly Leu Lys Pro
        50                  55                  60

Gly Val Asp Tyr Thr Ile Thr Val Tyr Ala Val Thr Asp Tyr Phe Asn
65                  70                  75                  80

Pro Thr Thr His Glu Tyr Ile Tyr Gln Thr Thr Pro Ile Ser Ile Asn
                85                  90                  95

Tyr Arg Thr Glu Ile Asp Lys Gly Ser Gly Ser Gly Ser Gly Ser Gly
                100                 105                 110

Ser Gly Ser Gly Ser Gly Ser Gly Ser Val Ser Asp Val Pro
                115                 120                 125

Arg Asp Leu Glu Val Val Ala Ala Thr Pro Thr Ser Leu Leu Ile Ser
        130                 135                 140

Trp Ser Ala Arg Leu Lys Val Ala Arg Tyr Tyr Arg Ile Thr Tyr Gly
145                 150                 155                 160

Glu Thr Gly Gly Asn Ser Pro Val Gln Glu Phe Thr Val Pro Lys Asn
                165                 170                 175

Val Tyr Thr Ala Thr Ile Ser Gly Leu Lys Pro Gly Val Asp Tyr Thr
                180                 185                 190

Ile Thr Val Tyr Ala Val Thr Arg Phe Arg Asp Tyr Gln Pro Ile Ser
            195                 200                 205

Ile Asn Tyr Arg Thr
        210

<210> SEQ ID NO 119
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (219)..(219)
<223> OTHER INFORMATION: Ser or Cys
```

```
<400> SEQUENCE: 119

Val Ser Asp Val Pro Arg Asp Leu Glu Val Val Ala Ala Thr Pro Thr
1               5                   10                  15

Ser Leu Leu Ile Ser Trp His Glu Arg Asp Gly Ser Arg Gln Tyr Tyr
            20                  25                  30

Arg Ile Thr Tyr Gly Glu Thr Gly Asn Ser Pro Val Gln Glu Phe
        35                  40                  45

Thr Val Pro Gly Gly Val Arg Thr Ala Thr Ile Ser Gly Leu Lys Pro
    50                  55                  60

Gly Val Asp Tyr Thr Ile Thr Val Tyr Ala Val Thr Asp Tyr Phe Asn
65                  70                  75                  80

Pro Thr Thr His Glu Tyr Ile Tyr Gln Thr Thr Pro Ile Ser Ile Asn
                85                  90                  95

Tyr Arg Thr Glu Ile Asp Lys Gly Ser Gly Ser Gly Ser Gly Ser Gly
            100                 105                 110

Ser Gly Ser Gly Ser Gly Ser Gly Ser Val Ser Asp Val Pro
            115                 120                 125

Arg Asp Leu Glu Val Val Ala Ala Thr Pro Thr Ser Leu Leu Ile Ser
130                 135                 140

Trp Ser Ala Arg Leu Lys Val Ala Arg Tyr Arg Ile Thr Tyr Gly
145                 150                 155                 160

Glu Thr Gly Gly Asn Ser Pro Val Gln Glu Phe Thr Val Pro Lys Asn
                165                 170                 175

Val Tyr Thr Ala Thr Ile Ser Gly Leu Lys Pro Gly Val Asp Tyr Thr
            180                 185                 190

Ile Thr Val Tyr Ala Val Thr Arg Phe Arg Asp Tyr Gln Pro Ile Ser
            195                 200                 205

Ile Asn Tyr Arg Thr Glu Ile Asp Lys Pro Xaa Gln
            210                 215                 220

<210> SEQ ID NO 120
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Gly Val Ser Asp Val Pro Arg Asp Leu Glu Val Val Ala Ala Thr
1               5                   10                  15

Pro Thr Ser Leu Leu Ile Ser Trp His Glu Arg Asp Gly Ser Arg Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Phe Asn Pro Thr Thr His Glu Tyr Ile Tyr Gln Thr Thr Pro Ile Ser
                85                  90                  95

Ile Asn Tyr Arg Thr Glu Ile Asp Lys Gly Ser Gly Ser Gly Ser Gly
            100                 105                 110

Ser Gly Ser Gly Ser Gly Ser Gly Ser Gly Ser Val Ser Asp
            115                 120                 125
```

```
Val Pro Arg Asp Leu Glu Val Ala Ala Thr Pro Thr Ser Leu Leu
    130                 135                 140

Ile Ser Trp Ser Ala Arg Leu Lys Val Ala Arg Tyr Tyr Arg Ile Thr
145                 150                 155                 160

Tyr Gly Glu Thr Gly Gly Asn Ser Pro Val Gln Glu Phe Thr Val Pro
                165                 170                 175

Lys Asn Val Tyr Thr Ala Thr Ile Ser Gly Leu Lys Pro Gly Val Asp
                180                 185                 190

Tyr Thr Ile Thr Val Tyr Ala Val Thr Arg Phe Arg Asp Tyr Gln Pro
            195                 200                 205

Ile Ser Ile Asn Tyr Arg Thr Glu Ile Asp Lys Pro Cys Gln His His
    210                 215                 220

His His His His
225

<210> SEQ ID NO 121
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (101)..(118)
<223> OTHER INFORMATION: This region may encompass 3, 6, or 9 "Pro-Ala"
      repeats

<400> SEQUENCE: 121

Val Ser Asp Val Pro Arg Asp Leu Glu Val Val Ala Ala Thr Pro Thr
1               5                   10                  15

Ser Leu Leu Ile Ser Trp His Glu Arg Asp Gly Ser Arg Gln Tyr Tyr
                20                  25                  30

Arg Ile Thr Tyr Gly Glu Thr Gly Gly Asn Ser Pro Val Gln Glu Phe
            35                  40                  45

Thr Val Pro Gly Gly Val Arg Thr Ala Thr Ile Ser Gly Leu Lys Pro
        50                  55                  60

Gly Val Asp Tyr Thr Ile Thr Val Tyr Ala Val Thr Asp Tyr Phe Asn
65                  70                  75                  80

Pro Thr Thr His Glu Tyr Ile Tyr Gln Thr Thr Pro Ile Ser Ile Asn
                85                  90                  95

Tyr Arg Thr Glu Pro Ala Pro Ala Pro Ala Pro Ala Pro Ala Pro Ala
                100                 105                 110

Pro Ala Pro Ala Pro Ala Val Ser Asp Val Pro Arg Asp Leu Glu Val
            115                 120                 125

Val Ala Ala Thr Pro Thr Ser Leu Leu Ile Ser Trp Ser Ala Arg Leu
        130                 135                 140

Lys Val Ala Arg Tyr Tyr Arg Ile Thr Tyr Gly Glu Thr Gly Gly Asn
145                 150                 155                 160

Ser Pro Val Gln Glu Phe Thr Val Pro Lys Asn Val Tyr Thr Ala Thr
                165                 170                 175

Ile Ser Gly Leu Lys Pro Gly Val Asp Tyr Thr Ile Thr Val Tyr Ala
            180                 185                 190

Val Thr Arg Phe Arg Asp Tyr Gln Pro Ile Ser Ile Asn Tyr Arg Thr
        195                 200                 205

Glu Ile Asp Lys Pro Cys Gln His His His His His His
    210                 215                 220
```

```
<210> SEQ ID NO 122
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Arg Phe Arg Asp
65                  70                  75                  80

Tyr Gln Pro Ile Ser Ile Asn Tyr Arg Thr Glu Ile Asp Lys Gly Ser
                85                  90                  95

Gly Ser Gly Ser Gly Ser Gly Ser Gly Ser Gly Ser Gly Ser Gly Ser
            100                 105                 110

Gly Ser Val Ser Asp Val Pro Arg Asp Leu Glu Val Val Ala Ala Thr
        115                 120                 125

Pro Thr Ser Leu Leu Ile Ser Trp His Glu Arg Asp Gly Ser Arg Gln
    130                 135                 140

Tyr Tyr Arg Ile Thr Tyr Gly Glu Thr Gly Gly Asn Ser Pro Val Gln
145                 150                 155                 160

Glu Phe Thr Val Pro Gly Gly Val Arg Thr Ala Thr Ile Ser Gly Leu
                165                 170                 175

Lys Pro Gly Val Asp Tyr Thr Ile Thr Val Tyr Ala Val Thr Asp Tyr
            180                 185                 190

Phe Asn Pro Thr Thr His Glu Tyr Ile Tyr Gln Thr Thr Pro Ile Ser
        195                 200                 205

Ile Asn Tyr Arg Thr
    210

<210> SEQ ID NO 123
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (219)..(219)
<223> OTHER INFORMATION: Ser or Cys

<400> SEQUENCE: 123

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
```

```
                    50                  55                  60
Gly Val Asp Tyr Thr Ile Thr Val Tyr Ala Val Thr Arg Phe Arg Asp
 65                  70                  75                  80

Tyr Gln Pro Ile Ser Ile Asn Tyr Arg Thr Glu Ile Asp Lys Gly Ser
                 85                  90                  95

Gly Ser Gly Ser Gly Ser Gly Ser Gly Ser Gly Ser Gly Ser Gly Ser
                100                 105                 110

Gly Ser Val Ser Asp Val Pro Arg Asp Leu Glu Val Val Ala Ala Thr
                115                 120                 125

Pro Thr Ser Leu Leu Ile Ser Trp His Glu Arg Asp Gly Ser Arg Gln
130                 135                 140

Tyr Tyr Arg Ile Thr Tyr Gly Glu Thr Gly Gly Asn Ser Pro Val Gln
145                 150                 155                 160

Glu Phe Thr Val Pro Gly Gly Val Arg Thr Ala Thr Ile Ser Gly Leu
                165                 170                 175

Lys Pro Gly Val Asp Tyr Thr Ile Thr Val Tyr Ala Val Thr Asp Tyr
                180                 185                 190

Phe Asn Pro Thr Thr His Glu Tyr Ile Tyr Gln Thr Pro Ile Ser
                195                 200                 205

Ile Asn Tyr Arg Thr Glu Ile Asp Lys Pro Xaa Gln
210                 215                 220
```

<210> SEQ ID NO 124
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Met Gly Val Ser Asp Val Pro Arg Asp Leu Glu Val Val Ala Ala Thr
  1               5                  10                  15

Pro Thr Ser Leu Leu Ile Ser Trp Ser Ala Arg Leu Lys Val Ala Arg
                 20                  25                  30

Tyr Tyr Arg Ile Thr Tyr Gly Glu Thr Gly Gly Asn Ser Pro Val Gln
                 35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Ile Asp Lys
                 85                  90                  95

Gly Ser Gly Ser Gly Ser Gly Ser Gly Ser Gly Ser Gly Ser Gly Ser
                100                 105                 110

Gly Ser Gly Ser Val Ser Asp Val Pro Arg Asp Leu Glu Val Val Ala
                115                 120                 125

Ala Thr Pro Thr Ser Leu Leu Ile Ser Trp His Glu Arg Asp Gly Ser
130                 135                 140

Arg Gln Tyr Tyr Arg Ile Thr Tyr Gly Glu Thr Gly Gly Asn Ser Pro
145                 150                 155                 160

Val Gln Glu Phe Thr Val Pro Gly Gly Val Arg Thr Ala Thr Ile Ser
                165                 170                 175

Gly Leu Lys Pro Gly Val Asp Tyr Thr Ile Thr Val Tyr Ala Val Thr
                180                 185                 190
```

```
Asp Tyr Phe Asn Pro Thr Thr His Glu Tyr Ile Tyr Gln Thr Thr Pro
            195                 200                 205

Ile Ser Ile Asn Tyr Arg Thr Glu Ile Asp Lys Pro Cys Gln His His
    210                 215                 220

His His His His
225

<210> SEQ ID NO 125
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (92)..(109)
<223> OTHER INFORMATION: This region may encompass 3, 6, or 9 "Pro-Ala"
      repeats
<220> FEATURE:
<221> NAME/KEY: MOD_RES
<222> LOCATION: (214)..(214)
<223> OTHER INFORMATION: Ser or Cys

<400> SEQUENCE: 125

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Arg Phe Arg Asp
65                  70                  75                  80

Tyr Gln Pro Ile Ser Ile Asn Tyr Arg Thr Glu Pro Ala Pro Ala Pro
            85                  90                  95

Ala Pro Ala Pro Ala Pro Ala Pro Ala Pro Ala Pro Ala Val Ser Asp
                100                 105                 110

Val Pro Arg Asp Leu Glu Val Val Ala Ala Thr Pro Thr Ser Leu Leu
            115                 120                 125

Ile Ser Trp His Glu Arg Asp Gly Ser Arg Gln Tyr Tyr Arg Ile Thr
        130                 135                 140

Tyr Gly Glu Thr Gly Gly Asn Ser Pro Val Gln Glu Phe Thr Val Pro
145                 150                 155                 160

Gly Gly Val Arg Thr Ala Thr Ile Ser Gly Leu Lys Pro Gly Val Asp
                165                 170                 175

Tyr Thr Ile Thr Val Tyr Ala Val Thr Asp Tyr Phe Asn Pro Thr Thr
            180                 185                 190

His Glu Tyr Ile Tyr Gln Thr Thr Pro Ile Ser Ile Asn Tyr Arg Thr
        195                 200                 205

Glu Ile Asp Lys Pro Xaa Gln
    210                 215

<210> SEQ ID NO 126
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 126

Val Ser Asp Val Pro Arg Asp Leu Glu Val Val Ala Ala Thr Pro Thr
1               5                   10                  15

Ser Leu Leu Ile Ser Trp Trp Ala Pro Val Asp Arg Tyr Gln Tyr Tyr
                20                  25                  30

Arg Ile Thr Tyr Gly Glu Thr Gly Gly Asn Ser Pro Val Gln Glu Phe
            35                  40                  45

Thr Val Pro Arg Asp Val Tyr Thr Ala Thr Ile Ser Gly Leu Lys Pro
        50                  55                  60

Gly Val Asp Tyr Thr Ile Thr Val Tyr Ala Val Thr Asp Tyr Lys Pro
65                  70                  75                  80

His Ala Asp Gly Pro His Thr Tyr His Glu Ser Pro Ile Ser Ile Asn
                85                  90                  95

Tyr Arg Thr Glu Ile Asp Lys Gly Ser Gly Ser Gly Ser Gly Ser Gly
            100                 105                 110

Ser Gly Ser Gly Ser Gly Ser Gly Ser Val Ser Asp Val Pro
        115                 120                 125

Arg Asp Leu Glu Val Val Ala Ala Thr Pro Thr Ser Leu Leu Ile Ser
    130                 135                 140

Trp Ser Ala Arg Leu Lys Val Ala Arg Tyr Tyr Arg Ile Thr Tyr Gly
145                 150                 155                 160

Glu Thr Gly Gly Asn Ser Pro Val Gln Glu Phe Thr Val Pro Lys Asn
                165                 170                 175

Val Tyr Thr Ala Thr Ile Ser Gly Leu Lys Pro Gly Val Asp Tyr Thr
            180                 185                 190

Ile Thr Val Tyr Ala Val Thr Arg Phe Arg Asp Tyr Gln Pro Ile Ser
            195                 200                 205

Ile Asn Tyr Arg Thr
        210

<210> SEQ ID NO 127
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (219)..(219)
<223> OTHER INFORMATION: Ser or Cys

<400> SEQUENCE: 127

Val Ser Asp Val Pro Arg Asp Leu Glu Val Val Ala Ala Thr Pro Thr
1               5                   10                  15

Ser Leu Leu Ile Ser Trp Trp Ala Pro Val Asp Arg Tyr Gln Tyr Tyr
                20                  25                  30

Arg Ile Thr Tyr Gly Glu Thr Gly Gly Asn Ser Pro Val Gln Glu Phe
            35                  40                  45

Thr Val Pro Arg Asp Val Tyr Thr Ala Thr Ile Ser Gly Leu Lys Pro
        50                  55                  60

Gly Val Asp Tyr Thr Ile Thr Val Tyr Ala Val Thr Asp Tyr Lys Pro
65                  70                  75                  80

His Ala Asp Gly Pro His Thr Tyr His Glu Ser Pro Ile Ser Ile Asn
                85                  90                  95

Tyr Arg Thr Glu Ile Asp Lys Gly Ser Gly Ser Gly Ser Gly Ser Gly
```

```
                100             105             110
Ser Gly Ser Gly Ser Gly Ser Gly Val Ser Asp Val Pro
            115             120             125
Arg Asp Leu Glu Val Val Ala Ala Thr Pro Thr Ser Leu Leu Ile Ser
130                 135                 140
Trp Ser Ala Arg Leu Lys Val Ala Arg Tyr Tyr Arg Ile Thr Tyr Gly
145                 150                 155                 160
Glu Thr Gly Gly Asn Ser Pro Val Gln Glu Phe Thr Val Pro Lys Asn
                165                 170                 175
Val Tyr Thr Ala Thr Ile Ser Gly Leu Lys Pro Gly Val Asp Tyr Thr
            180                 185                 190
Ile Thr Val Tyr Ala Val Thr Arg Phe Arg Asp Tyr Gln Pro Ile Ser
                195                 200                 205
Ile Asn Tyr Arg Thr Glu Ile Asp Lys Pro Xaa Gln
            210                 215                 220

<210> SEQ ID NO 128
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Gly Val Ser Asp Val Pro Arg Asp Leu Glu Val Val Ala Ala Thr
1               5                   10                  15
Pro Thr Ser Leu Leu Ile Ser Trp Trp Ala Pro Val Asp Arg Tyr Gln
            20                  25                  30
Tyr Tyr Arg Ile Thr Tyr Gly Glu Thr Gly Gly Asn Ser Pro Val Gln
        35                  40                  45
Glu Phe Thr Val Pro Arg Asp Val Tyr Thr Ala Thr Ile Ser Gly Leu
50                  55                  60
Lys Pro Gly Val Asp Tyr Thr Ile Thr Val Tyr Ala Val Thr Asp Tyr
65                  70                  75                  80
Lys Pro His Ala Asp Gly Pro His Thr Tyr His Glu Ser Pro Ile Ser
                85                  90                  95
Ile Asn Tyr Arg Thr Glu Ile Asp Lys Gly Ser Gly Ser Gly Ser Gly
            100                 105                 110
Ser Gly Ser Gly Ser Gly Ser Gly Ser Gly Ser Val Ser Asp
            115                 120                 125
Val Pro Arg Asp Leu Glu Val Val Ala Ala Thr Pro Thr Ser Leu Leu
130                 135                 140
Ile Ser Trp Ser Ala Arg Leu Lys Val Ala Arg Tyr Tyr Arg Ile Thr
145                 150                 155                 160
Tyr Gly Glu Thr Gly Gly Asn Ser Pro Val Gln Glu Phe Thr Val Pro
                165                 170                 175
Lys Asn Val Tyr Thr Ala Thr Ile Ser Gly Leu Lys Pro Gly Val Asp
            180                 185                 190
Tyr Thr Ile Thr Val Tyr Ala Val Thr Arg Phe Arg Asp Tyr Gln Pro
        195                 200                 205
Ile Ser Ile Asn Tyr Arg Thr Glu Ile Asp Lys Pro Cys Gln His His
210                 215                 220
His His His His
225
```

```
<210> SEQ ID NO 129
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (101)..(118)
<223> OTHER INFORMATION: This region may encompass 3, 6, or 9 "Pro-Ala"
      repeats
<220> FEATURE:
<221> NAME/KEY: MOD_RES
<222> LOCATION: (214)..(214)
<223> OTHER INFORMATION: Ser or Cys

<400> SEQUENCE: 129

Val Ser Asp Val Pro Arg Asp Leu Glu Val Val Ala Ala Thr Pro Thr
1               5                   10                  15

Ser Leu Leu Ile Ser Trp Trp Ala Pro Val Asp Arg Tyr Gln Tyr Tyr
            20                  25                  30

Arg Ile Thr Tyr Gly Glu Thr Gly Gly Asn Ser Pro Val Gln Glu Phe
        35                  40                  45

Thr Val Pro Arg Asp Val Tyr Thr Ala Thr Ile Ser Gly Leu Lys Pro
    50                  55                  60

Gly Val Asp Tyr Thr Ile Thr Val Tyr Ala Val Thr Asp Tyr Lys Pro
65                  70                  75                  80

His Ala Asp Gly Pro His Thr Tyr His Glu Ser Pro Ile Ser Ile Asn
                85                  90                  95

Tyr Arg Thr Glu Pro Ala Pro Ala Pro Ala Pro Ala Pro Ala Pro Ala
            100                 105                 110

Pro Ala Pro Ala Pro Ala Val Ser Asp Val Pro Arg Asp Leu Glu Val
        115                 120                 125

Val Ala Ala Thr Pro Thr Ser Leu Leu Ile Ser Trp Ser Ala Arg Leu
    130                 135                 140

Lys Val Ala Arg Tyr Tyr Arg Ile Thr Tyr Gly Glu Thr Gly Gly Asn
145                 150                 155                 160

Ser Pro Val Gln Glu Phe Thr Val Pro Lys Asn Val Tyr Thr Ala Thr
                165                 170                 175

Ile Ser Gly Leu Lys Pro Gly Val Asp Tyr Thr Ile Thr Val Tyr Ala
            180                 185                 190

Val Thr Arg Phe Arg Asp Tyr Gln Pro Ile Ser Ile Asn Tyr Arg Thr
        195                 200                 205

Glu Ile Asp Lys Pro Xaa Gln
    210                 215

<210> SEQ ID NO 130
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30
```

```
Arg Ile Thr Tyr Gly Glu Thr Gly Gly Asn Ser Pro Val Gln Glu Phe
            35                  40                  45

Thr Val Pro Lys Asn Val Tyr Thr Ala Thr Ile Ser Gly Leu Lys Pro
 50                  55                  60

Gly Val Asp Tyr Thr Ile Thr Val Tyr Ala Val Thr Arg Phe Arg Asp
 65                  70                  75                  80

Tyr Gln Pro Ile Ser Ile Asn Tyr Arg Thr Glu Ile Asp Lys Gly Ser
                 85                  90                  95

Gly Ser Gly Ser Gly Ser Gly Ser Gly Ser Gly Ser Gly Ser Gly Ser
            100                 105                 110

Gly Ser Val Ser Asp Val Pro Arg Asp Leu Glu Val Val Ala Ala Thr
            115                 120                 125

Pro Thr Ser Leu Leu Ile Ser Trp Trp Ala Pro Val Asp Arg Tyr Gln
130                 135                 140

Tyr Tyr Arg Ile Thr Tyr Gly Glu Thr Gly Gly Asn Ser Pro Val Gln
145                 150                 155                 160

Glu Phe Thr Val Pro Arg Asp Val Tyr Thr Ala Thr Ile Ser Gly Leu
                165                 170                 175

Lys Pro Gly Val Asp Tyr Thr Ile Thr Val Tyr Ala Val Thr Asp Tyr
            180                 185                 190

Lys Pro His Ala Asp Gly Pro His Thr Tyr His Glu Ser Pro Ile Ser
            195                 200                 205

Ile Asn Tyr Arg Thr
            210

<210> SEQ ID NO 131
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (219)..(219)
<223> OTHER INFORMATION: Ser or Cys

<400> SEQUENCE: 131

Val Ser Asp Val Pro Arg Asp Leu Glu Val Val Ala Ala Thr Pro Thr
 1               5                  10                  15

Ser Leu Leu Ile Ser Trp Ser Ala Arg Leu Lys Val Ala Arg Tyr Tyr
             20                  25                  30

Arg Ile Thr Tyr Gly Glu Thr Gly Gly Asn Ser Pro Val Gln Glu Phe
            35                  40                  45

Thr Val Pro Lys Asn Val Tyr Thr Ala Thr Ile Ser Gly Leu Lys Pro
 50                  55                  60

Gly Val Asp Tyr Thr Ile Thr Val Tyr Ala Val Thr Arg Phe Arg Asp
 65                  70                  75                  80

Tyr Gln Pro Ile Ser Ile Asn Tyr Arg Thr Glu Ile Asp Lys Gly Ser
                 85                  90                  95

Gly Ser Gly Ser Gly Ser Gly Ser Gly Ser Gly Ser Gly Ser Gly Ser
            100                 105                 110

Gly Ser Val Ser Asp Val Pro Arg Asp Leu Glu Val Val Ala Ala Thr
            115                 120                 125

Pro Thr Ser Leu Leu Ile Ser Trp Trp Ala Pro Val Asp Arg Tyr Gln
130                 135                 140

Tyr Tyr Arg Ile Thr Tyr Gly Glu Thr Gly Gly Asn Ser Pro Val Gln
```

```
                145                 150                 155                 160
Glu Phe Thr Val Pro Arg Asp Val Tyr Thr Ala Thr Ile Ser Gly Leu
                165                 170                 175

Lys Pro Gly Val Asp Tyr Thr Ile Thr Val Tyr Ala Val Thr Asp Tyr
                180                 185                 190

Lys Pro His Ala Asp Gly Pro His Thr Tyr His Glu Ser Pro Ile Ser
                195                 200                 205

Ile Asn Tyr Arg Thr Glu Ile Asp Lys Pro Xaa Gln
                210                 215                 220

<210> SEQ ID NO 132
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
                20                  25                  30

Tyr Tyr Arg Ile Thr Tyr Gly Glu Thr Gly Gly Asn Ser Pro Val Gln
                35                  40                  45

Glu Phe Thr Val Pro Lys Asn Val Tyr Thr Ala Thr Ile Ser Gly Leu
                50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
                100                 105                 110

Gly Ser Gly Ser Val Ser Asp Val Pro Arg Asp Leu Glu Val Val Ala
                115                 120                 125

Ala Thr Pro Thr Ser Leu Leu Ile Ser Trp Trp Ala Pro Val Asp Arg
                130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Tyr Thr Ala Thr Ile Ser
                165                 170                 175

Gly Leu Lys Pro Gly Val Asp Tyr Thr Ile Thr Val Tyr Ala Val Thr
                180                 185                 190

Asp Tyr Lys Pro His Ala Asp Gly Pro His Thr Tyr His Glu Ser Pro
                195                 200                 205

Ile Ser Ile Asn Tyr Arg Thr Glu Ile Asp Lys Pro Cys Gln His His
                210                 215                 220

His His His His
225

<210> SEQ ID NO 133
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<221> NAME/KEY: misc_feature
<222> LOCATION: (94)..(111)
<223> OTHER INFORMATION: This region may encompass 3, 6, or 9 "Pro-Ala" repeats
<220> FEATURE:
<221> NAME/KEY: MOD_RES
<222> LOCATION: (216)..(216)
<223> OTHER INFORMATION: Ser or Cys

<400> SEQUENCE: 133

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Pro Ala Pro
                85                  90                  95

Ala Pro Ala Pro Ala Pro Ala Pro Ala Pro Ala Pro Ala Pro Ala Val
            100                 105                 110

Ser Asp Val Pro Arg Asp Leu Glu Val Val Ala Ala Thr Pro Thr Ser
        115                 120                 125

Leu Leu Ile Ser Trp Trp Ala Pro Val Asp Arg Tyr Gln Tyr Tyr Arg
    130                 135                 140

Ile Thr Tyr Gly Glu Thr Gly Gly Asn Ser Pro Val Gln Glu Phe Thr
145                 150                 155                 160

Val Pro Arg Asp Val Tyr Thr Ala Thr Ile Ser Gly Leu Lys Pro Gly
                165                 170                 175

Val Asp Tyr Thr Ile Thr Val Tyr Ala Val Thr Asp Tyr Lys Pro His
            180                 185                 190

Ala Asp Gly Pro His Thr Tyr His Glu Ser Pro Ile Ser Ile Asn Tyr
        195                 200                 205

Arg Thr Glu Ile Asp Lys Pro Xaa Gln
    210                 215

<210> SEQ ID NO 134
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(5)
<223> OTHER INFORMATION: Any amino acid; this region may encompass 0-5 residues
<220> FEATURE:
<221> NAME/KEY: MOD_RES
<222> LOCATION: (14)..(18)
<223> OTHER INFORMATION: Any amino acid; this region may encompass 0-5 residues

<400> SEQUENCE: 134

Xaa Xaa Xaa Xaa Xaa His Glu Arg Asp Gly Ser Arg Gln Xaa Xaa Xaa
1               5                   10                  15

Xaa Xaa

<210> SEQ ID NO 135
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (10)..(14)
<223> OTHER INFORMATION: Any amino acid; this region may encompass 0-5
      residues

<400> SEQUENCE: 135

Xaa Xaa Xaa Xaa Xaa Gly Gly Val Arg Xaa Xaa Xaa Xaa Xaa
 1               5                  10

<210> SEQ ID NO 136
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (21)..(25)
<223> OTHER INFORMATION: Any amino acid; this region may encompass 0-5
      residues

<400> SEQUENCE: 136

Xaa Xaa Xaa Xaa Xaa Asp Tyr Phe Asn Pro Thr Thr His Glu Tyr Ile
 1               5                  10                  15

Tyr Gln Thr Thr Xaa Xaa Xaa Xaa Xaa
            20                  25

<210> SEQ ID NO 137
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (14)..(18)
<223> OTHER INFORMATION: Any amino acid; this region may encompass 0-5
      residues

<400> SEQUENCE: 137

Xaa Xaa Xaa Xaa Xaa Trp Ala Pro Val Asp Arg Tyr Gln Xaa Xaa Xaa
 1               5                  10                  15

Xaa Xaa

<210> SEQ ID NO 138

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (10)..(14)
<223> OTHER INFORMATION: Any amino acid; this region may encompass 0-5
      residues

<400> SEQUENCE: 138

Xaa Xaa Xaa Xaa Xaa Arg Asp Val Tyr Xaa Xaa Xaa Xaa Xaa
1               5                   10

<210> SEQ ID NO 139
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (21)..(25)
<223> OTHER INFORMATION: Any amino acid; this region may encompass 0-5
      residues

<400> SEQUENCE: 139

Xaa Xaa Xaa Xaa Xaa Asp Tyr Lys Pro His Ala Asp Gly Pro His Thr
1               5                   10                  15

Tyr His Glu Ser Xaa Xaa Xaa Xaa Xaa
                20                  25

<210> SEQ ID NO 140
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Gly Val Ser Asp Val Pro Arg Asp Leu Glu Val Val Ala Ala Thr
1               5                   10                  15

Pro Thr Ser Leu Leu Ile Ser Trp Thr Gln Gly Ser Thr His Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Met Val Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Phe Asp Arg Ser Thr His Glu Tyr Lys Tyr Arg Thr Thr Pro Ile Ser
                85                  90                  95

Ile Asn Tyr Arg Thr Glu Ile Asp Lys Pro Ser Gln His His His His
```

His His

<210> SEQ ID NO 141
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Glu Val Val Ala Ala Thr Pro Thr Ser Leu Leu Ile Ser Trp Thr Gln
1               5                   10                  15

Gly Ser Thr His Tyr Gln Tyr Tyr Arg Ile Thr Tyr Gly Glu Thr Gly
                20                  25                  30

Gly Asn Ser Pro Val Gln Glu Phe Thr Val Pro Gly Met Val Tyr Thr
            35                  40                  45

Ala Thr Ile Ser Gly Leu Lys Pro Gly Val Asp Tyr Thr Ile Thr Val
        50                  55                  60

Tyr Ala Val Thr Asp Tyr Phe Asp Arg Ser Thr His Glu Tyr Lys Tyr
65                  70                  75                  80

Arg Thr Thr Pro Ile Ser Ile Asn Tyr Arg Thr
                85                  90
```

<210> SEQ ID NO 142
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76 or 77
<220> FEATURE:
<221> NAME/KEY: MOD_RES
<222> LOCATION: (102)..(108)
<223> OTHER INFORMATION: This region may encompass SEQ ID NOS 9, 10,
      78, 79, 80, or 81

<400> SEQUENCE: 142

```
Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Thr Gln Gly Ser Thr His Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Met Val Tyr Thr Ala Thr Ile Ser Gly Leu
        50                  55                  60

Lys Pro Gly Val Asp Tyr Thr Ile Thr Val Tyr Ala Val Thr Asp Tyr
65                  70                  75                  80

Phe Asp Arg Ser Thr His Glu Tyr Lys Tyr Arg Thr Thr Pro Ile Ser
                85                  90                  95

Ile Asn Tyr Arg Thr Xaa Xaa Xaa Xaa Xaa Xaa Xaa
            100                 105
```

<210> SEQ ID NO 143
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 143

Ser Trp Thr Gln Gly Ser Thr His Tyr Gln
1               5                   10

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Pro Gly Met Val Tyr Thr
1               5

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Thr Asp Tyr Phe Asp Arg Ser Thr His Glu Tyr Lys Tyr Arg Thr Thr
1               5                   10                  15

Pro

<210> SEQ ID NO 146
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (14)..(18)
<223> OTHER INFORMATION: Any amino acid; this region may encompass 0-5
      residues

<400> SEQUENCE: 146

Xaa Xaa Xaa Xaa Xaa Thr Gln Gly Ser Thr His Tyr Gln Xaa Xaa Xaa
1               5                   10                  15

Xaa Xaa

<210> SEQ ID NO 147
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
```

```
<220> FEATURE:
<221> NAME/KEY: MOD_RES
<222> LOCATION: (10)..(14)
<223> OTHER INFORMATION: Any amino acid; this region may encompass 0-5
      residues

<400> SEQUENCE: 147

Xaa Xaa Xaa Xaa Xaa Gly Met Val Tyr Xaa Xaa Xaa Xaa Xaa
1               5                   10

<210> SEQ ID NO 148
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (21)..(25)
<223> OTHER INFORMATION: Any amino acid; this region may encompass 0-5
      residues

<400> SEQUENCE: 148

Xaa Xaa Xaa Xaa Xaa Asp Tyr Phe Asp Arg Ser Thr His Glu Tyr Lys
1               5                   10                  15

Tyr Arg Thr Thr Xaa Xaa Xaa Xaa Xaa
            20                  25

<210> SEQ ID NO 149
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Met Gly Val Ser Asp Val Pro Arg Asp Leu Glu Val Val Ala Ala Thr
1               5                   10                  15

Pro Thr Ser Leu Leu Ile Ser Trp Thr Gln Gly Ser Thr His Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Met Val Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Phe Asp Arg Ser Thr His Glu Tyr Lys Tyr Arg Thr Thr Pro Ile Ser
                85                  90                  95

Ile Asn Tyr Arg Thr Glu Ile Asp Lys Gly Ser Gly Ser Gly Ser Gly
            100                 105                 110

Ser Gly Ser Gly Ser Gly Ser Gly Ser Gly Ser Val Ser Asp
    115                 120                 125

Val Pro Arg Asp Leu Glu Val Val Ala Ala Thr Pro Thr Ser Leu Leu
130                 135                 140

Ile Ser Trp Ser Ala Arg Leu Lys Val Ala Arg Tyr Tyr Arg Ile Thr
145                 150                 155                 160
```

Tyr Gly Glu Thr Gly Gly Asn Ser Pro Val Gln Glu Phe Thr Val Pro
            165                 170                 175

Lys Asn Val Tyr Thr Ala Thr Ile Ser Gly Leu Lys Pro Gly Val Asp
        180                 185                 190

Tyr Thr Ile Thr Val Tyr Ala Val Thr Arg Phe Arg Asp Tyr Gln Pro
        195                 200                 205

Ile Ser Ile Asn Tyr Arg Thr Glu Ile Asp Lys Pro Cys Gln His His
    210                 215                 220

His His His His
225

<210> SEQ ID NO 150
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: MOD_RES
<222> LOCATION: (216)..(222)
<223> OTHER INFORMATION: This region may encompass SEQ ID NOS 9, 10,
      78, 79, 80, 81 or not present

<400> SEQUENCE: 150

Xaa Xaa Xaa Xaa Xaa Xaa Xaa Xaa Xaa Glu Val Val Ala Ala Thr
1               5                   10                  15

Pro Thr Ser Leu Leu Ile Ser Trp Thr Gln Gly Ser Thr His Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Met Val Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Phe Asp Arg Ser Thr His Glu Tyr Lys Tyr Arg Thr Thr Pro Ile Ser
                85                  90                  95

Ile Asn Tyr Arg Thr Glu Ile Asp Lys Gly Ser Gly Ser Gly Ser Gly
            100                 105                 110

Ser Gly Ser Gly Ser Gly Ser Gly Ser Gly Ser Val Ser Asp
        115                 120                 125

Val Pro Arg Asp Leu Glu Val Val Ala Ala Thr Pro Thr Ser Leu Leu
130                 135                 140

Ile Ser Trp Ser Ala Arg Leu Lys Val Ala Arg Tyr Tyr Arg Ile Thr
145                 150                 155                 160

Tyr Gly Glu Thr Gly Gly Asn Ser Pro Val Gln Glu Phe Thr Val Pro
            165                 170                 175

Lys Asn Val Tyr Thr Ala Thr Ile Ser Gly Leu Lys Pro Gly Val Asp
        180                 185                 190

Tyr Thr Ile Thr Val Tyr Ala Val Thr Arg Phe Arg Asp Tyr Gln Pro
        195                 200                 205

Ile Ser Ile Asn Tyr Arg Thr Xaa Xaa Xaa Xaa Xaa Xaa Xaa
    210                 215                 220

```
<210> SEQ ID NO 151
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: misc_feature
<222> LOCATION: (103)..(120)
<223> OTHER INFORMATION: This region may encompass 3, 6, or 9 "Pro-Ala"
      repeats
<220> FEATURE:
<221> NAME/KEY: MOD_RES
<222> LOCATION: (211)..(217)
<223> OTHER INFORMATION: This region may encompass SEQ ID NOS 9, 10,
      78, 79, 80, 81 or not present

<400> SEQUENCE: 151

Xaa Xaa Xaa Xaa Xaa Xaa Xaa Xaa Xaa Glu Val Val Ala Ala Thr
1               5                   10                  15

Pro Thr Ser Leu Leu Ile Ser Trp Thr Gln Gly Ser Thr His Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Met Val Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Phe Asp Arg Ser Thr His Glu Tyr Lys Tyr Arg Thr Thr Pro Ile Ser
                85                  90                  95

Ile Asn Tyr Arg Thr Glu Pro Ala Pro Ala Pro Ala Pro Ala Pro Ala
            100                 105                 110

Pro Ala Pro Ala Pro Ala Pro Ala Val Ser Asp Val Pro Arg Asp Leu
        115                 120                 125

Glu Val Val Ala Ala Thr Pro Thr Ser Leu Leu Ile Ser Trp Ser Ala
    130                 135                 140

Arg Leu Lys Val Ala Arg Tyr Tyr Arg Ile Thr Tyr Gly Glu Thr Gly
145                 150                 155                 160

Gly Asn Ser Pro Val Gln Glu Phe Thr Val Pro Lys Asn Val Tyr Thr
                165                 170                 175

Ala Thr Ile Ser Gly Leu Lys Pro Gly Val Asp Tyr Thr Ile Thr Val
            180                 185                 190

Tyr Ala Val Thr Arg Phe Arg Asp Tyr Gln Pro Ile Ser Ile Asn Tyr
        195                 200                 205

Arg Thr Xaa Xaa Xaa Xaa Xaa Xaa
    210                 215

<210> SEQ ID NO 152
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Gly Val Ser Asp Val Pro Arg Asp Leu Glu Val Val Ala Ala Thr
```

```
            1               5                  10                 15
Pro Thr Ser Leu Leu Ile Ser Trp Ser Ala Arg Leu Lys Val Ala Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
                100                 105                 110

Gly Ser Gly Ser Val Ser Asp Val Pro Arg Asp Leu Glu Val Val Ala
                115                 120                 125

Ala Thr Pro Thr Ser Leu Leu Ile Ser Trp Thr Gln Gly Ser Thr His
            130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Gly Met Val Tyr Thr Ala Thr Ile Ser
                165                 170                 175

Gly Leu Lys Pro Gly Val Asp Tyr Thr Ile Thr Val Tyr Ala Val Thr
                180                 185                 190

Asp Tyr Phe Asp Arg Ser Thr His Glu Tyr Lys Tyr Arg Thr Thr Pro
            195                 200                 205

Ile Ser Ile Asn Tyr Arg Thr Glu Ile Asp Lys Pro Cys Gln His His
        210                 215                 220

His His His His
225

<210> SEQ ID NO 153
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: MOD_RES
<222> LOCATION: (216)..(222)
<223> OTHER INFORMATION: This region may encompass SEQ ID NOS 9, 10,
      78, 79, 80, 81 or not present

<400> SEQUENCE: 153

Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Ser Ala Arg Leu Lys Val Ala Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80
```

```
Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Thr Gln Gly Ser Thr His
            130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Gly Met Val Tyr Thr Ala Thr Ile Ser
                165                 170                 175

Gly Leu Lys Pro Gly Val Asp Tyr Thr Ile Thr Val Tyr Ala Val Thr
            180                 185                 190

Asp Tyr Phe Asp Arg Ser Thr His Glu Tyr Lys Tyr Arg Thr Thr Pro
            195                 200                 205

Ile Ser Ile Asn Tyr Arg Thr Xaa Xaa Xaa Xaa Xaa Xaa
            210                 215                 220

<210> SEQ ID NO 154
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: misc_feature
<222> LOCATION: (94)..(111)
<223> OTHER INFORMATION: This region may encompass 3, 6, or 9 "Pro-Ala"
      repeats
<220> FEATURE:
<221> NAME/KEY: MOD_RES
<222> LOCATION: (211)..(217)
<223> OTHER INFORMATION: This region may encompass SEQ ID NOS 9, 10,
      78, 79, 80, 81 or not present

<400> SEQUENCE: 154

Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Pro Ala Pro
            85                  90                  95

Ala Pro Ala Pro Ala Pro Ala Pro Ala Pro Ala Pro Ala Pro Ala Val
            100                 105                 110

Ser Asp Val Pro Arg Asp Leu Glu Val Val Ala Ala Thr Pro Thr Ser
            115                 120                 125

Leu Leu Ile Ser Trp Thr Gln Gly Ser Thr His Tyr Gln Tyr Tyr Arg
```

```
                130                 135                 140
Ile Thr Tyr Gly Glu Thr Gly Asn Ser Pro Val Gln Glu Phe Thr
145                 150                 155                 160

Val Pro Gly Met Val Tyr Thr Ala Thr Ile Ser Gly Leu Lys Pro Gly
                165                 170                 175

Val Asp Tyr Thr Ile Thr Val Tyr Ala Val Thr Asp Tyr Phe Asp Arg
                180                 185                 190

Ser Thr His Glu Tyr Lys Tyr Arg Thr Thr Pro Ile Ser Ile Asn Tyr
            195                 200                 205

Arg Thr Xaa Xaa Xaa Xaa Xaa Xaa Xaa
        210                 215

<210> SEQ ID NO 155
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Gly Val Ser Asp Val Pro Arg Asp Leu Glu Val Val Ala Ala Thr
1               5                   10                  15

Pro Thr Ser Leu Leu Ile Ser Trp Tyr Trp Glu Gly Leu Pro Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Arg Asp Val Asn Thr Ala Thr Ile Ser Gly Leu
    50                  55                  60

Lys Pro Gly Val Asp Tyr Thr Ile Thr Val Tyr Ala Val Thr Asp Trp
65                  70                  75                  80

Tyr Asn Pro Asp Thr His Glu Tyr Ile Tyr His Thr Ile Pro Ile Ser
                85                  90                  95

Ile Asn Tyr Arg Thr Glu Ile Asp Lys Pro Ser Gln His His His His
            100                 105                 110

His His

<210> SEQ ID NO 156
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Val Val Ala Ala Thr Pro Thr Ser Leu Leu Ile Ser Trp Tyr Trp
1               5                   10                  15

Glu Gly Leu Pro Tyr Gln Tyr Tyr Arg Ile Thr Tyr Gly Glu Thr Gly
            20                  25                  30

Gly Asn Ser Pro Val Gln Glu Phe Thr Val Pro Arg Asp Val Asn Thr
        35                  40                  45

Ala Thr Ile Ser Gly Leu Lys Pro Gly Val Asp Tyr Thr Ile Thr Val
    50                  55                  60

Tyr Ala Val Thr Asp Trp Tyr Asn Pro Asp Thr His Glu Tyr Ile Tyr
65                  70                  75                  80

His Thr Ile Pro Ile Ser Ile Asn Tyr Arg Thr
                85                  90
```

<210> SEQ ID NO 157
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76 or 77
<220> FEATURE:
<221> NAME/KEY: MOD_RES
<222> LOCATION: (102)..(108)
<223> OTHER INFORMATION: This region may encompass SEQ ID NOS 9, 10,
      78, 79, 80, or 81

<400> SEQUENCE: 157

Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Tyr Trp Glu Gly Leu Pro Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Arg Asp Val Asn Thr Ala Thr Ile Ser Gly Leu
    50                  55                  60

Lys Pro Gly Val Asp Tyr Thr Ile Thr Val Tyr Ala Val Thr Asp Trp
65                  70                  75                  80

Tyr Asn Pro Asp Thr His Glu Tyr Ile Tyr Thr Ile Pro Ile Ser
                85                  90                  95

Ile Asn Tyr Arg Thr Xaa Xaa Xaa Xaa Xaa Xaa Xaa
            100                 105

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Trp Tyr Trp Glu Gly Leu Pro Tyr Gln
1               5                   10

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Pro Arg Asp Val Asn Thr
1               5

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Asp Trp Tyr Asn Pro Asp Thr His Glu Tyr Ile Tyr His Thr Ile
1               5                   10                  15
Pro

<210> SEQ ID NO 161
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (14)..(18)
<223> OTHER INFORMATION: Any amino acid; this region may encompass 0-5
      residues

<400> SEQUENCE: 161

Xaa Xaa Xaa Xaa Xaa Tyr Trp Glu Gly Leu Pro Tyr Gln Xaa Xaa Xaa
1               5                   10                  15
Xaa Xaa

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (10)..(14)
<223> OTHER INFORMATION: Any amino acid; this region may encompass 0-5
      residues

<400> SEQUENCE: 162

Xaa Xaa Xaa Xaa Xaa Arg Asp Val Asn Xaa Xaa Xaa Xaa Xaa
1               5                   10

<210> SEQ ID NO 163
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (21)..(25)
<223> OTHER INFORMATION: Any amino acid; this region may encompass 0-5
      residues

<400> SEQUENCE: 163

```
Xaa Xaa Xaa Xaa Xaa Asp Trp Tyr Asn Pro Asp Thr His Glu Tyr Ile
1               5                   10                  15

Tyr His Thr Ile Xaa Xaa Xaa Xaa Xaa
            20              25
```

<210> SEQ ID NO 164
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Met Gly Val Ser Asp Val Pro Arg Asp Leu Glu Val Val Ala Ala Thr
1               5                   10                  15

Pro Thr Ser Leu Leu Ile Ser Trp Tyr Trp Gly Leu Pro Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Arg Asp Val Asn Thr Ala Thr Ile Ser Gly Leu
        50                  55                  60

Lys Pro Gly Val Asp Tyr Thr Ile Thr Val Tyr Ala Val Thr Asp Trp
65                  70                  75                  80

Tyr Asn Pro Asp Thr His Glu Tyr Ile Tyr His Thr Ile Pro Ile Ser
                85                  90                  95

Ile Asn Tyr Arg Thr Glu Ile Asp Lys Gly Ser Gly Ser Gly Ser Gly
            100                 105                 110

Ser Gly Ser Gly Ser Gly Ser Gly Ser Gly Ser Gly Ser Val Ser Asp
        115                 120                 125

Val Pro Arg Asp Leu Glu Val Val Ala Ala Thr Pro Thr Ser Leu Leu
    130                 135                 140

Ile Ser Trp Ser Ala Arg Leu Lys Val Ala Arg Tyr Tyr Arg Ile Thr
145                 150                 155                 160

Tyr Gly Glu Thr Gly Gly Asn Ser Pro Val Gln Glu Phe Thr Val Pro
                165                 170                 175

Lys Asn Val Tyr Thr Ala Thr Ile Ser Gly Leu Lys Pro Gly Val Asp
            180                 185                 190

Tyr Thr Ile Thr Val Tyr Ala Val Thr Arg Phe Arg Asp Tyr Gln Pro
        195                 200                 205

Ile Ser Ile Asn Tyr Arg Thr Glu Ile Asp Lys Pro Cys Gln His His
    210                 215                 220

His His His His
225
```

<210> SEQ ID NO 165
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: MOD_RES
<222> LOCATION: (216)..(222)
<223> OTHER INFORMATION: This region may encompass SEQ ID NOS 9, 10, 78, 79, 80, 81 or not present

<400> SEQUENCE: 165

Xaa Xaa Xaa Xaa Xaa Xaa Xaa Xaa Xaa Glu Val Val Ala Ala Thr
1               5                   10                  15

Pro Thr Ser Leu Leu Ile Ser Trp Tyr Trp Glu Gly Leu Pro Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Arg Asp Val Asn Thr Ala Thr Ile Ser Gly Leu
    50                  55                  60

Lys Pro Gly Val Asp Tyr Thr Ile Thr Val Tyr Ala Val Thr Asp Trp
65                  70                  75                  80

Tyr Asn Pro Asp Thr His Glu Tyr Ile Tyr His Thr Ile Pro Ile Ser
                85                  90                  95

Ile Asn Tyr Arg Thr Glu Ile Asp Lys Gly Ser Gly Ser Gly Ser Gly
            100                 105                 110

Ser Gly Ser Gly Ser Gly Ser Gly Ser Gly Ser Val Ser Asp
        115                 120                 125

Val Pro Arg Asp Leu Glu Val Val Ala Ala Thr Pro Thr Ser Leu Leu
    130                 135                 140

Ile Ser Trp Ser Ala Arg Leu Lys Val Ala Arg Tyr Tyr Arg Ile Thr
145                 150                 155                 160

Tyr Gly Glu Thr Gly Gly Asn Ser Pro Val Gln Glu Phe Thr Val Pro
                165                 170                 175

Lys Asn Val Tyr Thr Ala Thr Ile Ser Gly Leu Lys Pro Gly Val Asp
            180                 185                 190

Tyr Thr Ile Thr Val Tyr Ala Val Thr Arg Phe Arg Asp Tyr Gln Pro
        195                 200                 205

Ile Ser Ile Asn Tyr Arg Thr Xaa Xaa Xaa Xaa Xaa Xaa Xaa
    210                 215                 220

<210> SEQ ID NO 166
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: misc_feature
<222> LOCATION: (103)..(120)
<223> OTHER INFORMATION: This region may encompass 3, 6, or 9 "Pro-Ala"
      repeats
<220> FEATURE:
<221> NAME/KEY: MOD_RES
<222> LOCATION: (211)..(217)
<223> OTHER INFORMATION: This region may encompass SEQ ID NOS 9, 10,
      78, 79, 80, 81 or not present

<400> SEQUENCE: 166

Xaa Xaa Xaa Xaa Xaa Xaa Xaa Xaa Xaa Glu Val Val Ala Ala Thr
1               5                   10                  15

Pro Thr Ser Leu Leu Ile Ser Trp Tyr Trp Glu Gly Leu Pro Tyr Gln
            20                  25                  30

Tyr Tyr Arg Ile Thr Tyr Gly Glu Thr Gly Gly Asn Ser Pro Val Gln

```
            35                  40                  45
Glu Phe Thr Val Pro Arg Asp Val Asn Thr Ala Thr Ile Ser Gly Leu
 50                  55                  60

Lys Pro Gly Val Asp Tyr Thr Ile Thr Val Tyr Ala Val Thr Asp Trp
 65                  70                  75                  80

Tyr Asn Pro Asp Thr His Glu Tyr Ile Tyr His Thr Ile Pro Ile Ser
                 85                  90                  95

Ile Asn Tyr Arg Thr Glu Pro Ala Pro Ala Pro Ala Pro Ala Pro Ala
                100                 105                 110

Pro Ala Pro Ala Pro Ala Val Ser Asp Val Pro Arg Asp Leu
            115                 120                 125

Glu Val Val Ala Ala Thr Pro Thr Ser Leu Leu Ile Ser Trp Ser Ala
130                 135                 140

Arg Leu Lys Val Ala Arg Tyr Tyr Arg Ile Thr Tyr Gly Glu Thr Gly
145                 150                 155                 160

Gly Asn Ser Pro Val Gln Glu Phe Thr Val Pro Lys Asn Val Tyr Thr
                165                 170                 175

Ala Thr Ile Ser Gly Leu Lys Pro Gly Val Asp Tyr Thr Ile Thr Val
                180                 185                 190

Tyr Ala Val Thr Arg Phe Arg Asp Tyr Gln Pro Ile Ser Ile Asn Tyr
                195                 200                 205

Arg Thr Xaa Xaa Xaa Xaa Xaa Xaa
                210                 215

<210> SEQ ID NO 167
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Met Gly Val Ser Asp Val Pro Arg Asp Leu Glu Val Val Ala Ala Thr
 1               5                  10                  15

Pro Thr Ser Leu Leu Ile Ser Trp Ser Ala Arg Leu Lys Val Ala Arg
                 20                  25                  30

Tyr Tyr Arg Ile Thr Tyr Gly Glu Thr Gly Gly Asn Ser Pro Val Gln
                 35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Ile Asp Lys
                 85                  90                  95

Gly Ser Gly Ser Gly Ser Gly Ser Gly Ser Gly Ser Gly Ser Gly Ser
                100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Tyr Trp Glu Gly Leu Pro
130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Asn Thr Ala Thr Ile Ser
                165                 170                 175
```

```
Gly Leu Lys Pro Gly Val Asp Tyr Thr Ile Thr Val Tyr Ala Val Thr
                180                 185                 190

Asp Trp Tyr Asn Pro Asp Thr His Glu Tyr Ile Tyr His Thr Ile Pro
            195                 200                 205

Ile Ser Ile Asn Tyr Arg Thr Glu Ile Asp Lys Pro Cys Gln His His
        210                 215                 220

His His His His
225

<210> SEQ ID NO 168
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: MOD_RES
<222> LOCATION: (216)..(222)
<223> OTHER INFORMATION: This region may encompass SEQ ID NOS 9, 10,
      78, 79, 80, 81 or not present

<400> SEQUENCE: 168

Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
        115                 120                 125

Ala Thr Pro Thr Ser Leu Leu Ile Ser Trp Tyr Trp Glu Gly Leu Pro
    130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Asn Thr Ala Thr Ile Ser
                165                 170                 175

Gly Leu Lys Pro Gly Val Asp Tyr Thr Ile Thr Val Tyr Ala Val Thr
            180                 185                 190

Asp Trp Tyr Asn Pro Asp Thr His Glu Tyr Ile Tyr His Thr Ile Pro
        195                 200                 205

Ile Ser Ile Asn Tyr Arg Thr Xaa Xaa Xaa Xaa Xaa Xaa Xaa
    210                 215                 220

<210> SEQ ID NO 169
<211> LENGTH: 217
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: misc_feature
<222> LOCATION: (94)..(111)
<223> OTHER INFORMATION: This region may encompass 3, 6, or 9 "Pro-Ala"
      repeats
<220> FEATURE:
<221> NAME/KEY: MOD_RES
<222> LOCATION: (211)..(217)
<223> OTHER INFORMATION: This region may encompass SEQ ID NOS 9, 10,
      78, 79, 80, 81 or not present

<400> SEQUENCE: 169

Xaa Xaa Xaa Xaa Xaa Xaa Xaa Xaa Xaa Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Asn Ser Pro Val Gln
        35                  40                  45

Glu Phe Thr Val Pro Lys Asn Val Tyr Thr Ala Thr Ile Ser Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Pro Ala Pro
                85                  90                  95

Ala Pro Ala Pro Ala Pro Ala Pro Ala Pro Ala Pro Ala Val
            100                 105                 110

Ser Asp Val Pro Arg Asp Leu Glu Val Val Ala Ala Thr Pro Thr Ser
            115                 120                 125

Leu Leu Ile Ser Trp Tyr Trp Glu Gly Leu Pro Tyr Gln Tyr Tyr Arg
        130                 135                 140

Ile Thr Tyr Gly Glu Thr Gly Gly Asn Ser Pro Val Gln Glu Phe Thr
145                 150                 155                 160

Val Pro Arg Asp Val Asn Thr Ala Thr Ile Ser Gly Leu Lys Pro Gly
                165                 170                 175

Val Asp Tyr Thr Ile Thr Val Tyr Ala Val Thr Asp Trp Tyr Asn Pro
            180                 185                 190

Asp Thr His Glu Tyr Ile Tyr His Thr Ile Pro Ile Ser Ile Asn Tyr
        195                 200                 205

Arg Thr Xaa Xaa Xaa Xaa Xaa Xaa
    210                 215

<210> SEQ ID NO 170
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Met Gly Val Ser Asp Val Pro Arg Asp Leu Glu Val Val Ala Ala Thr
1               5                   10                  15

Pro Thr Ser Leu Leu Ile Ser Trp Ala Ser Asn Arg Gly Thr Tyr Gln
```

```
                    20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Ser Thr Ala Thr Ile Ser Gly Leu
    50                  55                  60

Lys Pro Gly Val Asp Tyr Thr Ile Thr Val Tyr Ala Val Thr Asp Ala
65                  70                  75                  80

Phe Asn Pro Thr Thr His Glu Tyr Asn Tyr Phe Thr Thr Pro Ile Ser
                85                  90                  95

Ile Asn Tyr Arg Thr Glu Ile Asp Lys Pro Ser Gln His His His His
            100                 105                 110

His His

<210> SEQ ID NO 171
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Val Val Ala Ala Thr Pro Thr Ser Leu Leu Ile Ser Trp Ala Ser
1               5                   10                  15

Asn Arg Gly Thr Tyr Gln Tyr Tyr Arg Ile Thr Tyr Gly Glu Thr Gly
            20                  25                  30

Gly Asn Ser Pro Val Gln Glu Phe Thr Val Pro Gly Gly Val Ser Thr
        35                  40                  45

Ala Thr Ile Ser Gly Leu Lys Pro Gly Val Asp Tyr Thr Ile Thr Val
    50                  55                  60

Tyr Ala Val Thr Asp Ala Phe Asn Pro Thr Thr His Glu Tyr Asn Tyr
65                  70                  75                  80

Phe Thr Thr Pro Ile Ser Ile Asn Tyr Arg Thr
                85                  90

<210> SEQ ID NO 172
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76 or 77
<220> FEATURE:
<221> NAME/KEY: MOD_RES
<222> LOCATION: (102)..(108)
<223> OTHER INFORMATION: This region may encompass SEQ ID NOS 9, 10,
      78, 79, 80, or 81

<400> SEQUENCE: 172

Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Ala Ser Asn Arg Gly Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Ser Thr Ala Thr Ile Ser Gly Leu
```

```
            50                  55                  60
Lys Pro Gly Val Asp Tyr Thr Ile Thr Val Tyr Ala Val Thr Asp Ala
 65                  70                  75                  80

Phe Asn Pro Thr Thr His Glu Tyr Asn Tyr Phe Thr Thr Pro Ile Ser
                 85                  90                  95

Ile Asn Tyr Arg Thr Xaa Xaa Xaa Xaa Xaa Xaa Xaa
            100                 105
```

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

```
Ser Trp Ala Ser Asn Arg Gly Thr Tyr Gln
 1               5                  10
```

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

```
Pro Gly Gly Val Ser Thr
 1               5
```

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

```
Thr Asp Ala Phe Asn Pro Thr Thr His Glu Tyr Asn Tyr Phe Thr Thr
 1               5                  10                  15

Pro
```

<210> SEQ ID NO 176
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (14)..(18)
<223> OTHER INFORMATION: Any amino acid; this region may encompass 0-5
      residues

<400> SEQUENCE: 176

```
Xaa Xaa Xaa Xaa Xaa Ala Ser Asn Arg Gly Thr Tyr Gln Xaa Xaa Xaa
 1               5                  10                  15
```

Xaa Xaa

<210> SEQ ID NO 177
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (10)..(14)
<223> OTHER INFORMATION: Any amino acid; this region may encompass 0-5
      residues

<400> SEQUENCE: 177

Xaa Xaa Xaa Xaa Xaa Gly Gly Val Ser Xaa Xaa Xaa Xaa Xaa
1               5                   10

<210> SEQ ID NO 178
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (21)..(25)
<223> OTHER INFORMATION: Any amino acid; this region may encompass 0-5
      residues

<400> SEQUENCE: 178

Xaa Xaa Xaa Xaa Xaa Asp Ala Phe Asn Pro Thr Thr His Glu Tyr Asn
1               5                   10                  15

Tyr Phe Thr Thr Xaa Xaa Xaa Xaa Xaa
            20                  25

<210> SEQ ID NO 179
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Met Gly Val Ser Asp Val Pro Arg Asp Leu Glu Val Val Ala Ala Thr
1               5                   10                  15

Pro Thr Ser Leu Leu Ile Ser Trp Ala Ser Asn Arg Gly Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Ser Thr Ala Thr Ile Ser Gly Leu
    50                  55                  60

Lys Pro Gly Val Asp Tyr Thr Ile Thr Val Tyr Ala Val Thr Asp Ala
65                  70                  75                  80

```
Phe Asn Pro Thr Thr His Glu Tyr Asn Tyr Phe Thr Pro Ile Ser
                85                  90                  95

Ile Asn Tyr Arg Thr Glu Ile Asp Lys Gly Ser Gly Ser Gly
            100                 105                 110

Ser Gly Ser Gly Ser Gly Ser Gly Ser Gly Val Ser Asp
            115                 120                 125

Val Pro Arg Asp Leu Glu Val Val Ala Ala Thr Pro Thr Ser Leu Leu
130                 135                 140

Ile Ser Trp Ser Ala Arg Leu Lys Val Ala Arg Tyr Tyr Arg Ile Thr
145                 150                 155                 160

Tyr Gly Glu Thr Gly Gly Asn Ser Pro Val Gln Glu Phe Thr Val Pro
                165                 170                 175

Lys Asn Val Tyr Thr Ala Thr Ile Ser Gly Leu Lys Pro Gly Val Asp
                180                 185                 190

Tyr Thr Ile Thr Val Tyr Ala Val Thr Arg Phe Arg Asp Tyr Gln Pro
                195                 200                 205

Ile Ser Ile Asn Tyr Arg Thr Glu Ile Asp Lys Pro Cys Gln His His
                210                 215                 220

His His His His
225

<210> SEQ ID NO 180
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: MOD_RES
<222> LOCATION: (216)..(222)
<223> OTHER INFORMATION: This region may encompass SEQ ID NOS 9, 10,
      78, 79, 80, 81 or not present

<400> SEQUENCE: 180

Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Ala Ser Asn Arg Gly Thr Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Ser Thr Ala Thr Ile Ser Gly Leu
50                  55                  60

Lys Pro Gly Val Asp Tyr Thr Ile Thr Val Tyr Ala Val Thr Asp Ala
65                  70                  75                  80

Phe Asn Pro Thr Thr His Glu Tyr Asn Tyr Phe Thr Pro Ile Ser
                85                  90                  95

Ile Asn Tyr Arg Thr Glu Ile Asp Lys Gly Ser Gly Ser Gly
            100                 105                 110

Ser Gly Ser Gly Ser Gly Ser Gly Ser Gly Val Ser Asp
            115                 120                 125

Val Pro Arg Asp Leu Glu Val Val Ala Ala Thr Pro Thr Ser Leu Leu
130                 135                 140

Ile Ser Trp Ser Ala Arg Leu Lys Val Ala Arg Tyr Tyr Arg Ile Thr
```

```
                145                 150                 155                 160

Tyr Gly Glu Thr Gly Gly Asn Ser Pro Val Gln Glu Phe Thr Val Pro
                165                 170                 175

Lys Asn Val Tyr Thr Ala Thr Ile Ser Gly Leu Lys Pro Gly Val Asp
                180                 185                 190

Tyr Thr Ile Thr Val Tyr Ala Val Thr Arg Phe Arg Asp Tyr Gln Pro
                195                 200                 205

Ile Ser Ile Asn Tyr Arg Thr Xaa Xaa Xaa Xaa Xaa Xaa Xaa
                210                 215                 220

<210> SEQ ID NO 181
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: misc_feature
<222> LOCATION: (103)..(120)
<223> OTHER INFORMATION: This region may encompass 3, 6, or 9 "Pro-Ala"
      repeats
<220> FEATURE:
<221> NAME/KEY: MOD_RES
<222> LOCATION: (211)..(217)
<223> OTHER INFORMATION: This region may encompass SEQ ID NOS 9, 10,
      78, 79, 80, 81 or not present

<400> SEQUENCE: 181

Xaa Xaa Xaa Xaa Xaa Xaa Xaa Xaa Xaa Glu Val Val Ala Ala Thr
1               5                   10                  15

Pro Thr Ser Leu Leu Ile Ser Trp Ala Ser Asn Arg Gly Thr Tyr Gln
                20                  25                  30

Tyr Tyr Arg Ile Thr Tyr Gly Glu Thr Gly Gly Asn Ser Pro Val Gln
                35                  40                  45

Glu Phe Thr Val Pro Gly Gly Val Ser Thr Ala Thr Ile Ser Gly Leu
    50                  55                  60

Lys Pro Gly Val Asp Tyr Thr Ile Thr Val Tyr Ala Val Thr Asp Ala
65                  70                  75                  80

Phe Asn Pro Thr Thr His Glu Tyr Asn Tyr Phe Thr Thr Pro Ile Ser
                85                  90                  95

Ile Asn Tyr Arg Thr Glu Pro Ala Pro Ala Pro Ala Pro Ala Pro Ala
                100                 105                 110

Pro Ala Pro Ala Pro Ala Pro Ala Val Ser Asp Val Pro Arg Asp Leu
                115                 120                 125

Glu Val Val Ala Ala Thr Pro Thr Ser Leu Leu Ile Ser Trp Ser Ala
                130                 135                 140

Arg Leu Lys Val Ala Arg Tyr Tyr Arg Ile Thr Tyr Gly Glu Thr Gly
145                 150                 155                 160

Gly Asn Ser Pro Val Gln Glu Phe Thr Val Pro Lys Asn Val Tyr Thr
                165                 170                 175

Ala Thr Ile Ser Gly Leu Lys Pro Gly Val Asp Tyr Thr Ile Thr Val
                180                 185                 190

Tyr Ala Val Thr Arg Phe Arg Asp Tyr Gln Pro Ile Ser Ile Asn Tyr
                195                 200                 205
```

```
Arg Thr Xaa Xaa Xaa Xaa Xaa Xaa
    210                 215
```

```
<210> SEQ ID NO 182
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Asn Ser Pro Val Gln
    35                  40                  45

Glu Phe Thr Val Pro Lys Asn Val Tyr Thr Ala Thr Ile Ser Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Ala Ser Asn Arg Gly Thr
130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Gly Gly Val Ser Thr Ala Thr Ile Ser
                165                 170                 175

Gly Leu Lys Pro Gly Val Asp Tyr Thr Ile Thr Val Tyr Ala Val Thr
            180                 185                 190

Asp Ala Phe Asn Pro Thr Thr His Glu Tyr Asn Tyr Phe Thr Thr Pro
            195                 200                 205

Ile Ser Ile Asn Tyr Arg Thr Glu Ile Asp Lys Pro Cys Gln His His
    210                 215                 220

His His His His
225
```

```
<210> SEQ ID NO 183
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: MOD_RES
<222> LOCATION: (216)..(222)
<223> OTHER INFORMATION: This region may encompass SEQ ID NOS 9, 10,
      78, 79, 80, or 81 or not present

<400> SEQUENCE: 183
```

```
Xaa Xaa Xaa Xaa Xaa Xaa Xaa Xaa Xaa Glu Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
65                   70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Ala Ser Asn Arg Gly Thr
130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Gly Gly Val Ser Thr Ala Thr Ile Ser
                165                 170                 175

Gly Leu Lys Pro Gly Val Asp Tyr Thr Ile Thr Val Tyr Ala Val Thr
                180                 185                 190

Asp Ala Phe Asn Pro Thr Thr His Glu Tyr Asn Tyr Phe Thr Thr Pro
                195                 200                 205

Ile Ser Ile Asn Tyr Arg Thr Xaa Xaa Xaa Xaa Xaa Xaa Xaa
            210                 215                 220

<210> SEQ ID NO 184
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: misc_feature
<222> LOCATION: (94)..(111)
<223> OTHER INFORMATION: This region may encompass 3, 6, or 9 "Pro-Ala"
      repeats
<220> FEATURE:
<221> NAME/KEY: MOD_RES
<222> LOCATION: (211)..(217)
<223> OTHER INFORMATION: This region may encompass SEQ ID NOS 9, 10,
      78, 79, 80, 81 or not present

<400> SEQUENCE: 184

Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu
```

```
        50                  55                  60
Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Pro Ala Pro
                 85                  90                  95

Ala Pro Ala Pro Ala Pro Ala Pro Ala Pro Ala Pro Ala Pro Ala Val
            100                 105                 110

Ser Asp Val Pro Arg Asp Leu Glu Val Val Ala Ala Thr Pro Thr Ser
            115                 120                 125

Leu Leu Ile Ser Trp Ala Ser Asn Arg Gly Thr Tyr Gln Tyr Tyr Arg
            130                 135                 140

Ile Thr Tyr Gly Glu Thr Gly Gly Asn Ser Pro Val Gln Glu Phe Thr
145                 150                 155                 160

Val Pro Gly Gly Val Ser Thr Ala Thr Ile Ser Gly Leu Lys Pro Gly
                165                 170                 175

Val Asp Tyr Thr Ile Thr Val Tyr Ala Val Thr Asp Ala Phe Asn Pro
                180                 185                 190

Thr Thr His Glu Tyr Asn Tyr Phe Thr Thr Pro Ile Ser Ile Asn Tyr
            195                 200                 205

Arg Thr Xaa Xaa Xaa Xaa Xaa Xaa
            210                 215

<210> SEQ ID NO 185
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Gly Val Ser Asp Val Pro Arg Asp Leu Glu Val Val Ala Ala Thr
 1               5                  10                  15

Pro Thr Ser Leu Leu Ile Ser Trp Asp Ala Pro Thr Ser Arg Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gly Leu Ser Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Pro Ser Gln His His His His
            100                 105                 110

His His

<210> SEQ ID NO 186
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Glu Val Val Ala Ala Thr Pro Thr Ser Leu Leu Ile Ser Trp Asp Ala
 1               5                  10                  15
```

```
Pro Thr Ser Arg Tyr Gln Tyr Tyr Arg Ile Thr Tyr Gly Glu Thr Gly
            20                  25                  30

Gly Asn Ser Pro Val Gln Glu Phe Thr Val Pro Gly Gly Leu Ser Thr
            35                  40                  45

Ala Thr Ile Ser Gly Leu Lys Pro Gly Val Asp Tyr Thr Ile Thr Val
 50                  55                  60

Tyr Ala Val Thr Asp Tyr Lys Pro His Ala Asp Gly Pro His Thr Tyr
 65                  70                  75                  80

His Glu Ser Pro Ile Ser Ile Asn Tyr Arg Thr
                85                  90

<210> SEQ ID NO 187
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76 or 77
<220> FEATURE:
<221> NAME/KEY: MOD_RES
<222> LOCATION: (102)..(108)
<223> OTHER INFORMATION: This region may encompass SEQ ID NOS 9, 10,
      78, 79, 80 or 81

<400> SEQUENCE: 187

Xaa Xaa Xaa Xaa Xaa Xaa Xaa Xaa Xaa Xaa Glu Val Val Ala Ala Thr
 1               5                  10                  15

Pro Thr Ser Leu Leu Ile Ser Trp Asp Ala Pro Thr Ser Arg Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Gly Leu Ser Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Lys Pro His Ala Asp Gly Pro His Thr Tyr His Glu Ser Pro Ile Ser
                85                  90                  95

Ile Asn Tyr Arg Thr Xaa Xaa Xaa Xaa Xaa Xaa
            100                 105

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ser Trp Asp Ala Pro Thr Ser Arg Tyr Gln
 1               5                  10

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 189

Pro Gly Gly Leu Ser Thr
1               5

<210> SEQ ID NO 190
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (14)..(18)
<223> OTHER INFORMATION: Any amino acid; this region may encompass 0-5
      residues

<400> SEQUENCE: 190

Xaa Xaa Xaa Xaa Xaa Asp Ala Pro Thr Ser Arg Tyr Gln Xaa Xaa Xaa
1               5                   10                  15

Xaa Xaa

<210> SEQ ID NO 191
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (10)..(14)
<223> OTHER INFORMATION: Any amino acid; this region may encompass 0-5
      residues

<400> SEQUENCE: 191

Xaa Xaa Xaa Xaa Xaa Gly Gly Leu Ser Xaa Xaa Xaa Xaa Xaa
1               5                   10

<210> SEQ ID NO 192
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Met Gly Val Ser Asp Val Pro Arg Asp Leu Glu Val Val Ala Ala Thr
1               5                   10                  15

Pro Thr Ser Leu Leu Ile Ser Trp Asp Ala Pro Thr Ser Arg Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gly Leu Ser Thr Ala Thr Ile Ser Gly Leu
    50                  55                  60

```
Lys Pro Gly Val Asp Tyr Thr Ile Thr Val Tyr Ala Val Thr Asp Tyr
 65                  70                  75                  80

Lys Pro His Ala Asp Gly Pro His Thr Tyr His Glu Ser Pro Ile Ser
                 85                  90                  95

Ile Asn Tyr Arg Thr Glu Ile Asp Lys Gly Ser Gly Ser Gly Ser Gly
            100                 105                 110

Ser Gly Ser Gly Ser Gly Ser Gly Ser Gly Ser Gly Ser Val Ser Asp
            115                 120                 125

Val Pro Arg Asp Leu Glu Val Val Ala Ala Thr Pro Thr Ser Leu Leu
    130                 135                 140

Ile Ser Trp Ser Ala Arg Leu Lys Val Ala Arg Tyr Tyr Arg Ile Thr
145                 150                 155                 160

Tyr Gly Glu Thr Gly Gly Asn Ser Pro Val Gln Glu Phe Thr Val Pro
                165                 170                 175

Lys Asn Val Tyr Thr Ala Thr Ile Ser Gly Leu Lys Pro Gly Val Asp
            180                 185                 190

Tyr Thr Ile Thr Val Tyr Ala Val Thr Arg Phe Arg Asp Tyr Gln Pro
            195                 200                 205

Ile Ser Ile Asn Tyr Arg Thr Glu Ile Asp Lys Pro Cys Gln His His
    210                 215                 220

His His His His
225

<210> SEQ ID NO 193
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: MOD_RES
<222> LOCATION: (216)..(222)
<223> OTHER INFORMATION: This region may encompass SEQ ID NOS 9, 10,
      78, 79, 80, 81 or not present

<400> SEQUENCE: 193

Xaa Xaa Xaa Xaa Xaa Xaa Xaa Xaa Xaa Glu Val Val Ala Ala Thr
  1               5                  10                  15

Pro Thr Ser Leu Leu Ile Ser Trp Asp Ala Pro Thr Ser Arg Tyr Gln
                 20                  25                  30

Tyr Tyr Arg Ile Thr Tyr Gly Glu Thr Gly Gly Asn Ser Pro Val Gln
             35                  40                  45

Glu Phe Thr Val Pro Gly Gly Leu Ser Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Lys Pro His Ala Asp Gly Pro His Thr Tyr His Glu Ser Pro Ile Ser
                 85                  90                  95

Ile Asn Tyr Arg Thr Glu Ile Asp Lys Gly Ser Gly Ser Gly Ser Gly
            100                 105                 110

Ser Gly Ser Gly Ser Gly Ser Gly Ser Gly Ser Gly Ser Val Ser Asp
            115                 120                 125
```

```
Val Pro Arg Asp Leu Glu Val Val Ala Ala Thr Pro Thr Ser Leu Leu
    130                 135                 140

Ile Ser Trp Ser Ala Arg Leu Lys Val Ala Arg Tyr Tyr Arg Ile Thr
145                 150                 155                 160

Tyr Gly Glu Thr Gly Gly Asn Ser Pro Val Gln Glu Phe Thr Val Pro
                165                 170                 175

Lys Asn Val Tyr Thr Ala Thr Ile Ser Gly Leu Lys Pro Gly Val Asp
                180                 185                 190

Tyr Thr Ile Thr Val Tyr Ala Val Thr Arg Phe Arg Asp Tyr Gln Pro
            195                 200                 205

Ile Ser Ile Asn Tyr Arg Thr Xaa Xaa Xaa Xaa Xaa Xaa Xaa
210                 215                 220
```

<210> SEQ ID NO 194
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: misc_feature
<222> LOCATION: (103)..(120)
<223> OTHER INFORMATION: This region may encompass 3, 6, or 9 "Pro-Ala"
      repeats
<220> FEATURE:
<221> NAME/KEY: MOD_RES
<222> LOCATION: (211)..(217)
<223> OTHER INFORMATION: This region may encompass SEQ ID NOS 9, 10,
      78, 79, 80, 81 or not present

<400> SEQUENCE: 194

```
Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Asp Ala Pro Thr Ser Arg Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gly Leu Ser Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Ser Pro Ile Ser
                85                  90                  95

Ile Asn Tyr Arg Thr Glu Pro Ala Pro Ala Pro Ala Pro Ala Pro Ala
                100                 105                 110

Pro Ala Pro Ala Pro Ala Val Ser Asp Val Pro Arg Asp Leu
            115                 120                 125

Glu Val Val Ala Ala Thr Pro Thr Ser Leu Leu Ile Ser Trp Ser Ala
    130                 135                 140

Arg Leu Lys Val Ala Arg Tyr Tyr Arg Ile Thr Tyr Gly Glu Thr Gly
145                 150                 155                 160

Gly Asn Ser Pro Val Gln Glu Phe Thr Val Pro Lys Asn Val Tyr Thr
                165                 170                 175

Ala Thr Ile Ser Gly Leu Lys Pro Gly Val Asp Tyr Thr Ile Thr Val
            180                 185                 190
```

```
Tyr Ala Val Thr Arg Phe Arg Asp Tyr Gln Pro Ile Ser Ile Asn Tyr
        195                 200                 205

Arg Thr Xaa Xaa Xaa Xaa Xaa Xaa
    210                 215

<210> SEQ ID NO 195
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Asn Ser Pro Val Gln
        35                  40                  45

Glu Phe Thr Val Pro Lys Asn Val Tyr Thr Ala Thr Ile Ser Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Asp Ala Pro Thr Ser Arg
            130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Gly Gly Leu Ser Thr Ala Thr Ile Ser
                165                 170                 175

Gly Leu Lys Pro Gly Val Asp Tyr Thr Ile Thr Val Tyr Ala Val Thr
            180                 185                 190

Asp Tyr Lys Pro His Ala Asp Gly Pro His Thr Tyr His Glu Ser Pro
            195                 200                 205

Ile Ser Ile Asn Tyr Arg Thr Glu Ile Asp Lys Pro Cys Gln His His
        210                 215                 220

His His His His
225

<210> SEQ ID NO 196
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: MOD_RES
<222> LOCATION: (216)..(222)
```

<223> OTHER INFORMATION: This region may encompass SEQ ID NOS 9, 10,
      78, 79, 80, 81 or not present

<400> SEQUENCE: 196

Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
        115                 120                 125

Ala Thr Pro Thr Ser Leu Leu Ile Ser Trp Asp Ala Pro Thr Ser Arg
130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Gly Gly Leu Ser Thr Ala Thr Ile Ser
                165                 170                 175

Gly Leu Lys Pro Gly Val Asp Tyr Thr Ile Thr Val Tyr Ala Val Thr
            180                 185                 190

Asp Tyr Lys Pro His Ala Asp Gly Pro His Thr Tyr His Glu Ser Pro
        195                 200                 205

Ile Ser Ile Asn Tyr Arg Thr Xaa Xaa Xaa Xaa Xaa Xaa Xaa
    210                 215                 220

<210> SEQ ID NO 197
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: misc_feature
<222> LOCATION: (94)..(111)
<223> OTHER INFORMATION: This region may encompass 3, 6, or 9 "Pro-Ala"
      repeats
<220> FEATURE:
<221> NAME/KEY: MOD_RES
<222> LOCATION: (211)..(217)
<223> OTHER INFORMATION: This region may encompass SEQ ID NOS 9, 10,
      78, 79, 80, 81 or not present

<400> SEQUENCE: 197

Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Ser Ala Arg Leu Lys Val Ala Arg
            20                  25                  30

```
Tyr Tyr Arg Ile Thr Tyr Gly Glu Thr Gly Asn Ser Pro Val Gln
        35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Pro Ala Pro
                 85                  90                  95

Ala Pro Ala Pro Ala Pro Ala Pro Ala Pro Ala Pro Ala Pro Ala Val
            100                 105                 110

Ser Asp Val Pro Arg Asp Leu Glu Val Val Ala Ala Thr Pro Thr Ser
            115                 120                 125

Leu Leu Ile Ser Trp Asp Ala Pro Thr Ser Arg Tyr Gln Tyr Tyr Arg
130                 135                 140

Ile Thr Tyr Gly Glu Thr Gly Gly Asn Ser Pro Val Gln Glu Phe Thr
145                 150                 155                 160

Val Pro Gly Gly Leu Ser Thr Ala Thr Ile Ser Gly Leu Lys Pro Gly
                165                 170                 175

Val Asp Tyr Thr Ile Thr Val Tyr Ala Val Thr Asp Tyr Lys Pro His
            180                 185                 190

Ala Asp Gly Pro His Thr Tyr His Glu Ser Pro Ile Ser Ile Asn Tyr
        195                 200                 205

Arg Thr Xaa Xaa Xaa Xaa Xaa Xaa
        210                 215

<210> SEQ ID NO 198
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Met Gly Val Ser Asp Val Pro Arg Asp Leu Glu Val Val Ala Ala Thr
 1               5                  10                  15

Pro Thr Ser Leu Leu Ile Ser Trp Asp Ala Gly Ala Val Thr Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Arg Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Lys Pro His Ala Asp Gly Pro His Thr Tyr His Glu Tyr Pro Ile Ser
                 85                  90                  95

Ile Asn Tyr Arg Thr Glu Ile Asp Lys Pro Ser Gln His His His His
                100                 105                 110

His His

<210> SEQ ID NO 199
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 199

Glu Val Val Ala Ala Thr Pro Thr Ser Leu Leu Ile Ser Trp Asp Ala
1               5                   10                  15

Gly Ala Val Thr Tyr Gln Tyr Tyr Arg Ile Thr Tyr Gly Glu Thr Gly
            20                  25                  30

Gly Asn Ser Pro Val Gln Glu Phe Thr Val Pro Gly Val Arg Thr
        35                  40                  45

Ala Thr Ile Ser Gly Leu Lys Pro Gly Val Asp Tyr Thr Ile Thr Val
50                  55                  60

Tyr Ala Val Thr Asp Tyr Lys Pro His Ala Asp Gly Pro His Thr Tyr
65                  70                  75                  80

His Glu Tyr Pro Ile Ser Ile Asn Tyr Arg Thr
                85                  90

<210> SEQ ID NO 200
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76 or 77
<220> FEATURE:
<221> NAME/KEY: MOD_RES
<222> LOCATION: (102)..(108)
<223> OTHER INFORMATION: This region may encompass SEQ ID NOS 9, 10,
      78, 79, 80 or 81

<400> SEQUENCE: 200

Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Asp Ala Gly Ala Val Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Arg Thr Ala Thr Ile Ser Gly Leu
50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Tyr Pro Ile Ser
                85                  90                  95

Ile Asn Tyr Arg Thr Xaa Xaa Xaa Xaa Xaa Xaa Xaa
                100                 105

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser Trp Asp Ala Gly Ala Val Thr Tyr Gln
1               5                   10

<210> SEQ ID NO 202
<211> LENGTH: 17

```
-continued

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Thr Asp Tyr Lys Pro His Ala Asp Gly Pro His Thr Tyr His Glu Tyr
1               5                   10                  15

Pro

<210> SEQ ID NO 203
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (14)..(18)
<223> OTHER INFORMATION: Any amino acid; this region may encompass 0-5
      residues

<400> SEQUENCE: 203

Xaa Xaa Xaa Xaa Xaa Asp Ala Gly Ala Val Thr Tyr Gln Xaa Xaa Xaa
1               5                   10                  15

Xaa Xaa

<210> SEQ ID NO 204
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this region may encompass 0-5
      residues
<220> FEATURE:
<221> NAME/KEY: MOD_RES
<222> LOCATION: (21)..(25)
<223> OTHER INFORMATION: Any amino acid; this region may encompass 0-5
      residues

<400> SEQUENCE: 204

Xaa Xaa Xaa Xaa Xaa Asp Tyr Lys Pro His Ala Asp Gly Pro His Thr
1               5                   10                  15

Tyr His Glu Tyr Xaa Xaa Xaa Xaa Xaa
            20                  25

<210> SEQ ID NO 205
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Met Gly Val Ser Asp Val Pro Arg Asp Leu Glu Val Val Ala Ala Thr
1               5                   10                  15
```

```
Pro Thr Ser Leu Leu Ile Ser Trp Asp Ala Gly Ala Val Thr Tyr Gln
            20                  25                  30

Tyr Tyr Arg Ile Thr Tyr Gly Glu Thr Gly Asn Ser Pro Val Gln
        35                  40                  45

Glu Phe Thr Val Pro Gly Gly Val Arg Thr Ala Thr Ile Ser Gly Leu
     50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Tyr Pro Ile Ser
                85                  90                  95

Ile Asn Tyr Arg Thr Glu Ile Asp Lys Gly Ser Gly Ser Gly Ser Gly
                100                 105                 110

Ser Gly Ser Gly Ser Gly Ser Gly Ser Gly Ser Val Ser Asp
            115                 120                 125

Val Pro Arg Asp Leu Glu Val Val Ala Ala Thr Pro Thr Ser Leu Leu
130                 135                 140

Ile Ser Trp Ser Ala Arg Leu Lys Val Ala Arg Tyr Tyr Arg Ile Thr
145                 150                 155                 160

Tyr Gly Glu Thr Gly Gly Asn Ser Pro Val Gln Glu Phe Thr Val Pro
                165                 170                 175

Lys Asn Val Tyr Thr Ala Thr Ile Ser Gly Leu Lys Pro Gly Val Asp
                180                 185                 190

Tyr Thr Ile Thr Val Tyr Ala Val Thr Arg Phe Arg Asp Tyr Gln Pro
            195                 200                 205

Ile Ser Ile Asn Tyr Arg Thr Glu Ile Asp Lys Pro Cys Gln His His
                210                 215                 220

His His His His
225

<210> SEQ ID NO 206
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: MOD_RES
<222> LOCATION: (216)..(222)
<223> OTHER INFORMATION: This region may encompass SEQ ID NOS 9, 10,
      78, 79, 80, 81 or not present

<400> SEQUENCE: 206

Xaa Xaa Xaa Xaa Xaa Xaa Xaa Xaa Xaa Glu Val Val Ala Ala Thr
1               5                   10                  15

Pro Thr Ser Leu Leu Ile Ser Trp Asp Ala Gly Ala Val Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Arg Thr Ala Thr Ile Ser Gly Leu
     50                  55                  60

Lys Pro Gly Val Asp Tyr Thr Ile Thr Val Tyr Ala Val Thr Asp Tyr
65                  70                  75                  80
```

Lys Pro His Ala Asp Gly Pro His Thr Tyr His Glu Tyr Pro Ile Ser
              85                  90                  95

Ile Asn Tyr Arg Thr Glu Ile Asp Lys Gly Ser Gly Ser Gly
            100                 105                 110

Ser Gly Ser Gly Ser Gly Ser Gly Ser Gly Ser Val Ser Asp
        115                 120                 125

Val Pro Arg Asp Leu Glu Val Ala Ala Thr Pro Thr Ser Leu Leu
    130                 135                 140

Ile Ser Trp Ser Ala Arg Leu Lys Val Ala Arg Tyr Tyr Arg Ile Thr
145                 150                 155                 160

Tyr Gly Glu Thr Gly Gly Asn Ser Pro Val Gln Glu Phe Thr Val Pro
                165                 170                 175

Lys Asn Val Tyr Thr Ala Thr Ile Ser Gly Leu Lys Pro Gly Val Asp
                180                 185                 190

Tyr Thr Ile Thr Val Tyr Ala Val Thr Arg Phe Arg Asp Tyr Gln Pro
                195                 200                 205

Ile Ser Ile Asn Tyr Arg Thr Xaa Xaa Xaa Xaa Xaa Xaa Xaa
        210                 215                 220

<210> SEQ ID NO 207
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: misc_feature
<222> LOCATION: (103)..(120)
<223> OTHER INFORMATION: This region may encompass 3, 6, or 9 "Pro-Ala"
      repeats
<220> FEATURE:
<221> NAME/KEY: MOD_RES
<222> LOCATION: (211)..(217)
<223> OTHER INFORMATION: This region may encompass SEQ ID NOS 9, 10,
      78, 79, 80, 81 or not present

<400> SEQUENCE: 207

Xaa Xaa Xaa Xaa Xaa Xaa Xaa Xaa Xaa Xaa Glu Val Val Ala Ala Thr
1               5                   10                  15

Pro Thr Ser Leu Leu Ile Ser Trp Asp Ala Gly Ala Val Thr Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Tyr Pro Ile Ser
                85                  90                  95

Ile Asn Tyr Arg Thr Glu Pro Ala Pro Ala Pro Ala Pro Ala
            100                 105                 110

Pro Ala Pro Ala Pro Ala Val Ser Asp Val Pro Arg Asp Leu
        115                 120                 125

Glu Val Val Ala Ala Thr Pro Thr Ser Leu Leu Ile Ser Trp Ser Ala
    130                 135                 140

```
Arg Leu Lys Val Ala Arg Tyr Tyr Arg Ile Thr Tyr Gly Glu Thr Gly
145                 150                 155                 160

Gly Asn Ser Pro Val Gln Glu Phe Thr Val Pro Lys Asn Val Tyr Thr
                165                 170                 175

Ala Thr Ile Ser Gly Leu Lys Pro Gly Val Asp Tyr Thr Ile Thr Val
            180                 185                 190

Tyr Ala Val Thr Arg Phe Arg Asp Tyr Gln Pro Ile Ser Ile Asn Tyr
        195                 200                 205

Arg Thr Xaa Xaa Xaa Xaa Xaa Xaa
    210                 215
```

<210> SEQ ID NO 208
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 208

```
Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
        115                 120                 125

Ala Thr Pro Thr Ser Leu Leu Ile Ser Trp Asp Ala Gly Ala Val Thr
    130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Gly Gly Val Arg Thr Ala Thr Ile Ser
                165                 170                 175

Gly Leu Lys Pro Gly Val Asp Tyr Thr Ile Thr Val Tyr Ala Val Thr
            180                 185                 190

Asp Tyr Lys Pro His Ala Asp Gly Pro His Thr Tyr His Glu Tyr Pro
        195                 200                 205

Ile Ser Ile Asn Tyr Arg Thr Glu Ile Asp Lys Pro Cys Gln His His
    210                 215                 220

His His His His
225
```

<210> SEQ ID NO 209
<211> LENGTH: 222
<212> TYPE: PRT
<213> ORGANISM: Artificial Sequence
<220> FEATURE:
<223> OTHER INFORMATION: Description of Artificial Sequence: Synthetic

```
                  polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: MOD_RES
<222> LOCATION: (216)..(222)
<223> OTHER INFORMATION: This region may encompass SEQ ID NOS 9, 10,
      78, 79, 80, 81 or not present

<400> SEQUENCE: 209

Xaa Xaa Xaa Xaa Xaa Xaa Xaa Xaa Xaa Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
        115                 120                 125

Ala Thr Pro Thr Ser Leu Leu Ile Ser Trp Asp Ala Gly Ala Val Thr
    130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Gly Gly Val Arg Thr Ala Thr Ile Ser
                165                 170                 175

Gly Leu Lys Pro Gly Val Asp Tyr Thr Ile Thr Val Tyr Ala Val Thr
            180                 185                 190

Asp Tyr Lys Pro His Ala Asp Gly Pro His Thr Tyr His Glu Tyr Pro
        195                 200                 205

Ile Ser Ile Asn Tyr Arg Thr Xaa Xaa Xaa Xaa Xaa Xaa Xaa
    210                 215                 220

<210> SEQ ID NO 210
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: This region may encompass SEQ ID NOS 69, 70,
      71, 72, 73, 74, 75, 76, 77 or not present
<220> FEATURE:
<221> NAME/KEY: misc_feature
<222> LOCATION: (94)..(111)
<223> OTHER INFORMATION: This region may encompass 3, 6, or 9 "Pro-Ala"
      repeats
<220> FEATURE:
<221> NAME/KEY: MOD_RES
<222> LOCATION: (211)..(217)
<223> OTHER INFORMATION: This region may encompass SEQ ID NOS 9, 10,
      78, 79, 80, 81 or not present
```

<400> SEQUENCE: 210

```
Xaa Xaa Xaa Xaa Xaa Xaa Xaa Xaa Xaa Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
                35                  40                  45

Glu Phe Thr Val Pro Lys Asn Val Tyr Thr Ala Thr Ile Ser Gly Leu
        50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Pro Ala Pro
                85                  90                  95

Ala Pro Ala Pro Ala Pro Ala Pro Ala Pro Ala Pro Ala Pro Ala Val
            100                 105                 110

Ser Asp Val Pro Arg Asp Leu Glu Val Val Ala Ala Thr Pro Thr Ser
            115                 120                 125

Leu Leu Ile Ser Trp Asp Ala Gly Ala Val Thr Tyr Gln Tyr Tyr Arg
130                 135                 140

Ile Thr Tyr Gly Glu Thr Gly Gly Asn Ser Pro Val Gln Glu Phe Thr
145                 150                 155                 160

Val Pro Gly Gly Val Arg Thr Ala Thr Ile Ser Gly Leu Lys Pro Gly
                165                 170                 175

Val Asp Tyr Thr Ile Thr Val Tyr Ala Val Thr Asp Tyr Lys Pro His
            180                 185                 190

Ala Asp Gly Pro His Thr Tyr His Glu Tyr Pro Ile Ser Ile Asn Tyr
            195                 200                 205

Arg Thr Xaa Xaa Xaa Xaa Xaa Xaa
            210                 215
```

<210> SEQ ID NO 211
<211> LENGTH: 222
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 211

```
Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
                35                  40                  45

Glu Phe Thr Val Pro Lys Asn Val Tyr Thr Ala Thr Ile Ser Gly Leu
        50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Glu Lys
                85                  90                  95

Gly Ser Gly Cys Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
            115                 120                 125
```

```
Ala Thr Pro Thr Ser Leu Leu Ile Ser Trp Trp Ala Pro Val Asp Arg
        130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Tyr Thr Ala Thr Ile Ser
                165                 170                 175

Gly Leu Lys Pro Gly Val Asp Tyr Thr Ile Thr Val Tyr Ala Val Thr
                180                 185                 190

Asp Tyr Lys Pro His Ala Asp Gly Pro His Thr Tyr His Glu Ser Pro
                195                 200                 205

Ile Ser Ile Asn Tyr Arg Thr Glu His His His His His
        210                 215                 220
```

<210> SEQ ID NO 212
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

```
Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu
 50                 55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Glu Lys
                85                  90                  95

Gly Ser Gly Ser Gly Ser Gly Ser Gly Ser Gly Ser Gly Ser Gly Ser
                100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Trp Ala Pro Val Asp Arg
        130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Tyr Thr Ala Thr Ile Ser
                165                 170                 175

Gly Leu Lys Pro Gly Val Asp Tyr Thr Ile Thr Val Tyr Ala Val Thr
                180                 185                 190

Asp Tyr Lys Pro His Ala Asp Gly Pro His Thr Tyr His Glu Ser Pro
                195                 200                 205

Ile Ser Ile Asn Tyr Arg Thr Glu Gly Ser Gly Cys His His His His
        210                 215                 220

His His
225
```

<210> SEQ ID NO 213
<211> LENGTH: 222
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 213

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Cys Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Glu Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Trp Ala Pro Val Asp Arg
130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Tyr Thr Ala Thr Ile Ser
                165                 170                 175

Gly Leu Lys Pro Gly Val Asp Tyr Thr Ile Thr Val Tyr Ala Val Thr
            180                 185                 190

Asp Tyr Lys Pro His Ala Asp Gly Pro His Thr Tyr His Glu Ser Pro
            195                 200                 205

Ile Ser Ile Asn Tyr Arg Thr Glu His His His His His His
            210                 215                 220

<210> SEQ ID NO 214
<211> LENGTH: 222
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 214

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Glu Lys
                85                  90                  95

Gly Ser Gly Ser Gly Ser Gly Ser Gly Ser Gly Ser Gly Ser Gly Ser

```
                100             105                 110
Gly Ser Gly Ser Val Ser Asp Val Pro Arg Asp Leu Glu Val Val Ala
            115                 120                 125

Ala Thr Pro Thr Ser Leu Leu Ile Ser Trp Trp Ala Pro Val Asp Arg
130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Tyr Thr Ala Thr Ile Cys
                165                 170                 175

Gly Leu Lys Pro Gly Val Asp Tyr Thr Ile Thr Val Tyr Ala Val Thr
            180                 185                 190

Asp Tyr Lys Pro His Ala Asp Gly Pro His Thr Tyr His Glu Ser Pro
            195                 200                 205

Ile Ser Ile Asn Tyr Arg Thr Glu His His His His His
            210                 215                 220

<210> SEQ ID NO 215
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Cys Ile Asn Tyr Arg Thr Glu Ile Glu Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
            115                 120                 125

Ala Thr Pro Thr Ser Leu Leu Ile Ser Trp Trp Ala Pro Val Asp Arg
130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Tyr Thr Ala Thr Ile Ser
                165                 170                 175

Gly Leu Lys Pro Gly Val Asp Tyr Thr Ile Thr Val Tyr Ala Val Thr
            180                 185                 190

Asp Tyr Lys Pro His Ala Asp Gly Pro His Thr Tyr His Glu Ser Pro
            195                 200                 205

Ile Ser Ile Asn Tyr Arg Thr Glu His His His His His
            210                 215                 220

<210> SEQ ID NO 216
<211> LENGTH: 222
```

<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 216

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Glu Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
        115                 120                 125

Ala Thr Pro Thr Ser Leu Leu Ile Ser Trp Trp Ala Pro Val Asp Arg
    130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Tyr Thr Ala Thr Ile Ser
                165                 170                 175

Gly Leu Lys Pro Gly Val Asp Tyr Thr Ile Thr Val Tyr Ala Val Thr
            180                 185                 190

Asp Tyr Lys Pro His Ala Asp Gly Pro His Thr Tyr His Glu Ser Pro
        195                 200                 205

Ile Cys Ile Asn Tyr Arg Thr Glu His His His His His His
    210                 215                 220

<210> SEQ ID NO 217
<211> LENGTH: 4
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 217

Glu Ile Glu Lys
1

<210> SEQ ID NO 218
<211> LENGTH: 20
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 218

Gly Ser Gly Cys Gly Ser Gly Ser Gly Ser Gly Ser Gly Ser Gly Ser
1               5                   10                  15

Gly Ser Gly Ser

20

<210> SEQ ID NO 219
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Met Gly Val Ser Asp Val Pro Arg Asp Leu Glu Val Val Ala Ala Thr
1               5                   10                  15

Pro Thr Ser Leu Leu Ile Ser Trp Gln Val Pro Arg Pro Met Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Asp Val Tyr Thr Ala Thr Ile Ser Gly Leu
    50                  55                  60

Lys Pro Gly Val Asp Tyr Thr Ile Thr Val Tyr Ala Val Thr Asp Ser
65                  70                  75                  80

Tyr Asn Pro Ala Thr His Glu Tyr Lys Tyr His Gln Thr Pro Ile Ser
                85                  90                  95

Ile Asn Tyr Arg Thr Glu Ile Asp Lys Pro Ser Gln
            100                 105

<210> SEQ ID NO 220
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Met Gly Val Ser Asp Val Pro Arg Asp Leu Glu Val Val Ala Ala Thr
1               5                   10                  15

Pro Thr Ser Leu Leu Ile Ser Trp Gln Val Pro Arg Pro Met Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Asp Val His Thr Ala Thr Ile Ser Gly Leu
    50                  55                  60

Lys Pro Gly Val Asp Tyr Thr Ile Thr Val Tyr Ala Val Thr Asp Ser
65                  70                  75                  80

Tyr Asn Pro Ala Thr His Glu Tyr Lys Tyr His Gln Thr Pro Ile Ser
                85                  90                  95

Ile Asn Tyr Arg Thr Glu Ile Asp Lys Pro Ser Gln
            100                 105

<210> SEQ ID NO 221
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Met Gly Val Ser Asp Val Pro Arg Asp Leu Glu Val Val Ala Ala Thr
1               5                   10                  15

```
Pro Thr Ser Leu Leu Ile Ser Trp Gln Val Pro Arg Pro Met Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Tyr Asp Leu Thr Thr Ala Thr Ile Ser Gly Leu
 50                  55                  60

Lys Pro Gly Val Asp Tyr Thr Ile Thr Val Tyr Ala Val Thr Asp Ser
 65                  70                  75                  80

Tyr Asn Pro Ala Thr His Glu Tyr Lys Tyr His Gln Thr Pro Ile Ser
                 85                  90                  95

Ile Asn Tyr Arg Thr Glu Ile Asp Lys Pro Ser Gln
            100                 105
```

<210> SEQ ID NO 222
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

```
Met Gly Val Ser Asp Val Pro Arg Asp Leu Glu Val Val Ala Ala Thr
 1               5                  10                  15

Pro Thr Ser Leu Leu Ile Ser Trp Glu Ala Asn Pro Ser Arg Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro His Asp Leu Asn Thr Ala Thr Ile Ser Gly Leu
 50                  55                  60

Lys Pro Gly Val Asp Tyr Thr Ile Thr Val Tyr Ala Val Thr Asp Ser
 65                  70                  75                  80

Tyr Asn Pro Ala Thr His Glu Tyr Lys Tyr His Gln Thr Pro Ile Ser
                 85                  90                  95

Ile Asn Tyr Arg Thr Glu Ile Asp Lys Pro Ser Gln
            100                 105
```

<210> SEQ ID NO 223
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

```
Met Gly Val Ser Asp Val Pro Arg Asp Leu Glu Val Val Ala Ala Thr
 1               5                  10                  15

Pro Thr Ser Leu Leu Ile Ser Trp Tyr Pro Gly Ser Arg Thr Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Arg Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Tyr His Pro Ala Thr Tyr Glu His Glu Tyr His Ala His Pro Ile Ser
                 85                  90                  95
```

-continued

```
Ile Asn Tyr Arg Thr Glu Ile Asp Lys Pro Ser Gln
            100                 105
```

<210> SEQ ID NO 224
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

```
Met Gly Val Ser Asp Val Pro Arg Asp Leu Glu Val Val Ala Ala Thr
1               5                   10                  15

Pro Thr Ser Leu Leu Ile Ser Trp Thr Pro Ala Asn Lys Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Asp Gly Thr Thr Ala Thr Ile Ser Gly Leu
    50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Tyr Pro Ile Ser
                85                  90                  95

Ile Asn Tyr Arg Thr Glu Ile Asp Lys Pro Ser Gln
            100                 105
```

<210> SEQ ID NO 225
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

```
Met Gly Val Ser Asp Val Pro Arg Asp Leu Glu Val Val Ala Ala Thr
1               5                   10                  15

Pro Thr Ser Leu Leu Ile Ser Trp Gln Val Pro Arg Pro Met Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro His Asp Val Tyr Thr Ala Thr Ile Ser Gly Leu
    50                  55                  60

Lys Pro Gly Val Asp Tyr Thr Ile Thr Val Tyr Ala Val Thr Asp Ser
65                  70                  75                  80

Tyr Asn Pro Ala Thr His Glu Tyr Lys Tyr His Gln Thr Pro Ile Ser
                85                  90                  95

Ile Asn Tyr Arg Thr Glu Ile Asp Lys Pro Ser Gln
            100                 105
```

<210> SEQ ID NO 226
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

```
Met Gly Val Ser Asp Val Pro Arg Asp Leu Glu Val Val Ala Ala Thr
1               5                   10                  15

Pro Thr Ser Leu Leu Ile Ser Trp Gln Val Pro Arg Pro Met Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Gln Val Tyr Thr Ala Thr Ile Ser Gly Leu
    50                  55                  60

Lys Pro Gly Val Asp Tyr Thr Ile Thr Val Tyr Ala Val Thr Asp Ser
65                  70                  75                  80

Tyr Asn Pro Ala Thr His Glu Tyr Lys Tyr His Gln Thr Pro Ile Ser
                85                  90                  95

Ile Asn Tyr Arg Thr Glu Ile Asp Lys Pro Ser Gln
            100                 105
```

<210> SEQ ID NO 227
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 227

```
Met Gly Val Ser Asp Val Pro Arg Asp Leu Glu Val Val Ala Ala Thr
1               5                   10                  15

Pro Thr Ser Leu Leu Ile Ser Trp Gln Val Pro Arg Pro Met Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Tyr Asp Val Thr Thr Ala Thr Ile Ser Gly Leu
    50                  55                  60

Lys Pro Gly Val Asp Tyr Thr Ile Thr Val Tyr Ala Val Thr Asp Ser
65                  70                  75                  80

Tyr Asn Pro Ala Thr His Glu Tyr Lys Tyr His Gln Thr Pro Ile Ser
                85                  90                  95

Ile Asn Tyr Arg Thr Glu Ile Asp Lys Pro Ser Gln
            100                 105
```

<210> SEQ ID NO 228
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 228

```
Met Gly Val Ser Asp Val Pro Arg Asp Leu Glu Val Val Ala Ala Thr
1               5                   10                  15

Pro Thr Ser Leu Leu Ile Ser Trp Gln Val Pro Arg Pro Met Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro His Asp Leu Arg Thr Ala Thr Ile Ser Gly Leu
    50                  55                  60

Lys Pro Gly Val Asp Tyr Thr Ile Thr Val Tyr Ala Val Thr Asp Ser
65                  70                  75                  80
```

Tyr Asn Pro Ala Thr His Glu Tyr Lys Tyr His Gln Thr Pro Ile Ser
            85                  90                  95

Ile Asn Tyr Arg Thr Glu Ile Asp Lys Pro Ser Gln
            100                 105

<210> SEQ ID NO 229
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Met Gly Val Ser Asp Val Pro Arg Asp Leu Glu Val Val Ala Ala Thr
1               5                   10                  15

Pro Thr Ser Leu Leu Ile Ser Trp Gln Val Pro Arg Pro Met Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Asp Leu Val Thr Ala Thr Ile Ser Gly Leu
50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Ser Pro Ile Ser
            85                  90                  95

Ile Asn Tyr Arg Thr Glu Ile Asp Lys Pro Ser Gln
            100                 105

<210> SEQ ID NO 230
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Met Gly Val Ser Asp Val Pro Arg Asp Leu Glu Val Val Ala Ala Thr
1               5                   10                  15

Pro Thr Ser Leu Leu Ile Ser Trp Leu Pro Gly Lys Leu Arg Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro His Asp Leu Arg Thr Ala Thr Ile Ser Gly Leu
50                  55                  60

Lys Pro Gly Val Asp Tyr Thr Ile Thr Val Tyr Ala Val Thr Asn Met
65                  70                  75                  80

Met His Val Glu Tyr Ser Glu Tyr Pro Ile Ser Ile Asn Tyr Arg Thr
            85                  90                  95

Glu Ile Asp Lys Pro Ser Gln His
            100

<210> SEQ ID NO 231
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Met Gly Val Ser Asp Val Pro Arg Asp Leu Glu Val Val Ala Ala Thr
1               5                   10                  15

Pro Thr Ser Leu Leu Ile Ser Trp Val Ala Gly Ala Glu Asp Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro His Asp Leu Val Thr Ala Thr Ile Ser Gly Leu
    50                  55                  60

Lys Pro Gly Val Asp Tyr Thr Ile Thr Val Tyr Ala Val Thr Asp Met
65                  70                  75                  80

Met His Val Glu Tyr Thr Glu His Pro Ile Ser Ile Asn Tyr Arg Thr
                85                  90                  95

Glu Ile Asp Lys Pro Ser Gln
            100

<210> SEQ ID NO 232
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Met Gly Val Ser Asp Val Pro Arg Asp Leu Glu Val Val Ala Ala Thr
1               5                   10                  15

Pro Thr Ser Leu Leu Ile Ser Trp Gln Val Pro Arg Pro Met Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Met Val His Thr Ala Thr Ile Ser Gly Leu
    50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Pro Ser Gln
            100                 105

<210> SEQ ID NO 233
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Met Gly Val Ser Asp Val Pro Arg Asp Leu Glu Val Val Ala Ala Thr
1               5                   10                  15

Pro Thr Ser Leu Leu Ile Ser Trp Phe Val Thr His Val Ala Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Leu Ser Thr Ala Thr Ile Ser Gly Leu
    50                  55                  60

Lys Pro Gly Val Asp Tyr Thr Ile Thr Val Tyr Ala Val Thr Asp Tyr

```
                65                  70                  75                  80
Lys Pro His Ala Asp Gly Pro His Thr Tyr His Glu Ser Pro Ile Ser
                    85                  90                  95

Ile Asn Tyr Arg Thr Glu Ile Asp Lys Pro Ser Gln
                100                 105

<210> SEQ ID NO 234
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Met Gly Val Ser Asp Val Pro Arg Asp Leu Glu Val Val Ala Ala Thr
1               5                   10                  15

Pro Thr Ser Leu Leu Ile Ser Trp Glu Thr Glu Ser Asn Ala Tyr Gln
                20                  25                  30

Tyr Tyr Arg Ile Thr Tyr Gly Glu Thr Gly Gly Asn Ser Pro Val Gln
                35                  40                  45

Glu Phe Thr Val Pro Gly Gln Ile Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Ser Pro Ile Ser
                    85                  90                  95

Ile Asn Tyr Arg Thr Glu Ile Asp Lys Pro Ser Gln
                100                 105

<210> SEQ ID NO 235
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Met Gly Val Ser Asp Val Pro Arg Asp Leu Glu Val Val Ala Ala Thr
1               5                   10                  15

Pro Thr Ser Leu Leu Ile Ser Trp Met Thr Ser Pro Ser Val Tyr Gln
                20                  25                  30

Tyr Tyr Arg Ile Thr Tyr Gly Glu Thr Gly Gly Asn Ser Pro Val Gln
                35                  40                  45

Glu Phe Thr Val Pro Gly Pro Val Gln Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Lys Glu His Gln His Ala Pro His Gln Tyr Thr Ala His Pro Ile Ser
                    85                  90                  95

Ile Asn Tyr Arg Thr Glu Ile Asp Lys Pro Ser Gln
                100                 105

<210> SEQ ID NO 236
<211> LENGTH: 108
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 236

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Pro Val His Thr Ala Thr Ile Ser Gly Leu
    50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Pro Ser Gln
            100                 105

<210> SEQ ID NO 237
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Met Gly Val Ser Asp Val Pro Arg Asp Leu Glu Val Val Ala Ala Thr
1               5                   10                  15

Pro Thr Ser Leu Leu Ile Ser Trp Ser Thr Gly Arg Thr Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro His Asp Leu Asp Thr Ala Thr Ile Ser Gly Leu
    50                  55                  60

Lys Pro Gly Val Asp Tyr Thr Ile Thr Val Tyr Ala Val Thr Asp Ser
65                  70                  75                  80

Tyr Asn Pro Ala Thr His Glu Tyr Lys Tyr His Gln Thr Pro Ile Ser
                85                  90                  95

Ile Asn Tyr Arg Thr Glu Ile Asp Lys Pro Ser Gln
            100                 105

<210> SEQ ID NO 238
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Met Gly Val Ser Asp Val Pro Arg Asp Leu Glu Val Val Ala Ala Thr
1               5                   10                  15

Pro Thr Ser Leu Leu Ile Ser Trp Gln Val Pro Arg Pro Met Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Asp Val Ile Thr Ala Thr Ile Ser Gly Leu
    50                  55                  60

```
Lys Pro Gly Val Asp Tyr Thr Ile Thr Val Tyr Ala Val Thr Asp Met
 65                  70                  75                  80

Met His Val Glu Tyr Ala Glu Tyr Pro Ile Ser Ile Asn Tyr Arg Thr
                 85                  90                  95

Glu Ile Asp Lys Pro Ser Gln
            100
```

<210> SEQ ID NO 239
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

```
Met Gly Val Ser Asp Val Pro Arg Asp Leu Glu Val Val Ala Ala Thr
 1               5                  10                  15

Pro Thr Ser Leu Leu Ile Ser Trp Gln Val Pro Arg Pro Met Tyr Gln
                 20                  25                  30

Tyr Tyr Arg Ile Thr Tyr Gly Glu Thr Gly Gly Asn Ser Pro Val Gln
             35                  40                  45

Glu Phe Thr Val Pro Gly Gln Val Pro Thr Ala Thr Ile Ser Gly Leu
 50                  55                  60

Lys Pro Gly Val Asp Tyr Thr Ile Thr Val Tyr Ala Val Thr Asp Ser
 65                  70                  75                  80

Tyr Asn Pro Ala Thr His Glu Tyr Lys Tyr His Gln Thr Pro Ile Ser
                 85                  90                  95

Ile Asn Tyr Arg Thr Glu Ile Asp Lys Pro Ser Gln
            100                 105
```

<210> SEQ ID NO 240
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

```
Met Gly Val Ser Asp Val Pro Arg Asp Leu Glu Val Val Ala Ala Thr
 1               5                  10                  15

Pro Thr Ser Leu Leu Ile Ser Trp Gly Tyr Gln Ser Gly Gly Tyr Thr
                 20                  25                  30

Tyr Tyr Arg Ile Thr Tyr Gly Glu Thr Gly Gly Asn Ser Pro Val Gln
             35                  40                  45

Glu Phe Thr Val Pro His Asp Leu Arg Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Ala Tyr Lys Glu Tyr Gln Glu His Pro Ile Ser Ile Asn Tyr Arg Thr
                 85                  90                  95

Glu Ile Asp Lys Pro Ser Gln
            100
```

<210> SEQ ID NO 241
<211> LENGTH: 103
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 241

Met Gly Val Ser Asp Val Pro Arg Asp Leu Glu Val Val Ala Ala Thr
1               5                   10                  15

Pro Thr Ser Leu Leu Ile Ser Trp Trp Ile Gly Ile Pro Val Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Asp Gly Lys Thr Ala Thr Ile Ser Gly Leu
50                  55                  60

Lys Pro Gly Val Asp Tyr Thr Ile Thr Val Tyr Ala Val Thr Asp Met
65                  70                  75                  80

Met His Val Glu Tyr Ala Glu Tyr Pro Ile Ser Ile Asn Tyr Arg Thr
                85                  90                  95

Glu Ile Asp Lys Pro Ser Gln
            100

<210> SEQ ID NO 242
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Met Gly Val Ser Asp Val Pro Arg Asp Leu Glu Val Val Ala Ala Thr
1               5                   10                  15

Pro Thr Ser Leu Leu Ile Ser Trp Ser Lys Gly Ser Lys Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr His Val Tyr Thr Ala Thr Ile Ser Gly Leu
50                  55                  60

Lys Pro Gly Val Asp Tyr Thr Ile Thr Val Tyr Ala Val Thr Asp Tyr
65                  70                  75                  80

Tyr Asn Pro Ala Thr Tyr Glu Tyr Ile Tyr Leu Thr Thr Pro Ile Ser
                85                  90                  95

Ile Asn Tyr Arg Thr Glu Ile Asp Lys Pro Ser Gln
            100                 105

<210> SEQ ID NO 243
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Met Gly Val Ser Asp Val Pro Arg Asp Leu Glu Val Val Ala Ala Thr
1               5                   10                  15

Pro Thr Ser Leu Leu Ile Ser Trp Asn Pro Gly Ser Lys Ser Tyr Gln
            20                  25                  30

Tyr Tyr Arg Ile Thr Tyr Gly Glu Thr Gly Gly Asn Ser Pro Val Gln
        35                  40                  45
```

```
Glu Phe Thr Val Pro Gly Gly Val Arg Thr Ala Thr Ile Ser Gly Leu
 50                  55                  60

Lys Pro Gly Val Asp Tyr Thr Ile Thr Val Tyr Ala Val Thr Asp Phe
 65                  70                  75                  80

Tyr Asn Pro Asp Thr His Glu Tyr Leu Tyr Asn Gln Tyr Pro Ile Ser
                 85                  90                  95

Ile Asn Tyr Arg Thr Glu Ile Asp Lys Pro Ser Gln
            100                 105
```

<210> SEQ ID NO 244
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

```
Met Gly Val Ser Asp Val Pro Arg Asp Leu Glu Val Val Ala Ala Thr
 1               5                  10                  15

Pro Thr Ser Leu Leu Ile Ser Trp Gln Pro Gly Thr Thr His Tyr Gln
                 20                  25                  30

Tyr Tyr Arg Ile Thr Tyr Gly Glu Thr Gly Gly Asn Ser Pro Val Gln
             35                  40                  45

Glu Phe Thr Val Pro Tyr Asp Leu Met Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Tyr Asn Pro Asn Thr Tyr Glu Tyr Ile Tyr Leu Thr Thr Pro Ile Ser
                 85                  90                  95

Ile Asn Tyr Arg Thr Glu Ile Asp Lys Pro Ser Gln
            100                 105
```

<210> SEQ ID NO 245
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

```
Met Gly Val Ser Asp Val Pro Arg Asp Leu Glu Val Val Ala Ala Thr
 1               5                  10                  15

Pro Thr Ser Leu Leu Ile Ser Trp Ala Ile Gly Thr Ile Val Tyr Gln
                 20                  25                  30

Tyr Tyr Arg Ile Thr Tyr Gly Glu Thr Gly Gly Asn Ser Pro Val Gln
             35                  40                  45

Glu Phe Thr Val Pro Ala Gly Val Tyr Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Tyr Asp Trp Ala Thr His Glu Tyr Asn Tyr His Thr Ala Pro Ile Ser
                 85                  90                  95

Ile Asn Tyr Arg Thr Glu Ile Asp Lys Pro Ser Gln
            100                 105
```

<210> SEQ ID NO 246
<211> LENGTH: 108

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Met Gly Val Ser Asp Val Pro Arg Asp Leu Glu Val Val Ala Ala Thr
1               5                   10                  15

Pro Thr Ser Leu Leu Ile Ser Trp Thr Tyr Asn Asp Gly Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ala Val Tyr Thr Ala Thr Ile Ser Gly Leu
    50                  55                  60

Lys Pro Gly Val Asp Tyr Thr Ile Thr Val Tyr Ala Val Thr Asp Phe
65                  70                  75                  80

Tyr Asn Pro Ala Thr Tyr Glu Tyr Ile Tyr His Thr Thr Pro Ile Ser
                85                  90                  95

Ile Asn Tyr Arg Thr Glu Ile Asp Lys Pro Ser Gln
            100                 105

<210> SEQ ID NO 247
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Met Gly Val Ser Asp Val Pro Arg Asp Leu Glu Val Val Ala Ala Thr
1               5                   10                  15

Pro Thr Ser Leu Leu Ile Ser Trp Val Ser Leu Val Gly Phe Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val His Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Lys Pro His Ala Asp Gly Pro His Tyr His Glu Ser Pro Ile Ser
                85                  90                  95

Ile Asn Tyr Arg Thr Glu Ile Asp Lys Pro Ser Gln
            100                 105

<210> SEQ ID NO 248
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Met Gly Val Ser Asp Val Pro Arg Asp Leu Glu Val Val Ala Ala Thr
1               5                   10                  15

Pro Thr Ser Leu Leu Ile Ser Trp Ala Ser Arg Lys Glu Val Tyr Gln
            20                  25                  30

Tyr Tyr Arg Ile Thr Tyr Gly Glu Thr Gly Gly Asn Ser Pro Val Gln
```

```
                    35                   40                  45

Glu Phe Thr Val Pro Gly Trp Leu Asn Thr Ala Thr Ile Ser Gly Leu
 50                      55                  60

Lys Pro Gly Val Asp Tyr Thr Ile Thr Val Tyr Ala Val Thr Asp Tyr
 65                  70                  75                  80

Met His Val Glu Tyr Ala Glu Tyr Pro Ile Ser Ile Asn Tyr Arg Thr
                 85                  90                  95

Glu Ile Asp Lys Pro Ser Gln
            100
```

<210> SEQ ID NO 249
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

```
Met Gly Val Ser Asp Val Pro Arg Asp Leu Glu Val Val Ala Ala Thr
 1               5                  10                  15

Pro Thr Ser Leu Leu Ile Ser Trp Leu Ala Pro Phe Trp Arg Tyr Gln
                 20                  25                  30

Tyr Tyr Arg Ile Thr Tyr Gly Glu Thr Gly Gly Asn Ser Pro Val Gln
             35                  40                  45

Glu Phe Thr Val Pro Gly Gly Val Arg Thr Ala Thr Ile Ser Gly Leu
 50                  55                      60

Lys Pro Gly Val Asp Tyr Thr Ile Thr Val Tyr Ala Val Thr Asp Tyr
 65                  70                  75                  80

Lys Pro His Ala Asp Gly Pro His Thr Tyr His Glu Ser Pro Ile Ser
                 85                  90                  95

Ile Asn Tyr Arg Thr Glu Ile Asp Lys Pro Ser Gln
            100                 105
```

<210> SEQ ID NO 250
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

```
Met Gly Val Ser Asp Val Pro Arg Asp Leu Glu Val Val Ala Ala Thr
 1               5                  10                  15

Pro Thr Ser Leu Leu Ile Ser Trp Thr Pro Pro Gly His Gln His Gln
                 20                  25                  30

Tyr Tyr Arg Ile Thr Tyr Gly Glu Thr Gly Gly Asn Ser Pro Val Gln
             35                  40                  45

Glu Phe Thr Val Pro Gly Gln Val Thr Ala Thr Ile Ser Gly Leu
 50                  55                      60

Lys Pro Gly Val Asp Tyr Thr Ile Thr Val Tyr Ala Val Thr Asp Tyr
 65                  70                  75                  80

Tyr Asn Pro Ala Thr His Tyr Tyr Thr Tyr Thr Thr Pro Ile Ser
                 85                  90                  95

Ile Asn Tyr Arg Thr Glu Ile Asp Lys Pro Ser Gln
            100                 105
```

```
<210> SEQ ID NO 251
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Met Gly Val Ser Asp Val Pro Arg Asp Leu Glu Val Val Ala Ala Thr
1               5                   10                  15

Pro Thr Ser Leu Leu Ile Ser Trp Glu Ser Gly Ser Arg Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val His Thr Ala Thr Ile Ser Gly Leu
    50                  55                  60

Lys Thr Gly Val Asp Tyr Thr Ile Thr Val Tyr Ala Val Thr Asp Tyr
65                  70                  75                  80

Lys Pro His Ala Asp Gly Pro His Thr His Glu Tyr Pro Ile Ser
                85                  90                  95

Ile Asn Tyr Arg Thr Glu Ile Asp Lys Pro Ser Gln
            100                 105

<210> SEQ ID NO 252
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Met Gly Val Ser Asp Val Pro Arg Asp Leu Glu Val Val Ala Ala Thr
1               5                   10                  15

Pro Thr Ser Leu Leu Ile Ser Trp Glu Arg Thr Ser Thr His Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Arg Val Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Tyr Asn Pro Ala Thr His Glu Tyr Lys Tyr His Gln Thr Pro Ile Ser
                85                  90                  95

Ile Asn Tyr Arg Thr Glu Ile Asp Lys Pro Ser Gln
            100                 105

<210> SEQ ID NO 253
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Met Gly Val Ser Asp Val Pro Arg Asp Leu Glu Val Val Ala Ala Thr
1               5                   10                  15

Pro Thr Ser Leu Leu Ile Ser Trp Asn Ala Arg Thr Asp Ala Tyr Gln
            20                  25                  30
```

```
Tyr Tyr Arg Ile Thr Tyr Gly Glu Thr Gly Gly Asn Ser Pro Val Gln
            35                  40                  45

Glu Phe Thr Val Pro Arg Asp Leu Glu Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Lys Pro His Ala Asp Gly Pro His Thr Tyr Gln Glu Ser Pro Ile Ser
                85                  90                  95

Ile Asn Tyr Arg Thr Glu Ile Asp Lys Pro Ser Gln
            100                 105
```

<210> SEQ ID NO 254
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

```
Met Gly Val Ser Asp Val Pro Arg Asp Leu Glu Val Val Ala Ala Thr
 1               5                  10                  15

Pro Thr Ser Leu Leu Ile Ser Trp Gln Val Ser Ala Phe Arg Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Met Val Ser Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Lys Pro His Ala Asp Gly Pro His Thr Tyr Ser Glu Tyr Pro Ile Ser
                85                  90                  95

Ile Asn Tyr Arg Thr Glu Ile Asp Lys Pro Ser Gln
            100                 105
```

<210> SEQ ID NO 255
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

```
Met Gly Val Ser Asp Val Pro Arg Asp Leu Glu Val Val Ala Ala Thr
 1               5                  10                  15

Pro Thr Ser Leu Leu Ile Ser Trp Val Leu Gly Arg Arg Val Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Ala Val Tyr Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Phe Asn Pro Ala Thr His Glu Tyr Gln Tyr Glu Leu Thr Pro Ile Ser
                85                  90                  95

Ile Asn Tyr Arg Thr Glu Ile Asp Lys Pro Ser Gln
            100                 105
```

<210> SEQ ID NO 256
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Met Gly Val Ser Asp Val Pro Arg Asp Leu Glu Val Val Ala Ala Thr
1               5                   10                  15

Pro Thr Ser Leu Leu Ile Ser Trp Thr Pro Asn Ser Gly His Asn
            20                  25                  30

Tyr Tyr Arg Ile Thr Tyr Gly Glu Thr Gly Gly Asn Ser Pro Val Gln
        35                  40                  45

Glu Phe Thr Val Pro His Asp Leu Thr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Tyr Asn Pro Asn Thr Tyr Glu Tyr Thr Tyr Gln Phe Thr Pro Ile Ser
                85                  90                  95

Ile Asn Tyr Arg Thr Glu Ile Asp Lys Pro Ser Gln
            100                 105

<210> SEQ ID NO 257
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Met Gly Val Ser Asp Val Pro Arg Asp Leu Glu Val Val Ala Ala Thr
1               5                   10                  15

Pro Thr Ser Leu Leu Ile Ser Trp Val Val Pro Asn Trp Met Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Met Leu Glu Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Tyr Asn Pro Thr Thr Tyr Glu Tyr Thr Tyr Phe Thr Tyr Pro Ile Ser
                85                  90                  95

Ile Asn Tyr Arg Thr Glu Ile Asp Lys Pro Ser Gln
            100                 105

<210> SEQ ID NO 258
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Met Gly Val Ser Asp Val Pro Arg Asp Leu Glu Val Val Ala Ala Thr
1               5                   10                  15

Pro Thr Ser Leu Leu Ile Ser Trp Ser Gly Phe Met Arg Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Gln Val Tyr Thr Ala Thr Ile Ser Gly Leu
        50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Pro Ser Gln
            100                 105

<210> SEQ ID NO 259
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Met Gly Val Ser Asp Val Pro Arg Asp Leu Glu Val Val Ala Ala Thr
1               5                   10                  15

Pro Thr Ser Leu Leu Ile Ser Trp Asp Ser Glu Gly Pro Ser Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Tyr Ala Val Tyr Thr Ala Thr Ile Ser Gly Leu
        50                  55                  60

Lys Pro Gly Val Asp Tyr Thr Ile Thr Val Tyr Ala Val Thr Asp Tyr
65                  70                  75                  80

Tyr Asn Pro Arg Thr His Glu Leu Phe Phe Gln Gln Tyr Pro Ile Ser
                85                  90                  95

Ile Asn Tyr Arg Thr Glu Ile Asp Lys Pro Ser Gln
            100                 105

<210> SEQ ID NO 260
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Met Gly Val Ser Asp Val Pro Arg Asp Leu Glu Val Val Ala Ala Thr
1               5                   10                  15

Pro Thr Ser Leu Leu Ile Ser Trp Gln Val Pro Arg Pro Met Tyr Gln
            20                  25                  30

Tyr Tyr Arg Ile Thr Tyr Gly Glu Lys Gly Gly Asn Ser Pro Val Gln
            35                  40                  45

Glu Phe Thr Val Pro His Asp Leu Arg Thr Ala Thr Ile Ser Gly Leu
        50                  55                  60

Lys Pro Gly Val Asp Tyr Thr Ile Thr Val Tyr Ala Val Thr Asp Tyr
65                  70                  75                  80

Tyr Asp Pro Thr Ser Asn Leu Tyr Asn Tyr Asn Gln Thr Pro Ile Ser
                85                  90                  95

Ile Asn Tyr Arg Thr Glu Ile Asp Lys Pro Ser Gln
            100                 105

<210> SEQ ID NO 261
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Met Gly Val Ser Asp Val Pro Arg Asp Leu Glu Val Val Ala Ala Thr
1               5                   10                  15

Pro Thr Ser Leu Leu Ile Ser Trp Gln Val Gly Ser Val Val Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Arg Asp Val Leu Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Lys Pro Lys Pro Asp Gly Pro His Ile Tyr Gln Ala Val Pro Ile Ser
                85                  90                  95

Ile Asn Tyr Arg Thr Glu Ile Asp Lys Pro Ser Gln
            100                 105

<210> SEQ ID NO 262
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Met Gly Val Ser Asp Val Pro Arg Asp Leu Glu Val Val Ala Ala Thr
1               5                   10                  15

Pro Thr Ser Leu Leu Ile Ser Trp Asn Pro Ala Ser Lys Asp Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gln Val Pro Thr Ala Thr Ile Ser Gly Leu
    50                  55                  60

Lys Pro Gly Val Asp Tyr Thr Ile Thr Val Tyr Ala Val Thr Asp Phe
65                  70                  75                  80

Tyr Asn Pro Ala Thr His Glu Tyr Lys Tyr Asp Ser Thr Pro Ile Ser
                85                  90                  95

Ile Asn Tyr Arg Thr Glu Ile Asp Lys Pro Ser Gln
            100                 105

<210> SEQ ID NO 263
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Met Gly Val Ser Asp Val Pro Arg Asp Leu Glu Val Val Ala Ala Thr

```
 1               5                  10                 15
Pro Thr Ser Leu Leu Ile Ser Trp Arg Ser Ser Ala Thr Ala Tyr Gln
                20                  25                 30

Tyr Tyr Arg Ile Thr Tyr Gly Glu Thr Gly Gly Asn Ser Pro Val Gln
            35                  40                 45

Glu Phe Thr Val Pro Gly Arg Val Tyr Thr Ala Thr Ile Ser Gly Leu
        50                  55                  60

Lys Pro Gly Val Asp Tyr Thr Ile Thr Val Tyr Ala Val Thr Asp Phe
65                  70                  75                  80

Phe Asn Trp Ala Thr His Glu Tyr Ile Tyr His Ser Thr Pro Ile Ser
                85                  90                  95

Ile Asn Tyr Arg Thr Glu Ile Asp Lys Pro Ser Gln
                100                 105

<210> SEQ ID NO 264
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Met Gly Val Ser Asp Val Pro Arg Asp Leu Glu Val Val Ala Ala Thr
1               5                   10                  15

Pro Thr Ser Leu Leu Ile Ser Trp His Ser Gly Pro Arg Glu Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gln Val Tyr Thr Ala Thr Ile Ser Gly Leu
        50                  55                  60

Lys Pro Gly Val Asp Tyr Thr Ile Thr Val Tyr Ala Val Thr Asp Phe
65                  70                  75                  80

Phe Asn Pro Ile Thr His Tyr Tyr Tyr Glu Leu Thr Pro Ile Ser
                85                  90                  95

Ile Asn Tyr Arg Thr Glu Ile Asp Lys Pro Ser Gln
                100                 105

<210> SEQ ID NO 265
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Met Gly Val Ser Asp Val Pro Arg Asp Leu Glu Val Val Ala Ala Thr
1               5                   10                  15

Pro Thr Ser Leu Leu Ile Ser Trp Thr Val Gly Leu Ser Val Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Met Val Ser Thr Ala Thr Ile Ser Gly Leu
        50                  55                  60

Lys Pro Ser Val Asp Tyr Thr Ile Thr Val Tyr Ala Val Thr Asp Tyr
65                  70                  75                  80

Lys Pro His Ala Asp Gly Pro His Thr Tyr His Glu Tyr Pro Ile Ser
```

Ile Asn Tyr Arg Thr Glu Ile Asp Lys Pro Ser Gln
            100                 105

<210> SEQ ID NO 266
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Met Gly Val Ser Asp Val Pro Arg Asp Leu Glu Val Val Ala Ala Thr
1               5                   10                  15

Pro Thr Ser Leu Leu Ile Ser Trp Gly Gly His Arg Ala Val Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Ala Val Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Tyr Asn Pro Asp Thr His Glu Tyr Lys Tyr His Gln Tyr Pro Ile Ser
                85                  90                  95

Ile Asn Tyr Arg Thr Glu Ile Asp Lys Pro Ser Gln
            100                 105

<210> SEQ ID NO 267
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Met Gly Val Ser Asp Val Pro Arg Asp Leu Glu Val Val Ser Ala Thr
1               5                   10                  15

Pro Thr Ser Leu Leu Ile Ser Trp Gln Val Pro Arg Pro Met Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Trp Phe Lys Glu Tyr Arg Glu Asp Pro Ile Ser Ile Asn Tyr Arg Thr
                85                  90                  95

Glu Ile Asp Lys Pro Ser Gln
            100

<210> SEQ ID NO 268
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Met Gly Val Ser Asp Val Pro Arg Asp Leu Glu Val Val Ala Ala Thr
1               5                   10                  15

Pro Thr Ser Leu Leu Ile Ser Trp Ser Val Gly Met Ile Tyr Gln
            20                  25                  30

Tyr Tyr Arg Ile Thr Tyr Gly Glu Thr Gly Gly Asn Ser Pro Val Gln
                35                  40                  45

Glu Phe Thr Val Pro Gly Met Val Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Tyr Asn Pro Ala Thr His Glu Tyr Lys Tyr His Gln Thr Pro Ile Ser
            85                  90                  95

Ile Asn Tyr Arg Thr Glu Ile Asp Lys Pro Ser Gln
            100                 105

<210> SEQ ID NO 269
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Met Gly Val Ser Asp Val Pro Arg Asp Leu Glu Val Val Ala Ala Thr
1               5                   10                  15

Pro Thr Ser Leu Leu Ile Ser Trp Lys Ala Ser Tyr Thr Gly Tyr Asn
            20                  25                  30

Tyr Tyr Arg Ile Thr Tyr Gly Glu Thr Gly Gly Asn Ser Pro Val Gln
                35                  40                  45

Glu Phe Thr Val Pro Arg Asp Val Met Thr Ala Thr Ile Ser Gly Leu
    50                  55                  60

Lys Pro Gly Val Asp Tyr Thr Ile Thr Val Tyr Ala Val Thr Asp Phe
65                  70                  75                  80

Tyr Asn Pro Asp Thr His Gln Tyr Thr Tyr Arg Arg Ile Pro Ile Ser
            85                  90                  95

Ile Asn Tyr Arg Thr Glu Ile Asp Lys Pro Ser Gln
            100                 105

<210> SEQ ID NO 270
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Met Gly Val Ser Asp Val Pro Arg Asp Leu Glu Val Val Ala Ala Thr
1               5                   10                  15

Pro Thr Ser Leu Leu Ile Ser Trp Ser Val Gly Gln Val Phe Tyr Gln
            20                  25                  30

Tyr Tyr Arg Ile Thr Tyr Gly Glu Thr Gly Gly Asn Ser Pro Val Gln
                35                  40                  45

Glu Phe Thr Val Pro Tyr Asp Val Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Tyr Asn Pro Ala Thr His Glu Tyr Lys Tyr His Gln Thr Pro Ile Ser
                85                  90                  95

Ile Asn Tyr Arg Thr Glu Ile Asp Lys Pro Ser Gln
            100                 105

<210> SEQ ID NO 271
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Met Gly Val Ser Asp Val Pro Arg Asp Leu Glu Val Val Ala Ala Thr
1               5                   10                  15

Pro Thr Ser Leu Leu Ile Ser Trp Tyr Ser Gly Asp Tyr His Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro His Asp Leu Glu Thr Ala Thr Ile Ser Gly Leu
50                  55                  60

Lys Pro Gly Val Asp Tyr Thr Ile Thr Val Tyr Ala Val Thr Asp Tyr
65                  70                  75                  80

Tyr Asn Pro Ala Thr His Tyr Tyr Lys Tyr Glu Gln Thr Pro Ile Ser
                85                  90                  95

Ile Asn Tyr Arg Thr Glu Ile Asp Lys Pro Ser Gln
            100                 105

<210> SEQ ID NO 272
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Met Gly Val Ser Asp Val Pro Arg Asp Leu Glu Val Val Ala Ala Thr
1               5                   10                  15

Pro Thr Ser Leu Leu Ile Ser Trp Ile Val Gln Gly Gly Arg Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Met Val Thr Thr Ala Thr Ile Ser Gly Leu
50                  55                  60

Lys Pro Gly Val Asp Tyr Thr Ile Thr Val Tyr Ala Val Thr Asp Tyr
65                  70                  75                  80

Tyr Asn Pro Ser Thr His Glu Tyr Lys Tyr His Gln Thr Pro Ile Ser
                85                  90                  95

Ile Asn Tyr Arg Thr Glu Ile Asp Lys Pro Ser Gln
            100                 105

<210> SEQ ID NO 273
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Met Gly Val Ser Asp Val Pro Arg Asp Leu Glu Val Val Ala Ala Thr
1               5                   10                  15

Pro Thr Ser Leu Leu Ile Ser Trp Ser Ala Val Arg Trp Arg Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Val Arg Thr Ala Thr Ile Ser Gly Leu
50                  55                  60

Lys Pro Gly Val Asp Tyr Thr Ile Thr Val Tyr Ala Val Thr Asp Phe
65                  70                  75                  80

Tyr Asn Pro Arg Thr His Val Tyr Ile Tyr Asp Gln Phe Pro Ile Ser
                85                  90                  95

Ile Asn Tyr Arg Thr Glu Ile Asp Lys Pro Ser Gln
                100                 105

<210> SEQ ID NO 274
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Met Gly Val Ser Asp Val Pro Arg Asp Leu Glu Val Val Ala Ala Thr
1               5                   10                  15

Pro Thr Ser Leu Leu Ile Ser Trp Arg Ala Arg Arg Leu Gln Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Met Val Thr Ala Thr Ile Ser Gly Leu
50                  55                  60

Lys Pro Gly Val Asp Tyr Thr Ile Thr Val Tyr Ala Val Thr Asp Phe
65                  70                  75                  80

Tyr Asn Pro Ala Thr Met Glu Tyr Thr Tyr Gln Arg Thr Pro Ile Ser
                85                  90                  95

Ile Asn Tyr Arg Thr Glu Ile Asp Lys Pro Ser Gln
                100                 105

<210> SEQ ID NO 275
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Met Gly Val Ser Asp Val Pro Arg Asp Leu Glu Val Val Ala Ala Thr
1               5                   10                  15

Pro Thr Ser Leu Leu Ile Ser Trp Leu Gln Pro Leu Trp Arg Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Leu Asp Thr Ala Thr Ile Ser Gly Leu
50                  55                  60

```
Lys Pro Gly Val Asp Tyr Thr Ile Thr Val Tyr Ala Val Thr Asp Tyr
 65                  70                  75                  80

Lys Pro His Val Asp Gly Pro His Ala Tyr His Glu Tyr Pro Ile Ser
                 85                  90                  95

Ile Asn Tyr Arg Thr Glu Ile Asp Lys Pro Ser Gln
            100                 105

<210> SEQ ID NO 276
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Met Gly Val Ser Asp Val Pro Arg Asp Leu Glu Val Val Ala Ala Thr
 1               5                  10                  15

Pro Thr Ser Leu Leu Ile Ser Trp Asp Ala Ser Gln Gly Asn Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Ala Val Lys Thr Ala Thr Ile Ser Gly Leu
 50                  55                  60

Lys Pro Gly Val Asp Tyr Thr Ile Thr Val Tyr Ala Val Thr Asp Phe
 65                  70                  75                  80

Phe Asn Pro Ala Thr His Glu Tyr Ile Tyr His Thr Thr Pro Ile Ser
                 85                  90                  95

Ile Asn Tyr Arg Thr Glu Ile Asp Lys Pro Ser Gln
            100                 105

<210> SEQ ID NO 277
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Met Gly Val Ser Asp Val Pro Arg Asp Leu Glu Val Val Ala Ala Thr
 1               5                  10                  15

Pro Thr Ser Leu Leu Ile Ser Trp Cys Leu Asp Gly Gln Leu Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Ser Ile Val Thr Ala Thr Ile Ser Gly Leu
 50                  55                  60

Lys Pro Gly Val Asp Tyr Thr Ile Thr Val Tyr Ala Val Thr Asp Trp
 65                  70                  75                  80

Tyr Asn Leu Ala Thr His Glu Tyr Asn Tyr Arg Val Thr Pro Ile Ser
                 85                  90                  95

Ile Asn Tyr Arg Thr Glu Ile Asp Lys Pro Ser Gln
            100                 105

<210> SEQ ID NO 278
<211> LENGTH: 108
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 278

Met Gly Val Ser Asp Val Pro Arg Asp Leu Glu Val Val Ala Ala Thr
1               5                   10                  15

Pro Thr Ser Leu Leu Ile Ser Trp Asp Thr Ser Gly Ala Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Val Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Tyr Asp Pro Asp Ser His Tyr Tyr Asn Tyr Asn Met Val Pro Ile Ser
                85                  90                  95

Ile Asn Tyr Arg Thr Glu Ile Asp Lys Pro Ser Gln
            100                 105

<210> SEQ ID NO 279
<211> LENGTH: 108
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 279

Met Gly Val Ser Asp Val Pro Arg Asp Leu Glu Val Val Ala Ala Thr
1               5                   10                  15

Pro Thr Ser Leu Leu Ile Ser Trp Asp Ser Gly Asn Gly Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Arg Val Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Tyr Asn Pro Ala Thr His Glu Tyr Thr Tyr Glu Leu Arg Pro Ile Ser
                85                  90                  95

Ile Asn Tyr Arg Thr Glu Ile Asp Lys Pro Ser Gln
            100                 105

<210> SEQ ID NO 280
<211> LENGTH: 108
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 280

Met Gly Val Ser Asp Val Pro Arg Asp Leu Glu Val Val Ala Thr Thr
1               5                   10                  15

Pro Thr Ser Leu Leu Ile Ser Trp Arg Pro Thr Ser Gln Val Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Asn Val Tyr Thr Ala Thr Ile Ser Gly Leu

```
                    50                  55                  60
Lys Pro Gly Val Asp Tyr Thr Ile Thr Val Tyr Ala Val Thr Asp Phe
 65                  70                  75                  80

Phe Asn Tyr Ala Thr His Glu Tyr Ile Tyr His Thr Ile Pro Ile Ser
                 85                  90                  95

Ile Asn Tyr Arg Thr Glu Ile Asp Lys Pro Ser Gln
                100                 105
```

<210> SEQ ID NO 281
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

```
Met Gly Val Ser Asp Val Pro Arg Asp Leu Glu Val Val Ala Ala Thr
 1               5                  10                  15

Pro Thr Ser Leu Leu Ile Ser Trp Lys Ser Tyr Gly Ser Ala Tyr Gln
                20                  25                  30

Tyr Tyr Arg Ile Thr Tyr Gly Glu Thr Gly Gly Asn Ser Pro Val Gln
             35                  40                  45

Glu Phe Thr Val Pro Gly Asp Leu Gln Thr Ala Thr Ile Ser Gly Leu
 50                  55                  60

Lys Pro Gly Val Asp Tyr Thr Ile Thr Val Tyr Ala Ile Thr Asp Tyr
 65                  70                  75                  80

Tyr Asn Pro Asp Thr His Glu Tyr Lys Tyr His Val Ser Pro Ile Ser
                 85                  90                  95

Ile Asn Tyr Arg Thr Glu Ile Asp Lys Pro Ser Gln
                100                 105
```

<210> SEQ ID NO 282
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

```
Met Gly Val Ser Asp Val Pro Arg Asp Leu Glu Val Val Ala Ala Thr
 1               5                  10                  15

Pro Thr Ser Leu Leu Ile Ser Trp Ser Ser Val Met Gly Leu Tyr Gln
                20                  25                  30

Tyr Tyr Arg Ile Thr Tyr Gly Glu Thr Gly Gly Asn Ser Pro Val Gln
             35                  40                  45

Glu Phe Thr Val Pro Tyr Asp Val Tyr Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Tyr Asn Pro Ser Thr Tyr Glu Tyr Lys Tyr Asn Thr Thr Pro Ile Ser
                 85                  90                  95

Ile Asn Tyr Arg Thr Glu Ile Asp Lys Pro Ser Gln
                100                 105
```

<210> SEQ ID NO 283
<211> LENGTH: 108
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 283

Met Gly Val Ser Asp Val Pro Arg Asp Leu Glu Val Val Ala Ala Thr
1               5                   10                  15

Pro Thr Ser Leu Leu Ile Ser Trp Lys Thr Glu Pro Gly Arg His Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Arg Thr Ala Thr Ile Ser Gly Leu
50                  55                  60

Lys Pro Gly Val Asp Tyr Thr Ile Thr Val Tyr Ala Val Thr Asp Trp
65                  70                  75                  80

Tyr Asn Leu Val Ser His Glu Tyr Val Tyr His Thr Thr Pro Ile Ser
                85                  90                  95

Ile Asn Tyr Arg Thr Glu Ile Asp Lys Pro Ser Gln
            100                 105

<210> SEQ ID NO 284
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Met Gly Val Ser Asp Val Pro Arg Asp Leu Glu Val Val Ala Ala Thr
1               5                   10                  15

Pro Thr Ser Leu Leu Ile Ser Trp His Ala Gly Met Ala Val Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Asp Val Leu Thr Ala Thr Ile Ser Gly Leu
50                  55                  60

Lys Pro Gly Val Asp Tyr Thr Ile Thr Val Tyr Ala Val Thr Asp Phe
65                  70                  75                  80

Phe Asn Pro Val Thr His Glu Tyr Met Tyr His Thr Ile Pro Ile Ser
                85                  90                  95

Ile Asn Tyr Arg Thr Glu Ile Asp Lys Pro Ser Gln
            100                 105

<210> SEQ ID NO 285
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Met Gly Val Ser Asp Val Pro Arg Asp Leu Glu Val Val Ala Ala Thr
1               5                   10                  15

Pro Thr Ser Leu Leu Ile Ser Trp Val Ser Ala Arg Gly Arg Tyr Gln
            20                  25                  30

Tyr Tyr Arg Ile Thr Tyr Gly Glu Thr Gly Gly Asn Ser Pro Val Gln
        35                  40                  45

```
Glu Phe Thr Val Pro Gly Gly Val Arg Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Tyr Asn Leu Glu Thr Tyr Glu Tyr His Tyr Tyr Arg Thr Pro Ile Ser
                 85                  90                  95

Ile Asn Tyr Arg Thr Glu Ile Asp Lys Pro Ser Gln
                100                 105
```

<210> SEQ ID NO 286
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

```
Met Gly Val Ser Asp Val Pro Arg Asp Leu Glu Val Val Ala Ala Thr
 1               5                  10                  15

Pro Thr Ser Leu Leu Ile Ser Trp Trp Phe Gly Thr Ser Ser Tyr Gln
                 20                  25                  30

Tyr Tyr Arg Ile Thr Tyr Gly Glu Thr Gly Gly Asn Ser Pro Val Gln
             35                  40                  45

Glu Phe Thr Val Pro Gly Asp Leu Lys Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Phe Asn Pro Val Thr His Glu Tyr Glu Tyr His Thr Thr Pro Ile Ser
                 85                  90                  95

Ile Asn Tyr Arg Thr Glu Ile Asp Lys Pro Ser Gln
                100                 105
```

<210> SEQ ID NO 287
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

```
Met Gly Val Ser Asp Val Pro Arg Asp Leu Glu Val Val Ala Ala Thr
 1               5                  10                  15

Pro Thr Ser Leu Leu Ile Ser Trp Ser Ala Thr Arg Thr Leu Tyr Gln
                 20                  25                  30

Tyr Tyr Arg Ile Thr Tyr Gly Glu Thr Gly Gly Asn Ser Pro Val Gln
             35                  40                  45

Glu Phe Thr Val Pro Tyr Asp Val His Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Tyr Asn Met Val Thr Tyr Glu Tyr Asn Tyr His Leu Thr Pro Ile Ser
                 85                  90                  95

Ile Asn Tyr Arg Thr Glu Ile Asp Lys Pro Ser Gln
                100                 105
```

<210> SEQ ID NO 288

<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Met Gly Val Ser Asp Val Pro Arg Asp Leu Glu Val Val Ala Thr
1               5                   10                  15

Pro Thr Ser Leu Leu Ile Ser Trp Thr Lys Leu Leu Gly Gly Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Pro Val Tyr Thr Ala Thr Ile Ser Gly Leu
    50                  55                  60

Lys Pro Gly Val Asp Tyr Thr Ile Thr Val Tyr Ala Val Thr Asp Phe
65                  70                  75                  80

Phe Asn Pro Arg Thr His Glu Tyr Gln Tyr His Thr Thr Pro Ile Ser
                85                  90                  95

Ile Asn Tyr Arg Thr Glu Ile Asp Lys Pro Ser Gln
            100                 105

<210> SEQ ID NO 289
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Met Gly Val Ser Asp Val Pro Arg Asp Leu Glu Val Val Ala Ala Thr
1               5                   10                  15

Pro Thr Ser Leu Leu Ile Ser Trp Arg Ala Ser Gly Gly Leu Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Ser Val Asn Thr Ala Thr Ile Ser Gly Leu
    50                  55                  60

Lys Pro Gly Val Asp Tyr Thr Ile Thr Val Tyr Ala Val Thr Asp Phe
65                  70                  75                  80

Tyr Asn Pro Ala Thr Tyr Glu Tyr Ile Tyr His Thr Thr Pro Ile Ser
                85                  90                  95

Ile Asn Tyr Arg Thr Glu Ile Asp Lys Pro Ser Gln
            100                 105

<210> SEQ ID NO 290
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Met Gly Val Ser Asp Val Pro Arg Asp Leu Glu Val Val Ala Ala Thr
1               5                   10                  15

Pro Thr Ser Leu Leu Ile Ser Trp Ala Ala Gly Arg Ala Thr Tyr Gln
            20                  25                  30

```
Tyr Tyr Arg Ile Thr Tyr Gly Glu Thr Gly Asn Ser Pro Val Gln
            35                  40                  45

Glu Phe Thr Val Pro Tyr Asp Val Thr Ala Thr Ile Ser Gly Leu
 50                      55                  60

Lys Pro Gly Val Asp Tyr Thr Ile Thr Val Tyr Ala Val Thr Asp Phe
 65                  70                  75                  80

Tyr Asn Pro Ala Thr His Glu Tyr Tyr Glu Thr Thr Pro Ile Ser
                 85                  90                  95

Ile Asn Tyr Arg Thr Glu Ile Asp Lys Pro Ser Gln
                100                 105
```

<210> SEQ ID NO 291
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

```
Met Gly Val Ser Asp Val Pro Arg Asp Leu Glu Val Val Ala Ala Thr
 1               5                  10                  15

Pro Thr Ser Leu Leu Ile Ser Trp Tyr Ser Gln Pro Leu Thr Tyr Gln
                20                  25                  30

Tyr Tyr Arg Ile Thr Tyr Gly Glu Thr Gly Asn Ser Pro Val Gln
            35                  40                  45

Glu Phe Thr Val Pro His Asp Val Asn Thr Ala Thr Ile Ser Gly Leu
 50                      55                  60

Lys Pro Gly Val Asp Tyr Thr Ile Thr Val Tyr Ala Val Thr Asp Phe
 65                  70                  75                  80

Tyr Asn Pro Glu Thr His Glu Tyr Thr Tyr His Leu Thr Pro Ile Ser
                 85                  90                  95

Ile Asn Tyr Arg Thr Glu Ile Asp Lys Pro Ser Gln
                100                 105
```

<210> SEQ ID NO 292
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

```
Met Gly Val Ser Asp Val Pro Arg Asp Leu Glu Val Val Ala Ala Thr
 1               5                  10                  15

Pro Thr Ser Leu Leu Ile Ser Trp Ser Ser Ala Thr Arg Pro Tyr Gln
                20                  25                  30

Tyr Tyr Arg Ile Thr Tyr Gly Glu Thr Gly Asn Ser Pro Val Gln
            35                  40                  45

Glu Phe Thr Val Pro Gly Gly Val Arg Thr Ala Thr Ile Ser Gly Leu
 50                      55                  60

Lys Pro Gly Val Asp Tyr Thr Ile Thr Val Tyr Ala Val Thr Asp Phe
 65                  70                  75                  80

Phe Asn Pro Thr Thr His Glu Tyr Tyr Tyr His Thr Thr Pro Ile Ser
                 85                  90                  95

Ile Asn Tyr Arg Thr Glu Ile Asp Lys Pro Ser Gln
                100                 105
```

<210> SEQ ID NO 293
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Met Gly Val Ser Asp Val Pro Arg Asp Leu Glu Val Val Ala Ala Thr
1               5                   10                  15

Pro Thr Ser Leu Leu Ile Ser Trp Ser Val Glu Arg Ser Val Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Tyr Asn Pro Ser Thr His Glu Tyr Asn Tyr Leu Thr Thr Pro Ile Ser
                85                  90                  95

Ile Asn Tyr Arg Thr Glu Ile Asp Lys Pro Ser Gln
            100                 105

<210> SEQ ID NO 294
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Met Gly Val Ser Asp Val Pro Arg Asp Leu Glu Val Val Ala Ala Thr
1               5                   10                  15

Pro Thr Ser Leu Leu Ile Ser Trp Gln Asp Thr Ser Ser Tyr His Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Phe Asn Pro Ser Thr His Glu Tyr Ile Tyr Arg Thr Ile Pro Ile Ser
                85                  90                  95

Ile Asn Tyr Arg Thr Glu Ile Asp Lys Pro Ser Gln
            100                 105

<210> SEQ ID NO 295
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Met Gly Val Ser Asp Val Pro Arg Asp Leu Glu Val Val Ala Ala Thr
1               5                   10                  15

Pro Thr Ser Leu Leu Ile Ser Trp Ser Ser Ser His Arg Arg Tyr Gln

```
                20                  25                  30

Tyr Tyr Arg Ile Thr Tyr Gly Glu Thr Gly Gly Asn Ser Pro Val Gln
            35                  40                  45

Glu Phe Thr Val Pro Gly Ser Val Ala Thr Ala Ile Ser Gly Leu
50                      55                  60

Lys Pro Gly Val Asp Tyr Thr Ile Thr Val Tyr Ala Val Thr Asp Tyr
65                  70                  75                  80

Phe Asn Pro Asp Thr His Glu Tyr Leu Tyr His Ala Thr Pro Ile Ser
                85                  90                  95

Ile Asn Tyr Arg Thr Glu Ile Asp Lys Pro Ser Gln
                100                 105

<210> SEQ ID NO 296
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Met Gly Val Ser Asp Val Pro Arg Asp Leu Glu Val Val Ala Ala Thr
1               5                   10                  15

Pro Thr Ser Leu Leu Ile Ser Trp Asp Asn Ser Asn Ser Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Tyr Asp Leu Arg Thr Ala Thr Ile Ser Gly Leu
50                      55                  60

Lys Pro Gly Val Asp Tyr Thr Ile Thr Val Tyr Ala Val Thr Asp Tyr
65                  70                  75                  80

Lys Pro His Thr Glu Gly Glu His Thr Tyr His Glu Ser Pro Ile Ser
                85                  90                  95

Ile Asn Tyr Arg Thr Glu Ile Asp Lys Pro Ser Gln
                100                 105

<210> SEQ ID NO 297
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Met Gly Val Ser Asp Val Pro Arg Asp Leu Glu Val Val Ala Ala Thr
1               5                   10                  15

Pro Thr Ser Leu Leu Ile Ser Trp Arg Val Leu Val Asp Met Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Leu Thr Ala Thr Ile Ser Gly Leu
50                      55                  60

Lys Pro Gly Val Asp Tyr Thr Ile Thr Val Tyr Ala Val Thr Asp Tyr
65                  70                  75                  80

Lys Pro His Val Asp Gly Pro His Thr Tyr Tyr Glu Ser Pro Ile Ser
                85                  90                  95

Ile Asn Tyr Arg Thr Glu Ile Asp Lys Pro Ser Gln
```

-continued

```
                100                 105

<210> SEQ ID NO 298
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Met Gly Val Ser Asp Val Pro Arg Asp Leu Glu Val Val Ala Ala Thr
1               5                   10                  15

Pro Thr Ser Leu Leu Ile Ser Trp Met Phe Val Gly Met Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Gly Val His Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Phe Asn Pro Ala Thr His Glu Tyr Ile Tyr His Val Thr Pro Ile Ser
                85                  90                  95

Ile Asn Tyr Arg Thr Glu Ile Asp Lys Pro Ser Gln
                100                 105

<210> SEQ ID NO 299
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Met Gly Val Ser Asp Val Pro Arg Asp Leu Glu Val Val Ala Ala Thr
1               5                   10                  15

Pro Thr Ser Leu Leu Ile Ser Trp Thr Leu His Arg Lys Asn Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Val Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Tyr Asn Pro Ala Thr His Glu Tyr Asp Tyr Arg Thr Thr Pro Ile Ser
                85                  90                  95

Ile Asn Tyr Arg Thr Glu Ile Asp Lys Pro Ser Gln
                100                 105

<210> SEQ ID NO 300
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Met Gly Val Ser Asp Val Pro Arg Asp Leu Glu Val Val Ala Ala Thr
1               5                   10                  15
```

```
Pro Thr Ser Leu Leu Ile Ser Trp Thr Gln Gly Ser Thr His Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Met Val Tyr Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Phe Asp Arg Ser Thr His Glu Tyr Lys Tyr Arg Thr Thr Pro Ile Ser
                 85                  90                  95

Ile Asn Tyr Arg Thr Glu Ile Asp Lys Pro Ser Gln
            100                 105

<210> SEQ ID NO 301
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Met Gly Val Ser Asp Val Pro Arg Asp Leu Glu Val Val Ala Ala Thr
 1               5                  10                  15

Pro Thr Ser Leu Leu Ile Ser Trp Asp Ser Gly Glu Asn Asn Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Arg Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Tyr Asn Pro Lys Thr His Glu Tyr Asn Tyr Leu Thr Ile Pro Ile Ser
                 85                  90                  95

Ile Asn Tyr Arg Thr Glu Ile Asp Lys Pro Ser Gln
            100                 105

<210> SEQ ID NO 302
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Met Gly Val Ser Asp Val Pro Arg Asp Leu Glu Val Val Ala Ala Thr
 1               5                  10                  15

Pro Thr Ser Leu Leu Ile Ser Trp Gly Ser Pro Leu Ile Glu Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Gly Leu Ser Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Phe Asn Pro Ala Thr His Glu Tyr Thr Tyr His Val Ser Pro Ile Ser
                 85                  90                  95
```

Ile Asn Tyr Arg Thr Glu Ile Asp Lys Pro Ser Gln
            100                 105

<210> SEQ ID NO 303
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Met Gly Val Ser Asp Val Pro Arg Asp Leu Glu Val Val Ala Ala Thr
1               5                   10                  15

Pro Thr Ser Leu Leu Ile Ser Trp Ser Ala Thr Asn Lys Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Phe Asn Pro Thr Thr His Glu Tyr Ile Tyr Gln Thr Pro Ile Ser
                85                  90                  95

Ile Asn Tyr Arg Thr Glu Ile Asp Lys Pro Ser Gln
            100                 105

<210> SEQ ID NO 304
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Met Gly Val Ser Asp Val Pro Arg Asp Leu Glu Val Val Ala Ala Thr
1               5                   10                  15

Pro Thr Ser Leu Leu Ile Ser Trp Asp Asp Pro Ala Ala Asn Arg Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Asp Leu Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Tyr Asn Pro Ala Thr His Gln Tyr Lys Tyr Ser Gln Ser Pro Ile Ser
                85                  90                  95

Ile Asn Tyr Arg Thr Glu Ile Asp Lys Pro Ser Gln
            100                 105

<210> SEQ ID NO 305
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Met Gly Val Ser Asp Val Pro Arg Asp Leu Glu Val Val Ala Ala Thr
1               5                   10                  15

Pro Thr Ser Leu Leu Ile Ser Trp Tyr Trp Glu Gly Leu Pro Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Arg Asp Val Asn Thr Ala Thr Ile Ser Gly Leu
    50                  55                  60

Lys Pro Gly Val Asp Tyr Thr Ile Thr Val Tyr Ala Val Thr Asp Trp
65                  70                  75                  80

Tyr Asn Pro Asp Thr His Glu Tyr Ile Tyr His Thr Ile Pro Ile Ser
                85                  90                  95

Ile Asn Tyr Arg Thr Glu Ile Asp Lys Pro Ser Gln
            100                 105

<210> SEQ ID NO 306
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Met Gly Val Ser Asp Val Pro Arg Asp Leu Glu Val Val Ala Ala Thr
1               5                   10                  15

Pro Thr Ser Leu Leu Ile Ser Trp Ser Ala Pro Trp Arg Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Asp Val Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Leu Asn Pro Asn Thr Leu Glu Tyr Thr Tyr Gln Arg Ile Pro Ile Ser
                85                  90                  95

Ile Asn Tyr Arg Thr Glu Ile Asp Lys Pro Ser Gln
            100                 105

<210> SEQ ID NO 307
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Met Gly Val Ser Asp Val Pro Arg Asp Leu Glu Val Val Ala Ala Thr
1               5                   10                  15

Pro Thr Ser Leu Leu Ile Ser Trp Gln Ala Ala Asn His Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Phe
65                  70                  75                  80

Phe Asn Pro Val Thr His Glu Tyr Lys Tyr Arg Thr Ile Pro Ile Ser
                85                  90                  95

Ile Asn Tyr Arg Thr Glu Ile Asp Lys Pro Ser Gln
            100                 105

<210> SEQ ID NO 308
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Tyr Pro Ile Ser
                85                  90                  95

Ile Asn Tyr Arg Thr Glu Ile Asp Lys Pro Ser Gln
            100                 105

<210> SEQ ID NO 309
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Met Gly Val Ser Asp Val Pro Arg Asp Leu Glu Val Val Ala Ala Thr
1               5                   10                  15

Pro Thr Ser Leu Leu Ile Ser Trp Asn Asn Gly Gly Arg Asn Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Asp Val Tyr Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Tyr Pro Ile Ser
                85                  90                  95

Ile Asn Tyr Arg Thr Glu Ile Asp Lys Pro Ser Gln
            100                 105

<210> SEQ ID NO 310
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 310

Met Gly Val Ser Asp Val Pro Arg Asp Leu Glu Val Val Ala Ala Thr
1               5                   10                  15

Pro Thr Ser Leu Leu Ile Ser Trp Val Val Pro Gln Gly Met Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Ser Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Phe Asn Pro Ala Thr His Glu Tyr Asn Tyr His Ser Ile Pro Ile Ser
                85                  90                  95

Ile Asn Tyr Arg Thr Glu Ile Asp Lys Pro Ser Gln
            100                 105

<210> SEQ ID NO 311
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Met Gly Val Ser Asp Val Pro Arg Asp Leu Glu Val Val Ala Ala Thr
1               5                   10                  15

Pro Thr Ser Leu Leu Ile Ser Trp Ala Ser Asn Arg Gly Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Ser Thr Ala Thr Ile Ser Gly Leu
    50                  55                  60

Lys Pro Gly Val Asp Tyr Thr Ile Thr Val Tyr Ala Val Thr Asp Ala
65                  70                  75                  80

Phe Asn Pro Thr Thr His Glu Tyr Asn Tyr Phe Thr Thr Pro Ile Ser
                85                  90                  95

Ile Asn Tyr Arg Thr Glu Ile Asp Lys Pro Ser Gln
            100                 105

<210> SEQ ID NO 312
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Met Gly Val Ser Asp Val Pro Arg Asp Leu Glu Val Val Ala Ala Thr
1               5                   10                  15

Pro Thr Ser Leu Leu Ile Ser Trp Leu Pro Gly Lys Leu Arg Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro His Asp Leu Arg Thr Ala Thr Ile Ser Gly Leu
    50                  55                  60

Lys Pro Gly Val Asp Tyr Thr Ile Thr Val Tyr Ala Val Thr Asp Tyr
```

65                  70                  75                  80
Lys Pro His Ala Asp Gly Pro His Thr Tyr His Glu Ser Pro Ile Ser
                    85                  90                  95

Ile Asn Tyr Arg Thr Glu Ile Asp Lys Pro Ser Gln
                100                 105

<210> SEQ ID NO 313
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Met Gly Val Ser Asp Val Pro Arg Asp Leu Glu Val Val Ala Ala Thr
1               5                   10                  15

Pro Thr Ser Leu Leu Ile Ser Trp Asp Ala Pro Thr Ser Arg Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Tyr Pro Ile Ser
                    85                  90                  95

Ile Asn Tyr Arg Thr Glu Ile Asp Lys Pro Ser Gln
                100                 105

<210> SEQ ID NO 314
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Met Gly Val Ser Asp Val Pro Arg Asp Leu Glu Val Val Ala Ala Thr
1               5                   10                  15

Pro Thr Ser Leu Leu Ile Ser Trp Asp Ala Pro Thr Ser Arg Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Tyr Pro Ile Ser
                    85                  90                  95

Ile Asn Tyr Arg Thr Glu Ile Asp Lys Pro Ser Gln
                100                 105

<210> SEQ ID NO 315
<211> LENGTH: 108
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 315

Met Gly Val Ser Asp Val Pro Arg Asp Leu Glu Val Val Ala Ala Thr
1               5                   10                  15

Pro Thr Ser Leu Leu Ile Ser Trp Thr Pro Ala Asn Lys Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro His Asp Leu Val Thr Ala Thr Ile Ser Gly Leu
    50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Tyr Pro Ile Ser
                85                  90                  95

Ile Asn Tyr Arg Thr Glu Ile Asp Lys Pro Ser Gln
            100                 105

<210> SEQ ID NO 316
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro His Asp Leu Val Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Pro Ser Gln
            100                 105

<210> SEQ ID NO 317
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Met Gly Val Ser Asp Val Pro Arg Asp Leu Glu Val Val Ala Ala Thr
1               5                   10                  15

Pro Thr Ser Leu Leu Ile Ser Trp Thr Pro Ala Asn Lys Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro His Asp Leu Val Thr Ala Thr Ile Ser Gly Leu
    50                  55                  60

-continued

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Pro Ser Gln
            100                 105

<210> SEQ ID NO 318
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Met Gly Val Ser Asp Val Pro Arg Asp Leu Glu Val Val Ala Ala Thr
1               5                   10                  15

Pro Thr Ser Leu Leu Ile Ser Trp Thr Pro Ala Asn Lys Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asn Met
65                  70                  75                  80

Met His Val Glu Tyr Ser Glu Tyr Pro Ile Ser Ile Asn Tyr Arg Thr
                85                  90                  95

Glu Ile Asp Lys Pro Ser Gln
            100

<210> SEQ ID NO 319
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Met Gly Val Ser Asp Val Pro Arg Asp Leu Glu Val Val Ala Ala Thr
1               5                   10                  15

Pro Thr Ser Leu Leu Ile Ser Trp Asp Ala Gly Ala Val Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro His Asp Leu Val Thr Ala Thr Ile Ser Gly Leu
    50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Tyr Pro Ile Ser
                85                  90                  95

Ile Asn Tyr Arg Thr Glu Ile Asp Lys Pro Ser Gln
            100                 105

<210> SEQ ID NO 320
<211> LENGTH: 108
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 320

Met Gly Val Ser Asp Val Pro Arg Asp Leu Glu Val Val Ala Ala Thr
1               5                   10                  15

Pro Thr Ser Leu Leu Ile Ser Trp Asp Ala Pro Thr Ser Arg Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Leu Ser Thr Ala Thr Ile Ser Gly Leu
50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Pro Ser Gln
            100                 105

<210> SEQ ID NO 321
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Tyr Asp Val Tyr Thr Ala Thr Ile Ser Gly Leu
50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Tyr Pro Ile Ser
                85                  90                  95

Ile Asn Tyr Arg Thr Glu Ile Asp Lys Pro Ser Gln
            100                 105

<210> SEQ ID NO 322
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
            20                  25                  30

Tyr Tyr Arg Ile Thr Tyr Gly Glu Thr Gly Gly Asn Ser Pro Val Gln
        35                  40                  45
```

```
Glu Phe Thr Val Pro Tyr Asp Val Tyr Thr Ala Thr Ile Ser Gly Leu
 50                  55                  60

Lys Pro Gly Val Asp Tyr Thr Ile Thr Val Tyr Ala Val Thr Asp Met
 65                  70                  75                  80

Met His Val Glu Tyr Thr Glu His Pro Ile Ser Ile Asn Tyr Arg Thr
                 85                  90                  95

Glu Ile Asp Lys Pro Ser Gln His
                100
```

<210> SEQ ID NO 323
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

```
Met Gly Val Ser Asp Val Pro Arg Asp Leu Glu Val Val Ala Ala Thr
 1               5                  10                  15

Pro Thr Ser Leu Leu Ile Ser Trp Asp Ala Pro Ala Val Thr Tyr Gln
                20                  25                  30

Tyr Tyr Arg Ile Thr Tyr Gly Glu Thr Gly Gly Asn Ser Pro Val Gln
             35                  40                  45

Glu Phe Thr Val Pro Gly Gly Val Arg Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Lys Pro His Ala Asp Gly Pro His Thr Tyr His Glu Ser Pro Ile Ser
                 85                  90                  95

Ile Asn Tyr Arg Thr Glu Ile Asp Lys Pro Ser Gln
                100                 105
```

<210> SEQ ID NO 324
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

```
Met Gly Val Ser Asp Val Pro Arg Asp Leu Glu Val Val Ala Ala Thr
 1               5                  10                  15

Pro Thr Ser Leu Leu Ile Ser Trp Asp Ala Pro Thr Ser Arg Tyr Gln
                20                  25                  30

Tyr Tyr Arg Ile Thr Tyr Gly Glu Thr Gly Gly Asn Ser Pro Val Gln
             35                  40                  45

Glu Phe Thr Val Pro His Asp Leu Val Thr Ala Thr Ile Ser Gly Leu
 50                  55                  60

Lys Pro Gly Val Asp Tyr Thr Ile Thr Val Tyr Ala Val Thr Asp Tyr
 65                  70                  75                  80

Lys Pro His Ala Asp Gly Pro His Thr Tyr His Glu Ser Pro Ile Ser
                 85                  90                  95

Ile Asn Tyr Arg Thr Glu Ile Asp Lys Pro Ser Gln
                100                 105
```

<210> SEQ ID NO 325
<211> LENGTH: 108

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Met Gly Val Ser Asp Val Pro Arg Asp Leu Glu Val Val Ala Ala Thr
1               5                   10                  15

Pro Thr Ser Leu Leu Ile Ser Trp Asp Ala Gly Ala Val Thr Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Pro Ser Gln
            100                 105

<210> SEQ ID NO 326
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Met Gly Val Ser Asp Val Pro Arg Asp Leu Glu Val Val Ala Ala Thr
1               5                   10                  15

Pro Thr Ser Leu Leu Ile Ser Trp Asp Ala Pro Thr Ser Arg Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro His Asp Leu Val Thr Ala Thr Ile Ser Gly Leu
    50                  55                  60

Lys Pro Gly Val Asp Tyr Thr Ile Thr Val Tyr Ala Val Thr Asn Met
65                  70                  75                  80

Met His Val Glu Tyr Ser Glu Tyr Pro Ile Ser Ile Asn Tyr Arg Thr
                85                  90                  95

Glu Ile Asp Lys Pro Ser Gln
            100

<210> SEQ ID NO 327
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Met Gly Val Ser Asp Val Pro Arg Asp Leu Glu Val Val Ala Ala Thr
1               5                   10                  15

Pro Thr Ser Leu Leu Ile Ser Trp Asp Ala Gly Ala Val Thr Tyr Gln
            20                  25                  30

Tyr Tyr Arg Ile Thr Tyr Gly Glu Thr Gly Gly Asn Ser Pro Val Gln

```
                    35                  40                  45
Glu Phe Thr Val Pro Gly Gly Val Arg Thr Ala Thr Ile Ser Gly Leu
        50                  55                  60

Lys Pro Gly Val Asp Tyr Thr Ile Thr Val Tyr Ala Val Thr Asp Tyr
65                  70                  75                  80

Lys Pro His Ala Asp Gly Pro His Thr Tyr His Glu Tyr Pro Ile Ser
                85                  90                  95

Ile Asn Tyr Arg Thr Glu Ile Asp Lys Pro Ser Gln
            100                 105
```

<210> SEQ ID NO 328
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 328

```
atgggagttt ctgatgtgcc gcgcgacctg gaagtggttg ctgccacccc caccagcctg    60
ctgatcagct ggtctgcgcg tctgaaagtt gcgcgatatt accgcatcac ttacggcgaa   120
acaggaggca atagccctgt ccaggagttc actgtgccta aaaacgttta cacagctacc   180
atcagcggcc ttaaacctgg cgttgattat accatcactg tgtatgctgt cactaggttc   240
cgcgactacc agccaatttc cattaattac cgcacagaaa ttgacaaacc atgccagcac   300
caccaccacc accac                                                     315
```

<210> SEQ ID NO 329
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 329

```
atgggagttt ctgatgtgcc gcgcgacctg gaagtggttg ctgccacccc caccagcctg    60
ctgatcagct ggcaggttcc gcgtccgatg taccaatatt accgcatcac ttacggcgaa   120
acaggaggca atagccctgt ccaggagttc actgtgcctt acgacgttta cacagctacc   180
atcagcggcc ttaaacctgg cgttgattat accatcactg tgtatgctgt cactgactct   240
tacaacccgg ctactcatga atacaaatac catcagactc caatttccat taattaccgc   300
acagaaattg acaaaccatc ccagcaccat caccaccacc ac                       342
```

<210> SEQ ID NO 330
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 330

```
atgggagttt ctgatgtgcc gcgcgacctg gaagtggttg ctgccacccc caccagcctg    60
ctgatcagct ggcaggttcc gcgtccgatg taccaatatt accgcatcac ttacggcgaa   120
acaggaggca atagccctgt ccaggagttc actgtgcctt acgacgttca tacagctacc   180
atcagcggcc ttaaacctgg cgttgattat accatcactg tgtatgctgt cactgactct   240
```
tacaacccgg ctactcatga atacaaatac catcagactc caatttccat taattaccgc      300
acagaaattg acaaaccatc ccagcaccat caccaccacc ac                          342

<210> SEQ ID NO 331
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 331
atgggagttt ctgatgtgcc gcgcgacctg gaagtggttg ctgccacccc caccagcctg      60
ctgatcagct ggcaggttcc gcgtccgatg taccaatatt accgcatcac ttacggcgaa     120
acaggaggca atagccctgt ccaggagttc actgtgcctt acgacctgac tcagctacc      180 atcagcggcc ttaaacctgg cgttgattat accatcactg tgtatgctgt cactgactct     240
tacaacccgg ctactcatga atacaaatac catcagactc caatttccat taattaccgc     300
acagaaattg acaaaccatc ccagcaccat caccaccacc ac                          342

<210> SEQ ID NO 332
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 332
atgggagttt ctgatgtgcc gcgcgacctg gaagtggttg ctgccacccc caccagcctg      60
ctgatcagct gggaagctaa cccttctcgt tatcaatatt accgcatcac ttacggcgaa     120
acaggaggca atagccctgt ccaggagttc actgtgcctc atgacctgaa cacagctacc     180
atcagcggcc ttaaacctgg cgttgattat accatcactg tgtatgctgt cactgactct     240
tacaacccgg ctactcatga atacaaatac catcagactc caatttccat taattaccgc     300
acagaaattg acaaaccatc ccagcaccat caccaccacc ac                          342

<210> SEQ ID NO 333
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 333
atgggagttt ctgatgtgcc gcgcgacctg gaagtggttg ctgccacccc caccagcctg      60
ctgatcagct ggtacccagg atctcgcacc taccaatatt accgcatcac ttacggcgaa     120
acaggaggca atagccctgt ccaggagttc actgtgcctg gtggtgttcg tacagctacc     180
atcagcggcc ttaaacctgg cgttgattat accatcactg tgtatgctgt cactgactac     240
taccatccgg ctacttacga acatgaatac catgctcatc caatttccat taattaccgc     300
acagaaattg acaaaccatc ccagcaccat caccaccacc ac                          342

<210> SEQ ID NO 334
<211> LENGTH: 342
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 334

```
atgggagttt ctgatgtgcc gcgcgacctg gaagtggttg ctgccacccc caccagcctg      60
ctgatcagct ggacccctgc taataaatct taccaatatt accgcatcac ttacggcgaa     120
acaggaggca atagccctgt ccaggagttc actgtgcctt acgacggtac tacagctacc     180
atcagcggcc ttaaacctgg cgttgattat accatcactg tgtatgctgt cactgaccat     240
aaaccgcatg ctgacggtcc gcatacttac catgaatacc caatttccat taattaccgc     300
acagaaattg acaaaccatc ccagcaccat caccaccacc ac                         342
```

<210> SEQ ID NO 335
<211> LENGTH: 342
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 335

```
atgggagttt ctgatgtgcc gcgcgacctg gaagtggttg ctgccacccc caccagcctg      60
ctgatcagct ggcaggttcc gcgtccgatg taccaatatt accgcatcac ttacggcgaa     120
acaggaggca atagccctgt ccaggagttc actgtgcctc atgacgttta cacagctacc     180
atcagcggcc ttaaacctgg cgttgattat accatcactg tgtatgctgt cactgactct     240
tacaacccgg ctactcatga atacaaatac catcagactc caatttccat taattaccgc     300
acagaaattg acaaaccatc ccagcaccat caccaccacc ac                         342
```

<210> SEQ ID NO 336
<211> LENGTH: 342
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 336

```
atgggagttt ctgatgtgcc gcgcgacctg gaagtggttg ctgccacccc caccagcctg      60
ctgatcagct ggcaggttcc gcgtccgatg taccaatatt accgcatcac ttacggcgaa     120
acaggaggca atagccctgt ccaggagttc actgtgcctg gtcaggttta cacagctacc     180
atcagcggcc ttaaacctgg cgttgattat accatcactg tgtatgctgt cactgactct     240
tacaacccgg ctactcatga atacaaatac catcagactc caatttccat taattaccgc     300
acagaaattg acaaaccatc ccagcaccat caccaccacc ac                         342
```

<210> SEQ ID NO 337
<211> LENGTH: 342
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 337

```
atgggagttt ctgatgtgcc gcgcgacctg gaagtggttg ctgccacccc caccagcctg      60
ctgatcagct ggcaggttcc gcgtccgatg taccaatatt accgcatcac ttacggcgaa     120
acaggaggca atagccctgt ccaggagttc actgtgcctt acgacgttac tacagctacc     180
```
atcagcggcc ttaaacctgg cgttgattat accatcactg tgtatgctgt cactgactct    240
tacaacccgg ctactcatga atacaaatac catcagactc caatttccat taattaccgc    300
acagaaattg acaaaccatc ccagcaccat caccaccacc ac                       342

<210> SEQ ID NO 338
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 338
atgggagttt ctgatgtgcc gcgcgacctg gaagtggttg ctgccacccc caccagcctg    60
ctgatcagct ggcaggttcc gcgtccgatg taccaatatt accgcatcac ttacggcgaa    120
acaggaggca atagccctgt ccaggagttc actgtgcctc atgacctgcg tacagctacc    180
atcagcggcc ttaaacctgg cgttgattat accatcactg tgtatgctgt cactgactct    240
tacaacccgg ctactcatga atacaaatac catcagactc caatttccat taattaccgc    300
acagaaattg acaaaccatc ccagcaccat caccaccacc ac                       342

<210> SEQ ID NO 339
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 339
atgggagttt ctgatgtgcc gcgcgacctg gaagtggttg ctgccacccc caccagcctg    60
ctgatcagct ggcaggttcc gcgtccgatg taccaatatt accgcatcac ttacggcgaa    120
acaggaggca atagccctgt ccaggagttc actgtgcctt acgacctggt tacagctacc    180
atcagcggcc ttaaacctgg cgttgattat accatcactg tgtatgctgt cactgaccat    240
aaaccgcatg ctgacggtcc gcatacttac catgaatctc caatttccat taattaccgc    300
acagaaattg acaaaccatc ccagcaccat caccaccacc ac                       342

<210> SEQ ID NO 340
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 340
atgggagttt ctgatgtgcc gcgcgacctg gaagtggttg ctgccacccc caccagcctg    60
ctgatcagct ggttgccggg caagctgagg taccaatatt accgcatcac ttacggcgaa    120
acaggaggca atagccctgt ccaggagttc actgtgcctc atgacctgcg tacagctacc    180
atcagcggcc ttaaacctgg cgttgattat accatcactg tgtatgctgt cactaacatg    240
atgcatgttg aatactctga atacccaatt tccattaatt accgcacaga aattgacaaa    300
ccatcccagc accatcacca ccaccac                                        327

<210> SEQ ID NO 341
<211> LENGTH: 327

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 341
atgggagttt ctgatgtgcc gcgcgacctg gaagtggttg ctgccacccc caccagcctg      60
ctgatcagct gggtggccgg ggcggaggac taccaatatt accgcatcac ttacggcgaa     120
acaggaggca atagccctgt ccaggagttc actgtgcctc atgacctggt tacagctacc     180
atcagcggcc ttaaacctgg cgttgattat accatcactg tgtatgctgt cactgacatg     240
atgcatgttg aatacactga acatccaatt tccattaatt accgcacaga aattgacaaa     300
ccatcccagc accatcacca ccaccac                                         327

<210> SEQ ID NO 342
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 342
atgggagttt ctgatgtgcc gcgcgacctg gaagtggttg ctgccacccc caccagcctg      60
ctgatcagct ggcaggttcc gcgtccgatg taccaatatt accgcatcac ttacggcgaa     120
acaggaggca atagccctgt ccaggagttc actgtgcctg gtatggttca cacagctacc     180
atcagcggcc ttaaacctgg cgttgattat accatcactg tgtatgctgt cactgaccat     240
aaaccgcatg ctgacggtcc gcatacttac catgaatctc caatttccat taattaccgc     300
acagaaattg acaaaccatc ccagcaccat caccaccacc ac                        342

<210> SEQ ID NO 343
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 343
atgggagttt ctgatgtgcc gcgcgacctg gaagtggttg ctgccacccc caccagcctg      60
ctgatcagct ggttcgtgac gcacgtcgcc taccaatatt accgcatcac ttacggcgaa     120
acaggaggca atagccctgt ccaggagttc actgtgcctg gtggtctgtc cacagctacc     180
atcagcggcc ttaaacctgg cgttgattat accatcactg tgtatgctgt cactgactat     240
aaaccgcatg ctgacggtcc gcatacttac catgaatctc caatttccat taattaccgc     300
acagaaattg acaaaccatc ccagcaccat caccaccacc ac                        342

<210> SEQ ID NO 344
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 344
atgggagttt ctgatgtgcc gcgcgacctg gaagtggttg ctgccacccc caccagcctg      60
```

```
ctgatcagct gggagacgga gagcaacgcg taccaatatt accgcatcac ttacggcgaa      120
acaggaggca atagccctgt ccaggagttc actgtgcctg gtcagatcta cacagctacc      180
atcagcggcc ttaaacctgg cgttgattat accatcactg tgtatgctgt cactgactat      240
aaaccgcatg ctgacggtcc gcatacttac catgaatctc caatttccat taattaccgc      300
acagaaattg acaaaccatc ccagcaccat caccaccacc ac                         342
```

<210> SEQ ID NO 345
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 345

```
atgggagttt ctgatgtgcc gcgcgacctg gaagtggttg ctgccacccc caccagcctg       60
ctgatcagct ggatgacgtc gccctcggtg taccaatatt accgcatcac ttacggcgaa      120
acaggaggca atagccctgt ccaggagttc actgtgcctg gtccggttca gacagctacc      180
atcagcggcc ttaaacctgg cgttgattat accatcactg tgtatgctgt cactgactac      240
aaagaacatc agcatgctcc gcatcagtac actgctcatc caatttccat taattaccgc      300
acagaaattg acaaaccatc ccagcaccat caccaccacc ac                         342
```

<210> SEQ ID NO 346
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 346

```
atgggagttt ctgatgtgcc gcgcgacctg gaagtggttg ctgccacccc caccagcctg       60
ctgatcagct gggattcagg acgaggttcc tatcaatatt accgcatcac ttacggcgaa      120
acaggaggca atagccctgt ccaggagttc actgtgcctg gtccggttca tacagctacc      180
atcagcggcc ttaaacctgg cgttgattat accatcactg tgtatgctgt cactgaccat      240
aaaccgcatg ctgacggtcc gcatacttac catgaatctc caatttccat taattaccgc      300
acagaaattg acaaaccatc ccagcaccat caccaccacc ac                         342
```

<210> SEQ ID NO 347
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 347

```
atgggagttt ctgatgtgcc gcgcgacctg gaagtggttg ctgccacccc caccagcctg       60
ctgatcagct ggtcaacagg tcgcacaact tatcaatatt accgcatcac ttacggcgaa      120
acaggaggca atagccctgt ccaggagttc actgtgcctc atgacctgga cacagctacc      180
atcagcggcc ttaaacctgg cgttgattat accatcactg tgtatgctgt cactgactct      240
tacaacccgg ctactcatga atacaaatac catcagactc caatttccat taattaccgc      300
acagaaattg acaaaccatc ccagcaccat caccaccacc ac                         342
```

<210> SEQ ID NO 348
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 348
atgggagttt ctgatgtgcc gcgcgacctg gaagtggttg ctgccacccc caccagcctg    60
ctgatcagct ggcaggttcc gcgtccgatg taccaatatt accgcatcac ttacggcgaa   120
acaggaggca atagccctgt ccaggagttc actgtgcctt acgacgttat cacagctacc   180
atcagcggcc ttaaacctgg cgttgattat accatcactg tgtatgctgt cactgacatg   240
atgcatgttg aatacgctga atacccaatt tccattaatt accgcacaga aattgacaaa   300
ccatcccagc accatcacca ccaccac                                       327

<210> SEQ ID NO 349
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 349
atgggagttt ctgatgtgcc gcgcgacctg gaagtggttg ctgccacccc caccagcctg    60
ctgatcagct ggcaggttcc gcgtccgatg taccaatatt accgcatcac ttacggcgaa   120
acaggaggca atagccctgt ccaggagttc actgtgcctg gtcaggttcc aacagctacc   180
atcagcggcc ttaaacctgg cgttgattat accatcactg tgtatgctgt cactgactct   240
tacaacccgg ctactcatga atacaaatac catcagactc caatttccat taattaccgc   300
acagaaattg acaaaccatc ccagcaccat caccaccacc ac                      342

<210> SEQ ID NO 350
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 350
atgggagttt ctgatgtgcc gcgcgacctg gaagtggttg ctgccacccc caccagcctg    60
ctgatcagct ggggctacca aagtggcggc tatacctatt accgcatcac ttacggcgaa   120
acaggaggca atagccctgt ccaggagttc actgtgcctc atgacctgcg tacagctacc   180
atcagcggcc ttaaacctgg cgttgattat accatcactg tgtatgctgt cactgactac   240
gcttacaaag aataccagga acatccaatt tccattaatt accgcacaga aattgacaaa   300
ccatcccagc accatcacca ccaccac                                       327

<210> SEQ ID NO 351
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 351

```
atgggagttt ctgatgtgcc gcgcgacctg gaagtggttg ctgccacccc caccagcctg      60
ctgatcagct ggtggatcgg catcccggtg taccaatatt accgcatcac ttacggcgaa     120
acaggaggca atagccctgt ccaggagttc actgtgcctt acgacggtaa aacagctacc     180
atcagcggcc ttaaacctgg cgttgattat accatcactg tgtatgctgt cactgacatg     240
atgcatgttg aatacgctga atacccaatt ccattaatt accgcacaga aattgacaaa      300
ccatcccagc accatcacca ccaccac                                          327
```

<210> SEQ ID NO 352  
<211> LENGTH: 342  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 352

```
atgggagttt ctgatgtgcc gcgcgacctg gaagtggttg ctgccacccc caccagcctg      60
ctgatcagct ggtctaaagg ttcaaaatct taccaatatt accgcatcac ttacggcgaa     120
acaggaggca atagccctgt ccaggagttc actgtgcctt accatgttta cacagctacc     180
atcagcggcc ttaaacctgg cgttgattat accatcactg tgtatgctgt cactgactat     240
tataacccgg ctacttacga atacatatac cttacgactc caatttccat taattaccgc     300
acagaaattg acaaaccatc ccagcaccat caccaccacc ac                         342
```

<210> SEQ ID NO 353  
<211> LENGTH: 342  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 353

```
atgggagttt ctgatgtgcc gcgcgacctg gaagtggttg ctgccacccc caccagcctg      60
ctgatcagct ggaatcccgg ctccaaaagc taccaatatt accgcatcac ttacggcgaa     120
acaggaggca atagccctgt ccaggagttc actgtgcctg gtggtgttcg tacagctacc     180
atcagcggcc ttaaacctgg cgttgattat accatcactg tgtatgctgt cactgacttt     240
tacaatccgg atactcatga atacctatac aatcaatatc caatttccat taattaccgc     300
acagaaattg acaaaccatc ccagcaccat caccaccacc ac                         342
```

<210> SEQ ID NO 354  
<211> LENGTH: 342  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 354

```
atgggagttt ctgatgtgcc gcgcgacctg gaagtggttg ctgccacccc caccagcctg      60
ctgatcagct ggcaacccgg caccacacat tatcaatatt accgcatcac ttacggcgaa     120
acaggaggca atagccctgt ccaggagttc actgtgcctt acgacctgat gacagctacc     180
atcagcggcc ttaaacctgg cgttgattat accatcactg tgtatgctgt cactgactat     240
tacaacccga atacttatga gtatatatac ttgacgactc caatttccat taattaccgc     300
```
acagaaattg acaaaccatc ccagcaccat caccaccacc ac          342

<210> SEQ ID NO 355
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 355
atgggagttt ctgatgtgcc gcgcgacctg gaagtggttg ctgccacccc caccagcctg          60
ctgatcagct gggccatcgg caccatcgtc taccaatatt accgcatcac ttacggcgaa         120
acaggaggca atagccctgt ccaggagttc actgtgcctg ctggtgttta cacagctacc         180
atcagcggcc ttaaacctgg cgttgattat accatcactg tgtatgctgt cactgactat         240
tacgactggg ctactcatga atacaattac cacaccgctc caatttccat taattaccgc         300
acagaaattg acaaaccatc ccagcaccat caccaccacc ac          342

<210> SEQ ID NO 356
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 356
atgggagttt ctgatgtgcc gcgcgacctg gaagtggttg ctgccacccc caccagcctg          60
ctgatcagct ggacttataa tgatggcagc tatcaatatt accgcatcac ttacggcgaa         120
acaggaggca atagccctgt ccaggagttc actgtgcctt acgctgttta cacagctacc         180
atcagcggcc ttaaacctgg cgttgattat accatcactg tgtatgctgt cactgacttt         240
tacaatccgg ctacatatga atacatatat cacacgacac caatttccat taattaccgc         300
acagaaattg acaaaccatc ccagcaccat caccaccacc ac          342

<210> SEQ ID NO 357
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 357
atgggagttt ctgatgtgcc gcgcgacctg gaagtggttg ctgccacccc caccagcctg          60
ctgatcagct gggtctccct cgtgggcttc taccaatatt accgcatcac ttacggcgaa         120
acaggaggca atagccctgt ccaggagttc actgtgcctg gtggtgttca tacagctacc         180
atcagcggcc ttaaacctgg cgttgattat accatcactg tgtatgctgt cactgactat         240
aaaccgcatg ctgacggtcc gcatacttac catgaatctc caatttccat taattaccgc         300
acagaaattg acaaaccatc ccagcaccat caccaccacc ac          342

<210> SEQ ID NO 358
<211> LENGTH: 327
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 358

| atgggagttt ctgatgtgcc gcgcgacctg gaagtggttg ctgccacccc caccagcctg | 60 |
| ctgatcagct gggcctcgag gaaggaggtc taccaatatt accgcatcac ttacggcgaa | 120 |
| acaggaggca atagccctgt ccaggagttc actgtgcctg gttggttgaa cacagctacc | 180 |
| atcagcggcc ttaaacctgg cgttgattat accatcactg tgtatgctgt cactgactac | 240 |
| atgcatgttg aatacgctga atacccaatt tccattaatt accgcacaga aattgacaaa | 300 |
| ccatcccagc accatcacca ccaccac | 327 |

<210> SEQ ID NO 359
<211> LENGTH: 342
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 359

| atgggagttt ctgatgtgcc gcgcgacctg gaagtggttg ctgccacccc caccagcctg | 60 |
| ctgatcagct ggttggcgcc cttctggcgg taccaatatt accgcatcac ttacggcgaa | 120 |
| acaggaggca atagccctgt ccaggagttc actgtgcctg gtggtgttcg tacagctacc | 180 |
| atcagcggcc ttaaacctgg cgttgattat accatcactg tgtatgctgt cactgactat | 240 |
| aaaccgcatg ctgacggtcc gcatacttac catgaatctc caatttccat taattaccgc | 300 |
| acagaaattg acaaaccatc ccagcaccat caccaccacc ac | 342 |

<210> SEQ ID NO 360
<211> LENGTH: 342
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 360

| atgggagttt ctgatgtgcc gcgcgacctg gaagtggttg ctgccacccc caccagcctg | 60 |
| ctgatcagct ggacaccacc aggacatcaa catcaatatt accgcatcac ttacggcgaa | 120 |
| acaggaggca atagccctgt ccaggagttc actgtgcctg gtcaggttac tacagctacc | 180 |
| atcagcggcc ttaaacctgg cgttgattat accatcactg tgtatgctgt cactgactat | 240 |
| tacaacccag ctactcacta ttacacttat tatacgactc caatttccat taattaccgc | 300 |
| acagaaattg acaaaccatc ccagcaccat caccaccacc ac | 342 |

<210> SEQ ID NO 361
<211> LENGTH: 342
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 361

| atgggagttt ctgatgtgcc gcgcgacctg gaagtggttg ctgccacccc caccagcctg | 60 |
| ctgatcagct gggagtcggg gtccaggacg taccaatatt accgcatcac ttacggcgaa | 120 |
| acaggaggca atagccctgt ccaggagttc actgtgcctg gtggtgttca tacagctacc | 180 |

```
atcagcggcc ttaaaactgg cgttgattat accatcactg tgtatgctgt cactgactat    240
aaaccgcatg ctgacggtcc gcatacttac catgaatatc caatttccat taattaccgc    300
acagaaattg acaaaccatc ccagcaccat caccaccacc ac                       342
```

<210> SEQ ID NO 362
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 362

```
atgggagttt ctgatgtgcc gcgcgacctg gaagtggttg ctgccacccc caccagcctg    60
ctgatcagct gggagaggac ctccacccac taccaatatt accgcatcac ttacggcgaa    120
acaggaggca atagccctgt ccaggagttc actgtgcctg gtcgtgttta cacagctacc    180
atcagcggcc ttaaacctgg cgttgattat accatcactg tgtatgctgt cactgactac    240
tacaacccgg ctactcatga atacaaatac catcagactc caatttccat taattaccgc    300
acagaaattg acaaaccatc ccagcaccat caccaccacc ac                       342
```

<210> SEQ ID NO 363
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 363

```
atgggagttt ctgatgtgcc gcgcgacctg gaagtggttg ctgccacccc caccagcctg    60
ctgatcagct ggaatgctcg caccgacgct tatcaatatt accgcatcac ttacggcgaa    120
acaggaggca atagccctgt ccaggagttc actgtgcctc gtgacctgga aacagctacc    180
atcagcggcc ttaaacctgg cgttgattat accatcactg tgtatgctgt cactgactat    240
aaacctcatg cggacggacc gcatacttac caagagtcgc caatttccat taattaccgc    300
acagaaattg acaaaccatc ccagcaccat caccaccacc ac                       342
```

<210> SEQ ID NO 364
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 364

```
atgggagttt ctgatgtgcc gcgcgacctg gaagtggttg ctgccacccc caccagcctg    60
ctgatcagct ggcaggtgag cgcgttccgg taccaatatt accgcatcac ttacggcgaa    120
acaggaggca atagccctgt ccaggagttc actgtgcctg gtatggtttc tacagctacc    180
atcagcggcc ttaaacctgg cgttgattat accatcactg tgtatgctgt cactgactat    240
aaaccgcatg ctgacggtcc gcatacttac tctgaatacc caatttccat taattaccgc    300
acagaaattg acaaaccatc ccagcaccat caccaccacc ac                       342
```

<210> SEQ ID NO 365
<211> LENGTH: 342
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 365

| | | | | | |
|---|---|---|---|---|---|
| atgggagttt | ctgatgtgcc | gcgcgacctg | gaagtggttg | ctgccacccc | caccagcctg | 60 |
| ctgatcagct | gggtgctggg | caggagggtg | taccaatatt | accgcatcac | ttacggcgaa | 120 |
| acaggaggca | atagccctgt | ccaggagttc | actgtgcctg | tgctgttta | cacagctacc | 180 |
| atcagcggcc | ttaaacctgg | cgttgattat | accatcactg | tgtatgctgt | cactgactat | 240 |
| ttcaacccag | ctacccatga | ataccaatac | gagcttactc | caatttccat | taattaccgc | 300 |
| acagaaattg | acaaaccatc | ccagcaccat | caccaccacc | ac | | 342 |

<210> SEQ ID NO 366
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 366

| | | | | | |
|---|---|---|---|---|---|
| atgggagttt | ctgatgtgcc | gcgcgacctg | gaagtggttg | ctgccacccc | caccagcctg | 60 |
| ctgatcagct | ggactccacc | caattctggt | cataattatt | accgcatcac | ttacggcgaa | 120 |
| acaggaggca | atagccctgt | ccaggagttc | actgtgcctc | atgacctgac | tacagctacc | 180 |
| atcagcggcc | ttaaacctgg | cgttgattat | accatcactg | tgtatgctgt | cactgactat | 240 |
| tacaacccga | atacctatga | atacacatat | caattcactc | caatttccat | taattaccgc | 300 |
| acagaaattg | acaaaccatc | ccagcaccat | caccaccacc | ac | | 342 |

<210> SEQ ID NO 367
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 367

| | | | | | |
|---|---|---|---|---|---|
| atgggagttt | ctgatgtgcc | gcgcgacctg | gaagtggttg | ctgccacccc | caccagcctg | 60 |
| ctgatcagct | gggtcgtccc | gaactggatg | taccaatatt | accgcatcac | ttacggcgaa | 120 |
| acaggaggca | atagccctgt | ccaggagttc | actgtgcctg | gtatgctgga | aacagctacc | 180 |
| atcagcggcc | ttaaacctgg | cgttgattat | accatcactg | tgtatgctgt | cactgactat | 240 |
| tataacccga | ctacgtatga | atacacatac | tttacctatc | caatttccat | taattaccgc | 300 |
| acagaaattg | acaaaccatc | ccagcaccat | caccaccacc | ac | | 342 |

<210> SEQ ID NO 368
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 368

| | | | | | |
|---|---|---|---|---|---|
| atgggagttt | ctgatgtgcc | gcgcgacctg | gaagtggttg | ctgccacccc | caccagcctg | 60 |
| ctgatcagct | ggtccggcgg | gttcatgcgg | taccaatatt | accgcatcac | ttacggcgaa | 120 |

```
acaggaggca atagccctgt ccaggagttc actgtgcctg gtcaggttta cacagctacc    180
atcagcggcc ttaaacctgg cgttgattat accatcactg tgtatgctgt cactgactat    240
aaaccgcatg ctgacggtcc gcatacttac catgaatctc caatttccat taattaccgc    300
acagaaattg acaaaccatc ccagcaccat caccaccacc ac                       342
```

<210> SEQ ID NO 369
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 369

```
atgggagttt ctgatgtgcc gcgcgacctg gaagtggttg ctgccacccc caccagcctg    60
ctgatcagct gggattccga aggtccttct tatcaatatt accgcatcac ttacggcgaa    120
aaaggaggca atagccctgt ccaggagttc actgtgcctt acgctgttta cacagctacc    180
atcagcggcc ttaaacctgg cgttgattat accatcactg tgtatgctgt cactgactat    240
tacaacccga gaacgcatga attattttc cagcaatatc caatttccat taattaccgc    300
acagaaattg acaaaccatc ccagcaccat caccaccacc ac                       342
```

<210> SEQ ID NO 370
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 370

```
atgggagttt ctgatgtgcc gcgcgacctg gaagtggttg ctgccacccc caccagcctg    60
ctgatcagct ggcaggttcc gcgtccgatg taccaatatt accgcatcac ttacggcgaa    120
acaggaggca atagccctgt ccaggagttc actgtgcctc atgacctgcg tacagctacc    180
atcagcggcc ttaaacctgg cgttgattat accatcactg tgtatgctgt cactgactat    240
tacgacccga catctaatct gtacaattac aaccagactc caatttccat taattaccgc    300
acagaaattg acaaaccatc ccagcaccat caccaccacc ac                       342
```

<210> SEQ ID NO 371
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 371

```
atgggagttt ctgatgtgcc gcgcgacctg gaagtggttg ctgccacccc caccagcctg    60
ctgatcagct ggcaggtggg ctcggtggtg taccaatatt accgcatcac ttacggcgaa    120
acaggaggca atagccctgt ccaggagttc actgtgcctc gtgacgttct gacagctacc    180
atcagcggcc ttaaacctgg cgttgattat accatcactg tgtatgctgt cactgactat    240
aaaccgaagc ctgacggtcc acatatatac caggcagtgc caatttccat taattaccgc    300
acagaaattg acaaaccatc ccagcaccat caccaccacc ac                       342
```

<210> SEQ ID NO 372
<211> LENGTH: 342
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 372

```
atgggagttt ctgatgtgcc gcgcgacctg gaagtggttg ctgccacccc caccagcctg      60
ctgatcagct ggaaccctgc ttctaaagac tatcaatatt accgcatcac ttacggcgaa     120
acaggaggca atagccctgt ccaggagttc actgtgcctg gtcaggttcc gacagctacc     180
atcagcggcc ttaaacctgg cgttgattat accatcactg tgtatgctgt cactgacttt     240
tacaacccgg ctactcatga gtataaatat gactcgactc caatttccat taattaccgc     300
acagaaattg acaaaccatc ccagcaccat caccaccacc ac                         342
```

<210> SEQ ID NO 373
<211> LENGTH: 342
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 373

```
atgggagttt ctgatgtgcc gcgcgacctg gaagtggttg ctgccacccc caccagcctg      60
ctgatcagct ggagatcatc agcaaccgcc taccaatatt accgcatcac ttacggcgaa     120
acaggaggca atagccctgt ccaggagttc actgtgcctg gtcgtgttta cacagctacc     180
atcagcggcc ttaaacctgg cgttgattat accatcactg tgtatgctgt cactgacttt     240
ttcaactggg ccactcatga gtacatatac cactcaactc caatttccat taattaccgc     300
acagaaattg acaaaccatc ccagcaccat caccaccacc ac                         342
```

<210> SEQ ID NO 374
<211> LENGTH: 342
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 374

```
atgggagttt ctgatgtgcc gcgcgacctg gaagtggttg ctgccacccc caccagcctg      60
ctgatcagct ggcattccgg tccacgagaa tatcaatatt accgcatcac ttacggcgaa     120
acaggaggca atagccctgt ccaggagttc actgtgcctg gtcaggttta cacagctacc     180
atcagcggcc ttaaacctgg cgttgattat accatcactg tgtatgctgt cactgacttt     240
ttcaacccga ttacacatta ctattactac gagctgactc caatttccat taattaccgc     300
acagaaattg acaaaccatc ccagcaccat caccaccacc ac                         342
```

<210> SEQ ID NO 375
<211> LENGTH: 342
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 375

```
atgggagttt ctgatgtgcc gcgcgacctg gaagtggttg ctgccacccc caccagcctg    60
ctgatcagct ggacggtggg cctgagcgtg taccaatatt accgcatcac ttacggcgaa   120
acaggaggca atagccctgt ccaggagttc actgtgcctg gtatggtttc tacagctacc   180
atcagcggcc ttaaacctag cgttgattat accatcactg tgtatgctgt cactgactat   240
aaaccgcatg ctgacggtcc gcatacttac catgaatatc caatttccat taattaccgc   300
acagaaattg acaaaccatc ccagcaccat caccaccacc ac                      342
```

<210> SEQ ID NO 376  
<211> LENGTH: 342  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 376

```
atgggagttt ctgatgtgcc gcgcgacctg gaagtggttg ctgccacccc caccagcctg    60
ctgatcagct ggggggggca ccgggcggtg taccaatatt accgcatcac ttacggcgaa   120
acaggaggca atagccctgt ccaggagttc actgtgcctg gtgctgttta cacagctacc   180
atcagcggcc ttaaacctgg cgttgattat accatcactg tgtatgctgt cactgactac   240
tacaacccgg atactcatga atacaaatac catcaatatc caatttccat taattaccgc   300
acagaaattg acaaaccatc ccagcaccat caccaccacc ac                      342
```

<210> SEQ ID NO 377  
<211> LENGTH: 327  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 377

```
atgggagttt ctgatgtgcc gcgcgacctg gaagtggttt ctgccacccc caccagcctg    60
ctgatcagct ggcaggttcc gcgtccgatg taccaatatt accgcatcac ttacggcgaa   120
acaggaggca atagccctgt ccaggagttc actgtgcctg gtggtgttcg tacagctacc   180
atcagcggcc ttaaacctgg cgttgattat accatcactg tgtatgctgt cactgactac   240
tggttcaagg ataccgtga agacccaatt tccattaatt accgcacaga aattgacaaa   300
ccatcccagc accatcacca ccaccac                                      327
```

<210> SEQ ID NO 378  
<211> LENGTH: 342  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 378

```
atgggagttt ctgatgtgcc gcgcgacctg gaagtggttg ctgccacccc caccagcctg    60
ctgatcagct ggagcgtcgg gggcatgatc taccaatatt accgcatcac ttacggcgaa   120
acaggaggca atagccctgt ccaggagttc actgtgcctg gtatggttac tacagctacc   180
atcagcggcc ttaaacctgg cgttgattat accatcactg tgtatgctgt cactgactac   240
tacaacccgg ctactcatga atacaaatac catcagactc caatttccat taattaccgc   300
```

```
acagaaattg acaaaccatc ccagcaccat caccaccacc ac                    342

<210> SEQ ID NO 379
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 379
atgggagttt ctgatgtgcc gcgcgacctg gaagtggttg ctgccacccc caccagcctg    60
ctgatcagct ggtgggcccc cgtcgaccgg taccaatatt accgcatcac ttacggcgaa   120
acaggaggca atagccctgt ccaggagttc actgtgcctc gtgacgttta cacagctacc   180
atcagcggcc ttaaacctgg cgttgattat accatcactg tgtatgctgt cactgactat   240
aaaccgcatg ctgacggtcc gcatacttac catgaatctc aatttccat taattaccgc    300 acagaaattg acaaaccatc ccagcaccat caccaccacc ac                      342

<210> SEQ ID NO 380
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 380
atgggagttt ctgatgtgcc gcgcgacctg gaagtggttg ctgccacccc caccagcctg    60
ctgatcagct ggtgggcccc cgtcgaccgg taccaatatt accgcatcac ttacggcgaa   120
acaggaggca atagccctgt ccaggagttc actgtgcctc gtgacgttta cacagctacc   180
atcagcggcc ttaaacctgg cgttgattat accatcactg tgtatgctgt cactgactat   240
aaaccgcatg ctgacggtcc gcatacttac catgaatctc aatttccat taattaccgc    300 acagaaattg acaaaccatg ccagcaccac caccaccacc ac                      342

<210> SEQ ID NO 381
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 381
atgggagttt ctgatgtgcc gcgcgacctg gaagtggttg ctgccacccc caccagcctg    60
ctgatcagct ggaaagccag ctataccggc tacaactatt accgcatcac ttacggcgaa   120
acaggaggca atagccctgt ccaggagttc actgtgcctc gtgacgttat gacagctacc   180
atcagcggcc ttaaacctgg cgttgattat accatcactg tgtatgctgt cactgacttc   240
tacaatccgg atactcatca atacacatac cgtcgcattc aatttccat taattaccgc    300 acagaaattg acaaaccatc ccagcaccat caccaccacc ac                      342

<210> SEQ ID NO 382
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
```

-continued

<400> SEQUENCE: 382

```
atgggagttt ctgatgtgcc gcgcgacctg gaagtggttg ctgccacccc caccagcctg      60
ctgatcagct ggtcggtggg ccaggtcttc taccaatatt accgcatcac ttacggcgaa     120
acaggaggca atagccctgt ccaggagttc actgtgcctt acgacgttta cacagctacc     180
atcagcggcc ttaaacctgg cgttgattat accatcactg tgtatgctgt cactgactac     240
tacaacccgg ctactcatga atacaaatac catcagactc caatttccat taattaccgc     300
acagaaattg acaaaccatc ccagcaccat caccaccacc ac                        342
```

<210> SEQ ID NO 383
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 383

```
atgggagttt ctgatgtgcc gcgcgacctg gaagtggttg ctgccacccc caccagcctg      60
ctgatcagct ggtactctgg tgattaccat taccaatatt accgcatcac ttacggcgaa     120
acaggaggca atagccctgt ccaggagttc actgtgcctc atgacctgga aacagctacc     180
atcagcggcc ttaaacctgg cgttgattat accatcactg tgtatgctgt cactgactat     240
tacaacccgg ctactcatta ctacaagtac gagcagacac caatttccat taattaccgc     300
acagaaattg acaaaccatc ccagcaccat caccaccacc ac                        342
```

<210> SEQ ID NO 384
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 384

```
atgggagttt ctgatgtgcc gcgcgacctg gaagttgttg ctgccacccc caccagcctg      60
ctgatcagct ggatcgtcca ggggggggcgc taccaatatt accgcatcac ttacggcgaa     120
acaggaggca atagccctgt ccaggagttc actgtgcctg gtatggttac tacagctacc     180
atcagcggcc ttaaacctgg cgttgattat accatcactg tgtatgctgt cactgactat     240
tacaaccctt caactcatga atacaaatac catcagactc caatttccat taattaccgc     300
acagaaattg acaaaccatc ccagcaccat caccaccacc ac                        342
```

<210> SEQ ID NO 385
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 385

```
atgggagttt ctgatgtgcc gcgcgacctg gaagtggttg ctgccacccc caccagcctg      60
ctgatcagct ggtcggccgt ccgctggcgg taccaatatt accgcatcac ttacggcgaa     120
acaggaggca atagccctgt ccaggagttc actgtgcctg gtggtgttcg tacagctacc     180
atcagcggcc ttaaacctgg cgttgattat accatcactg tgtatgctgt cactgacttt     240
```

```
tacaacccgc gtactcatgt atacatatac gatcagttcc caatttccat taattaccgc    300
acagaaattg acaaaccatc ccagcaccat caccaccacc ac                      342
```

<210> SEQ ID NO 386
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 386

```
atgggagttt ctgatgtgcc gcgcgacctg gaagtggttg ctgccacccc caccagcctg    60
ctgatcagct ggagggccag gcgcttgcag taccaatatt accgcatcac ttacggcgaa   120
acaggaggca atagccctgt ccaggagttc actgtgcctg gtatggttac tacagctacc   180
atcagcggcc ttaaacctgg cgttgattat accatcactg tgtatgctgt cactgacttt   240
tacaacccgg ctactatgga gtacacatat cagcggactc caatttccat taattaccgc   300
acagaaattg acaaaccatc ccagcaccat caccaccacc ac                      342
```

<210> SEQ ID NO 387
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 387

```
atgggagttt ctgatgtgcc gcgcgacctg gaagtggttg ctgccacccc caccagcctg    60
ctgatcagct ggttgcagcc cctctggagg taccaatatt accgcatcac ttacggcgaa   120
acaggaggca atagccctgt ccaggagttc actgtgcctg gtggtctgga cacagctacc   180
atcagcggac ttaaacctgg cgttgattat accatcactg tgtatgctgt cactgactat   240
aaaccgcatg ttgacggtcc ccatgcttac catgaatatc caatttccat taattaccgc   300
acagaaattg acaaaccatc ccagcaccat caccaccacc ac                      342
```

<210> SEQ ID NO 388
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 388

```
atgggagttt ctgatgtgcc gcgcgacctg gaagtggttg ctgccacccc caccagcctg    60
ctgatcagct gggacgcctc caggggaac taccaatatt accgcatcac ttacggcgaa    120
acaggaggca atagccctgt ccaggagttc actgtgcctg gtgctgttaa aacagctacc   180
atcagcggcc ttaaacctgg cgttgattat accatcactg tgtatgctgt cactgacttt   240
ttcaacccgg ctactcatga atacatatac catacgactc caatttccat taattaccgc   300
acagaaattg acaaaccatc ccagcaccat caccaccacc ac                      342
```

<210> SEQ ID NO 389
<211> LENGTH: 342
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 389
atgggagttt ctgatgtgcc gcgcgacctg gaagtggttg ctgccacccc caccagcctg     60
ctgatcagct ggtgcctcga cgggcagttg taccaatatt accgcatcac ttacggcgaa    120
acaggaggca atagccctgt ccaggagttc actgtgcctg gttctatcgt tacagctacc    180
atcagcggcc ttaaacctgg cgttgattat accatcactg tgtatgctgt cactgactgg    240
tacaacctcg cgactcatga atacaactac cgtgtgactc aatttccat taattaccgc     300 acagaaattg acaaaccatc ccagcaccat caccaccacc ac                       342

<210> SEQ ID NO 390
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 390
atgggagttt ctgatgtgcc gcgcgacctg gaagtggttg ctgccacccc caccagcctg     60
ctgatcagct gggacacttc aggtgcttca tatcaatatt accgcatcac ttacggcgaa    120
acaggaggca atagccctgt ccaggagttc actgtgcctt actctgttta cacagctacc    180
atcagcggcc ttaaacctgg cgttgattat accatcactg tgtatgctgt cactgactat    240
tacgaccctg attcgcatta ttacaactac aatatggttc caatttccat taattaccgc    300
acagaaattg acaaaccatc ccagcaccat caccaccacc ac                       342

<210> SEQ ID NO 391
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 391
atgggagttt ctgatgtgcc gcgcgacctg gaagtggttg ctgccacccc caccagcctg     60
ctgatcagct gggattctgg taatggtact tatcaatatt accgcatcac ttacggcgaa    120
acaggaggca atagccctgt ccaggagttc actgtgcctt accgtgttta cacagctacc    180
atcagcggcc ttaaacctgg cgttgattat accatcactg tgtatgctgt cactgactat    240
tacaacccgg ctactcacga atatacatac gagctgcgtc aatttccat taattaccgc     300 acagaaattg acaaaccatc ccagcaccat caccaccacc ac                       342

<210> SEQ ID NO 392
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 392
atgggagttt ctgatgtgcc gcgcgacctg gaagtggttg ctaccacccc caccagcctg     60
ctgatcagct ggcggcccac cagccaggtc taccaatatt accgcatcac ttacggcgaa    120
```

```
acaggaggca atagccctgt ccaggagttc actgtgcctt acaacgttta cacagctacc    180
atcagcggcc ttaaacctgg cgttgattat accatcactg tgtatgctgt cactgacttt    240
tttaactatg ctactcacga atacatatac cataccattc caatttccat taattaccgc    300
acagaaattg acaaaccatc ccagcaccat caccaccacc ac                       342
```

<210> SEQ ID NO 393
<211> LENGTH: 342
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 393

```
atgggagttt ctgatgtgcc gcgcgacctg gaagtggttg ctgccacccc caccagcctg    60
ctgatcagct ggaagtcgta cgggtcggcc taccaatatt accgcatcac ttacggcgaa   120
acaggaggca atagccctgt ccaggagttc actgtgcctg gtgacctgca gacagctacc   180
atcagcggcc ttaaacctgg cgttgattat accatcactg tgtatgctat cactgactat   240
tacaacccgg atacacatga gtataaatac catgtgtcgc caatttccat taattaccgc   300
acagaaattg acaaaccatc ccagcaccat caccaccacc ac                       342
```

<210> SEQ ID NO 394
<211> LENGTH: 342
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 394

```
atgggagttt ctgatgtgcc gcgcgacctg gaagtggttg ctgccacccc caccagcctg    60
ctgatcagct ggtcgtcggt gatggggttg taccaatatt accgcatcac ttacggcgaa   120
acaggaggca atagccctgt ccaggagttc actgtgcctt acgacgttta cacagctacc   180
atcagcggcc ttaaacctgg cgttgattat accatcactg tgtatgctgt cactgactat   240 tacaacccctt ctacttatga atacaaatac aatacgactc caatttccat taattaccgc   300
acagaaattg acaaaccatc ccagcaccat caccaccacc ac                       342
```

<210> SEQ ID NO 395
<211> LENGTH: 342
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 395

```
atgggagttt ctgatgtgcc gcgcgacctg gaagtggttg ctgccacccc caccagcctg    60
ctgatcagct ggcacgccgg catggcggtg taccaatatt accgcatcac ttacggcgaa   120
acaggaggca atagccctgt ccaggagttc actgtgcctg gtgacgttct gacagctacc   180
atcagcggcc ttaaacctgg cgttgattat accatcactg tgtatgctgt cactgactat   240
ttcaatccgg ttactcatga atacatgtat catacgattc caatttccat taattaccgc   300
acagaaattg acaaaccatc ccagcaccat caccaccacc ac                       342
```

<210> SEQ ID NO 396

```
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 396
atgggagttt ctgatgtgcc gcgcgacctg gaagtggttg ctgccacccc caccagcctg      60
ctgatcagct gggtgtccgc gaggggcgg taccaatatt accgcatcac ttacggcgaa      120
acaggaggca atagccctgt ccaggagttc actgtgcctg gtggtgttcg tacagctacc      180
atcagcggcc ttaaacctgg cgttgattat accatcactg tgtatgctgt cactgactat      240
tacaacctag aaacttatga atatcattac tatcgcactc caatttccat taattaccgc      300
acagaaattg acaaaccatc ccagcaccat caccaccacc ac                         342

<210> SEQ ID NO 397
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 397
atgggagttt ctgatgtgcc gcgcgacctg gaagtggttg ctgccacccc caccagcctg      60
ctgatcagct ggtggttcgg cacctcgtcc taccaatatt accgcatcac ttacggcgaa      120
acaggaggca atagccctgt ccaggagttc actgtgcctg gtgacctgaa aacagctacc      180
atcagcggcc ttaaacctgg cgttgattat accatcactg tgtatgctgt cactgactat      240
tttaaccccg ttactcatga atacgaatat catacgactc caatttccat taattaccgc      300
acagaaattg acaaaccatc ccagcaccat caccaccacc ac                         342

<210> SEQ ID NO 398
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 398
atgggagttt ctgatgtgcc gcgcgacctg gaagtggttg ctgccacccc caccagcctg      60
ctgatcagct ggtccgcgac ccggaccctg taccaatatt accgaatcac ttacggcgaa      120
acaggaggca atagccctgt ccaggagttc actgtgcctt acgacgttca tacagctacc      180
atcagcggcc ttaaacctgg cgttgattat accatcactg tgtatgctgt cactgactat      240
tacaacatgg ttacttatga atacaactac catcttactc caatttccat taattaccgc      300
acagaaattg acaaaccatc ccagcaccat caccaccacc ac                         342

<210> SEQ ID NO 399
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 399
atgggagttt ctgatgtgcc gcgcgacctg gaagtggttg ttgccacccc caccagcctg      60
```
ctgatcagct ggaccaagtt gttgggcggg taccaatatt accgcatcac ttacggcgaa    120
acaggaggca atagccctgt ccaggagttc actgtgcctg gtcctgttta cacagctacc    180
atcagcggcc ttaaacctgg cgttgattat accatcactg tgtatgctgt cactgacttt    240
ttcaaccctc gtactcatga atatcaatat cacacgactc aatttccat taattaccgc     300 acagaaattg acaaaccatc ccagcaccat caccaccacc ac                       342

<210> SEQ ID NO 400
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 400
atgggagttt ctgatgtgcc gcgcgacctg gaagtggttg ctgccacccc caccagcctg    60
ctgatcagct ggagggcgtc gggcgggctg taccaatatt accgcatcac ttacggcgaa    120
acaggaggca atagccctgt ccaggagttc actgtgcctg gttctgttaa cacagctacc    180
atcagcggcc ttaaacctgg cgttgattat accatcactg tgtatgctgt cactgacttt    240
tacaacccgg ctacttatga gtacatatac cataccactc caatttccat taattaccgc   300
acagaaattg acaaaccatc ccagcaccat caccaccacc ac                       342

<210> SEQ ID NO 401
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 401
atgggagttt ctgatgtgcc gcgcgacctg gaagtggttg ctgccacccc caccagcctg    60
ctgatcagct gggcggccgg gcgcgccacg taccaatatt accgcatcac ttacggcgaa    120
acaggaggca atagccctgt ccaggagttc actgtgcctt acgacgttac tacagctacc   180
atcagcggcc ttaaacctgg cgttgattat accatcactg tgtatgctgt cactgacttt    240
tacaacccgg ctactcatga atactactat gagaccacgc caatttccat taattaccgc   300
acagaaattg acaaaccatc ccagcaccat caccaccacc ac                       342

<210> SEQ ID NO 402
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 402
atgggagttt ctgatgtgcc gcgcgacctg gaagtggttg ctgccacccc caccagcctg    60
ctgatcagct ggtactcgca gcccttgacg taccaatatt accgcatcac ttacggcgaa    120
acaggaggca atagccctgt ccaggagttc actgtgcctc atgacgttaa cacagctacc    180
atcagcggcc ttaaacctgg cgttgattat accatcactg tgtatgctgt cactgacttc    240
tacaacccgg agacacatga atacacttac cacctgactc caatttccat taattaccgc    300
acagaaattg acaaaccatc ccagcaccat caccaccacc ac                       342

<210> SEQ ID NO 403
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 403
atgggagttt ctgatgtgcc gcgcgacctg gaagtggttg ctgccacccc caccagcctg     60
ctgatcagct ggagttctgc aacaagacct taccaatatt accgcatcac ttacggcgaa    120
acaggaggca atagccctgt ccaggagttc actgtgcctg gtggtgttcg tacagctacc    180
atcagcggcc ttaaacctgg cgttgattat accatcactg tgtatgctgt cactgacttt    240
ttcaacccga ctacgcacga atactattat catacgactc caatttccat taattaccgc    300
acagaaattg acaaaccatc ccagcaccat caccaccacc ac                       342

<210> SEQ ID NO 404
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 404
atgggagttt ctgatgtgcc gcgcgacctg gaagtggttg ctgccacccc caccagcctg     60
ctgatcagct ggtccgtcga gaggtccgtg taccaatatt accgcatcac ttacggcgaa    120
acaggaggca atagccctgt ccaggagttc actgtgcctg gtggtgttcg tacagctacc    180
atcagcggcc ttaaacctgg cgttgattat accatcactg tgtatgctgt cactgactat    240
tacaacccgt ctactcatga atacaattac ctcacgactc caatttccat taattaccgc    300
acagaaattg acaaaccatc ccagcaccat caccaccacc ac                       342

<210> SEQ ID NO 405
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 405
atgggagttt ctgatgtgcc gcgcgacctg gaagtggttg ctgccacccc caccagcctg     60
ctgatcagct ggcaagatac ctccagttat catcaatatt accgcatcac ttacggcgaa    120
acaggaggca atagccctgt ccaggagttc actgtgcctg gtggtgttcg tacagctacc    180
atcagcggcc ttaaacctgg cgttgattat accatcactg tgtatgctgt cactgactat    240
ttcaacccgt ctacccatga atacatctac cgtaccattc caatttccat taattaccgc    300
acagaaattg acaaaccatc ccagcaccat caccaccacc ac                       342

<210> SEQ ID NO 406
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 406

| atgggagttt ctgatgtgcc gcgcgacctg gaagtggttg ctgccacccc caccagcctg | 60 |
| ctgatcagct ggtctagctc tcatcgccgc tatcaatatt accgcatcac ttacggcgaa | 120 |
| acaggaggca atagccctgt ccaggagttc actgtgcctg gttcggttgc tacagctacc | 180 |
| atcagcggcc ttaaacctgg cgttgattat accatcactg tgtatgctgt cactgactat | 240 |
| ttcaacccag acactcatga atacctatac catgccaccc caatttccat taattaccgc | 300 |
| acagaaattg acaaaccatc ccagcaccat caccaccacc ac | 342 |

<210> SEQ ID NO 407
<211> LENGTH: 342
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 407

| atgggagttt ctgatgtgcc gcgcgacctg gaagtggttg ctgccacccc caccagcctg | 60 |
| ctgatcagct gggataataa ttctaactca tatcaatatt accgcatcac ttacggcgaa | 120 |
| acaggaggca atagccctgt ccaggagttc actgtgcctt acgacctgcg tacagctacc | 180 |
| atcagcggcc ttaaacctgg cgttgattat accatcactg tgtatgctgt cactgactat | 240 |
| aaacctcata ctgagggtga gcatacttat catgaatcgc caatttccat taattaccgc | 300 |
| acagaaattg acaaaccatc ccagcaccat caccaccacc ac | 342 |

<210> SEQ ID NO 408
<211> LENGTH: 342
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 408

| atgggagttt ctgatgtgcc gcgcgacctg gaagtggttg ctgccacccc caccagcctg | 60 |
| ctgatcagct ggcgcgtgtt ggtcgacatg taccaatatt accgcatcac ttacggcgaa | 120 |
| acaggaggca atagccctgt ccaggagttc actgtgcctg gtggtgttct gacagctacc | 180 |
| atcagcggcc ttaaacctgg cgttgattat accatcactg tgtatgctgt cactgactat | 240 |
| aaaccgcatg ttgacgggcc gcacacctac tatgaatctc caatttccat taattaccgc | 300 |
| acagaaattg acaaaccatc ccagcaccat caccaccacc ac | 342 |

<210> SEQ ID NO 409
<211> LENGTH: 342
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 409

| atgggagttt ctgatgtgcc gcgcgacctg gaagtggttg ctgccacccc caccagcctg | 60 |
| ctgatcagct ggatgttcgt ggggatgtcc taccaatatt accgcatcac ttacggcgaa | 120 |
| acaggaggca atagccctgt ccaggagttc actgtgcctt acggtgttca tacagctacc | 180 |
| atcagcggcc ttaaacctgg cgttgattat accatcactg tgtatgctgt cactgactat | 240 | ttcaacccgg ctacgcatga atacatctac catgtgactc caatttccat taattaccgc    300 acagaaattg acaaaccatc ccagcaccat caccaccacc ac                       342

<210> SEQ ID NO 410
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 410
atgggagttt ctgatgtgcc gcgcgacctg gaagtggttg ctgccacccc caccagcctg    60
ctgatcagct ggacgctgca ccggaagaac taccaatatt accgcatcac ttacggcgaa    120
acaggaggca atagccctgt ccaggagttc actgtgcctg gtggtgttgt tacagctacc    180
atcagcggcc ttaaacctgg cgttgattat accatcactg tgtatgctgt cactgactat    240 tacaaccccgg caactcatga atacgactac cgaacaactc caatttccat taattaccgc    300
acagaaattg acaaaccatc ccagcaccat caccaccacc ac                       342

<210> SEQ ID NO 411
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 411
atgggagttt ctgatgtgcc gcgcgacctg gaagtggttg ctgccacccc caccagcctt    60
ctgatcagct ggacacaagg cagtactcat taccaatatt accgcatcac ttacggcgaa    120
acaggaggca atagccctgt ccaggagttc actgtgcctg gtatggttta cacagctacc    180
atcagcggcc ttaaacctgg cgttgattat accatcactg tgtatgctgt cactgactat    240
ttcgaccgct ctactcatga gtataaatac cgtacgactc caatttccat taattaccgc    300
acagaaattg acaaaccatc ccagcaccat caccaccacc ac                       342

<210> SEQ ID NO 412
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 412
atgggagttt ctgatgtgcc gcgcgacctg gaagtggttg ctgccacccc caccagcctg    60
ctgatcagct ggcacgaacg tgacggaagt agacaatatt accgcatcac ttacggcgaa    120
acaggaggca atagccctgt ccaggagttc actgtgcctg gtggtgttcg tacagctacc    180
atcagcggcc ttaaacctgg cgttgattat accatcactg tgtatgctgt cactgactat    240
tttaacccga ctacacatga atacatatat cagacaactc caatttccat taattaccgc    300
acagaaattg acaaaccatc ccagcaccat caccaccacc ac                       342

<210> SEQ ID NO 413
<211> LENGTH: 342
<212> TYPE: DNA
<213> ORGANISM: Artificial Sequence
<220> FEATURE:

-continued

<223> OTHER INFORMATION: Description of Artificial Sequence: Synthetic
      polynucleotide

<400> SEQUENCE: 413

```
atgggagttt ctgatgtgcc gcgcgacctg gaagtggttg ctgccacccc caccagcctg    60
ctgatcagct gggactccgg tgaaaacaat taccaatatt accgcatcac ttacggcgaa   120
acaggaggca atagccctgt ccaggagttc actgtgcctg gtggtgttcg tacagctacc   180
atcagcggcc ttaaacctgg cgttgattat accatcactg tgtatgctgt cactgactat   240
tacaacccga agactcatga atataattat cttactattc caatttccat taattaccgc   300
acagaaattg acaaaccatc ccagcaccat caccaccacc ac                      342
```

<210> SEQ ID NO 414
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 414

```
atgggagttt ctgatgtgcc gcgcgacctg gaagtggttg ctgccacccc caccagcctg    60
ctgatcagct gggggagccc cttgatcgag taccaatatt accgcatcac ttacggcgaa   120
acaggaggca atagccctgt ccaggagttc actgtgcctg gtggtctgtc tacagctacc   180
atcagcggcc tcaaacctgg cgttgattat accatcactg tgtatgctgt cactgactat   240
ttcaacccgg ctactcatga atacacatac catgtgagtc caatttccat taattaccgc   300
acagaaattg acaaaccatc ccagcaccat caccaccacc ac                      342
```

<210> SEQ ID NO 415
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 415

```
atgggagttt ctgatgtgcc gcgcgacctg gaagtggttg ctgccacccc caccagcctg    60
ctgatcagct ggtctgcaac aaacaaaact taccaatatt accgcatcac ttacggcgaa   120
acaggaggca atagccctgt ccaggagttc actgtgcctg gtggtgttcg tacagctacc   180
atcagcggcc ttaaacctgg cgttgattat accatcactg tgtatgctgt cactgactat   240
tttaacccga ctacacatga atacatatat cagacaactc caatttccat taattaccgc   300
acagaaattg acaaaccatc ccagcaccat caccaccacc ac                      342
```

<210> SEQ ID NO 416
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 416

```
atgggagttt ctgatgtgcc gcgcgacctg gaagtggttg ctgccacccc caccagcctg    60
ctgatcagct gggatgaccc agctgcaaac cgacaatatt accgcatcac ttacggcgaa   120
acaggaggca atagccctgt ccaggagttc actgtgcctt acgacctgcg tacagctacc   180
```

```
atcagcggcc ttaaacctgg cgttgattat accatcactg tgtatgctgt cactgactat    240
tacaacccgg ctaccatca atacaaatac tctcagagtc caatttccat taattaccgc    300
acagaaattg acaaaccatc ccagcaccat caccaccacc ac                      342
```

<210> SEQ ID NO 417
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 417

```
atgggagttt ctgatgtgcc gcgcgacctg gaagtggttg ctgccacccc caccagcctg    60
ctgatcagct ggtactggga ggggctgccc taccaatatt accgcatcac ttacggcgaa    120
acaggaggca atagccctgt ccaggagttc actgtgcctc gtgacgttaa cacagctacc    180
atcagcggcc ttaaacctgg cgttgattat accatcactg tgtatgctgt cactgactgg    240
tacaaccccg acaccatga gtatatatac catacgattc caatttccat taattaccgc    300
acagaaattg acaaaccatc ccagcaccat caccaccacc ac                      342
```

<210> SEQ ID NO 418
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 418

```
atgggagttt ctgatgtgcc gcgcgacctg gaagtggttg ctgccacccc caccagcctg    60
ctgatcagct ggagcgcgcc gtggcggacc taccaatatt accgcatcac ttacggcgaa    120
acaggaggca atagccctgt ccaggagttc actgtgcctt acgacgtttta cacagctacc    180 atcagcggcc ttaaacctgg cgttgattat accatcactg tgtatgctgt cactgactat    240 ttaaaccccta acacgcttga atacacctac cagcgcattc caatttccat taattaccgc    300
acagaaattg acaaaccatc ccagcaccat caccaccacc ac                      342
```

<210> SEQ ID NO 419
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 419

```
atgggagttt ctgatgtgcc gcgcgacctg gaagtggttg ctgccacccc caccagcctg    60
ctgatcagct ggcaggcggc caaccactcg taccaatatt accgcatcac ttacggcgaa    120
acaggaggca atagccctgt ccaggagttc actgtgcctg gtggtgttcg tacagctacc    180
atcagcggcc ttaaacctgg cgttgattat accatcactg tgtatgctgt cactgacttt    240
ttcaatcctg tcactcatga atacaaatac cgtacaattc caatttccat taattaccgc    300
acagaaattg acaaaccatc ccagcaccat caccaccacc ac                      342
```

<210> SEQ ID NO 420
<211> LENGTH: 342

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 420
atgggagttt ctgatgtgcc gcgcgacctg gaagtggttg ctgccacccc caccagcctg    60
ctgatcagct gggattcagg acgaggttcc tatcaatatt accgcatcac ttacggcgaa   120
acaggaggca atagccctgt ccaggagttc actgtgcctg gtggtgttcg tacagctacc   180
atcagcggcc ttaaacctgg cgttgattat accatcactg tgtatgctgt cactgactat   240
aaaccgcacg ctgacggtcc gcacacttac catgaatatc caatttccat taattaccgc   300
acagaaattg acaaaccatc ccagcaccat caccaccacc ac                      342

<210> SEQ ID NO 421
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 421
atgggagttt ctgatgtgcc gcgcgacctg gaagtggttg ctgccacccc caccagcctg    60
ctgatcagct ggaataacgg aggacgcaat tatcaatatt accgcatcac ttacggcgaa   120
acaggaggca atagccctgt ccaggagttc actgtgcctt acgacgttta cacagctacc   180
atcagcggcc ttaaacctgg cgttgattat accatcactg tgtatgctgt cactgactat   240
aaaccgcacg ctgacggtcc gcacacttac catgaatatc caatttccat taattaccgc   300
acagaaattg acaaaccatc ccagcaccat caccaccacc ac                      342

<210> SEQ ID NO 422
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 422
atgggagttt ctgatgtgcc gcgcgacctg gaagtggttg ctgccacccc caccagcctg    60
ctgatcagct gggtcgtgcc gcaggggatg taccaatatt accgcatcac ttacggcgaa   120
acaggaggca atagccctgt ccaggagttc actgtgcctg gtggtgtttc tacagctacc   180
atcagcggcc ttaaacctgg cgttgattat accatcactg tgtatgctgt cactgactat   240
ttcaacccgg caacccatga atacaattat cattcaattc caatttccat taattaccgc   300
acagaaattg acaaaccatc ccagcaccat caccaccacc ac                      342

<210> SEQ ID NO 423
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 423
atgggagttt ctgatgtgcc gcgcgacctg gaagtggttg ctgccacccc caccagcctg    60
```

```
ctgatcagct gggcgagcaa ccgggggacg taccaatatt accgcatcac ttacggcgaa      120
acaggaggca atagccctgt ccaggagttc actgtgcctg gtggtgtttc tacagctacc      180
atcagcggcc ttaaacctgg cgttgattat accatcactg tgtatgctgt cactgacgct      240
ttcaacccaa ctactcatga atacaattat tttacaactc caatttccat taattaccgc      300
acagaaattg acaaaccatc ccagcaccat caccaccacc ac                         342
```

<210> SEQ ID NO 424
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 424

```
atgggagttt ctgatgtgcc gcgcgacctg gaagtggttg ctgccacccc caccagcctg      60
ctgatcagct ggttgccggg caagctgagg taccaatatt accgcatcac ttacggcgaa     120
acaggaggca atagccctgt ccaggagttc actgtgcctc atgacctgcg tacagctacc     180
atcagcggcc ttaaacctgg cgttgattat accatcactg tgtatgctgt cactgactat     240
aaaccgcatg ctgacggtcc gcatacttac catgaatctc caatttccat taattaccgc     300
acagaaattg acaaaccatc ccagcaccat caccaccacc ac                        342
```

<210> SEQ ID NO 425
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 425

```
atgggagttt ctgatgtgcc gcgcgacctg gaagtggttg ctgccacccc caccagcctg      60
ctgatcagct gggacgctcc aacctcccgc taccaatatt accgcatcac ttacggcgaa     120
acaggaggca atagccctgt ccaggagttc actgtgcctg gtggtgttcg tacagctacc     180
atcagcggcc ttaaacctgg cgttgattat accatcactg tgtatgctgt cactgaccat     240
aaaccgcatg ctgacggtcc gcatacttac catgaatacc caatttccat taattaccgc     300
acagaaattg acaaaccatc ccagcaccat caccaccacc ac                        342
```

<210> SEQ ID NO 426
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 426

```
atgggagttt ctgatgtgcc gcgcgacctg gaagtggttg ctgccacccc caccagcctg      60
ctgatcagct gggacgctcc aacctcccgc taccaatatt accgcatcac ttacggcgaa     120
acaggaggca atagccctgt ccaggagttc actgtgcctg gtggtgttcg tacagctacc     180
atcagcggcc ttaaacctgg cgttgattat accatcactg tgtatgctgt cactgactat     240
aaaccgcacg ctgacggtcc gcacacttac catgaatatc caatttccat taattaccgc     300
acagaaattg acaaaccatc ccagcaccat caccaccacc ac                        342
```

<210> SEQ ID NO 427
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 427

```
atgggagttt ctgatgtgcc gcgcgacctg gaagtggttg ctgccacccc caccagcctg      60
ctgatcagct ggacccctgc taataaatct taccaatatt accgcatcac ttacggcgaa     120
acaggaggca atagccctgt ccaggagttc actgtgcctc atgacctggt tacagctacc     180
atcagcggcc ttaaacctgg cgttgattat accatcactg tgtatgctgt cactgaccat     240
aaaccgcatg ctgacggtcc gcatacttac catgaatacc caatttccat taattaccgc     300
acagaaattg acaaaccatc ccagcaccat caccaccacc ac                        342
```

<210> SEQ ID NO 428
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 428

```
atgggagttt ctgatgtgcc gcgcgacctg gaagtggttg ctgccacccc caccagcctg      60
ctgatcagct gggacgctcc ggctgttact taccagtatt accgcatcac ttacggcgaa     120
acaggaggca atagccctgt ccaggagttc actgtgcctc atgacctggt tacagctacc     180
atcagcggcc ttaaacctgg cgttgattat accatcactg tgtatgctgt cactgactat     240
aaaccgcatg ctgacggtcc gcatacttac catgaatctc caatttccat taattaccgc     300
acagaaattg acaaaccatc ccagcaccat caccaccacc ac                        342
```

<210> SEQ ID NO 429
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 429

```
atgggagttt ctgatgtgcc gcgcgacctg gaagtggttg ctgccacccc caccagcctg      60
ctgatcagct ggacccctgc taataaatct taccaatatt accgcatcac ttacggcgaa     120
acaggaggca atagccctgt ccaggagttc actgtgcctc atgacctggt tacagctacc     180
atcagcggcc ttaaacctgg cgttgattat accatcactg tgtatgctgt cactgaccat     240
aaaccgcatg ctgacggtcc gcatacttac catgaatctc caatttccat taattaccgc     300
acagaaattg acaaaccatc ccagcaccat caccaccacc ac                        342
```

<210> SEQ ID NO 430
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 430

```
atgggagttt ctgatgtgcc gcgcgacctg gaagtggttg ctgccacccc caccagcctg      60
ctgatcagct ggaccoctgc taataaatct taccaatatt accgcatcac ttacggcgaa     120
acaggaggca atagccctgt ccaggagttc actgtgcctg gtggtgttcg tacagctacc     180
atcagcggcc ttaaacctgg cgttgattat accatcactg tgtatgctgt cactaacatg     240
atgcatgttg aatactctga atacccaatt tccattaatt accgcacaga aattgacaaa     300
ccatcccagc accatcacca ccaccac                                         327
```

<210> SEQ ID NO 431
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 431

```
atgggagttt ctgatgtgcc gcgcgacctg gaagtggttg ctgccacccc caccagcctg      60
ctgatcagct gggacgctgg tgctgttact taccagtatt accgcatcac ttacggcgaa     120
acaggaggca atagccctgt ccaggagttc actgtgcctc atgacctggt tacagctacc     180
atcagcggcc ttaaacctgg cgttgattat accatcactg tgtatgctgt cactgaccat     240
aaaccgcatg ctgacggtcc gcatacttac catgaatacc caatttccat taattaccgc     300
acagaaattg acaaaccatc ccagcaccat caccaccacc ac                        342
```

<210> SEQ ID NO 432
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 432

```
atgggagttt ctgatgtgcc gcgcgacctg gaagtggttg ctgccacccc caccagcctg      60
ctgatcagct gggacgctcc aacctcccgc taccaatatt accgcatcac ttacggcgaa     120
acaggaggca atagccctgt ccaggagttc actgtgcctg gtggtctgtc cacagctacc     180
atcagcggcc ttaaacctgg cgttgattat accatcactg tgtatgctgt cactgactat     240
aaaccgcatg ctgacggtcc gcatacttac catgaatctc caatttccat taattaccgc     300
acagaaattg acaaaccatc ccagcaccat caccaccacc ac                        342
```

<210> SEQ ID NO 433
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 433

```
atgggagttt ctgatgtgcc gcgcgacctg gaagtggttg ctgccacccc caccagcctg      60
ctgatcagct gggacgctcc ggctgttact taccagtatt accgcatcac ttacggcgaa     120
acaggaggca atagccctgt ccaggagttc actgtgcctt acgacgttta cacagctacc     180
atcagcggcc ttaaacctgg cgttgattat accatcactg tgtatgctgt cactgactat     240
aaaccgcacg ctgacggtcc gcacacttac catgaatatc caatttccat taattaccgc     300
```
acagaaattg acaaaccatc ccagcaccat caccaccacc ac            342

<210> SEQ ID NO 434
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 434
atgggagttt ctgatgtgcc gcgcgacctg gaagtggttg ctgccacccc caccagcctg    60
ctgatcagct gggattcagg acgaggttcc tatcaatatt accgcatcac ttacggcgaa   120
acaggaggca atagccctgt ccaggagttc actgtgcctt acgacgttta cacagctacc   180
atcagcggcc ttaaacctgg cgttgattat accatcactg tgtatgctgt cactgacatg   240
atgcatgttg aatacactga acatccaatt tccattaatt accgcacaga aattgacaaa   300
ccatcccagc accatcacca ccaccac                                       327

<210> SEQ ID NO 435
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 435
atgggagttt ctgatgtgcc gcgcgacctg gaagtggttg ctgccacccc caccagcctg    60
ctgatcagct gggacgctcc ggctgttact taccagtatt accgcatcac ttacggcgaa   120
acaggaggca atagccctgt ccaggagttc actgtgcctg gtggtgttcg tacagctacc   180
atcagcggcc ttaaacctgg cgttgattat accatcactg tgtatgctgt cactgactat   240
aaaccgcatg ctgacggtcc gcatacttac catgaatctc caatttccat taattaccgc   300
acagaaattg acaaaccatc ccagcaccat caccaccacc ac                      342

<210> SEQ ID NO 436
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 436
atgggagttt ctgatgtgcc gcgcgacctg gaagtggttg ctgccacccc caccagcctg    60
ctgatcagct gggacgctcc aacctcccgc taccaatatt accgcatcac ttacggcgaa   120
acaggaggca atagccctgt ccaggagttc actgtgcctc atgacctggt tacagctacc   180
atcagcggcc ttaaacctgg cgttgattat accatcactg tgtatgctgt cactgactat   240
aaaccgcatg ctgacggtcc gcatacttac catgaatctc caatttccat taattaccgc   300
acagaaattg acaaaccatc ccagcaccat caccaccacc ac                      342

<210> SEQ ID NO 437
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 437

| atgggagttt | ctgatgtgcc | gcgcgacctg | gaagtggttg | ctgccacccc | caccagcctg | 60 |
| ctgatcagct | gggacgctgg | tgctgttact | taccagtatt | accgcatcac | ttacggcgaa | 120 |
| acaggaggca | atagccctgt | ccaggagttc | actgtgcctg | gtggtgttcg | tacagctacc | 180 |
| atcagcggcc | ttaaacctgg | cgttgattat | accatcactg | tgtatgctgt | cactgactat | 240 |
| aaaccgcatg | ctgacggtcc | gcatacttac | catgaatctc | caatttccat | taattaccgc | 300 |
| acagaaattg | acaaaccatc | ccagcaccat | caccaccacc | ac | | 342 |

<210> SEQ ID NO 438
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 438

| atgggagttt | ctgatgtgcc | gcgcgacctg | gaagtggttg | ctgccacccc | caccagcctg | 60 |
| ctgatcagct | gggacgctcc | aacctcccgc | taccaatatt | accgcatcac | ttacggcgaa | 120 |
| acaggaggca | atagccctgt | ccaggagttc | actgtgcctc | atgacctggt | tacagctacc | 180 |
| atcagcggcc | ttaaacctgg | cgttgattat | accatcactg | tgtatgctgt | cactaacatg | 240 |
| atgcatgttg | aatactctga | atacccaatt | tccattaatt | accgcacaga | aattgacaaa | 300 |
| ccatcccagc | accatcacca | ccaccac | | | | 327 |

<210> SEQ ID NO 439
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 439

| atgggagttt | ctgatgtgcc | gcgcgacctg | gaagtggttg | ctgccacccc | caccagcctg | 60 |
| ctgatcagct | gggacgctgg | tgctgttact | taccagtatt | accgcatcac | ttacggcgaa | 120 |
| acaggaggca | atagccctgt | ccaggagttc | actgtgcctg | gtggtgttcg | tacagctacc | 180 |
| atcagcggcc | ttaaacctgg | cgttgattat | accatcactg | tgtatgctgt | cactgactat | 240 |
| aaaccgcacg | ctgacggtcc | gcacacttac | catgaatatc | caatttccat | taattaccgc | 300 |
| acagaaattg | acaaaccatc | ccagcaccat | caccaccacc | ac | | 342 |

<210> SEQ ID NO 440
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 440

| atgggagttt | ctgatgtgcc | gcgcgacctg | gaagtggttg | ctgccacccc | caccagcctg | 60 |
| ctgatcagct | ggtatcctgg | ccaaccaaca | tatcaatatt | accgcatcac | ttacggcgaa | 120 |
| acaggaggca | atagccctgt | ccaggagttc | attgtgcctt | acctggttta | cacagctacc | 180 | atcagcggcc ttaaacctgg cgttgattat accatcactg tgtatgctgt cactgactac    240 gcttacaaag aatactctga atacccaatt tccattaatt accgcacaga aattgacaaa    300 ccatcccagc accatcacca ccaccac                                        327

<210> SEQ ID NO 441
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 441
atgggagttt ctgatgtgcc gcgcgacctg gaagtggttg ctgccacccc caccagcctg    60
ctgatcagct ggcaaagttc aaccagccaa tatcaatatt accgcatcac ttacggcgaa    120
acaggaggca atagccctgt ccaggagttc actgtgcctg gtggtgttcg tacagctacc    180
atcagcggcc ttaaacctgg cgttgattat accatcactg tgtatgctgt cactgaccat    240
aaaccgcatg ctgacggtcc gcatacttac catgaatctc caatttccat taattaccgc    300
acagaaattg acaaaccatc ccagcaccat caccaccacc ac                       342

<210> SEQ ID NO 442
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 442
atgggagttt ctgatgtgcc gcgcgacctg gaagtggttg ctgccacccc caccagcctg    60
ctgatcagct ggttgccggg caagctgagg taccaatatt accgcatcac ttacggcgaa    120
acaggaggca atagccctgt ccaggagttc actgtgcctc atgacctgcg tacagctacc    180
atcagcggcc ttaaacctgg cgttgattat accatcactg tgtatgctgt cactaacatg    240
atgcatgttg aatactctga atacccaatt tccattaatt accgcacaga aattgacaaa    300
ggtagcggct ctggttccgg cagcggctcc ggcagcggct ctggcagcgg ttctggttcc    360
gtttctgatg tgccgcgcga cctggaagtg gttgctgcca cccccaccag cctgctgatc    420
agctggtctg cgcgtctgaa agttgcgcga tattaccgca tcacttacgg cgaaacagga    480
ggcaatagcc ctgtccagga gttcactgtg cctaaaaacg tttacacagc taccatcagc    540
ggccttaaac ctggcgttga ttataccatc actgtgtatg ctgtcactag gttccgcgac    600
taccagccaa tttccattaa ttaccgcaca gaaattgaca aaccatgcca gcaccaccac    660
caccaccac                                                            669

<210> SEQ ID NO 443
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 443
atgggagttt ctgatgtgcc gcgcgacctg gaagtggttg ctgccacccc caccagcctg    60
ctgatcagct ggtctgcgcg tctgaaagtt gcgcgatatt accgcatcac ttacggcgaa    120

| | |
|---|---|
| acaggaggca atagccctgt ccaggagttc actgtgccta aaaacgttta cacagctacc | 180 |
| atcagcggcc ttaaacctgg cgttgattat accatcactg tgtatgctgt cactaggttc | 240 |
| cgcgactacc agccaatttc cattaattac cgcacagaaa ttgacaaagg tagcggctct | 300 |
| ggttccggca gcggctccgg cagcggctct ggcagcggtt ctggttccgt ttctgatgtg | 360 |
| ccgcgcgacc tggaagtggt tgctgccacc cccaccagcc tgctgatcag ctggttgccg | 420 |
| ggcaagctga ggtaccaata ttaccgcatc acttacggcg aaacaggagg caatagccct | 480 |
| gtccaggagt tcactgtgcc tcatgacctg cgtacagcta ccatcagcgg ccttaaacct | 540 |
| ggcgttgatt ataccatcac tgtgtatgct gtcactaaca tgatgcatgt tgaatactct | 600 |
| gaatacccaa tttccattaa ttaccgcaca gaaattgaca aaccatgcca gcaccaccac | 660 |
| caccaccac | 669 |

<210> SEQ ID NO 444
<211> LENGTH: 669
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 444

| | |
|---|---|
| atgggagttt ctgatgtgcc gcgcgacctg gaagtggttg ctgccacccc caccagcctg | 60 |
| ctgatcagct gggtggccgg ggcggaggac taccaatatt accgcatcac ttacggcgaa | 120 |
| acaggaggca atagccctgt ccaggagttc actgtgcctc atgacctggt tacagctacc | 180 |
| atcagcggcc ttaaacctgg cgttgattat accatcactg tgtatgctgt cactgacatg | 240 |
| atgcatgttg aatacactga acatccaatt tccattaatt accgcacaga aattgacaaa | 300 |
| ggtagcggct ctggttccgg cagcggctcc ggcagcggct ctggcagcgg ttctggttcc | 360 |
| gtttctgatg tgccgcgcga cctggaagtg gttgctgcca ccccaccag cctgctgatc | 420 |
| agctggtctg cgcgtctgaa agttgcgcga tattaccgca tcacttacgg cgaaacagga | 480 |
| ggcaatagcc ctgtccagga gttcactgtg cctaaaaacg tttacacagc taccatcagc | 540 |
| ggccttaaac ctggcgttga ttataccatc actgtgtatg ctgtcactag gttccgcgac | 600 |
| taccagccaa tttccattaa ttaccgcaca gaaattgaca aaccatgcca gcaccaccac | 660 |
| caccaccac | 669 |

<210> SEQ ID NO 445
<211> LENGTH: 669
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 445

| | |
|---|---|
| atgggagttt ctgatgtgcc gcgcgacctg gaagtggttg ctgccacccc caccagcctg | 60 |
| ctgatcagct ggtctgcgcg tctgaaagtt gcgcgatatt accgcatcac ttacggcgaa | 120 |
| acaggaggca atagccctgt ccaggagttc actgtgccta aaaacgttta cacagctacc | 180 |
| atcagcggcc ttaaacctgg cgttgattat accatcactg tgtatgctgt cactaggttc | 240 |
| cgcgactacc agccaatttc cattaattac cgcacagaaa ttgacaaagg tagcggctct | 300 |
| ggttccggca gcggctccgg cagcggctct ggcagcggtt ctggttccgt ttctgatgtg | 360 |
| ccgcgcgacc tggaagtggt tgctgccacc cccaccagcc tgctgatcag ctgggtggcc | 420 |

```
ggggcggagg actaccaata ttaccgcatc acttacggcg aaacaggagg caatagccct      480
gtccaggagt tcactgtgcc tcatgacctg gttacagcta ccatcagcgg ccttaaacct      540
ggcgttgatt ataccatcac tgtgtatgct gtcactgaca tgatgcatgt tgaatacact      600
gaacatccaa tttccattaa ttaccgcaca gaaattgaca aaccatgcca gcaccaccac      660
caccaccac                                                              669
```

<210> SEQ ID NO 446
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 446

```
atgggagttt ctgatgtgcc gcgcgacctg gaagtggttg ctgccacccc caccagcctg      60
ctgatcagct gggattcagg acgaggttcc tatcaatatt accgcatcac ttacggcgaa     120
acaggaggca atagccctgt ccaggagttc actgtgcctg gtccggttca tacagctacc     180
atcagcggcc ttaaacctgg cgttgattat accatcactg tgtatgctgt cactgaccat     240
aaaccgcatg ctgacggtcc gcatacttac catgaatctc caatttccat taattaccgc     300
acagaaattg acaaaggtag cggctctggt tccggcagcg gctccggcag cggtctggc     360 agcggttctg gttccgtttc tgatgtgccg cgcgacctgg aagtggttgc tgccacccc      420 accagcctgc tgatcagctg gtctgcgcgt ctgaaagttg cgcgatatta ccgcatcact     480
tacggcgaaa caggaggcaa tagccctgtc caggagttca ctgtgcctaa aaacgtttac     540
acagctacca tcagcggcct taaacctggc gttgattata ccatcactgt gtatgctgtc     600
actaggttcc gcgactacca gccaatttcc attaattacc gcacagaaat tgacaaacca     660
tgccagcacc accaccacca ccac                                            684
```

<210> SEQ ID NO 447
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 447

```
atgggagttt ctgatgtgcc gcgcgacctg gaagtggttg ctgccacccc caccagcctg      60
ctgatcagct ggtctgcgcg tctgaaagtt gcgcgatatt accgcatcac ttacggcgaa     120
acaggaggca atagccctgt ccaggagttc actgtgccta aaaacgttta cacagctacc     180
atcagcggcc ttaaacctgg cgttgattat accatcactg tgtatgctgt cactaggttc     240
cgcgactacc agccaatttc cattaattac cgcacagaaa ttgacaaagg tagcggctct     300
ggttccggca gcggctccgg cagcggtctc ggcagcggtt ctggttccgt ttctgatgtg     360
ccgcgcgacc tggaagtggt tgctgccacc cccaccagcc tgctgatcag ctgggattca     420
ggacgaggtt cctatcaata ttaccgcatc acttacggcg aaacaggagg caatagccct     480
gtccaggagt tcactgtgcc tggtccggtt catacagcta ccatcagcgg ccttaaacct     540
ggcgttgatt ataccatcac tgtgtatgct gtcactgacc ataaaccgca tgctgacggt     600
ccgcatactt accatgaatc tccaatttcc attaattacc gcacagaaat tgacaaacca     660
```

```
tgccagcacc accaccacca ccac                                          684

<210> SEQ ID NO 448
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 448
atgggtgttt ctgatgttcc gcgtgatctg gaggttgttg cagcaacccc gaccagcctg     60
ctgatttctt ggtgggcacc ggttgatcgt tatcagtatt atcgcatcac ctatggtgaa    120
accggtggta attctccggt tcaggaattt accgttcctc gcgacgttta taccgcaacc    180
attagcggtc tgaaaccggg tgttgattac accattaccg tttacgccgt taccgattat    240
aaaccgcatg cagatggtcc gcataccttat catgaaagcc cgattagcat taactatcgc    300
accgaaattg ataaaggtag cggtagcggt tcaggtagcg gatcaggttc tggttctggt    360
agtggtagcg gcagcgtttc agatgtgcct cgcgacctgg aagtggtggc agccacaccg    420
acttctctgc tgattagctg gtctgcacgt ctgaaagttg cccgttatta ccgtattact    480
tatggcgaaa caggcggaaa tagccctgtg caagaattta ccgtgccgaa aaatgtgtac    540
acagccacca tctctggcct gaaacctggc gtggactaca caatcacagt ttatgcagtg    600
acccgttttc gtgattatca gccgatcagc atcaattatc gtacagagat cgataaaccg    660
tgccagcatc accaccatca tcac                                          684

<210> SEQ ID NO 449
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 449
atgggtgttt ctgatgttcc gcgtgatctg gaggttgttg cagcaacccc gaccagcctg     60
ctgatttctt ggacccaggg tagcacacat tatcagtatt atcgcatcac ctatggtgaa    120
accggtggta attctccggt tcaggaattt accgttcctg gtatggttta taccgcaacc    180
attagcggtc tgaaaccggg tgttgattac accattaccg tttacgccgt taccgattat    240
ttcgatcggt ccacccatga atataaatat cggaccaccc cgattagcat taactatcgc    300
accgaaattg ataaaggtag cggtagcggt tcaggtagcg gatcaggttc tggttctggt    360
agtggtagcg gcagcgtttc agatgtgcct cgcgacctgg aagtggtggc agccacaccg    420
acttctctgc tgattagctg gtctgcacgt ctgaaagttg cccgttatta ccgtattact    480
tatggcgaaa caggcggaaa tagccctgtg caagaattta ccgtgccgaa aaatgtgtac    540
acagccacca tctctggcct gaaacctggc gtggactaca caatcacagt ttatgcagtg    600
acccgttttc gtgattatca gccgatcagc atcaattatc gtacagagat cgataaaccg    660
tgccagcatc accaccatca tcac                                          684

<210> SEQ ID NO 450
<211> LENGTH: 684
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 450

| | | |
|---|---|---|
| atgggtgttt ctgatgttcc gcgtgatctg gaggttgttg cagcaacccc gaccagcctg | 60 |
| ctgatttctt ggcatgaacg tgatggtagc cgtcagtatt atcgcatcac ctatggtgaa | 120 |
| accggtggta attctccggt tcaggaattt accgttcctg gcggtgttcg taccgcaacc | 180 |
| attagcggtc tgaaaccggg tgttgattac accattaccg tttacgccgt taccgattat | 240 |
| ttcaatccga ccacccatga atatatttat cagaccaccc cgattagcat taactatcgc | 300 |
| accgaaattg ataaaggtag cggtagcggt tcaggtagcg gatcaggttc tggttctggt | 360 |
| agtggtagcg gcagcgtttc agatgtgcct cgcgacctgg aagtggtggc agccacaccg | 420 |
| acttctctgc tgattagctg gtctgcacgt ctgaaagttg cccgttatta ccgtattact | 480 |
| tatggcgaaa caggcggaaa tagccctgtg caagaattta ccgtgccgaa aaatgtgtac | 540 |
| acagccacca tctctggcct gaaacctggc gtggactaca caatcacagt ttatgcagtg | 600 |
| acccgttttc gtgattatca gccgatcagc atcaattatc gtacagagat cgataaaccg | 660 |
| tgccagcatc accaccatca tcac | 684 |

<210> SEQ ID NO 451
<211> LENGTH: 684
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 451

| | | |
|---|---|---|
| atgggtgttt ctgatgttcc gcgtgatctg gaggttgttg cagcaacccc gaccagcctg | 60 |
| ctgatttctt ggtattggga aggtctgccg tatcagtatt atcgcatcac ctatggtgaa | 120 |
| accggtggta attctccggt tcaggaattc accgttcctc gcgacgttaa taccgcaacc | 180 |
| attagcggtc tgaaaccggg tgttgattac accattaccg tttacgccgt taccgattgg | 240 |
| tacaaccctg atacccatga atatatttat cataccattc cgattagcat taactatcgc | 300 |
| accgaaattg ataaaggtag cggtagcggt tcaggtagcg gatcaggttc tggttctggt | 360 |
| agtggtagcg gcagcgtttc agatgtgcct cgcgacctgg aagtggtggc agccacaccg | 420 |
| acttctctgc tgattagctg gtctgcacgt ctgaaagttg cccgttatta ccgtattact | 480 |
| tatggcgaaa caggcggaaa tagccctgtg caagaattta ccgtgccgaa aaatgtgtac | 540 |
| acagccacca tctctggcct gaaacctggc gtggactaca caatcacagt ttatgcagtg | 600 |
| acccgttttc gtgattatca gccgatcagc atcaattatc gtacagagat cgataaaccg | 660 |
| tgccagcatc accaccatca tcac | 684 |

<210> SEQ ID NO 452
<211> LENGTH: 684
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 452

| | | |
|---|---|---|
| atgggtgttt ctgatgttcc gcgtgatctg gaggttgttg cagcaacccc gaccagcctg | 60 |
| ctgatttctt gggcaagcaa tcgtggcacc tatcagtatt atcgcatcac ctatggtgaa | 120 |
| accggtggta attctccggt tcaggaattt accgttcctg gcggtgtttc taccgcaacc | 180 |

```
attagcggtc tgaaaccggg tgttgattac accattaccg tttacgccgt taccgatgca    240
tttaatccga ccacccatga atataattat tttaccaccc cgattagcat taactatcgc    300
accgaaattg ataaaggtag cggtagcggt tcaggtagcg gatcaggttc tggttctggt    360
agtggtagcg gcagcgtttc agatgtgcct cgcgacctgg aagtggtggc agccacaccg    420
acttctctgc tgattagctg gtctgcacgt ctgaaagttg cccgttatta ccgtattact    480
tatggcgaaa caggcggaaa tagccctgtg caagaattta ccgtgccgaa aaatgtgtac    540
acagccacca tctctggcct gaaacctggc gtggactaca caatcacagt ttatgcagtg    600
acccgttttc gtgattatca gccgatcagc atcaattatc gtacagagat cgataaaccg    660
tgccagcatc accaccatca tcac                                           684
```

<210> SEQ ID NO 453
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 453

```
atgggtgttt ctgatgttcc gcgtgatctg gaggttgttg cagcaacccc gaccagcctg     60
ctgatttctt gggatgcacc gacctctcgt tatcagtatt atcgcatcac ctatggtgaa    120
accggtggta attctccggt tcaggaattt accgttcctg gcggtctgag caccgcaacc    180
attagcggtc tgaaaccggg tgttgattac accattaccg tttacgccgt taccgattat    240
aaaccgcatg cagatggtcc gcataccctat catgaaagcc cgattagcat taactatcgc    300
accgaaattg ataaaggtag cggtagcggt tcaggtagcg gatcaggttc tggttctggt    360
agtggtagcg gcagcgtttc agatgtgcct cgcgacctgg aagtggtggc agccacaccg    420
acttctctgc tgattagctg gtctgcacgt ctgaaagttg cccgttatta ccgtattact    480
tatggcgaaa caggcggaaa tagccctgtg caagaattta ccgtgccgaa aaatgtgtac    540
acagccacca tctctggcct gaaacctggc gtggactaca caatcacagt ttatgcagtg    600
acccgttttc gtgattatca gccgatcagc atcaattatc gtacagagat cgataaaccg    660
tgccagcatc accaccatca tcac                                           684
```

<210> SEQ ID NO 454
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 454

```
atgggtgttt ctgatgttcc gcgtgatctg gaggttgttg cagcaacccc gaccagcctg     60
ctgatttctt gggatgcagg tgcagttacc tatcagtatt atcgcatcac ctatggtgaa    120
accggtggta attctccggt tcaggaattt accgttcctg gcggtgttcg taccgcaacc    180
attagcggtc tgaaaccggg tgttgattac accattaccg tttacgccgt taccgattat    240
aaaccgcatg cagatggtcc gcataccctat catgaatatc cgattagcat taactatcgc    300
accgaaattg ataaaggtag cggtagcggt tcaggtagcg gatcaggttc tggttctggt    360
agtggtagcg gcagcgtttc agatgtgcct cgcgacctgg aagtggtggc agccacaccg    420
```

-continued

| | |
|---|---|
| acttctctgc tgattagctg gtctgcacgt ctgaaagttg cccgttatta ccgtattact | 480 |
| tatggcgaaa caggcggaaa tagccctgtg caagaattta ccgtgccgaa aaatgtgtac | 540 |
| acagccacca tctctggcct gaaacctggc gtggactaca caatcacagt ttatgcagtg | 600 |
| acccgttttc gtgattatca gccgatcagc atcaattatc gtacagagat cgataaaccg | 660 |
| tgccagcatc accaccatca tcac | 684 |

<210> SEQ ID NO 455
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 455

| | |
|---|---|
| atgggtgttt ctgatgttcc gcgtgatctg gaagttgttg cagcaacccc gaccagcctg | 60 |
| ctgattagct ggtctgcacg tctgaaagtt gcccgttatt atcgcattac ctatggtgaa | 120 |
| accggtggta attctccggt tcaggaattt accgttccga aaatgtttta taccgcaacc | 180 |
| attagcggtc tgaaaccggg tgttgattac accattaccg tttatgcagt tacccgtttt | 240 |
| cgtgattatc agccgattag cattaactat cgcaccgaaa ttgataaagg tagcggtagc | 300 |
| ggttctggta gcggttcagg ttctggttct ggtagtggta gcggcagcgt ttcagacgtg | 360 |
| cctcgtgatt tagaagtggt ggcagccaca ccgacctcac tgctgatttc ttggtgggca | 420 |
| ccggttgatc gttatcagta ttatcgcatc acatacggcg aaacaggcgg aaatagccct | 480 |
| gtgcaagaat tcaccgtacc gcgtgatgtg tataccgcca caatttctgg tttaaaacct | 540 |
| ggcgtggact acacaatcac agtttatgcc gtgaccgatt ataaaccgca tgcagatggt | 600 |
| ccgcatacct atcatgaaag cccgatctct atcaattatc gcacagagat cgataaaccg | 660 |
| tgtcagcatc accaccatca tcac | 684 |

<210> SEQ ID NO 456
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 456

| | |
|---|---|
| atgggtgttt ctgatgttcc gcgtgatctg gaagttgttg cagcaacccc gaccagcctg | 60 |
| ctgattagct ggtctgcacg tctgaaagtt gcccgttatt atcgcattac ctatggtgaa | 120 |
| accggtggta attctccggt tcaggaattt accgttccga aaatgtttta taccgcaacc | 180 |
| attagcggtc tgaaaccggg tgttgattac accattaccg tttatgcagt tacccgtttt | 240 |
| cgtgattatc agccgattag cattaactat cgcaccgaaa ttgataaagg tagcggtagc | 300 |
| ggttctggta gcggttcagg ttctggttct ggtagtggta gcggcagcgt ttcagacgtg | 360 |
| cctcgtgatt tagaagtggt ggcagccaca ccgacctcac tgctgatttc ttggacccag | 420 |
| ggtagcacac attatcagta ttatcgcatc acatacggcg aaacaggcgg aaatagccct | 480 |
| gtgcaagaat tcaccgtacc gggtatggtg tataccgcca caatttctgg tttaaaacct | 540 |
| ggcgtggact acacaatcac agtttatgcc gtgaccgatt atttcgatcg cagcacccat | 600 |
| gaatataaat atcgtaccac cccgatctct atcaattatc gcacagagat cgataaaccg | 660 |
| tgtcagcatc accaccatca tcac | 684 |

<210> SEQ ID NO 457
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 457

```
atgggtgttt ctgatgttcc gcgtgatctg gaagttgttg cagcaacccc gaccagcctg      60
ctgattagct ggtctgcacg tctgaaagtt gcccgttatt atcgcattac ctatggtgaa     120
accggtggta attctccggt tcaggaattt accgttccga aaaatgttta taccgcaacc     180
attagcggtc tgaaaccggg tgttgattac accattaccg tttatgcagt tacccgtttt     240
cgtgattatc agccgattag cattaactat cgcaccgaaa ttgataaagg tagcggtagc     300
ggttctggta gcggttcagg ttctggttct ggtagtggta gcggcagcgt ttcagacgtg     360
cctcgtgatt tagaagtggt ggcagccaca ccgacctcac tgctgatttc ttggcatgaa     420
cgtgatggta gccgtcagta ttatcgcatc acatacggcg aaacaggcgg aaatagccct     480
gtgcaagaat tcaccgtacc gggtggtgtt cgtaccgcca caatttctgg tttaaaacct     540
ggcgtggact acacaatcac agtttatgcc gtgaccgatt atttcaatcc gaccacccac     600
gaatatattt atcagaccac cccgatctct atcaattatc gcacagagat cgataaaccg     660
tgtcagcatc accaccatca tcac                                            684
```

<210> SEQ ID NO 458
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 458

```
atgggtgttt ctgatgttcc gcgtgatctg gaagttgttg cagcaacccc gaccagcctg      60
ctgattagct ggtctgcacg tctgaaagtt gcccgttatt atcgcattac ctatggtgaa     120
accggtggta attctccggt tcaggaattt accgttccga aaaatgttta taccgcaacc     180
attagcggtc tgaaaccggg tgttgattac accattaccg tttatgcagt tacccgtttt     240
cgtgattatc agccgattag cattaactat cgcaccgaaa ttgataaagg tagcggtagc     300
ggttctggta gcggttcagg ttctggttct ggtagtggta gcggcagcgt ttcagacgtg     360
cctcgtgatt tagaagtggt ggcagccaca ccgacctcac tgctgatttc ttgggatgca     420
ccgaccagcc gttatcagta ttatcgcatc acatacggcg aaacaggcgg aaatagccct     480
gtgcaagaat tcaccgtacc gggtggtctg agcaccgcca caatttctgg tttaaaacct     540
ggcgtggact acacaatcac agtttatgcc gtgaccgatt ataaaccgca tgcagatggt     600
ccgcatacct atcatgaaag cccgatctct atcaattatc gcacagagat cgataaaccg     660
tgtcagcatc accaccatca tcac                                            684
```

<210> SEQ ID NO 459
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 459

```
atgggtgttt ctgatgttcc gcgtgatctg gaagttgttg cagcaacccc gaccagcctg      60
ctgattagct ggtctgcacg tctgaaagtt gcccgttatt atcgcattac ctatggtgaa     120
accggtggta attctccggt tcaggaattt accgttccga aaaatgttta taccgcaacc     180
attagcggtc tgaaaccggg tgttgattac accattaccg tttatgcagt tacccgtttt     240
cgtgattatc agccgattag cattaactat cgcaccgaaa ttgataaagg tagcggtagc     300
ggttctggta gcggttcagg ttctggttct ggtagtggta gcggcagcgt ttcagacgtg     360
cctcgtgatt tagaagtggt ggcagccaca ccgacctcac tgctgatttc ttgggatgcc     420
ggtgcagtta cctatcagta ttatcgcatc acatacggcg aaacaggcgg aaatagccct     480
gtgcaagaat tcaccgtacc gggtggtgtt cgtaccgcca caatttctgg tttaaaacct     540
ggcgtggact acacaatcac agtttatgcc gtgaccgatt ataaaccgca tgcagatggt     600
ccgcatacct atcatgaata tccgatctct atcaattatc gcacagagat cgataaaccg     660
tgtcagcatc accaccatca tcac                                            684
```

<210> SEQ ID NO 460
<211> LENGTH: 666
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 460

```
atgggcgtga gtgatgttcc gcgtgatctg gaagtggttg cagcaacccc gacgagcctg      60
ctgattagct ggtctgcccg cctgaaagtg gcacgttatt accgcatcac ctacggcgaa     120
acgggcggta actctccggt tcaggaattt accgtgccga aaaatgttta taccgcaacg     180
attagcggcc tgaaaccggg tgtggattat accatcacgg tgtacgcggt tacccgtttc     240
cgcgattacc agccgattag catcaactat cgtacggaaa ttgaaaaagg ctctggttgc     300
ggcagtggta gcggctctgg tagtggcagc ggttctggca gtggtagcgt gtctgacgtc     360
ccgcgcgacc tggaagttgt tgcagcgacc ccgaccagcc tgctgattag ttggtgggcc     420
ccggtggatc gttaccagta ttaccgcatc acctatggcg aaaccggtgg taacagcccg     480
gtgcaagaat ttaccgtgcc gcgtgatgtt tataccgcga ccatctctgg tctgaaaccg     540
ggcgttgact acacgattac cgtttacgcg gttaccgatt ataaaccgca tgccgatggt     600
ccgcatacgt accacgaaag tccgattagc atcaattatc ggaccgaaca tcaccatcac     660
catcac                                                                666
```

<210> SEQ ID NO 461
<211> LENGTH: 678
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 461

```
atgggcgtgt ctgatgttcc gcgtgatctg gaagtggttg cggccacccc gacgagtctg      60
ctgattagct ggtctgcccg cctgaaagtg gcacgttatt accgcatcac ctacggcgaa     120
acgggcggta acagcccggt tcaggaattt accgtgccga aaaatgttta taccgcaacg     180
```

```
atttctggcc tgaaaccggg tgtggattat accatcacgg tgtacgcggt tacccgtttc    240
cgcgattacc agccgattag catcaactat cgtacggaaa ttgaaaaagg cagtggtagc    300
ggctctggta gtggcagcgg ttctggcagt ggtagcggct ctggtagtgt aagcgacgtc    360
ccgcgcgatc tggaagtggt tgcagcgacc ccgacgagcc tgctgatttc ttggtgggcc    420
ccggtggatc gttaccagta ttaccgcatc acctatggcg aaaccggtgg caattctccg    480
gtgcaagaat tcaccgtgcc gcgtgatgtt tataccgcga cgattagcgg tctgaaaccg    540
ggcgttgact acacgattac cgtgtacgcg gttaccgatt ataaaccgca tgccgatggt    600
ccgcatacgt accacgaatc tccgattagt atcaattatc ggaccgaagg cagtggttgc    660
catcaccatc accatcac                                                  678
```

<210> SEQ ID NO 462
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 462

```
atgggcgtga gtgatgttcc gcgtgatctg gaagtggttg cagcaacccc gacgagcctg     60
ctgattagct ggtctgcccg cctgaaagtg gcacgttatt accgcatcac ctacggcgaa    120
acgggcggta acagcccggt tcaggaattt accgtgccga aaaatgttta taccgcaacg    180
atttgcggcc tgaaaccggg tgtggattat accatcacgg tgtacgcggt tacccgtttc    240
cgcgattacc agccgattag catcaactat cgtacggaaa ttgaaaaagg cagtggtagc    300
ggctctggta gtggcagcgg ttctggcagt ggtagcggct ctggtagtgt aagcgacgtc    360
ccgcgcgacc tggaagttgt tgcagcgacg ccgacgagcc tgctgatctc ttggtgggcc    420
ccggtggatc gttaccagta ttaccgcatc acctatggcg aaaccggtgg taactctccg    480
gtgcaagaat ttaccgtgcc gcgtgatgtt tataccgcga cgatttctgg tctgaaaccg    540
ggcgttgact acacgattac cgtttacgcg gttaccgatt ataaaccgca tgccgatggt    600
ccgcatacgt accacgaatc tccgattagt atcaattatc ggaccgaaca tcaccatcac    660
catcac                                                                666
```

<210> SEQ ID NO 463
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 463

```
atgggcgtga gtgatgttcc gcgtgatctg gaagtggttg cagcaacccc gacgagcctg     60
ctgattagct ggtctgcccg cctgaaagtg gcacgttatt accgcatcac ctacggcgaa    120
acgggcggta actctccggt tcaggaattt accgtgccga aaaatgttta taccgcaacg    180
attagcggcc tgaaaccggg tgtggattat accatcacgg tgtacgcggt tacccgtttc    240
cgcgattacc agccgattag catcaactat cgtacggaaa ttgaaaaagg cagtggtagc    300
ggctctggta gtggcagcgg ttctggcagt ggtagcggct ctggtagtgt aagcgacgtc    360
ccgcgcgacc tggaagttgt tgcagcgacg ccgacgagcc tgctgatctc ttggtgggcc    420
ccggtggatc gttaccagta ttaccgcatc acctatggcg aaaccggtgg taacagcccg    480
```

```
gtgcaagaat ttaccgtgcc gcgtgatgtt tataccgcga cgatttgtgg tctgaaaccg      540
ggcgttgact acacgattac cgtttacgcg gttaccgatt ataaaccgca tgccgatggt      600
ccgcatacgt accacgaatc tccgattagt atcaattatc ggaccgaaca tcaccatcac      660
catcac                                                                 666
```

<210> SEQ ID NO 464
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 464

```
atgggcgtga gtgatgttcc gcgtgatctg gaagtggttg cagcaacccc gacgagcctg       60
ctgattagct ggtctgcccg cctgaaagtg gcacgttatt accgcatcac ctacggcgaa      120
acgggcggta actctccggt tcaggaattt accgtgccga aaaatgttta taccgcaacg      180
attagcggcc tgaaaccggg tgtggattat accatcacgg tgtacgcggt tacccgtttc      240
cgcgattacc agccgatttg catcaactat cgtacgaaaa ttgaaaaagg cagtggtagc      300
ggctctggta gtggcagcgg ttctggcagt ggtagcggct ctggtagtgt aagcgacgtc      360
ccgcgcgacc tggaagttgt tgcagcgacg ccgacgagcc tgctgatctc ttggtgggcc      420
ccggtggatc gttaccagta ttaccgcatc acctatggcg aaaccggtgg taacagcccg      480
gtgcaagaat ttaccgtgcc gcgtgatgtt tataccgcga ccatctctgg tctgaaaccg      540
ggcgttgact acacgattac cgtttacgcg gttaccgatt ataaaccgca tgccgatggt      600
ccgcatacgt accacgaatc tccgattagt atcaattatc ggaccgaaca tcaccatcac      660
catcac                                                                 666
```

<210> SEQ ID NO 465
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 465

```
atgggcgtga gcgatgttcc gcgtgatctg gaagtggttg cagcaacccc gaccagcctg       60
ctgattagct ggtctgcccg cctgaaagtg gcacgttatt accgcatcac ctacggcgaa      120
acgggcggta acagtccggt tcaggaattt accgtgccga aaaatgttta taccgcaacg      180
attagcggcc tgaaaccggg tgtggattat accatcacgg tgtacgcggt tacccgtttc      240
cgcgattacc agccgattag catcaactat cgtacggaaa ttgaaaaagg cagtggtagc      300
ggctctggta gtggcagcgg ttctggcagt ggtagcggct ctggtagtgt aagcgacgtc      360
ccgcgcgacc tggaagttgt tgcagcgacg ccgaccagcc tgctgatcag ttggtgggcc      420
ccggtggatc gttaccagta ttaccgcatc acctatggcg aaaccggtgg taacagcccg      480
gtgcaagaat tcaccgtgcc gcgtgatgtt tataccgcga ccatctctgg tctgaaaccg      540
ggcgttgact acacgattac cgtttacgcg gttaccgatt ataaaccgca tgccgatggt      600
ccgcatacgt accacgaaag cccgatttgc atcaattatc ggaccgaaca tcaccatcac      660
catcac                                                                 666
```

-continued

```
<210> SEQ ID NO 466
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid; this region may encompass 1-15,
      2-15, 1-10, 2-10, 1-8, 2-8, 1-5, 2-5, 1-4, 2-4, 1-3, 2-3 or
      1-2 residues
<220> FEATURE:
<221> NAME/KEY: MOD_RES
<222> LOCATION: (26)..(35)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (46)..(55)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (64)..(83)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (89)..(98)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (105)..(114)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (118)..(137)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (147)..(156)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (174)..(183)
<223> OTHER INFORMATION: Any amino acid; this region may encompass 0-10,
      0-5, 1-10, 1-5 or 2-5 residues

<400> SEQUENCE: 466

Glu Val Val Ala Ala Thr Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa
            20                  25                  30

Xaa Xaa Xaa Ser Trp His Glu Arg Asp Gly Ser Arg Gln Xaa Xaa Xaa
        35                  40                  45

Xaa Xaa Xaa Xaa Xaa Xaa Xaa Tyr Tyr Arg Ile Thr Tyr Gly Glu Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Gln Glu Phe Thr Val Xaa Xaa Xaa Xaa Xaa Xaa Xaa
                85                  90                  95

Xaa Xaa Pro Gly Gly Val Arg Thr Xaa Xaa Xaa Xaa Xaa Xaa Xaa Xaa
            100                 105                 110
```

```
Xaa Xaa Ala Thr Ile Xaa Xaa Xaa Xaa Xaa Xaa Xaa Xaa Xaa Xaa
        115                 120                 125

Xaa Xaa Xaa Xaa Xaa Xaa Xaa Xaa Xaa Asp Tyr Thr Ile Thr Val Tyr
    130                 135                 140

Ala Val Xaa Xaa Xaa Xaa Xaa Xaa Xaa Xaa Thr Asp Tyr Phe
145                 150                 155                 160

Asn Pro Thr Thr His Glu Tyr Ile Tyr Gln Thr Thr Pro Xaa Xaa Xaa
                165                 170                 175

Xaa Xaa Xaa Xaa Xaa Xaa Xaa Ile Ser Ile Asn Tyr Arg Thr
            180                 185                 190

<210> SEQ ID NO 467
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid; this region may encompass 1-15,
      2-15, 1-10, 2-10, 1-8, 2-8, 1-5, 2-5, 1-4, 2-4, 1-3, 2-3 or
      1-2 residues
<220> FEATURE:
<221> NAME/KEY: MOD_RES
<222> LOCATION: (26)..(35)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (46)..(55)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (64)..(83)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (89)..(98)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (105)..(114)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (118)..(137)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (147)..(156)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (174)..(183)
<223> OTHER INFORMATION: Any amino acid; this region may encompass 0-10,
      0-5, 1-10, 1-5 or 2-5 residues

<400> SEQUENCE: 467

Glu Val Val Ala Ala Thr Xaa Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa Xaa
```

```
                 20                  25                  30
Xaa Xaa Xaa Ser Trp Trp Ala Pro Val Asp Arg Tyr Gln Xaa Xaa Xaa
             35                  40                  45

Xaa Xaa Xaa Xaa Xaa Xaa Xaa Tyr Tyr Arg Ile Thr Tyr Gly Glu Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Gln Glu Phe Thr Val Xaa Xaa Xaa Xaa Xaa Xaa Xaa Xaa
             85                  90                  95

Xaa Xaa Pro Arg Asp Val Tyr Thr Xaa Xaa Xaa Xaa Xaa Xaa Xaa Xaa
            100                 105                 110

Xaa Xaa Ala Thr Ile Xaa Xaa Xaa Xaa Xaa Xaa Xaa Xaa Xaa Xaa Xaa
            115                 120                 125

Xaa Xaa Xaa Xaa Xaa Xaa Xaa Xaa Asp Tyr Thr Ile Thr Val Tyr
            130                 135                 140

Ala Val Xaa Xaa Xaa Xaa Xaa Xaa Xaa Xaa Thr Asp Tyr Lys
145                 150                 155                 160

Pro His Ala Asp Gly Pro His Thr Tyr His Glu Ser Pro Xaa Xaa Xaa
            165                 170                 175

Xaa Xaa Xaa Xaa Xaa Xaa Xaa Ile Ser Ile Asn Tyr Arg Thr
            180                 185                 190

<210> SEQ ID NO 468
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid; this region may encompass 1-15,
      2-15, 1-10, 2-10, 1-8, 2-8, 1-5, 2-5, 1-4, 2-4, 1-3, 2-3 or
      1-2 residues
<220> FEATURE:
<221> NAME/KEY: MOD_RES
<222> LOCATION: (26)..(35)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (46)..(55)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (64)..(83)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (89)..(98)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (105)..(114)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (118)..(137)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
```

```
<221> NAME/KEY: MOD_RES
<222> LOCATION: (147)..(156)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (174)..(183)
<223> OTHER INFORMATION: Any amino acid; this region may encompass 0-10,
      0-5, 1-10, 1-5 or 2-5 residues

<400> SEQUENCE: 468

Glu Val Val Ala Ala Thr Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa
            20                  25                  30

Xaa Xaa Xaa Ser Trp Thr Gln Gly Ser Thr His Tyr Gln Xaa Xaa
        35                  40                  45

Xaa Xaa Xaa Xaa Xaa Xaa Xaa Tyr Tyr Arg Ile Thr Tyr Gly Glu Xaa
    50                  55                  60

Xaa Xaa Xaa Xaa Xaa Xaa Xaa Xaa Xaa Xaa Xaa Xaa Xaa Xaa Xaa
65              70                  75                  80

Xaa Xaa Xaa Gln Glu Phe Thr Val Xaa Xaa Xaa Xaa Xaa Xaa Xaa
            85                  90                  95

Xaa Xaa Pro Gly Met Val Tyr Thr Xaa Xaa Xaa Xaa Xaa Xaa Xaa
            100                 105                 110

Xaa Xaa Ala Thr Ile Xaa Xaa Xaa Xaa Xaa Xaa Xaa Xaa Xaa Xaa
        115                 120                 125

Xaa Xaa Xaa Xaa Xaa Xaa Xaa Xaa Xaa Asp Tyr Thr Ile Thr Val Tyr
    130                 135                 140

Ala Val Xaa Xaa Xaa Xaa Xaa Xaa Xaa Xaa Xaa Thr Asp Tyr Phe
145                 150                 155                 160

Asp Arg Ser Thr His Glu Tyr Lys Tyr Arg Thr Thr Pro Xaa Xaa Xaa
            165                 170                 175

Xaa Xaa Xaa Xaa Xaa Xaa Xaa Ile Ser Ile Asn Tyr Arg Thr
        180                 185                 190

<210> SEQ ID NO 469
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid; this region may encompass 1-15,
      2-15, 1-10, 2-10, 1-8, 2-8, 1-5, 2-5, 1-4, 2-4, 1-3, 2-3 or
      1-2 residues
<220> FEATURE:
<221> NAME/KEY: MOD_RES
<222> LOCATION: (26)..(35)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (46)..(55)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (64)..(83)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
```

```
<221> NAME/KEY: MOD_RES
<222> LOCATION: (89)..(98)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (105)..(114)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (118)..(137)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (147)..(156)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (174)..(183)
<223> OTHER INFORMATION: Any amino acid; this region may encompass 0-10,
      0-5, 1-10, 1-5 or 2-5 residues

<400> SEQUENCE: 469

Glu Val Val Ala Ala Thr Xaa Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa Xaa
            20                  25                  30

Xaa Xaa Xaa Ser Trp Tyr Trp Glu Gly Leu Pro Tyr Gln Xaa Xaa Xaa
        35                  40                  45

Xaa Xaa Xaa Xaa Xaa Xaa Xaa Tyr Tyr Arg Ile Thr Tyr Gly Glu Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Gln Glu Phe Thr Val Xaa Xaa Xaa Xaa Xaa Xaa Xaa Xaa
                85                  90                  95

Xaa Xaa Pro Arg Asp Val Asn Thr Xaa Xaa Xaa Xaa Xaa Xaa Xaa Xaa
            100                 105                 110

Xaa Xaa Ala Thr Ile Xaa Xaa Xaa Xaa Xaa Xaa Xaa Xaa Xaa Xaa Xaa
        115                 120                 125

Xaa Xaa Xaa Xaa Xaa Xaa Xaa Xaa Asp Tyr Thr Ile Thr Val Tyr
    130                 135                 140

Ala Val Xaa Xaa Xaa Xaa Xaa Xaa Xaa Xaa Xaa Thr Asp Trp Tyr
145                 150                 155                 160

Asn Pro Asp Thr His Glu Tyr Ile Tyr His Thr Ile Pro Xaa Xaa Xaa
                165                 170                 175

Xaa Xaa Xaa Xaa Xaa Xaa Xaa Ile Ser Ile Asn Tyr Arg Thr
            180                 185                 190

<210> SEQ ID NO 470
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid; this region may encompass 1-15,
      2-15, 1-10, 2-10, 1-8, 2-8, 1-5, 2-5, 1-4, 2-4, 1-3, 2-3 or
      1-2 residues
<220> FEATURE:
```

```
<221> NAME/KEY: MOD_RES
<222> LOCATION: (26)..(35)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (46)..(55)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (64)..(83)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (89)..(98)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (105)..(114)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (118)..(137)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (147)..(156)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (174)..(183)
<223> OTHER INFORMATION: Any amino acid; this region may encompass 0-10,
      0-5, 1-10, 1-5 or 2-5 residues

<400> SEQUENCE: 470

Glu Val Val Ala Ala Thr Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa
            20                  25                  30

Xaa Xaa Xaa Ser Trp Ala Ser Asn Arg Gly Thr Tyr Gln Xaa Xaa Xaa
        35                  40                  45

Xaa Xaa Xaa Xaa Xaa Xaa Xaa Tyr Tyr Arg Ile Thr Tyr Gly Glu Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Gln Glu Phe Thr Val Xaa Xaa Xaa Xaa Xaa Xaa Xaa
            85                  90                  95

Xaa Xaa Pro Gly Gly Val Ser Thr Xaa Xaa Xaa Xaa Xaa Xaa Xaa
            100                 105                 110

Xaa Xaa Ala Thr Ile Xaa Xaa Xaa Xaa Xaa Xaa Xaa Xaa Xaa Xaa
            115                 120                 125

Xaa Xaa Xaa Xaa Xaa Xaa Xaa Xaa Xaa Asp Tyr Thr Ile Thr Val Tyr
    130                 135                 140

Ala Val Xaa Xaa Xaa Xaa Xaa Xaa Xaa Xaa Thr Asp Ala Phe
145                 150                 155                 160

Asn Pro Thr Thr His Glu Tyr Asn Tyr Phe Thr Thr Pro Xaa Xaa Xaa
                165                 170                 175

Xaa Xaa Xaa Xaa Xaa Xaa Xaa Ile Ser Ile Asn Tyr Arg Thr
            180                 185                 190
```

```
<210> SEQ ID NO 471
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid; this region may encompass 1-15,
      2-15, 1-10, 2-10, 1-8, 2-8, 1-5, 2-5, 1-4, 2-4, 1-3, 2-3 or
      1-2 residues
<220> FEATURE:
<221> NAME/KEY: MOD_RES
<222> LOCATION: (26)..(35)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (46)..(55)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (64)..(83)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (89)..(98)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (105)..(114)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (118)..(137)
<223> OTHER INFORMATION: Any amino acid; this region may encompass 2-20,
      2-15, 2-10, 2-8, 5-20, 5-15, 5-10, 5-8, 6-20, 6-15, 6-10,
      6-8, 2-7, 5-7 or 6-7 residues
<220> FEATURE:
<221> NAME/KEY: MOD_RES
<222> LOCATION: (147)..(156)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (174)..(183)
<223> OTHER INFORMATION: Any amino acid; this region may encompass 0-10,
      0-5, 1-10, 1-5 or 2-5 residues

<400> SEQUENCE: 471

Glu Val Val Ala Ala Thr Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa
                20                  25                  30

Xaa Xaa Xaa Ser Trp Asp Ala Pro Thr Ser Arg Tyr Gln Xaa Xaa Xaa
        35                  40                  45

Xaa Xaa Xaa Xaa Xaa Xaa Xaa Tyr Tyr Arg Ile Thr Tyr Gly Glu Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Gln Glu Phe Thr Val Xaa Xaa Xaa Xaa Xaa Xaa Xaa
                85                  90                  95

Xaa Xaa Pro Gly Gly Leu Ser Thr Xaa Xaa Xaa Xaa Xaa Xaa Xaa Xaa
```

```
              100                 105                 110
Xaa Xaa Ala Thr Ile Xaa Xaa Xaa Xaa Xaa Xaa Xaa Xaa Xaa
        115                 120                 125

Xaa Xaa Xaa Xaa Xaa Xaa Xaa Xaa Asp Tyr Thr Ile Thr Val Tyr
        130                 135                 140

Ala Val Xaa Xaa Xaa Xaa Xaa Xaa Xaa Xaa Xaa Thr Asp Tyr Lys
145             150                 155                 160

Pro His Ala Asp Gly Pro His Thr Tyr His Glu Ser Pro Xaa Xaa Xaa
                165                 170                 175

Xaa Xaa Xaa Xaa Xaa Xaa Xaa Ile Ser Ile Asn Tyr Arg Thr
        180                 185                 190

<210> SEQ ID NO 472
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid; this region may encompass 1-15,
      2-15, 1-10, 2-10, 1-8, 2-8, 1-5, 2-5, 1-4, 2-4, 1-3, 2-3 or
      1-2 residues
<220> FEATURE:
<221> NAME/KEY: MOD_RES
<222> LOCATION: (26)..(35)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (46)..(55)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (64)..(83)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (89)..(98)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (105)..(114)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (118)..(137)
<223> OTHER INFORMATION: Any amino acid; this region may encompass 2-20,
      2-15, 2-10, 2-8, 5-20, 5-15, 5-10, 5-8, 6-20, 6-15, 6-10, 6-8,
      2-7, 5-7 or 6-7 residues
<220> FEATURE:
<221> NAME/KEY: MOD_RES
<222> LOCATION: (147)..(156)
<223> OTHER INFORMATION: Any amino acid; this region may encompass 0-10,
      0-5, 1-10, 1-5 or 2-5 residues
<220> FEATURE:
<221> NAME/KEY: MOD_RES
<222> LOCATION: (174)..(183)
<223> OTHER INFORMATION: Any amino acid; this region may encompass 0-10,
      0-5, 1-10, 1-5 or 2-5 residues

<400> SEQUENCE: 472

Glu Val Val Ala Ala Thr Xaa Xaa Xaa Xaa Xaa Xaa Xaa Xaa Xaa Xaa
1               5                   10                  15
```

```
Xaa Xaa Xaa Xaa Xaa Ser Leu Leu Ile Xaa Xaa Xaa Xaa Xaa
            20                  25                  30

Xaa Xaa Xaa Ser Trp Asp Ala Gly Ala Val Thr Tyr Gln Xaa Xaa Xaa
        35                  40                  45

Xaa Xaa Xaa Xaa Xaa Xaa Xaa Tyr Tyr Arg Ile Thr Tyr Gly Glu Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Gln Glu Phe Thr Val Xaa Xaa Xaa Xaa Xaa Xaa Xaa Xaa
                85                  90                  95

Xaa Xaa Pro Gly Gly Val Arg Thr Xaa Xaa Xaa Xaa Xaa Xaa Xaa Xaa
            100                 105                 110

Xaa Xaa Ala Thr Ile Xaa Xaa Xaa Xaa Xaa Xaa Xaa Xaa Xaa Xaa Xaa
        115                 120                 125

Xaa Xaa Xaa Xaa Xaa Xaa Xaa Xaa Asp Tyr Thr Ile Thr Val Tyr
    130                 135                 140

Ala Val Xaa Xaa Xaa Xaa Xaa Xaa Xaa Xaa Thr Asp Tyr Lys
145                 150                 155                 160

Pro His Ala Asp Gly Pro His Thr Tyr His Glu Tyr Pro Xaa Xaa Xaa
                165                 170                 175

Xaa Xaa Xaa Xaa Xaa Xaa Xaa Ile Ser Ile Asn Tyr Arg Thr
            180                 185                 190

<210> SEQ ID NO 473
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala or Tyr
<220> FEATURE:
<221> NAME/KEY: MOD_RES
<222> LOCATION: (8)..(8)
<223> OTHER INFORMATION: Any amino acid

<400> SEQUENCE: 473

Asp Tyr Xaa Gly Lys Pro Tyr Xaa Glu Tyr
1               5                   10

<210> SEQ ID NO 474
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala or Tyr
<220> FEATURE:
<221> NAME/KEY: MOD_RES
<222> LOCATION: (5)..(5)
<223> OTHER INFORMATION: Lys, Arg, Gln or Thr
<220> FEATURE:
<221> NAME/KEY: MOD_RES
<222> LOCATION: (8)..(8)
<223> OTHER INFORMATION: Any amino acid

<400> SEQUENCE: 474

Asp Tyr Xaa Tyr Xaa Pro Tyr Xaa Glu Tyr
```

<210> SEQ ID NO 475
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Asn
<220> FEATURE:
<221> NAME/KEY: MOD_RES
<222> LOCATION: (3)..(3)
<223> OTHER INFORMATION: Ala or Tyr
<220> FEATURE:
<221> NAME/KEY: MOD_RES
<222> LOCATION: (4)..(4)
<223> OTHER INFORMATION: Tyr or Phe
<220> FEATURE:
<221> NAME/KEY: MOD_RES
<222> LOCATION: (5)..(5)
<223> OTHER INFORMATION: Lys, Arg, Gln or Thr
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Tyr or His

<400> SEQUENCE: 475

Xaa Tyr Xaa Xaa Xaa Glu Tyr Xaa Glu Xaa
1               5                   10

<210> SEQ ID NO 476
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: His or Tyr
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Arg or Lys
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Glu or Thr
<220> FEATURE:
<221> NAME/KEY: MOD_RES
<222> LOCATION: (10)..(10)
<223> OTHER INFORMATION: Any amino acid

<400> SEQUENCE: 476

Asp Tyr Tyr Xaa Xaa Xaa Xaa Xaa Tyr Xaa
1               5                   10

```
<210> SEQ ID NO 477
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: His or Tyr
<220> FEATURE:
<221> NAME/KEY: MOD_RES
<222> LOCATION: (5)..(5)
<223> OTHER INFORMATION: Lys, His, Gln
<220> FEATURE:
<221> NAME/KEY: MOD_RES
<222> LOCATION: (6)..(6)
<223> OTHER INFORMATION: Arg or Lys
<220> FEATURE:
<221> NAME/KEY: MOD_RES
<222> LOCATION: (8)..(8)
<223> OTHER INFORMATION: Glu or Thr
<220> FEATURE:
<221> NAME/KEY: MOD_RES
<222> LOCATION: (10)..(10)
<223> OTHER INFORMATION: Gly or Pro

<400> SEQUENCE: 477

Asp Tyr Tyr Xaa Xaa Xaa Thr Xaa Tyr Xaa
1               5                   10

<210> SEQ ID NO 478
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Asn
<220> FEATURE:
<221> NAME/KEY: MOD_RES
<222> LOCATION: (6)..(6)
<223> OTHER INFORMATION: Glu or Asp
<220> FEATURE:
<221> NAME/KEY: MOD_RES
<222> LOCATION: (8)..(8)
<223> OTHER INFORMATION: Any amino acid

<400> SEQUENCE: 478

Xaa Met Met His Val Xaa Tyr Xaa Glu Tyr
1               5                   10

<210> SEQ ID NO 479
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 479

Asp Tyr Met His Xaa Xaa Tyr Xaa Glu Tyr
```

```
1               5                  10
```

<210> SEQ ID NO 480
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Met or Tyr
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Lys or Arg
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Val, Ile, Leu or Met

<400> SEQUENCE: 480

```
Asp Xaa Tyr His Xaa Xaa Xaa Xaa Tyr Gly
1               5                  10
```

<210> SEQ ID NO 481
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr or Phe
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid

<400> SEQUENCE: 481

```
Asp Xaa Xaa Asn Pro Xaa Thr His Glu Tyr Xaa Tyr Xaa Xaa Xaa
1               5                  10                  15
```

<210> SEQ ID NO 482
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr or Phe
<220> FEATURE:

```
<221> NAME/KEY: MOD_RES
<222> LOCATION: (5)..(5)
<223> OTHER INFORMATION: Pro or Leu
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid

<400> SEQUENCE: 482

Asp Xaa Xaa Asp Xaa Xaa Xaa His Xaa Tyr Xaa Tyr Xaa Xaa Xaa
1               5                   10                  15

<210> SEQ ID NO 483
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr or Phe
<220> FEATURE:
<221> NAME/KEY: MOD_RES
<222> LOCATION: (3)..(3)
<223> OTHER INFORMATION: Lys or Arg
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(11)
<223> OTHER INFORMATION: Thr or Ile
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(15)
<223> OTHER INFORMATION: Ser or Tyr

<400> SEQUENCE: 483

Asp Xaa Xaa Pro His Xaa Asp Gly Pro His Xaa Tyr Xaa Glu Xaa
1               5                   10                  15

<210> SEQ ID NO 484
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 484

Val Ser Asp Val Pro Arg Asp Leu Glu Val Val Ala Ala Thr Pro Thr
```

```
1               5                   10                  15
Ser Leu Leu Ile Ser Trp Gln Val Pro Arg Pro Met Tyr Gln Arg Tyr
                20                  25                  30

Tyr Arg Ile Thr Tyr Gly Glu Thr Gly Gly Asn Ser Pro Val Gln Glu
        35                  40                  45

Phe Thr Val Pro Gly Gly Val Arg Thr Ala Thr Ile Ser Gly Leu Lys
    50                  55                  60

Pro Gly Val Asp Tyr Thr Ile Thr Val Tyr Ala Val Thr Asp Tyr Met
65                  70                  75                  80

His Ser Glu Tyr Arg Gln Tyr Pro Ile Ser Ile Asn Tyr Arg Thr
            85                  90                  95

<210> SEQ ID NO 485
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 485

Val Ser Asp Val Pro Arg Asp Leu Glu Val Val Ala Ala Thr Pro Thr
1               5                   10                  15

Ser Leu Leu Ile Ser Trp Gln Val Pro Arg Pro Met Tyr Gln Tyr Tyr
                20                  25                  30

Arg Ile Thr Tyr Gly Glu Thr Gly Gly Asn Ser Pro Val Gln Glu Phe
            35                  40                  45

Thr Val Pro Gly Gly Val Arg Thr Ala Thr Ile Ser Gly Leu Lys Pro
    50                  55                  60

Gly Val Asp Tyr Thr Ile Thr Val Tyr Ala Val Thr Asp Tyr Met His
65                  70                  75                  80

Ser Glu Tyr Arg Gln Tyr Pro Ile Ser Ile Asn Tyr Arg Thr
                85                  90

<210> SEQ ID NO 486
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 486

Val Ser Asp Val Pro Arg Asp Leu Glu Val Val Ala Ala Thr Pro Thr
1               5                   10                  15

Ser Leu Leu Ile Ser Trp Gln Val Pro Arg Pro Met Tyr Gln Arg Tyr
                20                  25                  30

Tyr Arg Ile Thr Tyr Gly Glu Thr Gly Gly Asn Ser Pro Val Gln Glu
        35                  40                  45

Phe Thr Val Pro Gly Gly Val Arg Thr Ala Thr Ile Ser Gly Leu Lys
    50                  55                  60

Pro Gly Val Asp Tyr Thr Ile Thr Val Tyr Ala Val Thr Asp Tyr Met
65                  70                  75                  80

His Ser Glu Tyr Arg Gln Tyr Pro Ile Ser Ile Asn Tyr Arg Thr Glu
            85                  90                  95

Ile Asp Lys Pro Cys Gln
            100
```

```
<210> SEQ ID NO 487
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 487

His His His His His His
1               5

<210> SEQ ID NO 488
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: misc_feature
<222> LOCATION: (1)..(18)
<223> OTHER INFORMATION: This region may encompass 3, 6, or 9 "Pro-Ala"
      repeats

<400> SEQUENCE: 488

Pro Ala Pro Ala Pro Ala Pro Ala Pro Ala Pro Ala Pro Ala Pro Ala
1               5                   10                  15

Pro Ala

<210> SEQ ID NO 489
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Gly Ser Gly Cys
1

<210> SEQ ID NO 490
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

Met Gly Val Ser Asp Val Pro Arg Asp Leu Glu Val Val Ala Ala Thr
1               5                   10                  15

Pro Thr Ser Leu Leu Ile Ser Trp Gln Val Pro Arg Pro Met Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Gly Val Arg Thr Ala Thr Ile Ser Gly Leu
    50                  55                  60

Lys Pro Gly Val Asp Tyr Thr Ile Thr Val Tyr Ala Val Thr Asp Tyr
65                  70                  75                  80

Met His Ser Glu Tyr Arg Gln Tyr Pro Ile Ser Ile Asn Tyr Arg Thr
                85                  90                  95

Glu Ile Asp Lys Pro Ser Gln His His His His His
            100                 105
```

```
<210> SEQ ID NO 491
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Phe Lys Gly Asp Ser Phe Thr Arg Thr Pro Pro Leu Asp Pro Arg Glu
1               5                   10                  15

Leu Glu Ile

<210> SEQ ID NO 492
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 492

Glu Glu Lys Lys Val Cys Gln Gly Thr Ser Asn Lys Leu Thr Gln Leu
1               5                   10                  15

Gly Thr Phe Glu Asp His Phe Leu Ser Leu Gln Arg Met Phe Asn Asn
            20                  25                  30

Cys Glu Val Val Leu Gly Asn Leu Glu Ile Thr Tyr Val Gln Arg Asn
        35                  40                  45

Tyr Asp Leu Ser Phe Leu Lys Thr Ile Gln Glu Val Ala Gly Tyr Val
    50                  55                  60

Leu Ile Ala Leu Asn Thr Val Glu Arg Ile Pro Leu Glu Asn Leu Gln
65                  70                  75                  80

Ile Ile Arg Gly Asn Met Tyr Tyr Glu Asn Ser Tyr Ala Leu Ala Val
                85                  90                  95

Leu Ser Asn Tyr
            100

<210> SEQ ID NO 493
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Ile Gln Cys Ala His Tyr Ile Asp Gly Pro His Cys
1               5                   10

<210> SEQ ID NO 494
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Gly Ser Gly Ser Gly Ser Gly Ser Gly Ser Gly Ser Gly Ser Gly Ser
1               5                   10                  15

<210> SEQ ID NO 495
```

<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 495

```
atgggagttt ctgatgtgcc gcgcgacctg gaagtggttg ctgccacccc caccagcctg      60
ctgatcagct ggaaaacaga accaggccgc caccaatatt accgcatcac ttacggcgaa     120
acaggaggca atagccctgt ccaggagttc actgtgcctg gtggtgttcg tacagctacc     180
atcagcggcc ttaaacctgg cgttgattat accatcactg tgtatgctgt cactgactgg     240
tacaacctgg tttctcatga atacgtatac catactaccc caatttccat taattaccgc     300
acagaaattg acaaaccatc ccagcaccat caccaccacc ac                        342
```